US010844044B2

(12) United States Patent
Alvarado et al.

(10) Patent No.: US 10,844,044 B2
(45) Date of Patent: Nov. 24, 2020

(54) WDR5 INHIBITORS AND MODULATORS

(71) Applicant: Vanderbilt University, Nashville, TN (US)

(72) Inventors: Joseph R. Alvarado, Nashville, TN (US); Shaun R. Stauffer, Brentwood, TN (US); Rocco D. Gogliotti, Kingston Springs, TN (US); Changho Han, Nashville, TN (US); Kenneth M. Meyers, Nashville, TN (US); Jianhua Tian, Nashville, TN (US); Jonathan D. Macdonald, Nashville, TN (US); Stephen W. Fesik, Nashville, TN (US); Taekyu Lee, Brentwood, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 16/441,854

(22) Filed: Jun. 14, 2019

(65) Prior Publication Data
US 2020/0102288 A1    Apr. 2, 2020

Related U.S. Application Data

(60) Provisional application No. 62/685,040, filed on Jun. 14, 2018.

(51) Int. Cl.
| | | |
|---|---|---|
| C07D 401/10 | (2006.01) | |
| A61P 35/00 | (2006.01) | |
| C07D 401/14 | (2006.01) | |
| C07D 401/06 | (2006.01) | |
| C07D 405/10 | (2006.01) | |
| C07D 233/88 | (2006.01) | |
| C07D 403/10 | (2006.01) | |
| C07D 417/12 | (2006.01) | |
| C07D 401/12 | (2006.01) | |

(52) U.S. Cl.
CPC ............ *C07D 401/10* (2013.01); *A61P 35/00* (2018.01); *C07D 233/88* (2013.01); *C07D 401/06* (2013.01); *C07D 401/12* (2013.01); *C07D 401/14* (2013.01); *C07D 403/10* (2013.01); *C07D 405/10* (2013.01); *C07D 417/12* (2013.01)

(58) Field of Classification Search
CPC .. C07D 233/88; C07D 401/06; C07D 401/10; C07D 401/12; C07D 401/14; C07D 403/10; C07D 405/10; C07D 417/12; A61P 35/00
See application file for complete search history.

(56) References Cited

U.S. PATENT DOCUMENTS

| | | | |
|---|---|---|---|
| 7,476,688 B2 | 1/2009 | Suzuki et al. | |
| 10,160,763 B2 | 12/2018 | Fesik et al. | |
| 2004/0242627 A1 | 12/2004 | Suzuki et al. | |
| 2006/0079686 A1* | 4/2006 | Baxter | C07D 215/227 544/283 |
| 2008/0200445 A1* | 8/2008 | Zhu | C07D 413/04 514/210.02 |
| 2011/0288139 A1* | 11/2011 | Fuchs | C07D 235/32 514/395 |
| 2019/0084988 A1 | 3/2019 | Fesik et al. | |

FOREIGN PATENT DOCUMENTS

| | | | |
|---|---|---|---|
| WO | 200198276 A1 | | 12/2001 |
| WO | 2002088092 A1 | | 11/2002 |
| WO | 2009110985 A2 | | 9/2009 |
| WO | WO 2013/142396 | * | 9/2013 |
| WO | WO 2017/142821 | * | 8/2017 |
| WO | 2017147700 A1 | | 9/2017 |
| WO | 2017147701 A1 | | 9/2017 |
| WO | 2019046944 A1 | | 3/2019 |

OTHER PUBLICATIONS

McKittrick et al., Iminopyrimidinones: A novel pharmacophore for the development of orally active renin inhibitors, Bioorganic & Medicinal Chemistry Letters, 25, pp. 1592-1596 (2015).*
Acute Leukemia, Merck Manual (Online Edition) 6 pages, pp. 1-6 (2013).*
Simone, Oncology: Introduction, Cecil Textbook of Medicine, 20th Edition, vol. 1, pp. 1004-1010, 1996.*
Pearce et al., Failure modes in anticancer drug discovery and development, Cancer Drug Design and Discovery Edited by Stephen Neidle, Chapter 18, pp. 424-435 (2008).*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Aho et al., "Displacement of WDR5 from Chromatin by a WIN Site Inhibitor with Picomolar Affinity", Cell Reports 26, 2019, pp. 2916-2928.
Balgobind et al., "The heterogeneity of pediatric MLL-rearranged acute myeloid leukemia," Leukemia, 2011, 8, 1239-1248.
Cao et al. "Targeting MLL1 H3 K4 methyltransferase activity in MLL leukemia," Molecular Cell, 2014, 53, 247-261.
Carugo et al., "In Vivo Functional Platform Targeting Patient Derived Xenografts Identifies WDR5-Myc Association as a Critical Determinant of Pancreatic Cancer," Cell Reports, 2016, 16, 133-147.
Caslini et al., "Interaction of MLL Amino Terminal Sequences with Menin Is Required for Transformation," Cancer Res., 2007, 67, 7275-83.

(Continued)

*Primary Examiner* — Deepak R Rao
(74) *Attorney, Agent, or Firm* — Michael Best & Friedrich LLP

(57) ABSTRACT

Described are imino-azacycle-benzamide compounds that inhibit WDR5 and associated protein-protein interactions, pharmaceutical compositions including the compounds, and methods of using the compounds and compositions for treating disorders and conditions in a subject.

20 Claims, No Drawings

(56) References Cited

OTHER PUBLICATIONS

Chen et al., "Upregulated WDR5 promotes proliferation, self-renewal and chemoresistance in bladder cancer via mediating H3K4 trimethylation," Scientific Reports, 2015, 5:8293, 1-12.
Dai et al., "WDR5 Expression Is Prognostic of Breast Cancer Outcome," PLoSOne, 2015, 10, PMC4565643.
Dias et al., "Structural analysis of the KANSL1/WDR5/KANSL2 complex reveals that WDR5 is required for efficient assembly and chromatin targeting of the NSL complex," Genes & Development, 2014, 28, 929-942.
Dimartino et al., "Mll rearrangements in human malignancies: lessons from clinical and biological studies," Br. J. Haematol. 1999, 106, 614-626.
Ee et al., "An Embryonic Stem Cell-Specific NuRD Complex Functions through Interaction with WDR5," Stem Cell Reports, 2017, 8, 1488-96.
Karatas et al., "Discovery of a Highly Potent, Cell-Permeable Macrocyclic Peptidomimetic (MM-589) Targeting the WD Repeat Domain 5 Protein (WDR5)—Mixed Lineage Leukemia (MLL) Protein—Protein Interaction," J. Med. Chem., 2017, 60, 4818-4839.
Li et al., "MOF and H4 K16 acetylation play important roles in DNA damage repair by modulating recruitment of DNA damage repair protein Mdc1.," Molecular and Cellular Biology, 2010, 30, 5335-47.
Marschalek, "Mechanisms of leukemogenesis by MLL fusion proteins," Br. J. Haematol. 2011, 152, 141-54.
Milne et al., "Leukemogenic MLL Fusion Proteins Bind across a Broad Region of the Hox a9 Locus, Promoting Transcription and Multiple Histone Modifications," Cancer Res., 2005, 65, 11367-74.
Milne et al., "MLL Targets SET Domain Methyltransferase Activity to Hox Gene Promoters," Mol. Cell, 2002, 10, 1107-17.
Nakamura et al., "ALL-1 Is a Histone Methyltransferase that Assembles a Supercomplex of Proteins Involved in Transcriptional Regulation," Mol. Cell, 2002, 10, 1119-28.
Patel et al., "On the Mechanism of Multiple Lysine Methylation by the Human Mixed Lineage Leukemia Protein-1 (MLL1) Core Complex," J. Biol. Chem., 2009, 284, 24242-56.
Pigazzi et al., "MLL partner genes drive distinct gene expression profiles and genomic alterations in pediatric acute myeloid leukemia: an AIEOP study," Leukemia, 2011, 25, 560-563.
Pui et al., "Clinical heterogeneity in childhood acute lymphoblastic leukemia with 11q23 rearrangements," Leukemia, 2003, 4, 700-706.
Senisterra et al., "Small-molecule inhibition of MLL activity by disruption of its interaction with WDR5." Biochem. J., 2013, 449, 151-159.
Slany, "The molecular biology of mixed lineage leukemia," Haematologica, 2009, 94, 984-993.
Sun et al., "WDR5 Supports an N-Myc Transcriptional Complex That Drives a Protumorigenic Gene Expression Signature in Neuroblastoma," Cancer Research, 2015, 75, 5143-54.
Tamai etal., "11q23/MLL Acute Leukemia : Update of Clinical Aspects," J. Clin. Exp. Hematop., 2010, 50, 91-98.
Tan et al., "PI3K/AKT-mediated upregulation of WDR5 promotes colorectal cancer metastasis by directly targeting ZNF407," Cell Death & Disease, 2017, 8, 1-12.
Thachuk et al., "Involvement of a homolog of *Drosophila trithorax* by 11q23 chromosomal translocations in acute leukemias," Cell, 1992, 71, 691-700.
Thomas et al., "Interaction with WDR5 Promotes Target Gene Recognition and Tumorigenesis by MYC," Molecular Cell, 2015, 58, 440-52.
Tomizawa et al., "Outcome of risk-based therapy for infant acute lymphoblastic leukemia with or without an MLL gene rearrangement, with emphasis on late effects: a final report of two consecutive studies, MLL96 and MLL98, of the Japan Infant Leukemia Study Group," Leukemia, 2007, 21, 2258-63.
Yokoyama et al., "Leukemia proto-oncoprotein MLL forms a SET1-like histone methyltransferase complex with menin to regulate Hox gene expression," Mol. Cell Biol., 2004, 24, 5639-49.
Yokoyama et al., "The menin tumor suppressor protein is an essential oncogenic cofactor for MLL-associated leukemogenesis," Cell, 2005, 123, 207-18.
Yu et al., "MLL, a mammalian trithorax-group gene, functions as a transcriptional maintenance factor in morphogenesis," Proc. Natl. Acad. Sci., 1998, 95, 10632-10636.
Cantekin et al., Chemical Abstracts 2012: 701057 (Abstract of Angewandte Chemie, International Edition, 51 (26), pp. 6426-6431.

\* cited by examiner

WDR5 INHIBITORS AND MODULATORS

RELATED APPLICATIONS

This application claims priority to U.S. Provisional Application No. 62/685,040, filed Jun. 14, 2018, which is hereby incorporated by reference in its entirety.

STATEMENT OF GOVERNMENT INTEREST

This invention was made with government support under Contract No. HHSN261200800001E, awarded by the National Institutes of Health. The government has certain rights in the invention.

TECHNICAL FIELD

The present invention relates generally to compounds that inhibit the binding of transcription factors, regulatory regulators, and chromatin to WDR5 and methods of use thereof. In particular embodiments, the present invention provides compositions comprising imino-azacycle-benzamide compounds and methods of use thereof to inhibit or modulate the interaction of WDR5 with chromatin, cognate transcription and other regulatory factors, including for example the histone methyltransferase MLL1, for the treatment of leukemia, solid cancers and other diseases dependent on activity of WDR5.

BACKGROUND

Mixed lineage leukemia (MLL) presents a heterogeneous group of acute myeloid leukemia and acute lymphoblastic leukemia bearing features of more than one hematopoietic cell lineage. MLL accounts for about 80% of infant acute leukemia cases (Tomizawa, D.; et. al. *Leukemia*, 2007, 21, 2258-63.) and 10% of all acute leukemia cases (Marschalek, R. *Br. J. Haematol.* 2011, 152, 141-54.). MLL leukemia patients have a poor prognosis with overall 5-year survival ratio around 35% (Dimartino, J. F.; Cleary, M. L., *Br. J. Haematol.* 1999, 106, 614-626; Pui, C., et al. *Leukemia*, 2003, 4, 700-706.; Tomizawa, D.; et. al. *Leukemia*, 2007, 21, 2258-63.).

MLL is composed of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of *Drosophila* trithorax (Trx) (Thachuk, D. C.; et al. *Cell*, 1992, 71, 691-700.). Wild type MLL binds to regulatory regions of homeox (HOX) genes (Milne, T. A.; et al. *Cancer Res.*, 2005, 65, 11367-74.) through the amino terminal fragment while the catalytic C-terminal domain catalyzes the Histone 3 lysine 4 (H3K4) methylation via interaction with WDR5 and up regulates target gene transcription (Nakamura, T.; et al. *Mol. Cell*, 2002, 10, 1119-28; Yokoyama, A. et al. *Mol. Cell Biol.*, 2004, 24, 5639-49.; Milne, T. A.; et al. *Mol. Cell*, 2002, 10, 1107-17). Wild type MLL in conjunction with WDR5 is required for maintenance HOX genes expression and is widely expressed not only during embryo development but also in adult tissues including myeloid and lymphoid cells (Yu, B. D.; et al. *Proc. Natl. Acad. Sci.*, 1998, 95, 10632-10636.). Reciprocal translocations of MLL gene result in-frame fusion of the 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, C., et al. *Leukemia*, 2003, 4, 700-706; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, C.; et al. *Cancer Res.*, 2007, 67, 7275-83.; Yokoyama, A.; et al. *Cell*, 2005, 123, 207-18.). The numerous chromosomal translocations of MLL gene and partner genes add to the complexity of MLL leukemia treatment. Although HOX9 and MEIS1 overexpression are commonly observed among MLL leukemia patients, each rearrangement leads to distinct dysregulated target gene expression patterns and downstream events (Slany, R. K., Haematologica, 2009, 94, 984-993). Clinical studies reveal that MLL of different chromosomal translocations are associated with different prognosis and are treated differently under current protocols (Tamai, H., et al. *J. Clin. Exp. Hematop.*, 2010, 50, 91-98; Balgobind, B. V., et al. *Leukemia*, 2011, 8, 1239-1248; Pigazzi, M.; et al. Leukemia, 2011, 25, 560-563).

Intrinsic histone methyltransferase (HMT) activity of MLL1 is extremely low and requires a complex assembly of WDR5, RbBP5, ASH2L, and DPY30 protein partners for effective H3K4 trimethylation, the so-called WRAD complex (Patel, A.; et al. *J. Biol. Chem.*, 2009, 284, 24242-56). The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, F.; et al. *Molecular Cell*, 2014, 53, 247-61, Karatas, H.; et al. *J. Med. Chem.*, 2017, 60, 4818-4839.). In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. In addition to the highly characterized WDR5-MLL1 interaction, disruption of WDR5 with other transcription factors/epigenetic writers or displacement from chromatin itself could have a desirable benefit as a cancer treatment strategy. For example, WDR5 acts as a scaffold protein with the following chromatin complexes/structures, including histone H3 (via R2 residues, e.g. see Song, J.-J., et al. *J. Biol. Chem.* 2008, 283, 35258-64), NSL/MOF (Li, X., et al. *Molecular and Cellular Biology*, 2010, 30, 5335-47, Dias, J., et al. *Genes & Development*, 2014, 28, 929-942.), C/EBPα p30 (Senisterra, G., et al. *Biochem.* 1, 2013, 449, 151-159.), c-MYC (Thomas, L. R.; et al. *Molecular Cell*, 2015, 58, 440-52, herein incorporated by reference in its entirety), and the NuRD complex (Ee, L.-S., et al. *Stem Cell Reports*, 2017, 8, 1488-96.). In addition, WDR5 expression levels have been reported to be correlative and connected to patient prognosis in several other cancer types, including neuroblastoma (Sun, Y. et al. *Cancer Research*, 2015, 75, 5143-54.), breast cancer (Dai, X. et al. *PLoSOne*, 2015, 10, PMC4565643), bladder cancer (Chen, X. et al. *Scientific Reports*, 2015, 5, 8293.), and colorectal cancer (Tan, X. et al.

*CellDeath & Disease*, 2017, 8, PMC5386518). In addition, in an unbiased shRNA screen in human xenografts, WDR5 was identified as an important target in pancreatic cancer (Carugo, A. et al. *Cell Reports*, 2016, 16, 133-147.). Based on the growing number of complexes identified which utilize WDR5 to maintain tumor fitness and growth, the emerging importance of WDR5 in several cancer types is not unexpected. In the case of the c-MYC-WDR5 interaction, the MYC oncoprotein utilizes a molecularly defined interaction with WDR5 to bind to its target genes on chromatin. MYC is overexpressed in a majority of malignancies and contributes to an estimated 70,000-100,000 cancer deaths per year in the United States. Thus, disruption of WDR5 from chromatin as a strategy to displace MYC from its target genes may provide a beneficial strategy to treat MYC-driven tumors.

SUMMARY

The molecules described herein can inhibit or modulate the interaction of WDR5 with chromatin, cognate transcription and other regulatory factors, including for example the histone methyltransferase MLL1, and can provide a therapeutic approach to treat cancers associated with such interactions (e.g., the MLL1-WDR5 interaction).

In one aspect, the invention provides compounds of formula (I),

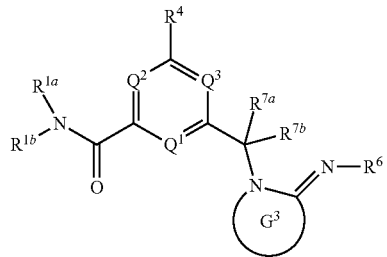

(I)

or a pharmaceutically acceptable salt thereof, wherein:

$Q^1$ is N or $CR^2$;

$Q^2$ is N or $CR^3$;

$Q^3$ is N or $CR^5$;

$R^{1a}$ is $G^1$ or $-(CR^aR^b)_n-G^1$;

n is 1, 2, or 3;

$R^a$ is hydrogen, $C_{1-4}$alkyl, $C_{1-4}$haloalkyl, $C_{3-6}$carbocycle, or $-C_{1-3}$alkylene-$C(O)YR^{20}$;

Y is O, NH, or $NC_{1-4}$alkyl;

$R^{20}$ is H, $C_{1-4}$alkyl, $C_{3-6}$cycloalkyl, or $-C_{1-3}$alkylene-$R^{30}$;

$R^{30}$ is $C(O)C_{1-4}$alkyl, $C(O)C_{3-6}$cycloalkyl, or phenyl, wherein the $C_{3-6}$cycloalkyl and phenyl are optionally substituted with 1-4 substituents independently selected from the group consisting of halogen, $C_{1-4}$alkyl, $-OC_{1-4}$alkyl, and $C_{1-4}$haloalkyl;

$R^b$ is hydrogen or $C_{1-4}$alkyl;

or alternatively $R^a$ and $R^b$ together with the carbon atom to which they are attached form a ring selected from a 3-8 membered saturated or partially unsaturated carbocyclic ring, a 3-8 membered saturated or partially unsaturated heterocyclic ring having 1-4 heteroatoms independently selected from nitrogen, oxygen, or sulfur;

or alternatively $R^a$ and $R^b$ are taken together to form an oxo group;

$R^{1b}$ is hydrogen, $C_{1-4}$alkyl, $C_{3-6}$cycloalkyl, or $-C_{1-3}$alkylene-$C_{3-6}$cycloalkyl;

$G^1$ is 6- to 12-membered aryl, a 5- to 12-membered heteroaryl, a 4- to 12-membered heterocyclyl, or a $C_{3-10}$carbocycle optionally fused to a phenyl or to a 5- to 6-membered heteroaryl, wherein $G^1$ is optionally substituted with 1-5 substituents independently selected from the group consisting of halogen, $C_{1-6}$alkyl, $C_{1-6}$haloalkyl, oxo, $-OR^{1c}$, $-NR^{1c}R^{1d}$, $-SR^{1c}$, cyano, $-C(O)OR^{1c}$, $-C(O)NR^{1c}R^{1d}$, $-C(O)R^{1e}$, $-SOR^{1e}$, $-SO_2R^{1e}$, $-SO_2NR^{1c}R^{1d}$, $-NR^{1c}C(O)R^{1e}$, $-NR^{1c}C(O)OR^{1d}$, $-NR^{1c}C(O)NR^{1c}R^{1d}$, $-NR^{1c}S(O)_2R^{1e}$, $-NR^{1c}S(O)_2NR^{1c}R^{1d}$, $C_{3-8}$cycloalkyl, and $-C_{1-3}$alkylene-$C_{3-8}$cycloalkyl, wherein the $C_{3-8}$cycloalkyl and $-C_{1-3}$alkylene-$C_{3-8}$cycloalkyl are optionally substituted with 1-4 substituents independently selected from $C_{1-4}$alkyl and halogen;

$R^2$ is hydrogen, halogen, $C_{1-4}$alkyl, or $C_{1-4}$haloalkyl;

$R^3$ is hydrogen, halogen, $C_{1-4}$alkyl, $C_{1-4}$haloalkyl, $-OR^{3a}$, $-NR^{3a}R^{3b}$, $-SR^{3a}$, cyano, $-C(O)OR^{3a}$, $-C(O)NR^{3a}R^{3b}$, $-C(O)R^{3c}$, $-SOR^{3c}$, $-SO_2R^{3c}$, $-SO_2NR^{3a}R^{3b}$, $-NR^{3a}C(O)R^{3c}$, $-NR^{3a}C(O)OR^{3b}$, $-NR^{3a}C(O)NR^{3a}R^{3b}$, $-NR^{3a}S(O)_2R^{3c}$, $-NR^{3a}S(O)_2NR^{3a}R^{3b}$, $C_{3-8}$cycloalkyl, or $-C_{1-3}$alkylene-$C_{3-8}$cycloalkyl, wherein the $C_{3-8}$cycloalkyl and $-C_{1-3}$alkylene-$C_{3-8}$cycloalkyl are optionally substituted with 1-4 substituents independently selected from $C_{1-4}$alkyl and halogen;

$R^4$ is hydrogen, halogen, $C_{1-6}$alkyl, $C_{1-6}$haloalkyl, $C_{1-6}$haloalkenyl, -L-$R^x$, $G^2$, -L-$G^2$, or -L-$C_{1-3}$alkylene-$G^2$;

L is O, S, $-NR^{4a}-$, $-S(O)-$, $-S(O)_2-$, $-S(O)_2NR^{4a}-$, $-C(O)NR^{4a}-$, $-C(O)-$, $-NR^{4a}C(O)-$, $-NR^{4a}C(O)O-$, $-NR^{4a}C(O)NR^{4a}-$, $-NR^{4a}S(O)_2-$, or $-NR^{4a}S(O)_2NR^{4a}-$;

$R^x$ is hydrogen, $C_{1-6}$alkyl, or $C_{1-6}$haloalkyl;

$G^2$ is a $C_{3-10}$carbocycle, a 6- to 12-membered aryl, a 5- to 12-membered heteroaryl, or a 4- to 12-membered heterocycle, wherein $G^2$ is optionally substituted with 1-5 substituents independently selected from the group consisting of halogen, $C_{1-6}$alkyl, $C_{1-6}$haloalkyl, oxo, $-OR^{4b}$, $-NR^{4b}R^{4c}$, $-SR^{4b}$, cyano, $-C(O)OR^{4b}$, $-C(O)NR^{4b}R^{4c}$, $-C(O)R^{4d}$, $-SOR^{4d}$, $-SO_2R^{4d}$, $-SO_2NR^{4b}R^{4c}$, $-NR^{4b}C(O)R^{4d}$, $-NR^{4b}C(O)OR^{4c}$, $-NR^{4b}C(O)NR^{4b}R^{4c}$, $-NR^{4b}S(O)_2R^{4d}$, $-NR^{4b}S(O)_2NR^{4b}R^{4c}$, $C_{3-8}$cycloalkyl, and $-C_{1-3}$alkylene-$C_{3-8}$cycloalkyl, wherein the $C_{3-8}$cycloalkyl and $-C_{1-3}$alkylene-$C_{3-8}$cycloalkyl are optionally substituted with 1-4 substituents independently selected from $C_{1-4}$alkyl and halogen;

$R^5$ is hydrogen, halogen, $C_{1-4}$alkyl, $C_{1-4}$haloalkyl, $-OR^5a$, $-NR^{5a}R^{5b}$, $-SR^{5a}$, cyano, $-C(O)OR^5a$, $-C(O)NR^{5a}R^{5b}$, $-C(O)R^{5c}$, $-SOR^5c$, $-SO_2R^{5c}$, $-SO_2NR^{5a}R^{5b}$, $-NR^{5a}C(O)R^{5c}$, $-NR^{5a}C(O)OR^{5b}$, $-NR^{5a}C(O)NR^{5a}R^{5b}$, $-NR^{5a}S(O)_2R^{5c}$, $-NR^{5a}S(O)_2NR^{5a}R^{5b}$, $C_{3-8}$cycloalkyl, or $-C_{1-3}$alkylene-$C_{3-8}$cycloalkyl, wherein the $C_{3-8}$cycloalkyl and $-C_{1-3}$alkylene-$C_{3-8}$cycloalkyl are optionally substituted with 1-4 substituents independently selected from $C_{1-4}$alkyl and halogen;

$G^3$ is a 5- to 12-membered heterocyclic ring system containing a first nitrogen at the point of attachment and optionally 1-4 additional heteroatoms selected from oxygen, nitrogen, and sulfur, $G^3$ optionally containing 1-2 double bonds and being optionally substituted with 1-4 substituents independently selected from the group consisting of halogen, oxo, $C_{1-6}$alkyl, $C_{1-6}$haloalkyl, $G^{3a}$, and $-C_{1-3}$alkylene-$G^{3a}$;

$G^{3a}$ is $C_{3-10}$carbocycle or a 6- to 12 membered aryl, wherein $G^{3a}$ is optionally substituted with 1-4 substituents independently selected from halogen, $C_{1-4}$alkyl, $C_{1-4}$haloalkyl, OH, and $-OC_{1-4}$alkyl;

$R^6$ is hydrogen, $C(O)C_{1-4}$alkyl, or $C(O)OC_{1-4}$alkyl;

$R^{7a}$ and $R^{7b}$ are independently selected from hydrogen, halogen, $C_{1-4}$alkyl, and $C_{1-4}$haloalkyl, or $R^{7a}$ and $R^{7b}$ are taken together to form an oxo group; and $R^{1c}$, $R^{1d}$, $R^{1e}$, $R^{3a}$, $R^{3b}$, $R^{3c}$, $R^{4a}$, $R^{4b}$, $R^{4c}$, $R^{4d}$, $R^{5a}$, $R^{5b}$, and $R^{5c}$, at each occurrence, are independently hydrogen, $C_{1-6}$alkyl, $C_{1-6}$haloalkyl, $C_{3-8}$cycloalkyl, or —$C_{1-6}$alkylene-$C_{3-8}$cycloalkyl, wherein the $C_{3-8}$cycloalkyl and —$C_{1-6}$alkylene-$C_{3-8}$cycloalkyl are optionally substituted with 1-4 substituents independently selected from $C_{1-4}$alkyl and halogen, wherein alternatively $R^{1c}$ and $R^{1d}$, $R^{3a}$ and $R^{3b}$, $R^{4b}$ and $R^{4c}$, and/or $R^{5a}$ and $R^{5b}$, each together with a common nitrogen atom to which each attaches form a 4- to 8-membered saturated or partially unsaturated heterocyclic ring, optionally substituted with 1-4 substituents independently selected from $C_{1-4}$alkyl, $C_{1-4}$haloalkyl, oxo, —OH, and —$OC_{1-4}$alkyl.

In another aspect, the invention provides a pharmaceutical composition comprising a compound of formula (I), or a pharmaceutically acceptable salt thereof, and a pharmaceutically acceptable carrier.

In another aspect, the invention provides a method for the treatment of cancer, comprising administering to a subject in need thereof a therapeutically effective amount of a compound of formula (I), or a pharmaceutically acceptable salt or composition thereof.

In another aspect, the invention provides a method for inhibiting the binding of MLL1 to WDR5, comprising administering to a subject in need thereof a therapeutically effective amount of a compound of formula (I), or a pharmaceutically acceptable salt or composition thereof.

In another aspect, the invention provides a compound of formula (I), or a pharmaceutically acceptable salt or composition thereof, for use in the treatment of cancer.

In another aspect, the invention provides a compound of formula (I), or a pharmaceutically acceptable salt or composition thereof, for use in the inhibition of binding of MLL1 to WDR5.

In another aspect, the invention provides the use of a compound of formula (I), or a pharmaceutically acceptable salt or composition thereof, in the manufacture of a medicament for the treatment of cancer.

In another aspect, the invention provides the use of a compound of formula (I), or a pharmaceutically acceptable salt or composition thereof, in the manufacture of a medicament for the inhibition of binding of MLL1 to WDR5.

In another aspect, the invention provides a kit comprising a compound of formula (I), or a pharmaceutically acceptable salt or composition thereof, and instructions for use.

DETAILED DESCRIPTION

Disclosed herein are inhibitors of WDR5 which bind at the WDR5 interaction or WIN-site. The inhibitors can be compounds of formula (I). Compounds of formula (I) can be used to treat cancers associated with the MLL1-WDR5 interaction. In one aspect, disclosed are compounds of formula (I) as WDR5-WIN-site inhibitors.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkylene," as used herein, refers to a divalent group derived from a straight or branched chain hydrocarbon, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "aryl," as used herein, refers to a phenyl or a phenyl appended to the parent molecular moiety and fused to a cycloalkyl group (e.g., indanyl), a phenyl group (i.e., naphthyl), or a non-aromatic heterocycle (e.g., benzo[d][1,3]dioxol-5-yl).

The term "cycloalkyl," as used herein, refers to a saturated ring system containing all carbon atoms as ring members and zero double bonds. A cycloalkyl may be a monocyclic cycloalkyl (e.g., cyclopropyl), a fused bicyclic cycloalkyl (e.g., decahydronaphthalenyl), or a bridged cycloalkyl in which two non-adjacent atoms of a ring are linked by an alkylene bridge of 1, 2, 3, or 4 carbon atoms (e.g., bicyclo[2.2.1]heptanyl). Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl," as used herein, means a non-aromatic monocyclic or multicyclic ring system containing all carbon atoms as ring members and at least one carbon-carbon double bond and preferably having from 5-10 carbon atoms per ring. A cycloalkenyl may be a monocyclic cycloalkenyl (e.g., cyclopentenyl), a fused bicyclic cycloalkenyl (e.g., octahydronaphthalenyl), or a bridged cycloalkenyl in which two non-adjacent atoms of a ring are linked by an alkylene bridge of 1, 2, 3, or 4 carbon atoms (e.g., bicyclo[2.2.1]heptenyl). Exemplary monocyclic cycloalkenyl rings include cyclopentenyl, cyclohexenyl or cycloheptenyl.

The term "carbocyclyl" or "carbocycle" means a "cycloalkyl" or a "cycloalkenyl."

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "heteroaryl," as used herein, refers to an aromatic monocyclic heteroatom-containing ring (monocyclic heteroaryl) or a bicyclic ring system containing at least one monocyclic heteroaryl (bicyclic heteroaryl). The monocyclic heteroaryl are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl is an 8- to 12-membered ring system having a monocyclic heteroaryl ring fused to a monocyclic aromatic or carbocyclic ring, a monocyclic heteroaryl, or a monocyclic heterocycle. The bicyclic heteroaryl group includes a 9-membered fused bicyclic aromatic ring system having four double bonds and at least one heteroatom contributing a lone electron pair to a fully aromatic 10×7 electron system, such as ring systems with a nitrogen atom at the ring junction (e.g., imidazopyridine) or a benzoxadiazolyl. The bicyclic heteroaryl is attached to the parent molecular moiety at an aromatic ring atom. Representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, a monocyclic heterocycle fused to a monocyclic heteroaryl, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocycle is attached to the parent molecular moiety at a non-aromatic ring atom (e.g., 2-oxaspiro[3.3]heptan-6-yl, indolin-1-yl, hexahydrocyclopenta[b]pyrrol-1(2H)-yl). Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1.3,7]decane), and oxa-adamantane (2-oxatricyclo[3.3.1.1.3,7]decane). The monocyclic, bicyclic, and tricyclic heterocycles are connected to the parent molecular moiety at a non-aromatic ring atom.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups may include, for example, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "allosteric site" as used herein refers to a ligand binding site that is topographically distinct from the orthosteric binding site.

The term "modulator" as used herein refers to a molecular entity (e.g., but not limited to, a ligand and a disclosed compound) that modulates the activity of the target receptor protein.

The term "ligand" as used herein refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

The terms "natural ligand" and "endogenous ligand" as used herein are used interchangeably, and refer to a naturally occurring ligand, found in nature, which binds to a receptor.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed are compounds of formula (I), wherein $R^{1a}$, $R^{1b}$, $R^4$, $R^6$, $R^{7a}$, $R^{7b}$, $Q^1$, $Q^2$, $Q^3$, and $G^3$ are as defined herein. Embodiments of formula (I) include the following descriptions of $R^{1a}$, $R^{1b}$, $R^4$, $R^6$, $R^{7a}$, $R^{7b}$, $Q^1$, $Q^2$, $Q^3$, and $G^3$, and any combinations thereof.

$G^3$ is a 5- to 12-membered heterocyclic ring system containing a first nitrogen at the point of attachment and optionally 1-4 additional heteroatoms selected from oxygen, nitrogen, and sulfur, $G^3$ optionally containing 1-2 double bonds and being optionally substituted with 1-4 substituents independently selected from the group consisting of halogen, oxo, $C_{1-6}$alkyl, $C_{1-6}$haloalkyl, $G^{3a}$, and —$C_{1-3}$alkylene-$G^{3a}$; and $G^{3a}$ is $C_{3-10}$carbocycle or a 6- to 12 membered aryl, wherein $G^{3a}$ is optionally substituted with 1-4 substituents independently selected from halogen, $C_{1-4}$alkyl, $C_{1-4}$haloalkyl, OH, and —$OC_{1-4}$alkyl. $G^3$ is substituted with the imine group

in the position adjacent to the first nitrogen atom, which is the point of attachment to the parent molecular moiety. In some embodiments, the 5- to 12-membered heterocyclic ring system of $G^3$ is a 5- to 8-membered monocyclic heterocycle or a 7- to 12-membered spiro heterocycle, optionally substituted as described herein. In some embodiments, the optional substituents are selected from halogen, oxo, $C_{1-4}$alkyl, $C_{3-8}$cycloalkyl, $C_{1-3}$alkylene-$C_{3-8}$cycloalkyl, or phenyl, the phenyl and cycloalkyl-containing substituents being further optionally substituted with 1-4 substituents independently selected from halogen, $C_{1-4}$alkyl, $C_{1-4}$haloalkyl, OH, and —$OC_{1-4}$alkyl. In some embodiments, the optional substituents are selected from halogen, oxo, $C_{1-4}$alkyl, $C_3$-6cycloalkyl, $C_{1-3}$alkylene-$C_{3-6}$cycloalkyl (e.g., —$CH_2$—$C_{3-6}$cycloalkyl), or phenyl, the phenyl and cycloalkyl-containing substituents being further optionally substituted with 1-4 substituents independently selected from halogen, $C_{1-4}$alkyl, $C_{1-4}$haloalkyl, OH, and —$OC_{1-4}$alkyl.

In some embodiments, $G^3$ is

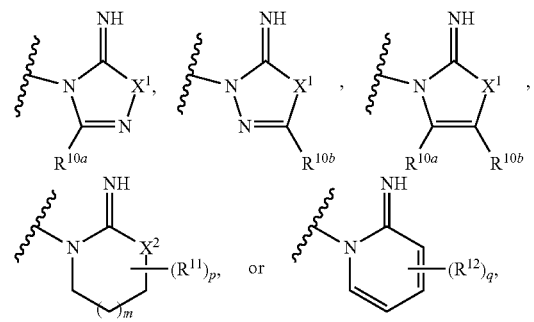

wherein $X^1$ is $NR^{13}$, O, or S; $X^2$ is $C(R^{14a})(R^{14b})$, $NR^{13}$, O, or S; $R^{10a}$ and $R^{10b}$ are independently hydrogen, $C_{1-4}$alkyl, or $C_{1-4}$haloalkyl; $R^{11}$, at each occurrence, is independently halogen, $C_{1-4}$alkyl, $C_{1-4}$haloalkyl, or two $R^{11}$ optionally form an oxo; $R^{12}$, at each occurrence, is independently halogen, $C_{1-4}$alkyl, or $C_{1-4}$ haloalkyl; $R^{13}$ is hydrogen, $C_{1-4}$alkyl, $C_{1-4}$haloalkyl, $C_{3-8}$cycloalkyl, $C_{1-3}$alkylene-$C_{3-8}$cycloalkyl, or phenyl, the phenyl and cycloalkyl-containing substituents being further optionally substituted with 1-4 substituents independently selected from halogen, $C_{1-4}$alkyl, $C_{1-4}$haloalkyl, OH, and —$OC_{1-4}$alkyl; $R^{14a}$ and $R^{14b}$ are independently hydrogen or $C_{1-4}$alkyl; m is 0, 1, or 2; p and q are each independently 0, 1, 2, 3, or 4; and $R^{1a}$, $R^{1b}$, $R^4$, $R^6$, $R^{7a}$, $R^{7b}$, $Q^1$, $Q^2$, and $Q^3$ are as defined herein. In further embodiments, $X^1$ is $NR^{13}$, $R^{13}$ is hydrogen, $C_{1-4}$alkyl, $C_{3-6}$cycloalkyl, $C_{1-3}$alkylene-$C_{3-6}$cycloalkyl (e.g., —$CH_2$—$C_{3-6}$cycloalkyl), or phenyl, the phenyl and cycloalkyl-containing substituents being further optionally substituted with 1-4 substituents independently selected from halogen, $C_{1-4}$alkyl, $C_{1-4}$haloalkyl, OH, and —$OC_{1-4}$alkyl;

In some embodiments, $G^3$ is

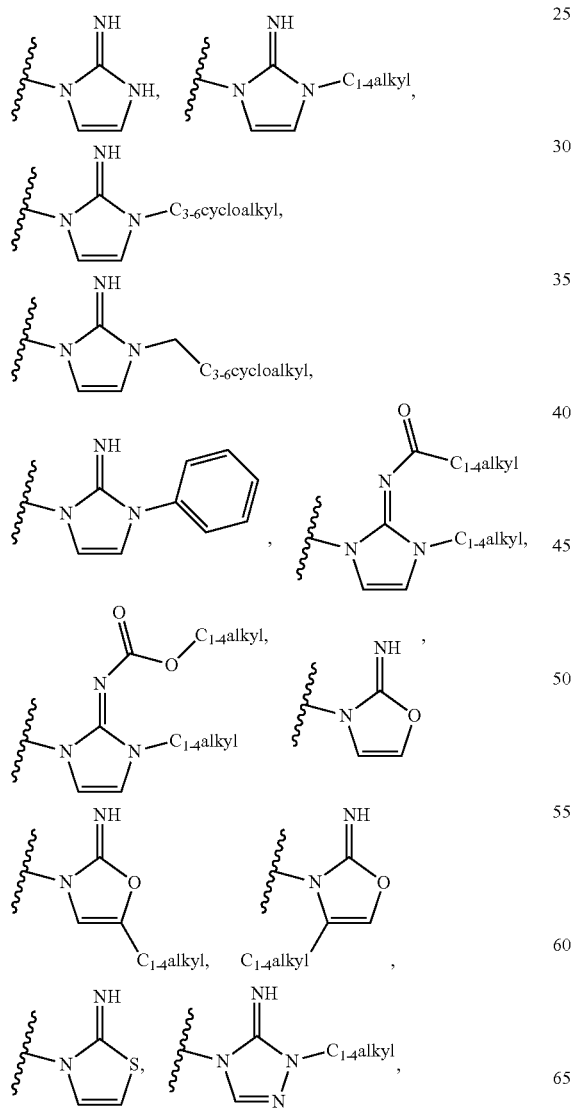

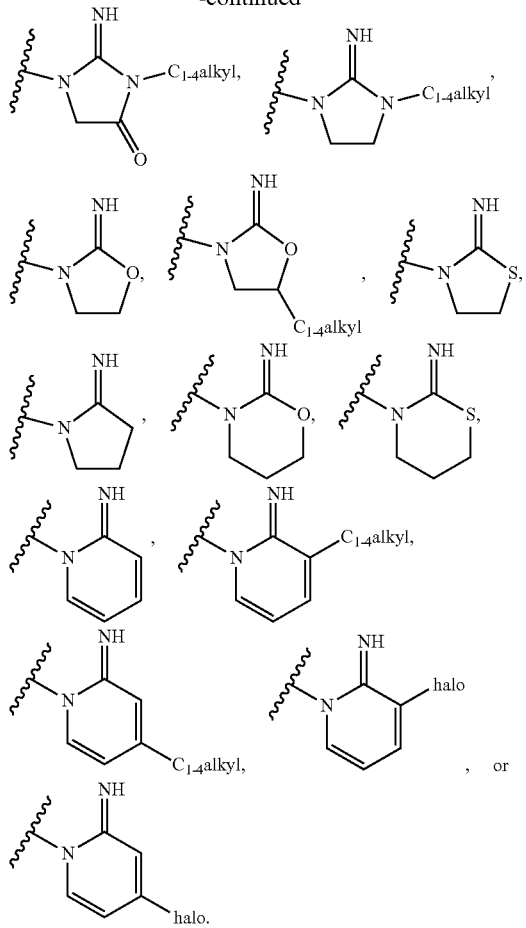

In some embodiments, $R^{1a}$ is $G^1$ or —$(CR^aR^b)_n$-$G^1$ (e.g., —$CR^aR^b$-$G^1$); wherein $G^1$ is 6- to 12-membered aryl (e.g., phenyl, naphthyl), a 5- to 12-membered heteroaryl, a 4- to 12-membered heterocyclyl, or a $C_{3-10}$carbocycle optionally fused to a phenyl (e.g., 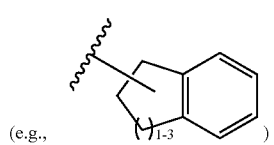 )

or to a 5- to 6-membered heteroaryl, wherein $G^1$ is optionally substituted as described herein and $R^a$ and $R^b$, and n are as defined herein.

In some embodiments, $R^{1a}$ is $G^{1a}$ or —$(CR^aR^b)$-$G^{1b}$; $G^{1a}$ is a 9- to 10-membered heteroaryl or a $C_{3-7}$carbocycle optionally fused to a phenyl (e.g., 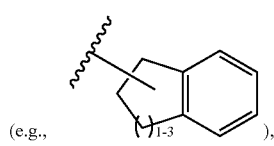 ), wherein $G^{1a}$ is optionally substituted with 1-4 substituents independently selected from the group consisting of halogen, $C_{1-6}$alkyl, $C_{1-6}$haloalkyl, oxo, —OR$^{1c}$, —NR$^{1c}$R$^{1d}$, —SR$^{1c}$, cyano, —C(O)OR, —C(O)NR$^{1c}$R$^{1d}$, —C(O)R$^{1e}$, —SOR$^{1e}$, —SO$_2$R$^{1e}$, —SO$_2$NR$^{1c}$R$^{1d}$, —NR$^{1c}$C(O)R$^{1e}$, —NR$^{1c}$C(O)OR$^{1d}$, NR$^{1c}$C(O)NR$^{1c}$R$^{1d}$, —NR$^{1c}$S(O)$_2$R$^{1e}$, —NR$^{1c}$S(O)$_2$NR$^{1c}$R$^{1d}$, $C_{3-8}$cycloalkyl, and —$C_{1-6}$alkylene-$C_{3-8}$cycloalkyl (e.g., —$C_{1-3}$alkylene-$C_{3-8}$cycloalkyl), wherein the $C_{3-8}$cycloalkyl and —$C_{1-6}$alkylene-$C_{3-8}$cycloalkyl (e.g., —$C_{1-3}$alkylene-$C_{3-8}$cycloalkyl) are optionally substituted with 1-4 substituents independently selected from $C_{1-4}$alkyl and halogen; and G$^{1b}$ is phenyl, a 5- to 6-membered heteroaryl, or a 4- to 8-membered heterocyclyl, wherein G$^{1b}$ is optionally substituted with 1-4 substituents independently selected from the group consisting of halogen, $C_{1-6}$alkyl, $C_{1-6}$ haloalkyl, oxo, —OR$^{1c}$, —NR$^{1c}$R$^{1d}$, —SR$^{1c}$, cyano, —C(O)OR$^{1c}$, —C(O)NR$^{1c}$R$^{1d}$, —C(O)R$^{1e}$, —SOR$^{1e}$, —SO$_2$R$^{1e}$, —SO$_2$NR$^{1c}$R$^{1d}$, —NR$^{1c}$C(O)R$^{1e}$, —NR$^{1c}$C(O)OR$^{1d}$, —NR$^{1c}$C(O)NR$^{1c}$R$^{1d}$, —NR$^{1c}$S(O)$_2$R$^{1e}$, —NR$^{1c}$S(O)$_2$NR$^{1c}$R$^{1d}$, $C_{3-8}$cycloalkyl, and —$C_{1-6}$alkylene-$C_{3-8}$cycloalkyl (e.g., —$C_{1-3}$alkylene-$C_{3-8}$cycloalkyl), wherein the $C_{3-8}$cycloalkyl and —$C_{1-6}$alkylene-$C_{3-8}$cycloalkyl (e.g., —$C_{1-3}$alkylene-$C_{3-8}$cycloalkyl) are optionally substituted with 1-4 substituents independently selected from $C_{1-4}$ alkyl and halogen. In further embodiments, G$^{1a}$ is a) a 5-membered monocyclic heteroaryl fused to a phenyl; b) $C_{3-7}$cycloalkyl; or c) a $C_{5-7}$cycloalkyl fused to a phenyl; wherein G$^{1a}$ is optionally substituted with 1-4 substituents independently selected from halogen, $C_{1-4}$alkyl, $C_{1-4}$ haloalkyl, and —OR$^{1c}$; and G$^{1b}$ is a) phenyl; b) a 5- to 6-membered heteroaryl; or c) a 4- to 8-membered heterocyclyl; wherein G$^{1b}$ is optionally substituted with 1-4 substituents independently selected from halogen, $C_{1-4}$alkyl, $C_{1-4}$haloalkyl, oxo, and —OR$^{1c}$. In still further embodiments, G$^{1a}$ is a) a 5-membered monocyclic heteroaryl containing 1-2 heteroatoms selected from O, N, and S, the heteroaryl being fused to a phenyl; b) $C_{3-7}$cycloalkyl; or c) a $C_{5-7}$ cycloalkyl fused to a phenyl, wherein the $C_{5-7}$cycloalkyl fused to a phenyl is optionally substituted with 1-2 substituents independently selected from halogen, $C_{1-4}$alkyl, or trifluoromethyl, and —OR$^{1c}$; G$^{1b}$ is a) phenyl optionally substituted with 1-3 substituents independently selected from the group consisting of halogen, $C_{1-4}$alkyl, $C_{1-4}$haloalkyl, and —OR$^{1C}$; b) a 5- to 6-membered heteroaryl optionally substituted with 1-3 substituents independently selected from the group consisting of halogen, $C_{1-6}$alkyl, $C_{1-6}$haloalkyl, and —OR$^{1c}$; c) a 4- to 8-membered saturated heterocyclyl containing one oxygen atom; or d) a pyridone optionally substituted with $C_{1-4}$alkyl; and R$^{1c}$ is $C_{1-4}$alkyl. In yet further embodiments, R$^{1a}$ is G$^{1a}$ and G$^{1a}$ is

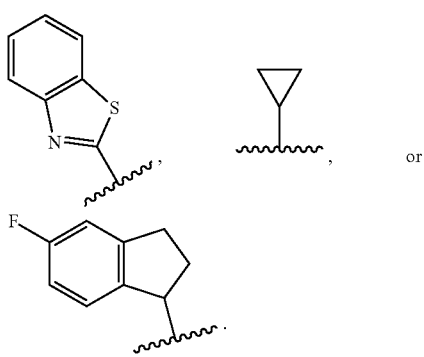

In further embodiments, R$^{1a}$ is —(CR$^a$R$^b$)-G$^{1b}$; and G$^{1b}$ is

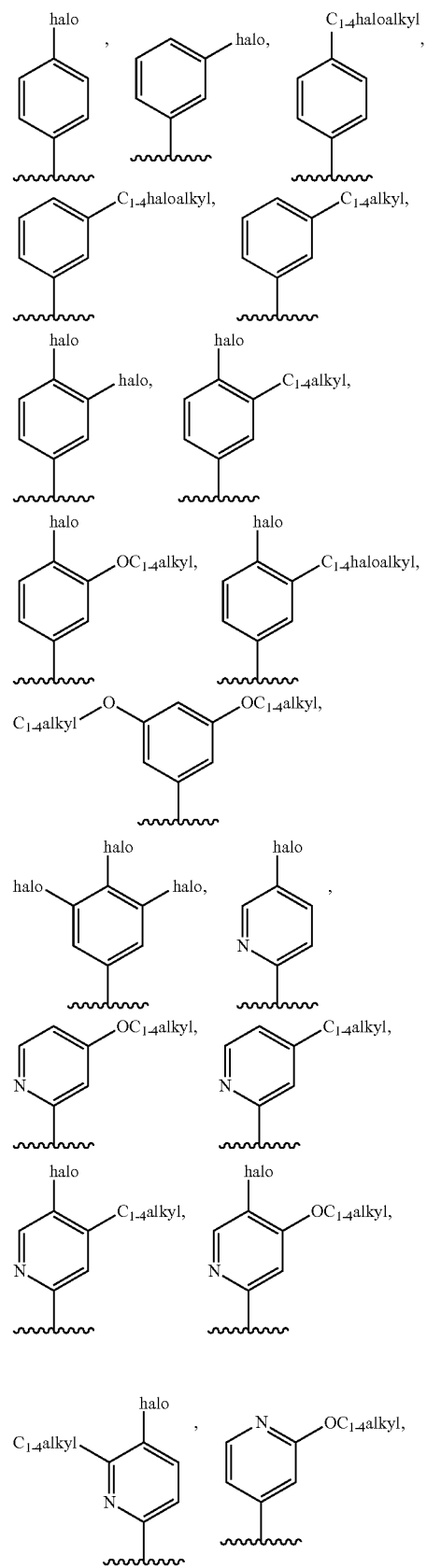

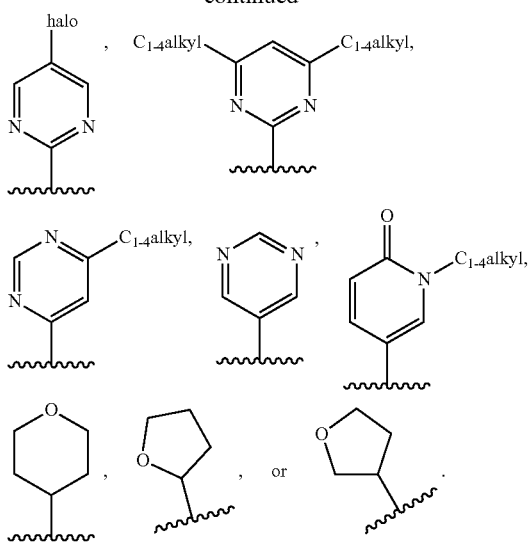

In still further embodiments, $G^{1b}$ is

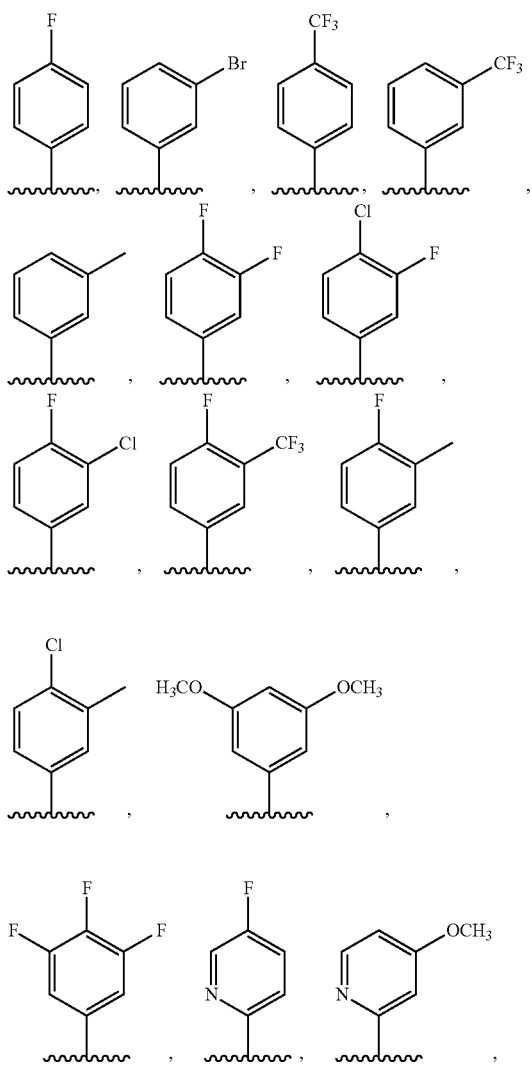

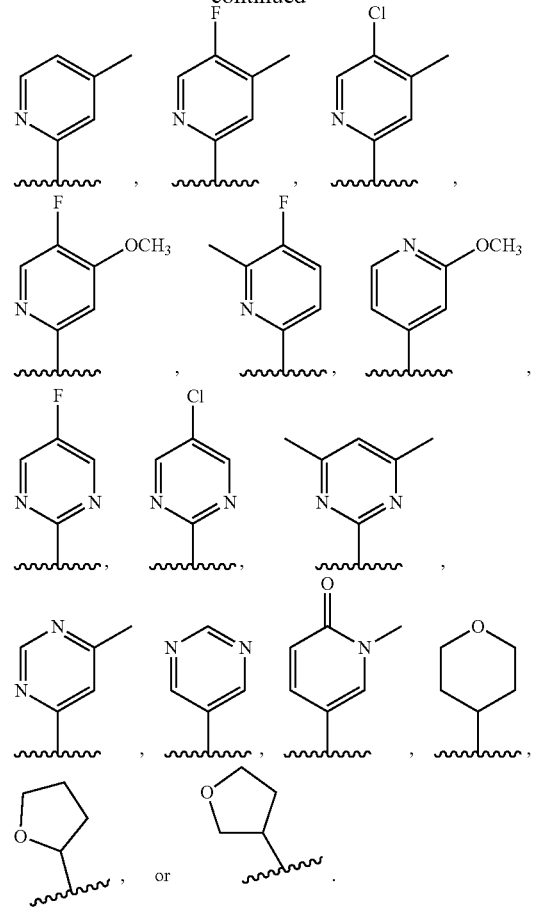

In some embodiments, $R^a$ is hydrogen, $C_{1-4}$alkyl, $C_{1-4}$haloalkyl, $C_{3-6}$carbocycle, —$C_{1-3}$alkylene-C(O)OH, —$C_{1-3}$alkylene-C(O)OC$_{1-4}$alkyl, or —$C_{1-3}$alkylene-C(O)YR$^{20}$; and Y is NH, or NC$_{1-4}$alkyl. In further embodiments, $R^a$ is hydrogen, $C_{1-2}$alkyl, $C_{1-2}$haloalkyl, $C_{3-4}$carbocycle, —$C_{1-3}$alkylene-C(O)OH, —$C_{1-3}$alkylene-C(O)OC$_{1-4}$alkyl, or —$C_{1-3}$alkylene-C(O)YR$^{20}$; Y is NH, or NC$_{1-4}$alkyl; $R^{20}$ is —$C_{1-3}$alkylene-R$^{30}$; and $R^{30}$ is C(O)C$_{1-4}$alkyl or phenyl, wherein the phenyl is optionally substituted with 1-4 substituents independently selected from the group consisting of halogen, $C_{1-4}$alkyl, —OC$_{1-4}$alkyl, and $C_{1-4}$haloalkyl.

In the embodiments described herein are further embodiments, wherein $R^b$ is hydrogen. For example, in the compounds described herein, $R^a$ may be hydrogen, $C_{1-2}$alkyl, $C_{1-2}$ haloalkyl, or $C_{3-4}$carbocycle; and $R^b$ is hydrogen. In the compounds described herein, $R^a$ may be —$C_{1-3}$alkylene-C(O)OH, —$C_{1-3}$alkylene-C(O)OC$_{1-4}$alkyl, or —$C_{1-3}$alkylene-C(O)YR$^{20}$; wherein Y is NH, or NC$_{1-4}$alkyl; $R^{20}$ is —$C_{1-3}$alkylene-R$^{30}$; and $R^{30}$ is C(O)C$_{1-4}$alkyl or phenyl, wherein the phenyl is optionally substituted with 1-4 substituents independently selected from the group consisting of halogen, $C_{1-4}$alkyl, —OC$_{1-4}$alkyl, and $C_{1-4}$haloalkyl; and $R^b$ is hydrogen.

In some embodiments, $R^a$ and $R^b$ together with the carbon atom to which they are attached form a ring selected form a 3-8 membered saturated or partially unsaturated carbocyclic ring. In further embodiments, $R^a$ and $R^b$ together with the carbon atom to which they are attached form a cyclobutane.

In the embodiments described herein are further embodiments, wherein $R^{1b}$ is hydrogen or $C_{1-4}$alkyl (e.g., methyl).

In some embodiments, $R^4$ is hydrogen, $C_{1-6}$haloalkyl, $C_{1-6}$haloalkenyl, -L-$R^x$, $G^2$, or -L-$C_{1-3}$alkylene-$G^2$; L is O; and $R^x$ is $C_{1-6}$alkyl or $C_{1-6}$haloalkyl. In further embodiments, $G^2$ is a $C_{3-7}$carbocycle, a 6- to 10-membered aryl, a 5- to 10-membered heteroaryl, or a 4- to 10-membered heterocycle, wherein $G^2$ is optionally substituted with 1-3 substituents independently selected from halogen, $C_{1-6}$alkyl, $C_{1-6}$haloalkyl, oxo, —$OR^{4b}$, cyano, —$C(O)OR^{4b}$, —$C(O)NR^{4b}R^{4c}$, and $C_{3-8}$cycloalkyl, wherein the $C_{3-8}$cycloalkyl is optionally substituted with 1-4 substituents independently selected from $C_{1-4}$alkyl and halogen. In further embodiments, $R^4$ is hydrogen, $C_{1-6}$haloalkyl, $C_{1-6}$haloalkenyl, —O—$R^x$, $G^2$, or —O—$C_{1-3}$alkylene-$C_{3-6}$cycloalkyl; $G^2$ is a) a $C_{3-6}$ cycloalkyl, optionally substituted with 1-3 substituents independently selected from the group consisting of halogen, $C_{1-4}$alkyl, and $C_{1-2}$haloalkyl; b) a 6- to 10-membered aryl, optionally substituted with 1-3 substituents independently selected from the group consisting of halogen, $C_{1-6}$alkyl, $C_{1-6}$haloalkyl, —$OR^{4b}$, cyano, —$C(O)OR^{4b}$, and —$C(O)NR^{4b}R^{4c}$; c) a 5- to 10-membered heteroaryl, optionally substituted with 1-3 substituents independently selected from the group consisting of halogen, $C_{1-6}$alkyl, $C_{1-6}$haloalkyl, —$OR^{4b}$, and $C_{3-6}$cycloalkyl; d) a 4- to 7-membered saturated nitrogen-containing heterocycle optionally substituted with 1-3 substituents independently selected from the group consisting of halogen, $C_{1-6}$alkyl, and $C_{1-6}$haloalkyl; or e) a pyridone, optionally substituted with $C_{1-4}$alkyl; and $R^{4b}$ and $R^{4c}$, at each occurrence, are independently hydrogen, $C_{1-4}$alkyl, or $C_{1-4}$haloalkyl. In still further embodiments, $G^2$ is a) a cyclopropyl optionally substituted with trifluoromethyl; b) a phenyl or benzodioxole, optionally substituted with 1-3 substituents independently selected from the group consisting of halogen, $C_{1-4}$alkyl, $C_{1-4}$haloalkyl, —$OR^{4b}$, cyano, —$C(O)OR^{4b}$, and —$C(O)NR^{4b}R^{4c}$; c) a pyrrolyl, pyrazolyl, imidazolyl, pyridinyl, pyrimidinyl, indazolyl, 5,6,7,8-tetrahydroquinazolinyl, or 6,7-dihydro-5H-cyclopenta[b]pyridinyl, optionally substituted with 1-3 substituents independently selected from the group consisting of halogen, $C_{1-4}$alkyl, $C_{1-4}$haloalkyl, —$OR^{4b}$, and $C_{3-6}$cycloalkyl; d) a pyrrolidinyl or morpholinyl, optionally substituted with 1-3 substituents independently selected from the group consisting of halogen, $C_{1-4}$alkyl, and $C_{1-4}$haloalkyl; or e) a pyridone, optionally substituted with $C_{1-4}$alkyl.

In the embodiments described herein are further embodiments wherein $Q^1$ is $CR^2$; $Q^2$ is $CR^3$; and $Q^3$ is $CR^5$ and $R^2$, $R^3$, and $R^5$ are as defined herein.

In the embodiments described herein are further embodiments wherein only one of $Q^1$, $Q^2$, and $Q^3$ is N. For example, in some embodiments, $Q^1$ is $CR^2$; $Q^2$ is N; and $Q^3$ is $CR^5$ and $R^2$ and $R^5$ are as defined herein. In some embodiments, $Q^1$ is $CR^2$; $Q^2$ is $CR^3$; and $Q^3$ is N, and $R^2$ and $R^3$ are as defined herein.

In the embodiments described herein are further embodiments wherein $R^2$ is hydrogen.

In the embodiments described herein are further embodiments wherein $R^3$ is hydrogen, halogen, or —$OR^3$a; and $R^{3a}$ is as defined herein. In further embodiments, $R^{3a}$ is $C_{1-4}$alkyl.

In the embodiments described herein are further embodiments wherein $R^5$ is hydrogen or halogen.

Throughout the embodiments and description of the compounds of the invention, all instances of haloalkyl may be fluoroalkyl (e.g., $C_{1-4}$haloalkyl may be $C_{1-4}$fluoroalkyl; $C_1$-2haloalkyl may be $C_{1-2}$fluoroalkyl).

In some embodiments, the compound of formula (I) is selected from the group consisting of:

TABLE 1

Exemplary compounds.

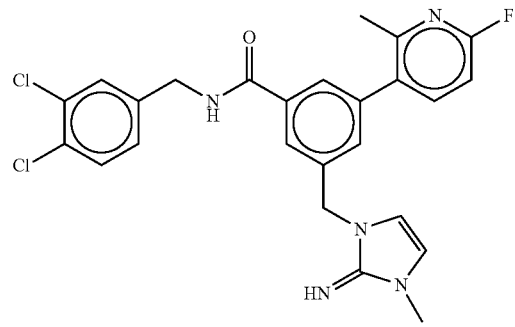

I-1

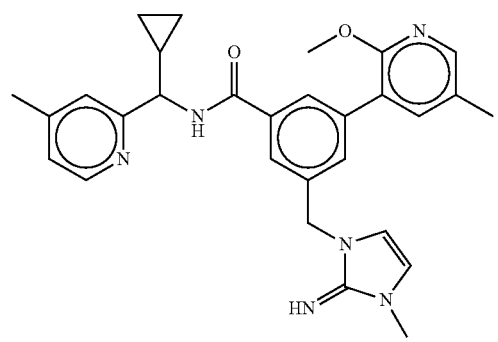

I-2

TABLE 1-continued
Exemplary compounds.
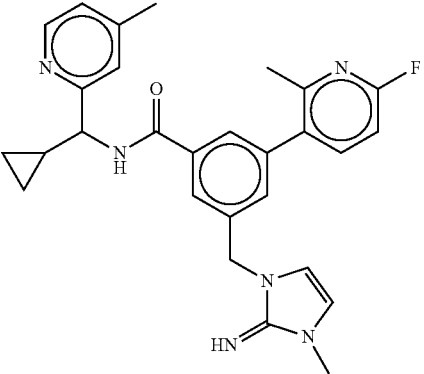
I-3
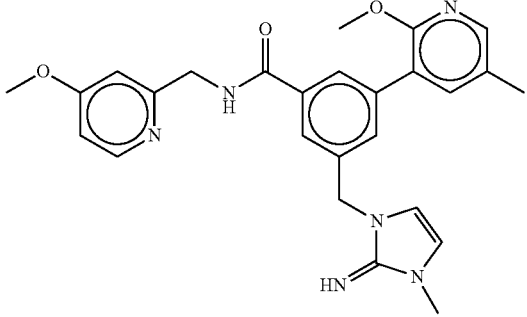
I-4
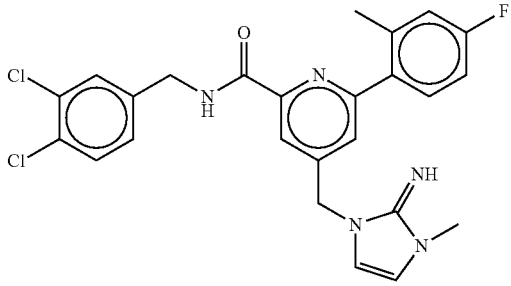
I-5
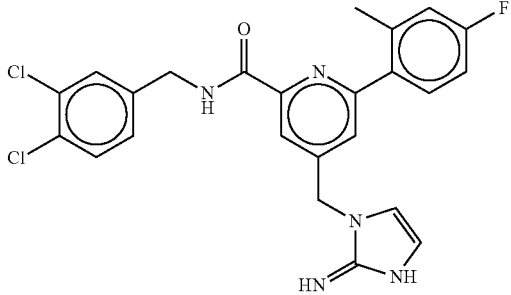
I-6
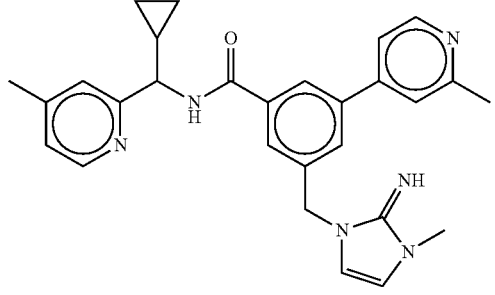
I-7

TABLE 1-continued
Exemplary compounds.
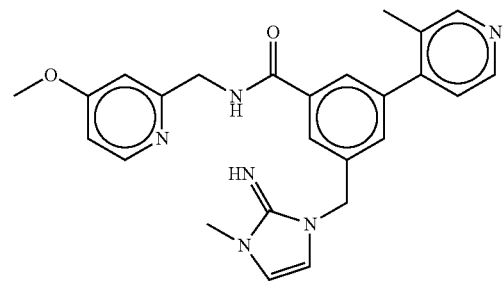
I-8
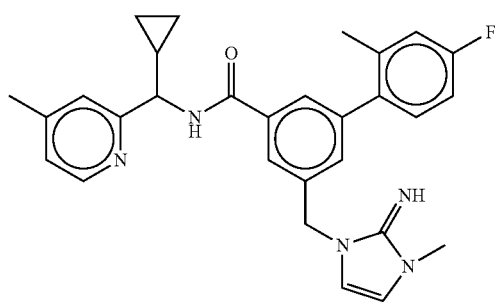
I-9
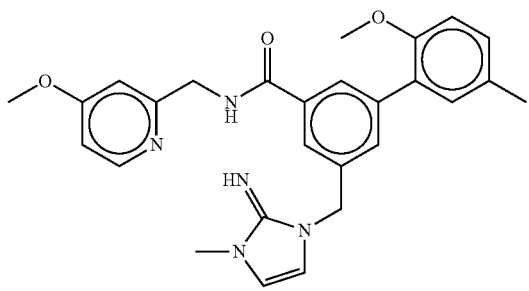
I-10
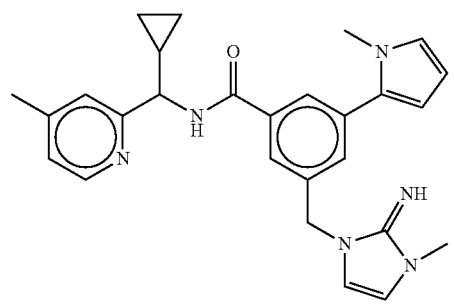
I-11
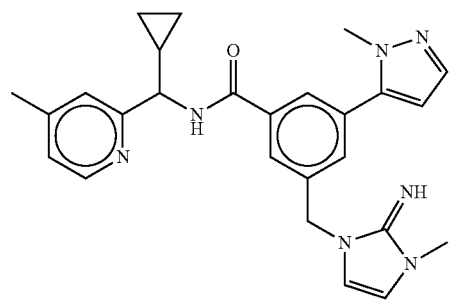
I-12

TABLE 1-continued
Exemplary compounds.
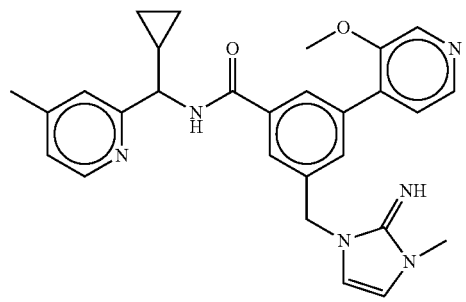
I-13
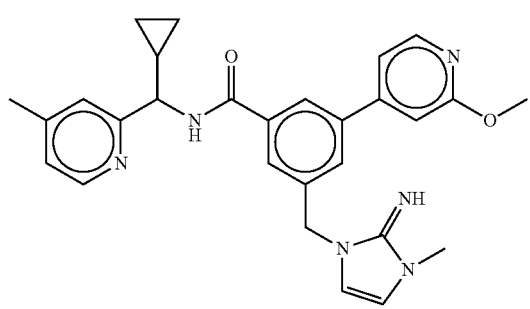
I-14
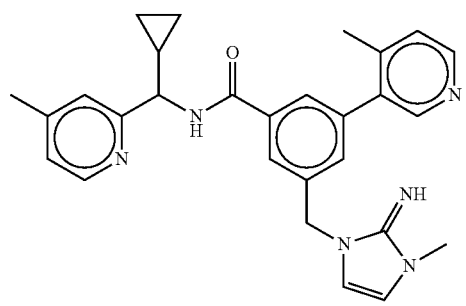
I-15
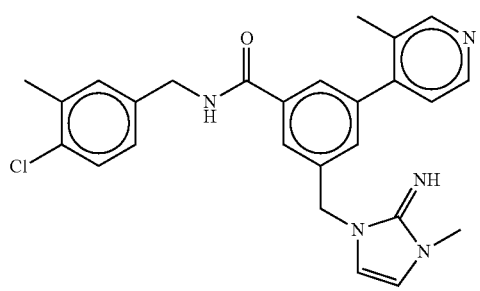
I-16
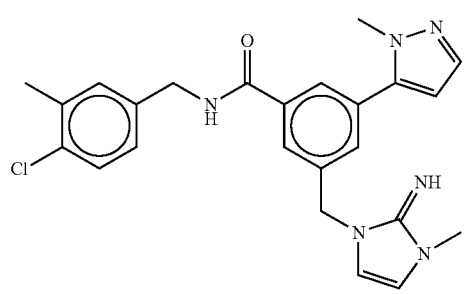
I-17

TABLE 1-continued
Exemplary compounds.
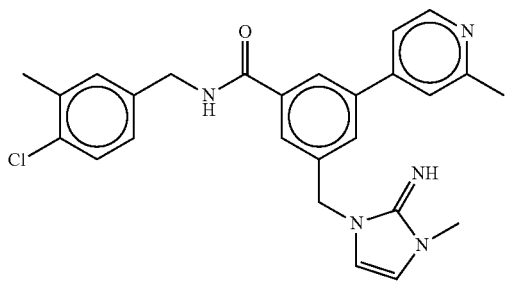
I-18
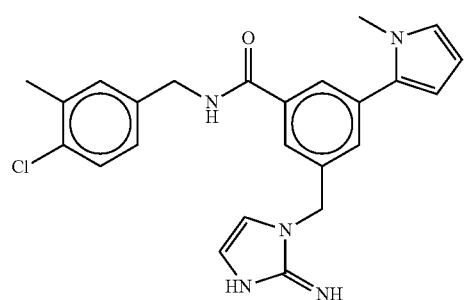
I-19
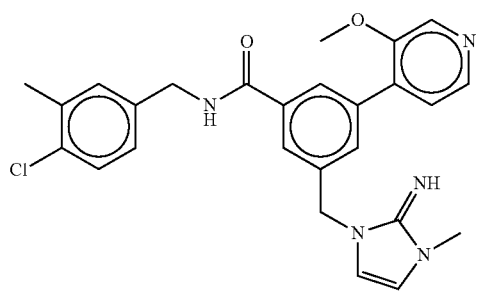
I-20
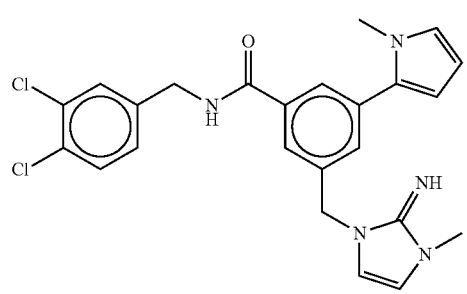
I-21
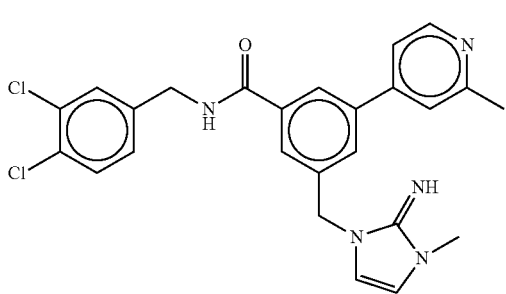
I-22

TABLE 1-continued
Exemplary compounds.
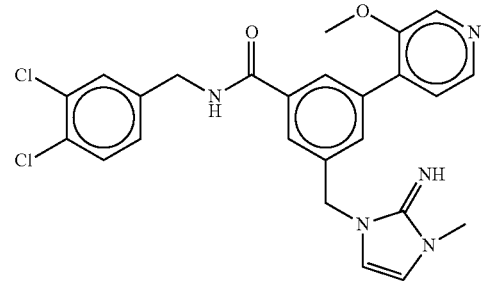
I-23
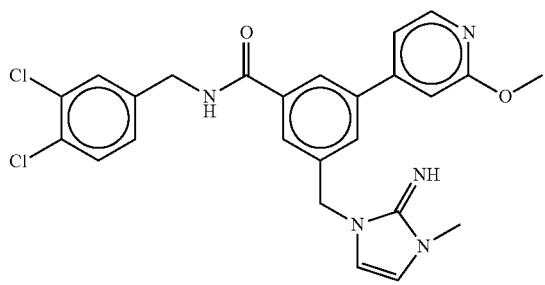
I-24
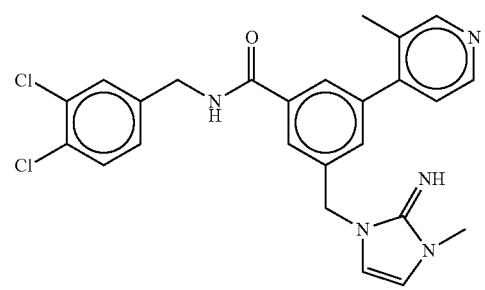
I-25
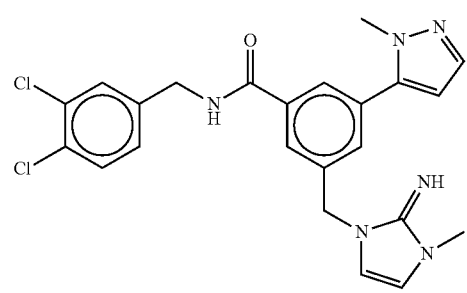
I-26
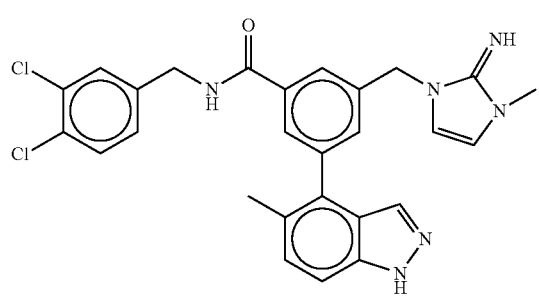
I-27

TABLE 1-continued
Exemplary compounds.
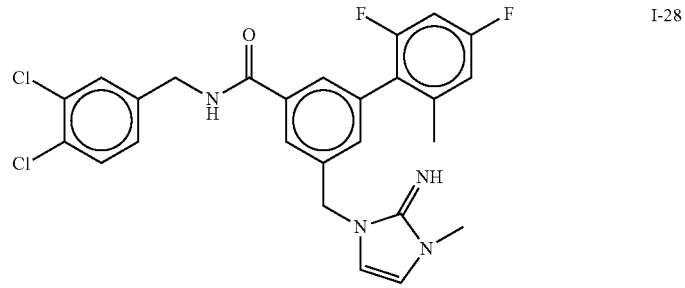 I-28
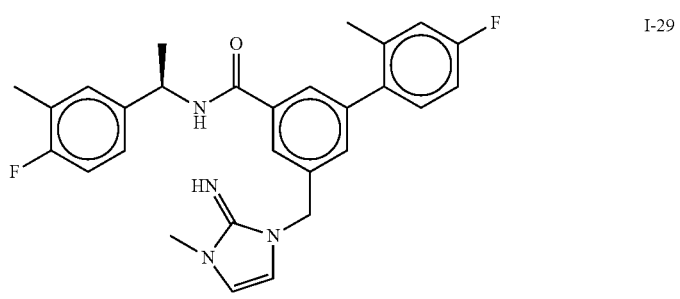 I-29
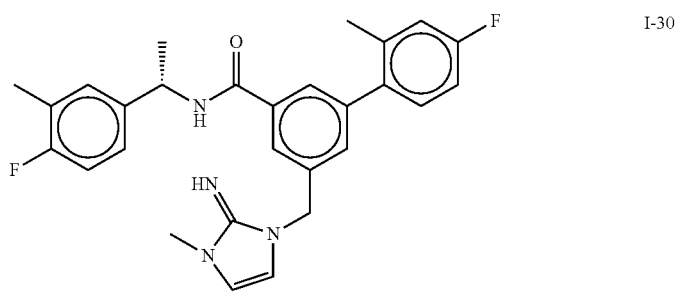 I-30
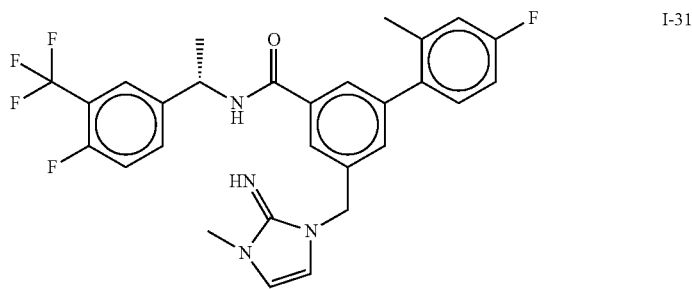 I-31
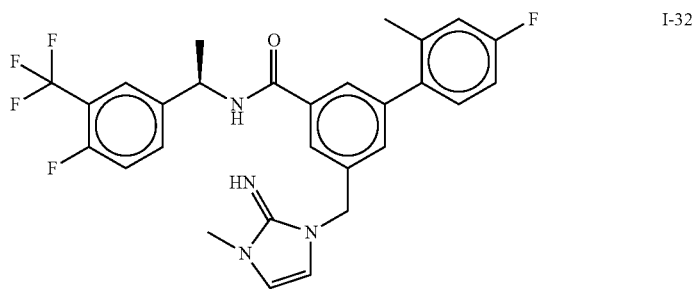 I-32

TABLE 1-continued
Exemplary compounds.
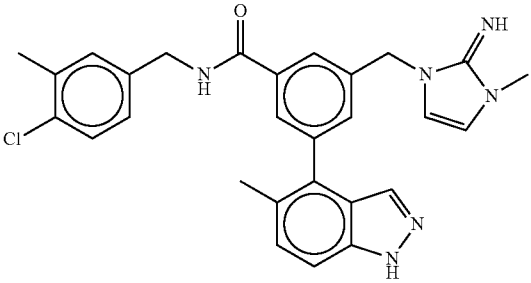 I-33
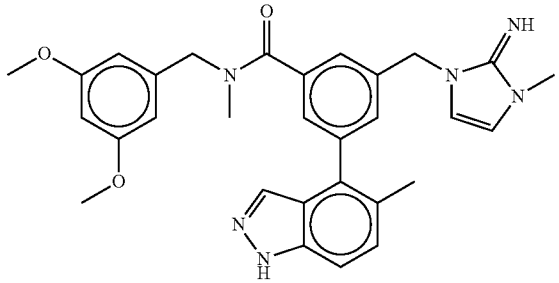 I-34
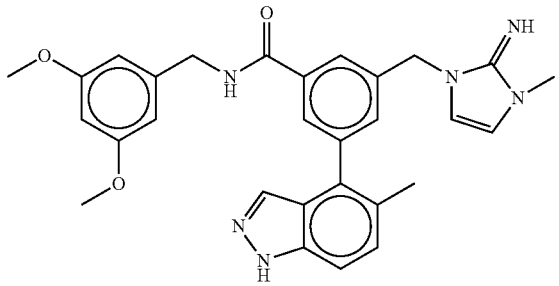 I-35
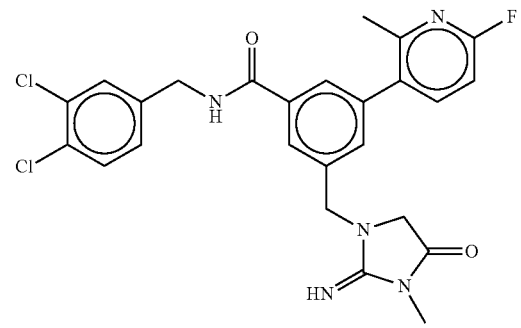 I-36
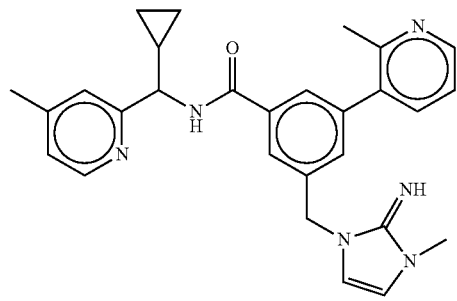 I-37

TABLE 1-continued
Exemplary compounds.
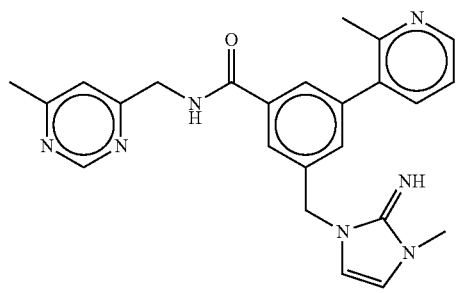 I-38
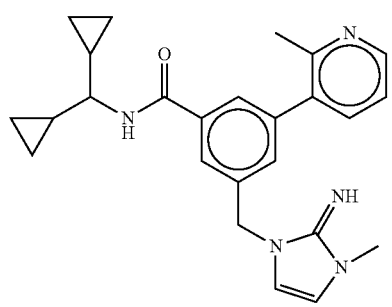 I-39
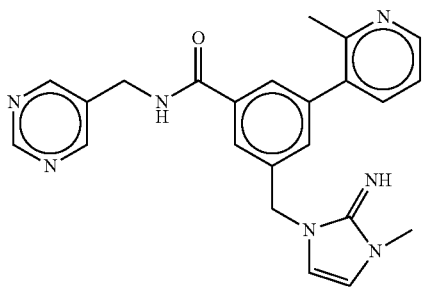 I-40
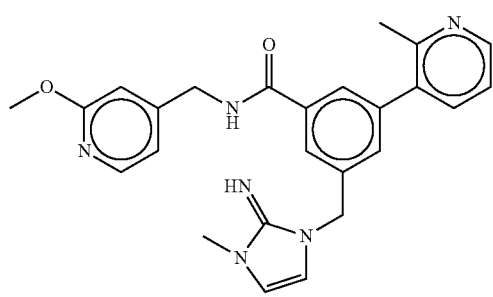 I-41
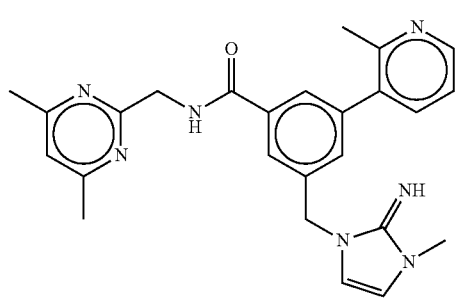 I-42

TABLE 1-continued
Exemplary compounds.
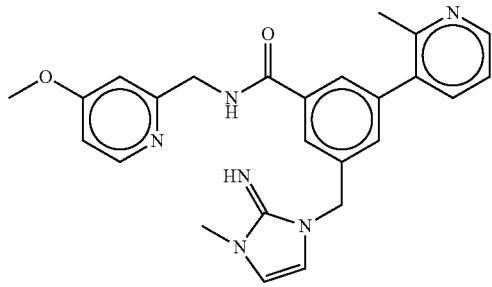
I-43
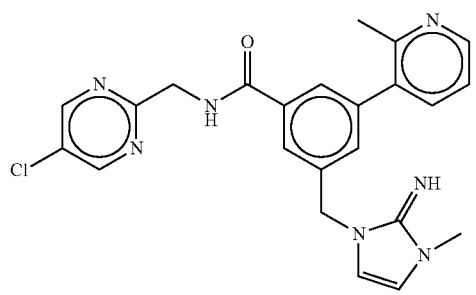
I-44
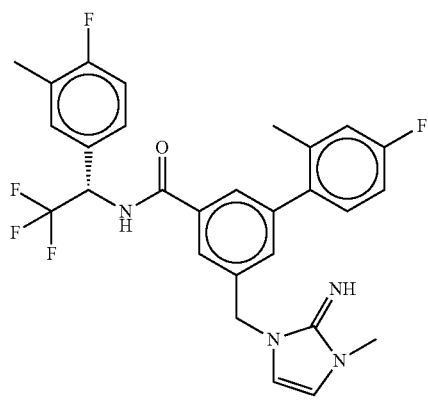
I-45
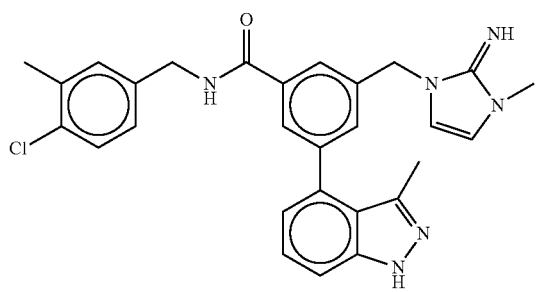
I-46
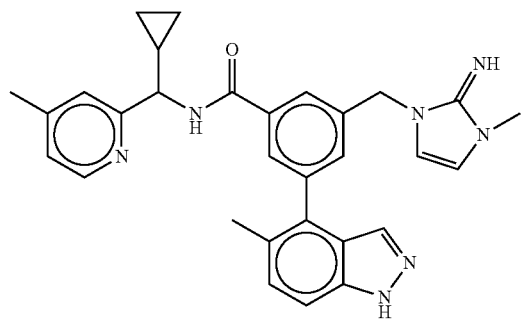
I-47

TABLE 1-continued
Exemplary compounds.
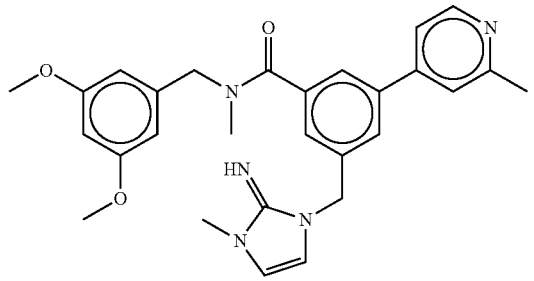
I-48
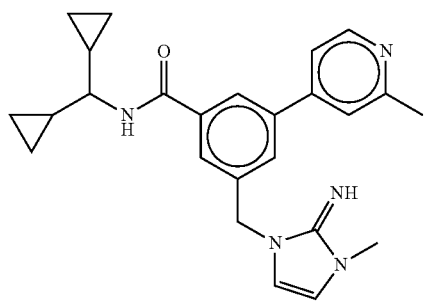
I-49
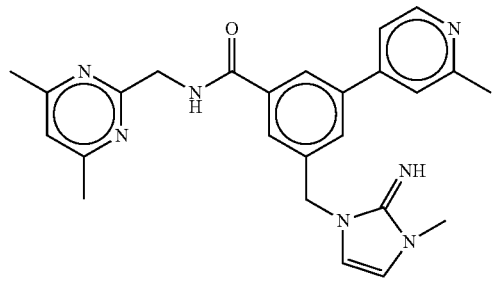
I-50
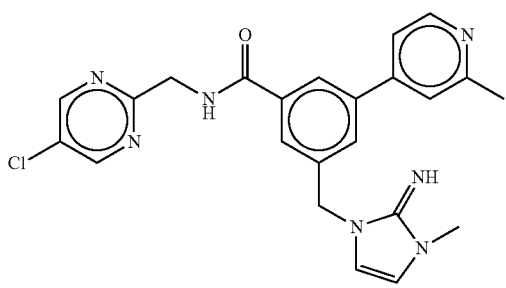
I-51
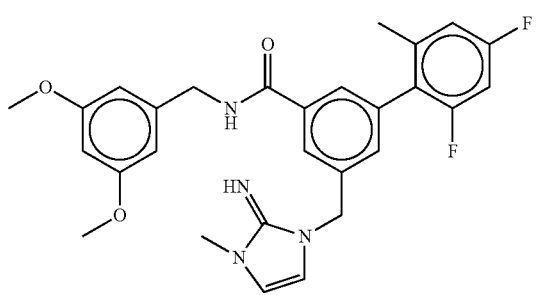
I-52

TABLE 1-continued
Exemplary compounds.
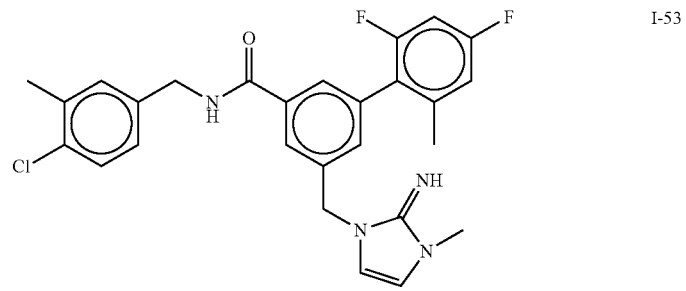
I-53
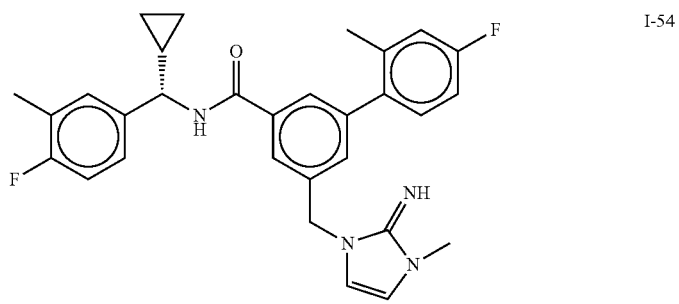
I-54
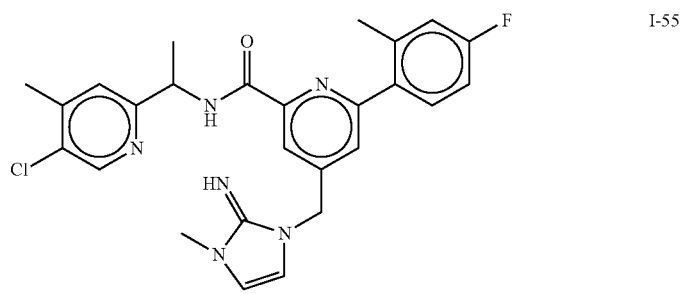
I-55
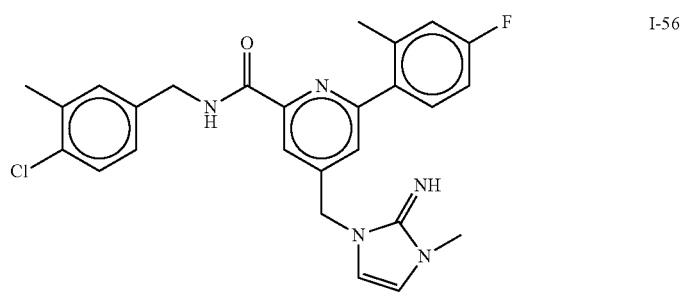
I-56
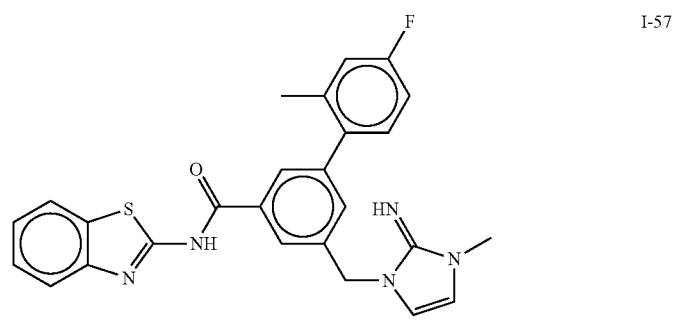
I-57

TABLE 1-continued

Exemplary compounds.

| | |
|---|---|
| (chemical structure) | I-58 |
| (chemical structure) | I-59 |
| (chemical structure) | I-60 |
| (chemical structure) | I-61 |
| (chemical structure) | I-62 |

TABLE 1-continued
Exemplary compounds.
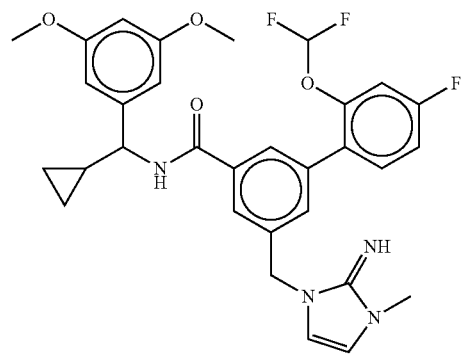
I-63
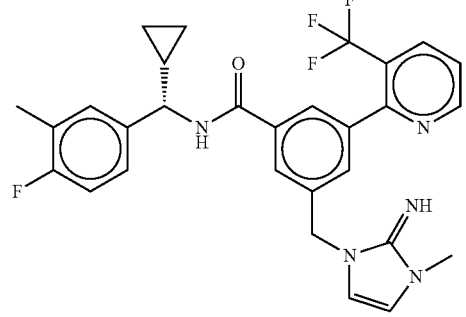
I-64
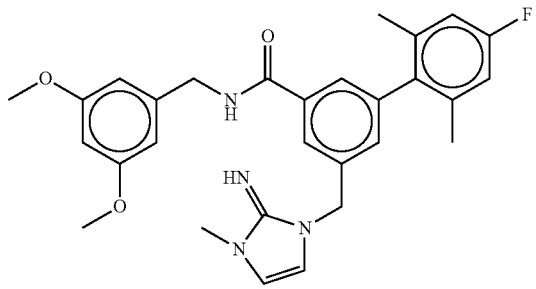
I-65
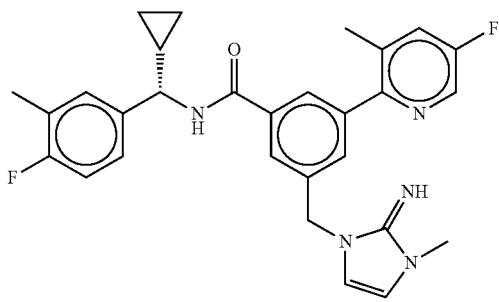
I-66
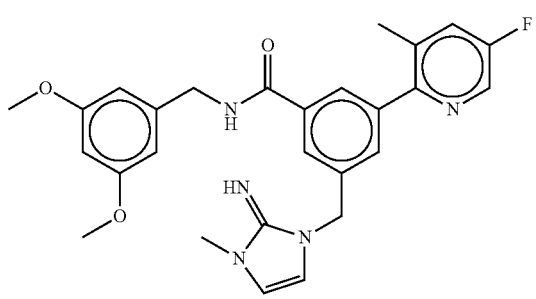
I-67

TABLE 1-continued
Exemplary compounds.
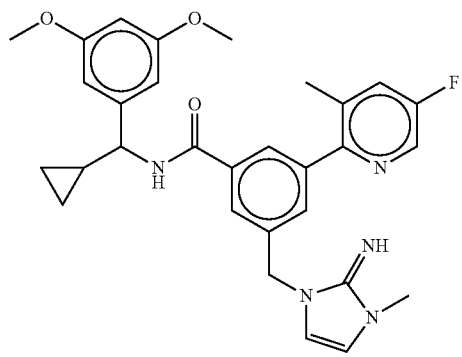
I-68
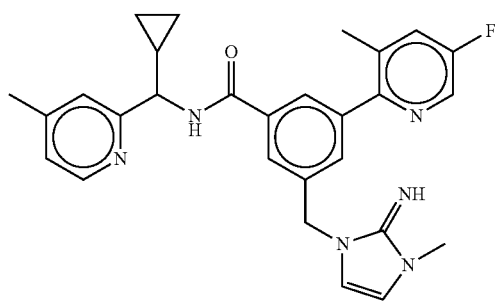
I-69
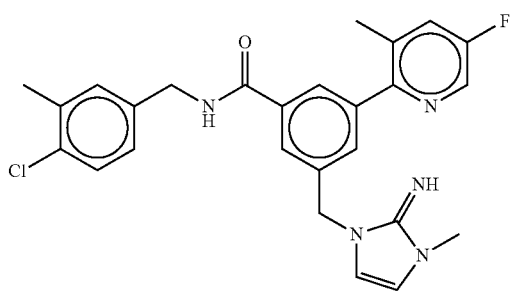
I-70
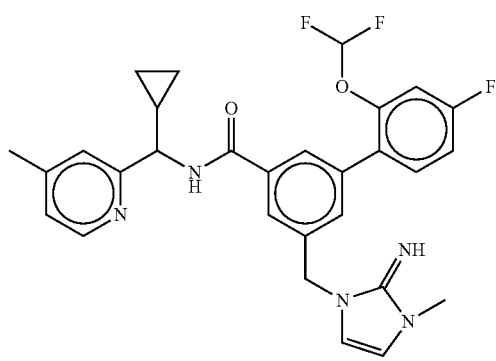
I-71

TABLE 1-continued
Exemplary compounds.
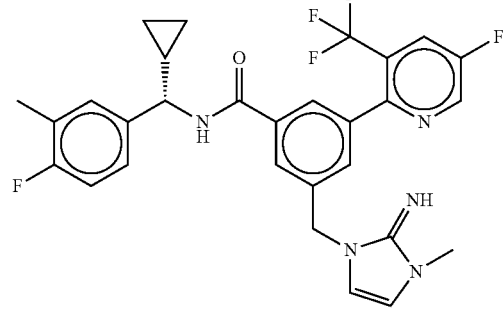
I-72
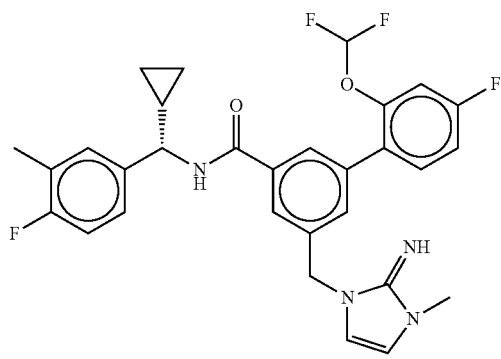
I-73
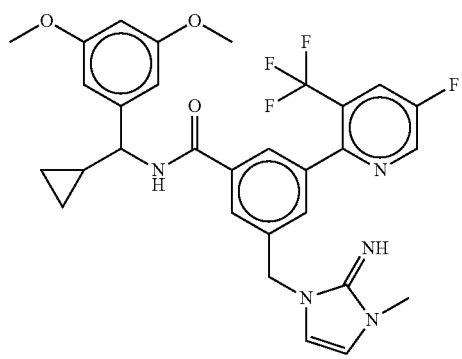
I-74
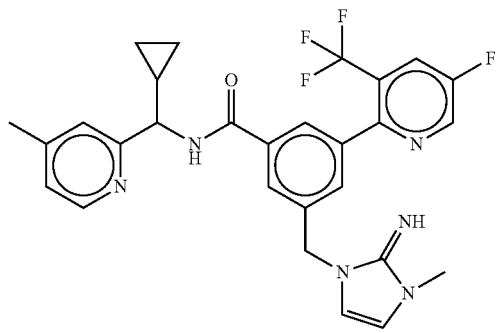
I-75

TABLE 1-continued
Exemplary compounds.
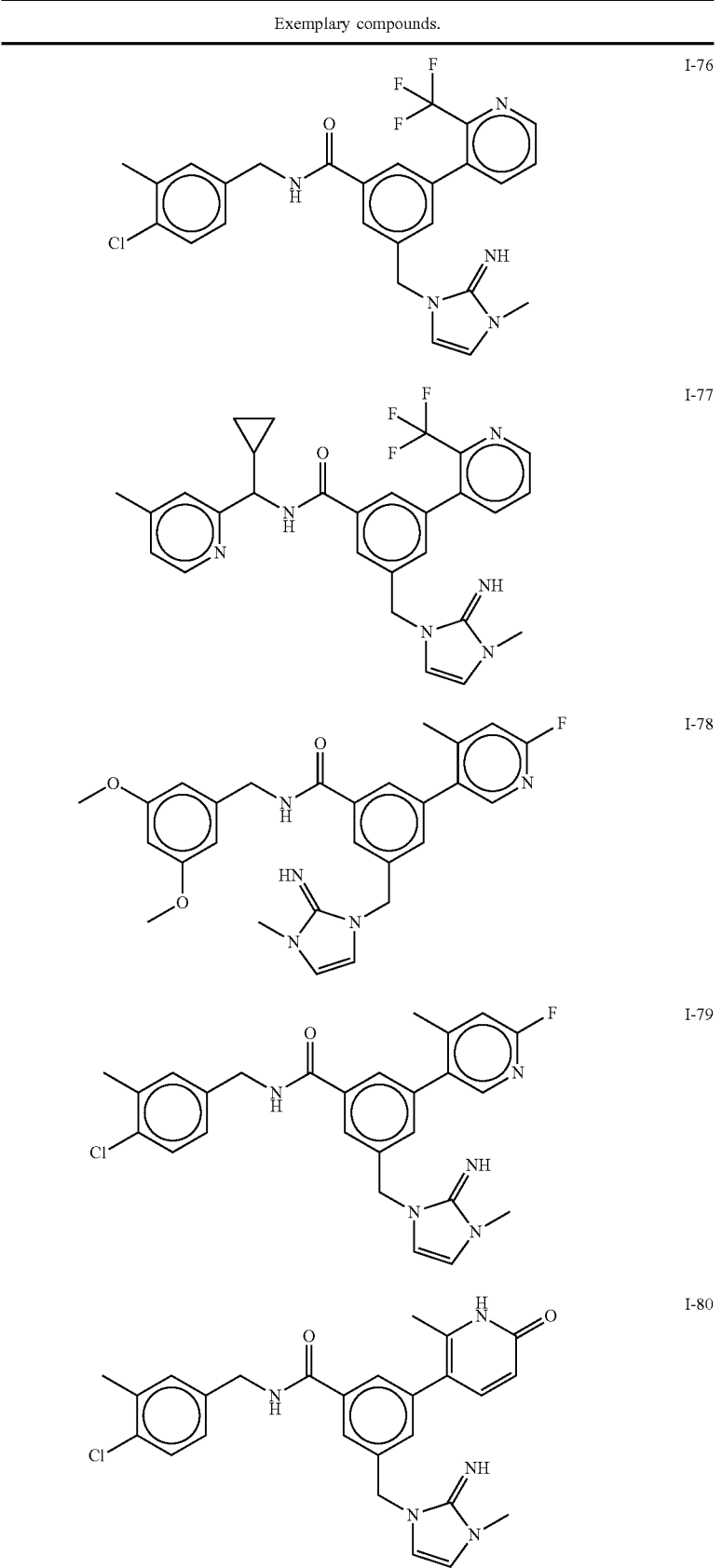
I-76
I-77
I-78
I-79
I-80

TABLE 1-continued
Exemplary compounds.
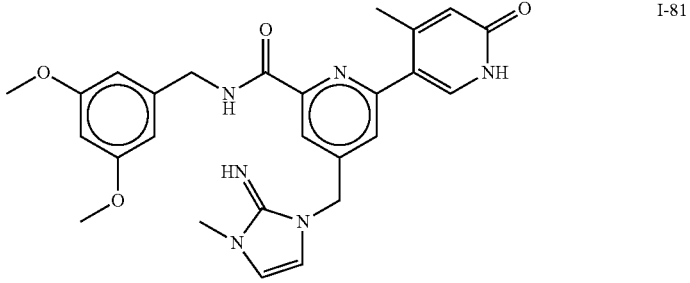 I-81
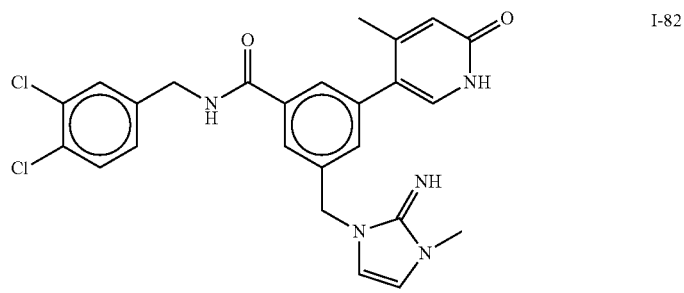 I-82
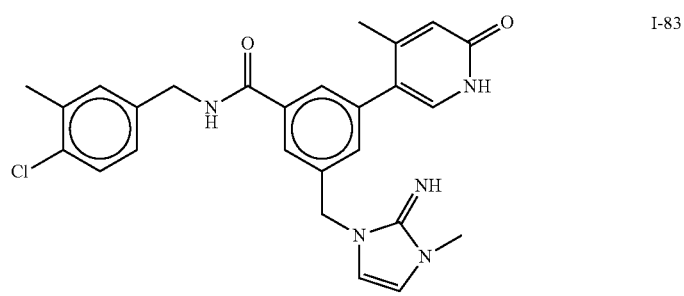 I-83
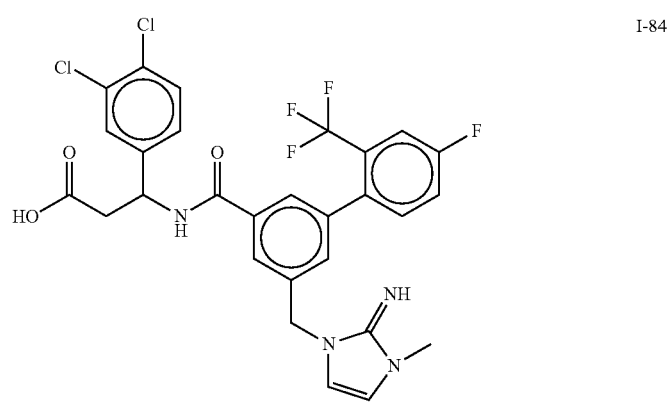 I-84

TABLE 1-continued
Exemplary compounds.
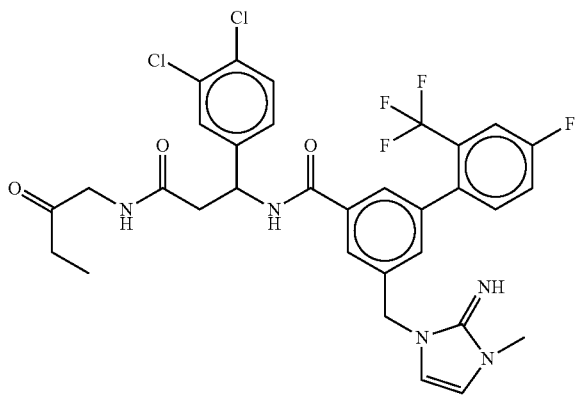
I-85
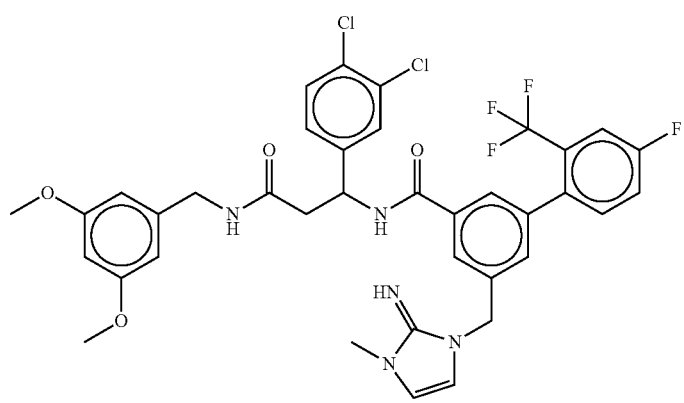
I-86
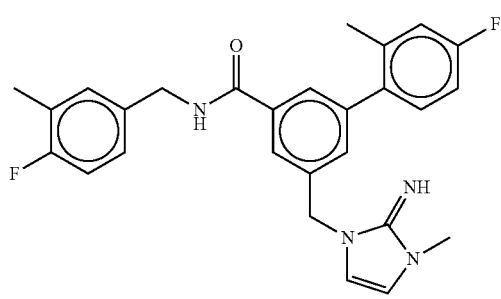
I-87
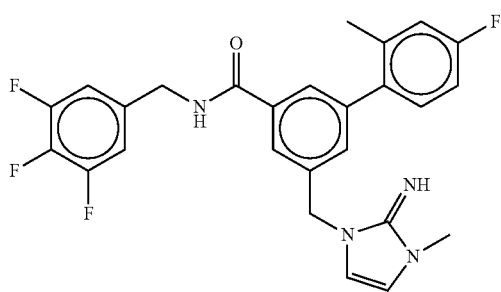
I-88

TABLE 1-continued

Exemplary compounds.

| Compound |
|---|
| I-89 |
| I-90 |
| I-91 |
| I-92 |
| I-93 |

TABLE 1-continued
Exemplary compounds.
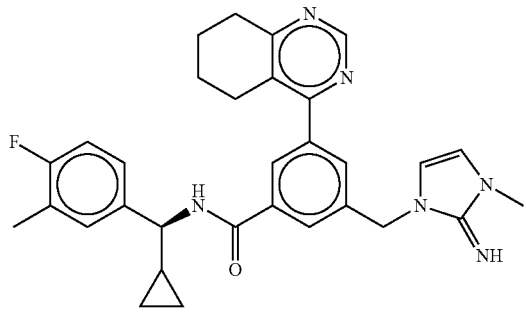
I-94
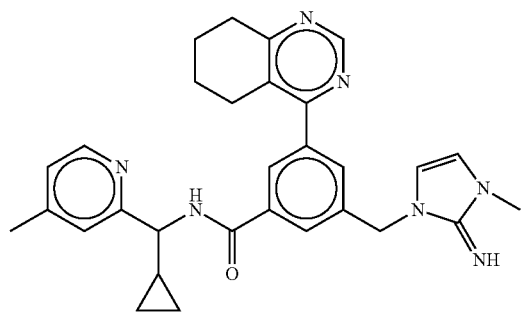
I-95
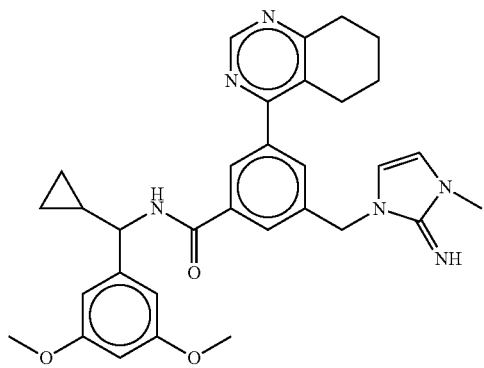
I-96
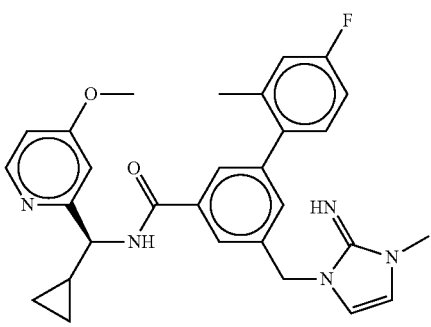
I-97

TABLE 1-continued
Exemplary compounds.
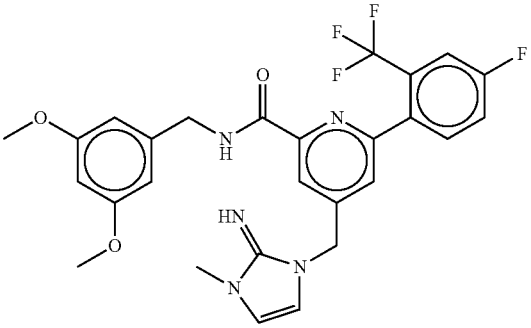
I-98
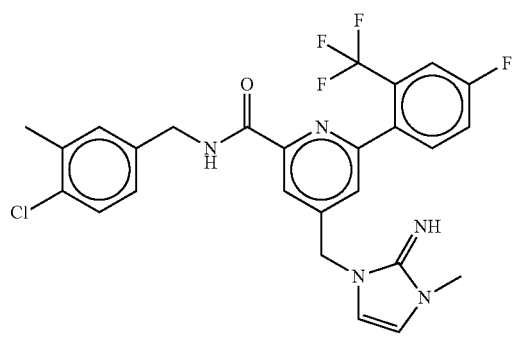
I-99
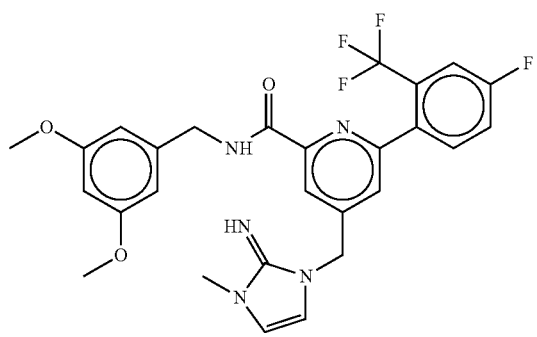
I-100
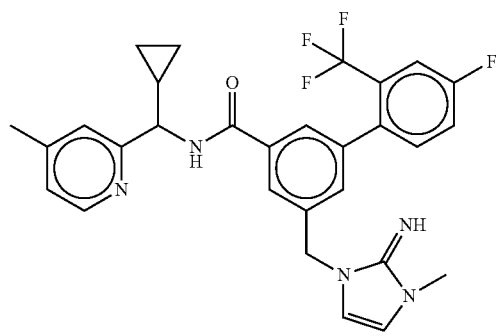
I-101

TABLE 1-continued
Exemplary compounds.
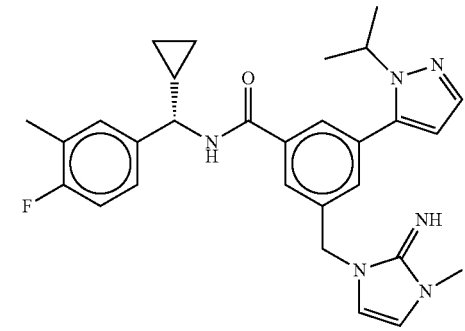
I-102
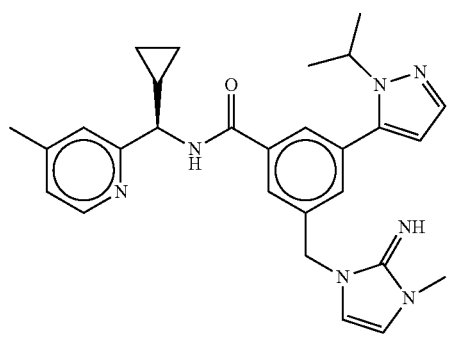
I-103
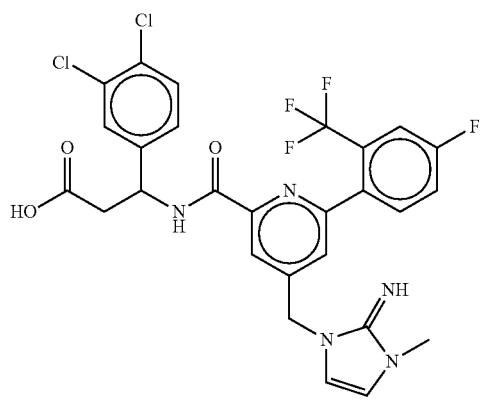
I-104
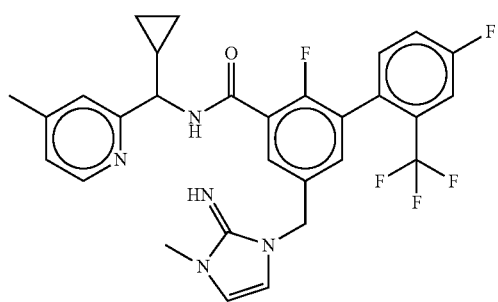
I-105

TABLE 1-continued
Exemplary compounds.
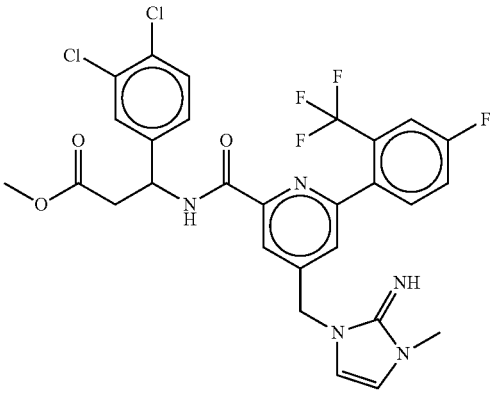
I-106
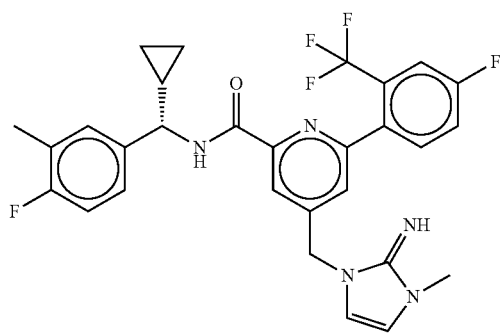
I-107
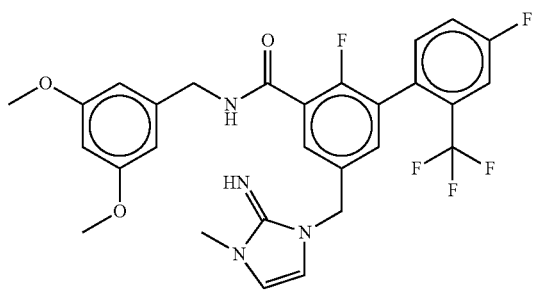
I-108
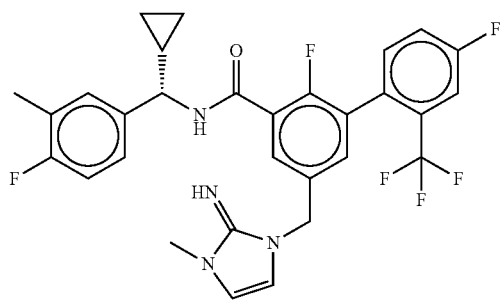
I-109

TABLE 1-continued
Exemplary compounds.
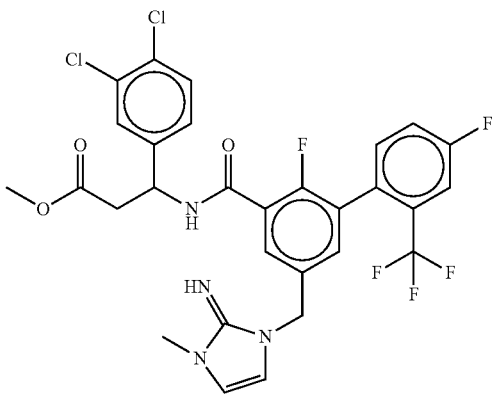
I-110
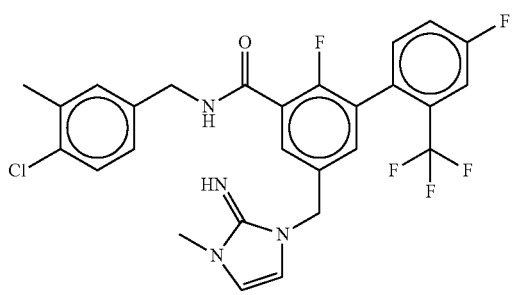
I-111
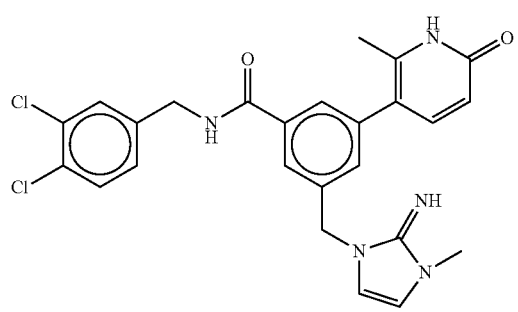
I-112
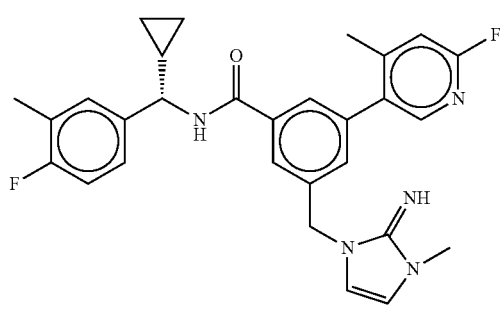
I-113

TABLE 1-continued
Exemplary compounds.
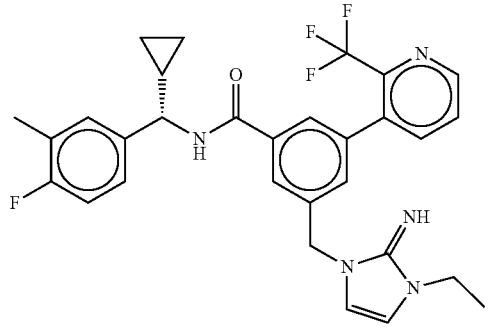
I-114
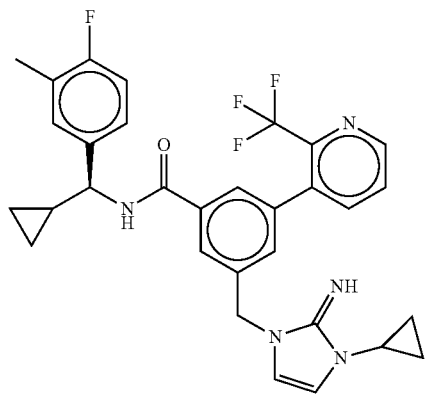
I-115
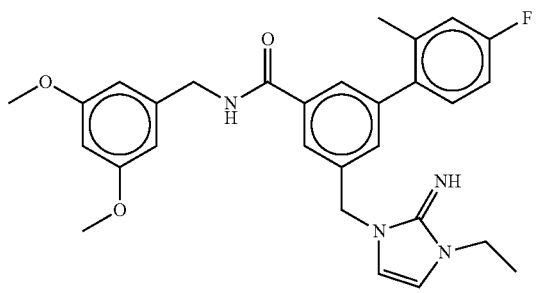
I-116
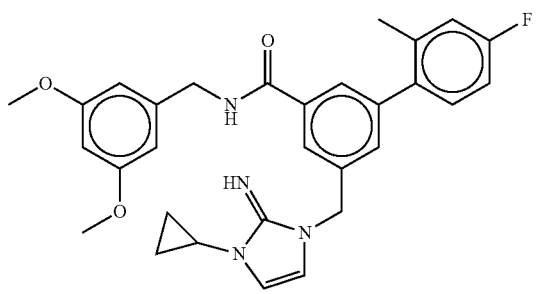
I-117

TABLE 1-continued
Exemplary compounds.
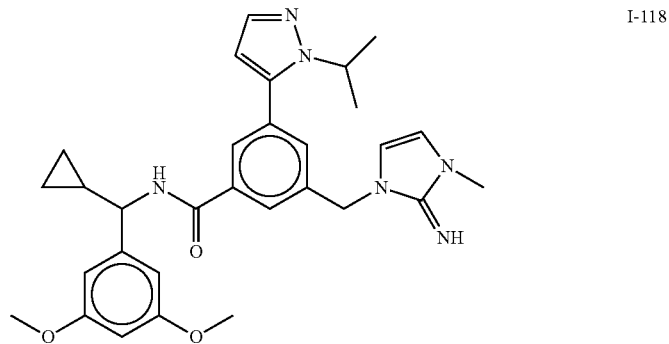
I-118
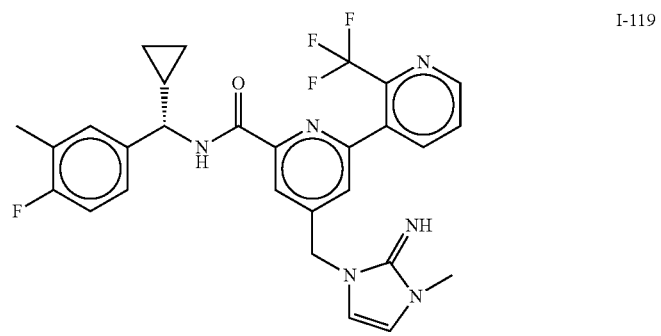
I-119
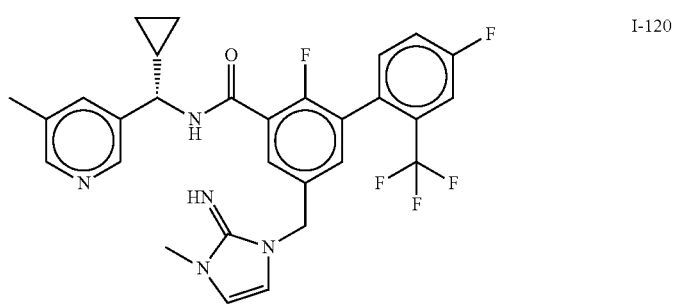
I-120
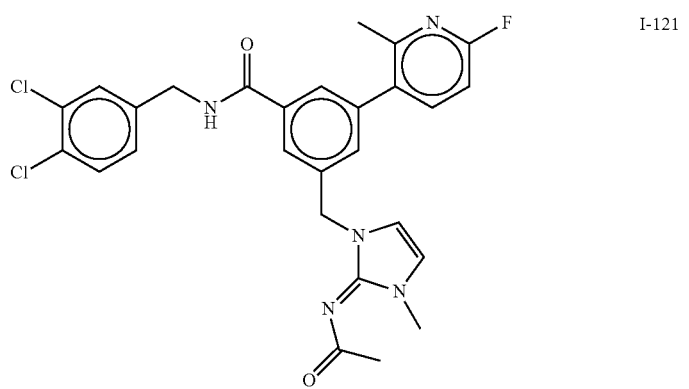
I-121

TABLE 1-continued
Exemplary compounds.
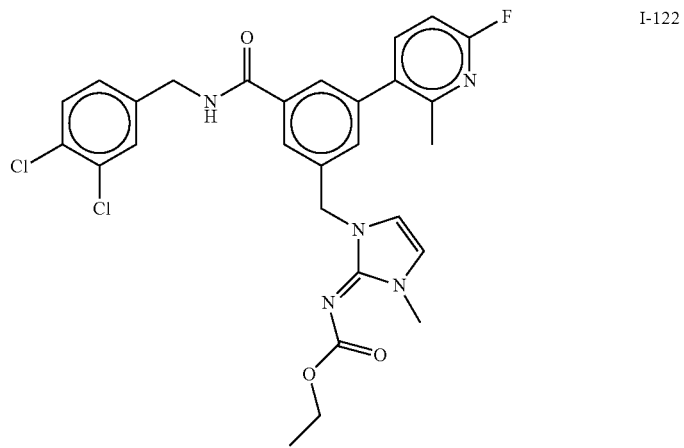
I-122
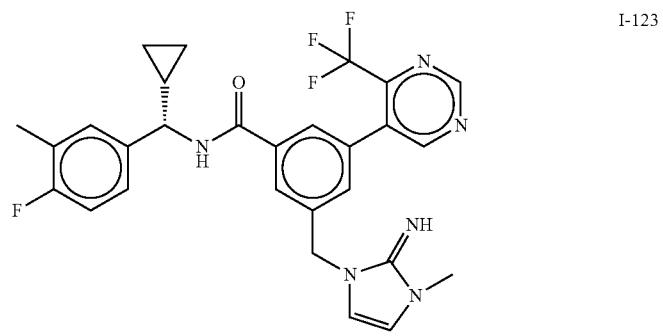
I-123
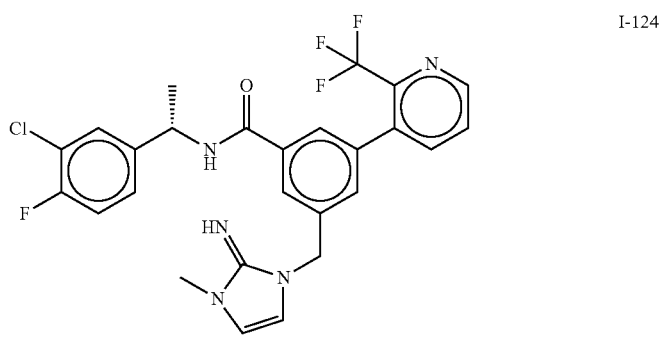
I-124
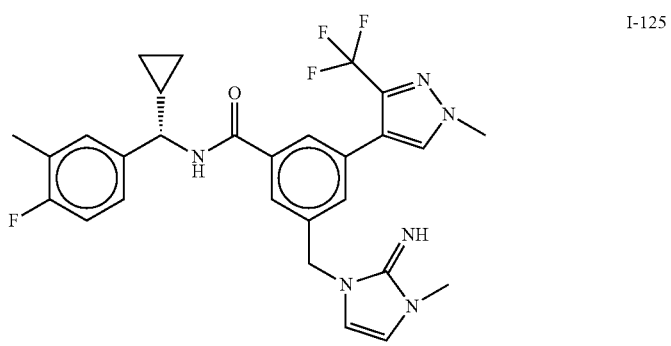
I-125

TABLE 1-continued
Exemplary compounds.
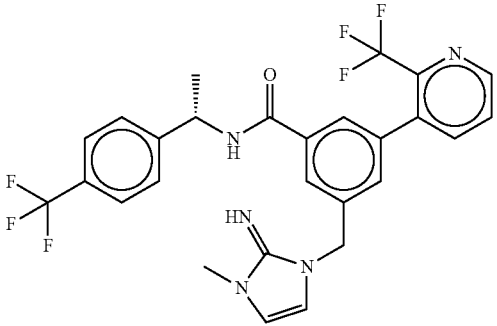
I-126
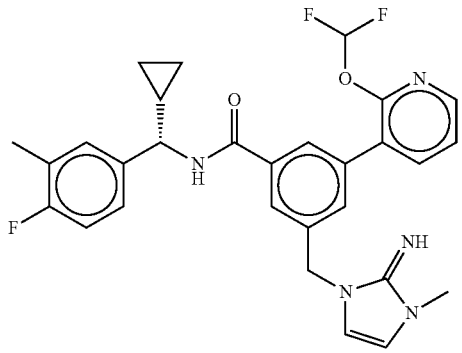
I-127
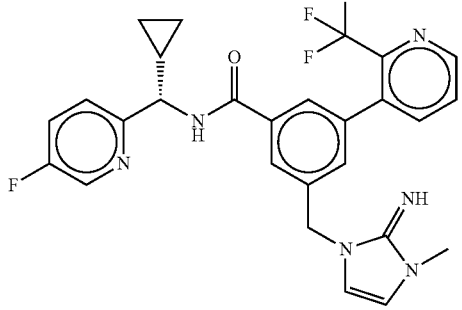
I-128
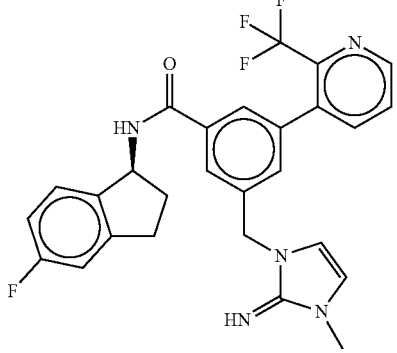
I-129

TABLE 1-continued
Exemplary compounds.
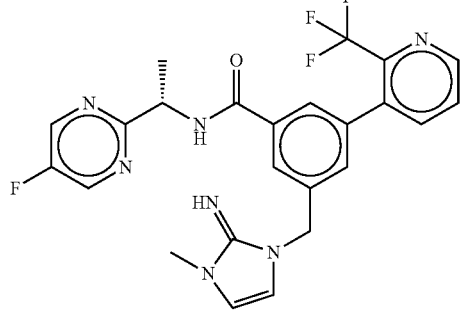
I-130
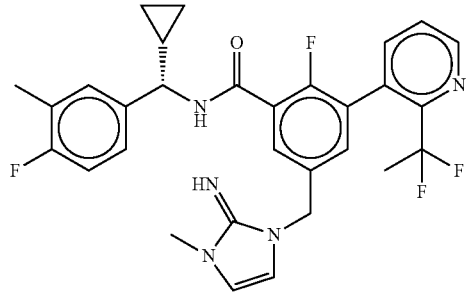
I-131
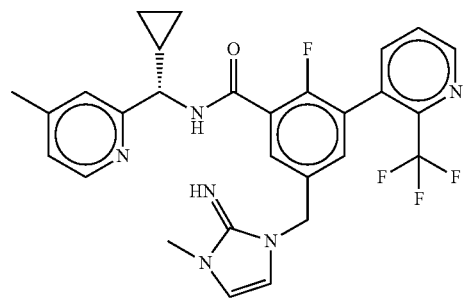
I-132
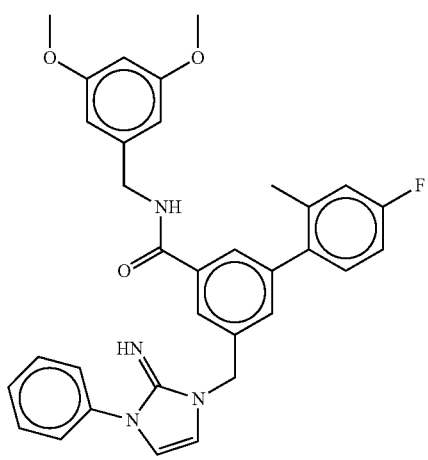
I-133

TABLE 1-continued
Exemplary compounds.
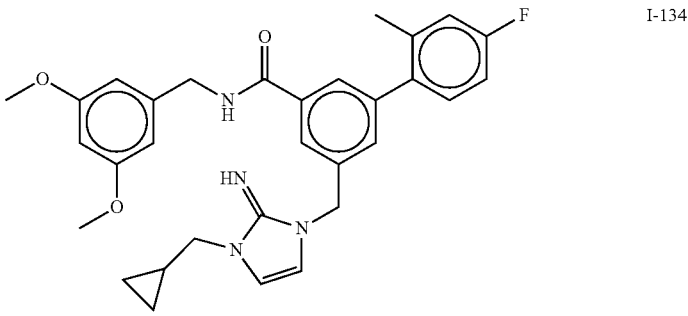
I-134
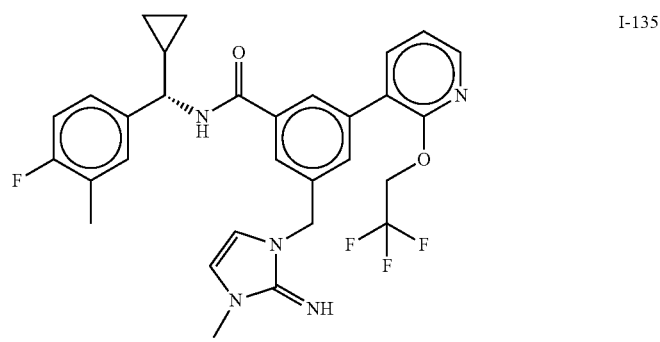
I-135
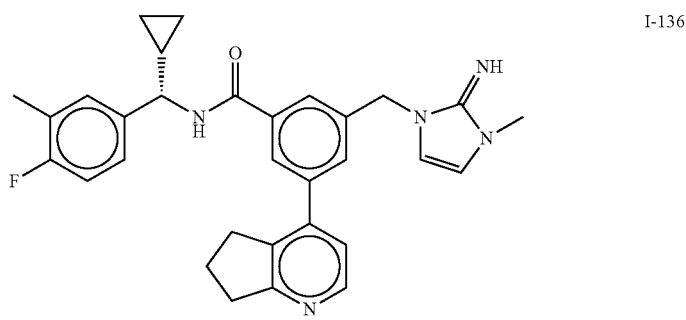
I-136
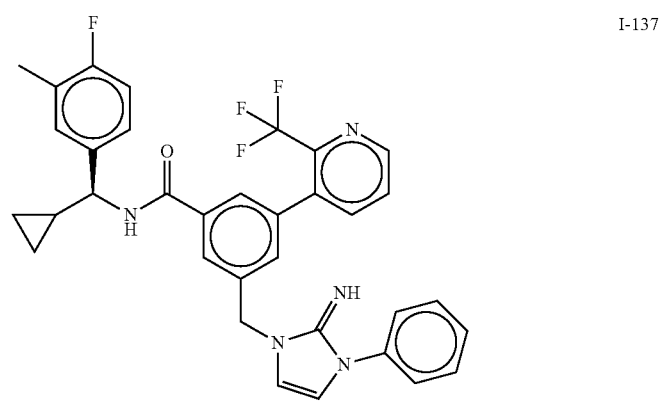
I-137

TABLE 1-continued
Exemplary compounds.
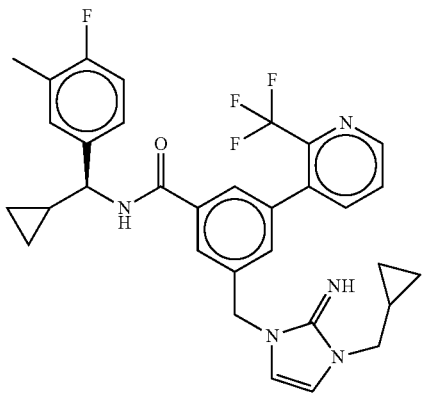
I-138
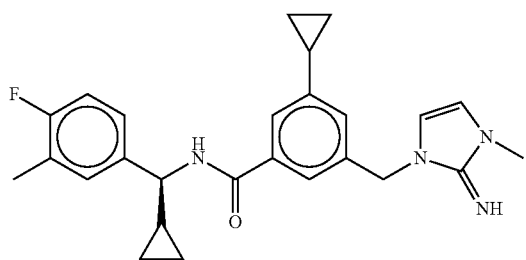
I-139
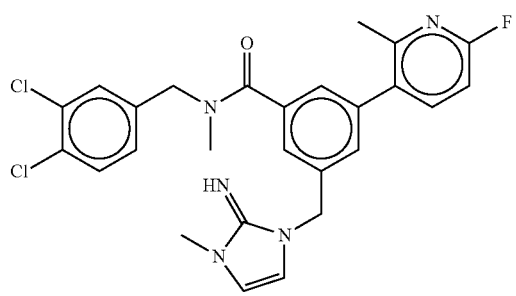
I-140
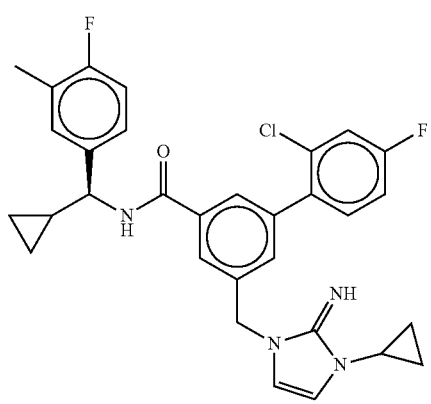
I-141

TABLE 1-continued
Exemplary compounds.
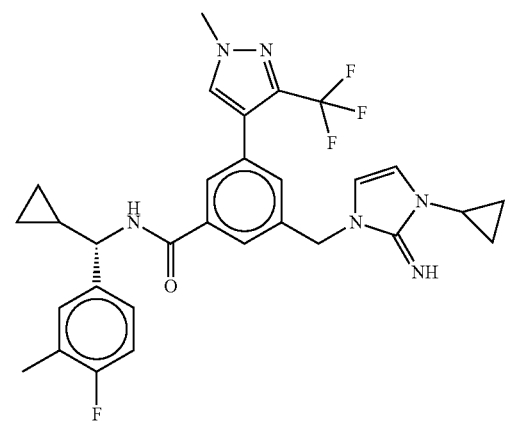
I-142
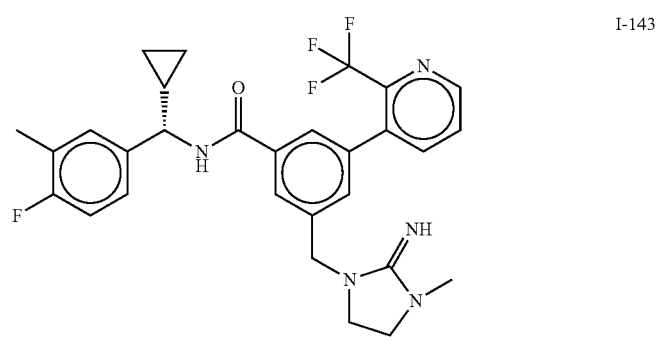
I-143
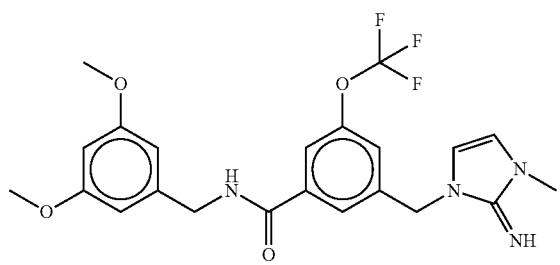
I-144
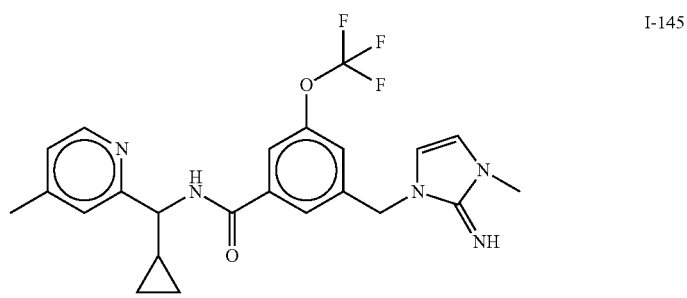
I-145

TABLE 1-continued
Exemplary compounds.
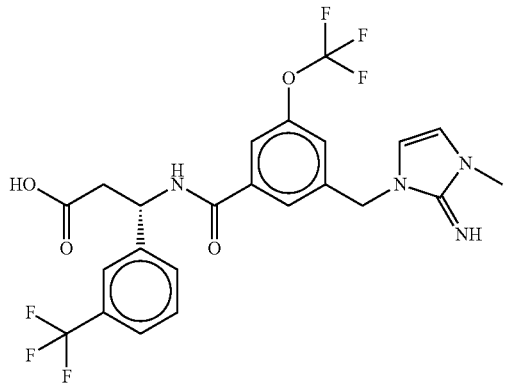
I-146
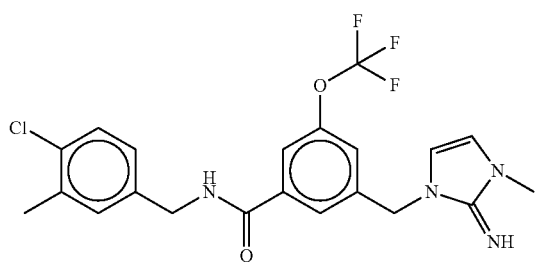
I-147
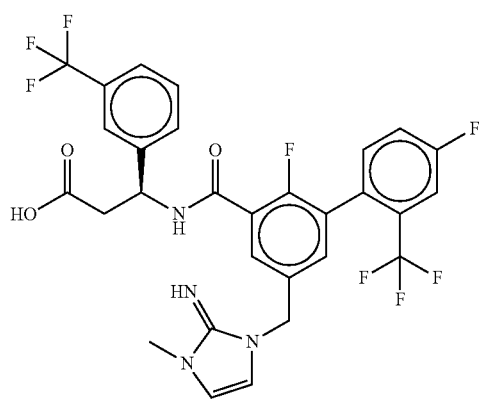
I-148
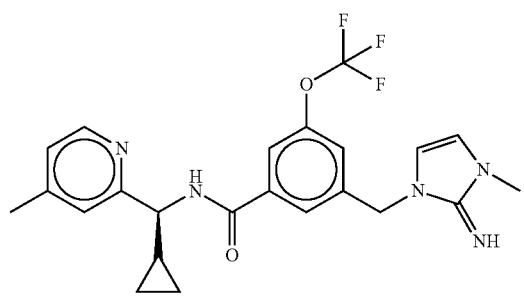
I-149

TABLE 1-continued
Exemplary compounds.
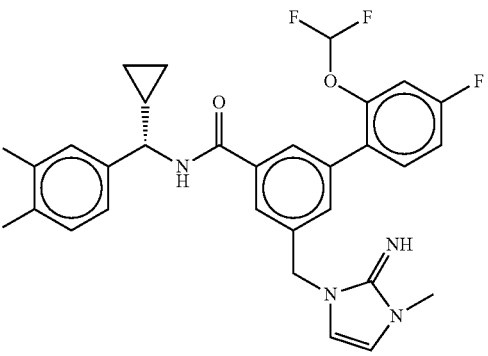
I-150
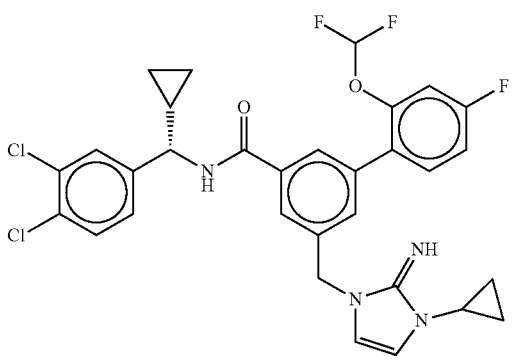
I-151
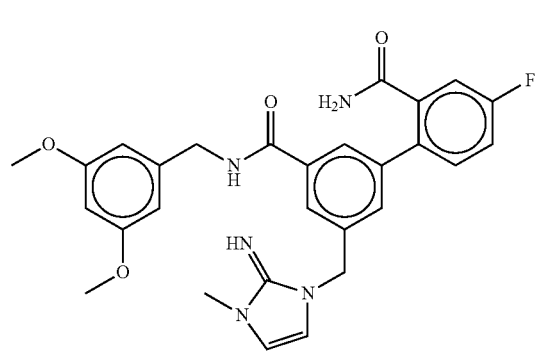
I-152
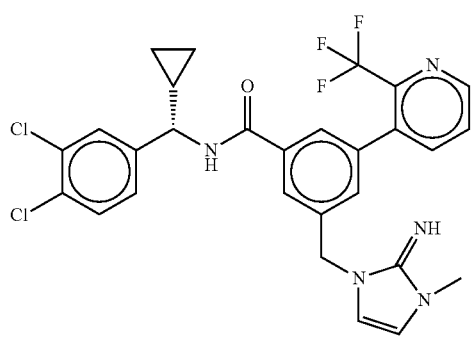
I-153

TABLE 1-continued
Exemplary compounds.
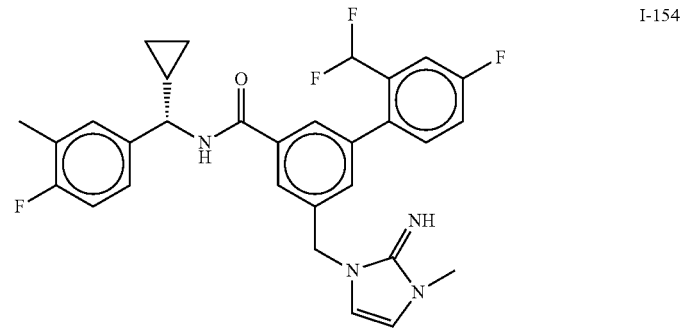 I-154
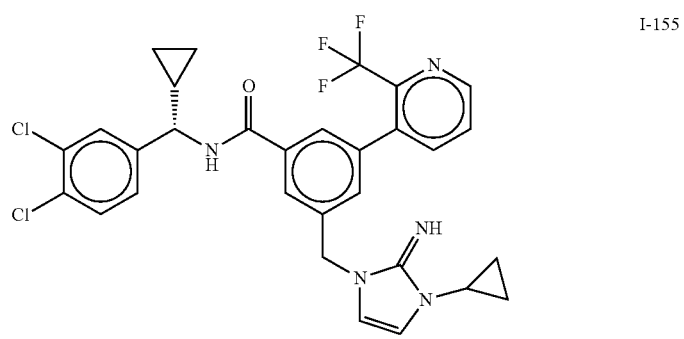 I-155
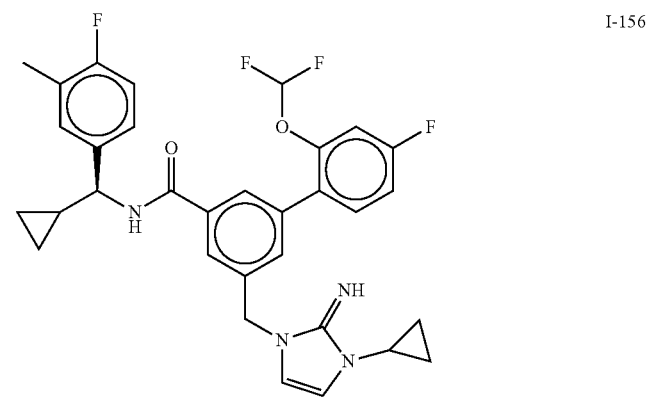 I-156
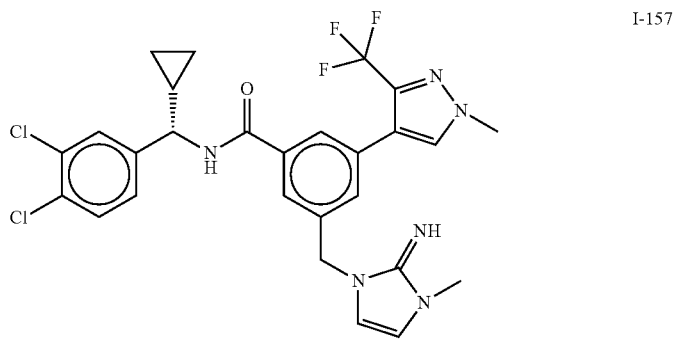 I-157

TABLE 1-continued
Exemplary compounds.
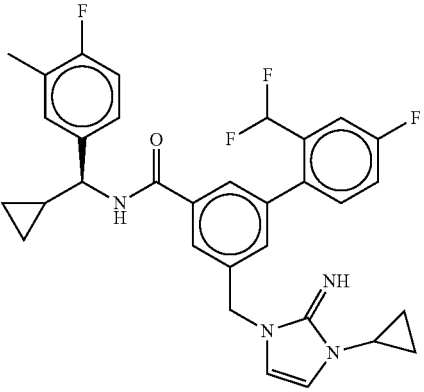
I-158
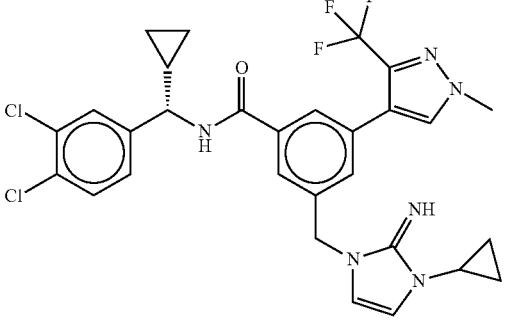
I-159
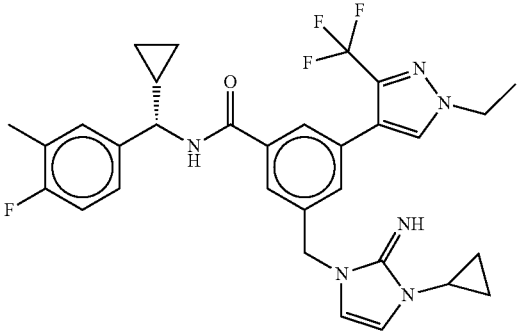
I-160
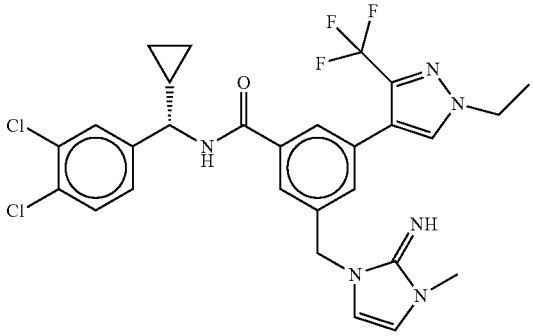
I-161

TABLE 1-continued

Exemplary compounds.

| Compound |
|---|
| I-162 |
| I-163 |
| I-164 |
| I-165 |

TABLE 1-continued
Exemplary compounds.
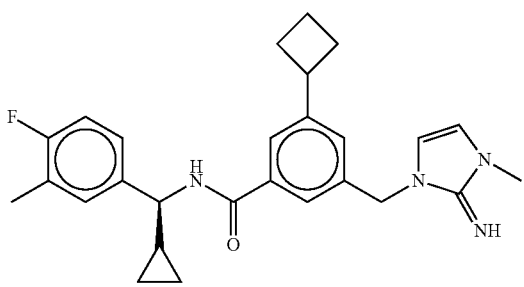
I-166
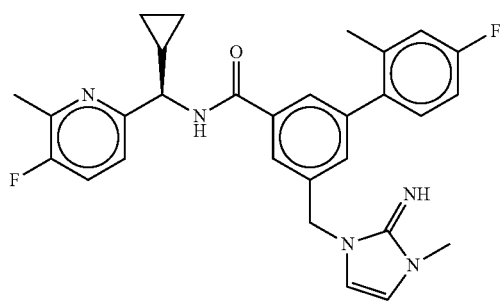
I-167
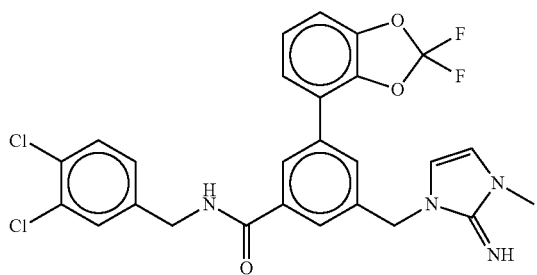
I-168
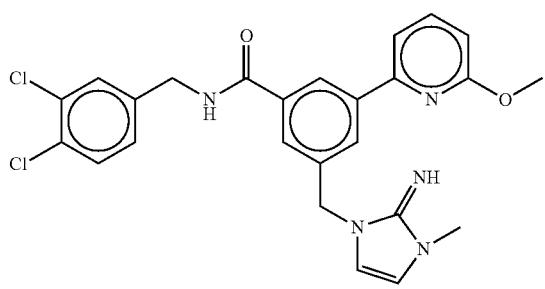
I-169
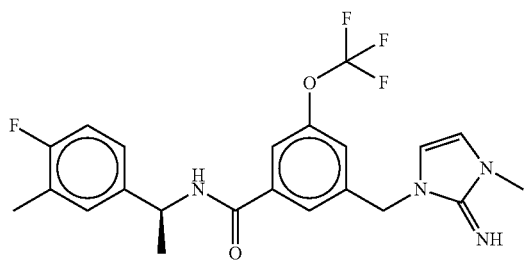
I-170

TABLE 1-continued
Exemplary compounds.
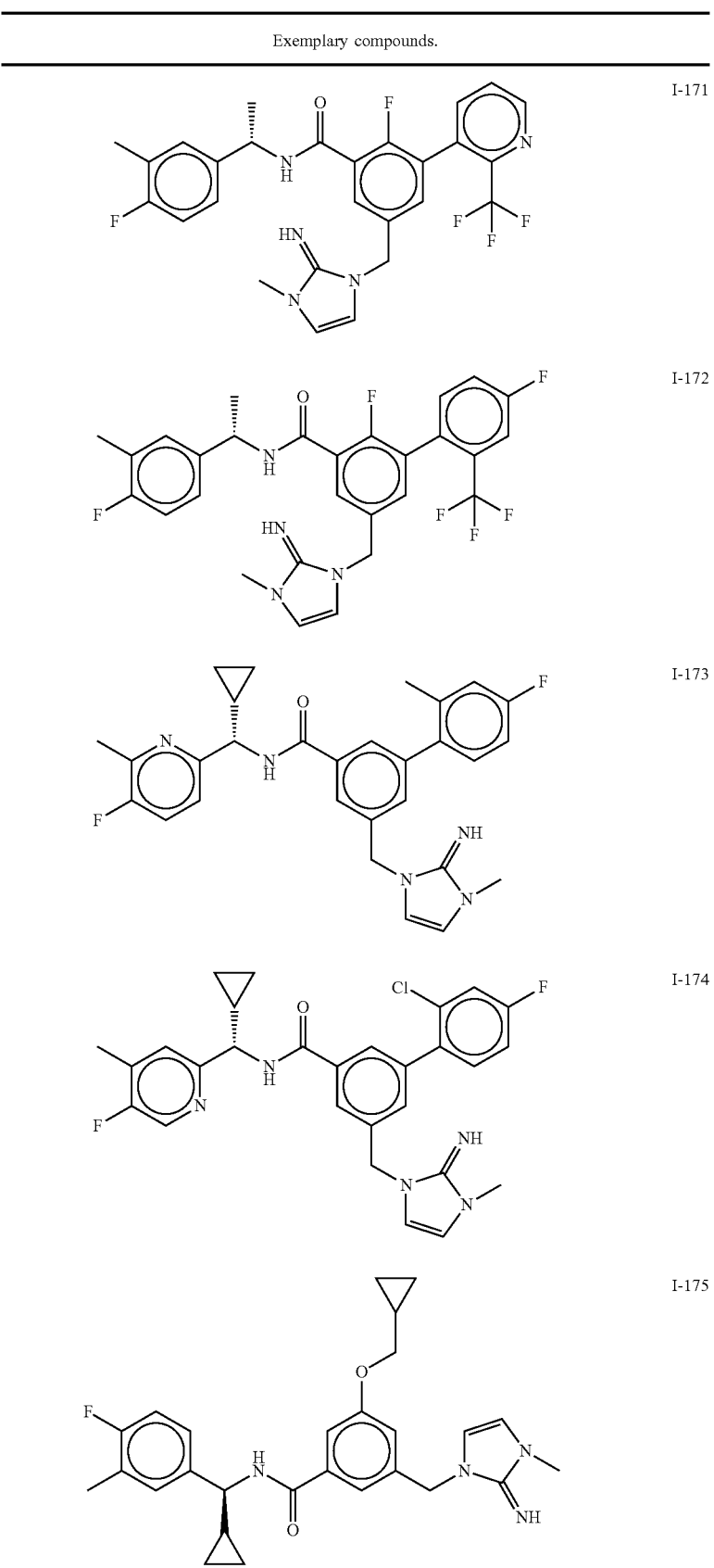
I-171
I-172
I-173
I-174
I-175

TABLE 1-continued

Exemplary compounds.

I-176

I-177

I-178

I-179

I-180

TABLE 1-continued
Exemplary compounds.
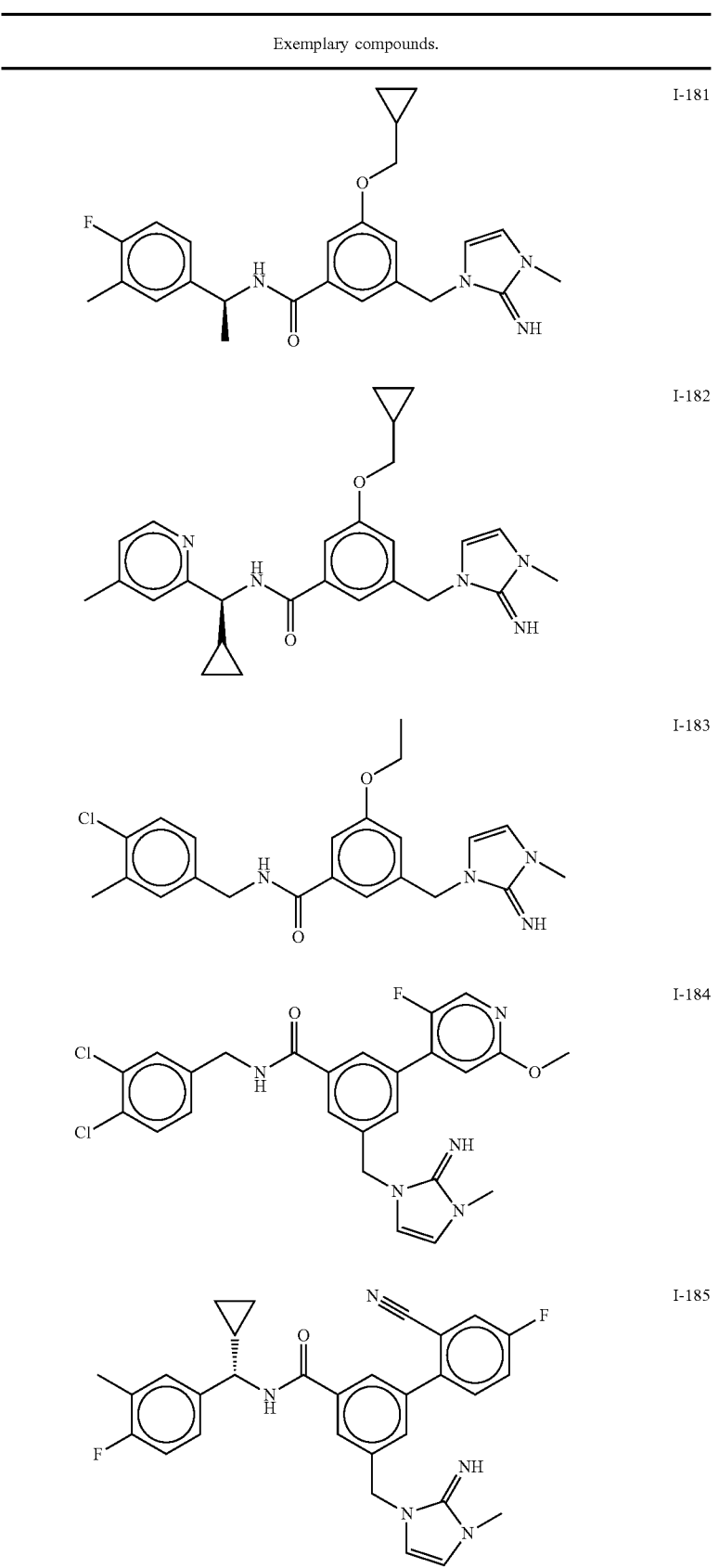
I-181
I-182
I-183
I-184
I-185

TABLE 1-continued
Exemplary compounds.
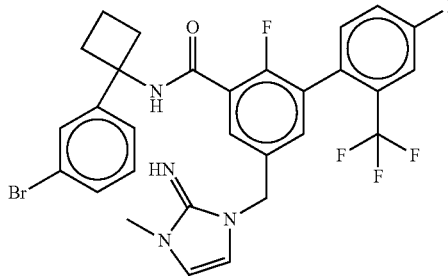 I-186
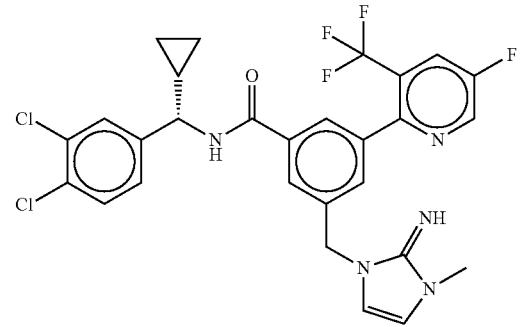 I-187
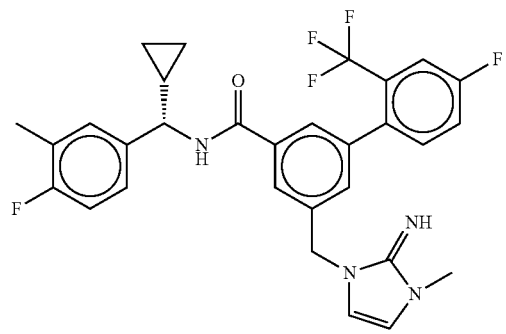 I-188
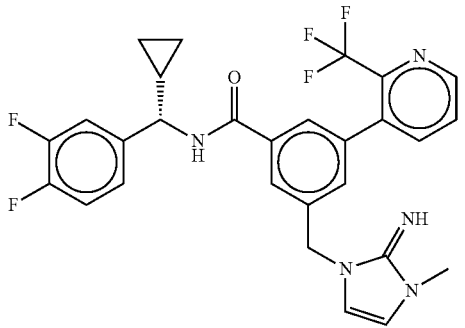 I-189

TABLE 1-continued
Exemplary compounds.
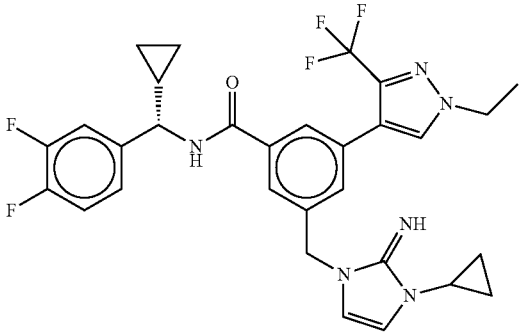
I-190
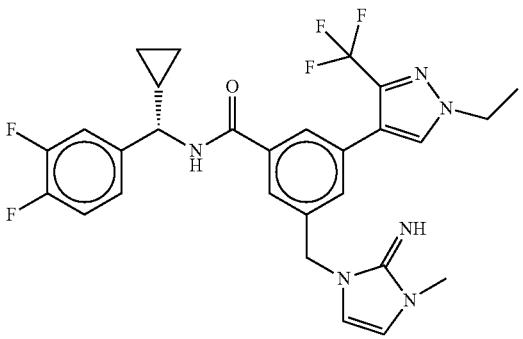
I-191
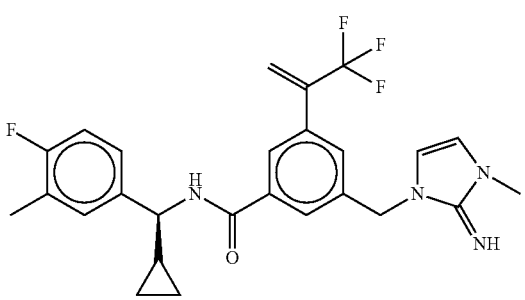
I-192
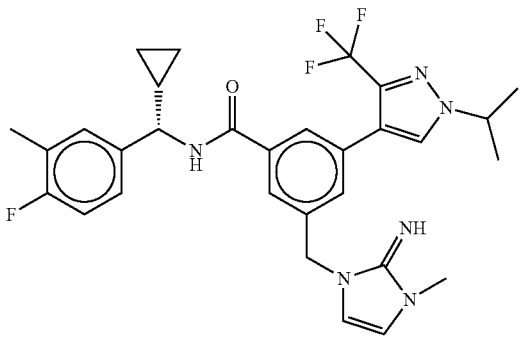
I-193

TABLE 1-continued
Exemplary compounds.
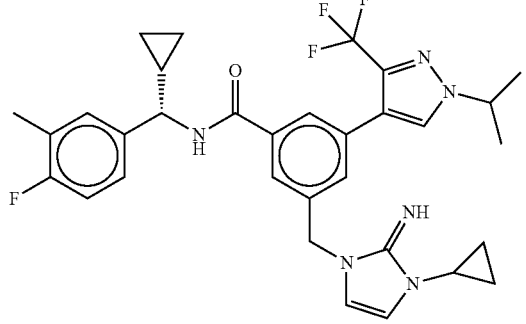
I-194
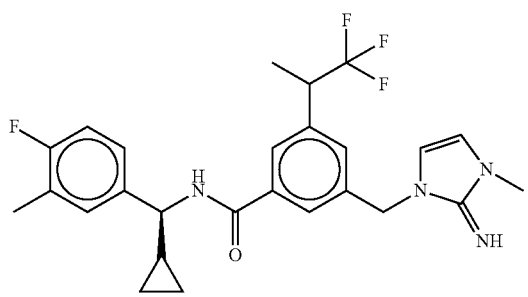
I-195
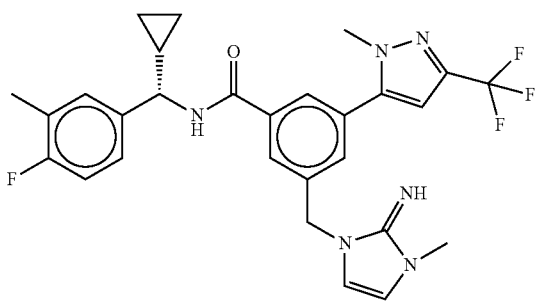
I-196
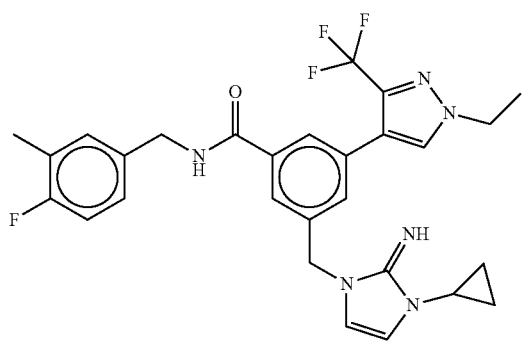
I-197

TABLE 1-continued
Exemplary compounds.
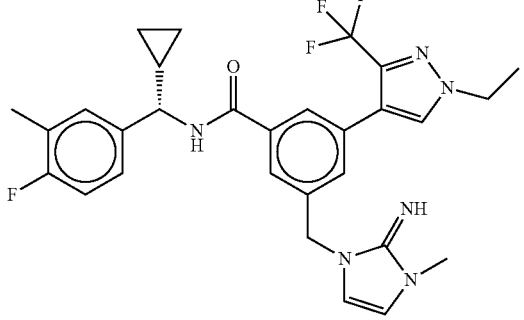
I-198
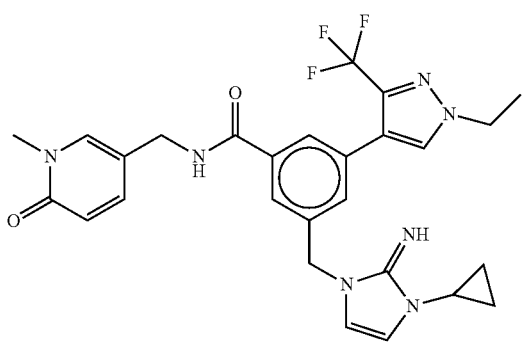
I-199
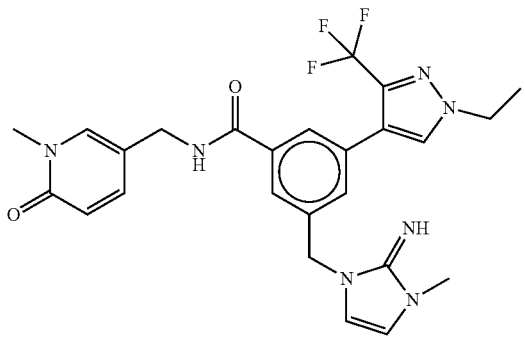
I-200
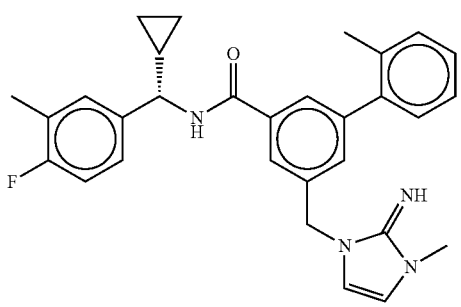
I-201

TABLE 1-continued
Exemplary compounds.
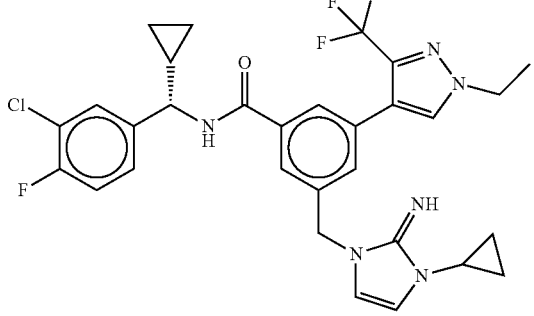
I-202
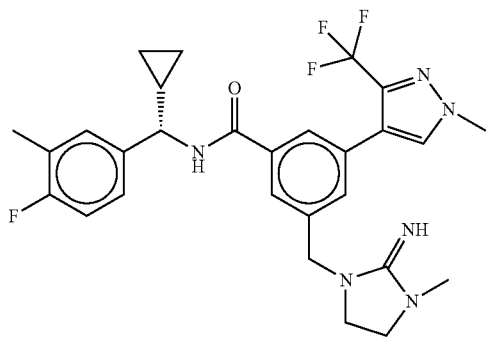
I-203
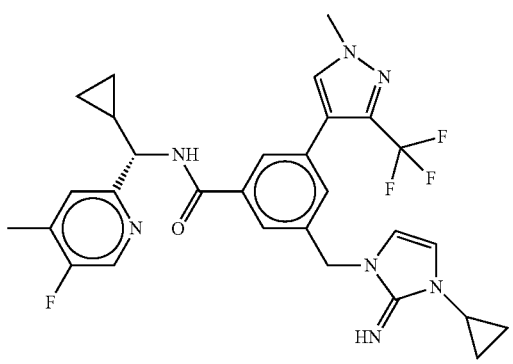
I-204
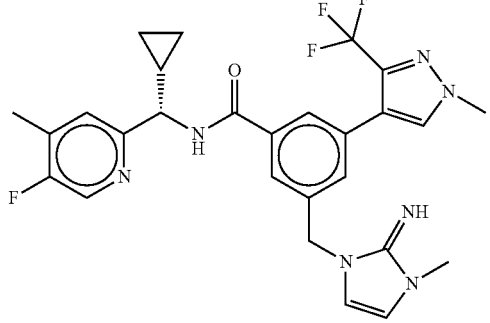
I-205

TABLE 1-continued
Exemplary compounds.
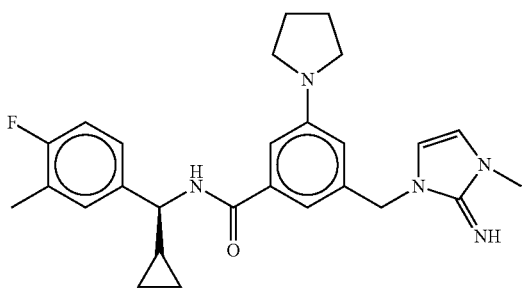
I-206
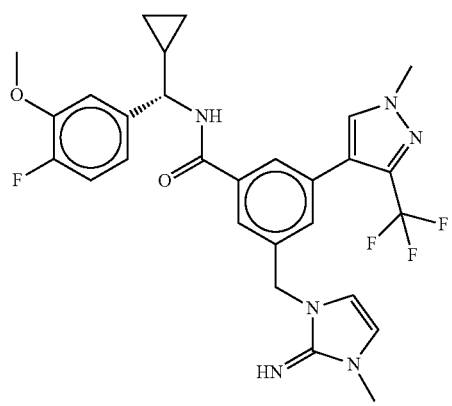
I-207
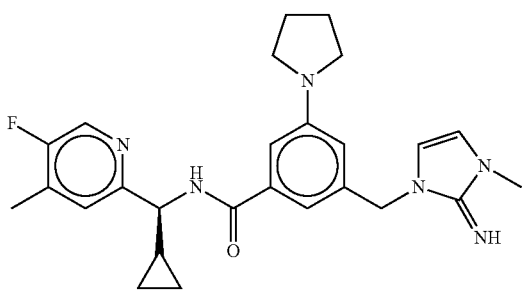
I-208
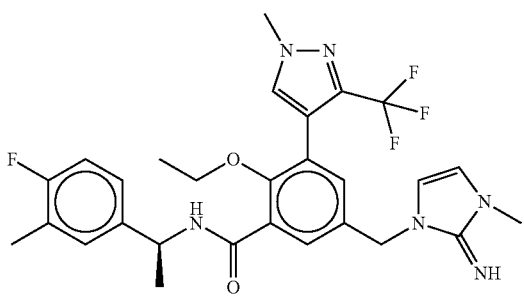
I-209
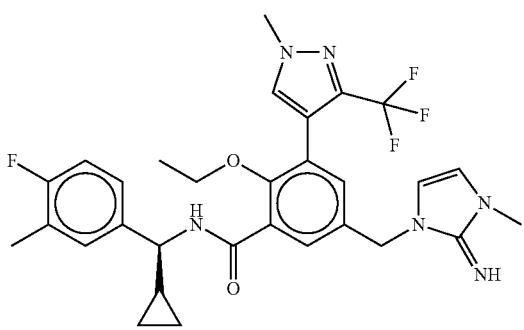
I-210

TABLE 1-continued
Exemplary compounds.
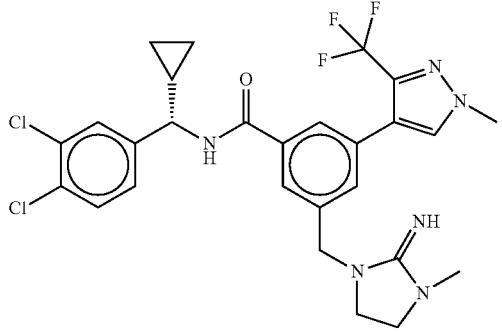
I-211
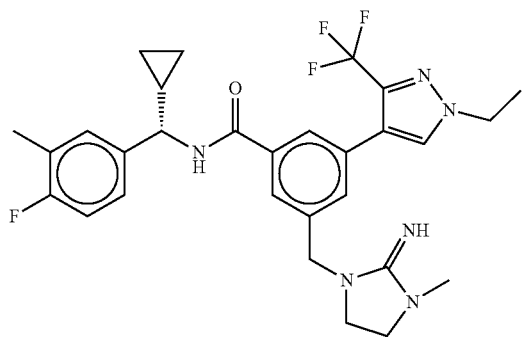
I-212
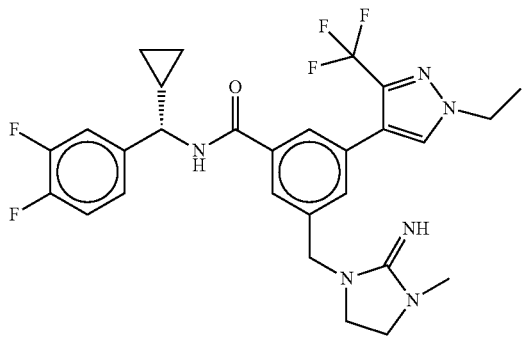
I-213
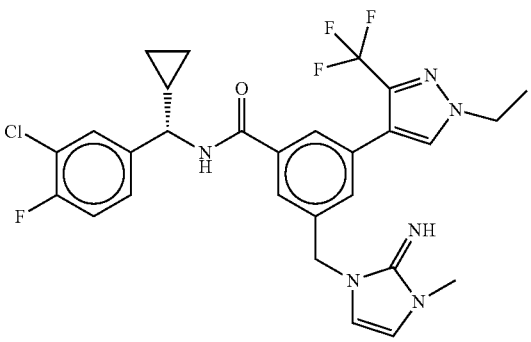
I-214

TABLE 1-continued
Exemplary compounds.
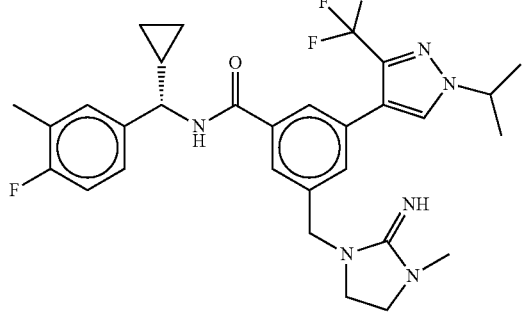 I-215
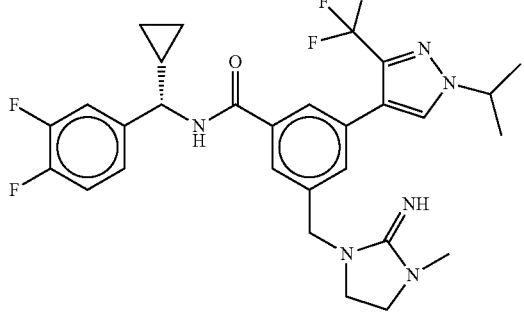 I-216
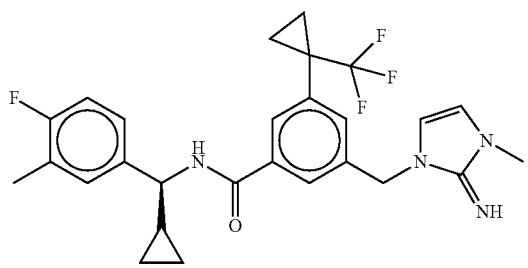 I-217
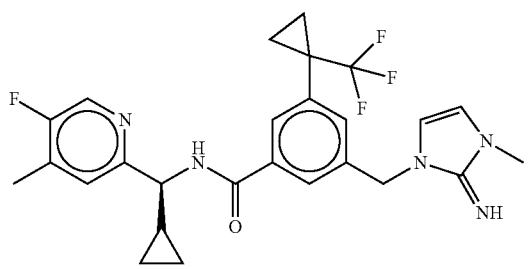 I-218
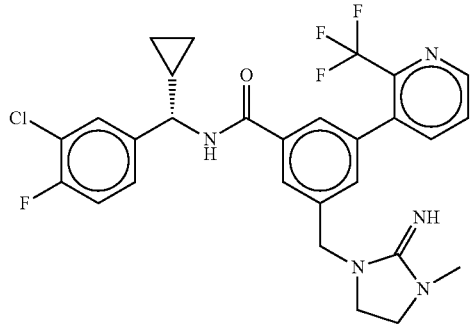 I-219

TABLE 1-continued
Exemplary compounds.
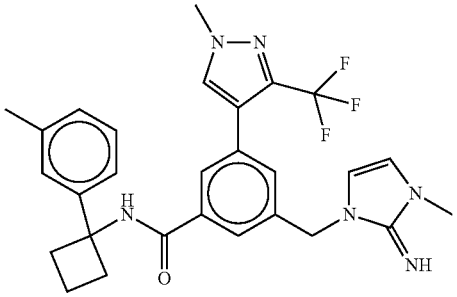
I-220
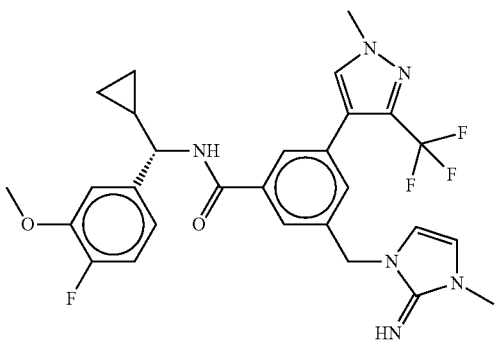
I-221
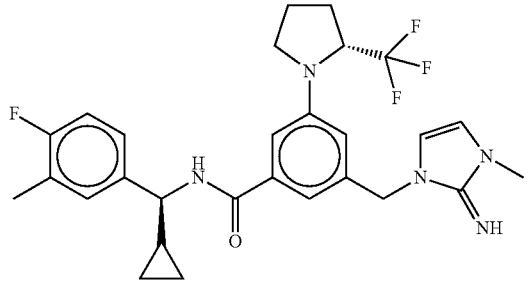
I-222
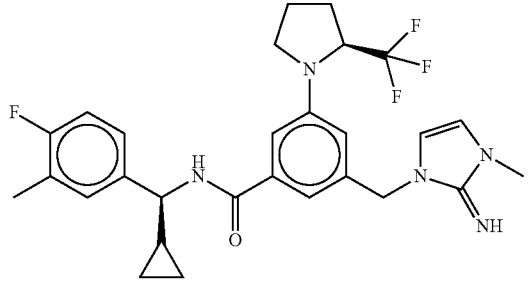
I-223
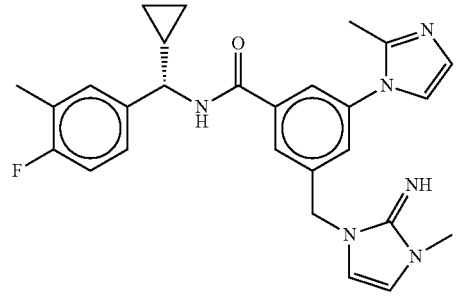
I-224

TABLE 1-continued
Exemplary compounds.
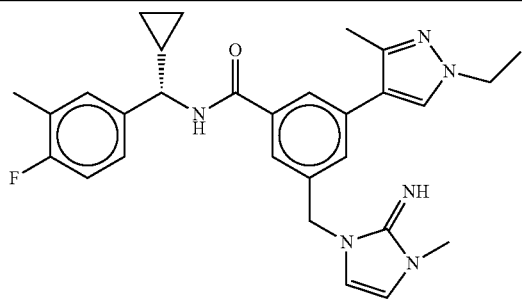 I-225
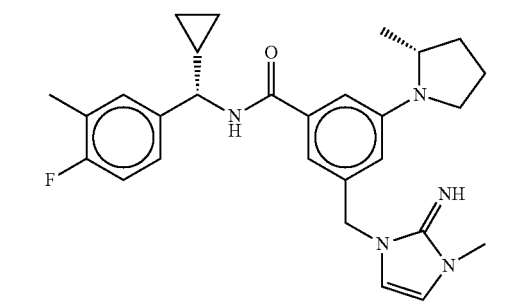 I-226
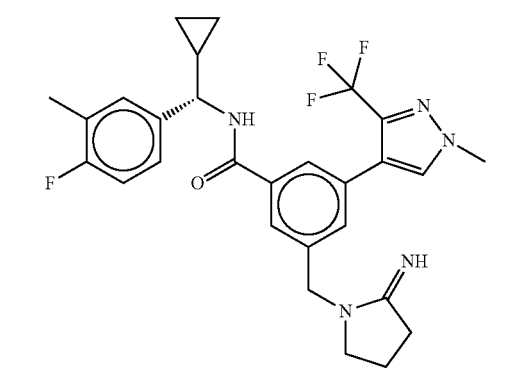 I-227
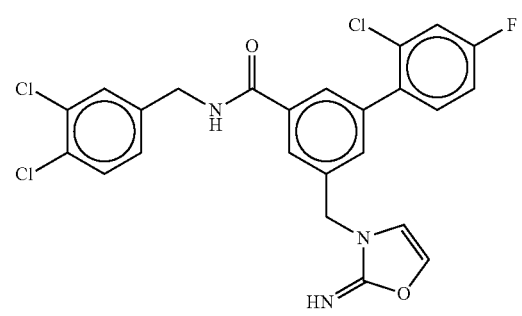 I-228
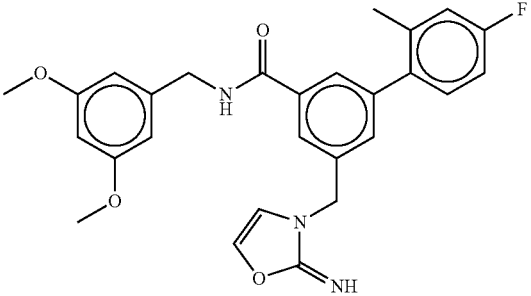 I-229

TABLE 1-continued
Exemplary compounds.
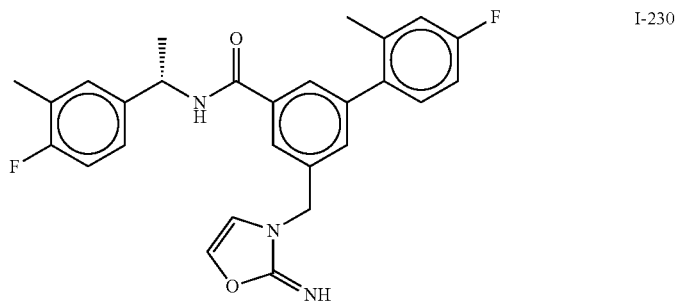
I-230
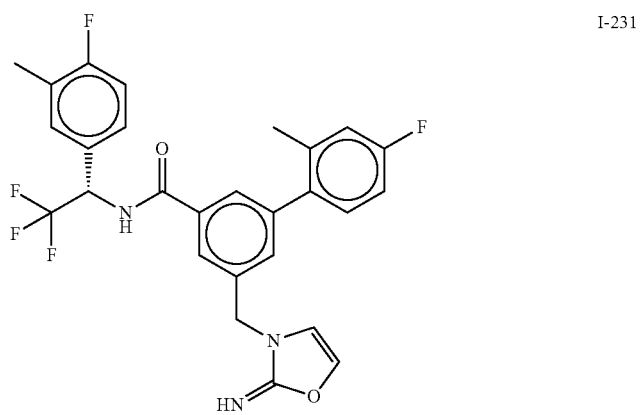
I-231
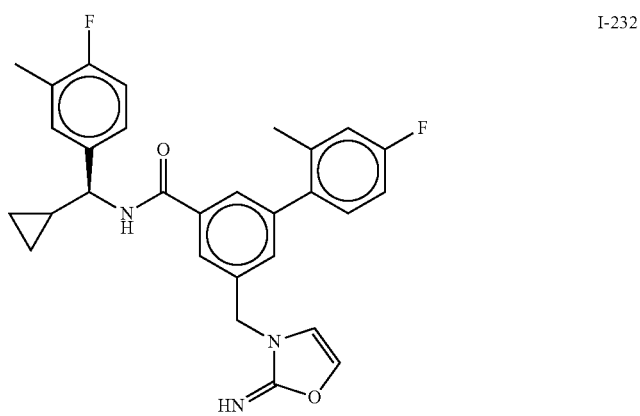
I-232
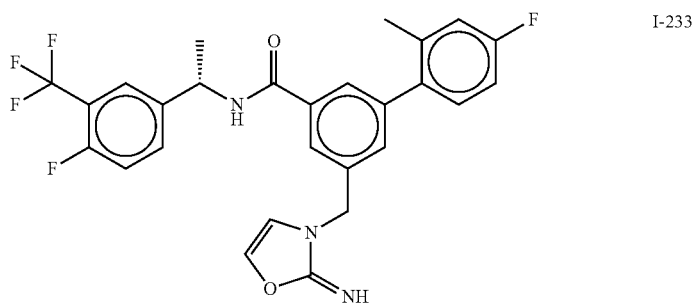
I-233

TABLE 1-continued
Exemplary compounds.
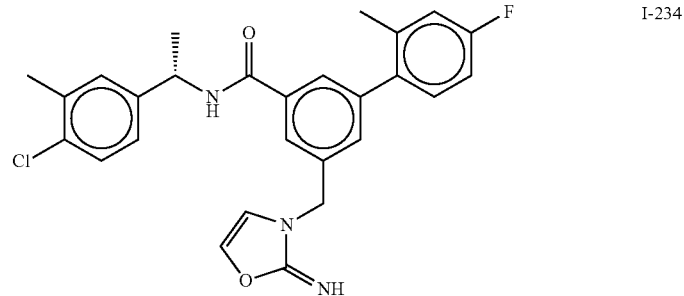
I-234
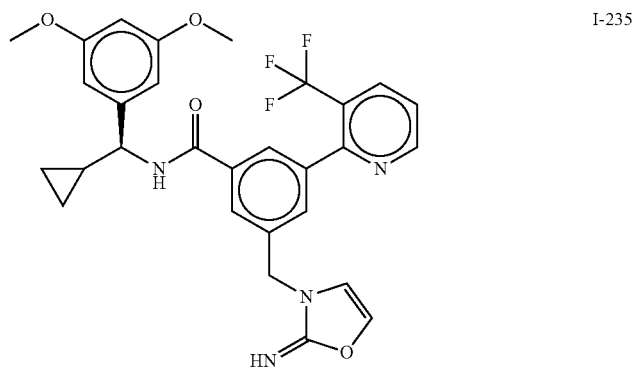
I-235
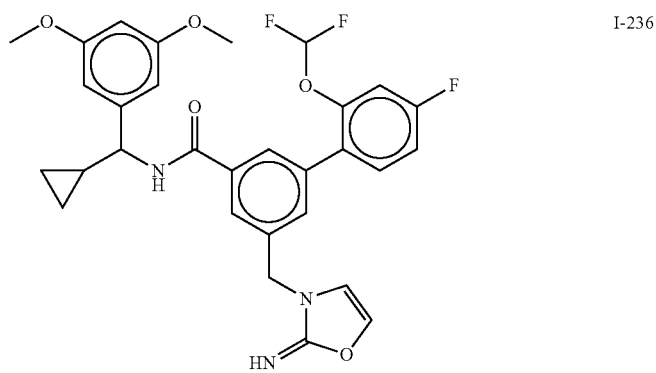
I-236
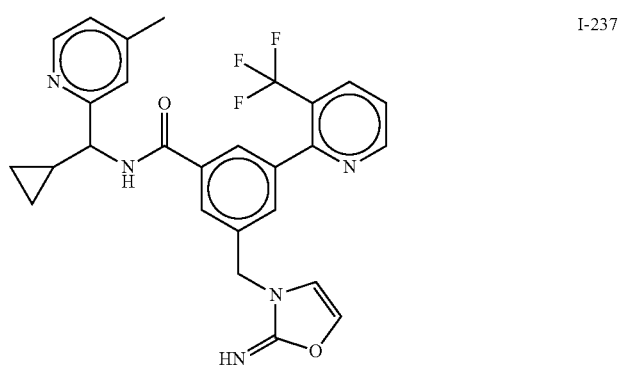
I-237

TABLE 1-continued
Exemplary compounds.
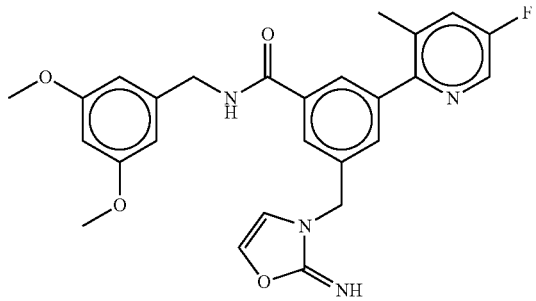
I-238
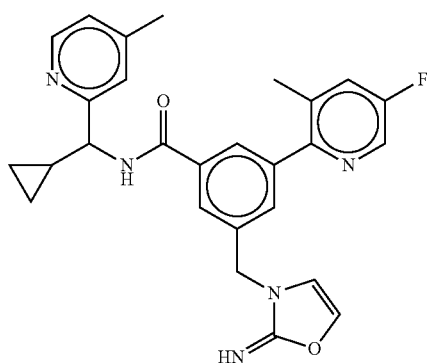
I-239
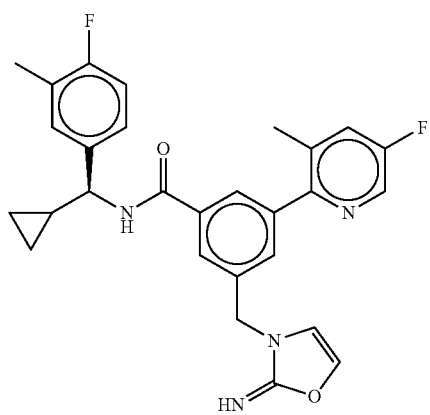
I-240
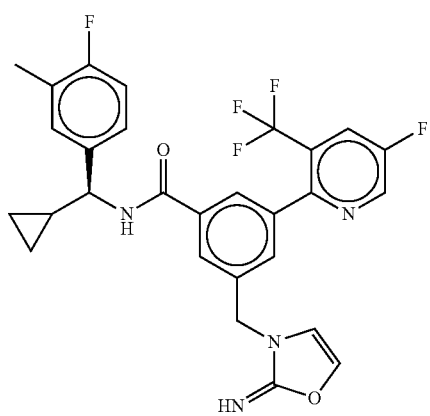
I-241

TABLE 1-continued
Exemplary compounds.
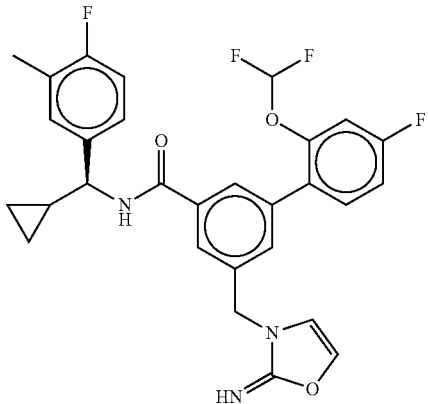
I-242
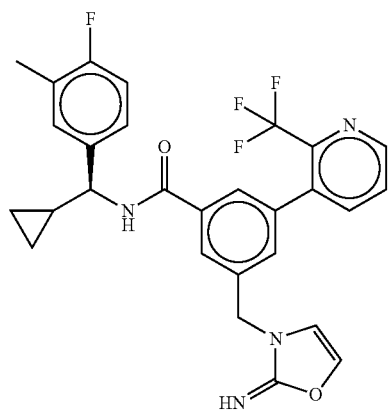
I-243
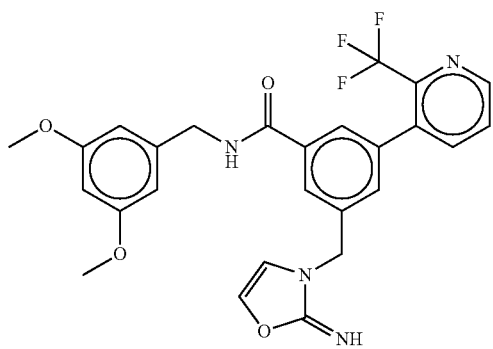
I-244
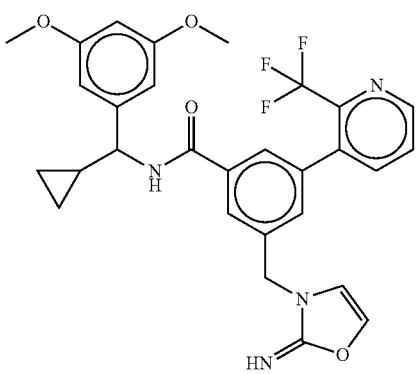
I-245

TABLE 1-continued
Exemplary compounds.
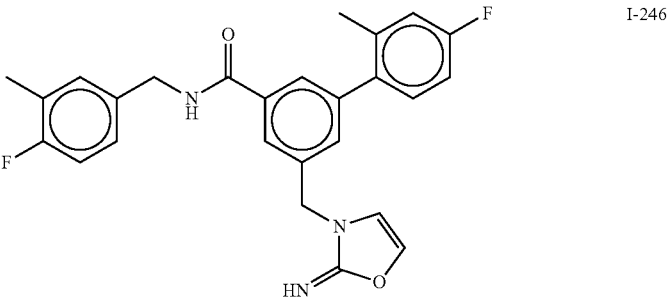
I-246
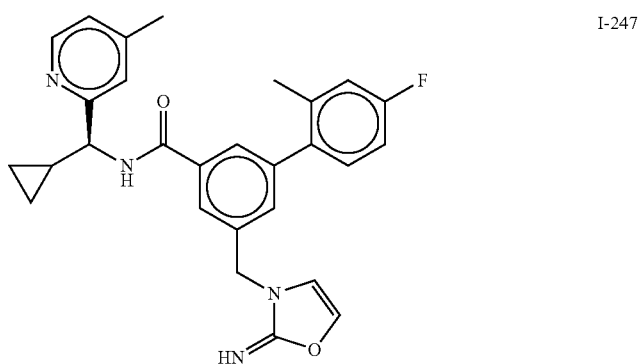
I-247
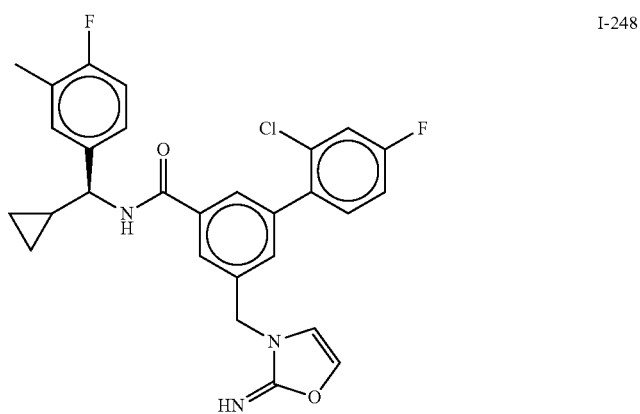
I-248
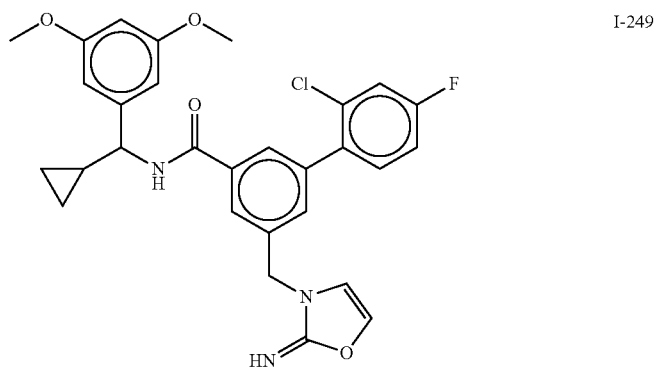
I-249

TABLE 1-continued
Exemplary compounds.
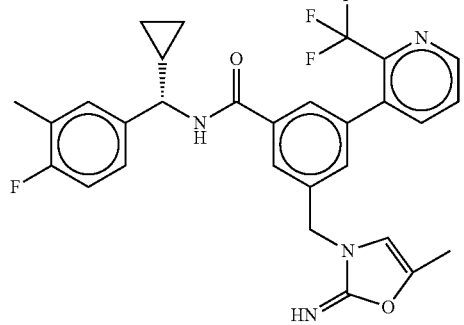
I-250
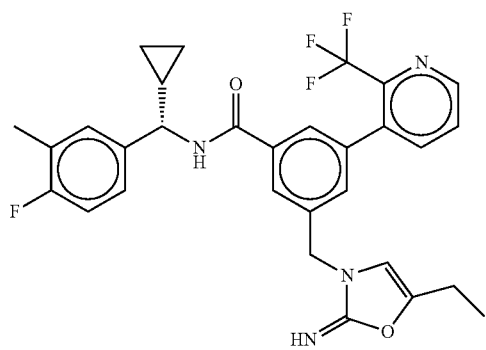
I-251
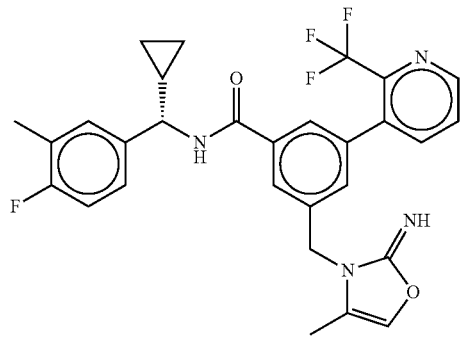
I-252
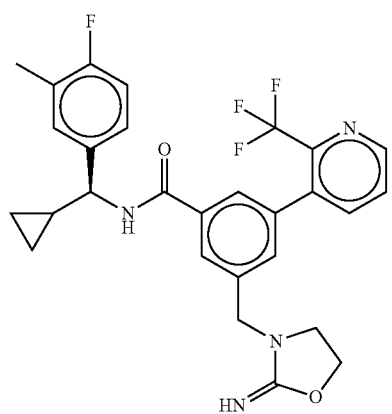
I-253

TABLE 1-continued
Exemplary compounds.
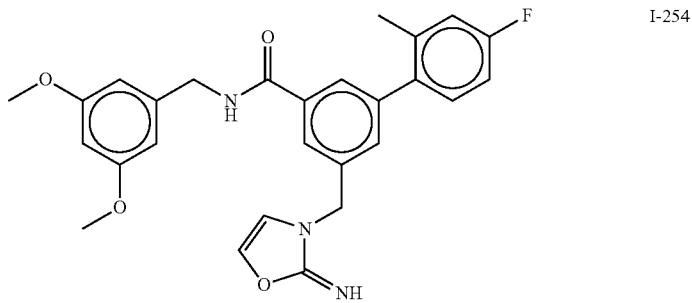
I-254
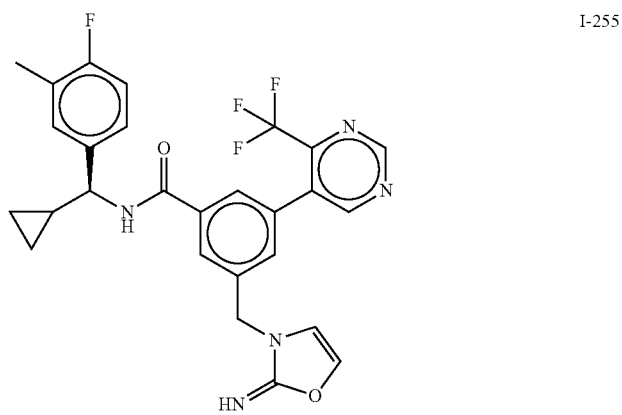
I-255
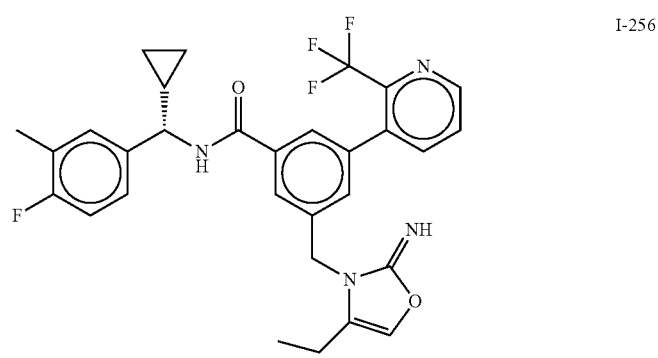
I-256
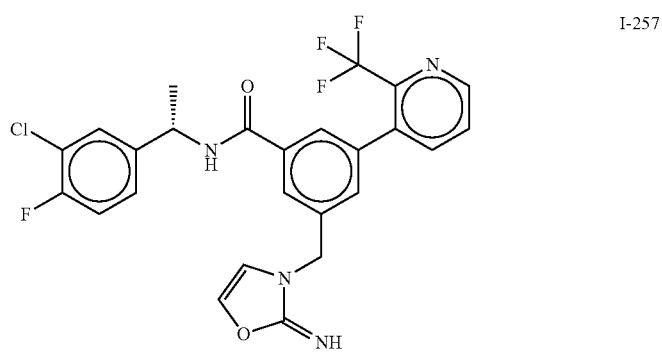
I-257

TABLE 1-continued
Exemplary compounds.
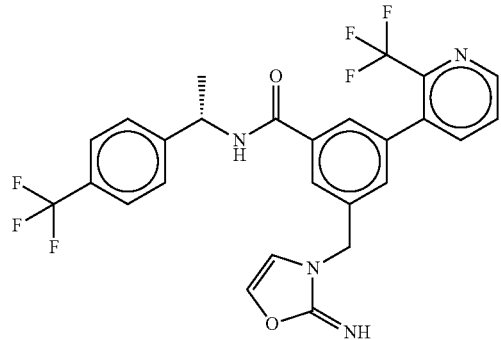
I-258
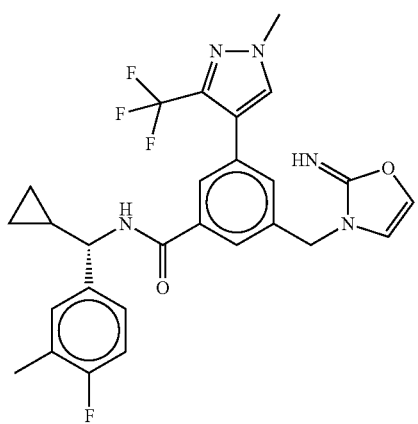
I-259
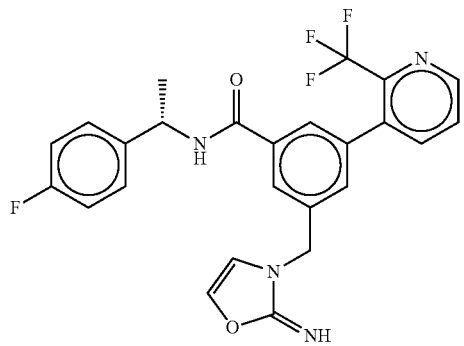
I-260
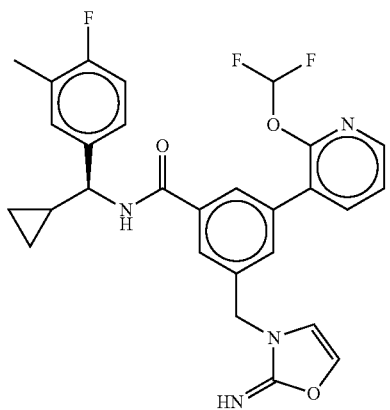
I-261

TABLE 1-continued
Exemplary compounds.
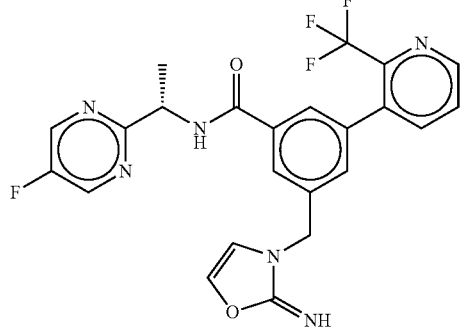
I-262
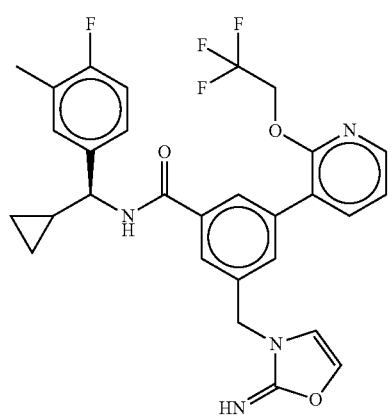
I-263
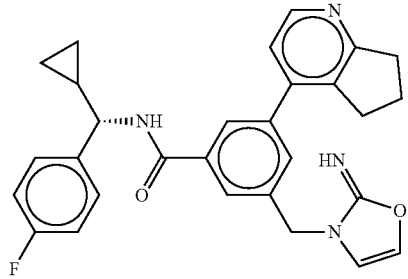
I-264
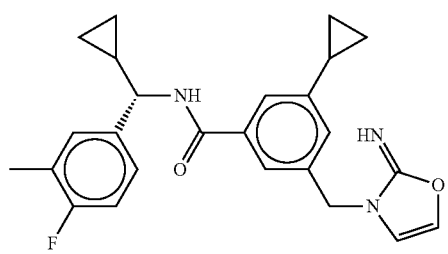
I-265
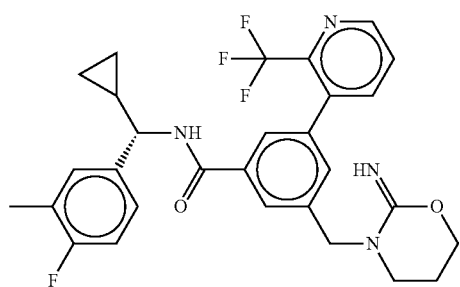
I-266

TABLE 1-continued
Exemplary compounds.
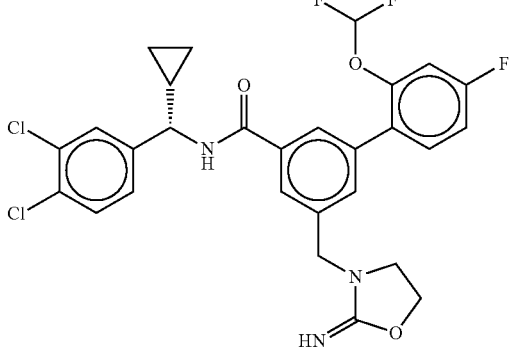
I-267
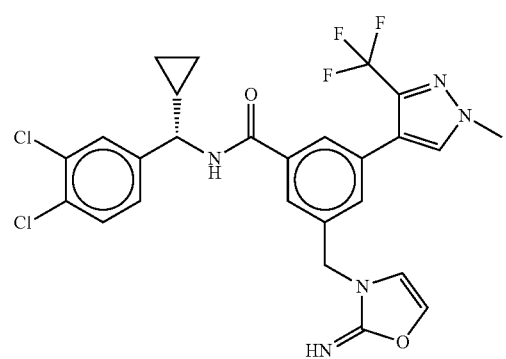
I-268
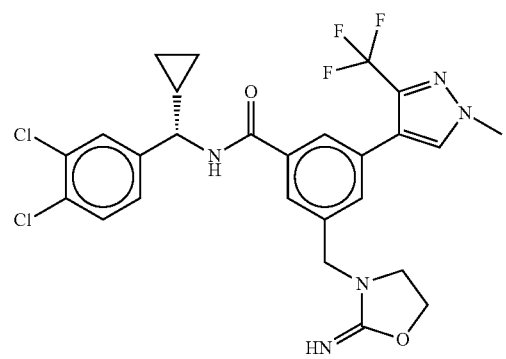
I-269
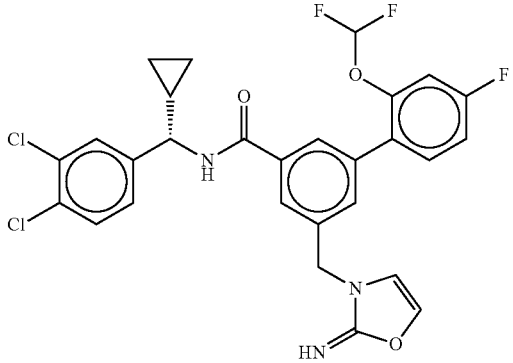
I-270

TABLE 1-continued
Exemplary compounds.
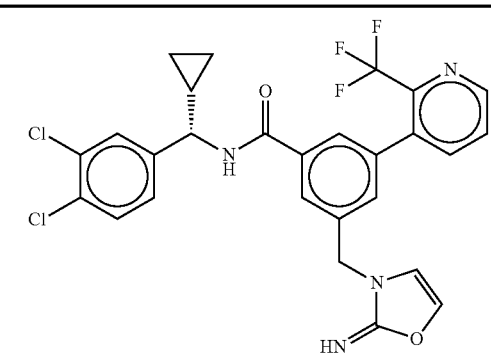
I-271
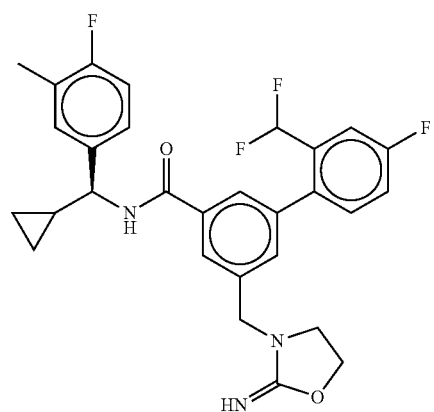
I-272
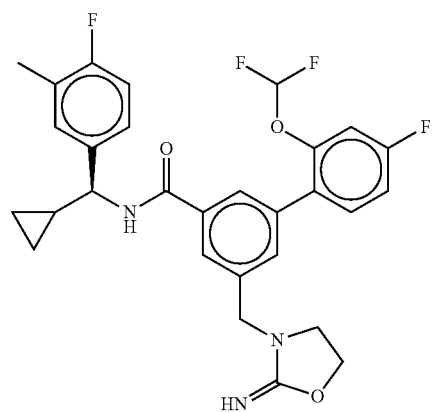
I-273
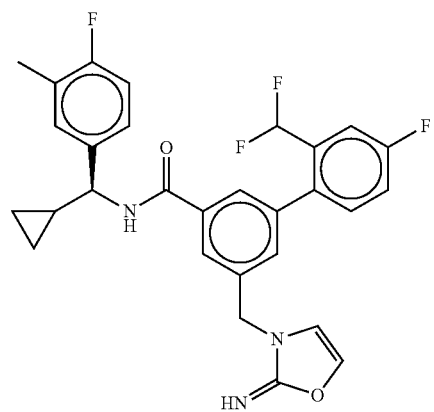
I-274

TABLE 1-continued
Exemplary compounds.
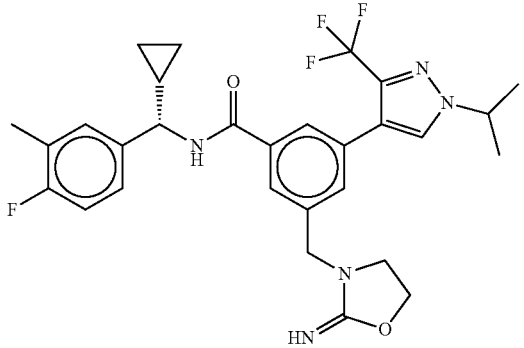
I-275
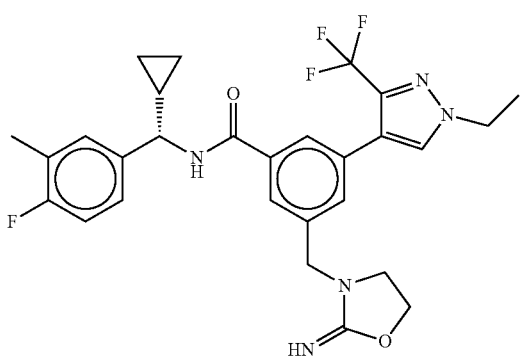
I-276
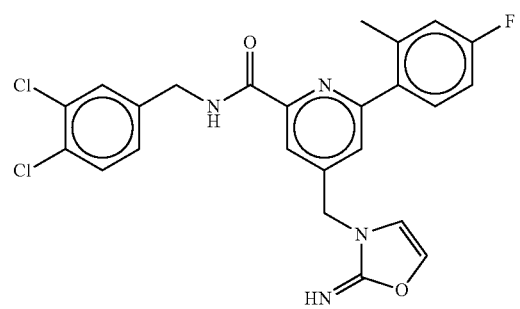
I-277
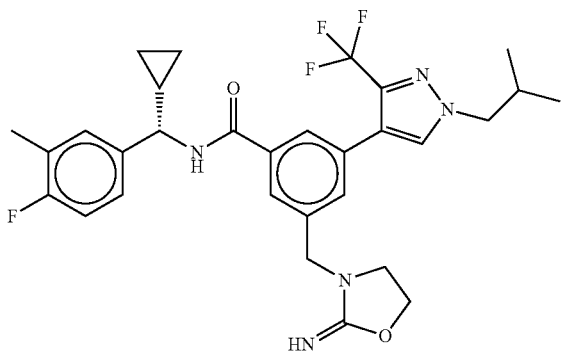
I-278

TABLE 1-continued
Exemplary compounds.
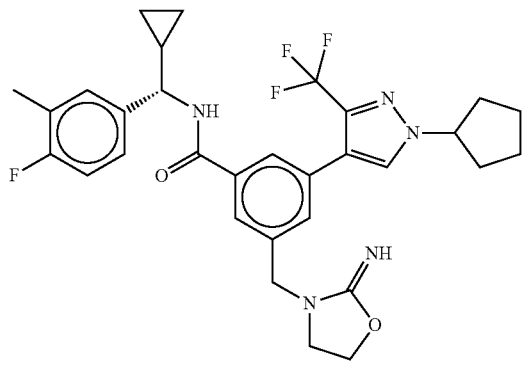
I-279
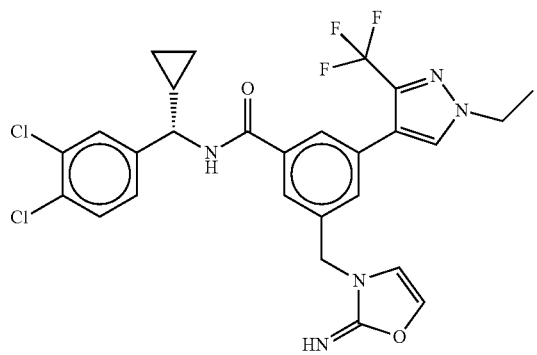
I-280
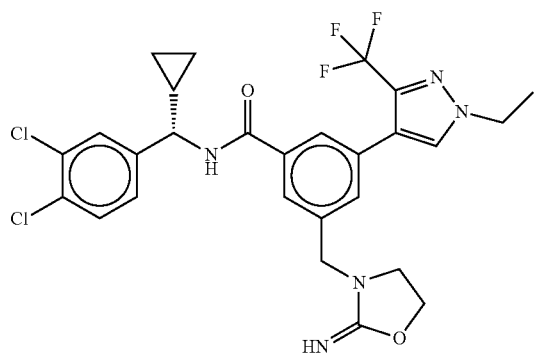
I-281
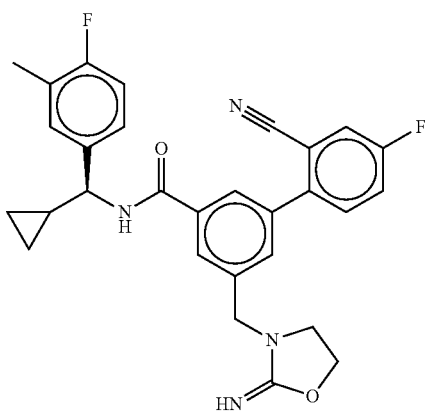
I-282

TABLE 1-continued
Exemplary compounds.
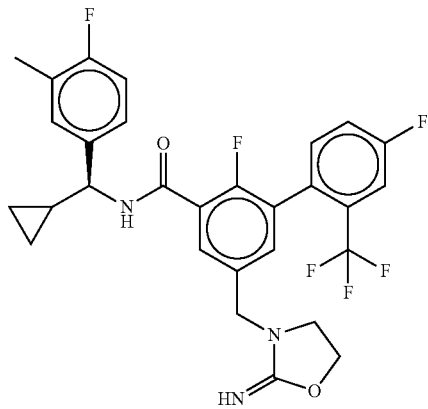
I-283
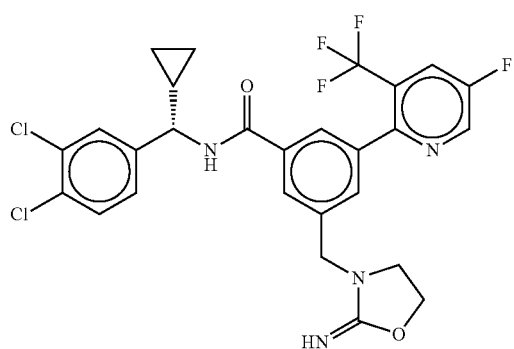
I-284
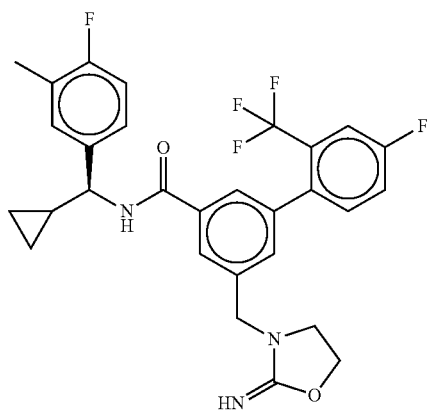
I-285
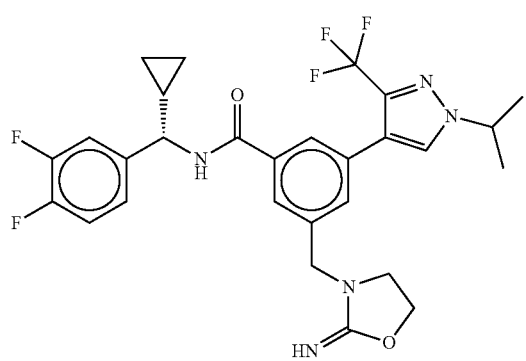
I-286

TABLE 1-continued
Exemplary compounds.
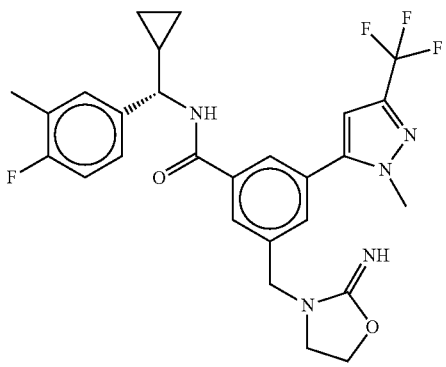
I-287
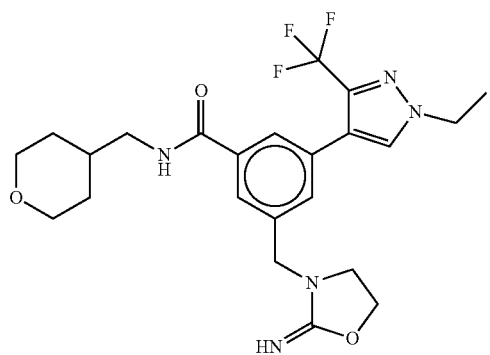
I-288
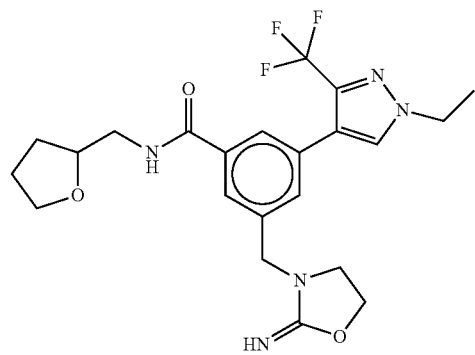
I-289
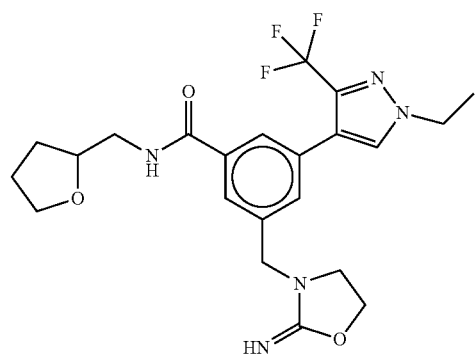
I-290

TABLE 1-continued
Exemplary compounds.
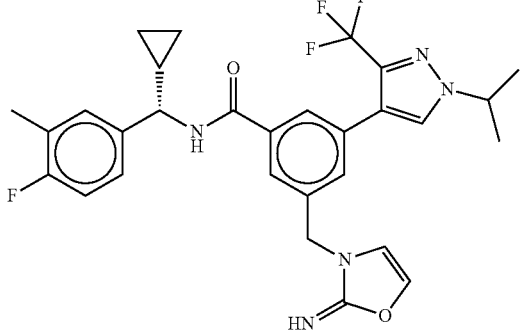
I-291
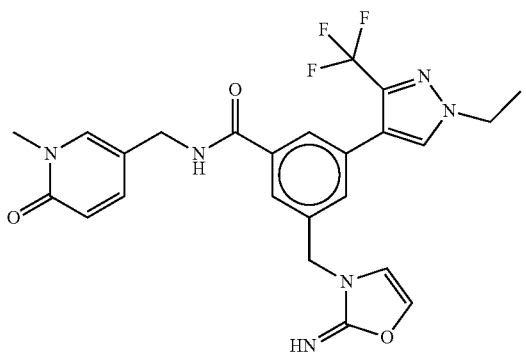
I-292
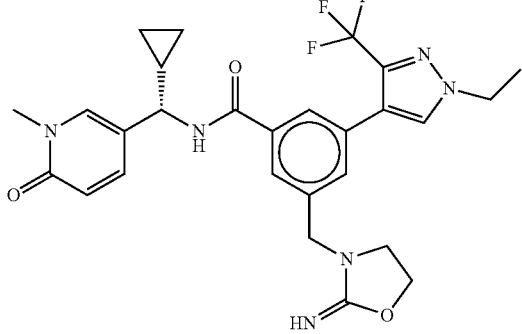
I-293
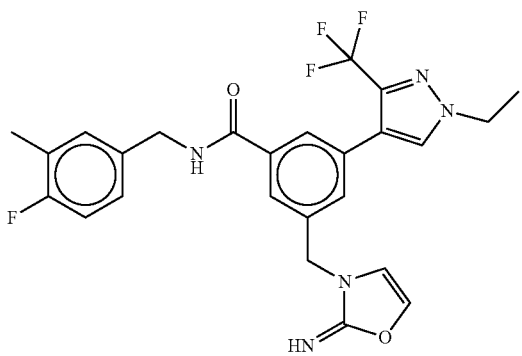
I-294

TABLE 1-continued
Exemplary compounds.
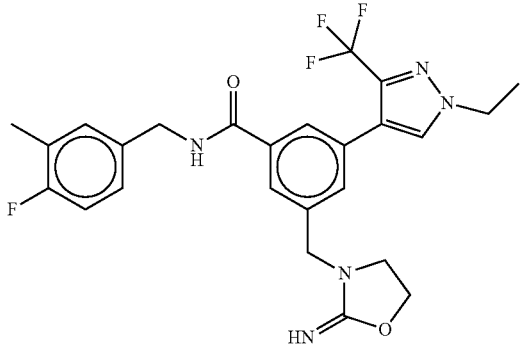
I-295
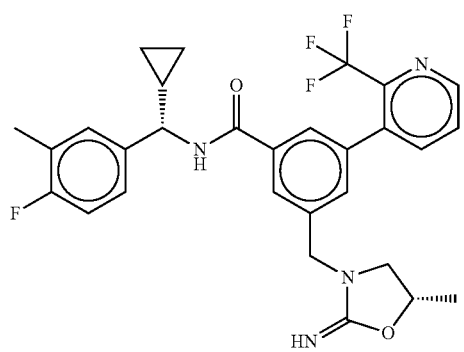
I-296
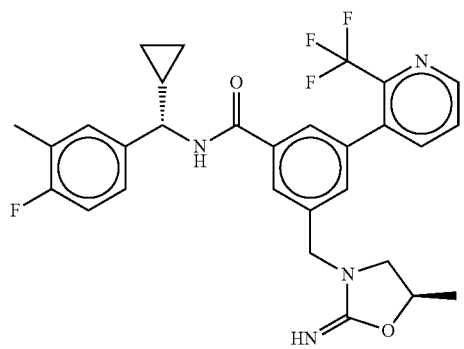
I-297
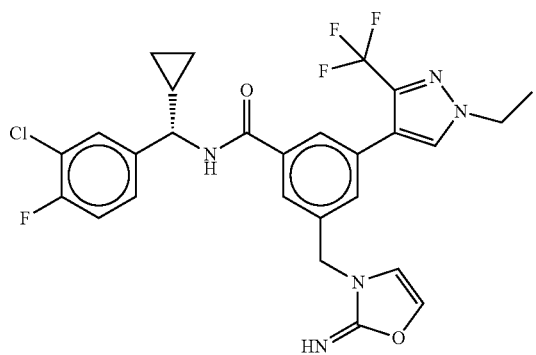
I-298

TABLE 1-continued
Exemplary compounds.
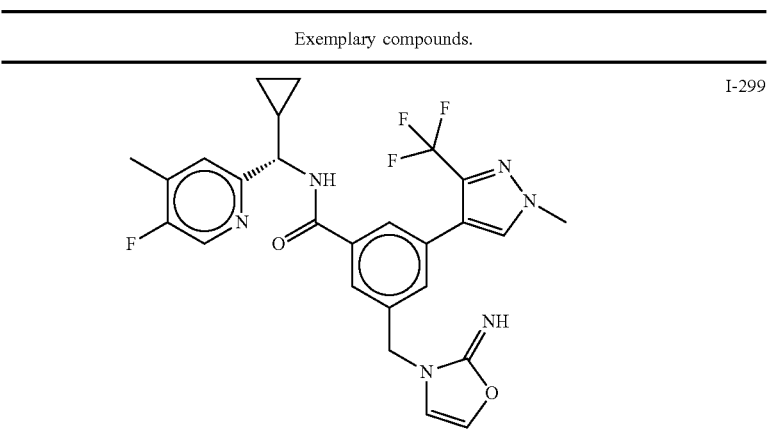
I-299
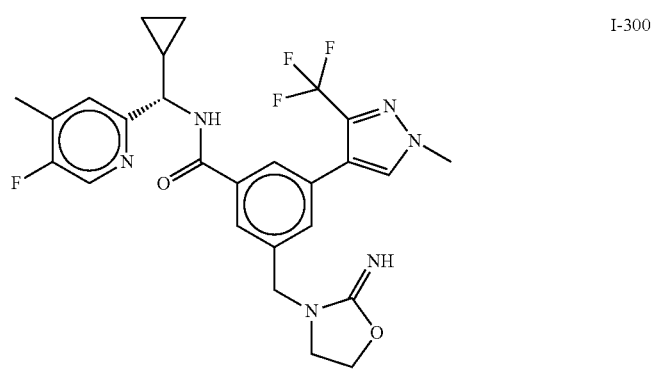
I-300
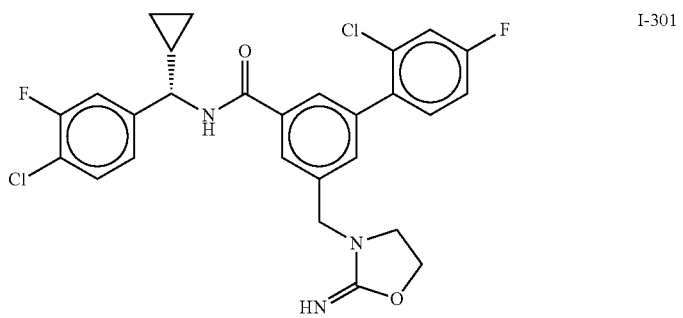
I-301
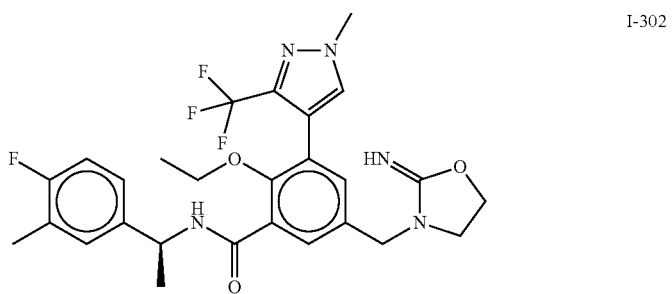
I-302

TABLE 1-continued
Exemplary compounds.
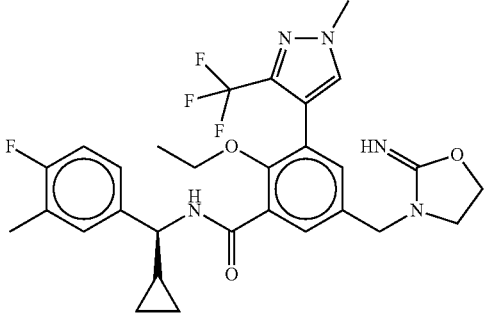
I-303
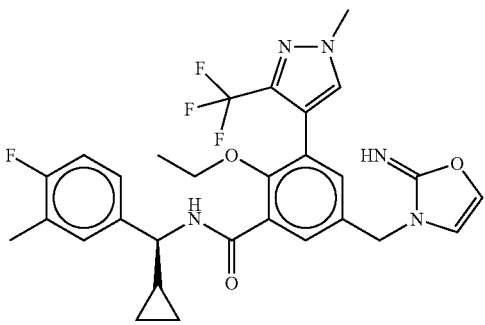
I-304
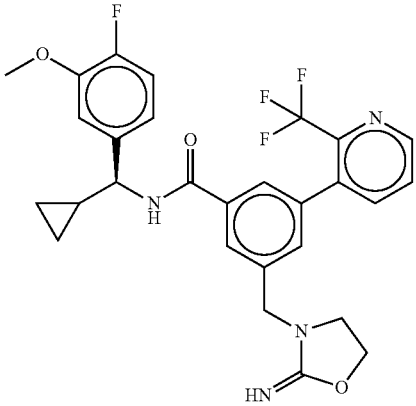
I-305
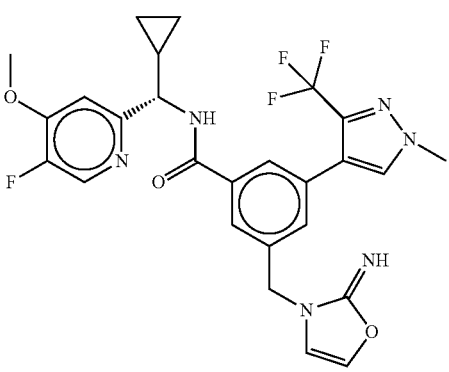
I-306

TABLE 1-continued
Exemplary compounds.
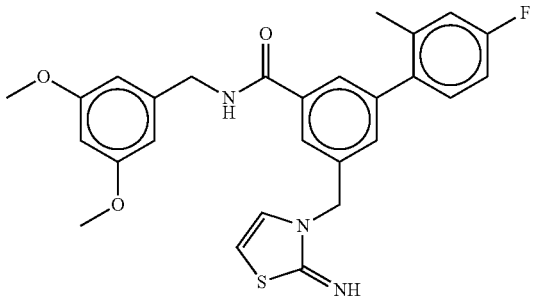 I-307
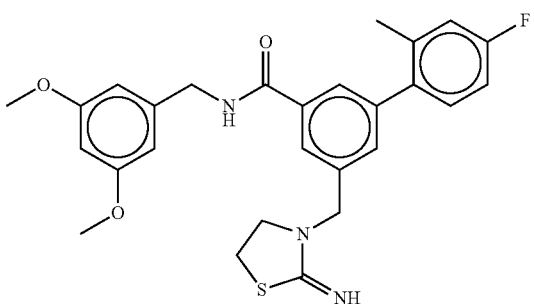 I-308
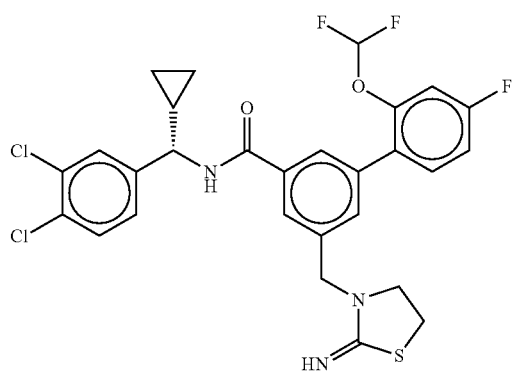 I-309
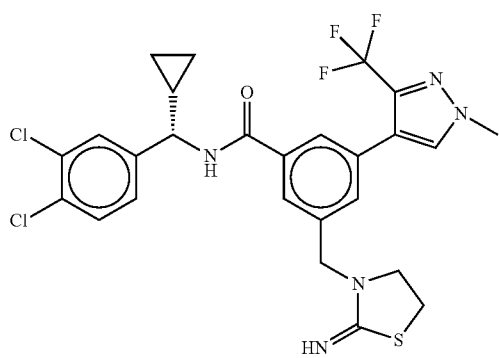 I-310

TABLE 1-continued
Exemplary compounds.
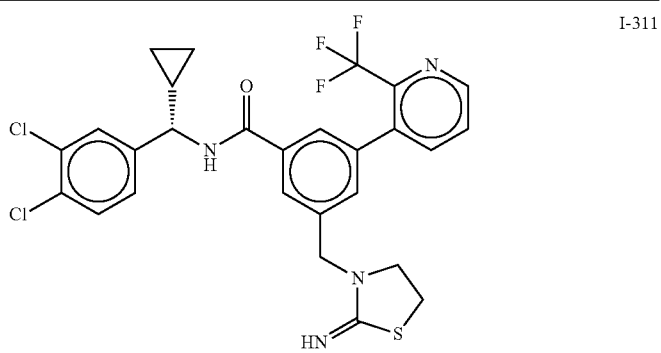
I-311
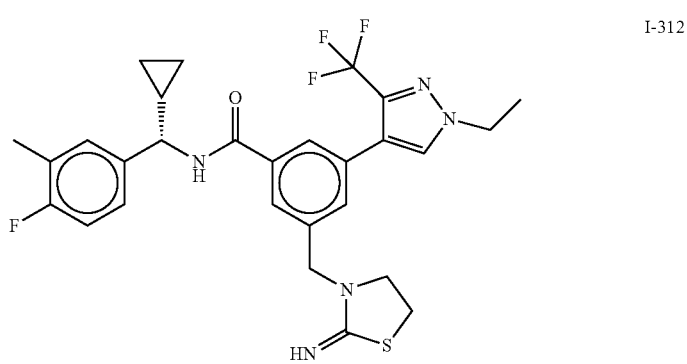
I-312
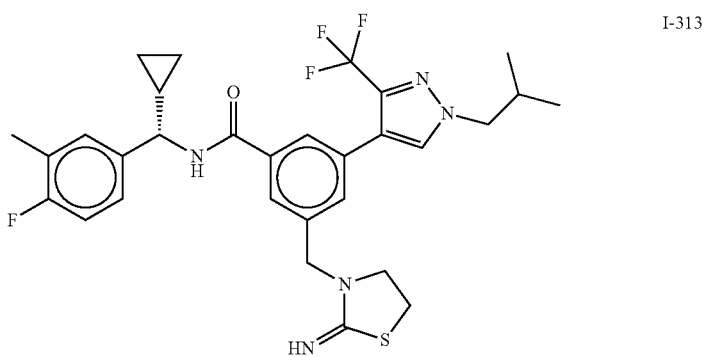
I-313
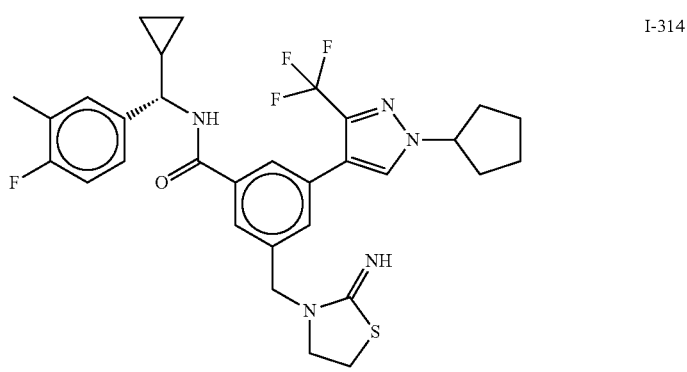
I-314

TABLE 1-continued
Exemplary compounds.
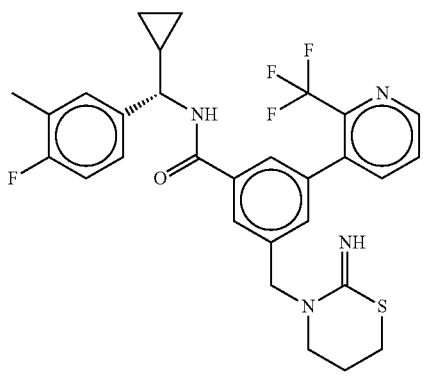
I-315
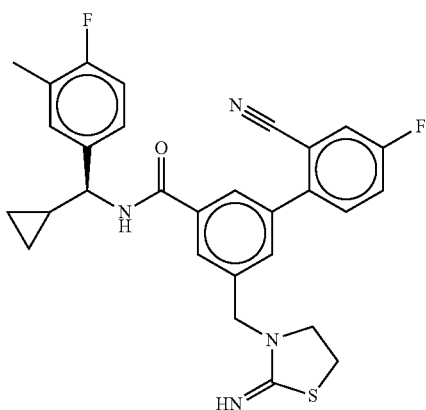
I-316
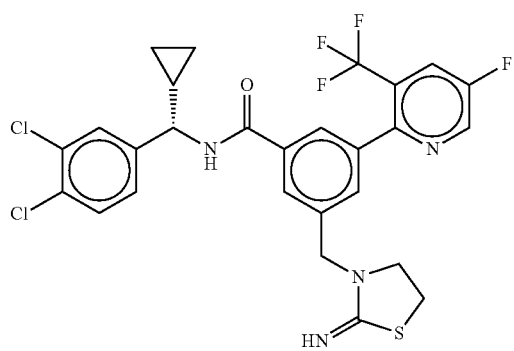
I-317
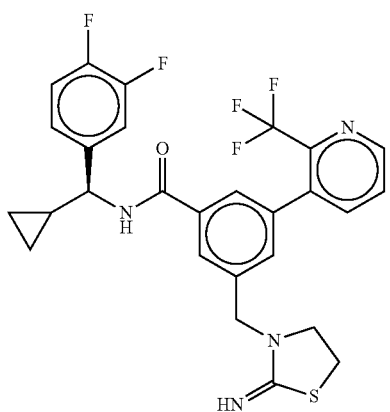
I-318

TABLE 1-continued
Exemplary compounds.
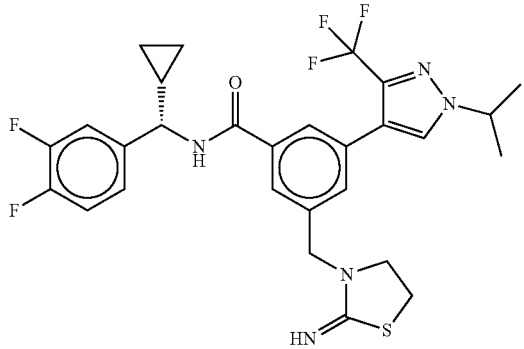
I-319
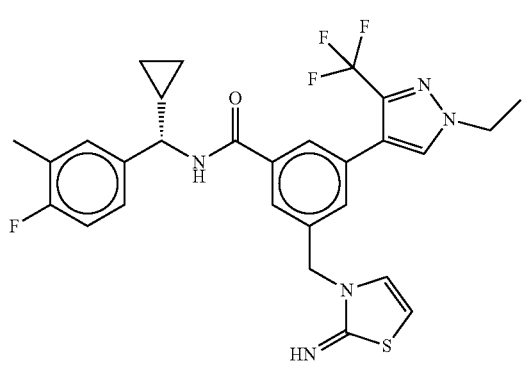
I-320
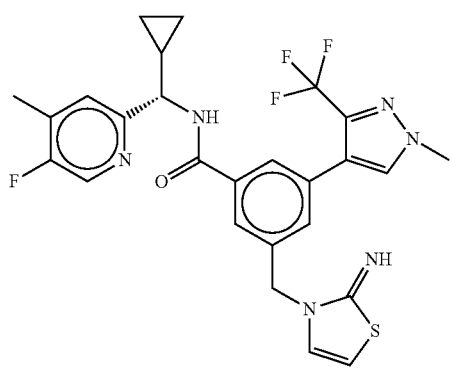
I-321
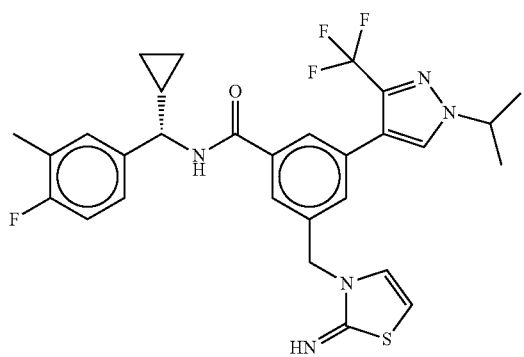
I-322

TABLE 1-continued
Exemplary compounds.
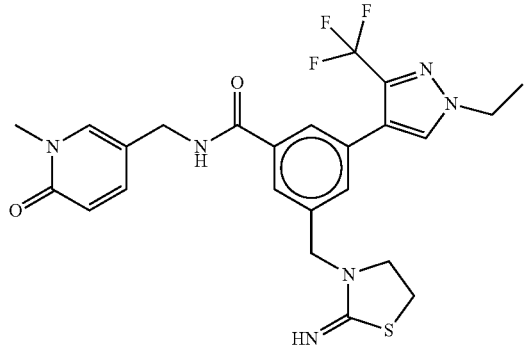
I-323
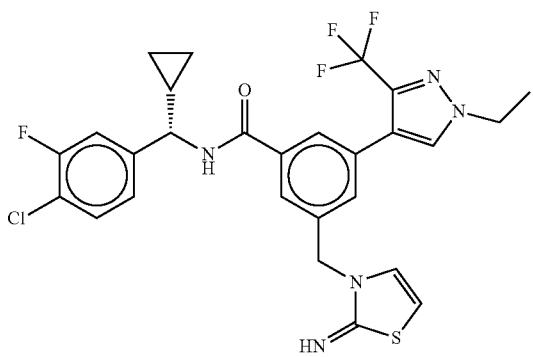
I-324
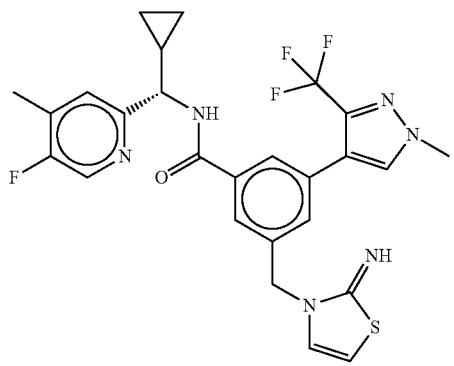
I-325
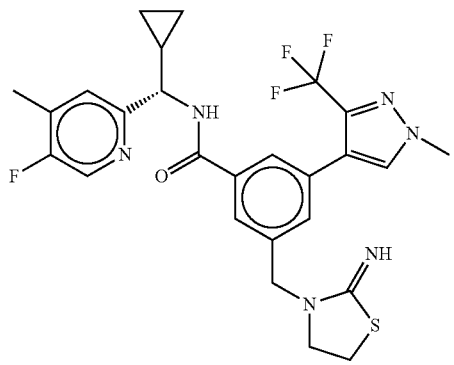
I-326

TABLE 1-continued
Exemplary compounds.
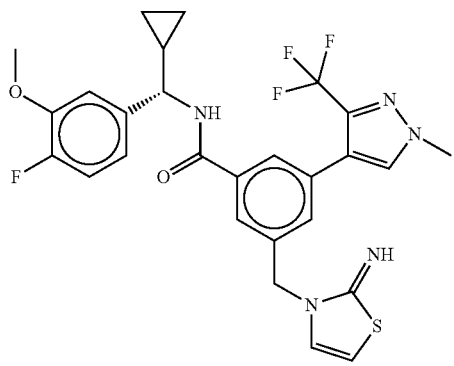
I-327
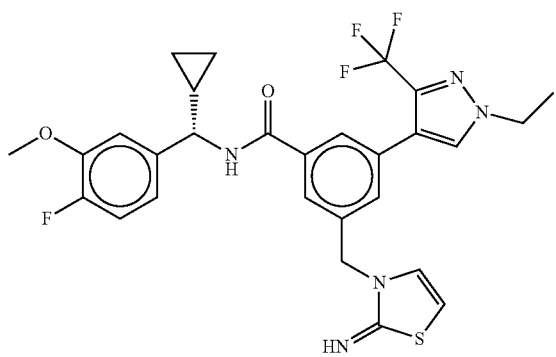
I-328
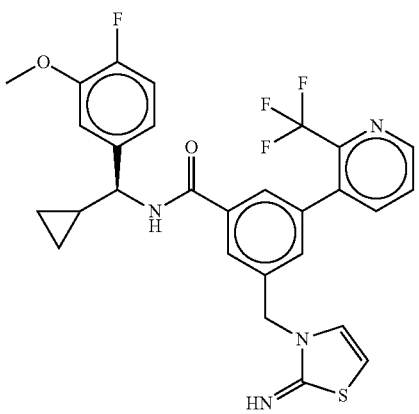
I-329
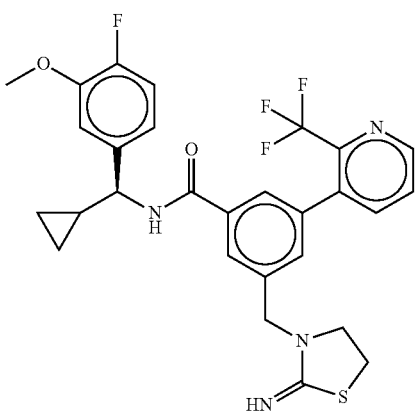
I-330

TABLE 1-continued
Exemplary compounds.
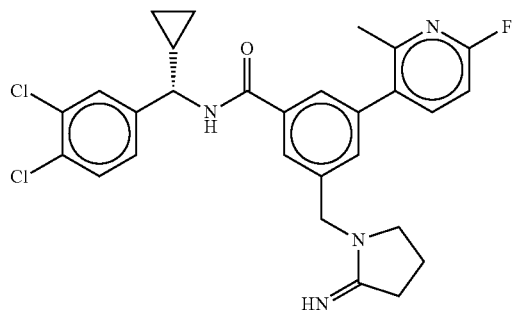
I-331
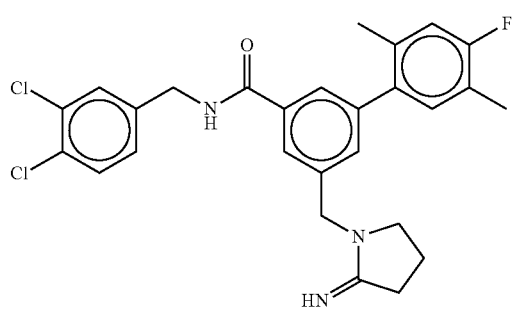
I-332
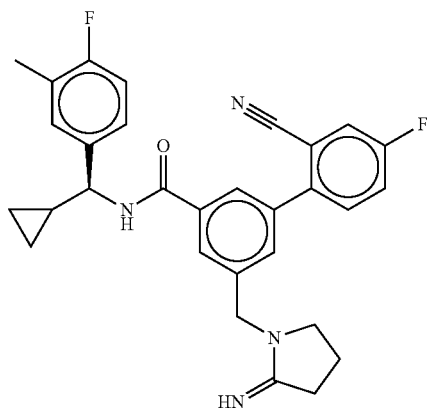
I-333
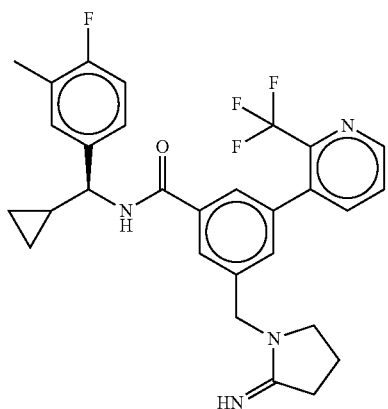
I-334

TABLE 1-continued
Exemplary compounds.
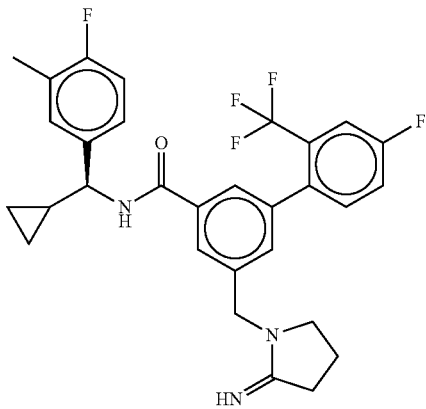
I-335
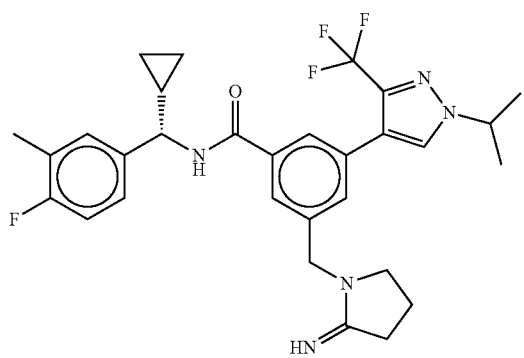
I-336
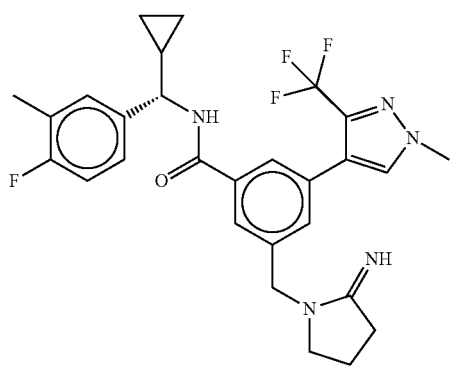
I-337
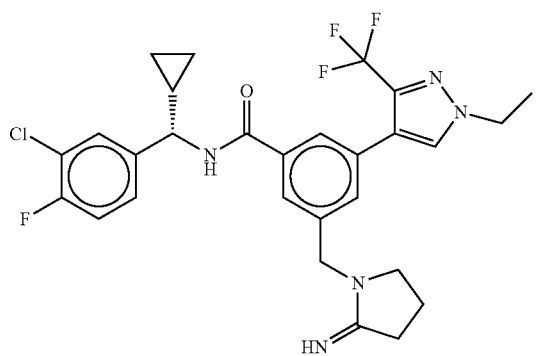
I-338

TABLE 1-continued
Exemplary compounds.
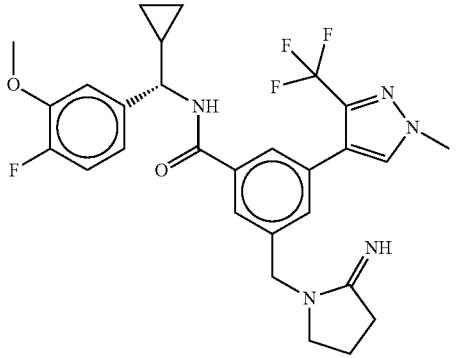
I-339
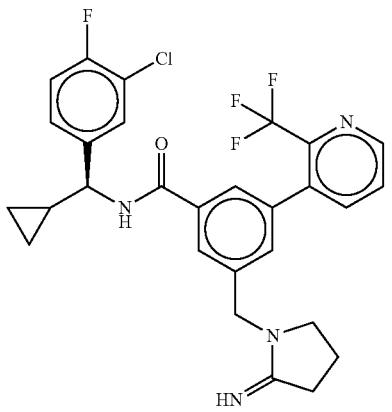
I-340
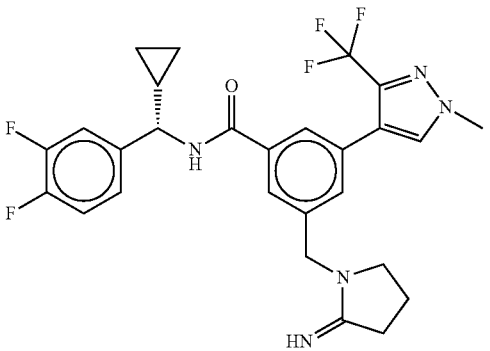
I-341
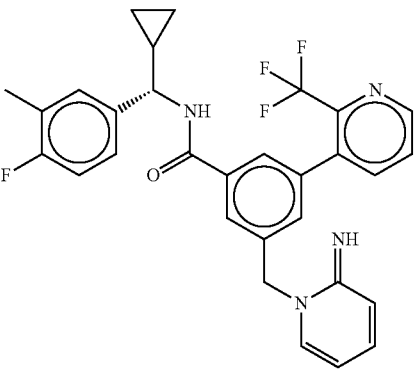
I-342

TABLE 1-continued
Exemplary compounds.
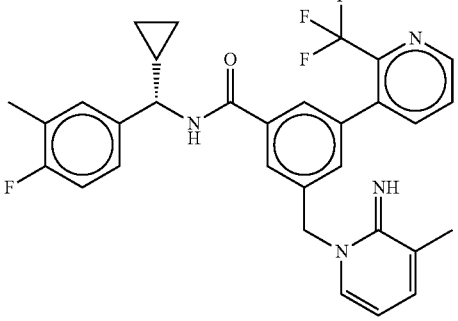
I-343
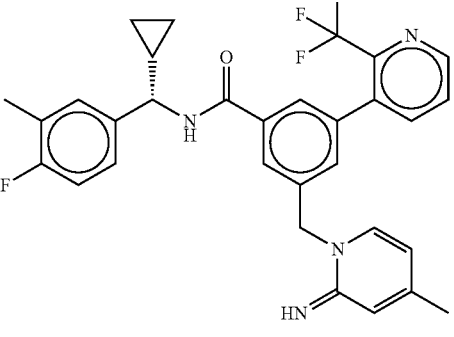
I-344
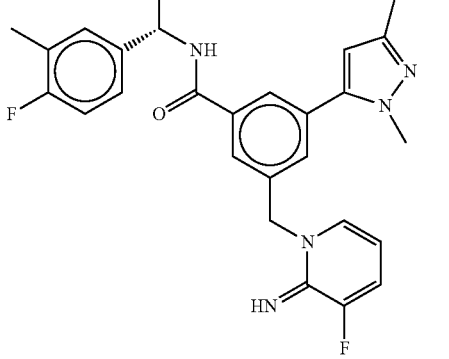
I-345
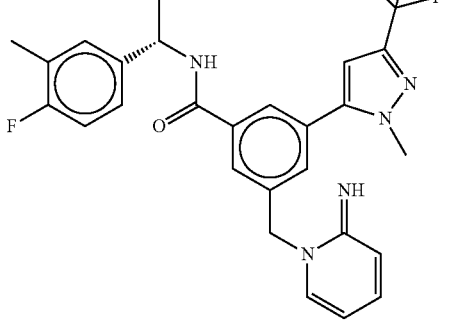
I-346

TABLE 1-continued
Exemplary compounds.
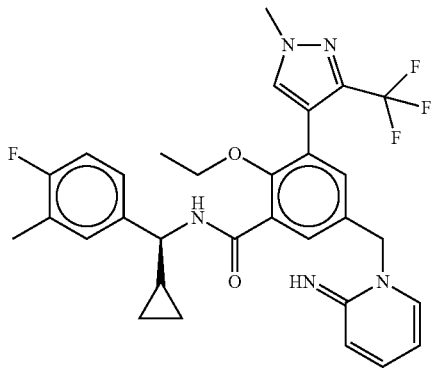
I-347
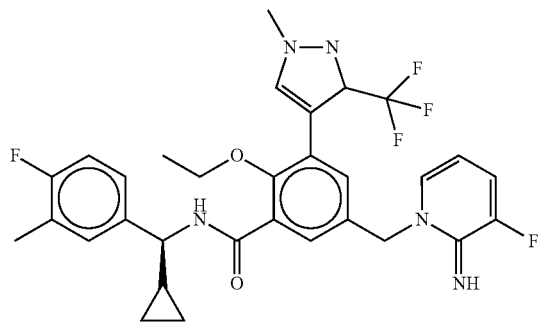
I-348
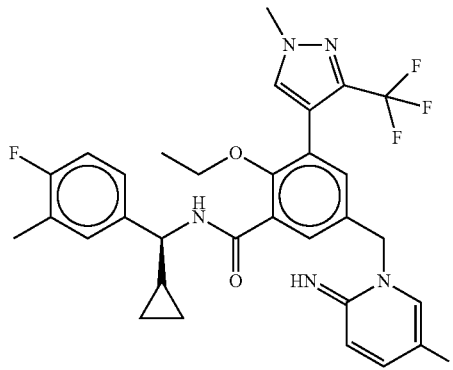
I-349
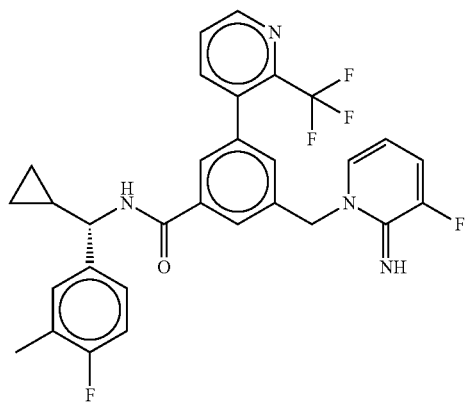
I-350

TABLE 1-continued
Exemplary compounds.
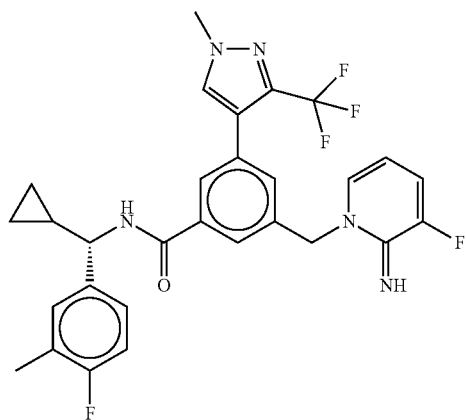
I-351
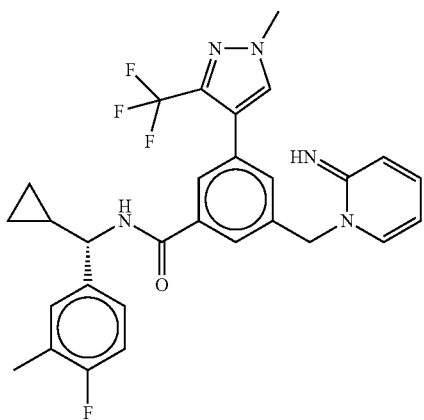
I-352
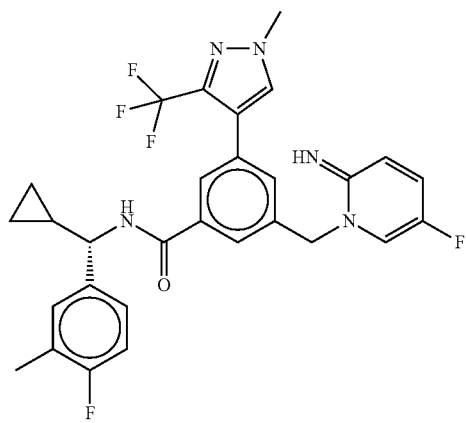
I-353

TABLE 1-continued
Exemplary compounds.
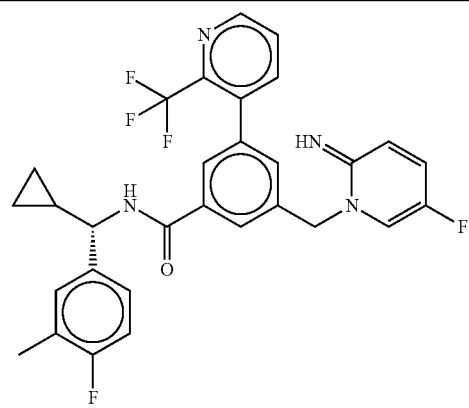
I-354
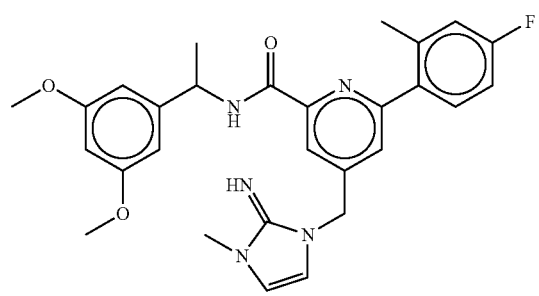
I-355
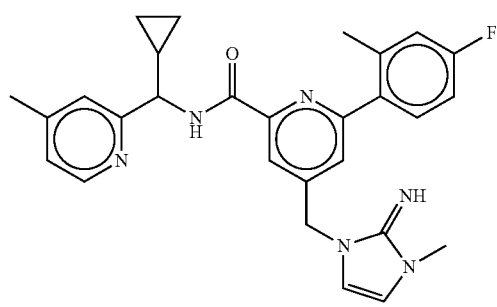
I-356
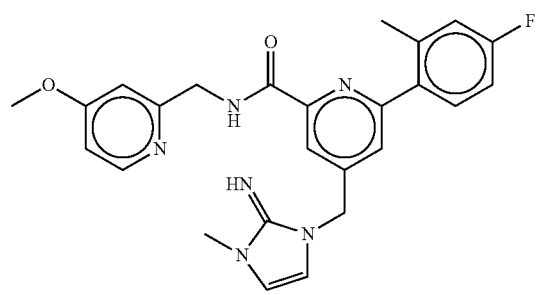
I-357
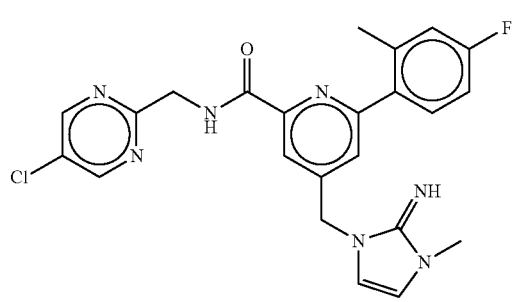
I-358

TABLE 1-continued
Exemplary compounds.
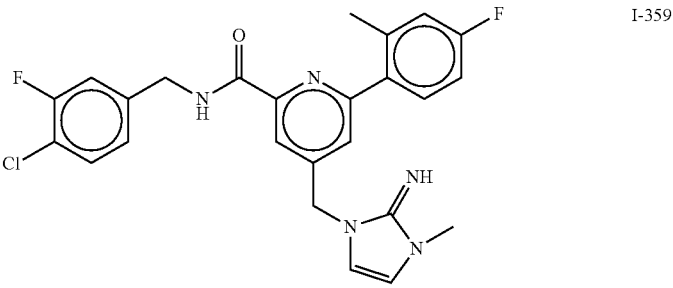 I-359
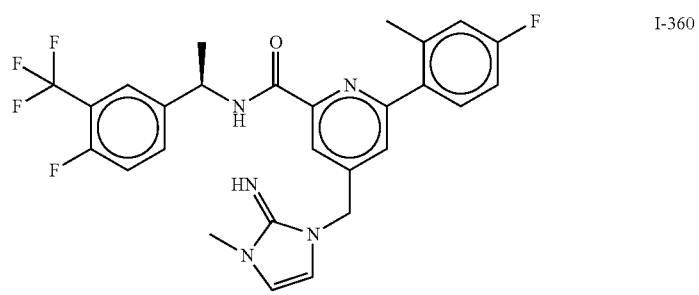 I-360
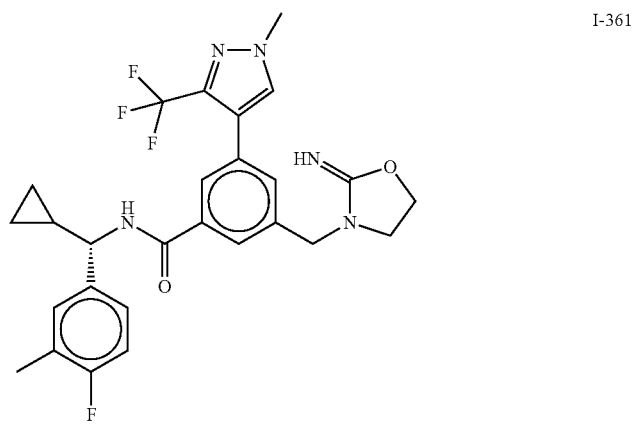 I-361
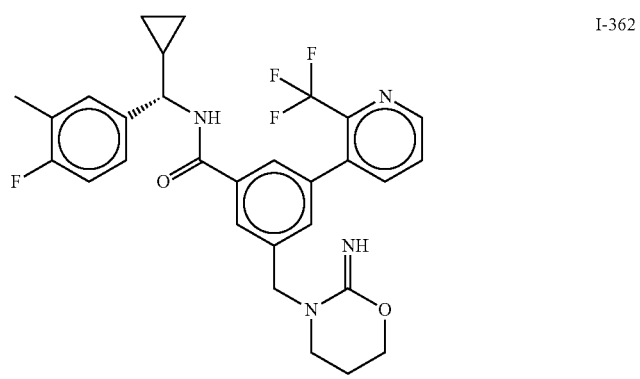 I-362

TABLE 1-continued

Exemplary compounds.

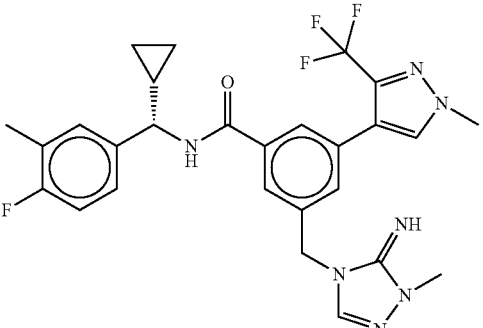

I-363

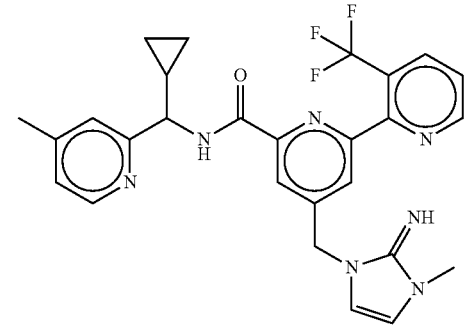

I-364

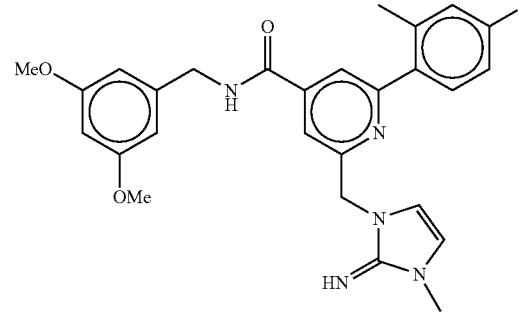

I-365

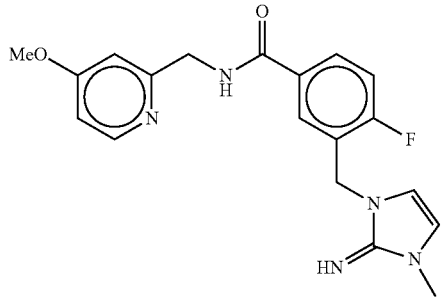

I-366 or a pharmaceutically acceptable salt thereof.

Compound names are assigned by using Struct=Name naming algorithm as part of CHEMDRAW® ULTRA.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

A. Binding to WDR5

The disclosed compounds may bind to WDR5 and prevent the association of MLL1 or other transcription factors and proteins dependent on WDR5. The compounds may bind to WDR5 and prevent oncogenic processes associated with MLL1, c-MYC, or other oncogenic proteins dependent on WDR5.

Compounds of formula (I) can bind to WDR5 resulting in a $K_i$ ranging from about 0.01 nM to about 250 μM. The compounds may have a $K_i$ of about 250 μM, about 200 μM, about 150 μM, about 100 μM, about 90 μM, about 80 μM, about 70 μM, about 60 μM, about 50 μM, about 40 μM, about 30 μM, about 20 μM, about 10 μM, about 9 μM, about 8 μM, about 7 μM, about 6 μM, about 5 μM, about 4 μM, about 3 μM, about 2 μM, about 1 μM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, about 1 nM, about 0.3 nM, about 0.1 nM, about 0.03 nM, or about 0.01 nM. Compounds of formula (I) can bind to WDR5 resulting in a $K_i$ of less than 250 μM, less than 200 μM, less than 150 μM, less than 100 μM, less than 90 μM, less than 80 μM, less than 70 μM, less than 60 μM, less than 50 μM, less than 40 μM, less than 30 μM, less than 20 μM, less than 10 μM, less than 9 μM, less than 8 μM, less than 7 μM, less than 6 μM, less than 5 μM, less than 4 μM, less than 3 μM, less than 2 μM, less than 1 μM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, less than 1 nM, less than 0.3 nM, less than 0.1 nM, or less than 0.03 nM.

B. General Synthesis

Compounds of formula (I) may be prepared by synthetic processes or by metabolic processes. Preparation of the compounds by metabolic processes includes those occurring in the human or animal body (in vivo) or processes occurring in vitro.

The compounds of the present disclosure can be prepared in a number of ways well known to one skilled in the art of organic synthesis. The compounds of the present disclosure can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the subject matter referenced herein. Compounds of formula (I) may be also prepared by metabolic processes. Preparation of the compounds by metabolic processes includes those occurring in the human or animal body (in vivo) or processes occurring in vitro.

The compounds of the disclosure may be prepared using the exemplary reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One having ordinary skill in the art may adjust one or more of the conditions described herein. One skilled in the art of organic synthesis understands that the functionality present on various portions of the edict molecule must be compatible with the reagents and reactions proposed. Not all compounds of the disclosure falling into a given class may be compatible with some of the reaction conditions required in some of the methods described. Such restrictions to the substituents, which are compatible with the reaction conditions, will be readily apparent to one skilled in the art and alternate methods can be used.

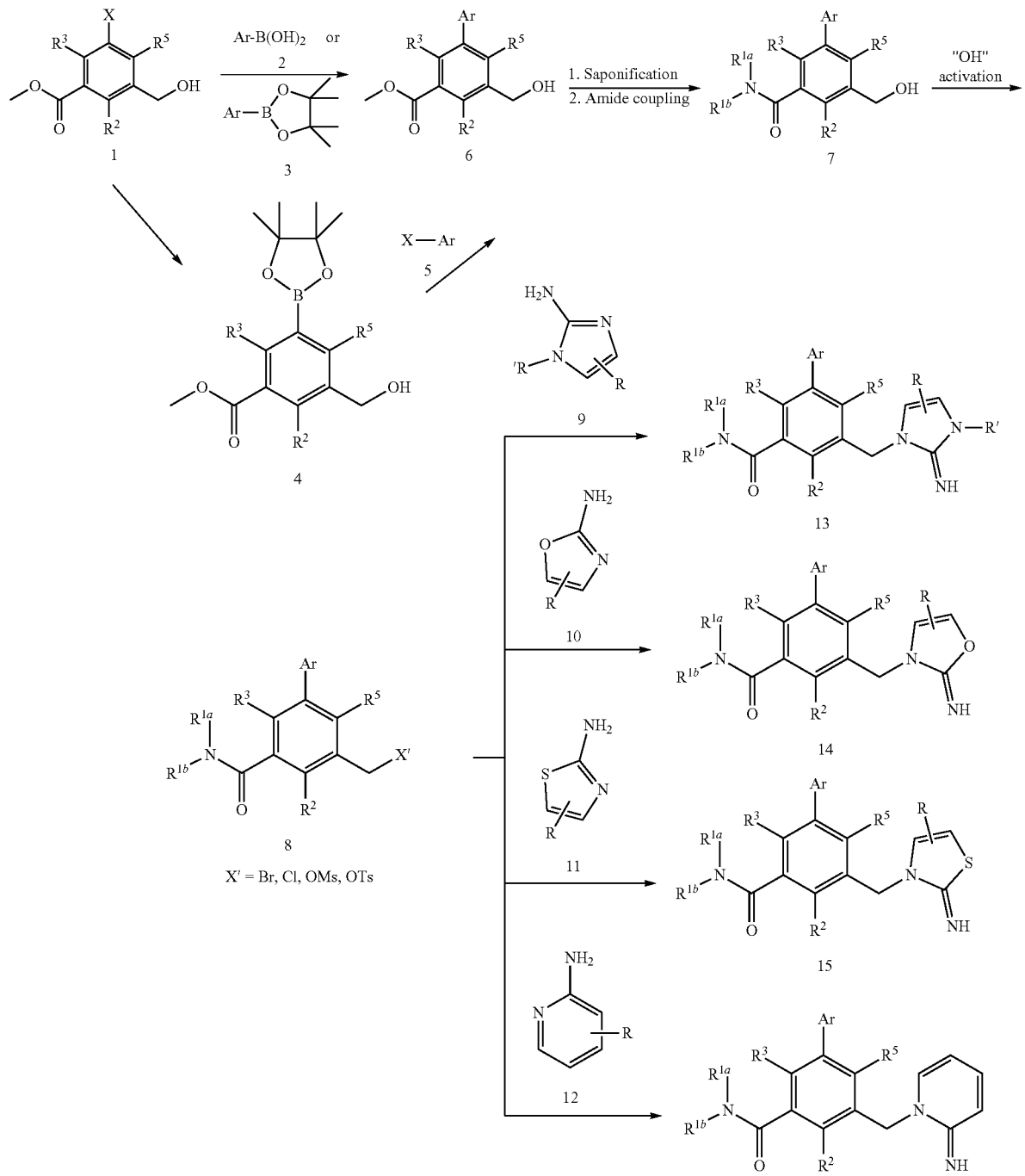

In some embodiments, provided compounds of this invention may be prepared as shown in Scheme 1. A variety of boronic acids 2 or borates 3, which are commercially available or can be prepared, can be coupled with benzyl alcohol 1, wherein X=Cl, Br, I, Triflates or diazoderivatives, via e.g., Suzuki-Miyaura coupling protocol to afford biaryl adducts 6 (Miyaura, N., Suzuki, A., *Chem. Rev.* (1995), 2457). One exemplary such procedure entails treatment of the aryl bromide, iodide or Triflate 1 with an aryl boronic acid in the presence of a catalytic Pd species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd catalyst, and a base such as $Na_2CO_3$, $Cs_2CO_3$, $K_2CO_3$, $Ba(OH)_2$ or $Et_3N$. Alternatively, biaryl adducts 6 can be prepared from Pinacolborates 4 which can be prepared from compounds 1 via Pd, such as $Pd(PPh_3)_4$, $Pd(PPh_3)_2Cl_2$, $Pd(OAc)_2$, $Pd_2(dba)_3$, catalyzed coupling of bis(pinacolato) diboron. Intermediates 4 can be coupled with a variety of aryl-halides or heteroaryl-halides 5 using Suzuki coupling protocol described above to give compounds 6. In some embodiments, a provided approach allows for great diversity in the subsequent coupling of indole boronic acids or borates with commercially available haloaromatic derivatives. Subsequent saponification of compounds 6 with appropriate bases, such as $Cs_2CO_3$, $K_2CO_3$, LiOH or NaOH, followed by amide coupling reaction with suitable amines using coupling reagents, but not limited to, HATU, EDC, PyBOP, DCC, HBTU, or TBTU at a number of conditions that are routine for those skilled in the art of organic synthesis gives amides 7. Hydroxy group of 7 may be activated by converting to chloride, bromide, iodide, Meslate or Toslate group at a number of conditions that are routine for those skilled in the art of organic synthesis to generate the versatile penultimate intermediates 8. Imidazole imines 13, oxazole imines 14, thiazole imines 15, and pyridine imines 16 can be generated from intermediates 8 via nucleophilic substitution protocols using corresponding amino-imidazoles 9, amino-oxazoles 10, amino-thiazoles 11, and amino-pyridines 12, respectively, in the presence of appropriate organic bases such as $Et_3N$ or DIPEA.

Scheme 2

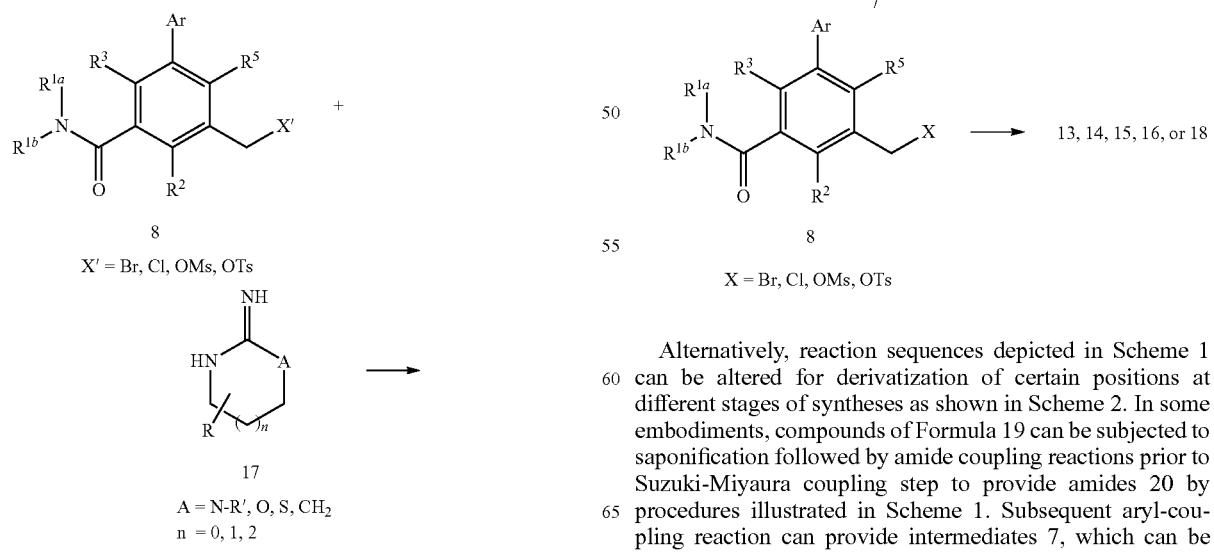

X' = Br, Cl, OMs, OTs

A = N-R', O, S, $CH_2$
n = 0, 1, 2

-continued

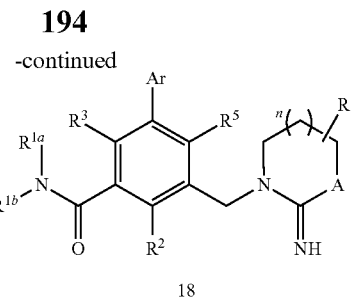

18

In some embodiments, compounds of Formula 18 may be synthesized by procedures illustrated in Scheme 2 from intermediates 8 using nucleophilic substitution conditions described in Scheme 1. A variety nucleophiles 17 can be applicable for the reaction for high diversity.

Scheme 3

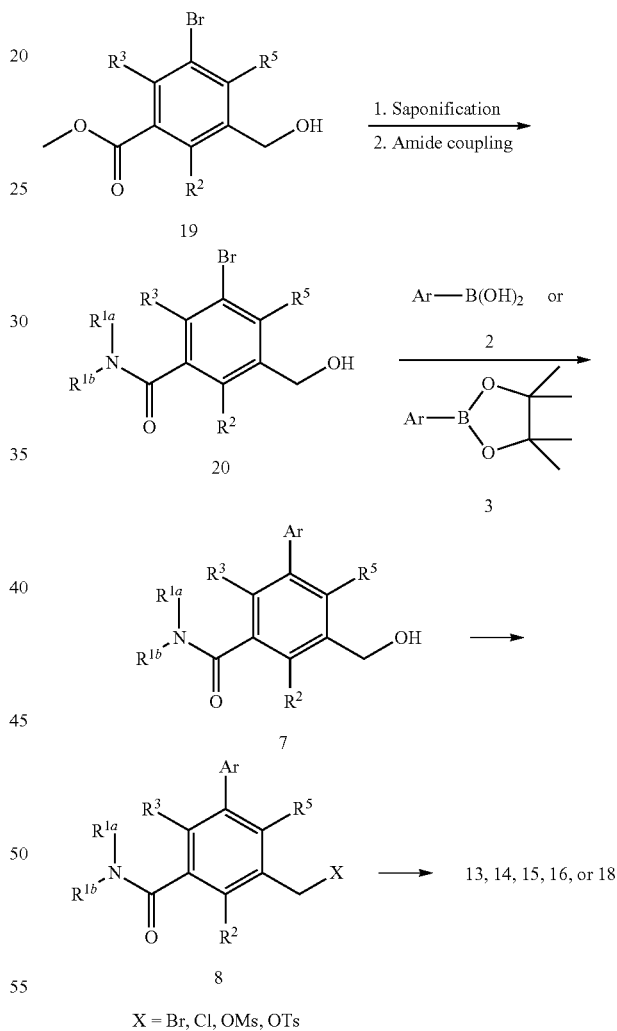

X = Br, Cl, OMs, OTs

Alternatively, reaction sequences depicted in Scheme 1 can be altered for derivatization of certain positions at different stages of syntheses as shown in Scheme 2. In some embodiments, compounds of Formula 19 can be subjected to saponification followed by amide coupling reactions prior to Suzuki-Miyaura coupling step to provide amides 20 by procedures illustrated in Scheme 1. Subsequent aryl-coupling reaction can provide intermediates 7, which can be further elaborated to give final compounds 13-16 and 18.

Scheme 4

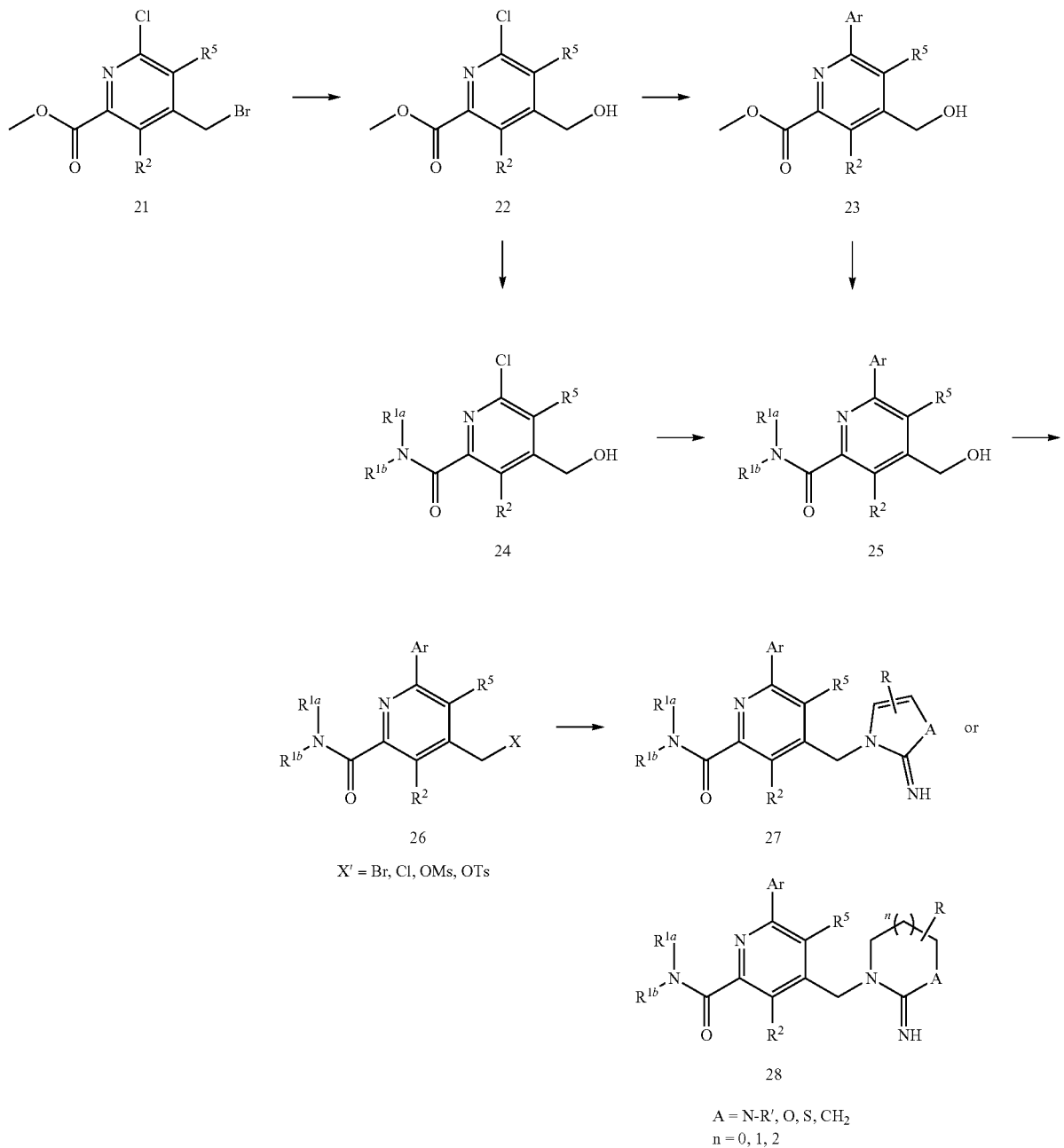

Exemplary method for preparing compounds of Formula 27 and 28 containing the core pyridyl group in Scheme 4 and proceeds from compounds of Formula 21. Intermediates 25 can be synthesized using Suzuki-Miyaura coupling protocol followed by saponification and amide-coupling sequence that described in Scheme 1. Alternatively, the reaction sequence can be reversed by conducting saponification and amide-coupling reactions prior to Suzuki-Miyaura coupling step as shown in Scheme 3. Finally, compounds of Formula 27 and 28 can be generated starting from compounds of Formula 25 applying the synthetic sequence outlined in Scheme 1 and 2.

Scheme 5

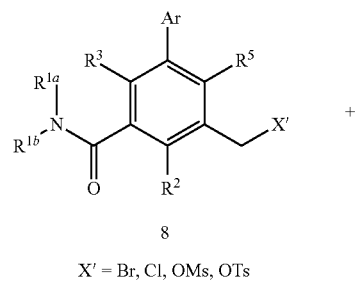

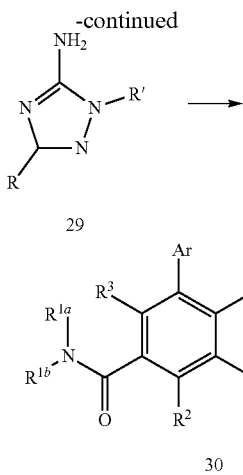

In some embodiments, triazole imine 30 can be generated from intermediates 8 using nucleophilic substitution protocols described in Scheme 1 using aminotriazole 29 as nucleophile.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

C. Examples

Abbreviations

The following abbreviations are employed in the Examples and elsewhere herein:
DCM=dichloromethane
EDC=1-Ethyl-3-(3-dimethylaminopropyl)carbodiimide
TEA=triethylamine
DMF=dimethylformamide
DMSO=dimethylsulfoxide
THF=tetrahydrofuran
$K_2CO_3$=potassium carbonate
$Cs_2CO_3$=cesium carbonate
ether=diethyl ether
NaOH=sodium hydroxide
KOH=potassium hydroxide
EtOAc=ethyl acetate
$Na_2CO_3$=sodium carbonate
$NaHCO_3$=sodium bicarbonate
$MgSO_4$=magnesium sulfate
$CH_2Cl_2$=methylene chloride
MeOH=methanol
EtOH=ethanol
Hex=hexanes
HCl=hydrochloric acid Pd(PPh$_3$)$_4$=tetrakis(triphenylphosphine)palladium(0)
Pd(OAc)$_2$=Palladium(II) acetate
TFA=trifluoroacetic acid
Et$_3$N=triethylamine
DIPEA=N,N-diisopropylethylamine
NaH=sodium hydride
NaN$_3$=sodium azide
TBAF=tetrabutyl ammonium fluoride
DTBAD=di-tert-butyl azodicarboxylate
HATU=2-(7-aza-1H-1-benzotriazole-1-yl)-1,1,3,3-tetramethyluronium hexafluorophosphate
NBS=N-bromo succinimide
AIBN=Azobisisobutyronitrile
min=minute(s)
h or hr=hour(s)
mL or ml=milliliter
g=gram(s)
mg=milligram(s)
mmol=millimole(s)
r.t.=room temperature
LRMS=low resolution mass spectrometry
NMR=nuclear magnetic resonance
(M+H)=the protonated mass of the free base of the compound
R$_T$=retention time (in minutes)

EXAMPLES

Microwave assisted reactions are performed in a single-mode reactor: Emrys™ Optimizer microwave reactor (Personal Chemistry A.B., currently Biotage).

Hydrogenation reactions are performed using an atmospheric balloon or using a Parr hydrogenation shaker apparatus.

Normal phase flash silica gel-based column chromatography is performed using ready-to-connect cartridges from ISCO, on irregular silica gel, particle size 15-40 µm on a Combi-flash Companion chromatography system from ISCO.

Low resolution mass spectra are obtained on an Agilent 1200 series 6130 mass spectrometer. Analytical HPLC is performed on an HP1100 with UV detection at 214 and 254 nm along with ELSD detection, LC/MS (J-Sphere80-C18, 3.0×50 mm, 4.1 min gradient, 5% [0.05% TFA/CH$_3$CN]: 95% [0.05% TFA/H$_2$O] to 100% [0.05% TFA/CH$_3$CN]. Preparative RP-HPLC purification is performed on a custom HP1100 automated purification system with collection triggered by mass detection or using a Gilson Inc. preparative UV-based system using a Phenomenex Luna C18 column (50×30 mm I.D., 5 µm) with an acetonitrile (unmodified)-water (0.1% TFA) custom gradient.

For LC-MS-characterization of the compounds of the present invention, the following methods are used.

Method 1:

The HPLC measurement is performed using an Agilent 1200 system comprising a binary pump with degasser, an autosampler, a column oven, a diode-array detector (DAD) and a column as specified in the respective methods below. Flow from the column is split to a SQ mass spectrometer and Polymer Labs ELSD. The MS detector is configured with an ES ionization source. Nitrogen is used as the nebulizer gas. The source temperature is maintained at 350° C. Data acquisition is performed with Agilent Chemstation software. Reversed phase HPLC is carried out on a Kinetex C18 column (2.6 µm, 2.1×30 µm) from Phenomenex, with a flow rate of 1.5 mL/min, at 45° C. The gradient conditions used are: 93% A (water+0.1% TFA), 7% B (acetonitrile), to 95% B in 1.1 minutes, returning to initial conditions at 1.11 minutes. Injection volume 1 µL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

Method 2:

Using method 1 instrument and column conditions. The gradient conditions used are: 93% A (water+0.1% TFA), 7% B (acetonitrile), to 95% B in 2.0 minutes, returning to initial conditions at 2.11 minutes. Injection volume 1 µL. Low-resolution mass spectra (single quadruple MSD detector) are acquired in electrospray mode by scanning from 100 to 700 in 0.25 seconds, step size of 0.1 and peak width of 0.03 minutes. The capillary needle voltage is 3.0 kV and the fragmentor voltage is 100V.

$^1$H NMR spectra are recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which is used as internal standard. Coupling constants (J-values) are reported in Hz.

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

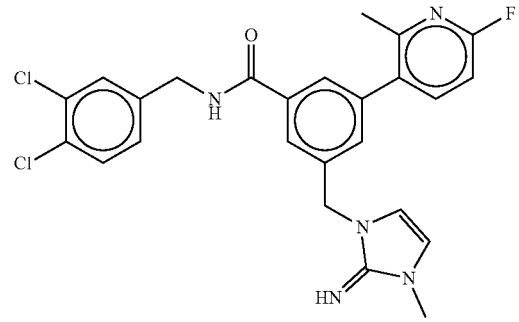

Example 1

N-(3,4-Dichlorobenzyl)-3-(6-fluoro-2-methylpyridin-3-yl)-5-((2-imino-3-methyl-2,3-dihydro-1H-imidazol-1-yl)methyl)benzamide Step A. Preparation of methyl 3-(6-fluoro-2-methylpyridin-3-yl)-5-(hydroxymethyl)benzoate Ar was bubbled into a mixture of methyl 3-bromo-5-(hydroxymethyl)benzoate (7.50 g, 31 mmol) and K$_2$CO$_3$ (10.7 g, 72.5 mmol) in 1,4 dioxane/water (4:1) (665 mL) for 5 min. Tetrakis(triphenylphospine)palladium (0) (2.68 g, 2.32 mmol) and (6-fluoro-2-methylpyridin-3-yl)boronic acid (6.4 g, 41.5 mmol) were added and the reaction was stirred for 6 h at 80° C. The reaction mixture was cooled to ambient temperature and concentrated under reduced pressure. The residue was dissolved in DCM, washed with water, dried with MgSO$_4$, filtered and concentrated under reduced pressure. The residue was purified by flash chromatography (Combi-flash Rf Hex/EtOAc=0-100% gradient) to afford the title compound (7.19 g, 83%). $^1$H NMR (400 MHz, d6 DMSO) δ 8.0 (s, 1H), 7.8 (t, 1H, J=7.9 Hz), 7.8 (s, 1H), 7.6 (s, 1H), 5.4 (broad S, 1H), 4.6 (s, 2H), 3.9 (s, 2H), 2.8 (s, 3H), 2.3 (s, 3H).

Step B. Preparation of 3-(6-fluoro-2-methylpyridin-3-yl)-5-(hydroxymethyl)benzoic acid A solution of methyl 3-(6-fluoro-2-methylpyridin-3-yl)-5-(hydroxymethyl)benzoate (7.19 g, 26.00 mmol) in THF (200 mL)/Methanol (50 mL)/water (50 ml) was treated with LiOH (1.13 g, 54.00 mmol) then stirred for 6 h at ambient temperature. The solvent was removed under reduced pressure and diluted with water. The aqueous solution was acidified with HCl aq. (1N) to pH=2. The resulting solid was filtered, washed with water and dried in a vacuum oven to afford the title compound (6.20 g, 91%)$^1$H NMR (400 MHz, D$_6$-DMSO) δ 7.98 (s, 1H) 7.9 (t, 1H, J=8.04 Hz), 7.8 (s, 1H), 7.6 (m, 1H), 7.56 (s, 1H), 7.1 (m, 1H) 5.40 (broad s, 1H), 4.62 (s, 2H), 2.30 (s, 3H), 7.1 (m, 1H), 5.4 (broad s, 1H), 4.6 (s, 2H), 2.4 (s, 3H).

Step C. Preparation of N-(3,4-dichlorobenzyl)-3-(6-fluoro-2-methylpyridin-3-yl)-5-(hydroxymethyl) benzamide A solution of 3-(6-fluoro-2-methylpyridin-3-yl)-5-(hydroxymethyl)benzoic acid (4.0 g, 15.3 mmol) and TEA (6.3 mL, 45.9 mmol) in DMF (70 mL) was cooled on an ice bath. EDC (3.0 g, 16.1 mmol) and HOBT (2.46 g, 16.1 mmol) were added to the reaction mixture and stirred for 5 min. (3,4-dichlorophenyl)methanamine (0.78 g, 4.2 mmol) was added and the reaction mixture was stirred for 18 h at ambient temperature. The DMF was removed under reduced pressure. The crude was dissolved in ethyl acetate, extracted with water, dried over MgSO4, filtered, and the solvent removed under reduced pressure. The residue was purified by flash chromatography (Combi-flash Rf, Hex/EtOAc=0-100% gradient) to afford the title compound (3.87 g, 60%). $^1$H NMR (400 MHz, D$_6$-DMSO) δ 9.1 (t, 1H, J=5.7 Hz), 7.9 (s, 1H), 7.8 (t, 1H, J=8.2 Hz), 7.7 (s, 1H), 7.6 (m, 2H), 7.5 (s, 1H), 7.3 (m, 1H), 7.1 (m, 1H), 5.3 (t, 1H, J=5.5 Hz), 4.6 (d, 2H, J=5.6), 4.4 (d, 2H, J=5.9 Hz), 2.3 (s, 3H).

Step D. Preparation of 3-(bromomethyl)-N-(3,4-dichlorobenzyl)-5-(6-fluoro-2-methylpyridin-3-yl) benzamide A solution of N-(3,4-dichlorobenzyl)-3-(6-fluoro-2-methylpyridin-3-yl)-5-(hydroxymethyl)benzamide (3.87 g, 9.25 mmol) and DCM (100 mL)/toluene (200 mL) was cooled on an ice bath. 1N Phosphorus tribromide (9.70 mL, 9.70 mmol) was added dropwise, and the reaction mixture was stirred for 18 h at ambient temperature. The reaction was quenched with water and sat. aq. NaHCO$_3$ to adjust pH=8. The organic layer was separated, washed with water, dried over MgSO$_4$, filtered, and concentrated under reduced pressure. The residue was purified by flash chromatography (Combi-flash Rf, Hex/EtOAc=0-60% gradient) to afford the title compound (2.81 g, 63%) $^1$H NMR (400 MHz, D$_6$-DMSO) δ 9.2 (t, 1H, J=5.5), 8.0 (s, 1H), 7.9 (m, 1H), 7.8 (s, 1H), 7.7 (s, 1H), 7.6 (m, 2H), 7.3 (m, 1H), 7.1 (m, 1H), 4.8 (s, 2H), 4.5 (d, 2H, J=5.5 Hz), 2.3 (s, 3H).

Step E. Example 1

A solution of 3-(bromomethyl)-N-(3,4-dichlorobenzyl)-5-(6-fluoro-2-methylpyridin-3-yl)benzamide (2.81 g, 5.80 mmol), DIPEA (2.55 mL, 14.5 mmol), and 1-methyl-1H-imidazol-2-amine (1.13 g, 11.60 mmol) in MeCN (150 mL) was stirred for 18 h at 80° C. The reaction mixture was cooled to ambient temperature and concentrated under reduced pressure. The crude material was purified by reverse phase HPLC (Phenomenex Gemini C18, H$_2$O/CH$_3$CN gradient to 10-80% MeCN 0.1% TFA). The desired fractions were combined and concentrated to dryness. The residue was dissolve in EtOAc, washed with sat. aq. NaHCO$_3$, dried over MgSO$_4$, and concentrated to afford the title compound (1.79 g, 62%). $^1$H NMR (400 MHz, D$_6$-DMSO) δ 9.22 (t, 1H, J=5.8 Hz), 7.90 (m, 4H), 7.57 (m, 2H), 7.32 (d, 1H, J=10.0 Hz), 7.14 (m, 2H), 7.07 (d, 1H, J=2.4 Hz), 5.22 (s, 2H), 4.48 (d, 2H, J=6.0 Hz), 3.47 (s, 3H), 2.39 (s, 3H); LCMS: 98% 254 nm R-r=0.99 min, MS (ES) 498 (M+H).

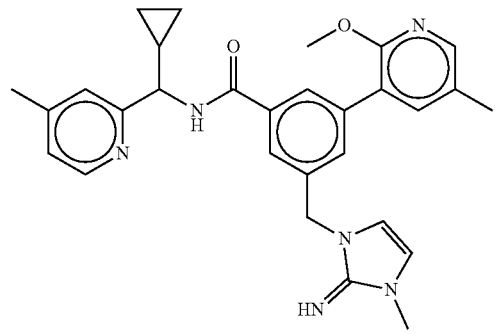

Example 2

N-(Cyclopropyl(4-methylpyridin-2-yl)methyl)-3-((2-imino-3-methyl-2,3-dihydro-1-imidazol-1-yl) methyl)-5-(2-methoxy-5-methylpyridin-3-yl)benzamide Step A. Preparation of methyl 3-(hydroxymethyl)-5-(2-methoxy-5-methylpyridin-3-yl)benzoate The title compound (0.88 g, 52%) was prepared following the procedure described in Example 1, Step A using methyl 3-bromo-5-(hydroxymethyl)benzoate (1.43 g, 5.86 mmol) and (2-methoxy-5-methylpyridin-3-yl)boronic acid (1.47 g, 8.80 mmol).

Step B. Preparation of 3-(hydroxymethyl)-5-(2-methoxy-5-methylpyridin-3-yl)benzoic Acid The title compound (0.76 g, 91%) was prepared following the procedure described in Example 1, Step B using methyl 3-(hydroxymethyl)-5-(2-methoxy-5-methylpyridin-3-yl) benzoate (0.88 g, 3.06 mmol).

Step C. Preparation of 3-(bromomethyl)-N-(cyclopropyl(4-methylpyridin-2-yl)methyl)-5-(2-methoxy-5-methylpyridin-3-yl)benzamide A solution of 3-(hydroxymethyl)-5-(2-methoxy-5-methylpyridin-3-yl)benzoic acid (0.20 g, 0.73 mmol) in THF (10 mL) was treated with DIPEA (0.57 mL, 3.28 mmol) and cooled in an ice bath. 2-chloro-1,3-dimethylimidazolinium chloride (0.14, 0.80 mmol) was added, and the resulting mixture was stirred for 60 min then treated with cyclopropyl (4-methylpyridin-2-yl)methanamine 2 HCl (0.19 g, 0.80 mmol). The reaction mixture was stirred for additional 18 h and concentrated in vacuo. The crude N-(cyclopropyl(4-methylpyridin-2-yl)methyl)-3-(hydroxymethyl)-5-(2-methoxy-5-methylpyridin-3-yl)benzamide (0.15 g, 0.36 mmol) was dissolved in THF (10 mL) and cooled in an ice bath. Triphenyl phosphine (0.19 g, 0.72 mmol) and NBS (0.13 g, 0.72 mmol) were added and the reaction mixture was stirred for additional 3 h then concentrated in vacuo. The residue was purified by flash chromatography (Combi-flash Rf, DCM/MeOH=0-5% gradient) to afford the title compound (0.11 g, 63%).

Step D. Example 2

The title compound (8 mg, 10%) was prepared following the procedure described in Example 1, Step E using 3-(bromomethyl)-N-(cyclopropyl(4-methylpyridin-2-yl)methyl)-5-(2-methoxy-5-methylpyridin-3-yl)benzamide (0.05 g, 0.10 mmol) and 1-methyl-1H-imidazol-2-amine (0.02 g, 0.20 mmol). LCMS: 98% 254 nm $R_T$=0.60 min, MS (ES) 497 (M+H).

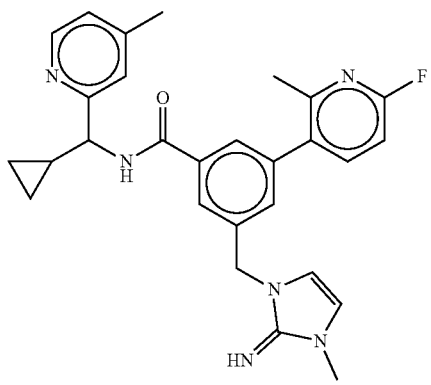

Example 3

N-(Cyclopropyl(4-methylpyridin-2-yl)methyl)-3-(6-fluoro-2-methylpyridin-3-yl)-5-((2-imino-3-methyl-2,3-dihydro-1H-imidazol-1-yl)methyl)benzamide Step A. Preparation of 3-(bromomethyl)-N-(cyclopropyl(4-ethylpyridin-2-yl)methyl)-5-(6-fluoro-2-methylpyridin-3-yl)benzamide The title compound (0.20 g, 67%) was prepared following the procedure described in Example 2, Step C using 3-(6-fluoro-2-methylpyridin-3-yl)-5-(hydroxymethyl)benzoic acid (0.30 g, 1.14 mmol) and cyclopropyl(4-methylpyridin-2-yl)methanamine (0.19 g, 0.80 mmol).

Step B. Example 3

The title compound (0.05 g, 94%) was prepared following the procedure described in Example 1, Step E using 3-(bromomethyl)-N-(cyclopropyl(4-methylpyridin-2-yl)methyl)-5-(6-fluoro-2-methylpyridin-3-yl)benzamide (0.05 g, 0.10 mmol) and 1-methyl-1H-imidazol-2-amine (0.02 g, 0.20 mmol). LCMS: 98% 254 nm $R_T$=0.69 min, MS (ES) 485 (M+H).

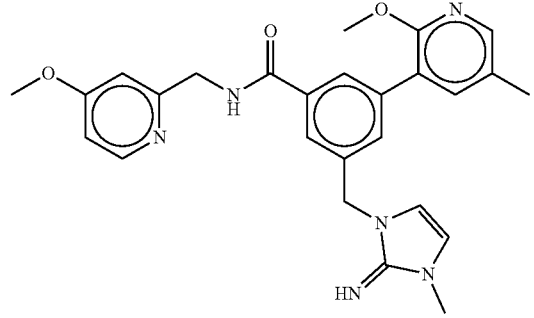

Example 4

3-((2-imino-3-methyl-2,3-dihydro-1H-imidazol-1-yl)methyl)-5-(2-m ethoxy-5-methylpyridin-3-yl)-N-((4-methoxypyridin-2-yl)methyl)benzamide Step A. Preparation of 3-(bromomethyl)-5-(2-m ethoxy-5-methylpyridin-3-yl)-N-((4-methoxypyridin-2-yl)methyl)benzamide The title compound (0.05 g, 15%) was prepared following the procedure described in Example 2, Step C using 3-(hydroxymethyl)-5-(2-methoxy-5-methylpyridin-3-yl)benzoic acid (0.30 g, 1.10 mmol) and (4-methoxypyridin-2-yl)methanamine (0.19 g, 0.80 mmol).

Step B. Example 4

The title compound (0.003 g, 50%) was prepared following the procedure described in Example 1, Step E using 3-(bromomethyl)-5-(2-methoxy-5-methylpyridin-3-yl)-N-((4-methoxypyridin-2-yl)methyl)benzamide (0.05 g, 0.11 mmol) and 1-methyl-1H-imidazol-2-amine (0.02 g, 0.24 mmol). LCMS: 98% co 254 nm $R_T$=0.68 min, MS (ES) 473 (M+H).

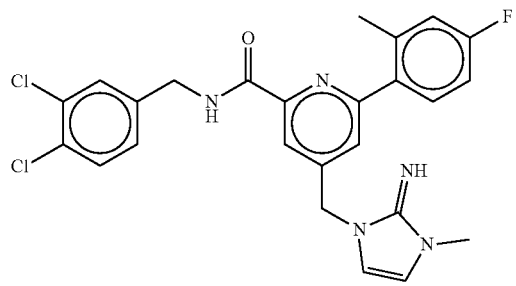

Example 5

N-(3,4-dichlorobenzyl)-6-(4-fluoro-2-methylphenyl)-4-((2-imino-3-methyl-2,3-dihydro-1H-imidazol-1-yl)methyl)picolinamide Step A. Preparation of methyl 4-(bromomethyl)-6-chloropicolinate A solution of methyl 6-chloro-4-methylpicolinate (6.00 g, 32.40 mmol) in $CCl_4$ (350 mL) and chlorobenzene (100 mL)

was refluxed through a Dean Stark trap to remove trace amount of water. The solution was cooled to ambient temperature and treated with N-Bromosuccinimide (NBS) (8.60 g, 48.6 mmol) and 2,2'azobis(2-methylpropionitrile (AIBN, 0.53 g, 3.24 mmol). The solution was heated to reflux for 18 h. An additional amount of NBS (8.00 g, 44.94 mmol) and AIBN (0.50 g, 3.0 mmol) was added and refluxing continued for an additional 6 h. The mixture was cooled to ambient temperature and concentrated under reduced pressure to approximately 25% of the original volume. The mixture was filtered and the filtrate was concentrated under reduced pressure. The residue was purified by flash chromatography (Combi-flash Rf, Hex/EtOAc=0-100% gradient) to afford the title compound (1.4 g 16%): $^1$H NMR (400 MHz, d$_6$ DMSO) δ 8.07 (s, 1H), 7.82 (s, 1H), 4.71 (s, 2H), 3.83 (s, 3H).

Step B. Preparation of 6-chloro-4-(hydroxymethyl)picolinic Acid

A solution of methyl 4-(bromomethyl)-6-chloropicolinate (1.40 g, 5.40 mmol) and NaOAc (0.87 g, 10.0 mmol) in MeOH (200 mL) was refluxed for 48 h. The reaction mixture was cooled to ambient temperature, concentrated under reduced pressure, and dissolved in EtOAc. The solution was washed with water, dried over MgSO$_4$, filtered, and the solvent removed under reduced pressure. The residue was dissolved in THF (40 mL)/MeOH (10 mL)/water (5 mL) and treated with 2 M aq. LiOH (6.80 mL, 13.5 mmol). The reaction mixture was stirred for 18 h at ambient temperature then additional 2 h at 50° C. The reaction mixture was cooled and concentrated under reduced pressure. The residue was dissolved in water and acidified to pH=1 with 1N aq. HCl. The resulting sold was filtered, washed with water, and dried to afford the title compound. (1.05 g, quant.). $^1$H NMR (400 MHz, d$_6$ DMSO) δ 7.91 (s, 1H), 7.47 (s, 1H), 4.59 (s, 2H).

Step C. Preparation of 6-chloro-N-(3,4-dichlorobenzyl)-4-(hydroxymethyl)picolinamide The title compound (1.71 g, 65%) was prepared following the procedure described in Example 1, Step C using 6-chloro-4-(hydroxymethyl)picolinic acid (1.43 g, 7.64 mmol) and (3,4-dichlorophenyl)methanamine (1.47 g, 8.4 mmol). $^1$H NMR (400 MHz, D$_6$-DMSO) δ 9.34 (t, 1H, J=6.2 Hz), 8.00 (s, 1H) 7.60 (m, 3H), 7.32 (d, 1H, J=9.7 Hz), 5.65 (t, 1H, J=5.8 Hz), 4.64 (d, 2H, J=5.4 Hz), 4.47 (d, 1H, J=6.5 Hz), 2.4 (s, 3H).

Step D. Preparation of N-(3,4-dichlorobenzyl)-6-(4-fluoro-2-methylphenyl)-4-(hydroxymethyl)picolinamide The title compound (0.23 g, 91%) was prepared following the procedure described in Example 1, Step A using 6-chloro-N-(3,4-dichlorobenzyl)-4-(hydroxymethyl)picolinamide (0.20 g, 0.58 mmol) and (4-fluoro-2-methylphenyl) boronic acid (0.13 g, 0.87 mmol). $^1$H NMR (400 MHz, CDCl3) δ7.84 (s, 1H), 7.70 (m, 1H), 7.63 (m, 1H), 7.50 (m, 1H), 7.46 (d, 1H, J=1.9 Hz), 7.42, (m, 2H), 7.21 (d, 1H, J=9.7 Hz), 6.85 (m, 1H), 6.75 (t, 1H, J=5.5 Hz), 4.62 (d, 2H, J=6.1 Hz), 4.56 (s, 2H), 2.43 (s, 3H).

Step E. Preparation of 4-(bromomethyl)-N-(3,4-dichlorobenzyl)-6-(4-fluoro-2-methylphenyl)picolinamide The title compound (0.40 g, 58%) was prepared following the procedure described in Example 1, Step D using N-(3,4-dichlorobenzyl)-6-(4-fluoro-2-methylphenyl)-4-(hydroxymethyl)picolinamide (0.40 g, 1.43 mmol) and 1M PBr$_3$/DCM (1.48 mL, 1.48 mmol). $^1$H NMR (400 MHz, d$_6$ DMSO) δ 9.36 (t, 1H, J=6.5 Hz), 8.10 (d, 1H, J=1.4 Hz), 7.80 (d, 1H, J=1.4 Hz), 7.56 (m, 3H), 7.31 (d, 1H, J=8.3 Hz), 7.19 (m, 2H), 4.83 (s, 2H), 4.51 (d, 2H, J=6.2 Hz), 2.39 (s, 3H).

Step F. Example 5

The title compound (0.33 g 79%) was prepared following the procedure described in Example 1, Step E using 4-(bromomethyl)-N-(3,4-dichlorobenzyl)-6-(4-fluoro-2-methylphenyl)picolinamide (0.40 g, 0.83 mmol) and 1-methyl-1H-imidazol-2-amine (0.16 g, 1.60 mmol). $^1$H NMR (400 MHz, D$_6$-DMSO) δ 9.40 (t, 1H, J=6.4 Hz), 7.97 (bs, 2H), 7.88 (s, 1H), 7.57 (m, 3H), 7.3 (d, 1H, J=8.5 Hz), 7.22 (m, 2H), 7.13 (d, 1H, J=2.5 Hz), 5.31 (s, 2H), 4.48 (d, 2H, J=6.5 Hz), 3.49 (s, 3H), 2.38 (s, 3H); LCMS: 98% 254 nm R$_T$=1.03 min, MS (ES) 499 (M+H).

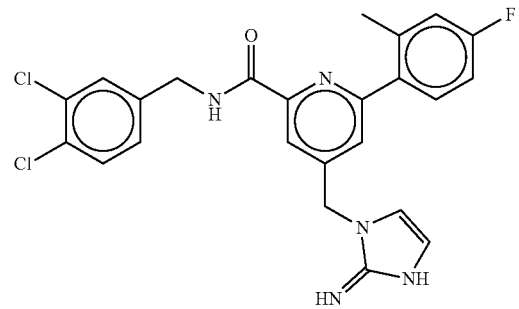

Example 6

N-(3,4-Dichlorobenzyl)-6-(4-fluoro-2-methylphenyl)-4-((2-imino-2,3-dihydro-1H-imidazol-1-yl)methyl)picolinamide To a solution of N-(3,4-dichlorobenzyl)-6-(4-fluoro-2-methylphenyl)-4-(hydroxymethyl)picolinamide (0.09 g, 0.22 mmol) and DIPEA (0.05 mL, 0.28 mmol) in DCM (6 mL) was added methanesulfonyl chloride (0.02 mL, 0.26 mmol) at 0° C. The reaction mixture was stirred for 2 h, diluted with DCM, washed with water, dried over MgSO$_4$, filtered and concentrated under reduced pressure. The residue was dissolved in MeCN (5 ml), treated with 1H-imidazol-2-amine (0.04 g, 0.44 mmol) and DIPEA (0.05 mL, 0.29 mmol). The solution was stirred for 18 h at 0° C., cooled and concentrated. The residue was purified by reverse phase HPLC (Phenomenex Gemini C18, H$_2$O/CH$_3$CN gradient from 30-90% CH$_3$CN, 0.1% TFA) to yield the title compound. (0.04 g, 37%). LC=98% 254 nm R$_T$=1.0, MS=485. LCMS: 98% 254 nm R$_T$=1.0 min, MS (ES) 485 (M+H).

207

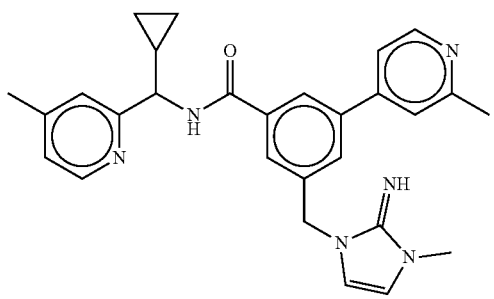

Example 7

N-(cyclopropyl(4-methylpyridin-2-yl)methyl)-3-((2-imino-3-ethyl-2,3-dihydro-1H-imidazol-1-yl)methyl)-5-(2-methylpyridin-4-yl)benzamide Step A. Preparation of 3-bromo-N-(cyclopropyl(4-methylpyridin-2-yl)methyl)-5-(hydroxymethyl)benzamide The title compound (0.21 g, 64%) was prepared following the procedure described in Example 2, Step C using 3-bromo-5-(hydroxymethyl)benzoic acid (0.20 g, 0.89 mmol), Et$_3$N (0.24 mL, 1.75 mmol), 2-chloro-1,3-dimethylimidazolinium chloride (0.16 g, 0.97 mmol), and cyclopropyl(4-methyl pyridin-2-yl)methanamine.2HCl (0.50 g, 2.10 mmol).

Step B. Preparation of N-(cyclopropyl(4-methylpyridin-2-yl)methyl)-3-(hydroxymethyl)-5-(2-methylpyridin-4-yl)benzamide The title compound (0.03 g, 5%) was prepared following the procedure described in Example 1, Step A using 3-bromo-N-(cyclopropyl(4-methylpyridin-2-yl)methyl)-5-(hydroxymethyl)benzamide (0.05 g, 0.14 mmol) and (2-methylpyridin-4-yl)boronic acid (0.03 g, 0.21 mmol).

Step C. Preparation of 3-(bromomethyl)-N-(cyclopropyl(4-methylpyridin-2-yl)methyl)-5-(2-methylpyridin-4-yl)benzamide The title compound (0.015 g, 44%) was prepared following the procedure described in Example 1, Step D using N-(cyclopropyl(4-methylpyridin-2-yl)methyl)-3-(hydroxymethyl)-5-(2-methylpyridin-4-yl)benzamide (0.03 g, 0.08 mmol) and 1M PBr$_3$/DCM (0.01 mL, 0.11 mmol).

Step D. Example 7

The title compound (5 mg, 14%) was prepared following the procedure described in Example 1, Step E using 3-(bromomethyl)-N-(cyclopropyl(4-methylpyridin-2-yl)methyl)-5-(2-methylpyridin-4-yl)benzamide (0.03 g, 0.08 mmol) and 1-methyl-1H-imidazol-2-amine (0.02 g, 0.15 mmol). LCMS: 90% 254 nm R$_T$=0.80 min, MS (ES) 467 (M+H).

208

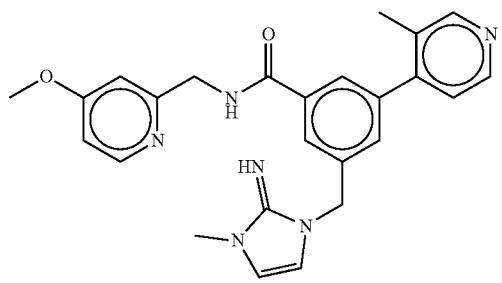

Example 8

3-((2-Imino-3-methyl-2,3-dihydro-1H-imidazol-1-yl)methyl)-N-((4-methoxypyridin-2-yl)methyl)-5-(3-methylpyridin-4-yl)benzamide Step A. Preparation of 3-bromo-5-(hydroxymethyl)-N-((4-methoxypyridin-2-yl)methyl)benzamide The title compound (0.33 g, 96%) was prepared following the procedure described in Example 2, Step C using 3-bromo-5-(hydroxymethyl)benzoic acid (0.20 g, 0.89 mmol), Et$_3$N (0.24 mL, 1.75 mmol), 2-chloro-1,3-dimethylimidazoliniumn chloride (0.16 g, 0.97 mmol), and (4-methoxypyridin-2-yl)methanamine (0.30 g, 2.10 mmol).

Step B. Preparation of 3-(hydroxymethyl)-N-((4-methoxypyridin-2-yl)methyl)-5-(3-methylpyridin-4-yl)benzamide The title compound (0.04 g, 50%) was prepared following the procedure described in Example 1, Step A using 3-bromo-5-(hydroxymethyl)-N-((4-methoxypyridin-2-yl)methyl)benzamide (0.08 g, 0.23 mmol) and (3-methylpyridin-4-yl)boronic acid (0.05 g, 0.35 mmol).

Step C. Preparation of 3-(bromomethyl)-N-((4-methoxypyridin-2-yl)methyl)-5-(3-methylpyridin-4-yl)benzamide The title compound (0.02 g, 45%) was prepared following the procedure described in Example 1, Step D using 3-(hydroxymethyl)-N-((4-methoxypyridin-2-yl)methyl)-5-(3-methylpyridin-4-yl)benzamide (0.04 g 0.12 mmol) and 1M PBr$_3$/DCM (0.01 mL, 0.11 mmol).

Step D. Example 8

The title compound (10 mg, 21%) was prepared following the procedure described in Example 1, Step E using 3-(bromomethyl)-N-((4-methoxypyridin-2-yl)methyl)-5-(3-methylpyridin-4-yl)benzamide (0.03 g, 0.07 mmol) and 1-methyl-1H-imidazol-2-amine (0.02 g, 0.15 mmol). LCMS: 98% 254 nm R$_T$=0.10 min, MS (ES) 443 (M+H).

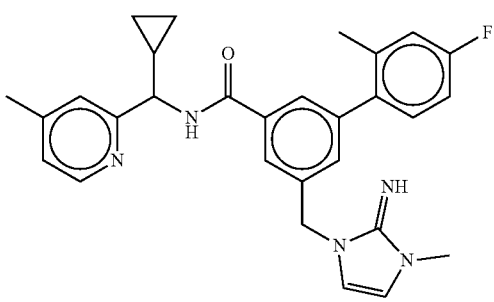

Example 9

N-(Cyclopropyl(4-methylpyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide Step A. Preparation of N-(cyclopropyl(4-methylpyridin-2-yl)methyl)-4'-fluoro-5-(hydroxymethyl)-2'-methyl-[1,1'-biphenyl]-3-carboxamide The title compound (0.05 g, 81%) was prepared following the procedure described in Example 1, Step A using 3-bromo-N-(cyclopropyl(4-methylpyridin-2-yl)methyl)-5-(hydroxymethyl)benzamide (0.05 g, 0.14 mmol) and (4-fluoro-2-methylphenyl)boronic acid (0.03 g, 0.21 mmol).

Step B. Preparation of 5-(bromomethyl)-N-(cyclopropyl(4-methylpyridin-2-yl)methyl)-4'-fluoro-2'-methyl-[1,1'-biphenyl]-3-carboxamide The title compound (0.06 g, quant.) was prepared following the procedure described in Example 1, Step D using N-(cyclopropyl(4-methylpyridin-2-yl)methyl)-4'-fluoro-5-(hydroxymethyl)-2'-methyl-[1,1'-biphenyl]-3-carboxamide (0.05 g, 0.12%) and 1M PBr$_3$/DCM (0.01 mL, 0.11 mmol).

Step C. Example 9

The title compound (2 mg, 13%) was prepared following the procedure described in Example 1, Step E using 5-(bromomethyl)-N-(cyclopropyl(4-methylpyridin-2-yl)methyl)-4'-fluoro-2'-methyl-[1,1'-biphenyl]-3-carboxamide (0.06 g, 0.13 mmol) and 1-methyl-1H-imidazol-2-amine (0.03 g, 0.26 mmol). LCMS: 98% 254 nm R$_T$=1.2 min, MS (ES) 484 (M+H).

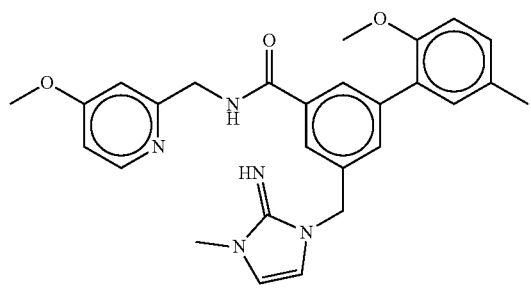

Example 10

5-((2-Imino-3-methyl-2,3-dihydro-1H-imidazol-1-yl)methyl)-2'-m ethoxy-N-((4-methoxypyridin-2-yl)methyl)-5'-methyl-[1,1'-biphenyl]-3-carboxamide Step A. Preparation of 5-(hydroxymethyl)-2'-methoxy-N-((4-methoxypyridin-2-yl)methyl)-5'-methyl-[1,1'-biphenyl]-3-carboxamide The title compound (0.06 g, 64%) was prepared following the procedure described in Example 1, Step A using 3-bromo-5-(hydroxymethyl)-N-((4-methoxypyridin-2-yl)methyl)benzamide (0.08 g, 0.23 mmol) and (2-methoxy-5-methylphenyl)boronic acid (0.06 g, 0.35 mmol).

Step B. Preparation of 5-(bromomethyl)-2'-methoxy-N-((4-methoxypyridin-2-yl)methyl)-5'-methyl-[1,1'-biphenyl]-3-carboxamide The title compound (0.05 g, quant.) was prepared following the procedure described in Example 1, Step D using 5-(hydroxymethyl)-2'-methoxy-N-((4-methoxypyridin-2-yl)methyl)-5'-methyl-[1,1'-biphenyl]-3-carboxamide (0.06 g 0.15 mmol) and 1M PBr$_3$/DCM (0.015 mL, 0.15 mmol).

Step C. Example 10

The title compound (40 mg, 56%) was prepared following the procedure described in Example 1, Step E using 5-(bromomethyl)-2'-methoxy-N-((4-methoxypyridin-2-yl)methyl)-5'-methyl-[1,1'-biphenyl]-3-carboxamide (0.05 g, 0.11 mmol) and 1-methyl-1H-imidazol-2-amine (0.03 g, 0.15 mmol). LCMS: 98% 254 nm R$_T$=0.70 min, MS (ES) 472 (M+H).

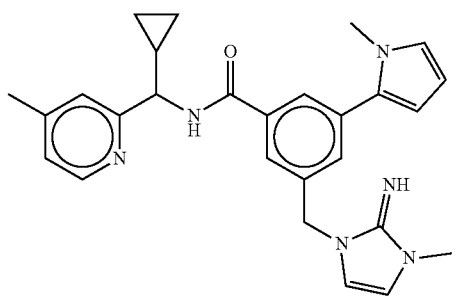

Example 11

N-(Cyclopropyl(4-methylpyridin-2-yl)methyl)-3-((2-imino-3-methyl-2,3-dihydro-1H-imidazol-1-yl)methyl)-5-(1-methyl-1H-pyrrol-2-yl)benzamide Step A. Preparation of N-(cyclopropyl(4-methylpyridin-2-yl)methyl)-3-(hydroxymethyl)-5-(1-methyl-1H-pyrrol-2-yl)benzamide Ar was bubbled into a mixture of 3-bromo-N-(cyclopropyl(4-methylpyridin-2-yl)methyl)-5-(hydroxymethyl)benzamide (0.11 g, 0.29 mmol), di-isopropyl amine (0.11 mL, 0.73 mmol), and 1-methyl-2-(4,4,5,5-tetramethyl-1,3,2-dioxaborolan-2-yl)-1H-pyrrole (0.09 g, 0.44 mmol) in DMF/water (4:1)(1 mL) for 5 min. Triphenylphosphine-3,3',3''-trisulfonic acid trisodium salt (0.05 g, 0.08 mmol) and Pd(OAc)$_2$ (0.01 g, 0.05 mmol) was added, and the reaction mixture was stirred for 6 h at 80° C. The reaction was cooled to ambient temperature and concentrated under reduced pressure. The residue was dissolved in DCM, washed with water, dried over MgSO$_4$, filtered and concentrated under reduced pressure. The residue was purified by flash chromatography (Combi-flash Rf, Hex/EtOAc=0-100% gradient) to afford the title compound (0.07 g, 64%).

Step B. Preparation of 3-((cyclopropyl(4-ethylpyridin-2-yl)ethylmethyl)carbamoyl)-5-(1-methyl-1H-pyrrol-2-yl)benzyl methanesulfonate A solution of N-(cyclopropyl(4-methylpyridin-2-yl)methyl)-3-(hydroxymethyl)-5-(1-methyl-1H-pyrrol-2-yl)benzamide (0.07 g, 0.19 mmol) and Et$_3$N (0.053 mL, 0.37 mmol) in DCM (5 mL) was cooled in an ice bath then methanesulfonyl chloride (0.015 mL, 0.22 mmol) was added. The reaction mixture was stirred for 2 h, diluted with DCM, washed with water, dried over MgSO$_4$, filtered and concentrated under reduced pressure to afforded the crude title compound. It was used in the next step without further purification.

Step C. Example 11

The title compound (40 mg, 24%) was prepared following the procedure described in Example 1, Step E using 3-((cyclopropyl(4-methylpyridin-2-yl)methyl)carbamoyl)-5-(1-methyl-1H-pyrrol-2-yl)benzyl methanesulfonate, 1-methyl-1H-imidazol-2-amine (0.06 g, 0.60 mmol) and TEA (0.08 mL, 0.60 mmol). LCMS: 98% 254 nm R$_T$=0.78 min, MS (ES) 455 (M+H).

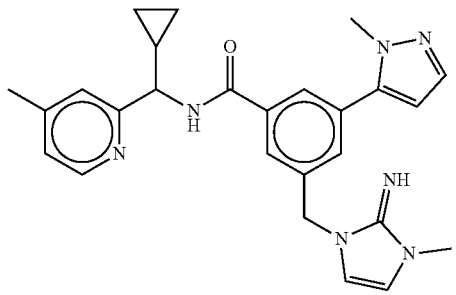

Example 12

N-(Cyclopropyl(4-methylpyridin-2-yl)methyl)-3-((2-imino-3-methyl-2,3-dihydro-1H-imidazol-1-yl)methyl)-5-(1-methyl-1H-pyrazol-5-yl)benzamide Step A. Preparation of N-(cyclopropyl(4-methylpyridin-2-yl)methyl)-3-(hydroxymethyl)-5-(1-methyl-1H-pyrazol-5-yl)benzamide The title compound (0.07 g, 63%) was prepared following the procedure described in Example 11 Step A using 3-bromo-N-(cyclopropyl(4-methylpyridin-2-yl)methyl)-5-(hydroxymethyl)benzamide (0.11 g, 0.29 mmol) and (1-methyl-1H-pyrazol-5-yl)boronic acid (1.5 eq.).

Step B. Preparation of 3-((cyclopropyl(4-methylpyridin-2-yl)methyl)carbamoyl)-5-(1-methyl-1H-pyrazol-5-yl)benzyl methanesulfonate The title compound was prepared following the procedure described in Example 11 Step B using N-(cyclopropyl(4-methylpyridin-2-yl)methyl)-3-(hydroxymethyl)-5-(1-methyl-1H-pyrazol-5-yl)benzamide (0.07 g, 0.18 mmol) and methanesulfonyl chloride (0.015 mL, 0.22 mmol).

Step C. Example 12

The title compound (50 mg, 62%) was prepared following the procedure described in Example 1, Step E using 3-((cyclopropyl(4-methylpyridin-2-yl)methyl)carbamoyl)-5-(1-methyl-1H-pyrazol-5-yl)benzyl methanesulfonate, 1-methyl-1H-imidazol-2-amine (0.06 g, 0.60 mmol) and TEA (0.08 mL, 0.60 mmol). LCMS: 98% 254 nm R$_T$=0.16 min, MS (ES) 456 (M+H).

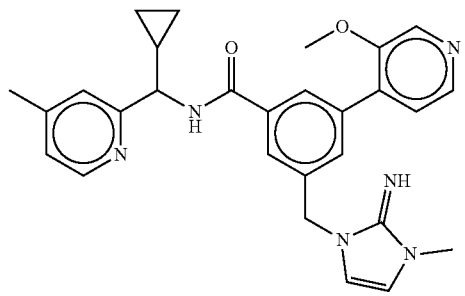

Example 13

N-(Cyclopropyl(4-methylpyridin-2-yl)methyl)-3-((2-imino-3-methyl-2,3-dihydro-1H-imidazol-1-yl)methyl)-5-(3-methoxypyridin-4-yl)benzamide Step A. Preparation of N-(cyclopropyl(4-methylpyridin-2-yl)methyl)-3-(hydroxymethyl)-5-(3-methoxypyridin-4-yl)benzamide The title compound (0.07 g, 55%) was prepared following the procedure described in Example 11 Step A using 3-bromo-N-(cyclopropyl(4-methylpyridin-2-yl)methyl)-5-(hydroxymethyl)benzamide (0.11 g, 0.29 mmol) and (3-methoxypyridin-4-yl)boronic acid (0.07 g, 0.44 mmol).

Step B. Preparation of 3-((cyclopropyl(4-methylpyridin-2-yl)methyl)carbamoyl)-5-(3-methoxypyridin-4-yl)benzyl methanesulfonate The title compound was prepared following the procedure described in Example 11 Step B using N-(cyclopropyl(4-methylpyridin-2-yl)methyl)-3-(hydroxymethyl)-5-(3-methoxypyridin-4-yl)benzamide (0.07 g, 0.18 mmol) and methanesulfonyl chloride (0.019 mL, 0.19 mmol).

Step C. Example 13

The title compound (10 mg, 7%) was prepared following the procedure described in Example 1, Step E using 3-((cyclopropyl(4-methylpyridin-2-yl)methyl)carbamoyl)-5-(3-methoxypyridin-4-yl)benzyl methanesulfonate, 1-methyl-1H-imidazol-2-amine (0.06 g, 0.60 mmol) and TEA (0.08 mL, 0.60 mmol). LCMS: 98% 254 nm R$_T$=0.13 min, MS (ES) 493 (M+H).

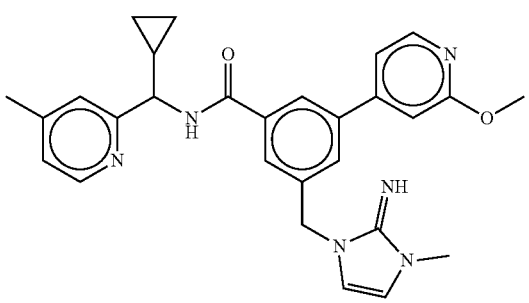

Example 14

N-(Cyclopropyl(4-methylpyridin-2-yl)methyl)-3-((2-imino-3-methyl-2,3-dihydro-1H-imidazol-1-yl)ethyl-methyl)-5-(2-methoxypyridin-4-yl)benzamide Step A. Preparation of N-(cyclopropyl(4-methyl-pyridin-2-yl)methyl)-3-(hydroxymethyl)-5-(2-methoxypyridin-4-yl)benzamide The title compound (0.07 g, 61%) was prepared following the procedure described in Example 11 Step A using 3-bromo-N-(cyclopropyl(4-methylpyridin-2-yl)methyl)-5-(hydroxymethyl)benzamide (0.11 g, 0.29 mmol) and (2-methoxypyridin-4-yl)boronic acid (0.07 g, 0.44 mmol).

Step B. Preparation of 3-((cyclopropyl(4-methyl-pyridin-2-yl)methyl)carbamoyl)-5-(2-methoxypyridin-4-yl)benzyl methanesulfonate The title compound was prepared following the procedure described in Example 11 Step B using N-(cyclopropyl(4-methylpyridin-2-yl)methyl)-3-(hydroxymethyl)-5-(2-methoxypyridin-4-yl)benzamide (0.07 g, 0.18 mmol) and methanesulfonyl chloride (0.015 mL, 0.12 mmol).

Step C. Example 14

The title compound (10 mg, 7%) was prepared following the procedure described in Example 1, Step E using 3-((cyclopropyl(4-methylpyridin-2-yl)methyl)carbamoyl)-5-(2-methoxypyridin-4-yl)benzyl methanesulfonate, 1-methyl-1H-imidazol-2-amine (0.06 g, 0.60 mmol) and TEA (0.08 mL, 0.60 mmol). LCMS: 98% 254 nm $R_T$=0.80 min, MS (ES) 483 (M+H).

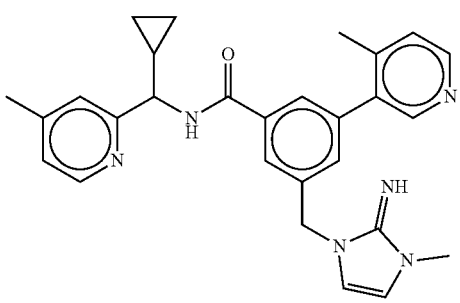

Example 15

N-(Cyclopropyl(4-methylpyridin-2-yl)methyl)-3-((2-imino-3-methyl-2,3-dihydro-1H-imidazol-1-yl)methyl)-5-(4-methylpyridin-3-yl)benzamide Step A. Preparation of N-(cyclopropyl(4-methyl-pyridin-2-yl)methyl)-3-(hydroxymethyl)-5-(4-methylpyridin-3-yl)benzamide The title compound (0.07 g, 61%) was prepared following the procedure described in Example 11 Step A using 3-bromo-N-(cyclopropyl(4-methylpyridin-2-yl)methyl)-5-(hydroxymethyl)benzamide (0.11 g, 0.29 mmol) and (4-methylpyridin-3-yl)boronic acid (0.06 g, 0.44 mmol).

Step B. Preparation of 3-((cyclopropyl(4-methyl-pyridin-2-yl)methyl)carbamoyl)-5-(4-methylpyridin-3-yl)benzyl methanesulfonate The title compound was prepared following the procedure described in Example 11 Step B using N-(cyclopropyl(4-methylpyridin-2-yl)methyl)-3-(hydroxymethyl)-5-(4-methylpyridin-3-yl)benzamide (0.07 g, 0.18 mmol) and methanesulfonyl chloride (0.015 mL, 0.21 mmol).

Step C. Example 15

The title compound (10 mg, 12%) was prepared following the procedure described in Example 1, Step E using 3-((cyclopropyl(4-methylpyridin-2-yl)methyl)carbamoyl)-5-(4-methylpyridin-3-yl)benzyl methanesulfonate, 1-methyl-1H-imidazol-2-amine (0.06 g, 0.60 mmol) and TEA (0.08 mL, 0.60 mmol). LCMS: 98% 254 nm $R_T$=0.13 min, MS (ES) 467 (M+H).

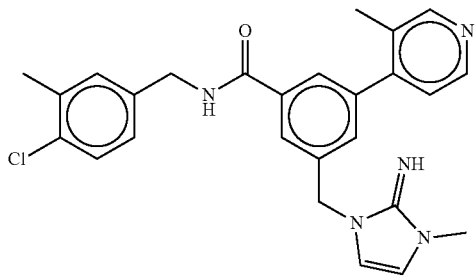

Example 16

N-(4-Chloro-3-methylbenzyl)-3-((2-imino-3-methyl-2,3-dihydro-1H-imidazol-1-yl)methyl)-5-(3-methyl-pyridin-4-yl)benzamide Step A. Preparation of 3-bromo-N-(4-chloro-3-methylbenzyl)-5-(hydroxymethyl)benzamide The title compound (0.79 g, 57%) was prepared following the procedure described in Example 1 Step C using 3-bromo-5-(hydroxymethyl)benzoic acid (0.86 g, 3.73 mmol) and (4-chloro-3-methylphenyl)methanamine (0.63 g, 4.10 mmol).

Step B. Preparation of N-(4-chloro-3-methylbenzyl)-3-(hydroxyethyl)-5-(3-methylpyridin-4-yl)benzamide The title compound (0.07 g, 580%) was prepared following the procedure described in Example 1 Step A using 3-bromo-N-(4-chloro-3-methylbenzyl)-5-(hydroxymethyl)benzamide (0.11 g, 0.31 mmol) and (3-methylpyridin-4-yl)boronic acid (0.06 g, 0.45 mmol),

Step C. Preparation of 3-((4-chloro-3-methylbenzyl)carbamoyl)-5-(3-methylpyridin-4-yl)benzyl methanesulfonate The title compound was prepared following the procedure described in Example 11 Step B using N-(4-chloro-3-methylbenzyl)-3-(hydroxymethyl)-5-(3-methylpyridin-4-yl)benzamide (0.07 g, 58%) and methanesulfonyl chloride (0.028 mL, 0.37 mmol).

Step D. Example 16

The title compound (8 mg, 26%) was prepared following the procedure described in Example 1, Step E using 3-((4-chloro-3-methylbenzyl)carbamoyl)-5-(3-methylpyridin-4-yl)benzyl methanesulfonate, 1-methyl-1H-imidazol-2-amine (0.06 g, 0.60 mmol) and DIPEA (0.11 mL, 0.60 mmol). LCMS: 98% 254 nm $R_T$=1.19 min, MS (ES) 460 (M+H).

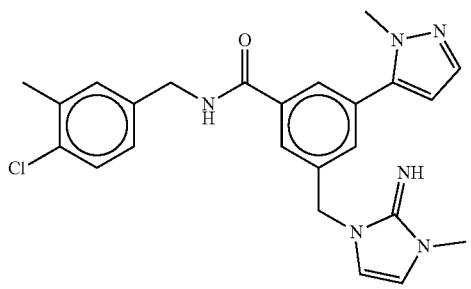

Example 17

N-(4-Chloro-3-methylbenzyl)-3-((2-imino-3-methyl-2,3-dihydro 1H-imidazol-1-yl)methyl)-5-(1-methyl-1H-pyrazol-5-yl)benzamide

Step A. Preparation of N-(4-chloro-3-methylbenzyl)-3-(hydroxymethyl)-5-(1-methyl-1H-pyrazol-5-yl)benzamide The title compound (0.07 g, 58%) was prepared following the procedure described in Example 1 Step A using 3-bromo-N-(4-chloro-3-methylbenzyl)-5-(hydroxymethyl)benzamide (0.1 g, 0.31 mmol) and (1-methyl-1H-pyrazol-5-yl)boronic acid (0.06 g, 0.45 mmol).

Step B. Preparation of 3-((4-chloro-3-methylbenzyl)carbamoyl)-5-(1-methyl-1H-pyrazol-5-yl)benzyl methanesulfonate The title compound was prepared following the procedure described in Example 11 Step B using N-(4-chloro-3-methylbenzyl)-3-(hydroxymethyl)-5-(1-methyl-1H-pyrazol-5-yl)benzamide (0.07 g, 58%) and methanesulfonyl chloride (0.028 mL, 0.37 mmol).

Step C. Example 17

The title compound (30 mg, 45%) was prepared following the procedure described in Example 1, Step E using 3-((4-chloro-3-methylbenzyl)carbamoyl)-5-(1-methyl-1H-pyrazol-5-yl)benzyl methanesulfonate, 1-methyl-1H-imidazol-2-amine (0.06 g, 0.60 mmol) and DIPEA (0.11 mL, 0.60 mmol). LCMS: 98% 254 nm $R_T$=0.87 min, MS (ES) 449 (M+H).

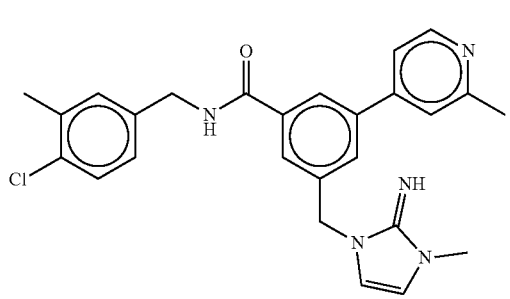

Example 18

N-(4-Chloro-3-methylbenzyl)-3-((2-imino-3-methyl-2,3-dihydro-1H-imidazol-1-yl)methyl)-5-(2-methylpyridin-4-yl)benzamide

Step A. Preparation of N-(4-chloro-3-methylbenzyl)-3-(hydroxymethyl)-5-(2-methylpyridin-4-yl)benzamide The title compound (0.08 g, 70%) was prepared following the procedure described in Example 1 Step A using 3-bromo-N-(4-chloro-3-methylbenzyl)-5-(hydroxymethyl)benzamide (0.11 g, 0.31 mmol) and (2-methylpyridin-4-yl)boronic acid (0.07 g, 0.45 mmol).

Step B. Preparation of 3-((4-chloro-3-methylbenzyl)carbamoyl)-5-(2-methylpyridin-4-yl)benzyl methanesulfonate The title compound was prepared following the procedure described in Example 11 Step B using N-(4-chloro-3-methylbenzyl)-3-(hydroxymethyl)-5-(2-methylpyridin-4-yl)benzamide (0.08 g, 70%) and methanesulfonyl chloride (0.028 mL, 0.37 mmol).

Step C. Example 18

The title compound (30 mg, 31%) was prepared following the procedure described in Example 1, Step E using 3-((4-chloro-3-methylbenzyl)carbamoyl)-5-(2-methylpyridin-4-yl)benzyl methanesulfonate, 1-methyl-1H-imidazol-2-amine (0.06 g, 0.60 mmol) and DIPEA (0.11 mL, 0.60 mmol). LCMS: 98% 254 nm $R_T$=1.22 min, MS (ES) 460 (M+H).

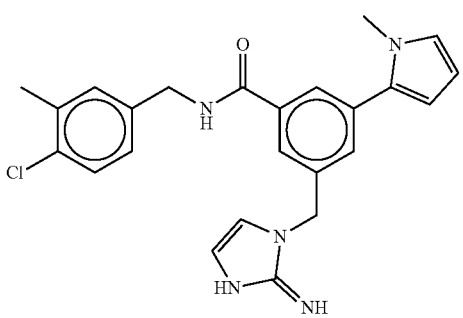

Example 19

N-(4-Chloro-3-methylbenzyl)-3-((2-imino-2,3-dihydro-1H-imidazol-1-yl)methyl)-5-(1-methyl-1H-pyrrol-2-yl)benzamide Step A. Preparation of N-(4-chloro-3-methylbenzyl)-3-(hydroxymethyl)-5-(1-methyl-1H-pyrrol-2-yl)benzamide The title compound (0.15 g, 98%) was prepared following the procedure described in Example 1 Step A using 3-bromo-N-(4-chloro-3-methylbenzyl)-5-(hydroxymethyl)benzamide (0.11 g, 0.31 mmol) and 1-methyl-2-(4,4,5,5-tetramethyl-1,3,2-dioxaborolan-2-yl)-1H-pyrrole (0.09 g, 0.45 mmol).

Step B. Preparation of 3-((4-chloro-3-methylbenzyl)carbamoyl)-5-(1-methyl-1H-pyrrol-2-yl)benzyl methanesulfonate The title compound was prepared following the procedure described in Example 11 Step B using N-(4-chloro-3-methylbenzyl)-3-(hydroxymethyl)-5-(1-methyl-1H-pyrrol-2-yl)benzamide (0.15 g, 98%) and methanesulfonyl chloride (0.028 mL, 0.37 mmol).

Step C. Example 19

The title compound (0.06 g, 91%) was prepared following the procedure described in Example 1, Step E using 3-((4-chloro-3-methylbenzyl)carbamoyl)-5-(1-methyl-1H-pyrrol-2-yl)benzyl methanesulfonate, 1-methyl-1H-imidazol-2-amine (0.06 g, 0.60 mmol) and DIPEA (0.11 mL, 0.60 mmol). LCMS: 98% 254 nm $R_T$=0.95 min, MS (ES) 434 (M+H).

Example 20

N-(4-Chloro-3-methylbenzyl)-3-((2-imino-3-methyl-2,3-dihydro-1H-imidazol-1-yl)methyl)-5-(3-methoxypyridin-4-yl)benzamide Step A. Preparation of N-(4-chloro-3-methylbenzyl)-3-(hydroxymethyl)-5-(3-methoxypyridin-4-yl)benzamide The title compound (0.06 g, 50%) was prepared following the procedure described in Example 1 Step A using 3-bromo-N-(4-chloro-3-methylbenzyl)-5-(hydroxymethyl)benzamide (0.11 g, 0.31 mmol) and (3-methoxypyridin-4-yl)boronic acid (0.07 g, 0.45 mmol).

Step B. Preparation of 3-((4-chloro-3-methylbenzyl)carbamoyl)-5-(3-methoxypyridin-4-yl)benzyl methanesulfonate The title compound was prepared following the procedure described in Example 11 Step B using N-(4-chloro-3-methylbenzyl)-3-(hydroxymethyl)-5-(3-methoxypyridin-4-yl)benzamide (0.06 g 0.15 mmol) and methanesulfonyl chloride (0.028 mL, 0.37 mmol).

Step C. Example 20

The title compound (0.011 g, 37%) was prepared following the procedure described in Example 1, Step E using 3-((4-chloro-3-methylbenzyl)carbamoyl)-5-(3-methoxypyridin-4-yl)benzyl methanesulfonate, 1-methyl-1H-imidazol-2-amine (0.06 g, 0.60 mmol) and DIPEA (0.11 mL, 0.60 mmol). LCMS: 98% 254 nm $R_T$=0.78 min, MS (ES) 476 (M+H).

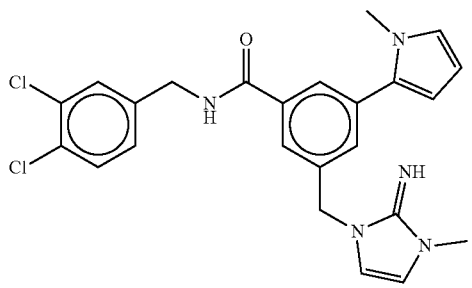

Example 21

N-(3,4-Dichlorobenzyl)-3-((2-imino-3-methyl-2,3-dihydro-1H-imidazol-1-yl)methyl)-5-(1-methyl-1H-pyrrol-2-yl)benzamide Step A. Preparation of 3-bromo-N-(3,4-dichlorobenzyl)-5-(hydroxymethyl)benzamide The title compound (1.05 g, 57%) was prepared following the procedure described in Example 1 Step C using 3-bromo-5-(hydroxymethyl)benzoic acid (1.00 g, 4.34 mmol) and (3,4-dichlorophenyl)methanamine (0.85 g, 4.77 mmol).

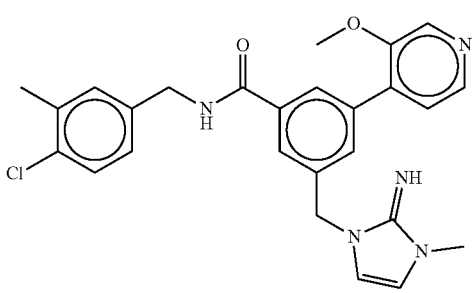

Step B. Preparation of N-(3,4-dichlorobenzyl)-3-(hydroxymethyl)-5-(1-methyl-1H-pyrrol-2-yl)benzamide The title compound (0.06 g, 51%) was prepared following the procedure described in Example 1 Step A using 3-bromo-N-(3,4-dichlorobenzyl)-5-(hydroxymethyl)benzamide (0.11 g, 0.29 mmol) and 1-methyl-2-(4,4,5,5-tetramethyl-1,3,2-dioxaborolan-2-yl)-1H-pyrrole (0.09 g, 0.44 mmol).

Step C. Preparation of 3-((3,4-dichlorobenzyl)carbamoyl)-5-(1-methyl-1H-pyrrol-2-yl)benzyl methanesulfonate The title compound was prepared following the procedure described in Example 11 Step B using N-(3,4-dichlorobenzyl)-3-(hydroxymethyl)-5-(1-methyl-1H-pyrrol-2-yl)benzamide and methanesulfonyl chloride.

Step D. Example 21

The title compound (6 mg, 4%) was prepared following the procedure described in Example 1, Step E using 3-((3,4-dichlorobenzyl)carbamoyl)-5-(1-methyl-1H-pyrrol-2-yl)benzyl methanesulfonate, 1-methyl-1H-imidazol-2-amine (0.05 g, 0.51 mmol) and DIPEA (0.09 mL, 0.51 mmol). LCMS: 98% 254 nm $R_T$=1.19 min, MS (ES) 469 (M+H).

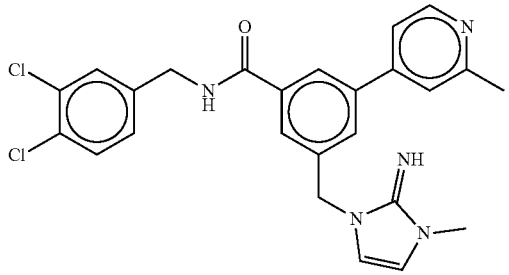

Example 22

N-(3,4-Dichlorobenzyl)-3-((2-imino-3-methyl-2,3-dihydro-1H-imidazol-1-yl)methyl)-5-(2-methylpyridin-4-yl)benzamide

Step A. Preparation of N-(3,4-dichlorobenzyl)-3-(hydroxymethyl)-5-(2-methylpyridin-4-yl)benzamide The title compound (0.04 g, 33%) was prepared following the procedure described in Example 1 Step A using 3-bromo-N-(3,4-dichlorobenzyl)-5-(hydroxymethyl)benzamide (0.11 g, 0.29 mmol) and (2-methylpyridin-4-yl)boronic acid (0.06 g, 0.44 mmol).

Step B. Preparation of 3-((3,4-dichlorobenzyl)carbamoyl)-5-(2-methylpyridin-4-yl)benzyl methanesulfonate The title compound was prepared following the procedure described in Example 11 Step B using N-(3,4-dichlorobenzyl)-3-(hydroxymethyl)-5-(2-methylpyridin-4-yl)benzamide (0.04 g, 0.10 mmol) and methanesulfonyl chloride (0.007 mL, 0.10 mmol),

Step C. Example 22

The title compound (0.016 g, 39%) was prepared following the procedure described in Example 1, Step E using 3-((3,4-dichlorobenzyl)carbamoyl)-5-(2-methylpyridin-4-yl)benzyl methanesulfonate, 1-methyl-1H-imidazol-2-amine (0.05 g, 0.51 mmol) and DIPEA (0.09 mL, 0.51 mmol). LCMS: 98% 254 nm $R_T$=1.2 min, MS (ES) 482 (M+2H).

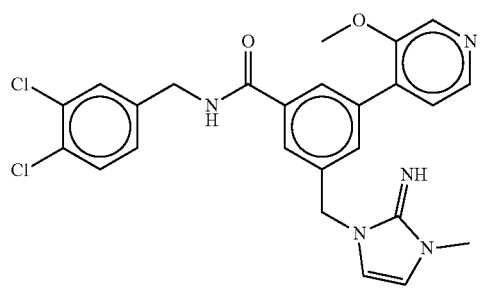

Example 23

N-(3,4-Dichlorobenzyl)-3-((2-imino-3-methyl-2,3-dihydro-1H-imidazol-1-yl)methyl)-5-(3-methoxypyridin-4-yl)benzamide

Step A. Preparation of N-(3,4-dichlorobenzyl)-3-(hydroxymethyl)-5-(3-methoxypyridin-4-yl)benzamide The title compound (0.08 g, 64%) was prepared following the procedure described in Example 1 Step A using 3-bromo-N-(3,4-dichlorobenzyl)-5-(hydroxymethyl)benzamide (0.11 g, 0.29 mmol) and (3-methoxypyridin-4-yl)boronic acid (0.07 g, 0.44 mmol).

Step B. Preparation of 3-((3,4-dichlorobenzyl)carbamoyl)-5-(3-methoxypyridin-4-yl)benzyl methanesulfonate The title compound was prepared following the procedure described in Example 11 Step B using N-(3,4-dichlorobenzyl)-3-(hydroxymethyl)-5-(3-methoxypyridin-4-yl)benzamide (0.08 g, 64%) and methanesulfonyl chloride (0.015 mL, 0.18 mmol).

Step C. Example 23

The title compound (0.017 g, 19%) was prepared following the procedure described in Example 1, Step E using 3-((3,4-dichlorobenzyl)carbamoyl)-5-(3-methoxypyridin-4-yl)benzyl methanesulfonate, 1-methyl-1H-imidazol-2-amine (0.05 g, 0.51 mmol) and DIPEA (0.09 mL, 0.51 mmol). LCMS: 98% 254 nm $R_T$=0.87 min, MS (ES) 497 (M+H).

221

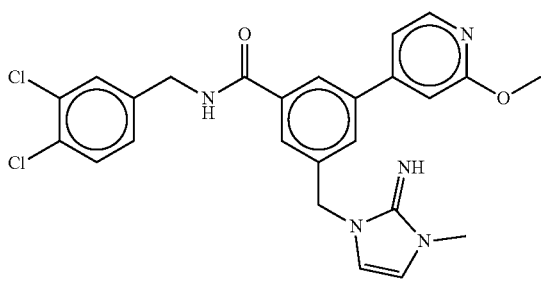

Example 24

N-(3,4-Dichlorobenzyl)-3-((2-imino-3-methyl-2,3-dihydro-1H-imidazol-1-yl) methyl)-5-(2-methoxypyridin-4-yl)benzamide Step A. Preparation of N-(3,4-dichlorobenzyl)-3-(hydroxymethyl)-5-(2-methoxypyridin-4-yl)benzamide The title compound (0.07 g, 47%) was prepared following the procedure described in Example 1 Step A using 3-bromo-N-(3,4-dichlorobenzyl)-5-(hydroxymethyl)benzamide (0.11 g, 0.29 mmol) and (2-methoxypyridin-4-yl) boronic acid (0.07 g, 0.44 mmol).

Step B. Preparation of 3-((3,4-dichlorobenzyl)carbamoyl)-5-(2-methoxypyridin-4-yl)benzyl methanesulfonate The title compound was prepared following the procedure described in Example 11 Step B using N-(3,4-dichlorobenzyl)-3-(hydroxymethyl)-5-(2-methoxypyridin-4-yl)benzamide (0.07 g 0.16 mmol) and methanesulfonyl chloride (0.015 mL, 0.19 mmol).

Step C. Example 24

The title compound (0.017 g, 120%) was prepared following the procedure described in Example 1, Step E using 3-((3,4-dichlorobenzyl)carbamoyl)-5-(2-methoxypyridin-4-yl)benzyl methanesulfonate, 1-methyl-1H-imidazol-2-amine (0.05 g, 0.51 mmol) and DIPEA (0.09 mL, 0.51 mmol). LCMS: 98% 254 nm $R_T$=1.2 min, MS (ES) 496 (M+H).

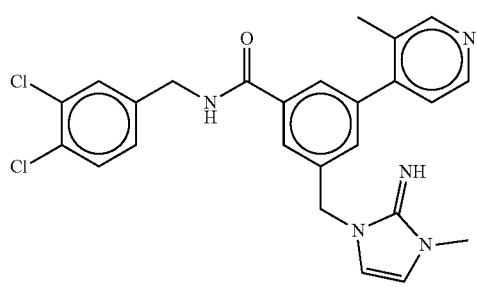

222

Example 25

N-(3,4-dichlorobenzyl)-3-((2-imino-3-methyl-2,3-dihydro-1H-imidazol-1-yl)methyl)-5-(3-methylpyridin-4-yl)benzamide Step A. Preparation of N-(3,4-dichlorobenzyl)-3-(hydroxymethyl)-5-(3-methylpyridin-4-yl)benzamide The title compound (0.06 g, 50%) was prepared following the procedure described in Example 1 Step A using 3-bromo-N-(3,4-dichlorobenzyl)-5-(hydroxymethyl)benzamide (0.11 g, 0.29 mmol) and (3-methylpyridin-4-yl)boronic acid (0.07 g, 0.44 mmol).

Step B. Preparation of 3-((3,4-dichlorobenzyl)carbamoyl)-5-(3-methylpyridin-4-yl)benzyl methanesulfonate The title compound was prepared following the procedure described in Example 11 Step B using N-(3,4-dichlorobenzyl)-3-(hydroxymethyl)-5-(3-methylpyridin-4-yl)benzamide and methanesulfonyl chloride (0.014 mL, 0.10 mmol).

Step C. Example 25

The title compound (0.01 g, 130%) was prepared following the procedure described in Example 1, Step E using 3-((3,4-dichlorobenzyl)carbamoyl)-5-(3-methylpyridin-4-yl)benzyl methanesulfonate, 1-methyl-1H-imidazol-2-amine (0.05 g, 0.51 mmol) and DIPEA (0.09 mL, 0.51 mmol). LCMS: 98% 254 nm $R_T$=0.75 min, MS (ES) 480 (M+H).

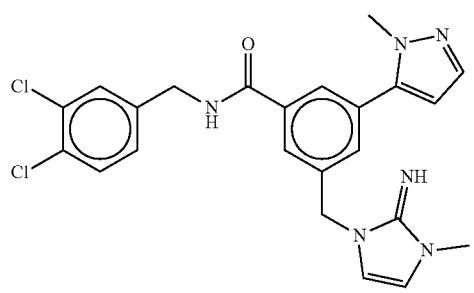

Example 26

N-(3,4-Dichlorobenzyl)-3-((2-imino-3-methyl-2,3-dihydro-1H-imidazol-1-yl)methyl)-5-(1-methyl-1H-pyrazol-5-yl)benzamide Step A. Preparation of N-(3,4-dichlorobenzyl)-3-(hydroxymethyl)-5-(1-methyl-1H-pyrazol-5-yl)benzamide The title compound (0.08 g, 72%) was prepared following the procedure described in Example 1 Step A using 3-bromo-N-(3,4-dichlorobenzyl)-5-(hydroxymethyl)benzamide (0.11 g, 0.29 mmol) and (1-methyl-1H-pyrazol-5-yl) boronic acid (0.05 g, 0.44 mmol).

Step B. Preparation of 3-((3,4-dichlorobenzyl)carbamoyl)-5-(1-methyl-1H-pyrazol-5-yl)benzyl methanesulfonate The title compound was prepared following the procedure described in Example 11 Step B using N-(3,4-dichlorobenzyl)-3-(hydroxymethyl)-5-(1-methyl-1H-pyrazol-5-yl)benzamide (0.08 g 0.21 mmol) and methanesulfonyl chloride (0.02 mL, 0.25 mmol).

Step C. Example 26

The title compound (0.06 g, 58%) was prepared following the procedure described in Example 1, Step E using 3-((3, 4-dichlorobenzyl)carbamoyl)-5-(1-methyl-1H-pyrazol-5-yl)benzyl methanesulfonate, 1-methyl-1H-imidazol-2-amine (0.05 g, 0.51 mmol) and DIPEA (0.09 mL, 0.51 mmol). LCMS: 98% 254 nm $R_T$=0.83 min, MS (ES) 470 (M+H).

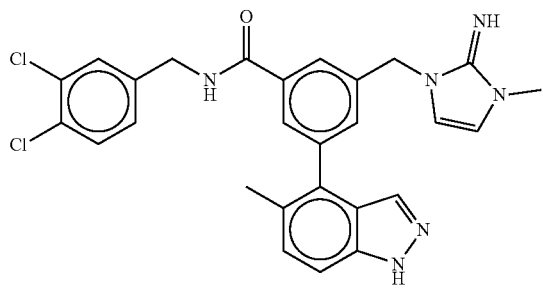

Example 27

N-(3,4-Dichlorobenzyl)-3-((2-imino-3-methyl-2,3-dihydro-1H-imidazol-1-yl)methyl)-5-(5-methyl-1H-indazol-4-yl)benzamide Step A. Preparation of methyl 3-(hydroxymethyl)-5-(5-methyl-1H-indazol-4-yl)benzoate The title compound (1.1 g, 84%) was prepared following the procedure described in Example 1 Step A using methyl 3-bromo-5-(hydroxymethyl)benzoate (1.07 g, 4.38 mmol) and (5-Methyl-1H-indazol-4-yl)boronic acid (925 mg, 5.25 mmol). LCMS: 98% 254 nm $R_T$=0.236 min, MS (ES) 297.3 (M+H).

Step B. Preparation of 3-(hydroxymethyl)-5-(5-methyl-1H-indazol-4-yl)benzoic Acid MeOH (0.5 mL) and 1M aq. NaOH (1.0 mL) were added to a solution of methyl 3-(hydroxymethyl)-5-(5-methyl-1H-indazol-4-yl)benzoate (78.6 mg, 0.27 mmol) in THF (0.5 mL). The reaction mixture was stirred at 40° C. for 6 h. After cooling to ambient temperature, the reaction mixture was neutralized with 1N HCl and concentrated under reduced pressure. The residue was purified by reverse phase HPLC (Phenomenex Gemini C18, H₂O/CH₃CN gradient from 5-95% CH₃CN, 0.1% TFA) to yield the title compound (26 mg, 34%). LCMS: $R_T$=0.220 min, MS (ES) 283.3 (M+H).

Step C. Preparation of N-(3,4-dichlorobenzyl)-3-(hydroxymethyl)-5-(5-methyl-1H-indazol-4-yl)benzamide (3,4-Dichlorophenyl)methanamine (19.3 mg, 0.11 mmol), HATU (41.7 mg, 0.11 mmol), DIPEA (0.05 mL, 0.27 mmol) were added to a solution of 3-(hydroxymethyl)-5-(5-methyl-1H-indazol-4-yl)benzoic acid (25.8 mg, 0.09 mmol) in DMF (1.0 mL). The reaction mixture was stirred at ambient temperature for 12 h. The reaction mixture was quenched by addition MeOH (0.5 mL), and the combined organics were concentrated under reduced pressure. The residue was purified by reverse phase HPLC (Phenomenex Gemini C18, H₂O/CH₃CN gradient from 5-95% CH₃CN, 0.1% TFA) to yield the title compound (26.3 mg, 65%). LCMS: $R_T$=1.690 min, MS (ES) 441.3 (M+H).

Step D. Preparation of 3-(bromomethyl)-N-(3,4-dichlorobenzyl)-5-(5-methyl-1H-indazol-4-yl)benzamide PBr₃ (0.01 mL, 0.12 mmol) was added to a solution of N-(3,4-dichlorobenzyl)-3-(hydroxymethyl)-5-(5-methyl-1H-indazol-4-yl)benzamide (26.3 mg, 0.06 mmol) in THF (1.0 mL). The reaction mixture was stirred at ambient temperature for 2 h and quenched with H₂O. The reaction mixture was extracted with CH₂Cl₂ (3×3.0 mL). The combined organics were concentrated under reduced pressure and used for the next step without further purification. LCMS: $R_T$=1.972 min, MS (ES) 504.2 (M+H).

Step E. Example 27

The title compound (12.3 mg, 39%) was prepared following the procedure described in Example 1, Step E using 3-(bromomethyl)-N-(3,4-dichlorobenzyl)-5-(5-methyl-1H-indazol-4-yl)benzamide (30.1 mg, 0.06 mmol), 1-methyl-1H-imidazol-2-amine (17.4 mg, 0.18 mmol) and DIPEA (0.05 mL, 0.30 mmol). LCMS: >95% 254 nm $R_T$=1.502 min, MS (ES) 520.4 (M+H).

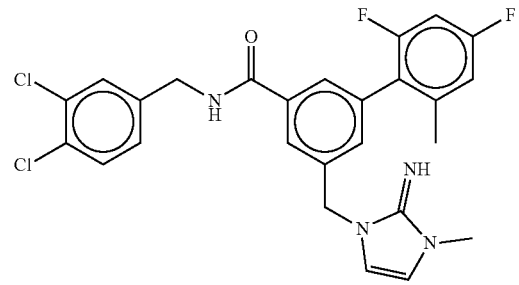

Example 28

N-(3,4-Dichlorobenzyl)-2',4'-difluoro-5-((2-imino-3-methyl-2,3-dihydro-1H-imidazo-1-yl)methyl)-6'-methyl-[1,1'-biphenyl]-3-carboxamide Step A. Preparation of methyl 3-(hydroxymethyl)-5-(4,4,5,5-tetramethyl-1,3,2-dioxaborolan-2-yl)benzoate Bis(pinacolato)diboron (358 mg, 1.41 mmol), KOAc (276 mg, 2.82 mmol), and PdCl₂(dppf) (69.0 mg, 0.094 mmol)

were added to a solution of methyl 3-bromo-5-(hydroxymethyl)benzoate (230 mg, 0.940 mmol) in 1,4-dioxane (9.4 mL). The reaction mixture was stirred at 85° C. 15 ht then concentrated. The residue was purified by flash chromatography (Combi-flash Rf, Hex/EtOAc=0-40% gradient) to afford the title compound (264 mg, quantitative): $^1$H NMR (400 MHz, CDCl$_3$) δ 8.39 (s, 1H), 8.15 (s, 1H), 7.99 (s, 1H), 4.75 (d, J=2.7 Hz, 2H), 3.92 (s, 3H), 1.35 (s, 12H).

Step B. Preparation of methyl 2',4'-difluoro-5-(hydroxymethyl)-6'-methyl-[1,1'-biphenyl]-3-carboxylate 2-Bromo-1,5-difluoro-3-methylbenzene (98.0 mg, 0.470 mmol), PdCl$_2$(dppf) (17.2 mg, 0.024 mmol), Na$_2$CO$_3$ (199 mg, 1.88 mmol) and water (3 mL) were added to a solution of methyl 3-(hydroxymethyl)-5-(4,4,5,5-tetramethyl-1,3,2-dioxaborolan-2-yl)benzoate (190 mg, 0.650 mmol) in DME (6 mL). The reaction mixture was stirred at 90° C. overnight. The reaction mixture was diluted with EtOAc and washed with water. The organic layer was dried (Na$_2$SO$_4$) and concentrated. The residue was purified by flash chromatography (Combi-flash Rf, Hex/EtOAc=0-50% gradient) to provide the title product (48 mg, 34% yield): $^1$H NMR (400 MHz, CDCl$_3$) δ 8.07 (s, 1H), 7.86 (s, 1H), 7.47 (s, 1H), 6.82 (d, J=9.2 Hz, 1H), 6.74 (dt, J=2.4, 9.2 Hz, 1H), 4.78 (d, J=5.2 Hz, 2H), 3.92 (s, 3H), 2.15 (s, 3H). The aqueous layer was acidified with 1 M HCl and extracted with EtOAc. The combined organic layers were dried (Na$_2$SO$_4$) and concentrated. The residue was purified by flash chromatography (Combi-flash Rf, DCM/MeOH=0-3% gradient) to afford 2',4'-difluoro-5-(hydroxymethyl)-6'-methyl-[1,1'-biphenyl]-3-carboxylic acid (72 mg, 55% yield): $^1$H NMR (400 MHz, CDCl$_3$) δ 7.98 (s, 1H), 7.77 (s, 1H), 7.38 (s, 1H), 6.75 (d, J=9.2 Hz, 1H), 6.66 (t, J=9.2 Hz, 1H), 4.67 (s, 2H), 2.07 (s, 3H).

Step C. Preparation of 2',4'-difluoro-5-(hydroxymethyl)-6'-methyl-[1,1'-biphenyl]-3-carboxylic Acid LiOHH$_2$O (18.5 mg, 0.44 mmol) was added to a mixture of methyl 2',4'-difluoro-5-(hydroxymethyl)-6'-methyl-[1,1'-biphenyl]-3-carboxylate (65.0 mg, 0.220 mmol), THF (3 mL), and water (1 mL). The reaction mixture was stirred at room temperature overnight. The reaction mixture was acidified with 1 M HCl and extracted with EtOAc. The organic layer was dried (Na$_2$SO$_4$) and concentrated to provide the desired product (61 mg, quantitative) which was used without further purification. 1H NM R (400 MHz, CD$_3$OD) δ 8.07 (s, 1H), 7.78 (s, 1H), 7.47 (s, 1H), 6.94 (d, J=9.2 Hz, 1H), 6.86 (dt, J=2.4, 9.2 Hz, 1H), 4.71 (s, 2H), 2.16 (s, 3H).

Step D. Preparation of N-(3,4-dichlorobenzyl)-2',4'-difluoro-5-(hydroxymethyl)-6'-methyl-[1,1'-biphenyl]-3-carboxamide The title compound (16.2 mg, 68%) was prepared following the procedure described in Example 1, Step C using 2',4'-difluoro-5-(hydroxymethyl)-6'-methyl-[1,1'-biphenyl]-3-carboxylic acid (15.0 mg, 0.054 mmol) and (3,4-Dichlorophenyl)methanamine (14.3 mg, 0.081 mmol). $^1$H NMR (400 MHz, CDCl$_3$) δ 7.80 (s, 1H), 7.58 (s, 1H), 7.43-7.38 (m, 3H), 7.16 (dd, J=2.0, 8.0 Hz, 1H), 6.80 (d, J=9.2 Hz, 1H), 6.72 (dt, J=2.4, 9.2 Hz, 1H), 6.65 (t, J=5.2 Hz, 1H), 4.77 (s, 2H), 4.56 (d, J=6.0 Hz, 2H), 2.12 (s, 3H).

Step E. Preparation of 5-(bromomethyl)-N-(3,4-dichlorobenzyl)-2',4'-difluoro-6'-methyl-[1,1'-biphenyl]-3-carboxamide The title compound (19 mg, quantitative) was prepared following Example 27, Step D using N-(3,4-dichlorobenzyl)-2',4'-difluoro-5-(hydroxymethyl)-6'-methyl-[1,1'-biphenyl]-3-carboxamide (16.2 mg, 0.037 mmol) and PBr$_3$ (10 µL, 0.111 mmol) in CH$_2$Cl$_2$ (1 mL). $^1$H NMR (400 MHz, CDCl$_3$) δ 7.83 (s, 1H), 7.58 (s, 1H), 7.45-7.40 (m, 3H), 7.20 (dd, J=2.0, 8.4 Hz, 1H), 6.82 (d, J=6.0 Hz, 1H), 6.74 (dt, J=2.4, 9.2 Hz, 1H), 6.52 (bs, 1H), 4.59 (d, J=6.0 Hz, 2H), 4.54 (s, 2H), 2.15 (s, 3H).

Step F. Example 28

1-Methyl-1H-imidazol-2-amine (11.0 mg, 0.110 mmol) was added to a solution of 5-(bromomethyl)-N-(3,4-dichlorobenzyl)-2',4'-difluoro-6'-methyl-[1,1'-biphenyl]-3-carboxamide (19.0 mg, 0.037 mmol) in MeCN (3 mL). The reaction mixture was heated at 80° C. in a microwave reactor for 30 min. The reaction mixture was concentrated and the residue was purified by reverse phase HPLC (Phenomenex Gemini C18, H$_2$O/CH$_3$CN gradient from 20-95% CH$_3$CN, 0.1% TFA). The fractions containing the desired product were combined and concentrated to ~2 mL. The mixture was basified with NaHCO$_3$ (sat.) and extracted with CH$_2$Cl$_2$/EtOAc (2/1, V/V). The combined organic layers were concentrated and dried under vacuum to provide the title product (7.8 mg, 40%). $^1$H NMR (400 MHz, CDCl$_3$) δ 8.51 (t, J=6.0 Hz, 1H), 7.99 (s, 1H), 7.85 (s, 1H), 7.46 (d, J=1.6 Hz, 1H), 7.31 (d, J=8.4 Hz, 1H), 7.23-7.20 (m, 2H), 6.80 (d, J=8.4 Hz, 1H), 6.70 (dt, J=2.4, 9.2 Hz, 1H), 6.48 (s, 2H), 5.14 (s, 2H), 4.51 (d, J=6.0 Hz, 2H), 3.47 (s, 3H), 2.10 (s, 3H); LC-MS: >89% 254 nm, R$_T$=1.17 min, MS (ES) 515 (M+H).

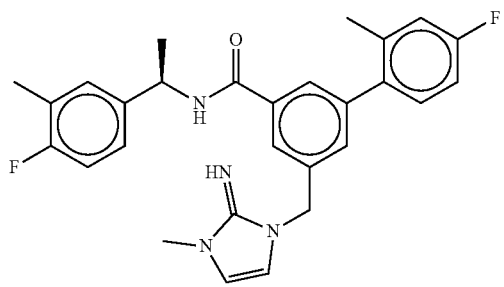

Example 29

(R)-4'-Fluoro-N-(1-(4-fluoro-3-methylphenyl)ethyl)-5-((2-imino-3-methyl-2,3-dihydro-imidazol-1-yl)methyl)-2'-methyl-[1,1'-biphenyl]-3-carboxamide The title compound was prepared (71 mg, 0.14 mmol) according to the procedures described in Example 1, Steps A-E substituting (4-fluoro-2-methylphenyl)boronic acid (5 g, 32.4 mmol) in Step A and the hydrochloride salt of (R)-1-(4-fluoro-3-methylphenyl)ethan-1-amine (0.3 g, 1.6 mmol) in Step C. $^1$H NMR (400 MHz, Chloroform-d) δ 8.42 (s, 1H), 7.90 (d, J=1.7 Hz, 1H), 7.73 (t, J=1.7 Hz, 1H), 7.68 (d, J=7.7 Hz, 1H), 7.22-7.18 (m, 2H), 7.06 (dd, J=8.4, 5.9 Hz, 1H), 6.95-6.85 (m, 4H), 6.45-6.42 (m, 2H), 5.20-5.07

(m, 3H), 3.49 (s, 3H), 2.20 (d, J=1.9 Hz, 3H), 2.14 (s, 3H), 1.56 (s, 3H); LC-MS: >95% 254 nm, R$_T$=1.063 min, MS (ES) 476 (M+H).

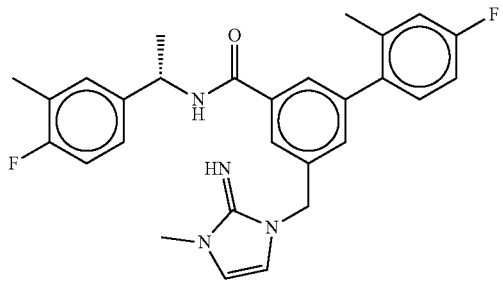

Example 30

(S)-4'-Fluoro-N-(1-(4-fluoro-3-methylphenyl)ethyl)-5-((2-imino-3-methyl-2,3-dihydro-1H-imidazol-1-yl)methyl)-2'-methyl-[1,1'-biphenyl]-3-carboxamide The title compound was prepared (95 mg, 0.20 mmol) according to the procedures described in Example 1, Steps A-E substituting (4-fluoro-2-methylphenyl)boronic acid (5 g, 32.4 mmol) in Step A and the hydrochloride salt of (S)-1-(4-fluoro-3-methylphenyl)ethan-1-amine (0.3 g, 1.6 mmol) in Step C. LC-MS: >95% 254 nm, R$_T$=1.047 min, MS (ES) 476 (M+H).

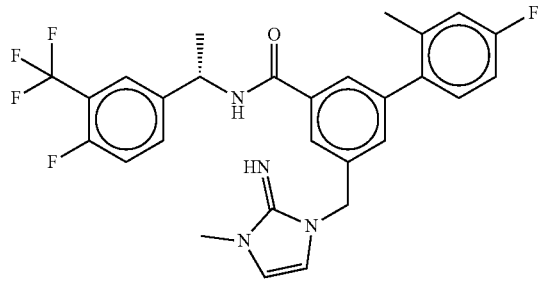

Example 31

(S)-4'-Fluoro-N-(1-(4-fluoro-3-(trifluoromethyl)phenyl)ethyl)-5-((2-imino-3-methyl-2,3-dihydro-1H-imidazol-1-yl)methyl)-2'-methyl-[1,1'-biphenyl]-3-carboxamide The title compound was prepared (65 mg, 0.12 mmol) according to the procedures described in Example 1, Steps A-E substituting (4-fluoro-2-methylphenyl)boronic acid (5 g, 32.4 mmol) in Step A and (S)-1-(4-fluoro-3-(trifluoromethyl)phenyl)ethan-1-amine (0.2 g, 0.82 mmol) in Step C. $^1$H NMR (400 MHz, Chloroform-d) δ 8.31 (s, 1H), 8.11 (d, J=7.5 Hz, 1H), 7.97 (d, J=1.7 Hz, 1H), 7.78 (t, J=1.7 Hz, 1H), 7.70-7.59 (m, 2H), 7.19 (t, J=1.6 Hz, 1H), 7.14-7.03 (m, 2H), 6.97-6.82 (m, 2H), 6.47 (s, 2H) 5.26 (p, J=7.3 Hz, 1H), 5.16 (s, 2H), 3.49 (s, 3H), 2.14 (s, 3H), 1.57 (d, J=7.1 Hz, 3H); LC-MS: >95% 254 nm, R$_T$=1.085 min, MS (ES) 530 (M+H).

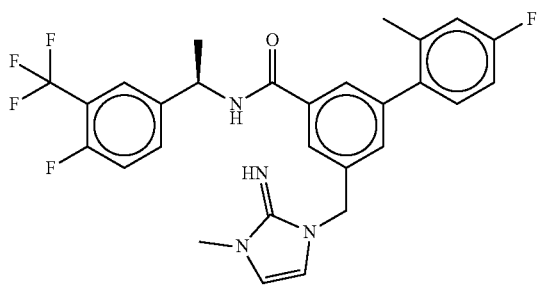

Example 32

(R)-4'-Fluoro-N-(1-(4-fluoro-3-(trifluoromethyl)phenyl)ethyl)-5-((2-imino-3-methyl-2,3-dihydro-1H-imidazol-1-yl)methyl)-2'-methyl-[1,1'-biphenyl]-3-carboxamide The title compound was prepared (87 mg, 0.16 mmol) according to the procedures described in Example 1, Steps A-E substituting (4-fluoro-2-methylphenyl)boronic acid (5 g, 32.4 mmol) in Step A and the hydrochloride salt of (R)-1-(4-fluoro-3-(trifluoromethyl)phenyl)ethan-1-amine (0.2 g, 0.82 mmol) in Step C. $^1$H NMR (400 MHz, Chloroform-d) δ 8.31 (s, 1H), 8.12 (d, J=7.5 Hz, 1H), 8.00 (t, J=1.7 Hz, 1H), 7.80 (t, J=1.6 Hz, 1H), 7.66 (ddd, J=18.0, 7.8, 3.8 Hz, 2H), 7.19 (t, J=1.6 Hz, 1H), 7.13-7.05 (m, 2H), 6.99-6.84 (m, 3H), 6.48 (s, 2H), 5.30-5.24 (m, 1H), 5.18 (s, 2H), 3.50 (s, 3H), 2.15 (s, 3H), 1.58 (d, J=7.1 Hz, 3H); LC-MS: >95% 254 nm, R$_T$=1.091 min, MS (ES) 530 (M+H).

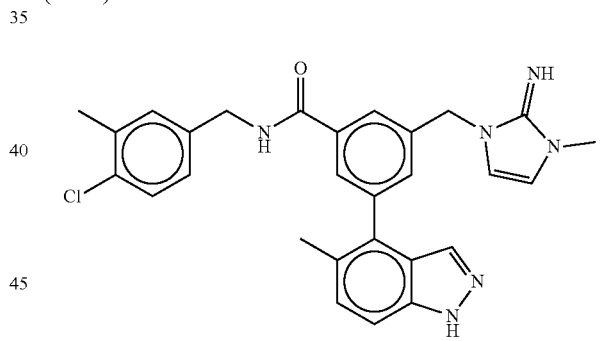

Example 33

N-(4-Chloro-3-methylbenzyl)-3-((2-imino-3-methyl-2,3-dihydro-1H-imidazol-1-yl)methyl)-5-(5-methyl-1H-indazol-4-yl)benzamide Step A. Preparation of N-(4-chloro-3-methylbenzyl)-3-(hydroxymethyl)-5-(5-methyl-1H-indazol-4-yl)benzamide (4-Chloro-3-methylphenyl)methanamine (44.1 mg, 0.28 mmol), EDCI (32.6 mg, 0.17 mmol), HOBt (25.9 mg, 0.17 mmol), and DMAP (20.8 mg, 0.17 mmol) were added to a solution of 3-(hydroxymethyl)-5-(5-methyl-1H-indazol-4-yl)benzoic acid (40.0 mg, 0.14 mmol) in DMF (0.5 mL). The reaction mixture was stirred at ambient temperature for 6 h and quenched with H$_2$O. The reaction mixture was extracted with CH$_2$Cl$_2$ (3×5.0 mL), and the combined organics were concentrated under reduced pressure. The residue was purified by reverse phase HPLC (Phenomenex Gemini C18, H₂O/CH₃CN gradient from 5-950% CH₃CN, 0.1% TFA) to yield the title compound (33.5 mg, 56% yield). LCMS: $R_T$=1.690 min, MS (ES) 420.9 (M+H).

Step B. Preparation of 3-(bromomethyl)-N-(4-chloro-3-methylbenzyl)-5-(5-methyl-1H-indazol-4-yl)benzamide The title compound was prepared from the procedure described in Example 27, Step D using N-(4-chloro-3-methylbenzyl)-3-(hydroxymethyl)-5-(5-methyl-1H-indazol-4-yl)benzamide (33.5 mg, 0.08 mmol). LCMS: $R_T$=1.970 min, MS (ES) 483.8 (M+H).

Step C. Example 33

The title compound (12.4 mg, 31% 2 step) was prepared from the procedure described in Example 1, Step E using 3-(bromomethyl)-N-(4-chloro-3-methylbenzyl)-5-(5-methyl-1H-indazol-4-yl)benzamide (38.5 mg, 0.08 mmol). LCMS: >950% 254 nm $R_T$=1.573 min, MS (ES) 500.0 (M+H).

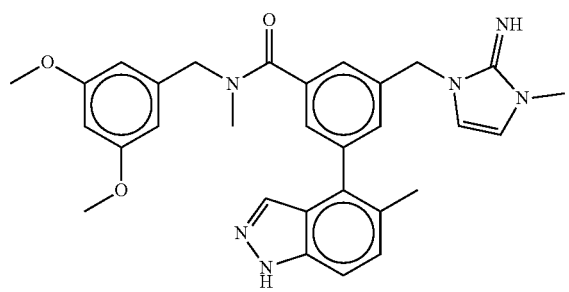

Example 34

N-(3,5-Dimethoxybenzyl)-3-((2-imino-3-methyl-2,3-dihydro-1H-imidazol-1-yl)methyl)-N-methyl-5-(5-methyl-1H-indazol-4-yl)benzamide Step A. Preparation of N-(3,5-dimethloxybenzyl)-3-(hydroxymethyl)-N-methyl-5-(5-methyl-1H-indazol-4-yl)benzamide The title compound (29.1 mg, 46% yield) was prepared from the procedure described in Example 33, Step A using 3-(hydroxymethyl)-5-(5-methyl-1H-indazol-4-yl)benzoic acid (40.0 mg, 0.14 mmol) and 1-(3,5-dimethoxyphenyl)-N-methylmethanamine (0.05 mL, 0.28 mmol). LCMS: $R_T$=r: 1.537 min, MS (ES) 446.5 (M+H)

Step B. Preparation of 3-(bromomethyl)-N-(3,5-dimethoxybenzyl)-N-methyl-5-(5-methyl-1H-indazol-4-yl)benzamide The title compound was prepared from the procedure described in Example 27, Step D using N-(4-chloro-3-methylbenzyl)-3-(hydroxymethyl)-5-(5-methyl-1H-indazol-4-yl)benzamide (33.5 mg, 0.08 mmol). LCMS: $R_T$=1.841 min, MS (ES) 509.4 (M+H).

Step C. Example 34

The title compound (21.8 mg, 61% 2 step) was prepared from the procedure described in Example 1, Step E using 3-(bromomethyl)-N-(3,5-dimethyldiethoxybenzyl)-N-methyl-5-(5-methyl-1H-indazol-4-yl)benzamide (33.2 mg, 0.07 mmol). LCMS: >94% 254 nm $R_T$=1.447 min, MS (ES) 525.6 (M+H).

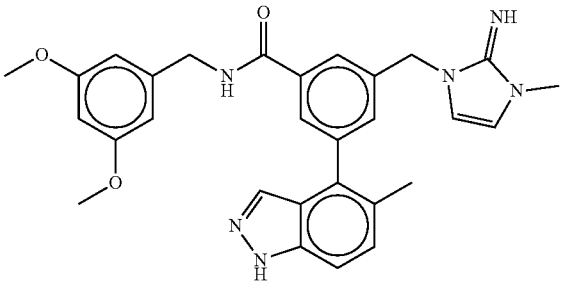

Example 35

N-(3,5-Dimethoxybenzyl)-3-((2-imino-3-methyl-2,3-dihydro-1H-imidazol-1-yl)methyl)-5-(5-methyl-1H-indazol-4-yl)benzamide Step A. Preparation of N-(3,5-dimethoxybenzyl)-3-(hydroxymethyl)-5-(5-methyl-1H-indazol-4-yl)benzamide The title compound (27.9 mg, 45%) was prepared from the procedure described in Example 33, Step A using 3-(hydroxymethyl)-5-(5-methyl-1H-indazol-4-yl)benzoic acid (40.0 mg, 0.14 mmol) and (3,5-dimethoxyphenyl)methanamine (0.04 mL, 0.28 mmol). LCMS: $R_T$=1.363 min, MS (ES) 432.5 (M+H).

Step B. Preparation of 3-(bromomethyl)-N-(3,5-dimethoxybenzyl)-5-(5-methyl-1H-indazol-4-yl)benzamide The title compound was prepared from the procedure described in Example 27, Step D using N-(3,5-dimethoxybenzyl)-3-(hydroxymethyl)-5-(5-methyl-1H-indazol-4-yl)benzamide (29.1 mg, 0.07 mmol). LCMS: $R_T$=1.807 min, MS (ES) 495.4 (M+H).

Step C. Example 35

The title compound (20.2 mg, 61% yield over 2 step) was prepared from the procedure described in Example 1, Step E using 3-(bromomethyl)-N-(3,5-dimethoxybenzyl)-5-(5-methyl-1H-indazol-4-yl)benzamide (31.8 mg, 0.06 mmol). LCMS: >94% 254 nm $R_T$=1.349 min, MS (ES) 511.6 (M+H).

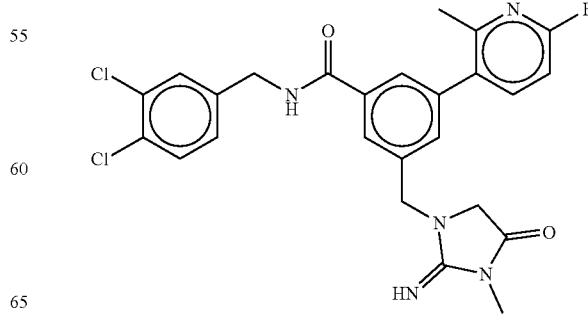

Example 36

N-(3,4-Dichlorobenzyl)-3-(6-fluoro-2-methylpyridin-3-yl)-5-((2-imino-3-methyl-4-oxoimidazolidin-1-yl)methyl)benzamide The title compound (0.03 g, 40%) was prepared from the procedure described in Example 1, Step E using 3-(bromomethyl)-N-(3,4-dichlorobenzyl)-5-(6-fluoro-2-methylpyridin-3-yl)benzamide (0.08 g, 0.16 mmol), 2-imino-3-methylimidazolidin-4-one HCl (0.05 g, 0.31 mmol) and DIPEA (0.07 mL, 0.39 mmol). LCMS: 98% 254 nm $R_T$=1.873 min, MS (ES) 713.1 (M+H).

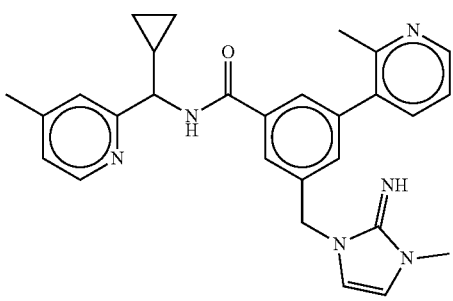

Example 37

N-(Cyclopropyl(4-methylpyridin-2-yl)methyl)-3-((2-imino-3-methyl-2,3-dihydro-1H-imidazol-1-yl)methyl)-5-(2-methylpyridin-3-yl)benzamide

Step A. Preparation of methyl 3-(hydroxymethyl)-5-(2-methylpyridin-3-yl)benzoate The title compound (2.85 g, 67%) was prepared following the procedure described in Example 1 Step A using methyl 3-bromo-5-(hydroxymethyl)benzoate (4.00 g, 16.40 mmol), and (2-methylpyridin-3-yl)boronic acid (6.4 g, 41.5 mmol).

Step B. Preparation of 3-(hydroxymethyl)-5-(2-methylpyridin-3-yl)benzoic Acid The title compound (2.1 g, 79%) was prepared following the procedure described in Example 1 Step B using methyl 3-(hydroxymethyl)-5-(2-methylpyridin-3-yl)benzoate. (2.85 g, 11.0 mmol).

Step C. Preparation of 3-(chloromethyl)-N-(cyclopropyl(4-methylpyridin-2-yl)methyl)-5-(2-methylpyridin-3-yl)benzamide A solution of 3-(hydroxymethyl)-5-(2-methylpyridin-3-yl)benzoic acid (0.40 g, 1.64 mmol) and DMF (drop) in EtOAc (65 mL) was treated with $SOCl_2$ (1.60 mL, 21.92 mmol). The reaction mixture was stirred for 3 h at ambient temperature then concentrated under reduced pressure to give crude 3-(chloromethyl)-5-(2-methylpyridin-3-yl)benzoyl chloride (0.46 g, quant). A solution of crude 3-(chloromethyl)-5-(2-methylpyridin-3-yl)benzoyl chloride (0.09 g, 0.33 mmol) in DCM (10 mL) was cooled in an Ice bath and treated with $Et_3N$ (0.11 mL, 0.83 mmol). Cyclopropyl(4-methylpyridin-2-yl)methanamine HCl (0.07 g, 0.33 mmol) was added and the reaction mixture was stirred for 18 h. The reaction mixture was washed with sat. aq. $NaHCO_3$, dried over $MgSO_4$, filtered, and concentrated under reduce pressure to yield the title compound (0.13 g, 97%).

Step D. Example 37

The title compound (0.09 g, 58%) was prepared following the procedure described in Example 1, Step E using 3-(chloromethyl)-N-(cyclopropyl(4-methylpyridin-2-yl)methyl)-5-(2-methylpyridin-3-yl)benzamide (0.13 g, 0.33 mmol), 1-methyl-1H-imidazol-2-amine (0.06 g, 0.66 mmol), and DIPEA (0.12 mL, 0.83 mmol). LCMS: 98% 254 nm $R_T$=0.78 min, MS (ES) 467 (M+H).

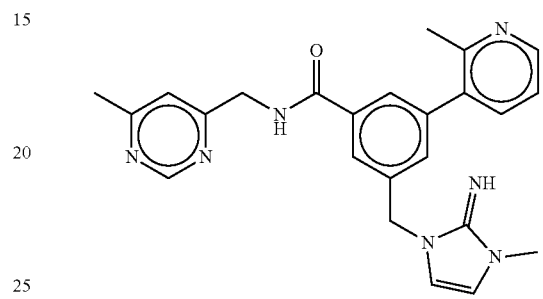

Example 38

3-((2-Imino-3-methyl-2,3-dihydro-1H-imidazol-1-yl)methyl)-5-(2-methylpyridin-3-yl)-N-((6-methylpyrimidin-4-yl)methyl)benzamide

Step A. Preparation of 3-(chloromethyl)-5-(2-methylpyridin-3-yl)-N-((6-methylpyrimidin-4-yl)methyl)benzamide The title compound was prepared following the procedure described in Example 37 Step C using crude 3-(chloromethyl)-5-(2-methylpyridin-3-yl)benzoyl chloride (0.09 g, 0.33 mmol) and (6-methylpyrimidin-4-yl)methanamine (0.04 g, 0.33 mmol).

Step B. Example 38

The title compound (2 mg, 2% 2 steps) was prepared following the procedure described in Example 1, Step E using 3-(chloromethyl)-5-(2-methylpyridin-3-yl)-N-((6-methylpyrimidin-4-yl)methyl)benzamide (0.12 g, 0.33 mmol), 1-methyl-1H-imidazol-2-amine (0.06 g, 0.66 mmol), and DIPEA (0.12 mL, 0.83 mmol). LCMS: 98% 254 nm $R_T$=0.69 min, MS (ES) 428 (M+H).

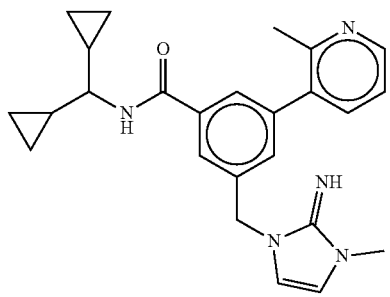

Example 39

N-(Dicyclopropylmethyl)-3-((2-imino-3-methyl-2,3-dihydro-1H-imidazol-1-yl)methyl)-5-(2-methylpyridin-3-yl)benzamide Step A. Preparation of 3-(chloromethyl)-N-(dicyclopropylmethyl)-5-(2-methylpyridin-3-yl)benzamide The title compound was prepared following the procedure described in Example 37 Step C using crude 3-(chloromethyl)-5-(2-methylpyridin-3-yl)benzoyl chloride (0.09 g, 0.33 mmol) and dicyclopropylmethanamine.2HCl (0.04 g, 0.25 mmol).

Step B. Example 39

The title compound (30 mg, 24% 2 steps) was prepared following the procedure described in Example 1, Step E using 3-(chloromethyl)-N-(dicyclopropylmethyl)-5-(2-methylpyridin-3-yl)benzamide (0.09 g, 0.26 mmol), 1-methyl-1H-imidazol-2-amine (0.06 g, 0.66 mmol), and DIPEA (0.12 mL, 0.83 mmol). LCMS: 98% 254 nm $R_T$=0.99 min, MS (ES) 416 (M+H).

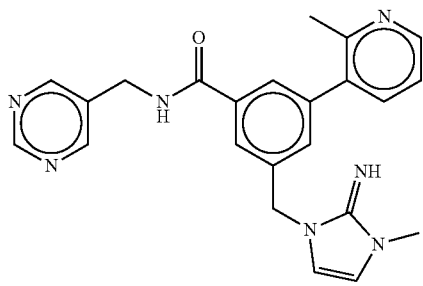

Example 40

3-((2-Imino-3-methyl-2,3-dihydro-1H-imidazol-1-yl)methyl)-5-(2-methylpyridin-3-yl)-N-(pyrimidin-5-ylmethyl)benzamide Step A. Preparation of 3-(chloromethyl)-5-(2-methylpyridin-3-yl)-N-(pyrimidin-5-ylmethyl)benzamide The title compound was prepared following the procedure described in Example 37 Step C using crude 3-(chloromethyl)-5-(2-methylpyridin-3-yl)benzoyl chloride (0.07 g, 0.26 mmol) and pyrimidin-5-ylmethanamine (0.03 g, 0.25 mmol).

Step B. Example 40

The title compound (20 mg, 20% 2 steps) was prepared following the procedure described in Example 1, Step E using 3-(chloromethyl)-5-(2-methylpyridin-3-yl)-N-(pyrimidin-5-ylmethyl)benzamide (0.09 g, 0.26 mmol), 1-methyl-1H-imidazol-2-amine (0.06 g, 0.66 mmol), and DIPEA (0.12 mL, 0.83 mmol). LCMS: 98% 254 nm $R_T$=0.60 min, MS (ES) 414 (M+H).

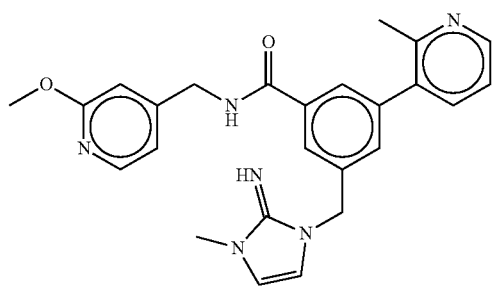

Example 41

3-((2-Imino-3-methyl-2,3-dihydro-1H-imidazol-1-yl)methyl)-N-((2-methoxypyridin-4-yl)methyl)-5-(2-methylpyridin-3-yl)benzamide Step A. Preparation of 3-(chloromethyl)-N-((2-methoxypyridin-4-yl)methyl)-5-(2-methylpyridin-3-yl)benzamide The title compound was prepared following the procedure described in Example 37 Step C using crude 3-(chloromethyl)-5-(2-methylpyridin-3-yl)benzoyl chloride (0.07 g, 0.26 mmol) and (2-methoxypyridin-4-yl)methanamine (0.03 g, 0.25 mmol).

Step B. Example 41

The title compound (20 mg, 24% 2 steps) was prepared following the procedure described in Example 1, Step E using crude 3-(chloromethyl)-N-((2-methoxypyridin-4-yl)methyl)-5-(2-methylpyridin-3-yl)benzamide (0.10 g, 0.26 mmol), 1-methyl-1H-imidazol-2-amine (0.06 g, 0.66 mmol), and DIPEA (0.12 mL, 0.83 mmol). LCMS: 98% 254 nm $R_T$=0.72 min, MS (ES) 443 (M+H).

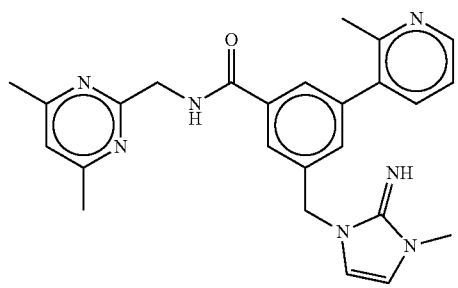

Example 42

N-((4,6-Dimethylpyrimidin-2-yl)methyl)-3-((2-imino-3-methyl-2,3-dihydro-1H-imidazol-1-yl)methyl)-5-(2-methylpyridin-3-yl)benzamide Step A. Preparation of 3-(chloromethyl)-N-((4,6-dimethylpyrimidin-2-yl)methyl)-5-(2-methylpyridin-3-yl)benzamide The title compound was prepared following the procedure described in Example 37 Step C using crude 3-(chloromethyl)-5-(2-methylpyridin-3-yl)benzoyl chloride (0.07 g, 0.26 mmol) and ((4,6-dimethylpyrimidin-2-yl)methanamine-2 HCl (0.05 g, 0.25 mmol).

Step B. Example 42

The title compound (30 mg, 28% 2 steps) was prepared following the procedure described in Example 1, Step E using crude 3-(chloromethyl)-N-((4,6-dimethylpyrimidin-2-yl)methyl)-5-(2-methylpyridin-3-yl)benzamide (0.10 g, 0.26 mmol), 1-methyl-1H-imidazol-2-amine (0.06 g, 0.66 mmol), and DIPEA (0.12 mL, 0.83 mmol). LCMS: 98% 254 nm $R_T$=0.74 min, MS (ES) 442 (M+H).

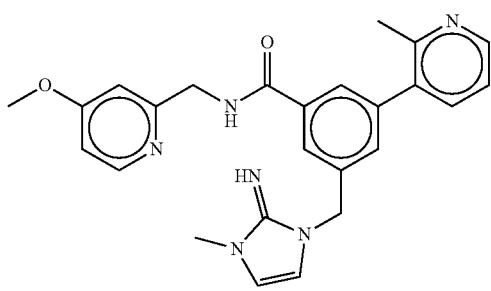

Example 43

3-((2-Imino-3-methyl-2,3-dihydro-1H-imidazol-1-yl)methyl)-N-((4-methoxypyridin-2-yl)methyl)-5-(2-methylpyridin-3-yl)benzamide Step A. Preparation of 3-(chloromethyl)-N-((4-methoxypyridin-2-yl)methyl)-5-(2-methylpyridin-3-yl)benzamide The title compound was prepared following the procedure described in Example 37 Step C using crude 3-(chloromethyl)-5-(2-methylpyridin-3-yl)benzoyl chloride (0.09 g, 0.33 mmol) and (4-methoxypyridin-2-yl)methanamine (0.03 g, 0.33 mmol).

Step B. Example 43

The title compound (2 mg, 20% 2 steps) was prepared following the procedure described in Example 1, Step E using crude 3-(chloromethyl)-N-((4-methoxypyridin-2-yl)methyl)-5-(2-methylpyridin-3-yl)benzamide (0.10 g, 0.26 mmol), 1-methyl-1H-imidazol-2-amine (0.06 g, 0.66 mmol), and DIPEA (0.12 mL, 0.83 mmol). LCMS: 98% 254 nm $R_T$=0.66 min, MS (ES) 443 (M+H).

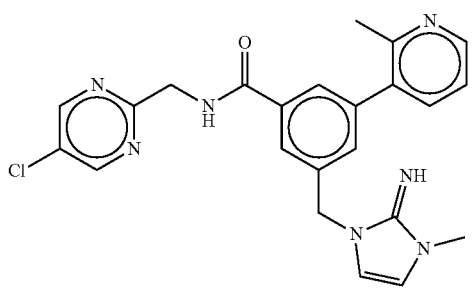

Example 44

N-((5-Chloropyrimidin-2-yl)methyl)-3-((2-imino-3-methyl-2,3-dihydro-1H-imidazol-1-yl)methyl)-5-(2-methylpyridin-3-yl)benzamide Step A. Preparation of 3-(chloromethyl)-N-((5-chloropyridin-2-yl)methyl)-5-(2-methylpyridin-3-yl)benzamide The title compound was prepared following the procedure described in Example 37 Step C using crude 3-(chloromethyl)-5-(2-methylpyridin-3-yl)benzoyl chloride (0.09 g, 0.33 mmol) and (5-chloropyrimidin-2-yl)methanamine (0.03 g, 0.33 mmol).

Step B. Example 44

The title compound (20 mg, 17% 2 steps) was prepared following the procedure described in Example 1, Step E using crude 3-(chloromethyl)-N-((5-chloropyrimidin-2-yl)methyl)-5-(2-methylpyridin-3-yl)benzamide (0.13 g, 0.33 mmol), 1-methyl-1H-imidazol-2-amine (0.06 g, 0.66 mmol), and DIPEA (0.12 mL, 0.83 mmol). LCMS: 98% 254 nm $R_T$=0.78 min, MS (ES) 448 (M+H).

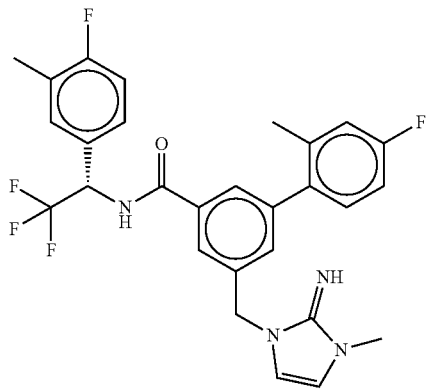

Example 45

(S)-4'-fluoro-5-((2-imino-3-methyl-2,3-dihydro-1H-imidazol-1-yl)methyl)-2'-methyl-N-(2,2,2-trifluoro-1-(4-fluor-3-methylphenyl)ethyl)-[1,1'-biphenyl]-3-carboxamide The title compound was prepared (17 mg, 0.032 mmol) according to the procedures described in Example 1, Steps A-E substituting (4-fluoro-2-methylphenyl)boronic acid (5 g, 32.4 mmol) in Step A and the hydrochloride salt of (S)-2,2,2-trifluoro-1-(4-fluoro-3-methylphenyl)ethan-1-amine (0.2 g, 0.82 mmol) in Step C. LC-MS: >95% 254 nm, $R_T$=1.083 min, MS (ES) 530 (M+H).

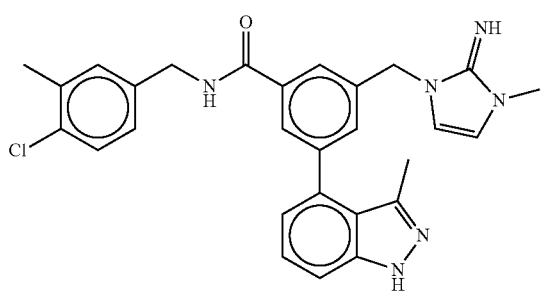

Example 46

N-(4-chloro-3-m ethylbenzyl)-3-((2-imino-3-methyl-2,3-dihydro-1H-imidazol-1-yl)methyl)-5-(3-methyl-1H-indazol-4-yl)benzamide Step A. Preparation of Preparation of 3-methyl-4-(4,4,5,5-tetramethyl-1,3,2-dioxaborolan-2-yl)-1H-indazole 4,4,4',54',5,5',5'-Octamethyl-2,2'-bi(1,3,2-dioxaborolane) (433.1 mg, 1.71 mmol), PdCl$_2$ (dppf (52.0 mg, 0.07 mmol), and KOAc (905.2 mg, 4.30 mmol) were added to a solution of 4-bromo-3-methyl-1H-indazole (300.0 mg, 1.42 mmol) in Dioxane (10.0 mL). The reaction mixture was degassed using Ar gas and stirred at 100° C. for 12 h. After cooling to ambient temperature, the reaction mixture was quenched with silica gel and concentrated under reduced pressure. The residue was purified by flash chromatography (Combi-flash Rf, Hex/EtOAc=0-10% gradient) to yield the title compound (351.5 mg, 95%). LCMS: R$_T$=1.462 min, MS (ES) 259.1 (M+H).

Step B. Preparation of methyl 3-(hydroxymethyl)-5-(3-methyl-1H-indazol-4-yl)benzoate The title compound (312.6 mg, 430%) was prepared from the procedure described in Example 1, Step A using methyl 3-bromo-5-(hydroxymethyl)benzoate (600.0 mg, 2.50 mmol) and 3-methyl-4-(4,4,5,5-tetramethyl-1,32-dioxaborolan-2-yl)-1H-indazole (758.4 mg, 2.90 mmol). LCMS: R-r=1.218 min, MS (ES) 297.3 (M+H).

Step C. Preparation of 3-(hydroxymethyl)-5-(3-methyl-1H-indazol-4-yl)benzoic Acid The title compound (88.6 mg, 29%) was prepared from the procedure described in Example 27, Step B using methyl 3-(hydroxymethyl)-5-(3-methyl-1H-indazol-4-yl)benzoate (312.6 mg, 1.05 mmol). LCMS: R$_T$=1.036 min, MS (ES) 283.3 (M+H).

Step D. Preparation of N-(4-chloro-3-methylbenzyl)-3-(hydroxymethyl)-5-(3-methyl-1H-indazol-4-yl)benzamide The title compound (30.2 mg, 67%) was prepared from the procedure described in Example 33, Step A using 3-(hydroxymethyl)-5-(3-methyl-1H-indazol-4-yl)benzoic acid (30.0 mg, 0.11 mmol) and (4-chloro-3-methylphenyl)methanamine (33.0 mL, 0.21 mmol). LCMS: R$_T$=1.469 min, MS (ES) 420.9 (M+H).

Step E. 3-(bromomethyl)-N-(4-chloro-3-methylbenzyl)-5-(3-methyl-1H-indazol-4-yl)benzamide The crude mixture of title compound was prepared from the procedure described in Example 27, Step D using N-(4-chloro-3-methylbenzyl)-3-(hydroxymethyl)-5-(3-methyl-1H-indazol-4-yl)benzamide (30.2 mg, 0.07 mmol). LCMS: R$_T$=1.773 min, MS (ES) 483.8 (M+H).

Step F. Example 46

The title compound (15.1 mg, 42% 2 step) was prepared from the procedure described in Example 1, Step E using 3-(bromomethyl)-N-(4-chloro-3-methylbenzyl)-5-(3-methyl-1H-indazol-4-yl)benzamide (34.7 mg, 0.07 mmol). $^1$H NMR (400 MHz, Methanol-d$_4$) δ 7.95 (t, J=1.5 Hz, 1H), 7.87 (t, J=1.6 Hz, 1H), 7.54-7.48 (m, 2H), 7.42 (dd, J=8.4, 7.0 Hz, 1H), 7.29 (d, J=8.2 Hz, 1H), 7.28-7.25 (m, 1H), 7.15 (dd, J=8.2, 1.8 Hz, 1H), 7.02 (dd, J=6.9, 0.7 Hz, 1H), 6.99 (d, J=2.5 Hz, 1H), 6.94 (d, J=2.5 Hz, 1H), 5.26 (s, 2H), 4.53 (s, 2H), 3.53 (s, 3H), 2.34 (s, 3H), 2.07 (s, 3H); LCMS: R$_T$=1.363 min, MS (ES) 500.0 (M+H).

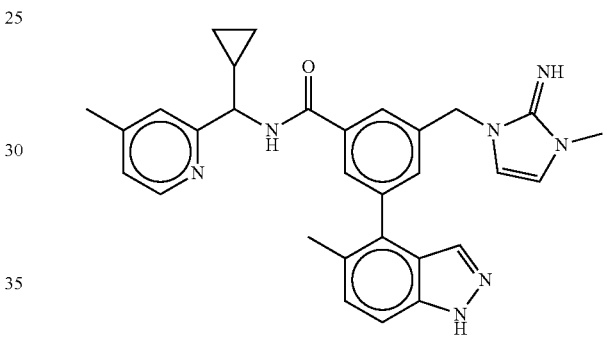

Example 47

N-(cyclopropyl(4-methylpyridin-2-yl)methyl)-3-((2-imino-3-methyl-2,3-dihydro-1H-imidazol-1-yl)methyl)-5-(5-methyl-1H-indazol-4-yl)benzamide Step A. Preparation of N-(cyclopropyl(4-methylpyridin-2-yl)methyl)-3-(hydroxymethyl)-5-(5-methyl-1H-indazol-4-yl)benzamide The title compound (42.5 mg, 93%) was prepared from the procedure described in Example 33, Step A using 3-(hydroxymethyl)-5-(5-methyl-1H-indazol-4-yl)benzoic acid (30.0 mg, 0.11 mmol), cyclopropyl(4-methylpyridin-2-yl)methanamine dihydrochloride (50.0 mL, 0.21 mmol), and DMAP (52.0 mg, 0.43 mmol). LCMS: R$_T$=1.064 min, MS (ES) 427.5 (M+H).

Step B. Preparation of 3-(bromomethyl)-N-(cyclopropyl(4-methylpyridin-2-yl)methyl)-5-(5-methyl-1H-indazol-4-yl)benzamide The crude mixture of title compound was prepared from the procedure described in Example 27, Step D using N-(cyclopropyl(4-methylpyridin-2-yl)methyl)-3-(hydroxymethyl)-5-(5-methyl-1H-indazol-4-yl)benzamide (48.9 mg, 0.11 mmol). LCMS: R$_T$=1.326 min, MS (ES) 490.4 (M+H).

Step C. Example 47

The title compound (12.2 mg, 21% 2 step) was prepared from the procedure described in Example 1, Step E using 3-(bromomethyl)-N-(cyclopropyl(4-methylpyridin-2-yl) methyl)-5-(5-methyl-1H-indazol-4-yl)benzamide (56.1 mg, 0.11 mmol). LCMS: $R_T$=1.039 min, MS (ES) 506.6 (M+H).

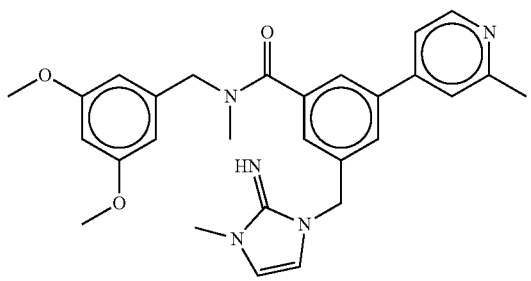

Example 48

N-(3,5-dimethoxybenzyl)-3-((2-imino-3-methyl-2,3-dihydro-1H-imidazol-1-yl)methyl)-N-methyl-5-(2-methylpyridin-4-yl)benzamide

Step A. Preparation of methyl 3-(hydroxymethyl)-5-(2-methylpyridin-4-yl)benzoate The title compound was prepared following the procedure described in Example 1 Step A using methyl 3-bromo-5-(hydroxymethyl)benzoate and (2-methylpyridin-4-yl)boronic acid.

Step B. Preparation of 3-(hydroxymethyl)-5-(2-methylpyridin-4-yl)benzoic Acid The title compound (1.65 g, 88%) was prepared following the procedure described in Example 1 Step B using methyl 3-(hydroxymethyl)-5-(2-methylpyridin-4-yl)benzoate. (1.99 g, 7.73 mmol).

Step C. Preparation of 3-(chloromethyl)-N-(3,5-dimethoxybenzyl)-N-methyl-5-(2-methylpyridin-4-yl)benzamide 3-(Hydroxymethyl)-5-(2-methylpyridin-4-yl)benzoic acid (0.60 g, 2.46 mmol) was converted to 3-(chloromethyl)-5-(2-methylpyridin-4-yl)benzoyl chloride (0.69 g, quant) which (0.07 g, 0.25 mmol) was coupled to 1-(3,5-dimethoxyphenyl)-N-methylmethanamine (0.04 g, 0.25 mmol) to afford the title compound (0.10 g, 0.25 mmol) by following the procedure described in Example 37 Step C.

Step D. Example 48

The title compound (0.07 g, 62%) was prepared following the procedure described in Example 1, Step E using crude 3-(chloromethyl)-N-(3,5-dimethoxybenzyl)-N-methyl-5-(2-methylpyridin-4-yl)benzamide (0.10 g, 0.25 mmol), 1-methyl-1H-imidazol-2-amine (0.05 g, 0.49 mmol), DIPEA (0.09 mL, 0.49 mmol). LCMS: 98% 254 nm $R_T$=1.0 min, MS (ES) 486 (M+H).

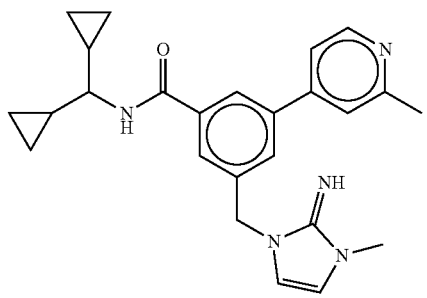

Example 49

N-(Dicyclopropylmethyl)-3-((2-imino-3-methyl-2,3-dihydro-1H-imidazol-1-yl)methyl)-5-(2-methylpyridin-4-yl)benzamide

Step A. Preparation of 3-(chloromethyl)-N-(dicyclopropylmethyl)-5-(2-methylpyridin-4-yl)benzamide The title compound was prepared following the procedure described in Example 37 Step C using crude 3-(chloromethyl)-5-(2-methylpyridin-4-yl)benzoyl chloride (0.07 g, 0.25 mmol) and dicyclopropylmethanamineHCl (0.04 g, 0.25 mmol).

Step B. Example 49

The title compound (50 mg, 470% 2 steps) was prepared following the procedure described in Example 1, Step E using crude 3-(chloromethyl)-N-(dicyclopropylmethyl)-5-(2-methylpyridin-4-yl)benzamide (0.10 g, 0.25 mmol), 1-methyl-1H-imidazol-2-amine (0.05 g, 0.49 mmol), and DIPEA (0.09 mL, 0.49 mmol). LCMS: 98% 254 nm $R_T$=0.98 min, MS (ES) 416 (M+H).

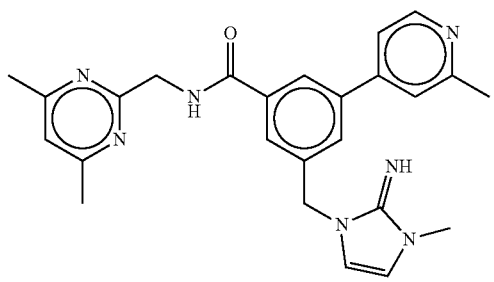

Example 50

N-((4,6-Dimethylpyrimidin-2-yl)methyl)-3-((2-imino-3-methyl-2,3-dihydro-1H-imidazol-1-yl) methyl)-5-(2-methylpyridin-4-yl)benzamide

Step A. Preparation of 3-(chloromethyl)-N-((4,6-dimethylpyrimidin-2-yl)methyl)-5-(2-methylpyridin-4-yl)benzamide The title compound was prepared following the procedure described in Example 37 Step C using crude 3-(chloromethyl)-5-(2-methylpyridin-4-yl)benzoyl chloride (0.07 g, 0.25 mmol) and (4,6-dimethylpyrimidin-2-yl)methanamine.2HCl (0.05 g, 0.25 mmol).

Step B. Example 50

The title compound (50 rig, 43% 2 steps) was prepared following the procedure described in Example 1, Step E using crude 3-(chloromethyl)-N-((4,6-dimethylpyrimidin-2-yl)methyl)-5-(2-methylpyridin-4-yl)benzamide (0.10 g, 0.25 mmol), 1-methyl-1H-imidazol-2-amine (0.05 g, 0.49 mmol), and DIPEA (0.09 mL, 0.49 mmol). LCMS: 98% 254 nm $R_T$=1.1 min, MS (ES) 443 (M+2H).

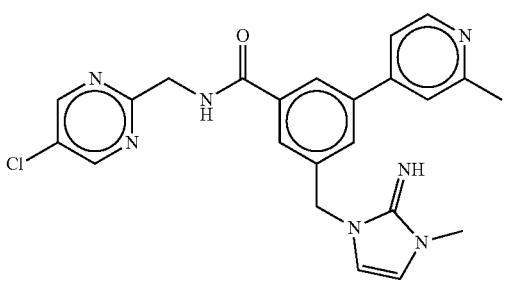

Example 51

N-((5-Chloropyrimidin-2-yl)methyl)-3-((2-imino-3-methyl-2,3-dihydro-1H-imidazol-1-yl)methyl)-5-(2-methylpyridin-4-yl)benzamide Step A. Preparation of 3-(chloromethyl)-N-((5-chloropyrimidin-2-yl)methyl)-5-(2-methylpyridin-4-yl)benzamidemide The title compound was prepared following the procedure described in Example 37 Step C using crude 3-(chloromethyl)-5-(2-methylpyridin-3-yl)benzoylchloride (0.07 g, 0.25 mmol) and (5-chloropyrimidin-2-yl)methanamineHCl (0.04 g, 0.25 mmol).

Step B. Example 51

The title compound (70 mg, 63% 2 steps) was prepared following the procedure described in Example 1, Step E using crude 3-(chloromethyl)-N-((5-chloropyrimidin-2-yl)methyl)-5-(2-methylpyridin-4-yl)benzamide (0.10 g, 0.25 mmol), 1-methyl-1H-imidazol-2-amine (0.05 g, 0.49 mmol), and DIPEA (0.09 mL, 0.49 mmol). LCMS: 98% 254 nm $R_T$=0.82 min, MS (ES) 448 (M+H).

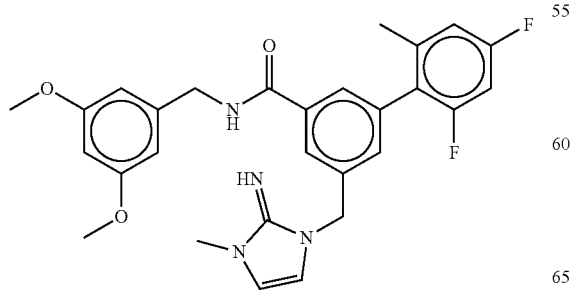

Example 52

N-(3,5-dimethoxybenzyl)-2',4'-difluoro-5-((2-imino-3-methyl-2,3-dihydro-1H-imidazol-1-yl)methyl)-6'-methyl-[1,1'-biphenyl]-3-carboxamide Step A. Preparation of N-(3,5-dimethoxybenzyl)-2',4'-difluoro-5-(hydroxymethyl)-6'-methyl-[1,1'-biphenyl]-3-carboxamide The title compound (26 mg, 81%) was prepared from the procedure described in Example 1, Step C using 2',4'-difluoro-5-(hydroxymethyl)-6'-methyl-[1,1'-biphenyl]-3-carboxylic acid and (3,5-dimethoxyphenyl)methanamine. $^1$H NMR (400 MHz, CDCl$_3$) δ 7.80 (s, 1H), 7.59 (s, 1H), 7.38 (s, 1H), 6.81 (d, J=9.2 Hz, 1H), 6.73 (dt, J=2.4, 9.2 Hz, 1H), 6.51-6.49 (m, 3H), 6.39 (t, J=2.0 Hz, 1H), 4.78 (s, 2H), 4.56 (d, J=5.6 Hz, 2H), 3.78 (s, 6H), 2.14 (s, 3H).

Step B. Preparation of 5-(bromomethyl)-N-(3,5-dimethoxybenzyl)-2',4'-difluoro-6'-methyl-[1,1'-biphenyl]-3-carboxamide The title compound (14 mg, 46%) was prepared from the procedure described in Example 27, Step D using N-(3,5-dimethoxybenzyl)-2',4'-difluoro-5-(hydroxymethyl)-6'-methyl-[1,1'-biphenyl]-3-carboxamide. LCMS: >75% 254 nm $R_T$=1.36 min, MS (ES) 490 (M+H).

Step C. Example 52

The title compound (10.9 mg, 72%) was prepared from the procedure described in Example 28, Step F using 5-(bromomethyl)-N-(3,5-dimethoxybenzyl)-2',4'-difluoro-6'-methyl-[1,1'-biphenyl]-3-carboxamide and 1-methyl-1H-imidazol-2-amine. $^1$H NMR (400 MHz, CDCl$_3$) δ 8.03 (t, J=6.0 Hz, 1H), 7.94 (s, 1H), 7.89 (s, 1H), 7.21 (s, 1H), 6.79 (d, J=9.2 Hz, 1H), 6.70 (dt, J=2.4, 9.2 Hz, 1H), 6.53 (d, J=2.0 Hz, 2H), 6.43 (dd, J=2.4, 6.8 Hz, 2H), 6.29 (t, J=2.0 Hz, 1H), 5.14 (s, 2H), 4.52 (d, J=6.0 Hz, 2H), 3.73 (s, 6H), 3.47 (s, 3H), 2.10 (s, 3H); LCMS: >90% 254 nm $R_T$=1.00 min, MS (ES) 507 (M+H).

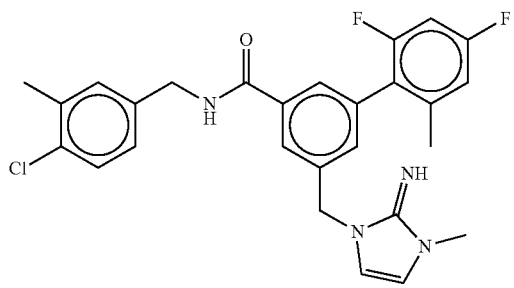

Example 53

N-(4-Chloro-3-methylbenzyl)-2',4'-difluoro-5-((2-imino-3-methyl-2,3-dihydro-1H-imidazol-1-yl)methyl)-6'-methyl-[1,1'-biphenyl]-3-carboxamide Step A. Preparation of N-(4-chloro-3-methylbenzyl)-2',4'-difluoro-5-(hydroxymethyl)-6'-methyl-[1,1'-biphenyl]-3-carboxamide The title compound (25 mg, 78%) was prepared from the procedure described in Example 1, Step C using 2',4'- difluoro-5-(hydroxymethyl)-6'-methyl-[1,1'-biphenyl]-3-carboxylic acid and (4-chloro-3-methylphenyl)methanamine. $^1$H NMR (400 MHz, CDCl$_3$) δ 7.81 (s, 1H), 7.58 (s, 1H), 7.38 (s, 1H), 7.30 (d, J=8.0 Hz, 1H), 7.21 (d, J=1.2 Hz, 1H), 7.10 (m, 1H), 6.82 (d, J=9.2 Hz, 1H), 6.71 (dt, J=2.4, 9.2 Hz, 1H), 6.49 (bs, 1H), 4.78 (s, 2H), 4.56 (d, J=5.6 Hz, 2H), 2.36 (s, 3H), 2.13 (s, 3H).

Step B. Preparation of 5-(bromo ethyl)-N-(4-chloro-3-methylbenzyl)-2',4'-difluoro-6'-methyl-[1,1'-biphenyl]-3-carboxamide The title compound (20 mg, 70%) was prepared from the procedure described in Example 27, Step D using N-(4-chloro-3-methylbenzyl)-2',4'-difluoro-5-(hydroxymethyl)-6'-methyl-[1,1'-biphenyl]-3-carboxamide. $^1$H NMR (400 MHz, CDCl$_3$) δ 7.84 (s, 1H), 7.58 (s, 1H), 7.44 (s, 1H), 7.32 (d, J=8.0 Hz, 1H), 7.23 (s, 1H), 7.12 (dd, J=2.0, 8.0 Hz, 1H), 6.83 (d, J=9.2 Hz, 1H), 6.75 (dt, =2.4, 9.2 Hz, 1H), 6.39 (bs, 1H), 4.59 (d, J=6.0 Hz, 2H), 4.55 (s, 2H), 2.38 (s, 3H), 2.15 (s, 3H).

Step C. Example 53

The title compound (12.3 mg, 59%) was prepared from the procedure described in Example 28, Step F using 5-(bromomethyl)-N-(4-chloro-3-methylbenzyl)-2',4'-difluoro-6'-methyl-[1,1'-biphenyl]-3-carboxamide and 1-methyl-1H-imidazol-2-amine. $^1$H NMR (400 MHz, CDCl$_3$) δ 8.03 (t, J=6.0 Hz, 1H), 7.94 (s, 1H), 7.89 (s, 1H), 7.21 (s, 1H), 6.79 (d, J=9.2 Hz, 1H), 6.70 (dt, J=2.4, 9.2 Hz, 1H), 6.53 (d, J=2.0 Hz, 2H), 6.43 (dd, J=2.4, 6.8 Hz, 2H), 6.29 (t, J=2.0 Hz, 1H), 5.14 (s, 2H), 4.52 (d, J=6.0 Hz, 2H), 3.73 (s, 6H), 3.47 (s, 3H), 2.10 (s, 3H); LCMS: >90% 254 nm R$_T$=1.12 min, MS (ES) 495 (M+H).

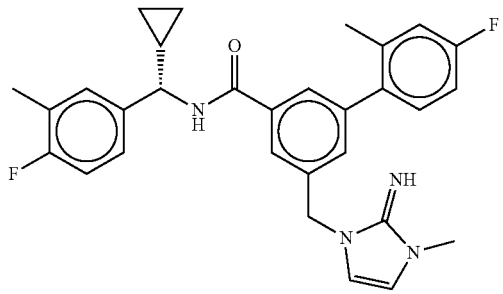

Example 54

(S)—N-(Cyclopropyl(4-fluoro-3-methylphenyl)methyl)-4'-fluoro-5-((2-imino-3-methyl-2,3-dihydro-1H-imidazol-1-yl)methyl)-2'-methyl-[1,1'-biphenyl]-3-carboxamide Title compound was prepared (33 mg, 0.066 mmol) as an orange solid according to the procedures described in Example 1, Steps A-E substituting (4-fluoro-2-methylphenyl)boronic acid (5 g, 32.4 mmol) in Step A and the hydrochloride salt of (S)-cyclopropyl(4-fluoro-3-methylphenyl)methanamine (0.3 g, 1.4 mmol) in Step C. LC-MS: >95% 254 nm, R$_T$=1.005 min, MS (ES) 502 (M+H).

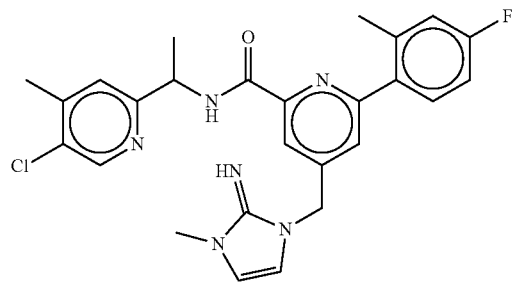

Example 55

N-(1-(5-Chloro-4-methylpyridin-2-yl)ethyl)-6-(4-fluoro-2-methylphenyl)-4-((2-imino-3-methyl-2,3-dihydro-1H-imidazol-1-yl)methyl)picolinamide

Step A. Preparation of methyl 6-(4-fluoro-2-methylphenyl)-4-(hydroxymethyl)picolinate The title compound (2.11 g, quant.) was prepared following the procedure described in Example 1 Step A using methyl 6-chloro-4-(hydroxymethyl)picolinate (1.80 g, 7.4 mmol) and (4-fluoro-2-methylphenyl)boronic acid (1.7 g, 11.1 mmol).

Step B. Preparation of 6-(4-fluoro-2-methylphenyl)-4-(hydroxymethyl)picolinic Acid The title compound (1.49 g, 75%) was prepared following the procedure described in Example 1 Step B using methyl 6-(4-fluoro-2-methylphenyl)-4-(hydroxymethyl)picolinate (2.11 g, 7.66 mmol).

Step C. Preparation of N-(1-(5-chloro-4-methylpyridin-2-yl)ethyl)-6-(4-fluoro-2-methylphenyl)-4-(hydroxymethyl)picolinamide The title compound (0.08 g, 52%) was prepared following the procedure described in Example 1, Step C using 6-(4-fluoro-2-methylphenyl)-4-(hydroxymethyl)picolinic acid (0.09 g, 0.35 mmol) and 1-(5-chloro-4-methylpyridin-2-yl)ethan-1-amine.2HCl (0.09 g, 0.38 mmol).

Step D. Preparation of 4-(bromomethyl)-N-(1-(5-chloro-4-methylpyridin-2-yl)ethyl)-6-(4-fluoro-2-methylphenyl)picolinamide The title compound was prepared following the procedure described in Example 1, Step D using N-(1-(5-chloro-4-methylpyridin-2-yl)ethyl)-6-(4-fluoro-2-methylphenyl)-4-(hydroxymethyl)picolinamide (0.08 g, 0.18 mmol).

Step E. Example 55

The title compound (0.07 g, 79% 2 steps) was prepared following the procedure described in Example 1, Step E using crude 4-(bromomethyl)-N-(1-(5-chloro-4-methylpyridin-2-yl)ethyl)-6-(4-fluoro-2-methylphenyl)picolinamide, 1-methyl-1H-imidazol-2-amine (0.04 g, 0.38 mmol), and DIPEA (0.14 mL, 0.80 mmol). LCMS: 98% 254 nm R$_T$=0.97 min, MS (ES) 493 (M+H).

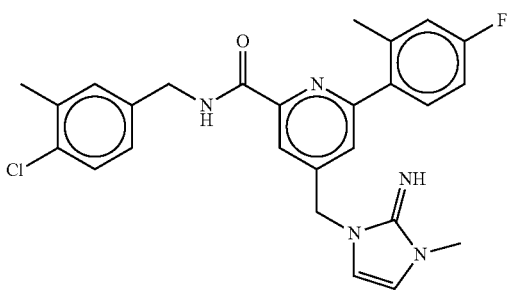

Example 56

N-(4-Chloro-3-methylbenzyl)-6-(4-fluoro-2-methyl-phenyl)-4-((2-imino-3-methyl-2,3-dihydro-1H-imidazol-1-yl)methyl)picolinamide Step A. Preparation of N-(4-chloro-3-methylbenzyl)-6-(4-fluoro-2-methylphenyl)-4-(hydroxymethyl)picolinamide The title compound was prepared following the procedure described in Example 1, Step C using 6-(4-fluoro-2-methylphenyl)-4-(hydroxymethyl)picolinic acid (0.09 g, 0.35 mmol) and (4-chloro-3-methylphenyl)methanamine (0.05 g, 0.38 mmol).

Step B. Preparation of 4-(bromomethyl)-N-(4-chloro-3-methylbenzyl)-6-(4-fluoro-2-methylphenyl)picolinamide The title compound was prepared following the procedure described in Example 1, Step D using crude N-(4-chloro-3-methylbenzyl)-6-(4-fluoro-2-methylphenyl)-4-(hydroxymethyl)picolinamide (0.07 g, 0.17 mmol).

Step C. Example 56

The title compound (0.07 g, 71% 2 steps) was prepared following the procedure described in Example 1, Step E using crude 4-(bromomethyl)-N-(4-chloro-3-methylbenzyl)-6-(4-fluoro-2-methylphenyl)picolinamide, 1-methyl-1H-imidazol-2-amine (0.04 g, 0.38 mmol), and DIPEA (0.14 mL, 0.80 mmol). LCMS: 98% 254 nm $R_T$=1.0 min, MS (ES) 478 (M+H).

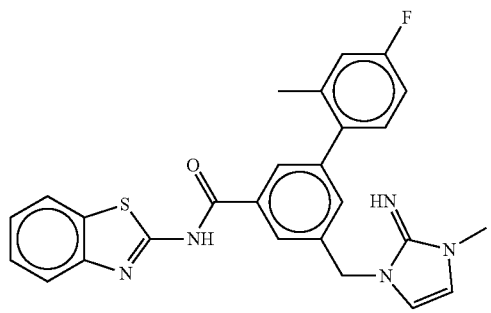

Example 57

N-(benzo[d]thiazol-2-yl)-4'-fluoro-5-((2-imino-3-methyl-2,3-dihydro-1H-imidazol-1-yl)methyl)-2'-methyl-[1,1'-biphenyl]-3-carboxamide The title compound was prepared (8 mg, 0.017 mmol) according to the procedures described in Example 1, Steps A-E substituting (4-fluoro-2-methylphenyl)boronic acid (5 g, 32.4 mmol) in Step A and benzo[d]thiazol-2-amine (0.3 g, 2.0 mmol) in Step C. LC-MS: >95% 254 nm, $R_T$=1.027 min, MS (ES) 473 (M+H).

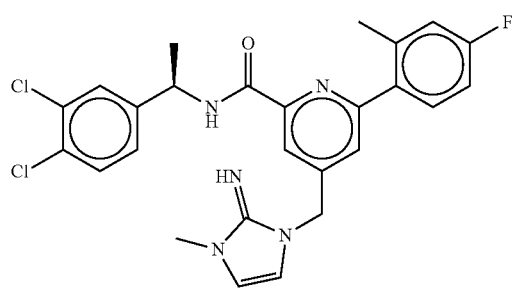

Example 58

(R)—N-(1-(3,4-Dichlorophenyl)ethyl)-6-(4-fluoro-2-methylphenyl)-4-((2-imino-3-methyl-2,3-dihydro-1H-imidazol-1-yl)methyl)picolinamide Step A. Preparation of (R)—N-(1-(3,4-dichlorophenyl)ethyl)-6-(4-fluoro-2-methylphenyl)-4-(hydroxymethyl)picolinamide The title compound (0.09 g, 0.21 mmol) was prepared following the procedure described in Example 1, Step C using 6-(4-fluoro-2-methylphenyl)-4-(hydroxymethyl)picolinic acid (0.09 g, 0.35 mmol) and (R)-1-(3,4-dichlorophenyl)ethan-1-amine.HCl (0.08 g, 0.38 mmol).

Step B. Preparation of (R)-4-(bromomethyl)-N-(1-(3,4-dichlorophenyl)ethyl)-6-(4-fluoro-2-methylphenyl)picolinamide The title compound was prepared following the procedure described in Example 1, Step D using crude (R)—N-(1-(3,4-dichlorophenyl)ethyl)-6-(4-fluoro-2-methylphenyl)-4-(hydroxymethyl)picolinamide (0.09 g, 0.21 mmol).

Step C. Example 58

The title compound (0.04 g, 33% 2 steps) was prepared following the procedure described in Example 1, Step E using crude (R)-4-(bromomethyl)-N-(1-(3,4-dichlorophenyl)ethyl)-6-(4-fluoro-2-methylphenyl)picolinamide, 1-methyl-1H-imidazol-2-amine (0.04 g, 0.38 mmol), and DIPEA (0.14 mL, 0.80 mmol). LCMS: 98% 254 nm $R_T$=1.07 min, MS (ES) 513 (M+H).

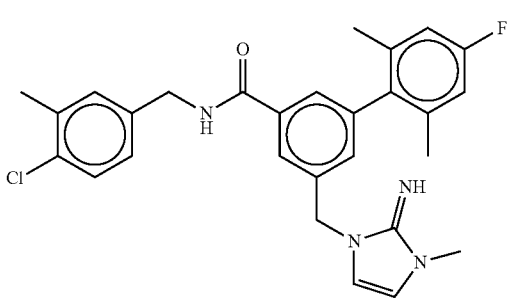

Example 59

N-(4-chloro-3-methylbenzyl)-4'-fluoro-5-((2-imino-3-methyl-2,3-dihydro-1H-imidazol-1-yl)methyl)-6'-methyl-[1,1'-biphenyl]-3-carboxamide

Step A. Preparation of methyl 4'-fluoro-5-(hydroxymethyl)-2',6'-dimethyl-[1,1'-biphenyl]-3-carboxylate The title compound (120 mg, 32%) was prepared from the procedure described in Example 28, Step B using methyl 3-(hydroxymethyl)-5-(4,4,5,5-tetramethyl-1,3,2-dioxaborolan-2-yl)benzoate and 2-bromo-5-fluoro-1,3-dimethylbenzene. ¹H NMR (400 MHz, CDCl₃) δ 8.05 (s, 1H), 7.75 (s, 1H), 7.35 (s, 1H), 6.82 (d, J=9.6 Hz, 2H), 4.81 (d, J=4.8 Hz, 2H), 3.94 (s, 3H), 2.01 (s, 6H).

Step B. Preparation of 4'-fluoro-5-(hydroxymethyl)-2',6'-dimethyl-[1,1'-biphenyl]-3-carboxylic Acid The title compound (119 mg, quant.) was prepared from the procedure described in Example 28, Step C using methyl 4'-fluoro-5-(hydroxymethyl)-2',6'-dimethyl-[1,1'-biphenyl]-3-carboxylate. ¹H NMR (400 MHz, CDCl₃/CD₃OD) δ 8.02 (s, 1H), 7.73 (s, 1H), 7.32 (s, 1H), 6.79 (d, J=9.6 Hz, 2H), 4.75 (s, 2H), 1.98 (s, 61H).

Step C. Preparation of N-(4-chloro-3-methylbenzyl)-4'-fluoro-5-(hydroxymethyl)-2',6'-dimethyl-[1,1'-biphenyl]-3-carboxamide The title compound (27 mg, 82%) was prepared from the procedure described in Example 1, Step C using 4'-fluoro-5-(hydroxymethyl)-2',6'-dimethyl-[1,1'-biphenyl]-3-carboxylic acid and (4-chloro-3-methylphenyl)methanamine. ¹H NMR (400 MHz, CD₃OD) δ 7.86 (s, 1H), 7.51 (s, 1H), 7.30-7.28 (m, 3H), 7.15 (dd, J=2.0, 8.4 Hz, 1H), 6.85 (d, J=9.6 Hz, 2H), 4.71 (s, 2H), 4.52 (s, 2H), 2.35 (s, 3H), 2.01 (s. 6H).

Step D. Preparation of 5-(bromomethyl)-N-(4-chloro-3-methylbenzyl)-4'-fluoro-2',6'-dimethyl-[1,1'-biphenyl]-3-carboxamide The title compound (27 mg, 82%) was prepared from the procedure described in Example 27, Step D using N-(4-chloro-3-methylbenzyl)-4'-fluoro-5-(hydroxymethyl)-2',6'-dimethyl-[1,1'-biphenyl]-3-carboxamide. LCMS: >88% 254 nm R_T=1.56 min, MS (ES) 474 (M+H).

Step E. Example 59

The title compound (7.6 mg, 23%) was prepared from the procedure described in Example 28, Step F using 5-(bromomethyl)-N-(4-chloro-3-methylbenzyl)-4'-fluoro-2',6'-dimethyl-[1,1'-biphenyl]-3-carboxamide and 1-methyl-1H-imidazol-2-amine. ¹H NMR (400 MHz, CDCl₃) δ 8.03 (t, J=6.0 Hz, 1H), 7.95 (s, 1H), 7.69 (s, 1H), 7.23-7.20 (m, 2H), 7.14-7.10 (m, 2H), 6.78 (d, J=9.2 Hz, 2H), 6.45 (m, 2H), 5.16 (s, 2H), 4.51 (d, J=6.0 Hz, 2H), 3.48 (s, 3H), 2.30 (s, 3H), 1.93 (s, 6H); LCMS: >90% 254 nm R_T=1.12 min, MS (ES) 491 (M+H).

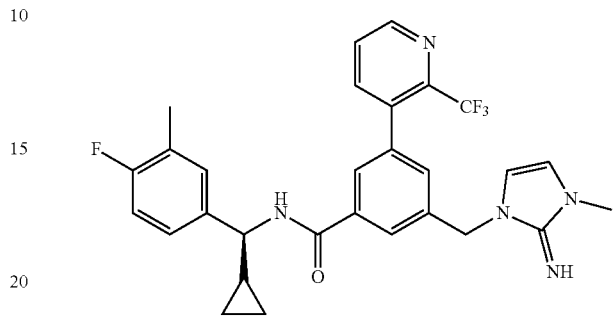

Example 60

(S)—N-(cyclopropyl(4-fluoro-3-methylphenyl)methyl)-3-((2-imino-3-methyl-2,3-dihydro-1H-imidazol-1-yl)methyl)-5-(2-(trifluoromethyl)pyridin-3-yl)benzamide

Step A. Preparation of methyl 3-bromo-5-(((tert-butyldiphenylsilyl)oxy)methyl)benzoate TBDPS-Cl (15.9 mL, 16.8 g, 61.21 mmol) was added to a solution of methyl 3-bromo-5-(hydroxymethyl)benzoate (10 g, 40.8 mmol) in CH₂Cl₂ (408 mL) at 23° C. and stirred for 1 h. The resultant heterogeneous reaction mixture was filtered and concentrated in vacuo. The residue was purified by flash chromatography (Combi-flash Rf, Hex/EtOAc=0-10% gradient) to afford the title compound (18.2 g, 37.6 mmol, 92%) as a white solid. ¹H NMR (400 MHz, Chloroform-d) δ 8.05 (s, 1H), 7.89 (s, 1H), 7.76-7.64 (m, 5H), 7.48-7.34 (m, 6H), 4.75 (s, 2H), 3.91 (s, 3H), 1.11 (s, 9H).

Step B. Preparation of methyl 3-(((tert-butyldiphenylsilyl)oxy)methyl)-5-(4,4,5,5-tetramethyl-1,3,2-dioxaborolan-2-yl)benzoate Bis(pinacolato)diboron (11.2 g, 44.2 mmol) was added to a mixture of methyl 3-bromo-5-(((tert-butyldiphenylsilyl)oxy)methyl)benzoate (17.6 g, 40.1 mmol), KOAc (11.8 g, 120.4 mmol) and PdCl₂(dppf) (3.2 g, 4.0 mmol) in Dioxane (401 mL) and degassed for 20 min; then stirred for 12 h at 85° C. The heterogeneous mixture was filtered through a pad of celite and concentrated in vaco. The residue was purified by flash chromatography (Combi-flash Rf, Hex/EtOAc=0-15% gradient) to afford the title compound (19.7 g, 37.1 mmol, 93%) as a white solid. ¹H NMR (400 MHz, Chloroform-d) δ 8.37 (s, 1H), 8.22 (s, 1H), 7.88 (s, 1H), 7.74-7.66 (m, 4H), 7.48-7.33 (m, 6H), 4.81 (s, 2H), 3.93 (s, 3H), 1.36 (s, 12H), 1.12 (s, 9H).

Step C. Preparation of methyl 3-(hydroxymethyl)-5-(2-(trifluoromethyl)pyridin-3-yl)benzoate Pd(PPh₃)₄ (0.2 g, 0.18 mmol) and potassium carbonate (3.6 g, 11.06 mmol) were added to a solution of 3-bromo- 2-(trifluoromethyl)pyridine (1 g, 4.4 mmol, 1 equiv) and methyl 3-(((tert-butyldiphenylsilyl)oxy)methyl)-5-(4,4,5,5-tetramethyl-1,3,2-dioxaborolan-2-yl)benzoate (2.7 g, 5.0 mmol) in Dioxane/H₂O (104 mL, 0.04 M, 4:1) and degassed for 20 min. The reaction mixture was then placed in a preheated oil bath and stirred for 14 h at 80° C. At 23° C., brine was added to the mixture and extracted with EtOAc. The combined organic layers were dried over Na₂SO₄ and concentrated in vacuo to give crude methyl 3-(((tert-butyldiphenylsilyl)oxy)methyl)-5-(2-(trifluoromethyl)pyridin-3-yl)benzoate, which was used without further purification. Tetra-n-butylammonium fluoride (9.82 mL, 1M in THF, 9.82 mmol) was added to a solution of crude methyl 3-(((tert-butyldiphenylsilyl)oxy)methyl)-5-(2-(trifluoromethyl)pyridin-3-yl)benzoate in THF (49 mL) at 0° C. and allowed to stir for 1 h. The reaction mixture was then concentrated in vacuo. The residue was purified by flash chromatography (Combi-flash Rf, Hex/EtOAc=0-60% gradient) to afford the title compound (1.2 g, 3.8 mmol, 86%) as a colorless oil. ¹H NMR (400 MHz, Chloroform-d) δ 8.74 (d, J=4.6 Hz, 1H), 8.11 (s, 1H), 7.93 (s, 1H), 7.73 (d, J=7.7 Hz, 1H), 7.62-7.51 (m, 2H), 4.82 (s, 2H), 3.93 (s, 3H), 1.23 (s, 1H); ¹H NMR (376 MHz, Chloroform-d) δ −61.25; LCMS: >95% 215, 254 nm R$_T$=0.815 min, MS (ES) 312.3 (M+H).

Step D. Preparation of 3-(hydroxymethyl)-5-(2-(trifluoromethyl)pyridin-3-yl)benzoic acid Lithium hydroxide (0.36 g, 15.0 mmol) was added to a solution of methyl 3-(hydroxymethyl)-5-(2-(trifluoromethyl)pyridin-3-yl)benzoate (1.2 g, 0.38 mmol) in THF/H₂O (4:1, 38 mL) and stirred for 5 h at 23° C. The aqueous layer was then collected and the organic layer was extracted with 2.5 N NaOH. The combined aqueous extraction layers were washed with Et₂O and then acidified with 3 N HCl to a pH of 4. The resultant acidic aqueous solution was extracted with EtOAc and the combined organic layers were dried over Na₂SO₄ and concentrated in vacuo to afford the title compound as a white solid. (1.0 g, 0.33 mmol, 89%). ¹H NMR (400 MHz, DMSO-d) δ 8.80 (d, J=3.8 Hz, 1H), 8.04-7.93 (m, 2H), 7.84-7.74 (m, 2H), 7.54 (s, 1H), 5.42 (s, 1H), 4.62 (s, 2H); ¹⁹F NMR (376 MHz, DMSO-d₆) δ −59.83.

Step E. Preparation of (S)—N-(cyclopropyl(4-fluoro-3-methylphenyl)methyl)-3-(hydroxymethyl)-5-(2-(trifluoromethyl)pyridin-3-yl)benzamide N,N-Diisopropylethylamine (0.22 g, 0.29 mL, 1.7 mmol) was added to a heterogeneous mixture of 3-(hydroxymethyl)-5-(2-(trifluoromethyl)pyridin-3-yl)benzoic acid (0.13 g, 0.42 mmol) in CH₂Cl₂ (2.1 mL) at 23° C. and stirred to homogeneity. Then at −10° C., 1-[Bis(dimethylamino)methylene]-1H-1,2,3-triazolo[4,5-b]pyridinium 3-oxid hexafluorophosphate (0.19 g, 0.51 mmol) was added to the solution and allowed to stir for 20 min. Next the HCl salt of (S)-cyclopropyl(4-fluoro-3-methylphenyl)methanamine (0.11 g, 0.49 mmol, 1.2 equiv) was added to the mixture and then stirred at −10° C. for 3 h. The reaction mixture was then concentrated in vacuo. The residue was purified by flash chromatography (Combi-flash Rf, Hex/EtOAc=0-80% gradient) to afford the title compound (0.18 g, 0.38 mmol, 90%) as a white solid. LCMS: >95% 215, 254 nm R$_T$=1.078 min, MS (ES) 459.4 (M+H).

Step F. Preparation of (S)-3-(bromomethyl)-N-(cyclopropyl(4-fluoro-3-methylphenyl)methyl)-5-(2-(trifluoromethyl)pyridin-3-yl)benzamide N-Bromosuccinimide (0.17 g, 0.38 mmol) was added to a solution of triphenylphosphine (0.25 g, 0.95 mmol) and (S)—N-(cyclopropyl(4-fluoro-3-methylphenyl)methyl)-3-(hydroxymethyl)-5-(2-(trifluoromethyl)pyridin-3-yl)benzamide (0.18 g, 0.38 mmol) in THF at 23° C. and stirred for 12 h. Brine was then added to the mixture and extracted with EtOAc. The combined organic layers were dried over Na₂SO₄ and concentrated in vacuo. The residue was purified by flash chromatography (Combi-flash Rf, Hex/EtOAc=0-80% gradient) to afford the title compound (0.18 g, 0.34 mmol, 91%) as an off white solid. ¹H NMR (400 MHz, Chloroform-d) δ 8.76 (d, J=5.7 Hz, 1H), 7.87 (s, 1H), 7.78-7.65 (m, 2H), 7.61-7.49 (m, 2H), 7.23 (d, J=6.9 Hz, 2H), 7.02-6.93 (m, 1H), 6.49 (d, J=7.6 Hz, 1H), 4.55 (m, 3H), 2.27 (d, J=1.6 Hz, 3H), 1.32-1.18 (m, 1H), 0.72-0.60 (m, 1H), 0.54 (dt, J=8.3, 4.7 Hz, 1H), 0.48-0.38 (m, 1H); ¹⁹F NMR (376 MHz, Chloroform-d) δ −61.09, −119.39; LC-MS: >95% 254 nm R$_T$=1.335 min, MS (ES) 449.2 (M+H).

Step G. Example 60

1-Methyl-1H-imidazol-2-amine (22 mg, 0.23 mmol) was added to a solution of (S)-3-(bromomethyl)-1N-(cyclopropyl(4-fluoro-3-methylphenyl)methyl)-5-(2-(trifluoromethyl)pyridin-3-yl)benzamide benzamide (60 mg, 0.12 mmol) in MeCN (1.2 mL, 0.1 M) at 23° C. The reaction mixture was then placed in a preheated reaction block at 50° C. and allowed to stir for 12 h. The mixture was filtered and concentrated. The title compound (52 mg, 0.1 mmol, 84%) was obtained as a light orange solid after reverse phase HPLC (Phenomenex Gemini C18, H₂O/CH₃CN gradient to 10-95% MeCN 0.1% TFA)). ¹H NMR (400 MHz, Chloroform-d) δ 8.71 (d, J=4.4 Hz, 1H), 8.03 (s, 1H), 7.91 (d, =7.8 Hz, 1H), 7.82 (s, 1H), 7.70 (d, J=7.7 Hz, 1H), 7.58-7.52 (m, 1H), 7.28 (s, 1H), 7.23 (d, J=15.6 Hz, 2H), 6.89 (t, J=8.9 Hz, 1H), 6.36 (dd, J=12.9, 2.4 Hz, 2H), 5.09 (s, 2H), 4.42 (t, J=8.5 Hz, 1H), 3.40 (s, 3H), 2.21 (s, 3H), 1.37 (tq, J=8.7, 4.9, 4.3 Hz, 1H), 0.58 (dd, J=8.2, 4.0 Hz, 2H), 0.46 (dd, J=9.4, 4.5 Hz, 1H), 0.34 (dd, J=9.3, 4.5 Hz, 1H); ¹⁹F NMR (376 MHz, Chloroform-d) δ −60.91, −119.96; LC-MS: >95% 254 nm, R$_T$=0.969 min, MS (ES) 538.5 (M+H).

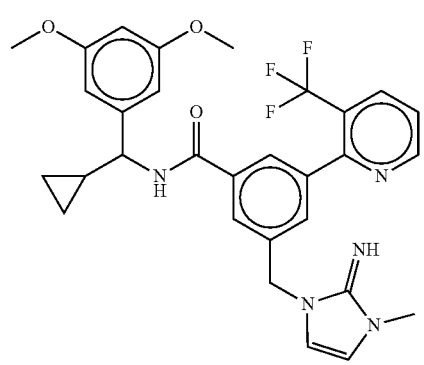

Example 61

N-(Cyclopropyl(3,5-dimethoxyphenyl)methyl)-3-((2-imino-3-methyl-2,3-dihydro-1H-imidazol-1-yl)methyl)-5-(3-(trifluoromethyl)pyridin-2-yl)benzamide The title compound was prepared (36 mg, 0.064 mmol) according to the procedures described in Example 60, Steps A-G substituting 2-bromo-3-(trifluoromethyl)pyridine (1 g, 4.4 mmol) in Step C and the hydrochloride salt of cyclopropyl(3,5-dimethoxyphenyl)methanamine (0.2 g, 0.82 mmol) in Step E. LC-MS: >95% 254 nm, $R_T$=0.932 min, MS (ES) 566 (M+H).

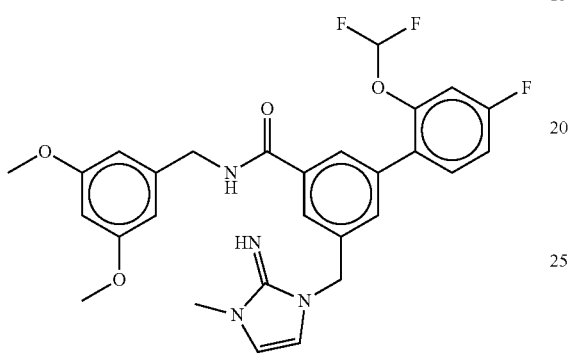

Example 62

2'-(Difluoromethoxy)-N-(3,5-dimethoxybenzyl)-4'-fluoro-5-((2-imino-3-methyl-2,3-dihydro-1H-imidazol-1-yl)methyl)-[1,1'-biphenyl]-3-carboxamide The title compound was prepared (89 mg, 0.17 mmol) according to the procedures described in Example 60, Steps A-G substituting 1-bromo-2-(difluoromethoxy)-4-fluorobenzene (1 g, 4.1 mmol) in Step C and (3,5-dimethoxyphenyl)methanamine (0.3 g, 1.8 mmol) in Step E. LC-MS: >95% 254 nm, $R_T$=0.951 min, MS (ES) 541 (M+H).

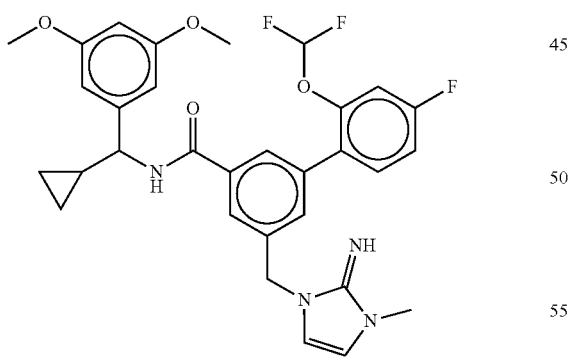

Example 63

N-(Cyclopropyl(3,5-dimethoxyphenyl)methyl)-2'-(difluoromethoxy)-4'-fluoro-5-((2-imino-3-methyl-2,3-dihydro-1H-imidazol-1-yl)methyl)-[1,1'-biphenyl]-3-carboxamide The title compound was prepared (77 mg, 0.13 mmol) according to the procedures described in Example 60, Steps A-G substituting 1-bromo-2-(difluoromethoxy)-4-fluorobenzene (1 g, 4.1 mmol) in Step C and the hydrochloride salt of cyclopropyl(3,5-dimethoxyphenyl)methanamine (0.2 g, 0.82 mmol) in Step E. LC-MS: >95% 254 nm, R 1.008 min, MS (ES) 581 (M H).

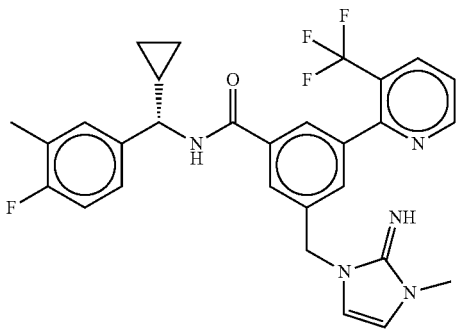

Example 64

(S)—N-(Cyclopropyl(4-fluoro-3-methylphenyl)methyl)-3-((2-imino-3-methyl-2,3-dihydro-1H-imidazol-1-yl)methyl)-5-(3-(trifluoromethyl)pyridin-2-yl)benzamide The title compound was prepared (32 mg, 0.06 mmol) according to the procedures described in Example 60, Steps A-G substituting 2-bromo-3-(trifluoromethyl)pyridine (1 g, 4.4 mmol) in Step C. LC-MS: >95% 254 nm, $R_T$=0.947 min, MS (ES) 538 (M+H).

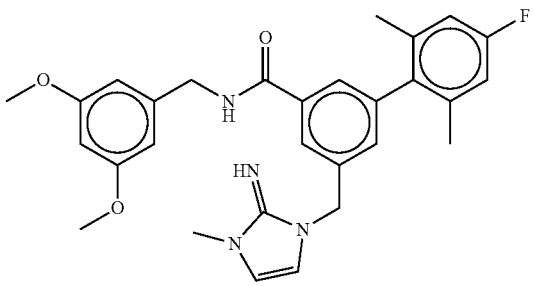

Example 65

N-(3,5-dimethoxybenzyl)-4'-fluoro-5-((2-imino-3-methyl-2,3-dihydro-1H-imidazol-1-yl)methyl)-2',6'-dimethyl-[1,1'-biphenyl]-3-carboxamide Step A. Preparation of N-(3,5-dimethoxybenzyl)-4'-fluoro-5-(hydroxymethyl)-2',6'-dimethyl-[1,1'-biphenyl]-3-carboxamide The title compound (23 mg, 68%) was prepared from the procedure described in Example 1, Step C using 4'-fluoro-5-(hydroxymethyl)-2',6'-dimethyl-[1,1'-biphenyl]-3-carboxylic acid and (3,5-dimethoxyphenyl)methanamine. $^1$H NMR (400 MHz, CDCl$_3$) δ 7.80 (s, 1H), 7.47 (s, 1H), 6.80 (d, J=9.2 Hz, 2H), 6.53-6.50 (m, 3H), 6.39 (t, J=2.4 Hz, 1H), 4.77 (d, J=3.2 Hz, 2H), 4.56 (d, J=6.0 Hz, 2H), 3.78 (s, 6H), 1.99 (s, 6H).

Step B. Preparation of 5-(bromomethyl)-N-(3,5-dimethoxybenzyl)-4'-fluoro-2',6'-dimethyl-[1,1'-biphenyl]-3-carboxamide The title compound (25 mg, 95%) was prepared from the procedure described in Example 27, Step D using N-(3,5-dimethoxybenzyl)-4'-fluoro-5-(hydroxymethyl)-2',6'-dimethyl-[1,1'-biphenyl]-3-carboxamide $^1$H NMR (400 MHz, CDCl$_3$) δ 7.81 (s, 1H), 7.47 (s, 1H), 7.32 (s, 1H), 6.81 (d, J=9.6 Hz, 2H), 6.51 (d, J=2.0 Hz, 2H), 6.48 (bs, 1H), 6.40 (t, J=2.0 Hz, 1H), 4.57 (d, J=5.6 Hz, 2-), 4.53 (s, 2-), 3.79 (s, 6H), 2.00 (s, 6H).

Step C. Example 65

The title compound (20 mg, 74%) was prepared from the procedure described in Example 28, Step F using 5-(bromomethyl)-N-(3,5-dimethoxybenzyl)-4'-fluoro-2',6'-dimethyl-[1,1'-biphenyl]-3-carboxamide and 1-methyl-1H-imidazol-2-amine. $^1$H NMR (400 MHz, CDCl$_3$) δ 7.91-7.90 (m, 2H), 7.66 (s, 1H), 7.10 (s, 1H), 6.78 (d, J=9.6 Hz, 2H), 6.52 (d, J=2.4 Hz, 2H), 6.45 (d, J=2.4 Hz, 1H), 6.41 (d, J=2.4 Hz, 1H), 6.30 (t, J=2.0 Hz, 1H), 5.16 (s, 2H), 4.52 (d, J=6.0 Hz, 2H), 3.73 (s, 6H), 3.48 (s, 3H), 1.93 (s, 61H); LCMS: >90% 254 nm R$_T$=1.03 min, MS (ES) 503 (M+H).

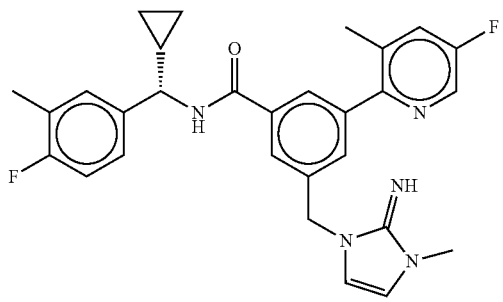

Example 66

(S)—N-(Cyclopropyl(4-fluoro-3-methylphenyl)methyl)-3-(5-fluoro-3-methylpyridin-2-yl)-5-((2-imino-3-methyl-2,3-dihydro-1H-imidazol-1-yl)methyl)benzamide The title compound was prepared (19 mg, 0.038 mmol) according to the procedures described in Example 60, Steps A-G substituting 2-chloro-5-fluoro-3-methylpyridine (1 g, 6.9 mmol) in Step C. LC-MS: >95% 254 nm, R$_T$=1.058 min, MS (ES) 502 (M+H).

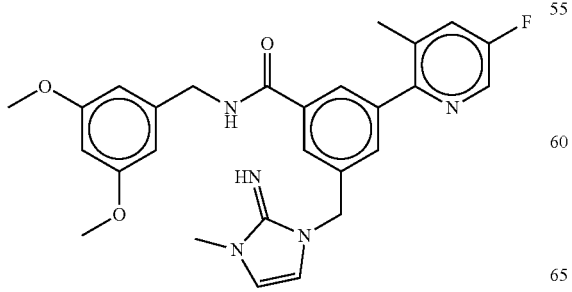

Example 67

N-(3,5-Dimethoxybenzyl)-3-(5-fluoro-3-methylpyridin-2-yl)-5-((2-imino-3-methyl-2,3-dihydro-1H-imidazol-1-yl)methyl)benzamide The title compound was prepared (46 mg, 0.094 mmol) according to the procedures described in Example 60, Steps A-G substituting 2-chloro-5-fluoro-3-methylpyridine (1 g, 6.9 mmol) in Step C and (3,5-dimethoxyphenyl)methanamine (0.3 g, 1.8 mmol) in Step E. LC-MS: >95% 254 nm, R$_T$=0.843 min, MS (ES) 490 (M+H).

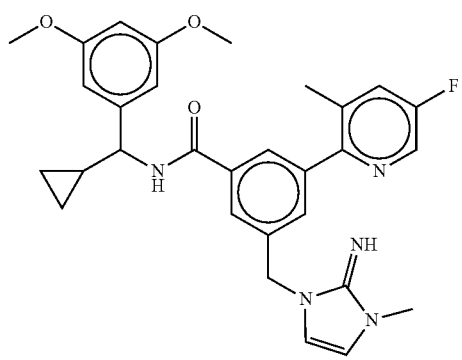

Example 68

N-(Cyclopropyl(3,5-dimethoxyphenyl)methyl)-3-(5-fluoro-3-methylpyridin-2-yl)-5-((2-imino-3-methyl-2,3-dihydro-1H-imidazol-1-yl)methyl)benzamide The title compound was prepared (45 mg, 0.085 mmol) according to the procedures described in Example 60, Steps A-G substituting 2-chloro-5-fluoro-3-methylpyridine (1 g, 6.9 mmol) in Step C and the hydrochloride salt of cyclopropyl(3,5-dimethoxyphenyl)methanamine (0.2 g, 0.82 mmol) in Step E. LC-MS: >95% 254 nm, R$_T$=0.916 min, MS (ES) 530 (M+H).

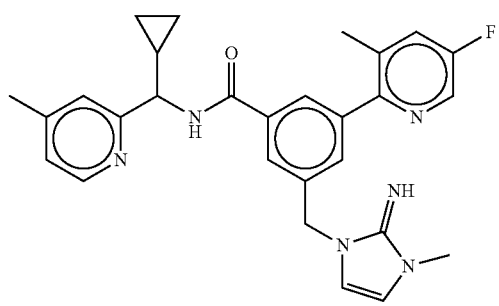

Example 69

N-(Cyclopropyl(4-methylpyridin-2-yl)-3-(5-fluoro-3-methylpyridin-2-yl)-5-((2-imino-3-methyl-2,3-dihydro-1H-imidazol-1-yl)methyl)benzamide The title compound was prepared (19 mg, 0.039 mmol) according to the procedures described in Example 60, Steps A-G substituting 2-chloro-5-fluoro-3-methylpyridine (1 g,

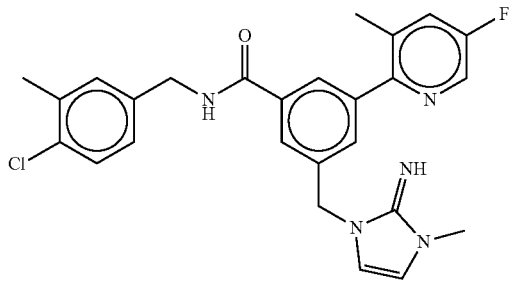

Example 70

N-(4-Chloro-3-m ethylbenzyl)-3-(5-fluoro-3-methyl-pyridin-2-yl)-5-((2-imino-3-methyl-2,3-dihydro-1H-imidazol-1-yl)methyl)benzamide The title compound was prepared (13 mg, 0.027 mmol) according to the procedures described in Example 60, Steps A-G substituting 2-chloro-5-fluoro-3-methylpyridine (1 g, 6.9 mmol) in Step C and (4-chloro-3-methylphenyl)methanamine (0.3 g, 1.9 mmol) in Step E. LC-MS: >95% 254 nm, $R_T$=0.938 min, MS (ES) 479 (M+H).

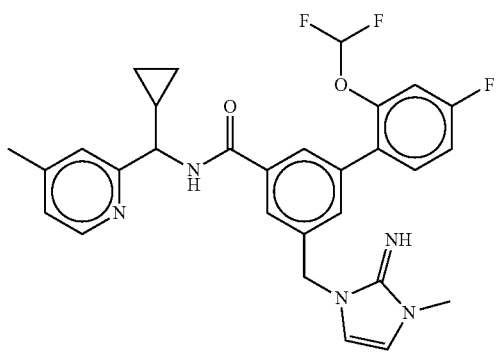

Example 71

N-(Cyclopropyl(4-methylpyridin-2-yl)methyl)-2'-(difluoromethoxy)-4'-fluoro-5-((2-imino-3-methyl-2,3-dihydro-1H-imidazol-1-yl)methyl)-[1,1'-biphenyl]-3-carboxamide The title compound was prepared (58 mg, 0.11 mmol) according to the procedures described in Example 60, Steps A-G substituting 1-bromo-2-(difluoromethoxy)-4-fluorobenzene (1 g, 4.1 mmol) in Step C and the dihydrochloride salt of cyclopropyl(4-methylpyridin-2-yl)methanamine (0.3 g, 1.3 mmol) in Step E. LC-MS: >95% 254 nm, $R_T$=0.805 min, MS (ES) 536 (M+H).

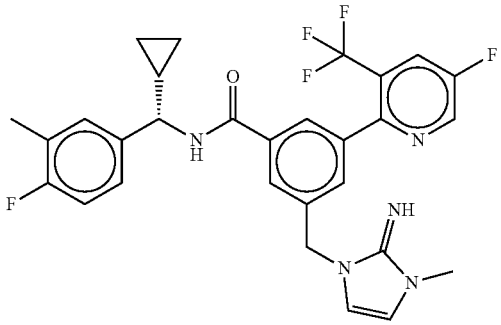

Example 72

(S)—N-(Cyclopropyl(4-fluoro-3-methylphenyl)methyl)-3-(5-fluoro-3-(trifluoromethyl)pyridin-2-yl)-5-((2-imino-3-methyl-2,3-dihydro-1H-imidazol-1-yl)methyl)benzamide Title compound was prepared (71 mg, 0.13 mmol) according to the procedures described in Example 60, Steps A-G substituting 2-chloro-5-fluoro-3-(trifluoromethyl)pyridine (1 g, 5.0 mmol) in Step C. LC-MS: >95% 254 nm, $R_T$=0.999 min, MS (ES) 557 (M+H).

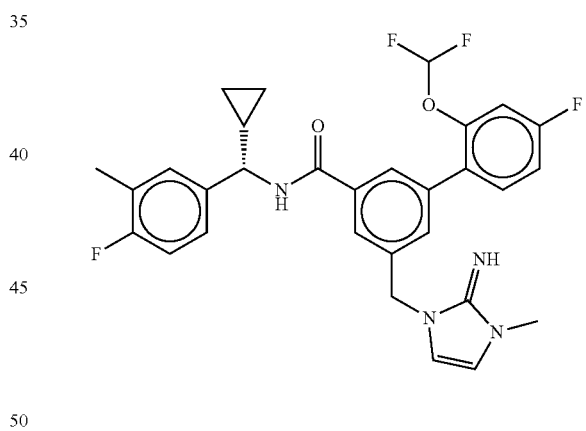

Example 73

(S)—N-(cyclopropyl(4-fluoro-3-methylphenyl)methyl)-2'-(difluoromethoxy)-4'-fluoro-5-((2-imino-3-methyl-2,3-dihydro-1-imidazol-1-yl)methyl)-[1,1'-biphenyl]-3-carboxamide The title compound was prepared (69 mg, 0.13 mmol) according to the procedures described in Example 60, Steps A-G substituting 1-bromo-2-(difluoromethoxy)-4-fluorobenzene (1 g, 4.1 mmol) in Step C. LC-MS: >95% 254 nm, $R_T$=1.067 min, MS (ES) 554 (M+H),

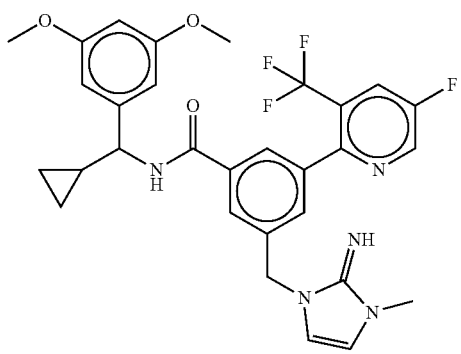

Example 74

N-(Cyclopropyl(3,5-dimethoxyphenyl)methyl)-3-(5-fluoro-3-(trifluoromethyl)pyridin-2-yl)-5-((2-imino-3-methyl-2,3-dihydro-1H-imidazol-1-yl)methyl)benzamide The title compound was prepared (42 mg, 0.072 mmol) according to the procedures described in Example 60, Steps A-G substituting 2-chloro-5-fluoro-3-(trifluoromethyl)pyridine (1 g, 5.0 mmol) in Step C and the hydrochloride salt of cyclopropyl(3,5-dimethoxyphenyl)methanamine (0.2 g, 0.82 mmol) in Step E. LC-MS: >95% 254 nm, $R_T$=0.969 min, MS (ES) 585 (M+H).

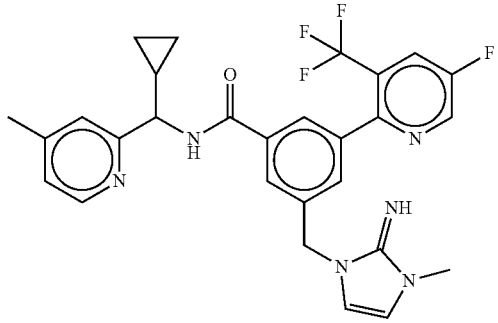

Example 75

N-(Cyclopropyl(4-methylpyridin-2-yl)methyl)-3-(5-fluoro-3-(trifluoromethyl)pyridin-2-yl)-5-((2-imino-3-methyl-2,3-dihydro-1H-imidazol-1-yl)methyl)benzamide The title compound was prepared (89 mg, 0.17 mmol) according to the procedures described in Example 60, Steps A-G substituting 2-chloro-5-fluoro-3-(trifluoromethyl)pyridine (1 g, 5.0 mmol) in Step C and the dihydrochloride salt of cyclopropyl(4-methylpyridin-2-yl)methanamine (0.3 g, 1.3 mmol) in Step E. LC-MS: >95% 254 nm, $R_T$=0.936 min, MS (ES) 515 (M+H).

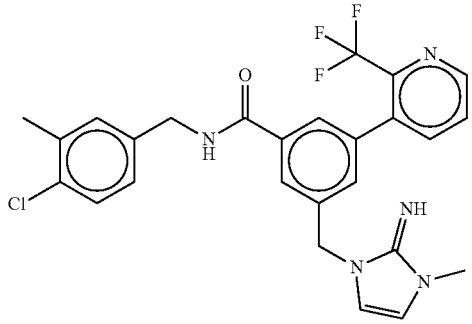

Example 76

N-(4-Chloro-3-methylbenzyl)-3-((2-imin-3-methyl-2,3-dihydro-1H-imidazol-1-yl)methyl)-5-(2-(trifluoromethyl)pyridin-3-yl)benzamide The title compound was prepared (67 mg, 0.13 mmol) according to the procedures described in Example 60, Steps A-G substituting (4-chloro-3-methylphenyl)methanamine (0.3 g, 1.9 mmol) in Step E. LC-MS: >95% 254 nm, $R_T$=0.936 min, MS (ES) 515 (M+H).

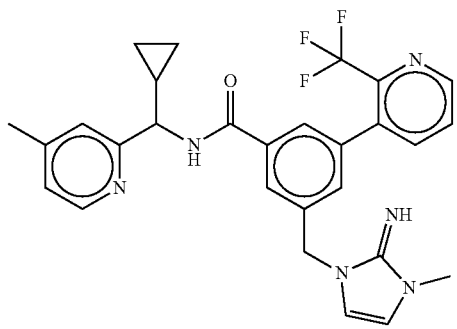

Example 77

N-(Cyclopropyl(4-methylpyridin-2-yl)methyl)-3-((2-imino-3-methyl-2,3-dihydro-1H-imidazol-1-yl)methyl)-5-(2-(trifluoromethyl)pyridin-3-yl)benzamide The title compound was prepared (45 mg, 0.086 mmol) according to the procedures described in Example 60, Steps A-G substituting the dihydrochloride salt of cyclopropyl(4-methylpyridin-2-yl)methanamine (0.3 g, 1.3 mmol) in Step E. LC-MS: >95% 254 nm, $R_T$=0.711 min, MS (ES) 522 (M+H).

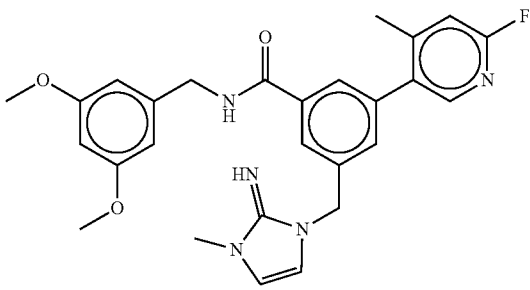

Example 78

N-(3,5-Dimethoxybenzyl)-3-(6-fluoro-4-methylpyridin-3-yl)-5-((2-imino-3-methy-2,3-dihydro-1H-imidazol-1-yl)methyl)benzamide Step A. Preparation of methyl 3-(6-fluoro-4-methylpyridin-3-yl)-5-(hydroxymethyl)benzoate 2-Fluoro-4-methylpyridine-5-boronic acid (3.51 g, 22.6 mmol), methyl 3-bromo-5-(hydroxymethyl)benzoate and Pd(dppf)Cl$_2$.DCM (616 mg, 0.75 mmol) were taken in anhydrous dioxane (76 mL) under an atmosphere of Ar, Na$_2$CO$_3$ (2.0M, 18.9 mL) was added and the mixture was refluxed for 16 h. The cooled solution was concentrated, then EtOAc (50 mL) added and the solution mixture was filtered through celite. The filtrate was washed with water (25 mL), brine (25 mL), concentrated and purified by ISCO flash column chromatography (120 g, 0-10% MeOH in CH$_2$Cl$_2$) to afford title compound (2.80 g, 10.2 mmol, 45%). LCMS (Method B): R$_T$=0.88 min, MS (ES) 276.1 (M+H).

Step B. Preparation of 3-(6-fluoro-4-methylpyridin-3-yi)-5-(hydroxymethyl)benzoic Acid Hydrochloride The title compound (2.20 g, 72%) was prepared from the procedure described in Example 1, Step B using methyl 3-(6-fluoro-4-methylpyridin-3-yl)-5-(hydroxymethyl)benzoate (2.80 g, 10.2 mmol). $^1$H NMR (400 MHz, DMSO-d$_6$) ∂$_H$ 8.06 (s, 1H), 7.99 (s, 1H), 7.76 (s, 1H), 7.55 (s, 1H), 7.22-7.18 (m, 1H), 4.62 (d, J=5.1 Hz, 2H), 3.31 (s, 4H), 2.28 (s, 3H); $^{19}$F NMR (376 MHz, DMSO-d$_6$) ∂$_F$-71.9; LCMS: R$_T$=0.73 min, MS (ES) 262.0 (M+H).

Step C. Preparation of N-(3,5-dimethoxybenzyl)-3-(6-fluoro-4-methyl pyridin-3-yl)-5-(hydroxymethyl) benzamide HATU (570 mg, 1.5 mmol) and pyridine (403 µL, 5.0 mmol) were added to a solution of 3-(6-fluoro-4-methylpyridin-3-yl)-5-(hydroxymethyl)benzoic acid hydrochloride (261 mg, 1.0 mmol) in CH$_2$Cl$_2$ (5 mL) at 0° C. The mixture was stirred for 15 min before the addition of 3,5-dimethoxybenzylamine (166 µL, 1.1 mmol). The reaction was subsequently stirred at r.t. for 18 h, then diluted with further CH$_2$Cl$_2$ and washed with water, concentrated and purified by ISCO flash chromatography (12 g, 0-5% MeOH in CH$_2$Cl$_2$) to afford the title compound (333 mg, 81%). LCMS: R$_T$=0.93 min, MS (ES) 411.1 (M+H).

Step D. Preparation of 3-(bromomethyl)-N-(3,5-dimethoxybenzyl)-5-(6-fluoro-4-methylpyridin-3-yl) benzamide N-(3,5-dimethoxybenzyl)-3-(6-fluoro-4-methylpyridin-3-yl)-5-(hydroxymethyl)benzamide (333 mg, 0.81 mmol) and PPh$_3$ (638 mg, 2.43 mmol) were combined in THF (4 mL) and cooled to 0° C. NBS (433 mg, 2.43 mmol) was added portion-wise, and upon complete addition the mixture was stirred at rt for 90 min. The mixture was diluted with EtOAc (50 mL) and washed with water (3×50 mL), sat. aq. NaCl (25 mL) and concentrated. The residue was purified by flash chromatography (Combi-flash Rf, DCM/MeOH=0-5% gradient) to afford the title compound (269 mg, 81%). $^1$H NMR (400 MHz, DMSO-d$_6$) ∂$_H$ 9.09 (t, J=6.0 Hz, 1H), 8.12 (s, 1H), 8.03 (t, J=1.7 Hz, 1H), 7.84 (t, J=1.7 Hz, 1H), 7.68 (t, J=1.7 Hz, 1H), 7.22 (s, 1H), 6.49 (d, J=2.3 Hz, 2H), 6.38 (t, J=2.3 Hz, 1H), 4.82 (s, 2H), 4.42 (d, J=6.0 Hz, 2H), 3.71 (s, 6H), 2.34-2.32 (s, 3H); LCMS: R$_T$=1.12 min, MS (ES) 473.0, 475.0 (M+H).

Step E. Example 78

3-(Bromomethyl)-(3,5-dimethoxybenzyl)-5-(6-fluoro-4-methylpyridin-3-yl)benzamide (47 mg, 0.10 mmol) and 2-amino-1-methylimidazole (19 mg, 0.20 mmol) were taken up in MeCN (1 mL) and heated to 80° C. for 16 h. Purification by reverse phase HPLC (Phenomenex Gemini C18, H$_2$O/CH$_3$CN gradient from 30-90% CH$_3$CN, 0.1% TFA) affords the title compound (10 mg, 20%). $^1$H NMR (400 MHz, MeOH-d$_4$) δ$_H$ 8.03 (s, 1H), 7.81 (d, J=1.7 Hz, 2H), 7.44 (t, J=1.7 Hz, 1H), 7.06 (s, 1H), 6.85 (d, J=2.6 Hz, 1H), 6.83 (d, J=2.6 Hz, 1H), 6.51 (d, J=2.3 Hz, 2H), 6.38 (t, J=2.3 Hz, 1H), 5.17 (s, 2H), 4.51 (s, 2H), 3.75 (s, 6H), 3.47 (s, 3H), 2.32 (s, 3H); LCMS: R$_T$=1.23 min, MS (ES) 490.0 (M+H).

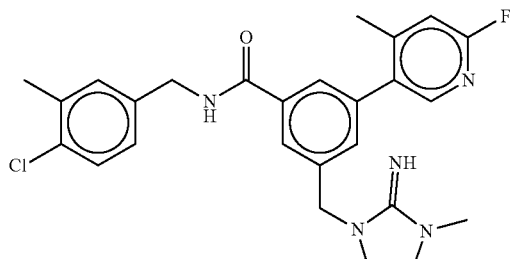

Example 79

N-(4-Chloro-3-methyl benzyl)-3-(6-fluoro-4-methyl pyridin-3-yl)-5-((2-imino-3-methyl-2,3-dihydro-1H-imidazol-1-yl)methyl)benzamide Step A. Preparation of N-(4-chloro-3-methylbenzyl)-3-(6-fluoro-4-methylpyridin-3-yl)-5-(hydroxymethyl)benzamide The title compound (338 mg, 85%) was prepared according to the procedure outlined for Example 78 Step C, using 3-methyl-4-chlorobenzylamine (147 µL, 1.1 mmol). LCMS: R$_T$=1.04 min, MS (ES) 399.1 (M+H).

Step B. Preparation of 3-(bromomethyl)-N-(4-chloro-3-methylbenzyl)-5-(6-fluoro-4-methylpyridin-3-yl)benzamide The title compound (128 mg, 33%) was prepared according to the procedure outlined for Example 78 Step D, from N-(4-chloro-3-methylbenzyl)-3-(6-fluoro-4-methylpyridin-3-yl)-5-(hydroxymethyl)benzamide (338 mg, 0.85 mmol). LCMS: $R_T$=1.25 min, MS (ES) 461, 463 (M+H).

Step C. Example 79

The title compound (7 mg, 15%) was prepared according to the procedure outlined for Example 78 Step E, from 3-(Bromomethyl)-N-(4-chloro-3-methylbenzyl)-5-(6-fluoro-4-methylpyridin-3-yl)benzamide (46 mg, 0.10 mmol). LCMS: $R_T$=1.38 min, MS (ES) 477.9

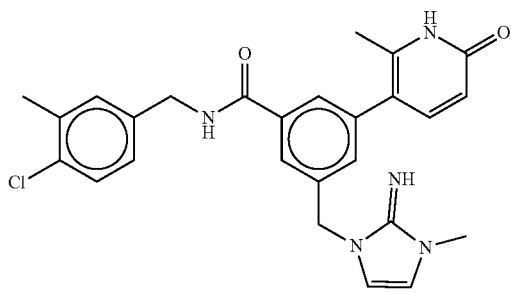

Example 80

N-(4-Chloro-3-m ethylbenzyl)-3-((2-imino-3-methyl-2,3-dihydro-1H-imidazol-1-yl)methyl)-5-(2-methyl-6-oxo-1,6-dihydropyridin-3-yl)benzamide N-(4-Chloro-3-methylbenzyl)-3-(6-fluoro-2-methylpyridin-3-yl)-5-((2-imino-3-methyl-2,3-dihydro-1H-imidazol-1-yl)methyl)benzamide (24 mg, 0.05 mmol) was stirred in a mixture of dioxane (0.5 mL) and hydrochloric acid (3 M, 0.5 mL) at 80° C. for 3 h. The mixture was concentrated and purified by reverse phase HPLC (Phenomenex Gemini C18, H₂O/CH₃CN gradient from 30-90% CH₃CN, 0.1% TFA) to yield the title compound (12 mg, 50%). LCMS: $R_t$=1.29 min, MS (ES) 476.0 (M+H).

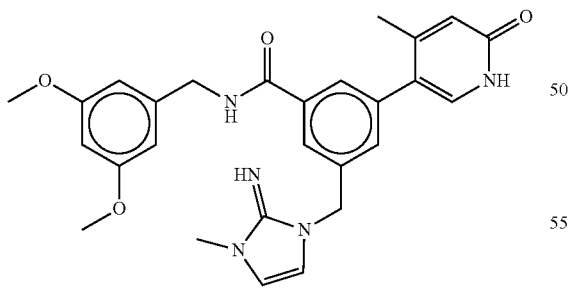

Example 81

N-(3,5-Dimethoxybenzyl)-3-((2-imino-3-methyl-2,3-dihydro-1H-imidazol-1-yl)methyl)-5-(4-methyl-6-oxo-1,6-dihydropyridin-3-yl)benzamide The title compound (9 mg, 37%) was synthesized according to the procedure outlined for Example 80 using N-(3,5-dimethoxybenzyl)-3-(6-fluoro-4-methylpyridin-3-yl)-5-((2-imino-3-methyl-2,3-dihydro-1H-imidazol-1-yl)methyl)benzamide (24 mg, 0.05 mmol). LCMS: $R_T$=0.74 min, MS (ES) 488 (M+H).

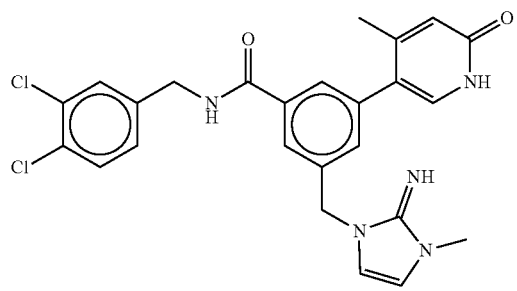

Example 82

N-(3,4-dichlorobenzyl)-3-((2-imino-3-methyl-2,3-dihydro-1H-imidazol-1-yl)methyl)-5-(4-methyl-6-oxo-1,6-dihydropyridin-3-yl)benzamide The title compound (6 mg, 24%) was synthesized according to the procedure outlined for Example 80 using 1N-(3,4-dichlorobenzyl)-3-(6-fluoro-2-methylpyridin-3-yl)-5-((2-imino-3-methyl-2,3-dihydro-1H-imidazol-1-yl)methyl)benzamide (24 mg, 0.05 mmol). ¹H NMR (400 MHz, MeOH-d₄) δ$_H$ 7.81-7.78 (m, 2H), 7.53 (d, J=2.1 Hz, 1H), 7.50 (d, J=8.2 Hz, 1H), 7.43 (t, J=1.7 Hz, 1H), 7.37 (s, 1H), 7.30 (dd, J=8.3, 2.1 Hz, 1H), 6.95 (s, 2H), 6.51 (s, 1H), 5.22 (s, 2H), 4.56 (s, 2H), 3.55 (s, 3H), 2.68 (s, 3H); LCMS: $R_T$=0.83 min, MS (ES) 496, 498 (M+H).

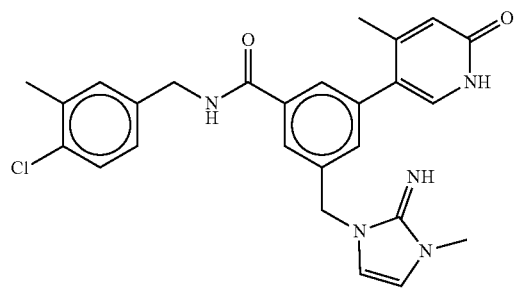

Example 83

N-(4-Chloro-3-methylbenzyl)-3-((2-imino-3-methyl-2,3-dihydro-1H-imidazol-1-yl)methyl)-5-(4-methyl-6-oxo-1,6-dihydropyridin-3-yl)benzamide The title compound (8 mg, 34%) was synthesized according to the procedure outlined for Example 80 using N-(4-chloro-3-methylbenzyl)-3-(6-fluoro-4-methylpyridin-3-yl)-5-((2-imino-3-methyl-2,3-dihydro-1H-imidazol-1-yl)methyl)benzamide (24 mg, 0.05 mmol). LCMS: $R_T$=0.82 min, MS (ES) 476.0 (M+H).

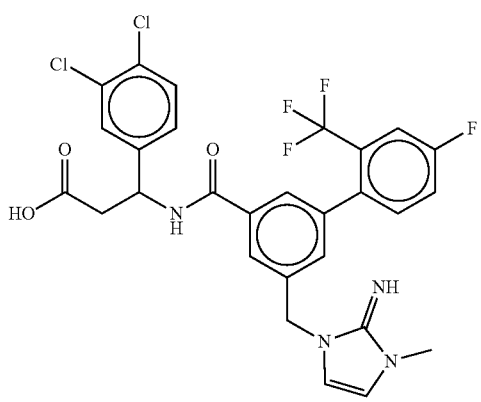

Example 84

3-(3,4-Dichlorophenyl)-3-(4'-fluoro-5-((2-imino-3-methyl-2,3-dihydro-1H-imidazol-1-yl)methyl)-2'-(trifluoromethyl)-[1,1'-biphenyl]-3-carboxamido)propanoic acid Step A. Preparation of methyl 3-bromo-5-((2-imino-3-methyl-2,3-dihydro-1H-imidazol-1-yl)methyl)benzoate The title compound (330.0 mg, 83%) was prepared following the procedure described in Example 1, Step E using methyl 3-bromo-5-(bromomethyl)benzoate (377.0 mg, 1.22 mmol). LCMS: $R_T$=0.219 min, MS (ES) 325.2 (M+H).

Step B. Preparation of methyl (Z)-3-bromo-5-((2-((tert-butoxycarbonyl)imino)-3-methyl-2,3-dihydro-1H-imidazol-1-yl)methyl)benzoate DMAP (62.2 mg, 0.51 mmol), and di-tert-butyl dicarbonate (1110.8 mg, 5.09 mmol) were added to a solution of methyl 3-bromo-5-((2-imino-3-methyl-2,3-dihydro-1H-imidazol-1-yl)methyl)benzoate (330.0 mg, 1.02 mmol) in DCE (5.0 mL). The reaction mixture was stirred at ambient temperature for 2.5 h and quenched with 2.0 mL of $H_2O$. The reaction mixture was extracted with $CH_2Cl_2$ (3×5.0 mL), and the combined organics were concentrated under reduced pressure. The residue was purified by flash chromatography (Combi-flash Rf, DCM/MeOH=0-20% gradient) to afford the title compound (153.3 mg, 35%). LCMS: $R_T$=1.206 min, MS (ES) 425.3 (M+H).

Step C. Preparation of methyl (Z)-5-((2-((tert-butoxycarbonyl)imino)-3-methyl-2,3-dihydro-1H-imidazol-1-yl)methyl)-4'-fluoro-2'-(trifluoromethyl)-[1,1'-biphenyl]-3-carboxylate The title compound (138.9 mg, 75%) was prepared from the procedure described in Example 1, Step A using methyl (Z)-3-bromo-5-((2-((tert-butoxycarbonyl)imino)-3-methyl-2,3-dihydro-1H-imidazol-1-yl)methyl)benzoate (153.3, 0.36 mmol) and (4-fluoro-2-(trifluoromethyl)phenyl)boronic acid (112.0 mg, 0.43 mmol). $^1$H NMR (400 MHz, Chlorform-d) δ 7.98 (s, 1H), 7.94 (s, 1H), 7.44 (dd, J=9.0, 2.3 Hz, 1H), 7.40 (s, 1H), 7.34-7.24 (m, 2H), 6.57 (d, J=2.5 Hz, 1H), 6.43 (d, J=2.5 Hz, 1H), 5.14 (s, 2H), 3.91 (s, 3H), 3.48 (s, 3H), 1.48 (s, 9H); LCMS: R, =1.424 min, MS (ES) 508.5 (M+H).

Step D. (Z)-5-((2-((tert-butoxycarbonyl)imino)-3-methyl-2,3-dihydro-1H-imidazol-1-yl)methyl)-4'-fluoro-2'-(trifluoromethyl)-[1,1'-biphenyl]-3-carboxylic Acid The crude title compound was prepared from the procedure described in Example 27, Step B using methyl (Z)-5-((2-((tert-butoxycarbonyl)imino)-3-methyl-2,3-dihydro-1H-imidazol-1-yl)methyl)-4'-fluoro-2'-(trifluoromethyl)-[1,1'-biphenyl]-3-carboxylate (138.9 mg, 0.27 mmol). It was utilized for the next reaction without further purifications. LCMS: $R_T$=1.325 min, MS (ES) 494.5 (M+H).

Step E. Preparation of Methyl 3-amino-3-(3,4-dichlorophenyl)propanoate

Thionyl chloride (0.46 mL, 6.41 mmol) was added dropwise to a solution of 3-amino-3-(3,4-dichlorophenyl)propanoic acid (500 mg, 2.14 mmol) in MeOH (10.0 mL) at 0° C. The reaction mixture was then stirred at 65° C. for 12 h and concentrated under reduced pressure. The crude mixture of title compound was used for next step without further purification. LCMS: $R_T$=0.145 min, MS (ES) 249.1 (M+H).

Step F. Preparation of methyl (Z)-3-(5-((2-((tert-butoxycarbonyl)imino)-3-methyl-2,3-dihydro-1H-imidazol-1-yl)methyl)-4'-fluoro-2'-(trifluoromethyl)-[1,1'-biphenyl]-3-carboxamido)-3-(3,4-dichlorophenyl)propanoate The crude title compound was prepared from the procedure described in Example 33, Step A using (Z)-5-((2-((tert-butoxycarbonyl)imino)-3-methyl-2,3-dihydro-1H-imidazol-1-yl)methyl)-4'-fluoro-2'-(trifluoromethyl)-[1,1'-biphenyl]-3-carboxylic acid (30.0 mg, 0.06 mmol) and methyl 3-amino-3-(3,4-dichlorophenyl)propanoate (16.6 mg, 0.07 mmol). LCMS: $R_T$=1.686 min, MS (ES) 724.6 (M+H).

Step G. Preparation of (Z)-3-(5-((2-((tert-butoxycarbonyl)imino)-3-methyl-2,3-dihydro-1H-imidazol-1-yl)ethyl)-4'-fluoro-2'-(trifluoromethyl)-[1,1'-biphenyl]-3-carboxamido)-3-(3,4-dichlorophenyl)propanoic acid The crude title compound was prepared from the procedure described in Example 27, Step B using methyl (Z)-3-(5-((2-((tert-butoxycarbonyl)imino)-3-methyl-2,3-dihydro-1H-imidazol-1-yl)methyl)-4'-fluoro-2'-(trifluoromethyl)-[1,1'-biphenyl]-3-carboxamido)-3-(3,4-dichlorophenyl)propanoate (44.0 mg, 0.06 mmol). LCMS: $R_T$=1.589 min, MS (ES) 710.5 (M+H).

Step H. Example 84

TFA (0.2 mL), and con. HCl (2 drops) were added to a solution of (Z)-3-(5-((2-((tert-butoxycarbonyl)imino)-3-methyl-2,3-dihydro-1H-imidazol-1-yl)methyl)-4'-fluoro-2'-(trifluoromethyl)-[1,1'-biphenyl]-3-carboxamido)-3-(3,4-dichlorophenyl)propanoic acid (43.1 mg, 0.06 mmol) in $CH_2Cl_2$ (2.0 mL). The reaction mixture was stirred at ambient temperature for 12 h then concentrated under reduced pressure. The residue was purified by reverse phase HPLC (Phenomenex Gemini C18, $H_2O$/$CH_3CN$ gradient from 5-95% $CH_3CN$, 0.1% TFA) to yield the title compound (18.4 mg, 49% 3 step). $^1$H NMR (400 MHz, Methanol-$d_4$) δ 7.84-7.76 (m, 2H), 7.62-7.56 (m, 2H), 7.49-7.45 (m, 3H), 7.35 (dd, J=8.4, 1.9 Hz, 2H), 6.97-6.87 (m, 2H), 5.48 (t, J=7.1 Hz, 1H), 5.22 (s, 2H), 3.53 (s, 3H), 2.95-2.81 (m, 2H); LCMS: $R_T$=1.443 min, MS (ES) 610.4 (M+H).

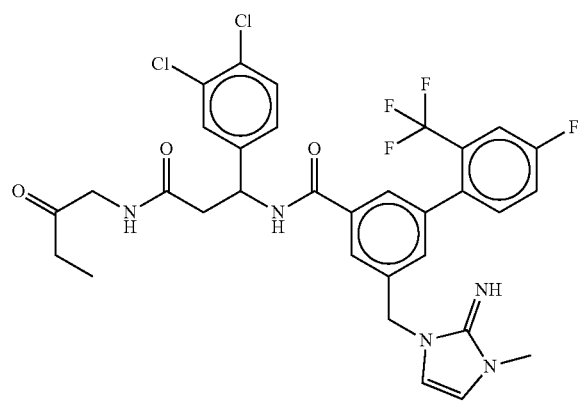

Example 85

N-(1-(3,4-Dichlorophenyl)-3-oxo-3-((2-oxobutyl)amino)propyl-4'-fluoro-5-((2-imino-3-methyl-2,3-dihydro-1H-imidazol-1-yl)methyl)-2'-(trifluoromethyl)-[1,1'-biphenyl]-3-carboxamide Step A. Preparation of tert-butyl (Z)-(1-((5-((1-(3,4-dichlorophenyl)-3-oxo-3-((2-oxobutyl)amino)propyl)carbamoyl)-4'-fluoro-2'-(trifluoromethyl)-[1,1'-biphenyl]-3-yl)methyl)-3-methyl-1,3-dihydro-2H-imidazol-2-ylidene)carbamate 1-(Aminomethyl)cyclopropan-1-ol (15.1 mg, 0.17 mmol) and DIPEA (0.09 mL, 0.52 mmol) were added to a solution of methyl (Z)-3-(5-(2-((tert-butoxycarbonyl)imino)-3-methyl-2,3-dihydro-1H-imidazol-1-yl)methyl)-4'-fluoro-2'-(trifluoromethyl)-[1,1'-biphenyl]-3-carboxamido)-3-(3,4-dichlorophenyl)propanoate (25.0 mg, 0.03 mmol) in THF (1.0 mL). The reaction mixture was stirred at 90° C. for 12 h, quenched with MeOH and concentrated under reduced pressure. The residue was purified by reverse phase HPLC (Phenomenex Gemini C18, H₂O/CH₃CN gradient from 5-95% CH₃CN, 0.1% TFA) to yield the title compound (23.9 mg, 88%) LCMS: $R_T$=1.575 min, MS (ES) 779.6 (M+H).

Step B. Example 85

The title compound (16.6 mg, 79%) was prepared from the procedure described in Example 84, Step H using tert-butyl (Z)-(1-((5-((1-(3,4-dichlorophenyl)-3-oxo-3-((2-oxobutyl)amino)propyl)carbamoyl)-4'-fluoro-2'-(trifluoromethyl)-[1,1'-biphenyl]-3-yl)methyl)-3-methyl-1,3-dihydro-2H-imidazol-2-ylidene)carbamate (23.9 mg, 0.03 mmol). ¹H NMR (400 MHz, Methanol-d₄) δ 7.82 (d, J=1.3 Hz, 2H), 7.61-7.55 (m, 2H), 7.50-7.44 (m, 3H), 7.38-7.31 (m, 2H), 6.93-6.85 (m, 2H), 5.50 (t, J=7.1 Hz, 1H), 5.20 (s, 2H), 4.04-3.89 (m, 1-H), 3.50 (s, 3H), 3.34 (s, 2H), 2.87 (dd, J=7.2, 3.7 Hz, 1H), 2.36 (q, J=7.3 Hz, 2H), 0.95 (t, J=7.3 Hz, 3H): LCMS: $R_T$=1.492 min, MS (ES) 679.5 (M+H).

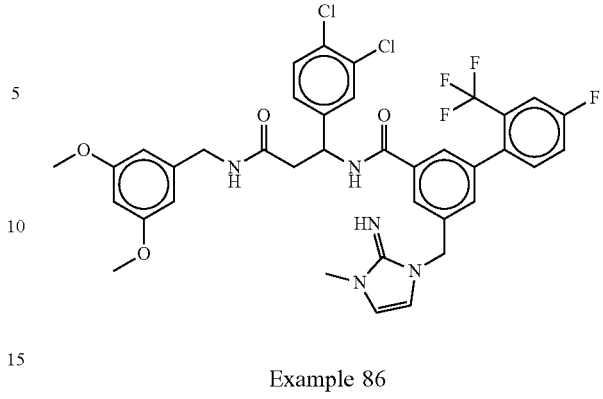

Example 86

1N-(1-(3,4-Dichlorophenyl)-3-((3,5-dimethoxybenzyl)amino)-3-oxopropyl)-4'-fluoro-5-((2-imino-3-methyl-2,3-dihydro-1H-imidazol-1-yl)methyl)-2'-(trifluoromethyl)-[1,1'-biphenyl]-3-carboxamide Step A. Preparation of tert-butyl (Z)-(1-((5-((1-(3,4-dichlorophenyl)-3-((3,5-dimethoxybenzyl)amino)-3-oxopropyl)carbamoyl)-4'-fluoro-2'-(trifluoromethyl)-[1,1'-biphenyl]-3-yl)methyl)-3-methyl-1,3-dihydro-2H-imidazol-2-ylidene)carbamate The title compound (11.9 mg, 40%) was prepared from the procedure described in Example 85, Step A using methyl (Z)-3-(5-((2-((tert-butoxycarbonyl)imino)-3-methyl-2,3-dihydro-1H-imidazol-1-yl)methyl)-4'-fluoro-2'-(trifluoromethyl)-[1, i-biphenyl]-3-carboxamido)-3-(3,4-dichlorophenyl)propanoate (25.0 mg, 0.03 mmol) and (3,5-dimethoxyphenyl)methanamine (0.03 mL, 0.17 mmol). LCMS: $R_T$=1.699 min, MS (ES) 859.7 (M+H).

Step B. Example 86

The title compound (3.2 mg, 30%) was prepared from the procedure described in Example 84, Step H using tert-butyl (Z)-(1-((5-((1-(3,4-dichlorophenyl)-3-((3,5-dimethoxybenzyl)amino)-3-oxopropyl)carbamoyl)-4'-fluoro-2'-(trifluoromethyl)-[1,1'-biphenyl]-3-yl)methyl)-3-methyl-1,3-dihydro-2H-imidazol-2-ylidene)carbamate (11.9 mg, 0.01 mmol). LCMS: $R_T$=1.593 min, MS (ES) 759.6 (M+H).

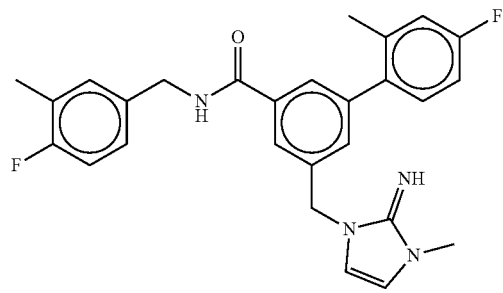

Example 87

4'-Fluoro-N-(4-fluoro-3-methylbenzyl)-5-((2-imino-3-methyl-2,3-dihydro-1H-imidazol-1-yl)methyl)-2'-methyl-[1,1'-biphenyl]-3-carboxamide The title compound was prepared (48 mg, 0.10 mmol) according to the procedures described in Example 1, Steps A-E substituting (4-fluoro-2-methylphenyl)boronic acid (5 g, 32.4 mmol) in Step A and (4-fluoro-3-methylphenyl)methanamine (0.3 g, 2.2 mmol) in Step C LC-MS: >95% 254 nm, $R_T$=0.976 min, MS (ES) 462 (M+H).

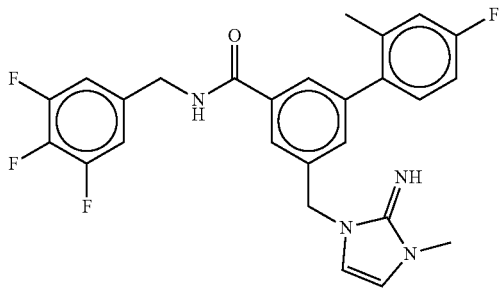

Example 88

4'-Fluoro-5-((2-imino-3-methyl-2,3-dihydro-1H-imidazol-1-yl)methyl)-2'-methyl-N-(3,4,5-trifluorobenzyl)-[1,1'-biphenyl]-3-carboxamide The title compound was prepared (37 mg, 0.077 mmol) according to the procedures described in Example 1, Steps A-E substituting (4-fluoro-2-methylphenyl)boronic acid (5 g, 32.4 mmol) in Step A and (2,3,4-trifluorophenyl)methanamine (0.3 g, 1.9 mmol) in Step C. LC-MS: >95% 254 nm, $R_T$=0.996 min, MS (ES) 484 (M+H).

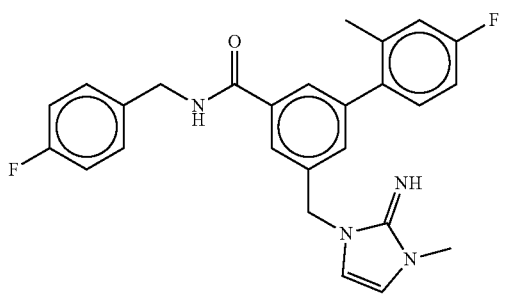

Example 89

4'-Fluoro-N-(4-fluorobenzyl)-5-((2-imino-3-methyl-2,3-dihydro-1H-imidazol-1-yl)methyl)-2'-methyl-[1,1'-biphenyl]-3-carboxamide The title compound was prepared (61 mg, 0.14 mmol) according to the procedures described in Example 1, Steps A-E substituting (4-fluoro-2-methylphenyl)boronic acid (5 g, 32.4 mmol) in Step A and (4-fluorophenyl)methanamine (0.3 g, 2.4 mmol) in Step C. LC-MS: >95% 254 nm, $R_T$=0.94 min, MS (ES) 448 (M+H).

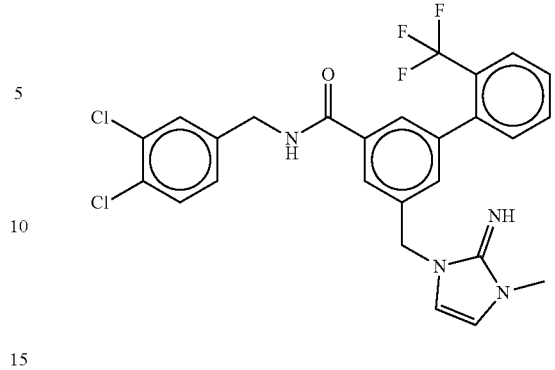

Example 90

N-(3,4-Dichlorobenzyl)-5-((2-imino-3-methyl-2,3-dihydro-1H-imidazol-1-yl)methyl)-2'-(trifluoromethyl)-[1,1'-biphenyl]-3-carboxamide Step A. Preparation of methyl 5-(hydroxymethyl)-2'-(trifluoromethyl)-[1,1'-biphenyl]-3-carboxylate (2-(Trifluoromethyl)phenyl)boronic acid (114 mg, 0.60 mmol), $PdCl_2(dppf)$ (12 mg, 0.016 mmol), $Et_3N$ (167 μL, 1.2 mmol) were added to a solution of methyl 3-bromo-5-(hydroxymethyl)benzoate (97.5 mg, 0.40 mmol) in EtOH (4 mL). The reaction mixture was stirred at 85° C. overnight, diluted with EtOAc and washed with water. The organic layer was dried ($Na_2SO_4$) and concentrated. The residue was purified by flash chromatography (Combi-flash Rf, Hex/EtOAc=0-60% gradient) to afford the title compound (100 mg, 80%). $^1$H NMR (400 MHz, $CDCl_3$) δ 8.09 (s, 1H), 7.95 (s, 1H), 7.77 (d, J=8.0 Hz, 1H), 7.56 (m, 3H), 7.33 (d, J=7.6 Hz, 1H), 4.81 (d, J=6.0 Hz, 2H), 3.94 (s, 3H), 1.79 (t, J=6.0 Hz, 1H).

Step B. Preparation of 5-(hydroxymethyl)-2'-(trifluoromethyl)-[1,1'-biphenyl]-3-carboxylic Acid The title compound (95 mg, quant.) was prepared from the procedure described in Example 28, Step C using methyl 5-(hydroxymethyl)-2'-(trifluoromethyl)-[1,1'-biphenyl]-3-carboxylate. $^1$H NMR (400 MHz, $CD_3OD_3$) δ 8.08 (s, 1H), 7.86 (s, 1H), 7.80 (d, J=7.6 Hz, 1H), 7.67 (m, 1H), 7.58 (m, 1H), 7.53 (s, 1H), 7.39 (d, J=7.6 Hz, 1H), 4.71 (s, 2H).

Step C. Preparation of N-(3,4-dichlorobenzyl)-5-(hydroxymethyl)-2'-(trifluoromethyl)-[1,1'-biphenyl]-3-carboxamide The title compound (66 mg, 72%) was prepared from the procedure described in Example 1, Step C using 5-(hydroxymethyl)-2'-(trifluoromethyl)-[1,1'-biphenyl]-3-carboxylic acid and (3,4-Dichlorophenyl)methanamine. $^1$H NMR (400 MHz, $CDCl_3$) δ 7.85 (s, 1H), 7.76 (d, J=8.0 Hz, 1H), 7.67 (s, 1H), 7.57 (m, 1H), 7.50 (m, 2H), 7.43 (m, 2H), 7.33 (d, J=7.2 Hz, 1H), 7.20 (m, 1H), 6.48 (brs, 1H), 4.81 (d, J=6.0 Hz, 2H), 4.61 (d, J=6.0 Hz, 2H), 1.81 (t, J=6.0 Hz, 1H).

Step D. Preparation of 5-(bromomethyl)-N-(3,4-dichlorobenzyl)-2'-(trifluoromethyl)-[1,1'-biphenyl]-3-carboxamide The title compound (76 mg, quant.) was prepared from the procedure described in Example 27, Step D using N-(3,4-dichlorobenzyl)-5-(hydroxymethyl)-2'-(trifluoromethyl)-[1,1'-biphenyl]-3-carboxamide. $^1$H NMR (400 MHz, CDCl$_3$) δ 7.88 (s, 1H), 7.77 (d, J=7.6 Hz, 1H), 7.66 (s, 1H), 7.60 (m, 1H), 7.53 (m, 1H), 7.43 (m, 2H), 7.34 (d, J=7.6 Hz, 1H), 7.21 (m, 1H), 6.47 (brs, 1H), 4.61 (d, J=6.0 Hz, 2H), 4.55 (s, 2H).

Step E. Example 90

The title compound (27 mg, 54%) was prepared from the procedure described in Example 28, Step F using 5-(bromomethyl)-N-(3,4-dichlorobenzyl)-2'-(trifluoromethyl)-[1,1'-biphenyl]-3-carboxamide and 1-methyl-1H-imidazol-2-amine. $^1$H NMR (400 MHz, CDCl$_3$) δ 8.63 (t, J=5.6 Hz, 1H), 7.98 (s, 1H), 7.89 (s, 1H), 7.70 (d, J=7.6 Hz, 1H), 7.53 (m, 2H), 7.42 (s, 1H), 7.27 (m, 3H), 7.16 (d, J=7.6 Hz, 1H), 6.42 (m, 2H), 5.08 (s, 2H), 4.46 (d, J=5.6 Hz, 2H), 3.41 (s, 3H); LCMS: >95% 254 nm R$_T$=1.593 min, MS m(ES) 533 (M+H).

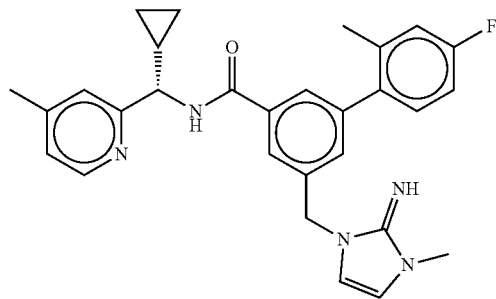

Example 91

(S)—N-(Cyclopropyl(4-methylpyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide Step A. Preparation of (S,E)-2,2-dimethyl-N-((4-methylpyridin-2-yl)methylene)propane-1-sulfinamide Cesium carbonate (2.0 g, 6.2 mmol) was added to a solution of (S)-2-methylpropane-2-sulfinamide (0.5 g, 4.1 mmol) and 4-methylpicolinaldehyde (0.5 g, 4.1 mmol) in DCM (10 mL). The reaction mixture was stirred at rt for 16 h and quenched with water (10 mL). The organic layer was separated, dried with MgSO$_4$ and concentrated. The residue was purified by flash chromatography (Combi-flash Rf, Hex/EtOAc=5-75% gradient) to afford the title compound (0.8 g, 88% yield). LCMS method 1: R$_T$=0.97 min, MS (ES) 225.2 (M+H).

Step B. Preparation of (S)—N—((S)-cyclopropyl(4-methylpyridin-2-yl)methyl)-2,2-dimethylpropane-1-sulfinamide 1.0 M Cyclopropyl magnesium bromide solution in 2-methyltetrahydrofuran (8.9 mL, 8.9 mmol) was added to a −78° C. solution of (S,E)-2,2-dimethyl-N-((4-methylpyridin-2-yl)methylene)propane-1-sulfinamide (1.0 g, 4.4 mmol) in THF (30 mL). After 30 minutes, the reaction was quenched by addition of sat. aq. NH$_4$Cl (30 mL). The mixture was stirred for 30 min then filtered. The filtrate was extracted 3×50 mL of EtOAc. The combined organic layers were dried with (MgSO$_4$), filtered, and concentrated. The major diasteromer was isolated by reverse phase HPLC (Phenomenex Gemini C18, H$_2$O/CH$_3$CN gradient from 5-95% CH$_3$CN, 0.2% NH$_4$OH) to yield the title compound (520 mg, 43%).

Step C. Preparation of (S)-cyclopropyl(4-methylpyridin-2-yl)methanamine hydrochloride 4.0 N HCl in dioxane solution (4.8 mL, 19.5 mmol) was added to a solution of (S)—N—((S)-cyclopropyl(4-methylpyridin-2-yl)methyl)-2,2-dimethylpropane-1-sulfinamide (520 mg, 1.95 mmol) in THF (30 mL). The reaction was stirred at rt for 45 min then it was diluted with ether (15 mL) and hexanes (15 mL) to yield a white precipitate. The precipitate was filtered and dried under vacuum to yield the title compound (330 mg, 85%).

Step D. Preparation of (S)—N-(cyclopropyl(4-methylpyridin-2-yl)methyl)-4'-fluoro-5-(hydroxymethyl)-2'-methyl-[1,1'-biphenyl]-3-carboxamide HATU (0.51 g, 1.3 mmol) and TEA (0.62 mL, 3.55 mmol) were added to a −20° C. solution of 4'-fluoro-5-(hydroxymethyl)-2'-methyl-[1,1'-biphenyl]-3-carboxylic acid (230 mg, 0.89 mmol) in DCM (8 mL). The reaction mixture was stirred at −20° C. for 30 min then (S)-cyclopropyl(4-methylpyridin-2-yl)methanamine hydrochloride (0.19 g, 0.98 mmol) was added. The reaction was allowed to warm to rt over 16 h. 1 M Na$_2$CO$_3$ was added and the layers were separated. The organic layer was dried with MgSO$_4$ and concentrated. The residue was purified by flash chromatography (Combi-flash Rf, DCM/MeOH=0-5% gradient) to afford the title compound (0.18 g, 51%). LCMS method 2: R$_T$=1.24 min, MS (ES) 405.0 (M+H).

Step E. (S)-(5-((cyclopropyl(4-methylpyridin-2-yl)methyl)carbamoyl)-4'-fluoro-2'-methyl-[1,1'-biphenyl]-3-yl)methyl methanesulfonate TEA (60 μL, 0.45 mmol) and methanesulfonyl chloride (25 μL, 0.33 mmol) were sequentially added to a solution of (S)—N-(cyclopropyl(4-methylpyridin-2-yl)methyl)-4'-fluoro-5-(hydroxymethyl)-2'-methyl-[1,1'-biphenyl]-3-carboxamide (90 mg, 0.22 mmol) in 5 DCM (5 mL). After stirring at rt for 1 h, the reaction was quenched with sat aq. NaHCO$_3$ solution. The organic layer was separated, dried with MgSO$_4$, and concentrated to provide the title compound (107 mg, 100%). LCMS method 2: R$_T$=1.31 min, MS (ES) 483.0 (M+H).

Step F. Example 91 i-Methyl-1H-imidazol-2-amine (32 mg, 0.33 mmol) and DIPEA (77 μL, 0.44 mmol) were sequentially added to a solution of (S)-(5-((cyclopropyl(4-methylpyridin-2-yl) methyl)carbamoyl)-4'-fluoro-2'-methyl-[1,1'-biphenyl]-3-yl)methyl methanesulfonate (107 mg, 0.22 mmol) in MeCN (1 mL). The reaction was heated at 55° C. for 16 h then concentrated. The residue was purified by reverse phase HPLC (Phenomenex Gemini C18, H$_2$O/CH$_3$CN gradient from 5-95% CH$_3$CN, 0.1% TFA) to yield the title compound (10.0 mg, 9%). $^1$H NMR (CDCl$_3$) δ 8.4 (d, J=5.2 Hz, 1H), 7.84 (d, J=7.9 Hz, 1H), 7.78 (bs, 1H), 7.68 (bs, 1H), 7.27 (s, 1H), 7.17-7.13 (m, 1H), 7.10 (s, 1H), 7.02 (d, J=4.7 Hz, 1H), 6.97-6.89 (m, 2H), 6.13-6.11 (m, 2H), 4.89 (s, 2H), 4.67 (t, J=8.2 Hz, 1H), 3.25 (s, 3H), 2.35 (s, 3H), 2.20 (s, 3H), 1.34-1.28 (m, 1H), 0.651-0.39 (series of m, 4H); LCMS method 2: $R_T$=0.99 min, MS (ES) 484.0 (M+H)

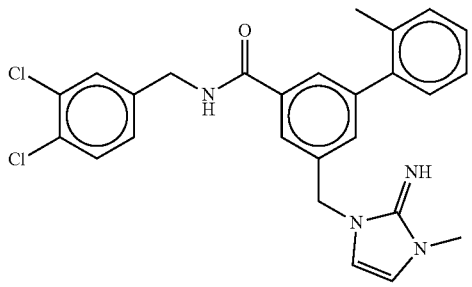

Example 92

N-(3,4-dichlorobenzyl)-5-((2-imino-3-methyl-2,3-dihydro-1H-imidazol-1-yl)methyl)-2'-methyl-[1,1'-biphenyl]-3-carboxamide Step A. Preparation of methyl 5-(hydroxymethyl)-2'-methyl-[1,1'-biphenyl]-3-carboxylate The title compound (116 mg, 93%) was prepared from the procedure described in Example 90, Step A using methyl 3-bromo-5-(hydroxymethyl)benzoate and o-tolylboronic acid: $^1$H NMR (400 MHz, CDCl$_3$) δ 8.02 (s, 1H), 7.95 (s, 1H), 7.56 (s, 1H), 7.22 (m, 4H), 4.82 (d, J=5.6 Hz, 2H), 3.96 (s, 3H), 2.25 (s, 3H), 1.77 (t, J=5.6 Hz, 1H).

Step B. Preparation of 5-(hydroxymethyl)-2'-methyl-[1,1'-biphenyl]-3-carboxylic acid The title compound (110 mg, quant.) was prepared from the procedure described in Example 28, Step C using methyl 5-(hydroxymethyl)-2'-methyl-[1,1'-biphenyl]-3-carboxylate. $^1$H NMR (400 MHz, CD$_3$OD$_3$) δ 7.96 (s, 1H), 7.87 (s, 1H), 7.46 (s, 1H), 7.17 (m, 4H), 4.68 (s, 2H), 2.20 (s, 3H).

Step C. Preparation of N-(3,4-dichlorobenzyl)-5-(hydroxymethyl)-2'-methyl-[1,1'-biphenyl]-3-carboxamide The title compound (67 mg, 79%) was prepared from the procedure described in Example 1, Step C using 5-(hydroxymethyl)-2'-methyl-[1,1'-biphenyl]-3-carboxylic acid and (3,4-Dichlorophenyl)methanamine. 1H NMR (400 MHz, CDCl$_3$) δ 7.80 (s, 1H), 7.66 (s, 1H), 7.44 (m, 3H), 7.25 (m, 5H), 6.48 (br, 1H), 4.81 (d, J=5.6 Hz, 2H), 4.62 (d, J=5.6 Hz, 2H), 2.26 (s, 3H), 1.79 (t, J=5.6 Hz, 1H).

Step D. Preparation of 5-(bromomethyl)-N-(3,4-dichlorobenzyl)-2'-methyl-[1,1'-biphenyl]-3-carboxamide The title compound (76 mg, quant.) was prepared from the procedure described in Example 27, Step D using N-(3,4-dichlorobenzyl)-5-(hydroxymethyl)-2'-methyl-[1,1'-biphenyl]-3-carboxamide. H NMR (400 MHz, CDCl$_3$) δ 7.82 (s, 1H), 7.65 (s, 1H), 7.52 (s, 1H), 7.42 (m, 2H), 7.27 (m, 51H), 4.61 (d, J=6.0 Hz, 2H), 4.55 (s, 2H), 2.26 (s, 3H).

Step E. Example 92

The title compound (21 mg, 66%) was prepared from the procedure described in Example 28, Step F using 5-(bromomethyl)-N-(3,4-dichlorobenzyl)-2'-methyl-[, 1'-biphenyl]-3-carboxamide and 1-methyl-1H-imidazol-2-amine. $^1$H NMR (400 MHz, CDCl$_3$) δ 8.48 (t, J=5.6 Hz, 1H), 7.87 (m, 2H), 7.41 (s, 1H), 7.27 (m, 6H), 7.09 (d, J=7.6 I-z, 1H), 6.42 (m, 2H), 5.09 (s, 2H), 4.47 (d, J=5.6 Hz, 2H), 3.42 (s, 3H), 2.15 (s, 3H); LCMS: >95% 254 nm $R_T$=1.08 min, MS m(ES) 479 (M+H).

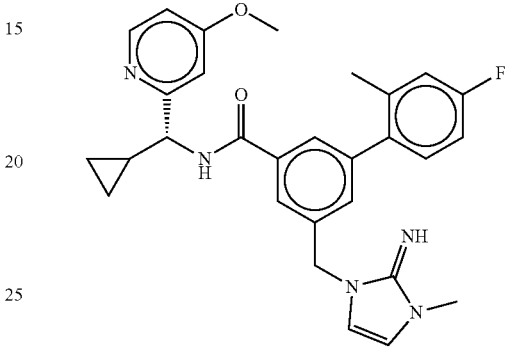

Example 93

(R)—N-(Cyclopropyl(4-methoxypyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide Step A. Preparation of (R,E)-N-((4-methoxypyridin-2-yl)methylene)-2,2-dimethylpropane-1-sulfinamide The title compound (1.2 g, 34%) was prepared from the procedure described in Example 91, Step A using 4-methoxypicolinaldehyde (0.7 g, 5.1 mmol), (R)-2-methylpropane-2-sulfinamide (0.6 g, 5.1 mmol), and cesium carbonate (2.5 g, 7.7 mmol).

Step B. Preparation of (R)—N—((R)-cyclopropyl(4-methoxypyridin-2-yl)methyl)-2,2-dimethylpropane-1-sulfinamide The title compound (0.5 g, 100%) was prepared as the major diasteromer isolated from the procedure described in Example 91, Step B using (R,E)-N-((4-methoxypyridin-2-yl)methylene)-2,2-dimethylpropane-1-sulfinamide (1.2 g, 5.1 mmol), and 1.0 M Cyclopropyl magnesium bromide solution in 2-methyltetrahydrofuran (10.2 mL, 10.2 mmol).

Step C. Preparation of (R)-cyclopropyl(4-methoxypyridin-2-yl)methanamine hydrochloride The title compound (0.37 g, 97%) was prepared from the procedure described in Example 91, Step C using (R)—N—((R)-cyclopropyl(4-methoxypyridin-2-yl)methyl)-2,2-dimethylpropane-1-sulfinamide (0.5 g, 1.8 mmol) and 4.0 N HCl in dioxane solution (4.5 mL, 18 mmol) LCMS method 2: $R_T$=0.31 min, MS (ES) 179.2 (M+H).

Step D. Preparation of (R)—N-(cyclopropyl(4-methoxypyridin-2-yl)methyl)-4'-fluoro-5-(hydroxymethyl)-2'-methyl-[1,1'-biphenyl]-3-carboxamide The title compound (0.31 g, quant.) was prepared from the procedure described in Example 91, Step D using 4'-fluoro-5-(hydroxymethyl)-2'-methyl-[1,1'-biphenyl]-3-carboxylic acid (0.18 g, 0.67 mmol), and (R)-cyclopropyl(4-methoxypyridin-2-yl)methanamine hydrochloride (0.16 g, 0.74 mmol). LCMS method 2: $R_T$=1.11 min, MS (ES) 421.0 (M+H).

Step E. Preparation of (R)-5-(bromomethyl)-N-(cyclopropyl(4-methoxypyridin-2-yl)methyl)-4'-fluoro-2'-methyl-[1,1'-biphenyl]-3-carboxamide Phosphorous tribromide (37 µL, 0.4 mmol) was added to a ice cooled solution of (R)—N-(cyclopropyl(4-methoxypyridin-2-yl)methyl)-4'-fluoro-5-(hydroxymethyl)-2'-methyl-[1,1'-biphenyl]-3-carboxamide (0.14 g, 0.33 mmol) in THF (15 mL). The reaction was stirred and warmed to rt over 16 h. The reaction was diluted with water and EtOAc. The layers were separated and the organic layer was dried with MgSO$_4$ and concentrated to provide the title compound (0.160 g, 100%). LCMS method 2: $R_T$=1.32 min, MS (ES) 482.9 (M+H)

Step F. Example 93

The title compound (17 mg, 16%) was prepared from the procedure described in Example 91, Step F using (R)-5-(bromomethyl)-N-(cyclopropyl(4-methoxypyridin-2-yl)methyl)-4'-fluoro-2'-methyl-[1,1'-biphenyl]-3-carboxamide (0.1 g, 0.21 mmol), 1-methyl-1H-imidazol-2-amine (30 mg, 0.31 mmol) and DIPEA (66 µL, 0.41 mmol). $^1$H NMR (CDCl$_3$) δ 8.34 (d, J=6.0 Hz, 1H), 8.13-8.09 (m, 1H), 7.80 (bs, 1H), 7.69 (bs, 1H), 7.27 (s, 1H), 7.11-7.08 (m, 1H), 6.94-6.86 (m, 2H), 6.83 (d, J=2.7 Hz, 1H), 6.70-6.68 (m, 1H), 6.29-6.26 (m, 2H), 5.13-5.03 (m, 2H), 4.61 (t, J=8.3 Hz, 1H), 3.84 (s, 3H), 3.40 (s, 3H), 2.17 (s, 3H), 1.38-1.29 (m, 1H), (0.64-0.40, series of m, 4H). LCMS method 1: $R_T$=0.8 min, MS (ES) 500.1 (M+H).

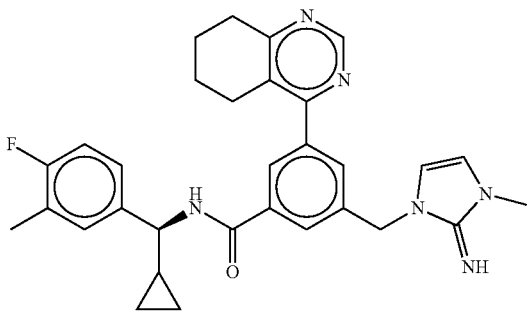

Example 94

(S)—N-(Cyclopropyl(4-fluoro-3-methylphenyl)methyl)-3-((2-imino-3-methyl-2,3-dihydro-1H-imidazol-1-yl)methyl)-5-(5,6,7,8-tetrahydroquinazolin-4-yl)benzamide The title compound was prepared (17 mg, 0.032 mmol) according to the procedures described in Example 60, Steps A-G substituting 4-chloro-5,6,7,8-tetrahydroquinazoline (1 g, 5.9 mmol) in Step C. LC-MS: >95% 254 nm, $R_T$=0.923 min, MS (ES) 525.6 (M+H).

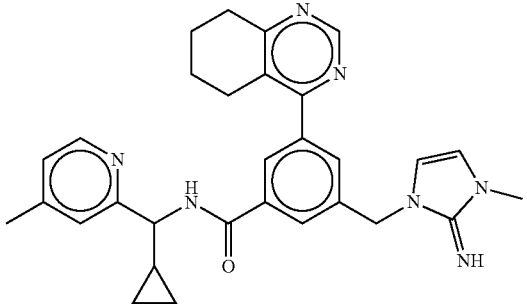

Example 95

N-(Cyclopropyl(4-methylpyridin-2-yl)methyl)-3-((2-imino-3-methyl-2,3-dihydro-1H-imidazol-1-yl)methyl)-5-(5,6,7,8-tetrahydroquinazolin-4-yl)benzamide The title compound was prepared (11 mg, 0.022 mmol) to the procedures described in Example 60, Steps A-G substituting 4-chloro-5,6,7,8-tetrahydroquinazoline (1 g, 5.9 mmol) in Step C and the dihydrochloride salt of cyclopropyl (4-methylpyridin-2-yl)methanamine (0.3 g, 1.3 mmol) in Step E. LC-MS: >95% 254 nm, $R_T$=0.706 min, MS (ES) 508.6 (M+H).

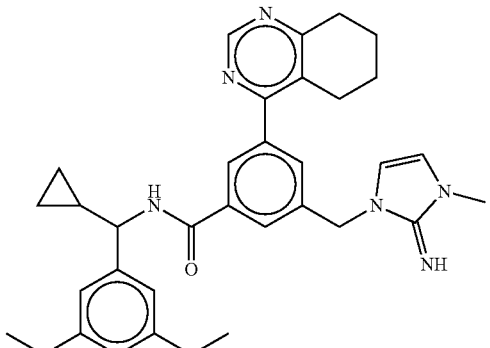

Example 96

N-(Cyclopropyl(3,5-dimethoxyphenyl)methyl)-3-((2-imino-3-methyl-2,3-dihydro-1H-imidazol-1-yl)methyl)-5-(5,6,7,8-tetrahydroquinazolin-4-yl)benzamide The title compound was prepared (14 mg, 0.025 mmol) according to the procedures described in Example 60, Steps A-G substituting 4-chloro-5,6,7,8-tetrahydroquinazoline (1 g, 5.9 mmol) in Step C and the hydrochloride salt of cyclopropyl(3,5-dimethoxyphenyl)methanamine (0.2 g, 0.82 mmol) in Step E. LC-MS: >95% 254 nm, $R_T$=0.883 min, MS (ES) 553 (M+H).

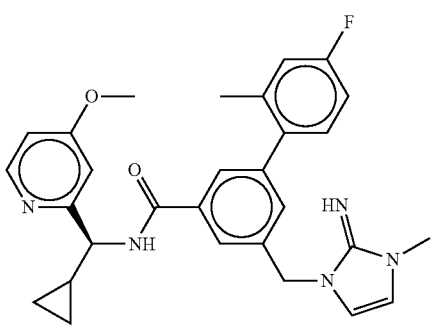

Example 97

(S)—N-(Cyclopropyl(4-methoxypyridin-2-yl)methyl)-4-fluoro-5-((2-imino-3-methyl-2,3-dihydro-1H-imidazol-1-yl)methyl)-2'-methyl-[1,1'-biphenyl]-3-carboxamide Step A. Preparation of (S)-cyclopropyl(4-methoxypyridin-2-yl)methanamine hydrochloride The title compound (0.11 g, 100%) was prepared from the procedure described in Example 91, step C using (R)—N—((S)-cyclopropyl(4-methoxypyridin-2-yl)methyl)-2-methyl-propane-2-sulfinamide (0.15 g, 0.53 mmol) (the minor diasteromer from Example 93, step B) and 4.0 M HCl in dioxane (1.3 mL, 5.3 mmol).

Step B. Preparation of (S)—N-(cyclopropyl(4-methoxypyridin-2-yl)methyl)-4'-fluoro-5-(hydroxymethyl)-2'-methyl-[1,1'-biphenyl]-3-carboxamide The title compound (0.17 g, 81%) was prepared from the procedure described in Example 91, Step D using 4'-fluoro-5-(hydroxymethyl)-2'-methyl-[1,1'-biphenyl]-3-carboxylic acid (0.13 g, 0.48 mmol), and (S)-cyclopropyl(4-methoxypyridin-2-yl)methanamine hydrochloride (0.11 g, 0.53 mmol). LCMS method 2: $R_T$=1.11 min, MS (ES) 421.0 (M+H).

Step C. Preparation of (S)-(5-(((cyclopropyl(4-methoxypyridin-2-yl)methyl)carbamoyl)-4'-fluoro-2'-methyl-[1,1'-biphenyl]-3-yl)methyl methanesulfonate The title compound (0.19 g, 100%) was prepared from the procedure described in Example 91, Step E using (S)—N-(cyclopropyl(4-methoxypyridin-2-yl)methyl)-4'-fluoro-5-(hydroxymethyl)-2'-methyl-[1,1'-biphenyl]-3-carboxamide (0.16 g, 0.39 mmol), DIPEA (136 µL, 0.78 mmol), and methanesulfonyl chloride (45 µL, 0.58 mmol).

Step D. Example 97

The title compound (7 mg, 7%) was prepared from the procedure described in Example 91, Step F using (S)-(5-((cyclopropyl(4-methoxypyridin-2-yl)methyl)carbamoyl)-4'-fluoro-2'-methyl-[1,1'-biphenyl]-3-yl)methyl methanesulfonate (0.1 g, 0.2 mmol), 1-methyl-1H-imidazol-2-amine (29 mg, 0.30 mmol) and DIPEA (70 µL, 0.40 mmol). 1H NMR (CDCl$_3$) δ 8.34 (d, J=6.0 Hz, 1H), 8.13-8.09 (m, 1H), 7.80 (bs, 1H), 7.69 (bs, 1H), 7.27 (s, 1H), 7.11-7.08 (m, 1H), 6.94-6.86 (m, 2H), 6.83 (d, J=2.7 Hz, 1H), 6.70-6.68 (m, 1H), 6.29-6.26 (m, 2H), 5.13-5.03 (m, 2H), 4.61 (t, J=8.3 Hz, 1H), 3.84 (s, 3H), 3.40 (s, 3H), 2.17 (s, 3H), 1.38-1.29 (m, 1H), (0.64-0.40, series of m, 4H). LCMS method 1: $R_T$=0.8 min, MS (ES) 500.1 (M+H).

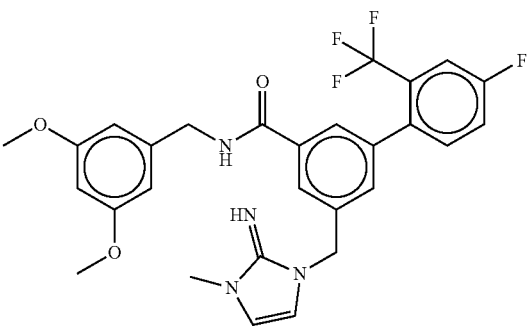

Example 98

N-(3,5-Dimethoxybenzyl)-4'-fluoro-5-((2-imino-3-methyl-2,3-dihydro-1H-imidazol-1-yl)methyl)-2'-(trifluoromethyl)-[1,1'-biphenyl]-3-carboxamide Step A. Preparation of methyl 4'-fluoro-5-(hydroxymethyl)-2'-(trifluoromethyl)-[1,1'-biphenyl]-3-carboxylate The crude mixture of title compound was prepared from the procedure described in Example 1, Step A using methyl 3-bromo-5-(hydroxymethyl)benzoate (500.0 mg, 2.04 mmol) and (4-fluoro-2-(trifluoromethyl)phenyl)boronic acid (509.1 mg, 2.45 mmol). LCMS: $R_T$=1.609 min, MS (ES) 329.3 (M+H).

Step B. Preparation of 4'-fluoro-5-(hydroxymethyl)-2'-(trifluoromethyl)-[1,1'-biphenyl]-3-carboxylic acid The crude title compound was prepared from the procedure described in Example 27, Step B using methyl 4'-fluoro-5-(hydroxymethyl)-2'-(trifluoromethyl)-[1,1'-biphenyl]-3-carboxylate (670.0 mg, 2.04 mmol). LCMS: $R_T$=1.321 min, MS (ES) 315.2 (M+H).

Step C. Preparation of N-(3,5-dimethoxybenzyl)-4'-fluoro-5-(hydroxymethyl)-2'-(trifluoromethyl)-[1,1'-biphenyl]-3-carboxamide The title compound (364.4 mg, 82%) was prepared from the procedure described in Example 33, Step A using 4'-fluoro-5-(hydroxymethyl)-2'-(trifluoromethyl)-[1,1'-biphenyl]-3-carboxylic acid (300.0 mg, 0.95 mmol) and (3,5-dimethoxyphenyl)methanamine (319.3 mg, 1.91 mmol). LCMS: $R_T$=1.630 min, MS (ES) 464.4 (M+H).

Step D. Preparation of 5-(bromomethyl)-N-(3,5-dimethoxybenzyl)-4'-fluoro-2'-(trifluoromethyl)-[1,1'-biphenyl]-3-carboxamide The crude title compound was prepared from the procedure described in Example 27, Step D using N-(3,5-dimethoxybenzyl)-4'-fluoro-5-(hydroxymethyl)-2'-(trifluoromethyl)-[1,1'-biphenyl]-3-carboxamide (34.9 mg, 0.08 mmol). LCMS: $R_T$=1.923 min, MS (ES) 527.3 (M+H).

Step E. Example 98

The title compound (32.0 mg, 78% 2 step) was prepared from the procedure described in Example 1, Step E using 5-(bromomethyl)-N-(3,5-dimethoxybenzyl)-4'-fluoro-2'-(trifluoromethyl)-[1,1'-biphenyl]-3-carboxamide (39.6 mg, 0.08 mmol). $^1$H NMR (400 MHz, Methanol-$d_4$) δ 7.84 (d, J=1.7 Hz, 1H), 7.81 (d, J=1.7 Hz, 1H), 7.57 (dt, J=9.1, 1.6 Hz, 1H), 7.46 (d, J=1.6 Hz, 1H), 7.44 (d, J=1.6 Hz, 1H), 7.35 (s, 1H), 6.91 (d, J=2.5 Hz, 1H), 6.89 (d, J=2.5 Hz, 1H), 6.49 (d, J=2.3 Hz, 2H), 6.36 (t, J=2.3 Hz, 1H), 5.21 (s, 2H), 4.49 (s, 2H), 3.73 (s, 6H), 3.51 (s, 3H); LCMS: $R_T$=1.186 min, MS (ES) 543.5 (M+H).

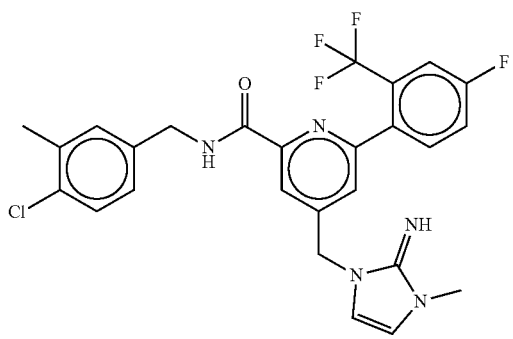

Example 99

N-(4-Chloro-3-methylbenzyl)-6-(4-fluoro-2-(trifluoromethyl)phenyl)-4-((2-imino-3-methyl-2,3-dihydro-1H-imidazol-1-yl)methyl)picolinamide Step A. Preparation of methyl 6-chloro-4-((2-imino-3-methyl-2,3-dihydro-1H-imidazol-1-yl)methyl)picolinate The crude title compound was prepared from the procedure described in Example 1, Step E using methyl 4-(bromomethyl)-6-chloropicolinate (300.0 mg, 1.13 mmol). LCMS: $R_T$=0.225 min, MS (ES) 281.7 (M+H).

Step B. Preparation of methyl (Z)-4-((2-((tert-butoxycarbonyl)imino)-3-methyl-2,3-dihydro-1H-imidazol-1-yl)methyl)-6-chloropicolinate The title compound (323.7 mg, 74% 2 step) was prepared from the procedure described in Example 84, Step B using methyl 6-chloro-4-((2-imino-3-methyl-2,3-dihydro-1H-imidazol-1-yl)methyl)picolinate (318.4 mg, 1.13 mmol). LCMS: $R_T$=0.180 min, MS (ES) 381.8 (M+H).

Step C. Preparation of methyl (Z)-4-((2-((tert-butoxycarbonyl)imino)-3-methyl-2,3-dihydro-1H-imidazol-1-yl)methyl)-6-(4-fluoro-2-(trifluoromethyl)phenyl)picolinate The crude title compound was prepared from the procedure described in Example 1, Step A using methyl (Z)-4-((2-((tert-butoxycarbonyl)imino)-3-methyl-2,3-dihydro-1H-imidazol-1-yl)methyl)-6-chloropicolinate (318.4 mg, 1.13 mmol) and (4-fluoro-2-(trifluoromethyl)phenyl)boronic acid (212.1 mg, 1.02 mmol). LCMS: $R_T$=0.194 min, MS (ES) 509.5 (M+H).

Step D. Preparation of (Z)-4-((2-((tert-butoxycarbonyl)imino)-3-methyl-2,3-dihydro-1H-imidazol-1-yl)methyl)-6-(4-fluoro-2-(trifluoromethyl)phenyl)picolinic Acid The crude title compound was prepared from the procedure described in Example 27, Step B using methyl (Z)-4-((2-((tert-butoxycarbonyl)imino)-3-methyl-2,3-dihydro-1H-imidazol-1-yl)methyl)-6-(4-fluoro-2-(trifluoromethyl)phenyl)picolinate (432.2 mg, 0.85 mmol). LCMS: $R_T$=0.175 min, MS (ES) 495.5 (M+H).

Step E. Preparation of tert-butyl (—Z)(1-((2-((4-chloro-3-methylbenzyl)carbamoyl)-6-(4-fluoro-2-(trifluoromethyl)phenyl)pyridin-4-yl)methyl)-3-methyl-1,3-dihydro-2H-imidazol-2-ylidene) carbamate The title compound (8.5 mg, 18% 3 step) was prepared from the procedure described in Example 33, Step A using (Z)-4-((2-((tert-butoxycarbonyl)imino)-3-methyl-2,3-dihydro-1H-imidazol-1-yl)methyl)-6-(4-fluoro-2-(trifluoromethyl)phenyl)picolinic acid (35.0 mg, 0.07 mmol) and (4-chloro-3-methylphenyl)methanamine (0.02 mL, 0.14 mmol). LCMS: $R_T$=1.511 min, MS (ES) 633.1 (M+H).

Step F. Example 99

The title compound (5.0 mg, 68%) was prepared from the procedure described in Example 84, Step H using tert-butyl (Z)-(1-((2-((4-chloro-3-methylbenzyl)carbamoyl)-6-(4-fluoro-2-(trifluoromethyl)phenyl)pyridin-4-yl)methyl)-3-methyl-1,3-dihydro-2H-imidazol-2-ylidene)carbamate (8.5 mg, 0.01 mmol). LCMS: $R_T$=1.377 min, MS (ES) 532.9 (M+H).

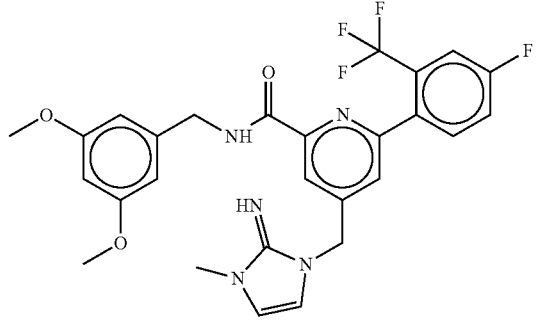

Example 100

N-(3,5-Dimethoxybenzyl)-6-(4-fluoro-2-(trifluoromethyl)phenyl)-4-((2-imino-3-methyl-2,3-dihydro-1-imidazol-1-yl)methyl)picolinamide Step A. Preparation of tert-butyl (Z)$_1$-((2-((3,5-dimethoxybenzyl)carbamoyl)-6-(4-fluoro-2-(trifluoromethyl)phenyl)pyridin-4-yl)methyl)-3-methyl-1,3-dihydro-2H-imidazol-2-ylidene)carbamate The title compound (9.2 mg, 20% 3 step) was prepared from the procedure described in Example 33, Step A using (Z)-4-((2-((tert-butoxycarbonyl)imino)-3-methyl-2,3-dihydro-1H-imidazol-1-yl)methyl)-6-(4-fluoro-2-(trifluoromethyl)phenyl)picolinic acid (35.0 mg, 0.07 mmol) and (3,5-dimethoxyphenyl)methanamine (23.7 mg, 0.14 mmol). LCMS: $R_T$=1.391 min, MS (ES) 644.6 (M+H).

Step B. Example 100

The title compound (1.9 mg, 24%) was prepared from the procedure described in Example 84, Step H using tert-butyl (Z)-(1-((2-((3,5-dimethoxybenzyl)carbamoyl)-6-(4-fluoro-2-(trifluoromethyl)phenyl)pyridin-4-yl)methyl)-3-methyl-1,3-dihydro-2H-imidazol-2-ylidene)carbamate (9.2 mg, 0.01 mmol). LCMS: $R_T$=1.268 min, MS (ES) 544.5 (M+H).

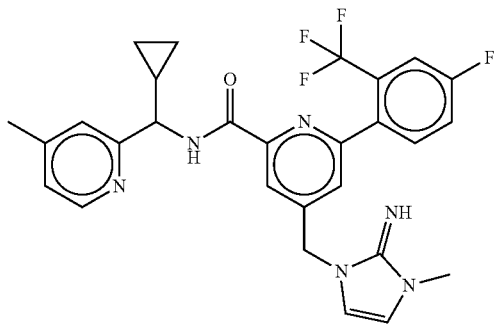

Example 101

N-(Cyclopropyl(4-methylpyridin-2-yl)methyl)-6-(4-fluoro-2-(trifluoromethyl)phenyl)-4-((2-imino-3-methyl-2,3-dihydro-1H-imidazol-1-yl)methyl)picolinamide Step A. Preparation of tert-butyl (Z)-(1-((2-((cyclopropyl(4-methylpyridin-2-yl)methyl)carbamoyl)-6-(4-fluoro-2-(trifluoromethyl)phenyl)pyridin-4-yl)methyl)-3-methyl-1,3-dihydro-2H-imidazol-2-ylidene)carbamate The title compound (28.5 mg, 63% 3 step) was prepared from the procedure described in Example 33, Step A using (Z)-4-((2-((tert-butoxycarbonyl)imino)-3-methyl-2,3-dihydro-1H-imidazol-1-yl)methyl)-6-(4-fluoro-2-(trifluoromethyl)phenyl)picolinic acid (35.0 mg, 0.07 mmol) and cyclopropyl(4-methylpyridin-2-yl)methanamine dihydrochloride (33.3 mg, 0.14 mmol). LCMS: $R_T$=1.208 min, MS (ES) 639.7 (M+H).

Step B. Example 101

The title compound (8.3 mg, 34%) was prepared from the procedure described in Example 84, Step H using tert-butyl (Z)-(1-((2-((cyclopropyl(4-methylpyridin-2-yl)methyl)carbamoyl)-6-(4-fluoro-2-(trifluoromethyl)phenyl)pyridin-4-yl)methyl)-3-methyl-1,3-dihydro-2H-imidazol-2-ylidene)carbamate (28.5 mg, 0.04 mmol). $^1$H NMR (400 MHz, Methanol-$d_4$) δ 8.31 (d, J=5.1 Hz, 1H), 7.91 (d, J=1.5 Hz, 1H), 7.73-7.63 (m, 2H), 7.57-7.49 (m, 2H), 7.26 (s, 1H), 7.13 (d, J=4.5 Hz, 1H), 6.70-6.61 (m, 2H), 4.48 (d, J=8.9 Hz, 1H), 3.35 (s, 3H), 2.36 (s, 3H), 1.38-1.26 (m, 1H), 0.60 (m, 1H), 0.49 (m, 3H); LCMS: $R_T$=1.107 min, MS (ES) 539.6 (M+H).

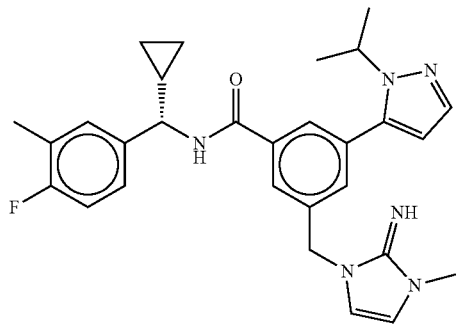

Example 102

(S)—N-(Cyclopropyl(4-fluoro-3-methylphenyl)methyl)-3-((2-imino-3-methyl-2,3-dihydro-1H-imidazol-1-yl)methyl)-5-(1-isopropyl-1H-pyrazol-5-yl)benzamide The title compound was prepared (0.1 g, 0.2 mmol) according to the procedures described in Example 60, Steps A-G substituting 5-bromo-1-isopropyl-1H-pyrazole (1 g, 5.3 mmol) in Step C. LC-MS: >95% 254 nm, $R_T$=0.925 min, MS (ES) 502 (M+H).

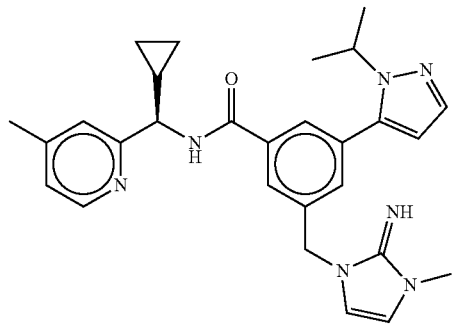

Example 103

(R)—N-(Cyclopropyl(4-methylpyridin-2-yl)methyl)-3-((2-imino-3-ethyl-2,3-dihydro-1H-imidazol-1-yl)methyl)-5-(1-isopropyl-1H-pyrazol-5-yl)benzamide The title compound was prepared (75 mg, 0.16 mmol) according to the procedures described in Example 60, Steps A-G substituting 5-bromo-1-isopropyl-1H-pyrazole (1 g, 5.3 mmol) in Step C and the dihydrochloride salt of (R)-cyclopropyl(4-methylpyridin-2-yl)methanamine (0.3 g, 1.3 mmol) in Step E. LC-MS: >950% 254 nm, $R_T$=0.102 min, MS (ES) 485 (M+H).

281

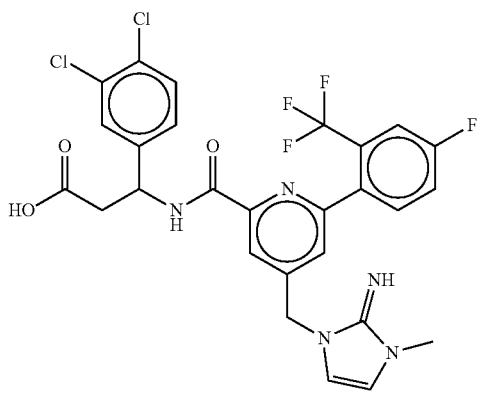

Example 104

3-(3,4-Dichlorophenyl)-3-(6-(4-fluoro-2-(trifluoromethyl)phenyl)-4-((2-imino-3-methyl-2,3-dihydro-1H-imidazol-1-yl)methyl)picolinamido)propanoic acid Step A. Preparation of methyl (Z)-3-(4-((2-((tert-butoxycarbonyl)imino)-3-methyl-2,3-dihydro-1H-imidazol-1-yl)methyl)-6-(4-fluoro-2-(trifluoromethyl)phenyl)picolinamido)-3-(3,4-dichlorophenyl) propanoate The title compound (20.3 mg, 27% 3 step) was prepared from the procedure described in Example 33, Step A using (Z)-4-((2-((tert-butoxycarbonyl)imino)-3-methyl-2,3-dihydro-1H-imidazol-1-yl)methyl)-6-(4-fluoro-2-(trifluoromethyl)phenyl)picolinic acid (50.0 mg, 0.1 mmol) and methyl 3-amino-3-(3,4-dichlorophenyl)propanoate (50.2 mg, 0.2 mmol). LCMS: $R_T$=1.479 min, MS (ES) 725.5 (M+H).

Step B. Preparation of (Z)-3-(4-((2-((tert-butoxycarbonyl)imino)-3-methyl-2,3-dihydro-1H-imidazol-1-yl)methyl)-6-(4-fluoro-2-(trifluoromethyl)phenyl) picolinamido)-3-(3,4-dichlorophenyl)propanoic Acid The crude title compound was prepared from the procedure described in Example 27, Step B using methyl (Z)-3-(4-((2-((tert-butoxycarbonyl)imino)-3-methyl-2,3-dihydro-1H-imidazol-1-yl)methyl)-6-(4-fluoro-2-(trifluoromethyl) phenyl)picolinamido)-3-(3,4-dichlorophenyl)propanoate (20.3 mg, 0.03 mmol). LCMS: $R_T$=1.274 min, MS (ES) 711.5 (M+H).

Step C. Example 104

The title compound (7.0 mg, 40% 2 step) was prepared from the procedure described in Example 84, Step H using (Z)-3-(4-((2-((tert-butoxycarbonyl)imino)-3-methyl-2,3-dihydro-1H-imidazol-1-yl)methyl)-6-(4-fluoro-2-(trifluoromethyl)phenyl)picolinamido)-3-(3,4-dichlorophenyl)propanoic acid (20.0 mg, 0.03 mmol). LCMS: $R_T$=1.290 min, MS (ES) 611.4 (M+H).

282

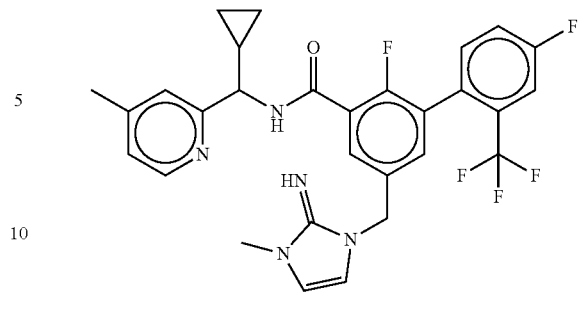

Example 105

N-(Cyclopropyl(4-methylpyridin-2-yl)methyl)-2,4'-difluoro-5-((2-imino-3-methyl-2,3-dihydro-1H-imidazol-1-yl)methyl)-2'-(trifluoromethyl)-[1,1'-biphenyl]-3-carboxamide Step A. Preparation of methyl 3-bromo-2-fluoro-5-methylbenzoate The title compound (678.4 mg, 91%) was prepared from the procedure described in Example 84, Step E using 3-bromo-2-fluoro-5-methylbenzoic acid (700.0 mg, 3.00 mmol). LCMS: $R_T$=1.651 min, MS (ES) 248.1 (M+H).

Step B. Preparation of methyl 2,4'-difluoro-5-methyl-2'-(trifluoromethyl)-[1,1'-biphenyl]-3-carboxylate The title compound (724.5 mg, 79%) was prepared from the procedure described in Example 1, Step A using methyl 3-bromo-2-fluoro-5-methylbenzoate (678.4 mg, 2.75 mmol) and (4-fluoro-2-(trifluoromethyl)phenyl)boronic acid (685.1 mg, 3.3 mmol). LCMS: $R_T$=1.891 min, MS (ES) 331.3 (M+H).

Step C. Preparation of methyl 5-(bromomethyl)-2,4'-difluoro-2'-(trifluoromethyl)-[1,1'-biphenyl]-3-carboxylate N-bromosuccinimide (210.2 mg, 1.2 mmol), benzoyl peroxide (4.4 mg, 0.02 mmol), and acetic acid (0.05 mL, 0.9 mmol) were added to a solution of methyl 2,4'-difluoro-5-methyl-2'-(trifluoromethyl)-[1,1'-biphenyl]-3-carboxylate (300.0 mg, 0.9 mmol) in $CCl_4$ (8.0 mL). The reaction mixture was stirred at 90° C. for 4.5 h. The mixture was cooled to ambient temperature, quenched with $H_2O$ (2.0 mL) and extracted with $CH_2Cl_2$ (3×10.0 mL). The combined organics were dried over $Na_2SO_4$, filtered and concentrated under reduced pressure to yield the title compound which was used for the next step without further purification. LCMS: $R_T$=1.905 min, MS (ES) 410.2 (M+H).

Step D. Preparation of methyl 2,4'-difluoro-5-((2-imino-3-methyl-2,3-dihydro-1H-imidazol-1-yl) methyl)-2'-(trifluoromethyl)-[1,1'-biphenyl]-3-carboxylate The crude title compound was prepared from the procedure described in Example 1, Step E using methyl 5-(bromomethyl)-2,4'-difluoro-2'-(trifluoromethyl)-[1,1'-biphenyl]-3-carboxylate (371.7 mg, 0.9 mmol). LCMS: $R_T$=0.180 min, MS (ES) 426.4 (M+H).

Step E. Preparation of methyl (Z)-5-((2-((tert-butoxycarbonyl)imino)-3-methyl-2,3=dihydro-1H-imidazol-1-yl)methyl)-2,4'-difluoro-2'-(trifluoromethyl)-[1,1'-biphenyl]-3-carboxylate The title compound (377.3 mg, 79% 3 step) was prepared from the procedure described in Example 84, Step B using methyl 2,4'-difluoro-5-((2-imino-3-methyl-2,3-dihydro-1H-imidazol-1-yl)methyl)-2'-(trifluoromethyl)-[1,1'-biphenyl]-3-carboxylate (386.4 mg, 0.91 mmol). LCMS: $R_T$=1.305 min, MS (ES) 526.5 (M+H).

Step F. Preparation of (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic Acid The crude title compound was prepared from the procedure described in Example 27, Step B using methyl (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylate (377.3 mg, 0.72 mmol). LCMS: $R_T$=1.192 min, MS (ES) 512.5 (M+H).

Step G. Preparation of tert-butyl (Z)-(1-((5-((cyclopropyl(4-methylpyridin-2-yl)methyl)carbamoyl)-4',6-difluoro-2'-(trifluoromethyl)-[1,1'-biphenyl]3-yl)methyl)-3-methyl-1,3-dihydro-2H-imidazol-2-ylidene)carbamate The title compound (7.7 mg, 15% 2 step) was prepared from the procedure described in Example 33, Step A using (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic acid (40.0 mg, 0.08 mmol) and cyclopropyl(4-methylpyridin-2-yl)methanamine dihydrochloride (36.8 mg, 0.16 mmol). LCMS: $R_T$=1.244 min, MS (ES) 656.7 (M+H).

Step H. Example 105

The title compound (4.4 mg, 67%) was prepared from the procedure described in Example 84, Step H using tert-butyl (Z)-(1-((5-((cyclopropyl(4-methylpyridin-2-yl)methyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate (7.7 mg, 0.01 mmol). LCMS: $R_T$=1.103 min, MS (ES) 556.6 (M+H).

Example 106

Methyl 3-(3,4-dichlorophenyl)-3-(6-(4-fluoro-2-(trifluoromethyl)phenyl)-4-((2-imino-3-methyl-2,3-dihydro-1H-imidazol-1-yl)methyl)picolinamido)propanoate The title compound (6.8 mg) was obtained from Example 104, Step C as a MeOH transesterification by-product. LCMS: $R_T$=1,398 min, MS (ES) 625.4 (M+H).

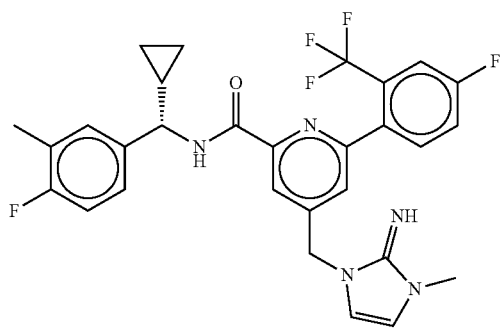

Example 107

(S)—N-(Cyclopropyl(4-fluoro-3-methylphenyl)methyl)-6-(4-fluoro-2-(trifluoromethyl)phenyl)-4-((2-imino-3-methyl-2,3-dihydro-1H-imidazol-1-yl)methyl)picolinamide Step A. Preparation of tert-butyl (S,Z)-(1-((2-((cyclopropyl(4-fluoro-3-methylphenyl)methyl)carbamoyl)-6-(4-fluoro-2-(trifluoromethyl)phenyl)pyridin-4-yl)methyl)-3-methyl-1,3-dihydro-2H-imidazol-2-ylidene)carbamate The title compound (14.4 mg, 27% 3 step) was prepared from the procedure described in Example 33, Step A using (Z)-4-((2-((tert-butoxycarbonyl)imino)-3-methyl-2,3-dihydro-1H-imidazol-1-yl)methyl)-6-(4-fluoro-2-(trifluoromethyl)phenyl)picolinic acid (40.0 mg, 0.08 mmol) and (S)-cyclopropyl(4-fluoro-3-methylphenyl)methanamine hydrochloride (34.9 mg, 0.2 mmol). LCMS: $R_T$=1.553 min, MS (ES) 656.7 (M+H).

Step B. Example 107

The title compound (1.4 mg, 11%) was prepared from the procedure described in Example 84, Step H using tert-butyl (S,Z)-(1-((2-((cyclopropyl(4-fluoro-3-methylphenyl)methyl)carbamoyl)-6-(4-fluoro-2-(trifluoromethyl)phenyl)pyridin-4-yl)methyl)-3-methyl-1,3-dihydro-2H-imidazol-2-ylidene)carbamate (14.4 mg, 0.02 mmol). LCMS: $R_T$=1.457 min, MS (ES) 556.6 (M+H).

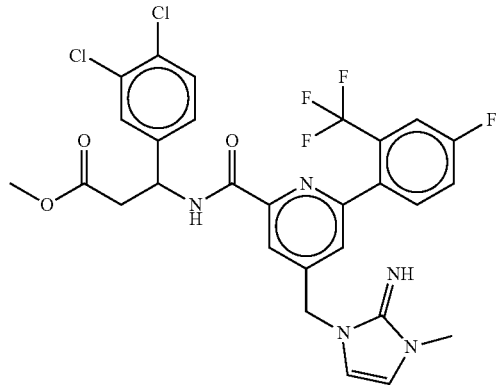

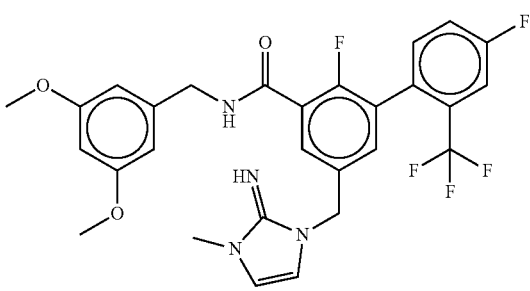

Example 108

N-(3,5-Dimethoxybenzyl)-2,4'-difluoro-5-((2-imino-3-methyl-2,3-dihydro-1H-imidazol-1-yl)methyl)-2'-(trifluoromethyl)-[1,1'-biphenyl]-3-carboxamide Step A. Preparation of tert-butyl (Z)-(1-((5-((3,5-dimethoxybenzyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate The title compound (26.4 mg, 51%) was prepared from the procedure described in Example 33, Step A using (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic acid (40.0 mg, 0.08 mmol) and (3,5-dimethoxyphenyl)methanamine (26.2 mg, 0.16 mmol). LCMS: $R_T$=1.396 min, MS (ES) 661.6 (M+H).

Step B. Example 108

The title compound (16.5 mg, 73%) was prepared from the procedure described in Example 84, Step H using tert-butyl (Z) 1-(1(5-((3,5-dimethoxybenzyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate (26.4 mg, 0.02 mmol). LCMS: $R_T$=1.258 min, MS (ES) 561.5 (M+H).

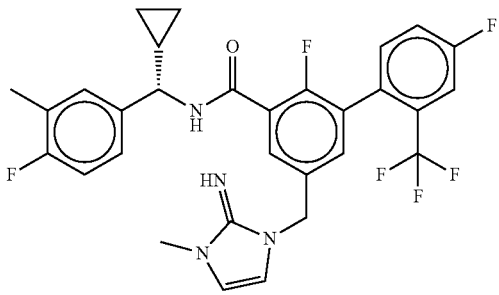

Example 109

(S)—N-(Cyclopropyl(4-fluoro-3-methylphenyl)methyl)-2,4-difluoro-5-((2-imino-3-methyl-2,3-dihydro-1H-imidazol-1-yl)methyl)-2'-(trifluoromethyl)-[1,1'-biphenyl]-3-carboxamide Step A. Preparation of tert-butyl (S,Z)-(1-((5-((cyclopropyl(4-fluoro-3-methylphenyl)ethyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate The title compound (26.1 mg, 49%) was prepared from the procedure described in Example 33, Step A using (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic acid (40.0 mg, 0.08 mmol) and (S)-cyclopropyl(4-fluoro-3-methylphenyl)methanamine hydrochloride (33.7 mg, 0.16 mmol). LCMS: $R_T$=1.532 min, MS (ES) 673.7 (M+H).

Step B. Example 109

The title compound (11.1 mg, 49%) was prepared from the procedure described in Example 84, Step H using tert-butyl (S,Z)-(1-((5-(((cyclopropyl(4-fluoro-3-methylphenyl)methyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate (26.1 mg, 0.04 mmol). LCMS: $R_T$=1.421 min, MS (ES) 573.6 (M+H).

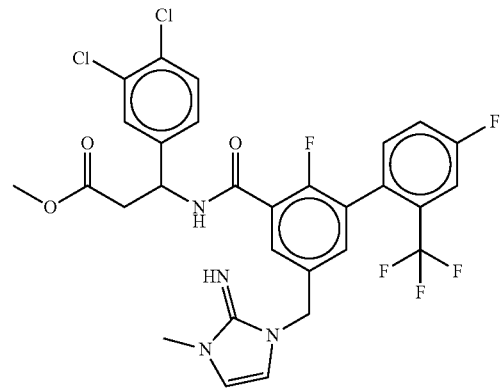

Example 110

Methyl 3-(3,4-dichlorophenyl)-3-(2,4'-difluoro-5-((2-imino-3-methyl-2,3-dihydro-1H-imidazol-1-yl)methyl)-2'-(trifluoromethyl)-[1,1'-biphenyl]-3-carboxamido)propanoate Step A. Preparation of methyl (Z)-3-(5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxamido)-3-(3,4-dichlorophenyl)propanoate The title compound (10.8 mg, 18%) was prepared from the procedure described in Example 33, Step A using (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic acid (40.0 mg, 0.08 mmol) and methyl 3-amino-3-(3,4-dichlorophenyl)propanoate (38.8 mg, 0.16 mmol). LCMS: $R_T$=1.526 min, MS (ES) 742.5 (M+H).

Step B. Example 110

The title compound (6.5 mg, 69%) was prepared from the procedure described in Example 84, Step H using methyl (Z)-3-(5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxamido)-3-(3,4-dichlorophenyl)propanoate (10.8 mg, 0.01 mmol). LCMS: $R_T$=1.418 min, MS (ES) 642.4 (M+H).

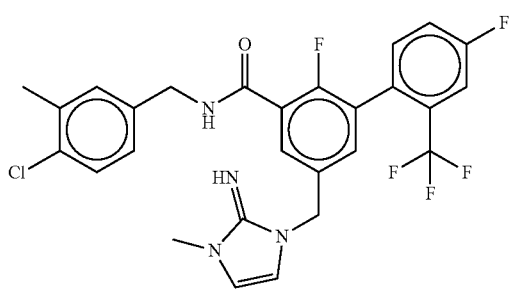

Example 111

N-(4-Chloro-3-methylbenzyl)-2,4'-difluoro-5-((2-imino-3-methyl-2,3-dihydro-1H-imidazol-1-yl)methyl)-2'-(trifluoromethyl)-[1,1'-biphenyl]-3-carboxamide Step A. Preparation of tert-butyl (Z)-(1-((5-((4-chloro-3-methylbenzyl)carbamoyl)-4',6-difloro-2'-(trifluoromethyl)-[1,1'-biphenyl]-3-yl)methyl)-3-methyl-1,3-dihydro-2H-imidazol-2-ylidene)carbamate The title compound (22.9 mg, 45%) was prepared from the procedure described in Example 33, Step A using (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic acid (40.0 mg, 0.08 mmol) and (4-chloro-3-methylphenyl)methanamine (24.3 mg, 0.16 mmol). LCMS: $R_T$=1.482 min, MS (ES) 650.1 (M+H).

Step B. Example 11

The title compound (16.6 mg, 85%) was prepared from the procedure described in Example 84, Step H using tert-butyl (Z)-(1-((5-((4-chloro-3-methylbenzyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate (22.9 mg, 0.04 mmol). LCMS: $R_T$=1.383 min, MS (ES) 549.9 (M+H).

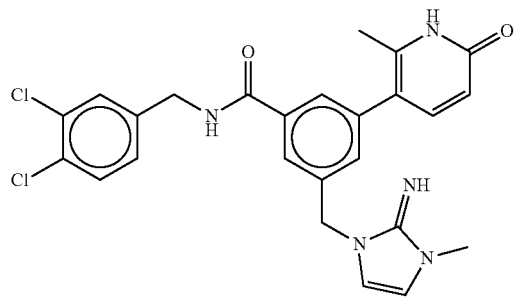

Example 112

N-(3,4-Cichlorobenzyl)-3-((2-imino-3-methyl-2,3-dihydro-1-imidazol-1-yl)methyl)-5-(2-methyl-6-oxo-1,6-dihydropyridin-3-yl)benzamide The title compound (6 mg, 25%) was synthesized according to the procedure outlined for Example 80 using N-(3,4-dichlorobenzyl)-3-(6-fluoro-2-methylpyridin-3-yl)-5-((2-imino-3-methyl-2,3-dihydro-1H-imidazol-1-yl)methyl)benzamide (24 mg, 0.05 mmol). LCMS: $R_T$=1.04 min, MS (ES) 495.9 (M+H).

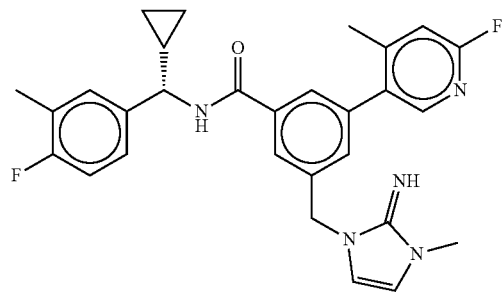

Example 113

(S)—N-(Cyclopropyl(4-fluoro-3-methylphenyl)methyl)-3-(6-fluoro-4-methylpyridin-3-yl)-5-((2-imino-3-methyl-2,3-dihydro-1H-imidazol-1-yl)methyl)benzamide Step A. Preparation of (S)—N-(cyclopropyl(4-fluoro-3-methylphenyl)methyl)-3-(6-fluoro-4-methylpyridin-3-yl)-5-(hydroxymethyl)benzamide The title compound (410 mg, 97%) was prepared according to the procedure outlined for Example 78 Step C, using (S)-cyclopropyl(4-fluoro-3-methylphenyl)methanamine hydrochloride (259 mg, 1.2 mmol). LCMS: $R_T$=1.04 min, MS (ES) 423 (M+H).

Step B. Preparation of (S)-3-(bromomethyl)-N-(cyclopropyl(4-fluoro-3-methylphenyl)methyl)-5-(6-fluoro-4-methylpyridin-3-yl)benzamide The title compound (218 mg, 46%) was prepared according to the procedure outlined for Example 78 Step D, from (S)—N-(cyclopropyl(4-fluoro-3-methylphenyl)methyl)-3-

(6-fluoro-4-methylpyridin-3-yl)-5-(hydroxymethyl)benzamide (410 mg, 0.97 mmol). LCMS: $R_T$=1.28 min, MS (ES) 485, 487 (M+H).

Step C. Example 113

Title compound (42 mg, 19%) was prepared according to the procedure outlined for Example 78 Step E, from (S)-3-(bromomethyl)-N-(cyclopropyl(4-fluoro-3-methylphenyl)methyl)-5-(6-fluoro-4-methylpyridin-3-yl)benzamide (218 mg, 0.45 mmol). LCMS: $R_T$=1.23 min, MS (ES) 503.0 (M+H)$^+$.

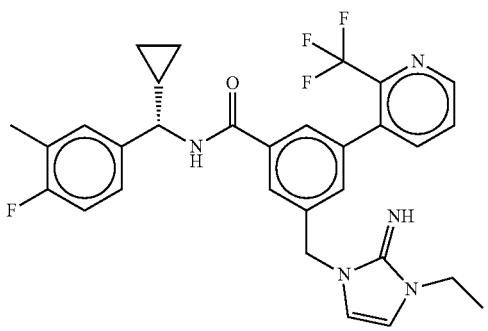

Example 114

(S)—N-(Cyclopropyl(4-fluoro-3-methylphenyl)methyl)-3-((3-ethyl-2-imino-2,3-dihydro-1H-imidazol-1-yl)methyl)-5-(2-(trifluoromethyl)pyridin-3-yl)benzamide The title compound was prepared (22 mg, 0.04 mmol) according to the procedures described in Example 60, Steps A-G substituting 1-ethyl-1H-imidazol-2-amine (25 mg, 0.22 mmol) in Step G. $^1$H NMR (400 MHz, Chloroform-d) δ 8.72 (dd, J=4.7, 1.6 Hz, 1H), 7.94 (s, 1H), 7.75-7.68 (m, 2H), 7.53 (dd, J=7.8, 4.7 Hz, 1H), 7.38 (s, 1H), 7.29 (s, 1H), 7.26-7.22 (m, 3H), 6.93 (dd, J=10.2, 7.9 Hz, 1H), 6.19 (dd, J=19.7, 2.7 Hz, 2H), 4.94 (s, 2H), 4.55-4.43 (m, 1H), 3.63 (q, J=7.3 Hz, 2H), 2.24 (d, J=1.9 Hz, 3H), 1.29 (d, J=7.3 Hz, 3H), 0.62 (dt, J=7.8, 2.5 Hz, 2H), 0.51 (dt, J=7.9, 4.5 Hz, 1H), 0.39 (ddd, J=10.6, 4.9, 2.1 Hz, 1H); LC-MS: >95% 254 nm, $R_T$=0.99 min, MS (ES) 552.2 (M+H).

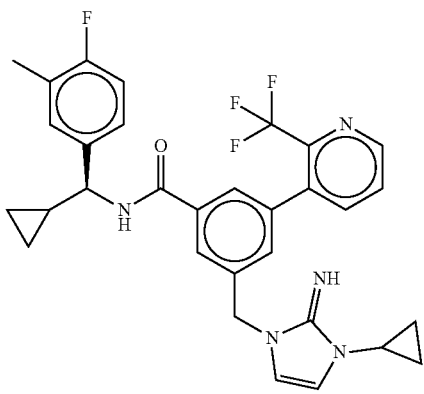

Example 115

(S)—N-(Cyclopropyl(4-fluoro-3-methylphenyl)methyl)-3-((3-cyclopropyl-2-imino-2,3-dihydro-1H-imidazol-1-yl)methyl)-5-(2-(trifluoromethyl)pyridin-3-yl)benzamide Title compound was prepared (25 mg, 0.044 mmol) as a tan solid according to the procedures described in Example 60, Steps A-G substituting 1-cyclopropyl-1H-imidazol-2-amine (25 mg, 0.20 mmol) in Step G. LC-MS: >95% 254 nm, $R_T$=0.981 min, MS (ES) 564.2 (M+H).

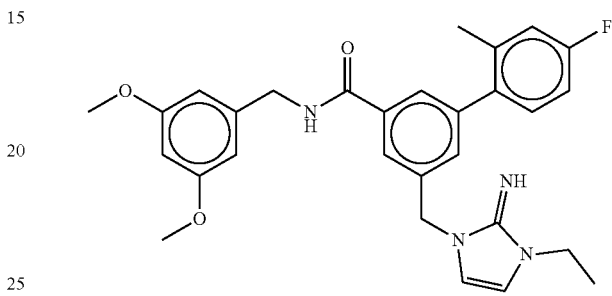

Example 116

N-(3,5-Dimethoxybenzyl)-5-((3-ethyl-2-imino-2,3-dihydro-1H-imidazol-1-yl)methyl)-4'-fluoro-2'-methyl-[1,1'-biphenyl]-3-carboxamide The title compound was prepared (23 mg, 0.045 mmol) according to the procedures described in Example 1, Steps A-E substituting (4-fluoro-2-methylphenyl)boronic acid (5 g, 32.4 mmol) in Step A, (3,5-dimethoxyphenyl)methanamine (0.3 g, 1.8 mmol) in Step C and 1-ethyl-1H-imidazol-2-amine (25 mg, 0.22 mmol) in Step E. LC-MS: >95% 254 nm, $R_T$=0.963 min, MS (ES) 503.2 (M+H).

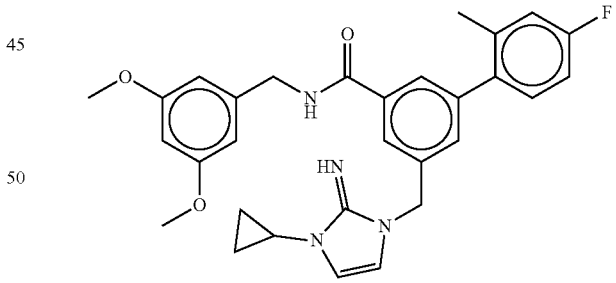

Example 117

5-((3-Cyclopropyl-2-imino-2,3-dihydro-1H-imidazol-1-yl)methyl)-N-(3,5-dimethoxybenzyl)-4'-fluoro-2'-methyl-[1,1'-biphenyl]-3-carboxamide The title compound was prepared (27 mg, 0.051 mmol) as a white solid according to the procedures described in Example 1, Steps A-E substituting (4-fluoro-2-methylphenyl)boronic acid (5 g, 32.4 mmol) in Step A, (3,5-dimethoxyphenyl)methanamine (0.3 g, 1.8 mmol) in Step C and 1-cyclopropyl-1H-imidazol-2-amine (25 mg, 0.20 mmol) in Step E. LC-MS: >95% 254 nm, $R_T$=0.961 min, MS (ES) 515.2 (M+H).

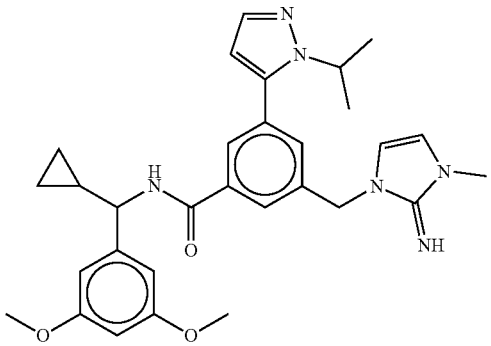

Example 118

N-(Cyclopropyl(3,5-dimethoxyphenyl)methyl)-3-((2-imino-3-methyl-2,3-dihydro-1H-imidazol-1-yl)methyl)-5-(1-isopropyl-1H-pyrazol-5-yl)benzamide The title compound was prepared (0.11 g, 0.21 mmol) according to the procedures described in Example 60, Steps A-G substituting 5-bromo-1-isopropyl-1H-pyrazole (1 g, 5.3 mmol) in Step C and the hydrochloride salt of cyclopropyl (3,5-dimethoxyphenyl)methanamine (0.2 g, 0.82 mmol) in Step E. $^1$H NMR (400 MHz, Chloroform-d) δ 7.84 (s, 1H), 7.74 (t, J=1.7 Hz, 1H), 7.56 (d, J=1.8 Hz, 1H), 7.31 (d, J=1.7 Hz, 1H), 7.05 (d, J=7.9 Hz, 1H), 6.61 (d, J=2.3 Hz, 2H), 6.36 (t, J=2.3 Hz, 1H), 6.24 (d, J=1.8 Hz, 1H), 6.18-6.13 (m, 2H), 4.91 (d, J=2.0 Hz, 2H), 4.56-4.45 (m, 2H), 3.78 (s, 6H), 3.24 (s, 3H), 1.44 (dd, J=6.6, 1.3 Hz, 6H), 1.32-1.25 (m, 1H), 0.67-0.60 (m, 2H), 0.56-0.52 (m, 1H), 0.46-0.42 (m, 1H); LC-MS: >95% 254 nm, $R_T$=0.911 min, MS (ES) 529.3 (M+H).

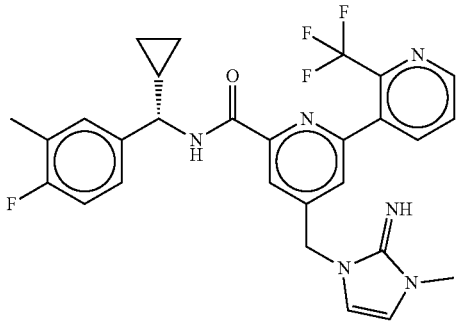

Example 119

(S)—N-(Cyclopropyl(4-fluoro-3-methylphenyl)methyl)-4-((2-imino-3-methyl-2,3-dihydro-1H-imidazol-1-yl)methyl)-2'-(trifluoromethyl)-[2,3'-bipyridine]-6-carboxamide Step A. Preparation of (Z)-4-((2-((tert-butoxycarbonyl)imino)-3-methyl-2,3-dihydro-1H-imidazol-1-yl)methyl)-2'-(trifluoromethyl)-[2,3'-bipyridine]-6-carboxylic Acid The title compound (37.8 mg, 14%) was prepared from the procedure described in Example 1, Step A using methyl (Z)-4-((2-((tert-butoxycarbonyl)imino)-3-methyl-2,3-dihydro-1H-imidazol-1-yl)methyl)-6-chloropicolinate (22.9 mg, 0.04 mmol) and (2-(trifluoromethyl)pyridin-3-yl)boronic acid. The methyl ester was hydrolyzed during the reaction to form the title compound. LCMS: $R_T$=0.937 min, MS (ES) 478.4 (M+H).

Step B. Preparation of tert-butyl (S,Z)$_1$-((6-((cyclopropyl(4-fluoro-3-methylphenyl)methyl)carbamoyl)-2'-(trifluoromethyl)-[2,3'-bipyridin]-4-yl)methyl)-3-methyl-1,3-dihydro-2H-imidazol-2-ylidene) carbamate The title compound (14.8 mg, 29%) was prepared from the procedure described in Example 33, Step A using (Z)-4-((2-((tert-butoxycarbonyl)imino)-3-methyl-2,3-dihydro-1H-imidazol-1-yl)methyl)-2'-(trifluoromethyl)-[2,3'-bipyridine]-6-carboxylic acid (37.8 mg, 0.08 mmol) and (S)-cyclopropyl(4-fluoro-3-methylphenyl)methanamine hydrochloride (34.2 mg, 0.16 mmol). LCMS: $R_T$=1.424 min, MS (ES) 639.7 (M+H).

Step C. Example 119

The title compound (1.4 mg, 11%) was prepared from the procedure described in Example 84, Step H using tert-butyl (S,Z)-(1-((6-((cyclopropyl(4-fluoro-3-methylphenyl)methyl)carbamoyl)-2'-(trifluoromethyl)-[2,3'-bipyridin]-4-yl)methyl)-3-methyl-1,3-dihydro-2H-imidazol-2-ylidene)carbamate (14.8 mg, 0.02 mmol). LCMS: $R_1$=1.332 min, MS (ES) 539.6 (M+H).

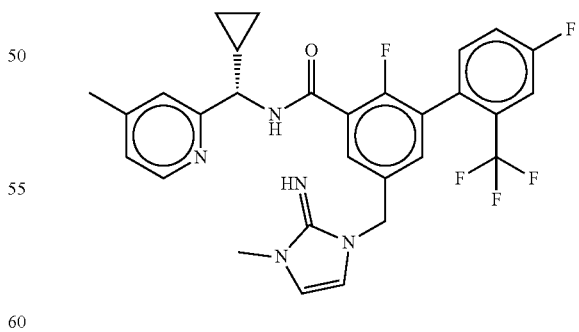

Example 120

(S)—N-(Cyclopropyl(4-methylpyridin-2-yl)methyl)-2,4'-difluoro-5-((2-imino-3-methyl-2,3-dihydro-1H-imidazol-1-yl)methyl)-2'-(trifluoromethyl)-[1,1'-biphenyl]-3-carboxamide Step A. Preparation of tert-butyl (S,Z)-(1-((5-((cyclopropyl(4-methylpyridin-2-yl)methyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate The title compound (23.3 mg, 51%) was prepared from the procedure described in Example 33, Step A using (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic acid (35.0 mg, 0.08 mmol) and (S)-cyclopropyl(4-methylpyridin-2-yl)methanamine dihydrochloride (32.2 mg, 0.14 mmol). LCMS: $R_T$=1.241 min, MS (ES) 656.7 (M+H).

Step B. Example 120

The title compound (12.9 mg, 65%) was prepared from the procedure described in Example 84, Step H using tert-butyl (S,Z)-(1-((5-((cyclopropyl(4-methylpyridin-2-yl)methyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate (23.3 mg, 0.04 mmol). LCMS: $R_T$=1.116 min, MS (ES) 556.6 (M+H).

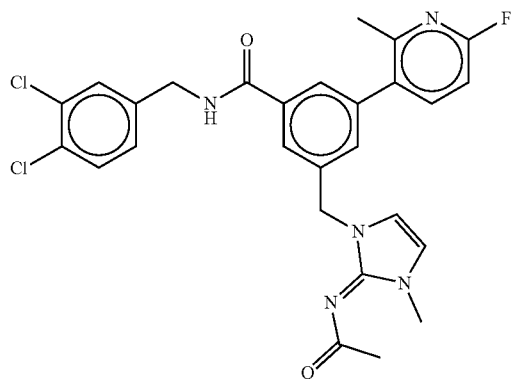

Example 121

(E)-3-((2-(acetylimino)-3-methyl-2,3-dihydro-1H-imidazol-1-yl)methyl)-N-(3,4-dichlorobenzyl)-5-(6-fluoro-2-methylpyridin-3-yl)benzamide 1 M aq. Na$_2$CO$_3$ (0.4 mL, 0.4 mmol) and acetic anhydride (14 µL, 0.15 mmol) were sequentially added to a solution of N-(3,4-dichlorobenzyl)-3-(6-fluoro-2-methylpyridin-3-yl)-5-(((1-methyl-1H-imidazol-2-yl)amino)methyl)benzamide, Example 1, (50 mg, 0.1 mmol) in THF (1 mL). The reaction was stirred at rt for 16 h then diluted with water and EtOAc. The layers were separated and the organic layer was dried with MgSO$_4$ and concentrated to dryness. The residue was purified by flash chromatography (Combi-flash Rf, DCM/MeOH=0-5% gradient) to provide the title compound (17 mg, 31%). $^1$H NMR (CDCl$_3$) δ 8.42 (t, J=6.2 Hz, 1H), 7.89 (s, 1H), 7.62-7.59 (m, 2H), 7.54 (d, J=1.8 Hz, 1H), 7.38 (d, J=9.1 Hz, 1H), 7.31 (s, 1H), 6.83 (dd, J=8.1, 3.2 Hz, 1H), 6.73 (d, J=2.4 Hz, 1H), 6.66 (d, J=2.4 Hz, 1H), 5.11 (s, 2H), 4.58 (d, J=6.2 Hz, 2H), 3.53 (s, 3H), 2.42 (s, 3H), 2.06 (s, 3H), LCMS method 2: $R_T$=1.22 min, MS (ES) 539.8 (M+).

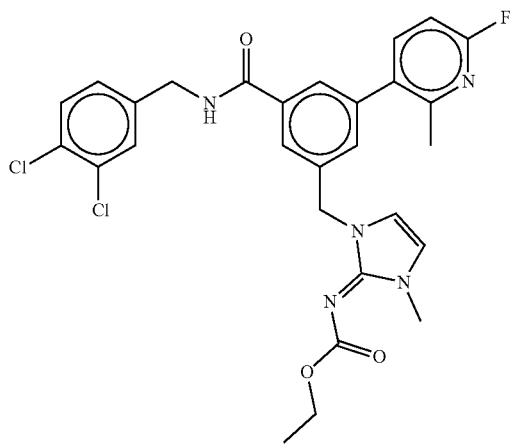

Example 122

Ethyl (1-(3-((3,4-dichlorobenzyl)carbamoyl)-5-(6-fluoro-2-methyl pyridin-3-yl)benzyl)-3-methyl-1,3-dihydro-2H-imidazol-2-ylidene)carbamate The title compound (28 mg, 49%) was prepared from the procedure described in Example 121 using N-(3,4-dichlorobenzyl)-3-(6-fluoro-2-methylpyridin-3-yl)-5-(((1-methyl-1H-imidazol-2-yl)amino)methyl)benzamide, Example 1, (50 mg, 0.1 mmol) and ethyl chloroformate (14 µL, 0.15 mmol). $^1$H NMR (DMSO d6) δ 9.13 (d, J=5.9 Hz, 1H), 7.87-7.80 (m, 3H), 7.60 (s, 1H), 7.58-7.56 (m, 1H), 7.42 (bs, 1H), 7.31 (dd, J=7.9, 2.2 Hz, 1H), 7.13-7.10 (m, 2H), 7.03 (d, J=2.5 Hz, 1H), 5.11 (s, 2H), 4.46 (d, J=5.9 Hz, 2H), 3.85 (q, J=7.0 Hz, 2H), 3.32 (s, 3H), 2.35 (s, 3H), 1.05 (t, J=7.0 Hz, 3H). LCMS method 2: $R_T$=1.28 min, MS (ES) 569.8 (M+).

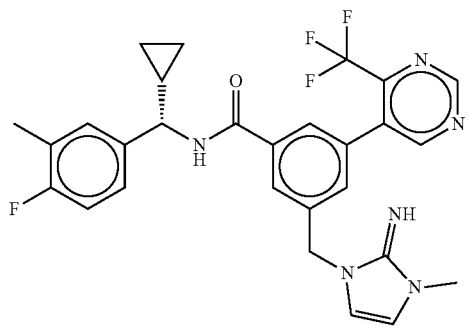

Example 123

(S)—N-(Cyclopropyl(4-fluoro-3-methylphenyl)methyl)-3-((2-imino-3-methyl-2,3-dihydro-1H-imidazol-1-yl)methyl)-5-(4-(trifluoromethyl)pyrimidin-5-yl)benzamide The title compound was prepared (22 mg, 0.041 mmol) according to the procedures described in Example 60 substituting 5-bromo-4-(trifluoromethyl)pyrimidine (1 g, 4.4 mmol) in Step C. LC-MS: >95% 254 nm, $R_T$=0.935 min, MS (ES) 539.2 (M+H).

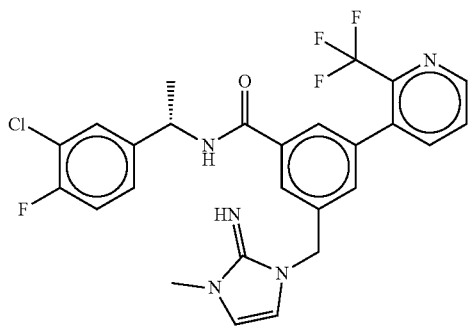

Example 124

(S)—N-(1-(3-chloro-4-fluorophenyl)ethyl)-3-((2-imino-3-methyl-2,3-dihydro-1H-imidazol-1-yl)methyl)-5-(2-(trifluoromethyl)pyridin-3-yl)benzamide The title compound was prepared (30 mg, 0.056 mmol) according to the procedures described in Example 60, Steps A-G substituting the hydrochloride salt of (S)-1-(3-chloro-4-fluorophenyl)ethan-1-amine (64 mg, 0.3 mmol) in Step E. LC-MS: >95% 254 nm, $R_T$=0.927 min, MS (ES) 532.1 (M+H).

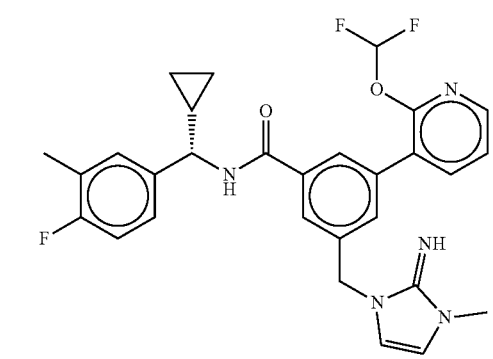

Example 125

(S)—N-(Cyclopropyl(4-fluoro-3-methylphenyl)methyl)-3-((2-imino-3-methyl-2,3-dihydro-1H-imidazol-1-yl)methyl)-5-(1-methyl-3-(trifluoromethyl)-1H-pyrazol-4-yl)benzamide The title compound was prepared (39 mg, 0.072 mmol) according to the procedures described in Example 60, Steps A-G substituting 4-bromo-1-methyl-3-(trifluoromethyl)-1H-pyrazole (1 g, 4.3 mmol) in Step C. LC-MS: >95% 254 nm, $R_T$=0.962 min, MS (ES) 541.2 (M+H).

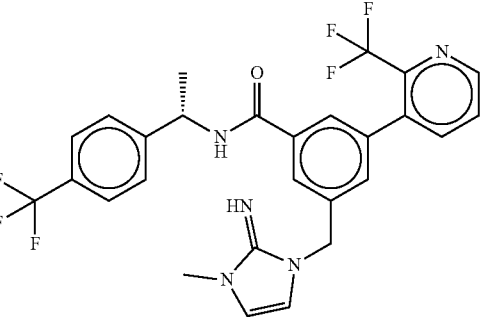

Example 126

(S)-3-((2-Imino-3-methyl-2,3-dihydro-1H-imidazol-1-yl)methyl)-N-(1-(4-(trifluoromethyl)phenyl)ethyl)-5-(2-(trifluoromethyl)pyridin-3-yl)benzamide The title compound was prepared (32 mg, 0.058 mmol) according to the procedures described in Example 60, Steps A-G substituting the hydrochloride salt of (S)-1-(4-(trifluoromethyl)phenyl)ethan-1-amine (68 g, 0.3 mmol) in Step E. LC-MS: >95% 254 nm, $R_T$=0.971 min, MS (ES) 548.1 (M+1).

Example 127

(S)—N-(Cyclopropyl(4-fluoro-3-methylphenyl)methyl)-3-(2-(difluoromethoxy)pyridin-3-yl)-5-((2-imino-3-methyl-2,3-dihydro-1H-imidazol-1-yl)methyl)benzamide The title compound was prepared (14 mg, 0.026 mmol) according to the procedures described in Example 60, Steps A-G substituting 3-bromo-2-(difluoromethoxy)pyridine (1 g, 4.4 mmol) in Step C. LC-MS: >95% 254 nm, $R_T$=0.999 min, MS (ES) 536.2 (M+H).

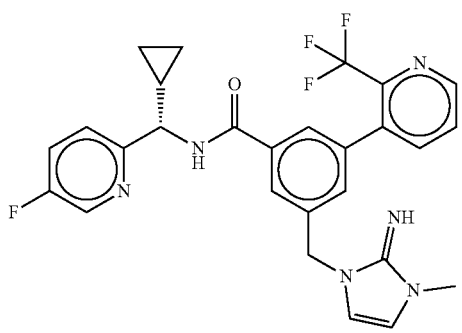

Example 128

(S)—N-(Cyclopropyl(5-fluoropyridin-2-yl)methyl)-3-((2-imino-3-methyl-2,3-dihydro-1H-imidazol-1-yl)methyl)-5-(2-(trifluoromethyl)pyridin-3-yl)benzamide The title compound was prepared (50 mg, 0.095 mmol) according to the procedures described in Example 60, Steps A-G substituting the di-hydrochloride salt of (S)-cyclopropyl(5-fluoropyridin-2-yl)methanamine (78 g, 0.36 mmol) in Step E. LC-MS: >95% 254 nm, $R_T$=0.832 min, MS (ES) 525.1 (M+H).

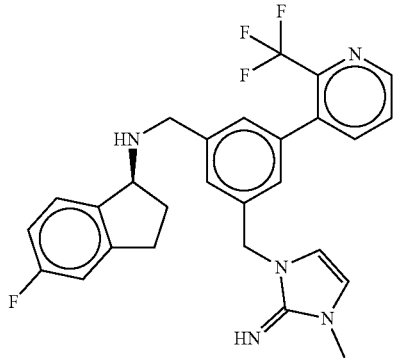

Example 129

(S)—N-(5-Fluoro-2,3-dihydro-1H-inden-1-yl)-3-((2-imino-3-methyl-2,3-dihydro-1H-imidazol-1-yl)methyl)-5-(2-(trifluoromethyl)pyridin-3-yl)benzamide The title compound was prepared (16 mg, 0.031 mmol) according to the procedures described in Example 60, Steps A-G substituting the hydrochloride salt of (S)-5-fluoro-2,3-dihydro-1H-inden-1-amine (57 g, 0.3 mmol) in Step E. LC-MS: >95% 254 nm, $R_T$=0.905 min, MS (ES) 510.2 (M+H).

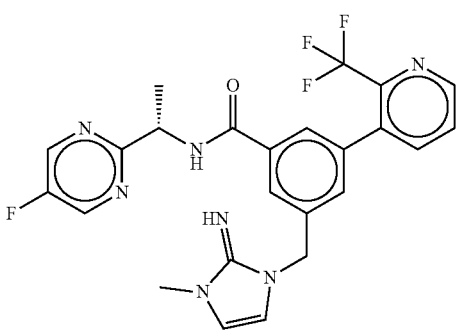

Example 130

(S)—N-(1-(5-Fluoropyrimidin-2-yl)ethyl)-3-((2-imino-3-methyl-2,3-dihydro-1H-imidazol-1-yl)methyl)-5-(2-(trifluoromethyl)pyridin-3-yl)benzamide The title compound was prepared (61 mg, 0.12 mmol) according to the procedures described in Example 60, Steps A-G substituting the hydrochloride salt of (S)-1-(5-fluoropyrimidin-2-yl)ethan-1-amine (97 g, 0.55 mmol) in Step E. LC-MS: >95% 254 nm, $R_T$=0.706 min, MS (ES) 500.2 (M+H).

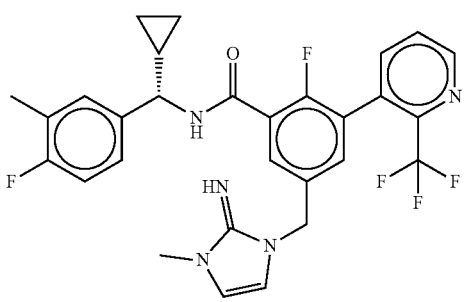

Example 131

(S)—N-(Cyclopropyl(4-fluoro-3-methylphenyl)methyl)-2-fluoro-5-((2-imino-3-methyl-2,3-dihydro-1H-imidazol-1-yl)methyl)-3-(2-(trifluoromethyl)pyridin-3-yl)benzamide Step A. Preparation of methyl 2-fluoro-5-methyl-3-(2-(trifluoromethyl)pyridin-3-yl)benzoate The title compound (187.8 mg, 24%) was prepared from the procedure described in Example 1, Step A using methyl 3-bromo-2-fluoro-5-methylbenzoate (600.0 mg, 2.4 mmol) and (2-(trifluoromethyl)pyridin-3-yl)boronic acid (556.4 mg, 2.9 mmol). LCMS: $R_T$=1.650 min, MS (ES) 314.3 (M+H).

Step B. Preparation of methyl 5-(bromomethyl)-2-fluoro-3-(2-(trifluoromethyl)pyridin-3-yl)benzoate The crude mixture of title compound was prepared from the procedure described in Example 105, Step C using methyl 2-fluoro-5-methyl-3-(2-(trifluoromethyl)pyridin-3-yl)benzoate (173.0 mg, 0.55 mmol). LCMS: $R_T$=1.690 min, MS (ES) 393.2 (M+H).

Step C. Preparation of methyl 2-fluoro-5-((2-imino-3-methyl-2,3-dihydro-1H-imidazol-1-yl)methyl)-3-(2-(trifluoromethyl)pyridin-3-yl)benzoate The crude title compound was prepared from the procedure described in Example 1, Step E using methyl 5-(bromomethyl)-2-fluoro-3-(2-(trifluoromethyl)pyridin-3-yl)benzoate (229.2 mg, 0.58 mmol). LCMS: $R_T$=1.015 min, MS (ES) 409.4 (M+H).

Step D. Preparation of methyl (E)-5-((2-((tert-butoxycarbonyl)imino)-3-methyl-2,3-dihydro-1H-imidazol-1-yl)methyl)-2-fluoro-3-(2-(trifluoromethyl)pyridin-3-yl)benzoate The title compound (164.3 mg, 550% 3 step) was prepared from the procedure described in Example 84, Step B using methyl 2-fluoro-5-((2-imino-3-methyl-2,3-dihydro-1H-imidazol-1-yl)methyl)-3-(2-(trifluoromethyl)pyridin-3-yl)benzoate (239 mg, 0.58 mmol). LCMS: $R_T$=1.167 min, MS (ES) 509.5 (M+H).

Step E. Preparation of (E)-5-((2-((tert-butoxycarbonyl)imino)-3-methyl-2,3-dihydro-1H-imidazol-1-yl)methyl)-2-fluoro-3-(2-(trifluoromethyl)pyridin-3-yl)benzoic Acid The crude title compound was prepared from the procedure described in Example 27, Step B using methyl (E)-5-((2-((tert-butoxycarbonyl)imino)-3-methyl-2,3-dihydro-1H-imidazol-1-yl)methyl)-2-fluoro-3-(2-(trifluoromethyl)pyridin-3-yl)benzoate (164 mg, 0.32 mmol). LCMS: $R_T$=1.062 min, MS (ES) 495.5 (M+H).

Step F. Preparation of tert-butyl (S,E)-(1-(3-((cyclopropyl(4-fluoro-3-methylphenyl)methyl)carbamoyl)-4-fluoro-5-(2-(trifluoromethyl)pyridin-3-yl)benzyl)-3-methyl-1,3-dihydro-2H-imidazol-2-ylidene)carbamate The title compound (10.4 mg, 26% 2 step) was prepared from the procedure described in Example 33, Step A using (E)-5-((2-((tert-butoxycarbonyl)imino)-3-methyl-2,3-dihydro-1H-imidazol-1-yl)methyl)-2-fluoro-3-(2-(trifluoromethyl)pyridin-3-yl)benzoic acid (30 mg, 0.06 mmol) and (S)-cyclopropyl(4-fluoro-3-methylphenyl)methanamine hydrochloride (26.2 mg, 0.12 mmol). LCMS: $R_T$=1.437 min, MS (ES) 656.7 (M+H).

Step G. Example 131

The title compound (7.0 mg, 79%) was prepared from the procedure described in Example 84, Step H using tert-butyl (S,E)-(1-(3-((cyclopropyl(4-fluoro-3-methylphenyl)methyl)carbamoyl)-4-fluoro-5-(2-(trifluoromethyl)pyridin-3-yl)benzyl)-3-methyl-1,3-dihydro-2H-imidazol-2-ylidene)carbamate (10.4 mg, 0.02 mmol). LCMS: $R_T$=1.313 min, MS (ES) 556.6 (M+H).

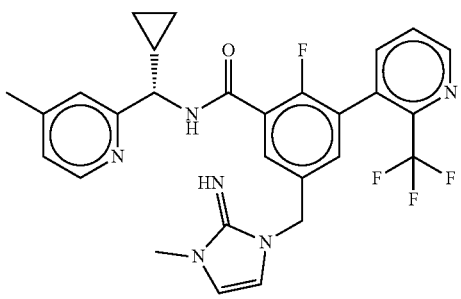

Example 132

(S)—N-(Cyclopropyl(4-methylpyridin-2-yl)methyl)-2-fluoro-5-((2-imino-3-methyl-2,3-dihydro-1H-imidazol-1-yl)methyl)-3-(2-(trifluoromethyl)pyridin-3-yl)benzamide Step A. Preparation of tert-butyl (S,E)-(1-(3-((cyclopropyl(4-methylpyridin-2-yl)methyl)carbamoyl)-4-fluoro-5-(2-(trifluoromethyl)pyridin-3-yl)benzyl)-3-methyl-1,3-dihydro-2H-imidazol-2-ylidene)carbamate The title compound (13.0 mg, 33% 2 step) was prepared from the procedure described in Example 33, Step A using (E)-5-((2-((tert-butoxycarbonyl)imino)-3-methyl-2,3-dihydro-1H-imidazol-1-yl)methyl)-2-fluoro-3-(2-(trifluoromethyl)pyridin-3-yl)benzoic acid (30.0 mg, 0.06 mmol) and (S)-cyclopropyl(4-methylpyridin-2-yl)methanamine dihydrochloride (28.5 mg, 0.12 mmol). LCMS: $R_T$=1.110 min, MS (ES) 639.7 (M+H).

Step B. Example 132

The title compound (4.5 mg, 41%) was prepared from the procedure described in Example 84, Step H using tert-butyl (S,E)-(1-(3-((cyclopropyl(4-methylpyridin-2-yl)methyl)carbamoyl)-4-fluoro-5-(2-(trifluoromethyl)pyridin-3-yl)benzyl)-3-methyl-1,3-dihydro-2H-imidazol-2-ylidene)carbamate (13.0 mg, 0.02 mmol). LCMS: $R_T$=0.956 min, MS (ES) 539.6 (M+H).

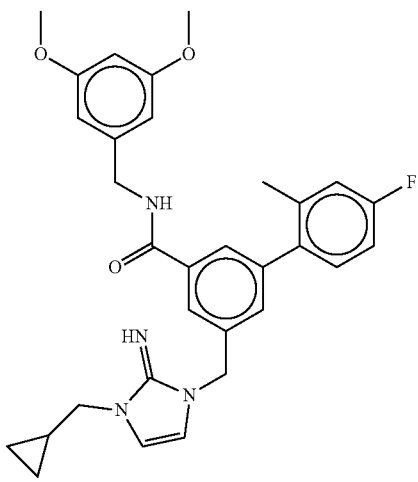

Example 133

N-(3,5-Dimethoxybenzyl)-4'-fluoro-5-((2-imino-3-phenyl-2,3-dihydro-1H-imidazol-1-yl)methyl)-2'-methyl-[1,1'-biphenyl]-3-carboxamide The title compound was prepared (19 mg, 0.034 mmol) according to the procedures described in Example 1, Steps A-E substituting (4-fluoro-2-methylphenyl)boronic acid (5 g, 32.4 mmol) in Step A, (3,5-dimethoxyphenyl)methanamine (0.3 g, 1.8 mmol) in Step C and 1-phenyl-1H-imidazol-2-amine (20 mg, 0.13 mmol) in Step E. LC-MS: >95% 254 nm, $R_T$=0.986 min, MS (ES) 551.2 (M+H).

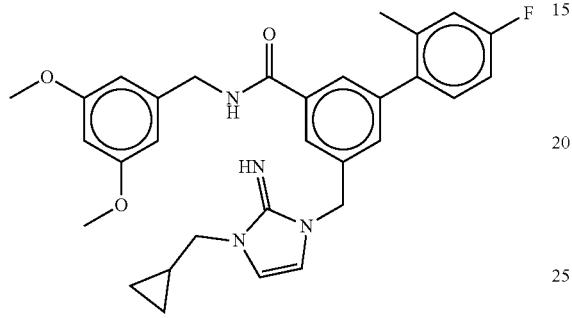

Example 134

5-((3-(Cyclopropylmethyl)-2-imino-2,3-dihydro-1H-imidazol-1-yl)methyl)-N-(3,5-dimethoxybenzyl)-4'-fluoro-2'-methyl-[1,1'-biphenyl]-3-carboxamide The title compound was prepared (23 mg, 0.044 mmol) according to the procedures described in Example 1, Steps A-E substituting (4-fluoro-2-methylphenyl)boronic acid (5 g, 32.4 mmol) in Step A (3,5-dimethoxyphenyl)methanamine (0.3 g, 1.8 mmol) in Step C and 1-(cyclopropylmethyl)-1H-imidazol-2-amine (17 mg, 0.13 mmol) in Step E. LC-MS: >95% 254 nm, $R_T$=0.971 min, MS (ES) 529.2 (M+H).

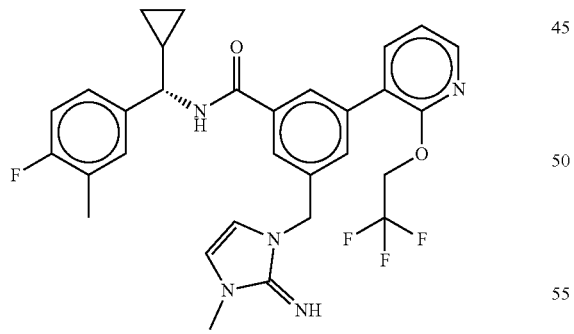

Example 135

(S)—N-(Cyclopropyl(4-fluoro-3-methylphenyl)methyl)-3-((2-imino-3-methyl-2,3-dihydro-1H-imidazol-1-yl)methyl)-5-(2-(2,2,2-trifluoroethoxy)pyridin-3-yl)benzamide The title compound was prepared (45 mg, 0.081 mmol) according to the procedures described in Example 60, Steps A-G substituting 3-bromo-2-(2,2,2-trifluoroethoxy)pyridine (1 g, 3.9 mmol) in Step C. LC-MS: >95% 254 nm, $R_4$=0.992 min, MS (ES) 555.1 (M+H).

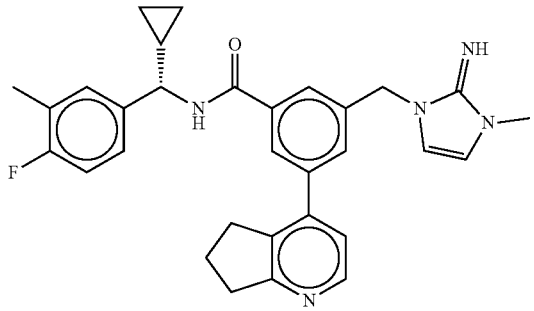

Example 136

(S)—N-(Cyclopropyl(4-fluoro-3-methylphenyl)methyl)-3-(6,7-dihydro-5H-cyclopenta[b]pyridin-4-yl)-5-((2-imino-3-methyl-2,3-dihydro-1H-imidazol-1-yl)methyl)benzamide The title compound was prepared (50 mg, 0.098 mmol) according to the procedures described in Example 60, Steps A-G substituting 4-chloro-6,7-dihydro-5H-cyclopenta[b]pyridine (1 g, 6.5 mmol) in Step C. LC-MS: >95% 254 nm, $R_T$=0.817 min, MS (ES) 510.2 (M+H).

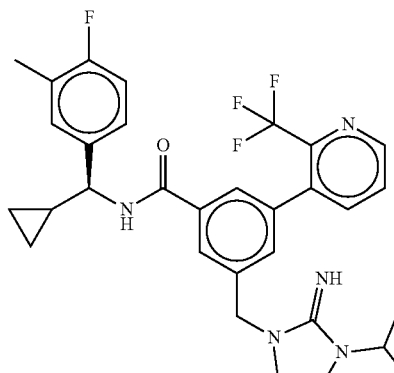

Example 137

(S)—N-(Cyclopropyl(4-fluoro-3-methylphenyl)methyl)-3-((2-imino-3-phenyl-2,3-dihydro-1H-imidazol-1-yl)methyl)-5-(2-(trifluoromethyl)pyridin-3-yl)benzamide The title compound was prepared (19 mg, 0.031 mmol) according to the procedures described in Example 60, Steps A-G substituting 1-phenyl-1H-imidazol-2-amine (20 mg, 0.13 mmol) in Step G. $^1$H NJ R (400 MHz, Chloroform-d) δ 8.82 (dd, J=5.0, 1.6 Hz, 1H), 8.20 (d, J=1.8 Hz, 1H), 8.09 (dd, J=8.0, 1.7 Hz, 1H), 7.99 (d, J=1.7 Hz, 1H), 7.57 (s, 1H), 7.54-7.33 (m, 8H), 7.28 (dd, J=5.5, 2.6 Hz, 1H), 6.92 (dd, J=9.6, 8.2 Hz, 1H), 6.47 (d, J=2.7 Hz, 1H), 6.41 (d, J=2.7 Hz, 1H), 5.14 (d, J=4.5 Hz, 2H), 4.53-4.45 (m, 1H), 2.24 (d, J=2.0 Hz, 3H), 1.35 (dddd, J=12.9, 9.5, 8.1, 4.9 Hz, 1H), 0.61 (dt, J=8.1, 2.6 Hz, 2H), 0.49 (ddd, J=10.8, 4.8, 2.1 Hz, 1H), 0.36 (ddd, J=9.5, 4.8, 1.5 Hz, 1H); LC-MS: >95% 254 nm, $R_T$=1.009 min, MS (ES) 600.2 (M+H).

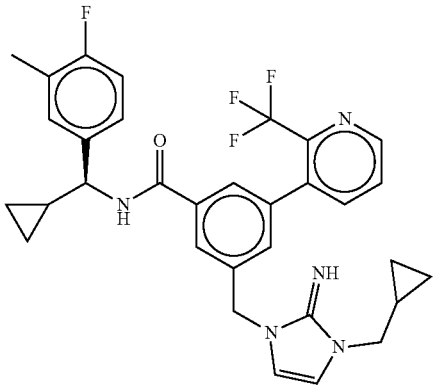

Example 138

(S)—N-(Cyclopropyl(4-fluoro-3-methylphenyl)methyl)-3-((3-(cyclopropylmethyl)-2-imino-2,3-dihydro-1H-imidazol-1-yl)methyl)-5-(2-(trifluoromethyl)pyridin-3-yl)benzamide The title compound was prepared (20 mg, 0.034 mmol) according to the procedures described in Example 60, Steps A-G substituting 1-(cyclopropylmethyl)-1H-imidazol-2-amine (17 mg, 0.13 mmol) in Step G. $^1$H NMR (400 MHz, Chloroform-d) δ 8.80 (dd, J=4.9, 1.6 Hz, 1H), 8.12-8.04 (m, 2H), 8.02 (d, 0.1=1.7 Hz, 1H), 7.91 (d, J=7.8 Hz, 1H), 7.45 (dd, J=8.0, 4.8 Hz, 1H), 7.40 (s, 1H), 7.26 (s, 2H), 6.89 (dd, J=9.6, 8.3 Hz, 1H), 6.61 (d, J=2.6 Hz, 1H), 6.38 (d, J=2.6 Hz, 1H), 5.13 (d, J=3.3 Hz, 2H), 4.42 (dd, J=9.3, 7.8 Hz, 1H), 3.65 (d, J=7.3 Hz, 2H), 2.21 (d, J=2.0 Hz, 3H), 1.43-1.32 (m, 1H), 1.09 (tt, J=7.7, 4.8 Hz, 1H), 0.66-0.56 (m, 4H), 0.49-0.42 (m, 1H), 0.34 (dd, J=6.5, 4.2 Hz, 3H); LC-MS: >95% 254 nm, $R_T$=1.006 min, MS (ES) 678.2 (M+H).

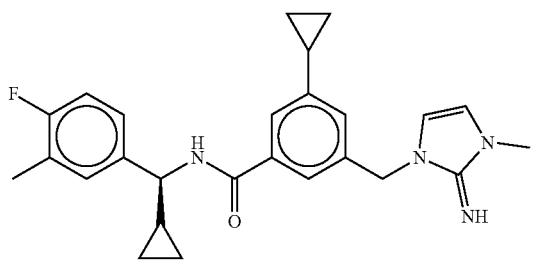

Example 139

(S)-3-Cyclopropyl-N-(cyclopropyl(4-fluoro-3-methylphenyl)methyl)-5-((2-imino-3-methyl-2,3-dihydro-1H-imidazol-1-yl)methyl)benzamide Step A. Preparation of methyl 3-cyclopropyl-5-(hydroxymethyl)benzoate Pd(OAc)$_2$ (45 mg, 0.2 mmol), RuPhos (100 mg, 0.2 mmol), K$_3$PO$_4$ (1.3 g, 6.1 mmol) and cyclopropylboronic acid (263 mg, 3.06 mmol) were added to a solution of methyl 3-bromo-5-(hydroxymethyl)benzoate (500 mg, 2.0 mmol) in toluene (20 mL). The reaction mixture was degassed using Ar gas then stirred at 100° C. for 20 h. The reaction mixture was filtered through Celite pad (washed with EtOAc) and concentrated. The residue was purified by flash chromatography (Combi-flash Rf, 1-Hex/EtOAc=0-50% gradient) to afford the title compound (260 mg, 62%). LCMS method 2: $R_T$=1.28 min, MS (ES) 207.1 (M+H).

Step B. Preparation of 3-cyclopropyl-5-(hydroxymethyl)benzoic Acid

LiOH (261 mg, 10.9 mmol) was added to a solution of methyl 3-cyclopropyl-5-(hydroxymethyl)benzoate (450 mg, 2.2 mmol) in THF/MeOH/H$_2$O (10 mL, 4:1:1). The reaction mixture was stirred at rt for 2 h. The reaction was acidified with 1 M HCl solution until pH<4.0. The mixture was extracted with EtOAc(3×10 mL). The organic layers were combined, dried over MgSO$_4$, and concentrated to obtain the title compound (358 mg, 85%).

Step C. Preparation of (S)-3-cyclopropyl-N-(cyclopropyl(4-fluoro-3-methylphenyl)methyl)-5-(hydroxymethyl)benzamide The title compound (256 mg, 0.72 mmol) was prepared from the procedure described in Example 91, Step D using 3-cyclopropyl-5-(hydroxymethyl)benzoic acid (0.15 g, 0.78 mmol) and (S)-cyclopropyl(4-fluoro-3-methylphenyl)methanamine hydrochloride (0.2 g, 0.94 mmol). LCMS method 2: $R_T$=1.62 min, MS (ES) 354.1 (M+H).

Step D. Preparation of (S)-3-(bromomethyl)-5-cyclopropyl-N-(cyclopropyl(4-fluoro-3-methylphenyl)methyl)benzamide PPh$_3$ (0.38 g, 1.5 mmol) and NBS (0.26 g, 1.5 mmol) were added to a solution of (S)-3-cyclopropyl-N-(cyclopropyl(4-fluoro-3-methylphenyl)methyl)-5-(hydroxymethyl)benzamide (0.26 g, 0.72 mmol) THF (10 mL) at 0° C. The reaction was warmed to rt overnight then concentrated. The residue was purified by flash chromatography (Combi-flash Rf, Hex/EtOAc=5-25% gradient) to afford the title compound (202 mg, 67%). LCMS method 2: $R_T$=1.94 min, MS (ES) 415.9 (M+).

Step E. Example 139

The title compound (20 mg, 38%) was prepared from the procedure described in Example 91, Step F using (S)-3-(bromomethyl)-5-cyclopropyl-N-(cyclopropyl(4-fluoro-3-methylphenyl)methyl)benzamide (50 mg, 0.12 mmol), 1-methyl-1H-imidazol-2-amine (17 mg, 0.18 mmol) and DIPEA (42 µL, 0.24 mmol). $^1$H NMR (CDCl$_3$) δ 7.61 (s, 1H), 7.45 (s, 1H), 7.37 (d, J=8.3 Hz, 1H), 7.26-7.22 (m, 2H), 7.04 (m, 1H), 6.92 (t, J=8.2 Hz, 1H), 6.27 (d, J=2.6 Hz, 1H), 6.22 (d, J=2.6 Hz, 1H), 4.89 (s, 2H), 4.45 (d, J=8.7 Hz, 1H), 3.38 (s, 3H), 2.23 (s, 3H), 1.90-1.84 (m, 1H), 1.34-1.27 (m, 1H), 0.99-0.94 (m, 2H), 0.71-0.67 (m, 2H), 0.64-0.59 (m, 2H), 0.52-0.47 (m, 1H), 0.39-0.34 (m, 1H). LCMS method 2: $R_T$=1.28 min, MS (ES) 333.0 (M+H).

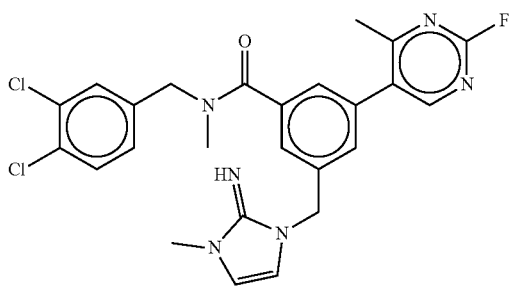

Example 140

(N-(3,4-Dichlorobenzyl)-3-(6-fluoro-2-methylpyridin-3-yl)-5-((2-imino-3-methyl-2,3-dihydro-1H-imidazol-1-yl)methyl)-N-methylbenzamide Step A. Preparation of tert-butyl (E)-(1-(3-((3,4-dichlorobenzyl)carbamoyl)-5-(6-fluoro-2-methylpyridin-3-yl)benzyl)-3-methyl-1,3-dihydro-2H-imidazol-2-ylidene)carbamate The title compound (75 mg, 83%) was prepared from the procedure described in Example 121, using N-(3,4-dichlorobenzyl)-3-(6-fluoro-2-methylpyridin-3-yl)-5-(((1-methyl-1H-imidazol-2-yl)amino)methyl)benzamide, Example 1, (75 mg, 0.15 mmol) and di-tert-butyl-dicarbonate (52 µL, 0.225 mmol). LCMS method 2: $R_T$=1.37 min, MS (ES) 597.9 (M+).

Step B. Preparation of tert-butyl (E)-(1-(3-((3,4-dichlorobenzyl)(methyl)carbamoyl)-5-(6-fluoro-2-methylpyridin-3-yl)benzyl)-3-methyl-1,3-dihydro-2H-imidazol-2-ylidene)carbamate 60% NaH (7 mg, 0.19 mmol) was added to a 0° C. solution of tert-butyl (E)-(1-(3-((3,4-di chlorobenzyl)carbamoyl)-5-(6-fluoro-2-methylpyridin-3-yl)benzyl)-3-methyl-1,3-dihydro-2H-imidazol-2-ylidene)carbamate (75 mg, 0.125 mmol) in DMF (1 mL). After 30 min, iodomethane (9 µL, 0.15 mmol) was added, and the reaction was stirred for 20 h at rt. The reaction was quenched with brine (2 mL) and extracted with EtOAc (3×5 mL). The combined organic layer was dried with MgSO$_4$ and concentrated. The residue was purified by flash chromatography (Combi-flash Rf, DCM/MeOH=0-5% gradient) to afford the title compound (35 mg, 46%).

Step C. Example 140

To a solution of tert-butyl (E)-(1-(3-((3,4-dichlorobenzyl)(methyl)carbamoyl)-5-(6-fluoro-2-methylpyridin-3-yl)benzyl)-3-methyl-1,3-dihydro-2H-imidazol-2-ylidene)carbamate (35 mg, 0.057 mmol) in THF (1 mL) was added 3 drops of concentrated HCl. The reaction mixture was stirred at rt for 4 h then concentrated. The residue was purified by reverse phase HPLC (Phenomenex Gemini C18, H$_2$O/CH$_3$CN gradient from 5-95% CH$_3$CN, 0.1% TFA) to yield the title compound (17 mg, 58%). LCMS method 2: $R_T$=1.26 min, MS (ES) 511.9 (M+).

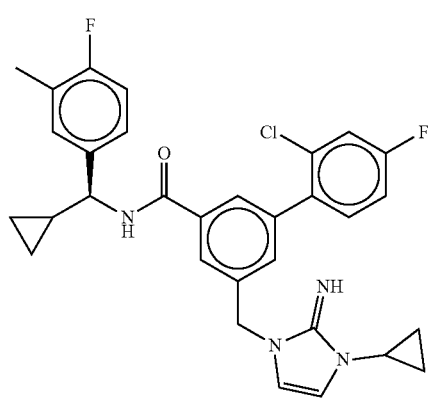

Example 141

(S)-2'-Chloro-N-(cyclopropyl(4-fluoro-3-methylphenyl)methyl)-5-((3-cyclopropyl-2-imino-2,3-dihydro-1H-imidazol-1-yl)methyl)-4'-fluoro-[1,1'-biphenyl]-3-carboxamide The title compound was prepared (15 mg, 0.027 mmol) according to the procedures described in Example 1, Steps A-E substituting (2-chloro-4-fluorophenyl)boronic acid (1 g, 5.7 mmol) in Step A, the hydrochloride salt of (R)-1-(4-fluoro-3-methylphenyl)ethan-1-amine (0.3 g, 1.6 mmol) in Step C and 1-cyclopropyl-1H-imidazol-2-amine (25 mg, 0.20 mmol) in Step E. $^1$H NMR (400 MHz, Chloroform-d) δ 8.11 (t, J=1.7 Hz, 1H), 7.90-7.85 (m, 2H), 7.38 (t, J=1.6 Hz, 1H), 7.30 (ddd, J=8.5, 5.5, 2.8 Hz, 3H), 7.20 (dd, J=8.5, 2.6 Hz, 1H), 7.04 (td, J=8.2, 2.6 Hz, 1H), 6.92 (dd, J=9.6, 8.1 Hz, 1H), 6.39-632 (m, 2H), 5.13 (s, 2H), 4.51-4.39 (m, 1H), 2.95 (tt, J=7.1, 3.7 Hz, 1H), 2.24 (d, J=1.9 Hz, 3H), 1.50-1.36 (m, 1H), 1.12-1.06 (m, 2H), 0.96-0.86 (m, 2H), 0.62 (ddt, J=8.2, 6.7, 4.0 Hz, 2H), 0.53-0.46 (m, 1H), 0.40-0.32 (m, 1H); LC-MS: >95% 254 nm, $R_T$=1.084 min, MS (ES) 549.2 (M+H).

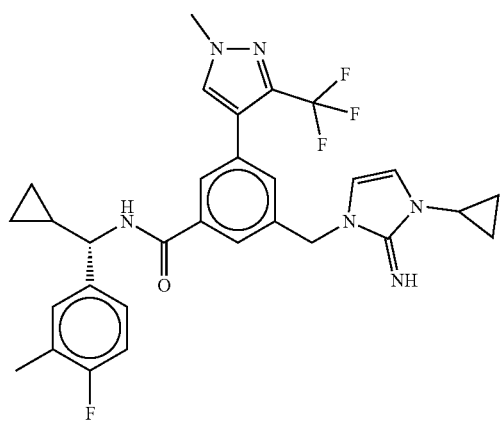

Example 142

(S)—N-(Cyclopropyl(4-fluoro-3-methylphenyl)methyl)-3-((3-cyclopropyl-2-imino-2,3-dihydro-1H-imidazol-1-yl)methyl)-5-(1-methyl-3-(trifluoromethyl)-1H-pyrazol-4-yl)benzamide The title compound was prepared (24 mg, 0.034 mmol) according to the procedures described in Examples 125 and 60, Steps A-G substituting 1-cyclopropyl-1H-imidazol-2-amine (14 mg, 0.11 mmol) in Step G. LC-MS: >95% 254 nm, $R_T$=0.978 min, MS (ES) 567.2 (M+H).

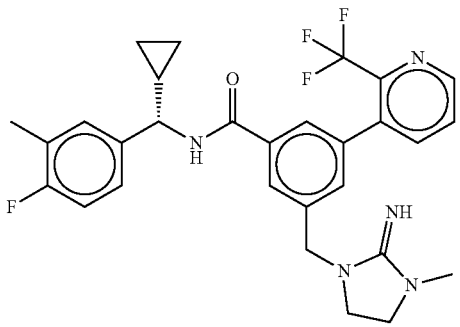

Example 143

(S)—N-(Cyclopropyl(4-fluoro-3-methylphenyl)methyl)-3-((2-imino-3-methylimidazolidin-1-yl)methyl)-5-(2-(trifluoromethyl)pyridin-3-yl)benzamide The title compound was prepared (10 mg, 0.019 mmol) according to the procedures described in Example 60, Steps A-G substituting 1-methyl-4,5-dihydro-1H-imidazol-2-amine (12 mg, 0.12 mmol) in Step G. LC-MS: >95% 254 nm, $R_T$=0.980 min, MS (ES) 540.2 (M+H).

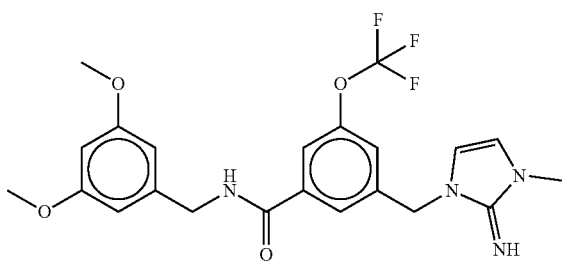

Example 144

N-(3,5-Dimethoxybenzyl)-3-((2-imino-3-methyl-2,3-dihydro-1H-imidazol-1-yl)methyl)-5-(trifluoromethoxy)benzamide

Step A. Preparation of methyl 3-methyl-5-(trifluoromethoxy)benzoate

The title compound (998 mg, 93%) was prepared from the procedure described in Example 84, Step E using 3-methyl-5-(trifluoromethoxy)benzoic acid (1000.0 mg, 4.54 mmol), LCMS: $R_T$=1.788 min, MS (ES) 235.2 (M+H).

Step B. Preparation of methyl 3-(bromomethyl)-5-(trifluoromethoxy)benzoate

The title compound (1046.6 mg, 78%) was prepared from the procedure described in Example 105, Step C using methyl 3-methyl-5-(trifluoromethoxy)benzoate (998 mg, 4.26 mmol). LCMS: $R_T$=1.807 min, MS (ES) 314.1 (M+H).

Step C. Preparation of methyl 3-((2-imino-3-methyl-2,3-dihydro-1H-imidazol-1-yl)methyl)-5-(trifluoromethoxy)benzoate The crude title compound was prepared from the procedure described in Example 1, Step E using methyl 3-(bromomethyl)-5-(trifluoromethoxy)benzoate (1047 mg, 3.34 mmol). LCMS: $R_T$=1.028 min, MS (ES) 330.3 (M+H).

Step D. Preparation of methyl (E)-3-((2-((tert-butoxycarbonyl)imino)-3-methyl-2,3-dihydro-1H-imidazol-1-yl)methyl)-5-(trifluoromethoxy)benzoate The title compound (1.26 g, 87%) was prepared from the procedure described in Example 84, Step B using methyl 3-((2-imino-3-methyl-2,3-dihydro-1H-imidazol-1-yl)methyl)-5-(trifluoromethoxy)benzoate (1.10 g, 3.34 mmol). LCMS: $R_T$=1.232 min, MS (ES) 430.4 (M+H).

Step E. Preparation of (E)-3-((2-((tert-butoxycarbonyl)imino)-3-methyl-2,3-dihydro-1H-imidazol-1-yl)methyl)-5-(trifluoromethoxy)benzoic Acid The crude title compound was prepared from the procedure described in Example 27, Step B using methyl (E)-3-((2-((tert-butoxycarbonyl)imino)-3-methyl-2,3-dihydro-1H-imidazol-1-yl)methyl)-5-(trifluoromethoxy)benzoate (1259 mg, 2.93 mmol). LCMS: $R_T$=1.133 min, MS (ES) 416.4 (M+H).

Step F. Preparation of tert-butyl (E)-(1-(3-((3,5-dimethoxybenzyl)carbamoyl)-5-(trifluoromethoxy)benzyl)-3-methyl-1,3-dihydro-2H-imidazol-2-ylidene)carbamate The title compound (18.4 mg, 38% 2 step) was prepared from the procedure described in Example 33, Step A using (E)-3-((2-((tert-butoxycarbonyl)imino)-3-methyl-2,3-dihydro-1H-imidazol-1-yl)methyl)-5-(trifluoromethoxy)benzoic acid (35.0 mg, 0.08 mmol) and (3,5-dimethoxyphenyl)methanamine (28.2 mg, 0.17 mmol). LCMS: $R_T$=1.317 min, MS (ES) 565.6 (M+H).

Step G. Example 144

The title compound (12.3 mg, 81%) was prepared from the procedure described in Example 84, Step H using tert-butyl (E)-(1-(1-(3-((3,5-dimethoxybenzyl)carbamoyl)-5-(trifluoromethoxy)benzyl)-3-methyl-1,3-dihydro-2H-imidazol-2-ylidene)carbamate (18.4 mg, 0.03 mmol). LCMS: $R_T$=1.186 min, MS (ES) 465.5 (M+H).

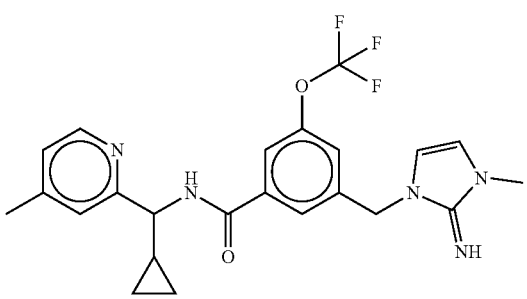

Example 145

N-(Cyclopropyl(4-methylpyridin-2-yl)methyl)-3-((2-imino-3-methyl-2,3-dihydro-1H-imidazol-1-yl)methyl)-5-(trifluoromethoxy)benzamide Step A. Preparation of tert-butyl (E)-(1-(3-((cyclopropyl(4-methylpyridin-2-yl)methyl)carbamoyl)-5-(trifluoromethoxy)benzyl)-3-methyl-1,3-dihydro-2H-imidazol-2-ylidene)carbamate The title compound (29.2 mg, 61% 2 step) was prepared from the procedure described in Example 33, Step A using (E)-3-((2-((tert-butoxycarbonyl)imino)-3-methyl-2,3-dihydro-1H-imidazol-1-yl)methyl)-5-(trifluoromethoxy)benzoic acid (35.0 mg, 0.08 mmol) and cyclopropyl(4-methylpyridin-2-yl)methanamine dihydrochloride (39.6 mg, 0.17 mmol). LCMS: $R_T$=1.093 min, MS (ES) 560.6 (M+H).

Step B. Example 145

The title compound (13.9 mg, 57%) was prepared from the procedure described in Example 84, Step H using tert-butyl (E)-(1-(3-((cyclopropyl(4-methylpyridin-2-yl)methyl)carbamoyl)-5-(trifluoromethoxy)benzyl)-3-methyl-1,3-dihydro-2H-imidazol-2-ylidene)carbamate (29.2 mg, 0.05 mmol). LCMS: $R_T$=0.904 min, MS (ES) 460.5 (M+H).

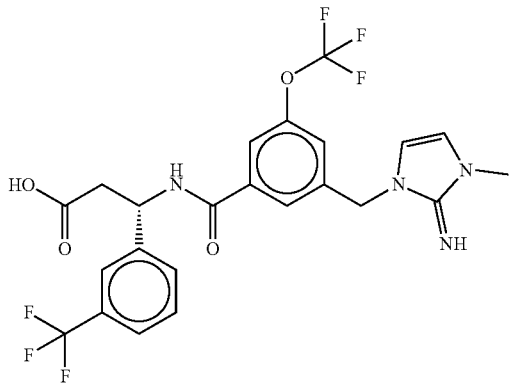

Example 146

(S)-3-(3-((2-Imino-3-methyl-2,3-dihydro-1H-imidazol-1-yl)methyl)-5-(trifluoromethoxy)benzamido)-3-(3-(trifluoromethyl)phenyl)propanoic acid Step A. Preparation of methyl (S,E)-3-(3-((2-((tert-butoxycarbonyl)imino)-3-methyl-2,3-dihydro-1H-imidazol-1-yl)methyl)-5-(trifluoromethoxy)benzamido)-3-(3-(trifluoromethyl)phenyl)propanoate The title compound (27.6 mg, 50% 2 step) was prepared from the procedure described in Example 33, Step A using (E)-3-((2-((tert-butoxycarbonyl)imino)-3-methyl-2,3-dihydro-1H-imidazol-1-yl)methyl)-5-(trifluoromethoxy)benzoic acid (35.0 mg, 0.08 mmol) and methyl (S)-3-amino-3-(3-(trifluoromethyl)phenyl)propanoate hydrochloride (47.8 mg, 0.17 mmol). LCMS: $R_T$=1.437 min, MS (ES) 645.6 (M+H).

Step B. Preparation of (S,E)-3-(3-((2-((tert-butoxycarbonyl)imino)-3-methyl-2,3-dihydro-1H-imidazol-1-yl)methyl)-5-(trifluoromethoxy)benzamido)-3-(3-(trifluoromethyl)phenyl)propanoic Acid The crude title compound was prepared from the procedure described in Example 27, Step B using methyl (S,E)-3-(3-((2-((tert-butoxycarbonyl)imino)-3-methyl-2,3-dihydro-1H-imidazol-1-yl)methyl)-5-(trifluoromethoxy)benzamido)-3-(3-(trifluoromethyl)phenyl)propanoate (27.6 mg, 0.04 mmol). LCMS: $R_T$=1.344 min, MS (ES) 631.5 (M+H).

Step C. Example 146

The title compound (15.3 mg, 67% 2 step) was prepared from the procedure described in Example 84, Step H using (S,E)-3-(3-((2-((tert-butoxycarbonyl)imino)-3-methyl-2,3-dihydro-1H-imidazol-1-yl)methyl)-5-(trifluoromethoxy)benzamido)-3-(3-(trifluoromethyl)phenyl)propanoic acid (27.0 mg, 0.04 mmol). LCMS: $R_T$=1.216 min, MS (ES) 531.4 (M+H).

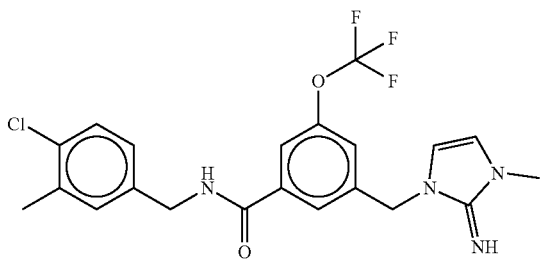

Example 147

N-(4-Chloro-3-methylbenzyl)-3-((2-imino-3-methyl-2,3-dihydro-1H-imidazol-1-yl)methyl)-5-(trifluoromethoxy)benzamide Step A. Preparation of tert-butyl (E)-(1-(3-((4-chloro-3-methylbenzyl)carbamoyl)-5-(trifluoromethoxy)benzyl)-3-methyl-1,3-dihydro-2H-imidazol-2-ylidene)carbamate The title compound (20.3 mg, 420% 2 step) was prepared from the procedure described in Example 33, Step A using (E)-3-((2-((tert-butoxycarbonyl)imino)-3-methyl-2,3-dihydro-1H-imidazol-1-yl)methyl)-5-(trifluoromethoxy)benzoic acid (35.0 mg, 0.08 mmol) and (4-chloro-3-methylphenyl)methanamine (0.02 mL, 0.17 mmol). LCMS: $R_T$=1.440 min, MS (ES) 554.0 (M+H).

Step B. Example 147

The title compound (14.8 mg, 89%) was prepared from the procedure described in Example 84, Step H using tert-butyl (E)-(1-(3-((4-chloro-3-methylbenzyl)carbamoyl)-5-(trifluoromethoxy)benzyl)-3-methyl-1,3-dihydro-2H-imidazol-2-ylidene)carbamate (20.3 mg, 0.04 mmol). LCMS: $R_T$=1.297 min, MS (ES) 453.9 (M+H).

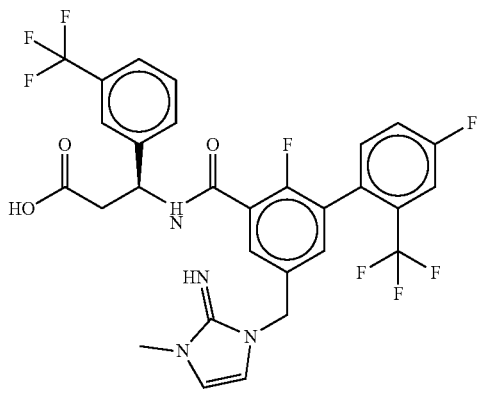

Example 148

(S)-3-(2,4'-Difluoro-5-((2-imino-3-methyl-2,3-dihydro-1H-imidazol-1-yl)methyl)-2'-(trifluoromethyl)-[1,1'-biphenyl]-3-carboxamido)-3-(3-(trifluoromethyl)phenyl)propanoic acid Step A. Preparation of methyl (S,Z)-3-(5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxamido)-3-(3-(trifluoromethyl)phenyl)propanoate The title compound (23.6 mg, 46% 2 step) was prepared from the procedure described in Example 33, Step A using (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic acid (35.0 mg, 0.08 mmol) and methyl (S)-3-amino-3-(3-(trifluoromethyl)phenyl)propanoate hydrochloride (38.8 mg, 0.14 mmol). LCMS: $R_T$=1.545 min, MS (ES) 741.7 (M+H).

Step B. Preparation of (S,Z)-3-(5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxamido)-3-(3-(trifluoromethyl)phenyl)propanoic acid The crude title compound was prepared from the procedure described in Example 27, Step B using methyl (S,Z)-3-(5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxamido)-3-(3-(trifluoromethyl)phenyl)propanoate (23.6 mg, 0.03 mmol). LCMS: $R_T$=1.445 min, MS (ES) 727.6 (M+H).

Step C. Example 148

The title compound (14.8 mg, 74% 2 step) was prepared from the procedure described in Example 84, Step H using (S,Z)-3-(5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxamido)-3-(3-(trifluoromethyl)phenyl)propanoic acid (23.2 mg, 0.03 mmol). LCMS: $R_T$=1.335 min, MS (ES) 627.5 (M+H).

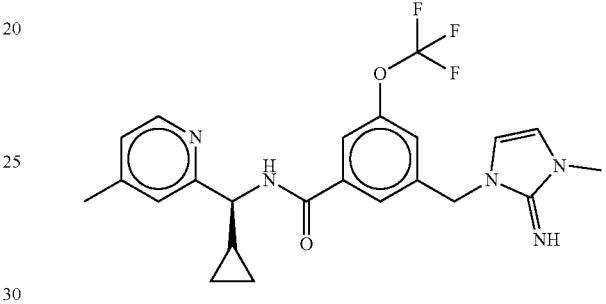

Example 149

(S)—N-(Cyclopropyl(4-methylpyridin-2-yl)methyl)-3-((2-imino-3-methyl-2,3-dihydro-1H-imidazol-1-yl)methyl)-5-(trifluoromethoxy)benzamide Step A. Preparation of tert-butyl (S,E)-(1-(3-((cyclopropyl(4-methylpyridin-2-yl)methyl)carbamoyl)-5-(trifluoromethoxy)benzyl)-3-methyl-1,3-dihydro-2H-imidazol-2-ylidene)carbamate The title compound (28.8 mg, 61% 2 step) was prepared from the procedure described in Example 33, Step A using (E)-3-((2-((tert-butoxycarbonyl)imino)-3-methyl-2,3-dihydro-1H-imidazol-1-yl)methyl)-5-(trifluoromethoxy)benzoic acid (35.0 mg, 0.08 mmol) and (S)-cyclopropyl(4-methylpyridin-2-yl)methanamine dihydrochloride (39.6 mL, 0.17 mmol). LCMS: $R_T$=1.092 min, MS (ES) 560.6 (M+H).

Step B. Example 149

The title compound (13.3 mg, 56%) was prepared from the procedure described in Example 84, Step H using tert-butyl (S,E)-(1-(3-((cyclopropyl(4-methylpyridin-2-yl)methyl)carbamoyl)-5-(trifluoromethoxy)benzyl)-3-methyl-1,3-dihydro-2H-imidazol-2-ylidene)carbamate (28.8 mg, 0.05 mmol). LCMS: $R_T$=0.898 min, MS (ES) 460.5 (M+H).

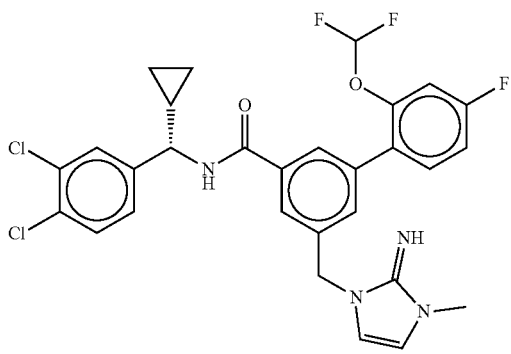

Example 150

(S)—N-(Cyclopropyl(3,4-dichlorophenyl)methyl)-2'-(difluoromethoxy)-4'-fluoro-5-((2-imino-3-methyl-2,3-dihydro-1H-imidazol-1-yl)methyl)-[1,1'-biphenyl]-3-carboxamide The title compound was prepared (27 mg, 0.045 mmol) according to the procedures described in Example 60, Steps A-G substituting 1-bromo-2-(difluoromethoxy)-4-fluorobenzene (1 g, 4.1 mmol) in Step C and the hydrochloride salt of (S)-cyclopropyl(3,4-dichlorophenyl)methanamine (0.3 g, 1.1 mmol) in Step E. LC-MS: >95% 254 nm, $R_T$=1.522 min, MS (ES) 589.3 (M+H).

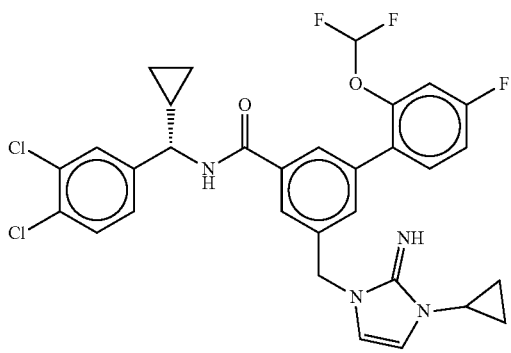

Example 151

(S)—N-(Cyclopropyl(3,4-dichlorophenyl)methyl)-5-((3-cyclopropyl-2-imino-2,3-dihydro-1H-imidazol-1-yl)methyl)-2'-(difluoromethoxy)-4'-fluoro-[1,1'-biphenyl]-3-carboxamide The title compound was prepared (27 mg, 0.045 mmol) according to the procedures described in Examples 150 and 60, Steps A-G substituting 1-cyclopropyl-1H-imidazol-2-amine (13 mg, 0.1 mmol) in Step G. $^1$H NMR (400 MHz, Chloroform-d) δ 8.11 (d, J=7.6 Hz, 1H), 7.99 (d, J=1.7 Hz, 1H), 7.90 (t, J=1.6 Hz, 1H), 7.58 (d, J=1.7 Hz, 1H), 7.41-7.33 (m, 4H), 7.03-6.94 (m, 2H), 6.53 6.16 (m, 3H), 5.15-5.02 (m, 2H), 4.38 (dd, J=9.5, 7.4 Hz, 1H), 3.41 (s, 3H), 1.38 (ddt, J=12.6, 8.1, 3.9 Hz, 1H), 0.67-0.59 (m, 2H), 0.51-0.44 (m, 1H), 0.37 (dd, J=9.1, 4.3 Hz, 1H); LC-MS: >95% 254 nm, $R_T$=1.546 min, MS (ES) 615.2 (M+H).

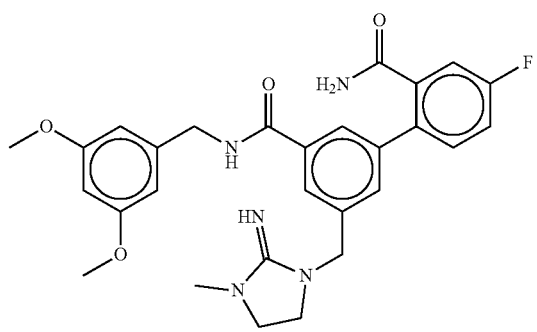

Example 152

N3'-(3,5-dimethoxybenzyl)-4-fluoro-5'-((2-imino-3-methyl-2,3-dihydro-1H-imidazol-1-yl)methyl)-[1,1'-biphenyl]-2,3'-dicarboxamide Step A. Preparation of methyl 2'-carbamoyl-4'-fluoro-5-(hydroxymethyl)-[1,1'-biphenyl]-3-carboxylate The title compound (195 mg, 51%) was prepared from the procedure described in Example 1, Step A using methyl 3-bromo-5-(hydroxymethyl)benzoate (0.5 g, 2.0 mmol) and (2-cyano-4-fluorophenyl)boronic acid (0.42 g, 2.55 mmol).

Step B. Preparation of 2'-carbamoyl-4'-fluoro-5-(hydroxymethyl)-[1,1'-biphenyl]-3-carboxylic Acid The title compound (0.26 g, 93%) was prepared from the procedure described in Example 139, Step B using methyl 2'-carbamoyl-4'-fluoro-5-(hydroxymethyl)-[1,1'-biphenyl]-3-carboxylate (0.195 g, 1.0 mmol) and LiOH (0.12 g, 5.0 mmol).

Step C. Preparation of N3'-(3,5-dimethoxybenzyl)-4-fluoro-5'-(hydroxymethyl)-[1,1'-biphenyl]-2,3'-dicarboxamide The title compound (113 mg, 57%) was prepared from the procedure described in Example 91, Step D using 2'-carbamoyl-4'-fluoro-5-(hydroxymethyl)-[1,1'-biphenyl]-3-carboxylic acid (0.13 g, 0.46 mmol) and 3,5-dimethoxybenzylamine (77 µL, 0.51 mmol). LCMS method 2: $R_T$=1.27 min, MS (ES) 439.0 (M+H).

Step D. Preparation of 5'-(bromomethyl)-N3'-(3,5-dimethoxybenzyl)-4-fluoro-[1,1'-biphenyl]-2,3'-dicarboxamide The title compound (57 mg, 34%) was prepared from the procedure described in Example 139, Step D using N3'-(3,5-dimethoxybenzyl)-4-fluoro-5'-(hydroxymethyl)-[1,1'-biphenyl]-2,3'-dicarboxamide (0.14 g, 0.33 mmol), PPh$_3$ (0.17 g, 0.66 mmol) and NBS (0.12 g, 0.66 mmol). LCMS method 2: $R_T$=1.51 min, MS (ES) 500.8 (M+).

Step E. Example 152

The title compound (14 mg, 24%) was prepared from the procedure described in Example 91, Step F using 5'-(bromomethyl)-N3'-(3,5-dim ethoxybenzyl)-4-fluoro-[1,1'-biphenyl]-2,3'-dicarboxamide (57 mg, 0.11 mmol), 1-methyl-1H-imidazol-2-amine (16 mg, 0.17 mmol) and DIPEA (39 µL, 0.23 mmol). $^1$H NMR (DMSO $d_6$) δ 9.03 (t, J=6.1 Hz, 1H), 7.83 (s, 1H), 7.76 (s, 2H), 7.48-7.31 (series of m, 6H), 6.52-6.49 (m, 4H), 6.39-6.37 (m, 1H), 4.86 (s, 2H), 4.41 (d, J=6.1 Hz, 2H), 3.72 (s, 6H), 3.16 (s, 3H); LCMS method 2: $R_T$=1.08 min, MS (ES) 518.0 (M+H).

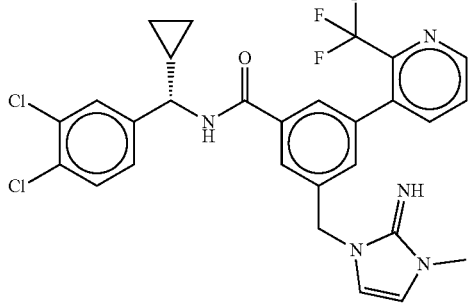

Example 153

(S)—N-(Cyclopropyl(3,4-dichlorophenyl)methyl)-3-((2-imino-3-methyl-2,3-dihydro-1H-imidazol-1-yl)methyl)-5-(2-(trifluoromethyl)pyridin-3-yl)benzamide The title compound was prepared (8 mg, 0.014 mmol) according to the procedures described in Example 60, Steps A-G substituting the hydrochloride salt of (S)-cyclopropyl (3,4-dichlorophenyl)methanamine (0.3 g, 1.1 mmol) in Step E. LC-MS: >95% 254 nm, $R_T$=1.021 min, MS (ES) 574.1 (M+H).

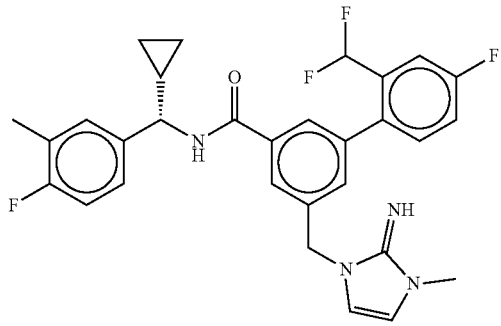

Example 154

(S)—N-(Cyclopropyl(4-fluoro-3-methylphenyl)methyl)-2'-(difluoromethyl)-4'-fluoro-5-((2-imino-3-methyl-2,3-dihydro-1H-imidazol-1-yl)methyl)-[1,1'-biphenyl]-3-carboxamide The title compound was prepared (21 mg, 0.039 mmol) according to the procedures described in Example 60, Steps A-G substituting 1-bromo-2-(difluoromethyl)-4-fluorobenzene (1 g, 4.4 mmol) in Step C. LC-MS: >95% 254 nm, $R_T$=1.038 min, MS (ES) 537.2 (M+H).

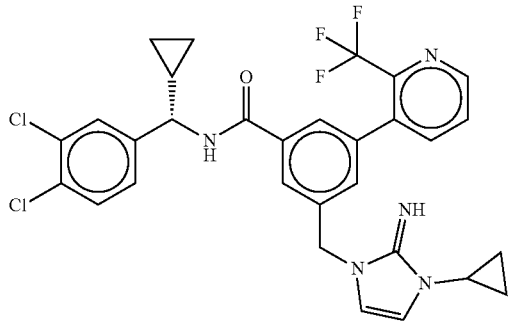

Example 155

(S)—N-(Cyclopropyl(3,4-dichlorophenyl)methyl)-3-((3-cyclopropyl-2-imino-2,3-dihydro-1H-imidazol-1-yl)methyl)-5-(2-(trifluoromethyl)pyridin-3-yl)benzamide The title compound was prepared (16 mg, 0.026 mmol) according to the procedures described in Examples 153 and 60, Steps A-G substituting 1-cyclopropyl-1H-imidazol-2-amine (13 mg, 0.1 mmol) in Step G. LC-MS: >95% 254 nm, $R_T$=1.030 min, MS (ES) 600.2 (M+H).

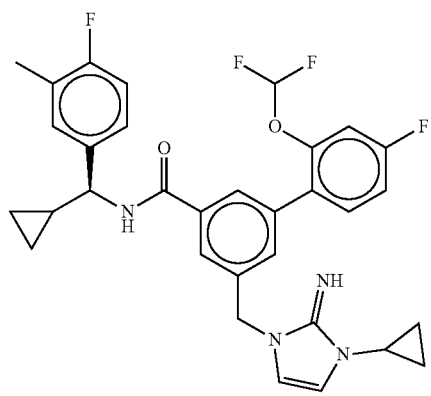

Example 156

(S)—N-(cyclopropyl(4-fluoro-3-methylphenyl)methyl)-5-((3-cyclopropyl-2-imino-2,3-dihydro-1H-imidazol-1-yl)methyl)-2'-(difluoromethoxy)-4'-fluoro-[1,1'-biphenyl]-3-carboxamide The title compound was prepared (29 mg, 0.05 mmol) as a tan solid according to the procedures described in Example 60, Steps A-G substituting 1-bromo-2-(difluoromethoxy)-4-fluorobenzene (1 g, 4.1 mmol) in Step C and 1-cyclopropyl-1H-imidazol-2-amine (17 mg, 0.13 mmol) in Step G. LC-MS, >95% (254 nm), $R_T$=1.042 min, m/z=579.2 [M+H]

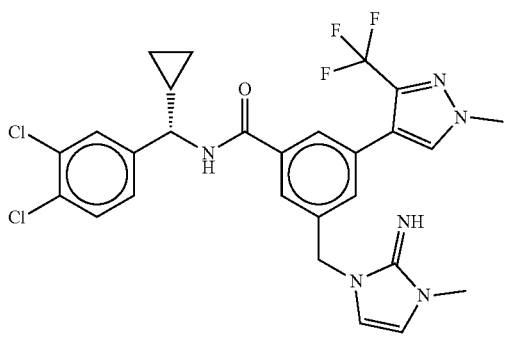

Example 157

(S)—N-(Cyclopropyl(3,4-dichlorophenyl)methyl)-3-((2-imino-3-methyl-2,3-dihydro-1H-imidazol-1-yl)methyl)-5-(1-methyl-3-(trifluoromethyl)-1H-pyrazol-4-yl)benzamide The title compound was prepared (12 mg, 0.021 mmol) according to the procedures described in Examples 125 and 60, Steps A-G substituting the hydrochloride salt of (S)-cyclopropyl(3,4-dichlorophenyl)methanamine (0.3 g, 1.1 mmol) in Step E. LC-MS: >95% 254 nm, $R_T$=1.415 min, MS (ES) 577.1 (M+H).

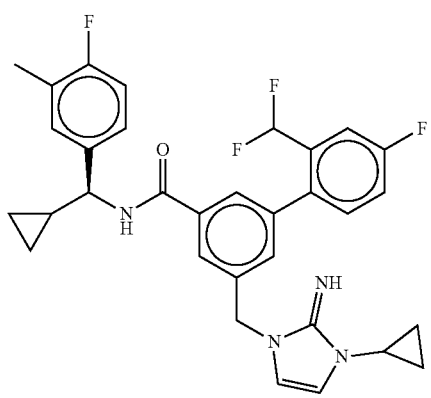

Example 158

(S)—N-(Cyclopropyl(4-fluoro-3-methylphenyl)methyl)-5-((3-cyclopropyl-2-imino-2,3-dihydro-1H-imidazol-1-yl)methyl)-2'-(difluoromethyl)-4'-fluoro-[1,1'-biphenyl]-3-carboxamide The title compound was prepared (16 mg, 0.028 mmol) according to the procedures described in Examples 154 and 60, Steps A-G substituting 1-cyclopropyl-1H-imidazol-2-amine (12 mg, 0.1 mmol) in Step G. LC-MS: >95% 254 nm, $R_T$=1.065 min, MS (ES) 563.2 (M+H).

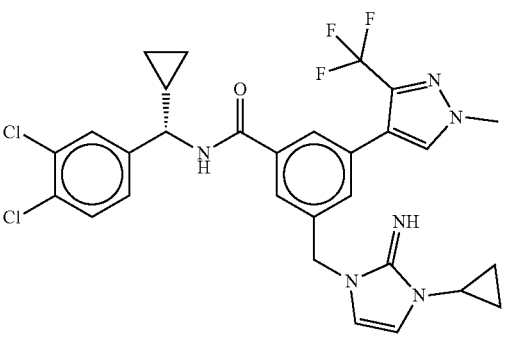

Example 159

(S)—N-(cyclopropyl(3,4-dichlorophenyl)methyl)-3-((3-cyclopropyl-2-imino-2,3-dihydro-1H-imidazol-1-yl)methyl)-5-(1-methyl-3-(trifluoromethyl)-1H-pyrazol-4-yl)benzamide The title compound was prepared (22 mg, 0.036 mmol) as a tan solid according to the procedures described in Examples 157 and 60, Steps A-G substituting 1-cyclopropyl-1H-imidazol-2-amine (13 mg, 0.1 mmol) in Step G. LC-MS: >95% 254 nm, $R_T$=1.484 min, MS (ES) 603.1 (M+H).

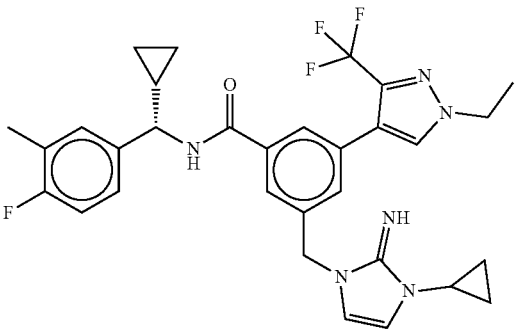

Example 160

(S)—N-(Cyclopropyl(4-fluoro-3-methylphenyl)methyl)-3-((3-cyclopropyl-2-imino-2,3-dihydro-1H-imidazol-1-yl)methyl)-5-(1-ethyl-3-(trifluoromethyl)-1H-pyrazol-4-yl)benzamide Title compound was prepared (23 mg, 0.04 mmol) according to the procedures described in Example 60, Steps A-G substituting 4-bromo-1-ethyl-3-(trifluoromethyl)-1H-pyrazole (1 g, 4.1 mmol) in Step C and 1-cyclopropyl-1H-imidazol-2-amine (12 mg, 0.1 mmol) in Step G. LC-MS: >95% 254 nm, $R_T$=1.029 min, MS (ES) 581.2 (M+H).

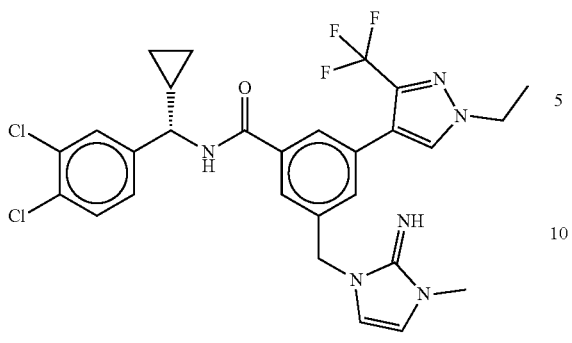

Example 161

(S)—N-(Cyclopropyl(3,4-dichlorophenyl)methyl)-3-(1-ethyl-3-(trifluoromethyl)-1H-pyrazol-4-yl)-5-((2-imino-3-methyl-2,3-dihydro-1H-imidazol-1-yl)methyl)benzamide The title compound was prepared (35 mg, 0.059 mmol) as an orange solid according to the procedures described in Examples 157 and 60 Steps A-G, substituting 4-bromo-1-ethyl-3-(trifluoromethyl)-1H-pyrazole (1 g, 4.1 mmol) in Step C. LC-MS: >95% 254 nm, $R_T$=i=1.045 min, MS (ES) 591.1 (M+H).

Example 163

(S)—N-(Cyclopropyl(4-fluoro-3-methylphenyl)methyl)-3-((3-cyclopropyl-2-imino-2,3-dihydro-1H-imidazol-1-yl)methyl)-5-(1-isobutyl-3-(trifluoromethyl)-1H-pyrazol-4-yl)benzamide The title compound was prepared (20 mg, 0.032 mmol) as a tan solid according to the procedures described in Example 60, Steps A-G substituting 4-bromo-1-isobutyl-3-(trifluoromethyl)-1H-pyrazole (1 g, 3.6 mmol) in Step C and 1-cyclopropyl-1H-imidazol-2-amine (11 mg, 0.09 mmol) in Step G. LC-MS: >95% 254 nm, $R_T$=1.077 min, MS (ES) 609.2 (M+H).

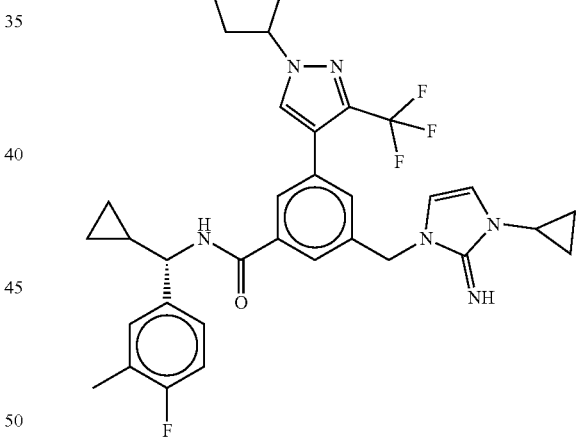

Example 162

(S)—N-(Cyclopropyl(3,4-dichlorophenyl)methyl)-3-((3-cyclopropyl-2-imino-2,3-dihydro-1H-imidazol-1-yl)methyl)-5-(1-ethyl-3-(trifluoromethyl)-1H-pyrazol-4-yl)benzamide The title compound was prepared (27 mg, 0.044 mmol) according to the procedures described in Examples 161 and 60, Steps A-G substituting 1-cyclopropyl-1H-imidazol-2-amine (17 mg, 0.14 mmol) in Step G. LC-MS: >95% 254 nm, $R_T$=1.068 min, MS (ES) 617.1 (M+H).

Example 164

(S)-3-(1-Cyclopentyl-3-(trifluoromethyl)-1H-pyrazol-4-yl)-N-(cyclopropyl(4-fluoro-3-methylphenyl)methyl)-5-((3-cyclopropyl-2-imino-2,3-dihydro-1H-imidazol-1-yl)methyl)benzamide The title compound was prepared (9 mg, 0.014 mmol) as a tan solid according to the procedures described in Example 60, Steps A-G substituting 4-bromo-1-cyclopentyl-3-(trifluoromethyl)-1H-pyrazole (1 g, 3.5 mmol) in Step C and 1-cyclopropyl-1H-imidazol-2-amine (11 mg, 0.09 mmol) in Step G. LC-MS: >95% 254 nm, $R_T$=1.115 min, MS (ES) 612.2 (M+H).

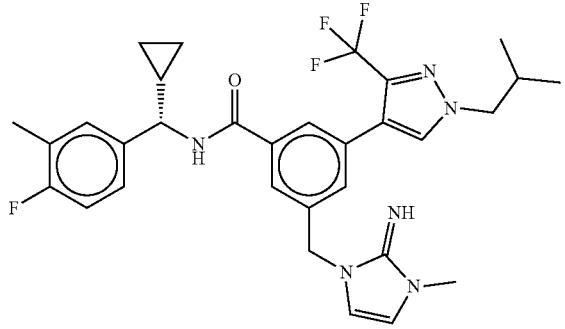

Example 165

(S)—N-(Cyclopropyl(4-fluoro-3-methylphenyl)methyl)-3-((2-imino-3-methyl-2,3-dihydro-1H-imidazol-1-yl)methyl)-5-(1-isobutyl-3-(trifluoromethyl)-1H-pyrazol-4-yl)benzamide Title compound was prepared (17 mg, 0.029 mmol) as an orange solid according to the procedures described in Example 60, Steps A-G substituting 4-bromo-1-isobutyl-3-(trifluoromethyl)-1H-pyrazole (1 g, 3.6 mmol) in Step C. LC-MS: >95% 254 nm, $R_T$=1.073 min, MS (ES) 583.2 (M+H).

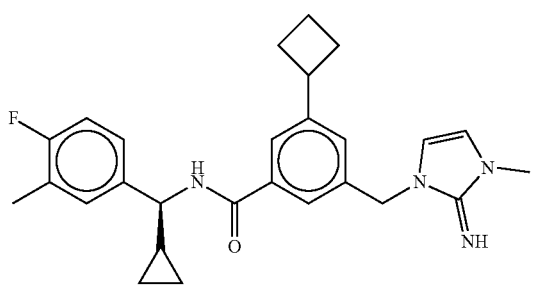

Example 166

(S)-3-Cyclobutyl-N-(cyclopropyl(4-fluoro-3-methylphenyl)methyl)-5-((2-imino-3-methyl-2,3-dihydro-1H-imidazol-1-yl)methyl)benzamide Step A. Preparation of methyl 3-bromo-5-(((tert-butyldiphenylsilyl)oxy)methyl)benzoate Imidazole (0.55 g, 8.2 mmol) and tert-butyl(chloro)diphenylsilane (1.59 mL, 6.1 mmol) were added to a solution of methyl 3-bromo-5-(hydroxymethyl)benzoate (1.0 g, 4.1 mmol) in DCM (20 mL). The organic layer was separated, dried with MgSO₄ and concentrated. The residue was purified by flash chromatography (Combi-flash Rf, Hex/EtOAc=1-5% gradient) to afford the title compound (1.8 g, 91%). LCMS method 3: $R_T$=1.99 min, MS (ES) 484.9 (M+H).

Step B. Preparation of methyl 3-(((tert-butyidiphenylsilyl)oxy)methyl)-5-cyclobutylbenzoate The title compound (185 mg, 26%) was prepared from the procedure described in Example 139, Step A using 3-bromo-5-(((tert-butyldiphenylsilyl)oxy)methyl)benzoate (0.75 g, 1.55 mmol) and cyclobutylboronic acid (232 mg, 2.3 mmol). LCMS method 3: $R_T$=2.20 min, MS (ES) 459.0 (M+H).

Step C. Preparation of 3-cyclobutyl-5-(hydroxymethyl)benzoic acid

The title compound (60 mg, 72%) was prepared from the procedure described in Example 139, Step B using methyl 3-(((tert-butyldiphenylsilyl)oxy)methyl)-5-cyclobutylbenzoate (185 mg, 0.4 mmol) and LiOH (48 mg, 2.0 mmol). LCMS method 2: $R_T$=1.22 min, MS (ES) 207.1 (M+H).

Step D. Preparation of (S)-3-cyclobutyl-N-(cyclopropyl(4-fluoro-3-methylphenyl)methyl)-5-(hydroxymethyl)benzamide The title compound (63 mg, 59%) was prepared from the procedure described in Example 91, Step D using 3-cyclobutyl-5-(hydroxymethyl)benzoic acid (60 mg, 0.29 mmol), and (S)-cyclopropyl(4-fluoro-3-methylphenyl)methanamine hydrochloride (94 mg, 0.44 mmol). LCMS method 2: $R_T$=1.72 min, MS (ES) 368.1 (M+H).

Step E. Preparation of (S)-3-(bromomethyl)-5-cyclobutyl-N-(cyclopropyl(4-fluoro-3-methylphenyl)methyl)benzamide The title compound (48 mg, 65%) was prepared from the procedure described in Example 139, Step D using (S)-3-cyclobutyl-N-(cyclopropyl(4-fluoro-3-methylphenyl)methyl)-5-(hydroxymethyl)benzamide (63 mg, 0.17 mmol), PPh₃ (89 mg, 0.34 mmol) and NBS (61 mg, 0.34 mmol). LCMS method 2: $R_T$=2.07 min, MS (ES) 429.9 (M+).

Step F. Example 166

The title compound (14 mg, 27%) was prepared from the procedure described in Example 91, Step F using (S)-3-(bromomethyl)-5-cyclobutyl-N-(cyclopropyl(4-fluoro-3-methylphenyl)methyl)benzamide (50 mg, 0.12 mmol), 1-methyl-1H-imidazol-2-amine (17 mg, 0.17 mmol) and DIPEA (40 PL, 0.23 mmol). ¹H NMR (CDCl₃) δ 7.65-7.62 (m, 2H), 7.56-7.54 (m, 1H), 7.27-7.23 (m, 2H), 7.10 (s, 1H), 6.90 (t, J=9.2 Hz, 1H), 6.34 (d, J=2.7 Hz, 1H), 6.27 (d, J=2.7 Hz, 1H), 4.97-4.89 (m, 2H), 4.44 (t, J=8.4 Hz, 1H), 3.49 (t, J=8.5 Hz, 1H), 3.42 (s, 3H), 2.33-2.25 (m, 2H), 2.25 (s, 3H), 2.12-1.96 (series of m, 3H), 1.85-1.78 (m, 1H), 1.41-1.31 (m, 1H), 0.63-0.59 (m, 2H), 0.51-0.47 (m, 1H), 0.37-0.33 (m, 1H). LCMS method 2: $R_T$=1.37 min, MS (ES) 447.1 (M+).

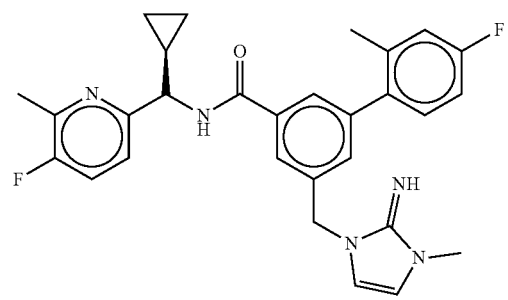

Example 167

(R)—N-(Cyclopropyl(5-fluoro-6-methylpyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide

Step A. Preparation of 5-fluoro-6-methylpicolinaldehyde

Isopropylmagnesium chloride lithium chloride complex solution 1.3 M in THF (8.1 mL, 10.5 mmol) was added dropwise to 0° C. solution of 6-bromo-3-fluoro-2-methylpyridine (1.0 g, 5.25 mmol) in THF (40 mL). The reaction was stirred and warmed to rt over 20 h. DMF (1.0 mL, 13.2 mmol) was added, and the reaction mixture was stirred at rt for an additional 20 h. The reaction was quenched with sat. aq. NH$_4$Cl (40 mL) and extracted with EtOAc (3×40 mL). The combined organic layer was dried with MgSO$_4$ and concentrated to give the title compound (1.0 g, quant.) as a yellow oil.

Step B. Preparation of (S,E)-N-((5-fluoro-6-methylpyridin-2-yl)methylene)-2-methylpropane-2-sulfinamide The title compound (280 mg, 16%) was prepared from the procedure described in Example 91, Step A using 5-fluoro-6-methylpicolinaldehyde (1.0 g, 7.2 mmol), cesium carbonate (3.5 g, 10.8 mmol), and (S)-2-methylpropane-2-sulfinamide (0.87 g, 7.2 mmol). LCMS method 2: R$_T$=1.41 min, MS (ES) 243.1 (M+H).

Step C. Preparation of (S)—N—((R)-cyclopropyl(5-fluoro-6-methylpyridin-2-yl)methyl)-2-methylpropane-2-sulfinamide The title compound (72 mg, 0.25 mmol) was isolated as the minor diastereomer from the procedure described in Example 91, Step B using (S,E)-N-((5-fluoro-6-methylpyridin-2-yl)methylene)-2-methylpropane-2-sulfinamide (0.28 g, 1.1 mmol) and 1.0 M Cyclopropyl magnesium bromide solution in 2-methyltetrahydrofuran (2.3 mL, 2.3 mmol). LCMS method 2: R$_T$=1.40 min, MS (ES) 185.1 (M+H).

Step D. Preparation of (R)-cyclopropyl(5-fluoro-6-methylpyridin-2-yl)methanamine hydrochloride The title compound (55 mg. 0.25 mmol) was prepared from the procedure described in Example 91, Step C using (S)—N—((R)-cyclopropyl(5-fluoro-6-methylpyridin-2-yl)methyl)-2-methylpropane-2-sulfinamide (72 mg, 0.25 mmol) and 4.0 M HCl in dioxane (0.63 mL, 2.5 mmol). LCMS method 2: R$_T$=0.19 min, MS (ES) 181.2 (M+H).

Step E. Preparation of (R)—N-(cyclopropyl(5-fluoro-6-methylpyridin-2-yl)methyl)-4'-fluoro-5-(hydroxymethyl)-2'-methyl-[1,1'-biphenyl]-3-carboxamide The title compound (88 mg, 100%) was prepared from the procedure described in Example 91, Step D using 4'-fluoro-5-(hydroxymethyl)-2'-methyl-[1,1'-biphenyl]-3-carboxylic acid (54 mg, 0.21 mmol) and (R)-cyclopropyl(5-fluoro-6-methylpyridin-2-yl)methanamine hydrochloride (54 mg, 0.25 mmol). LCMS method 2: R$_T$=1.68 min, MS (ES) 423.0 (M+H).

Step F. Preparation of (R)-5-(bromomethyl)-N-(cyclopropyl(5-fluoro-6-methylpyridin-2-yl)methyl)-4'-fluoro-2'-methyl-[1,1'-biphenyl]-3-carboxamide The title compound (112 mg, 100%) was prepared from the procedure described in Example 93, Step E using (R)—N-(cyclopropyl(5-fluoro-6-methylpyridin-2-yl)methyl)-4'-fluoro-5-(hydroxymethyl)-2'-methyl-[1,1'-biphenyl]-3-carboxamide (105 mg, 0.25 mmol) and PBr$_3$ (47 µL, 0.5 mmol). LCMS method 2: R$_T$=2.02 min, MS (ES) 484.9 (M+).

Step G. Example 167

The title compound (6 mg, 12%) was prepared from the procedure described in Example 91, Step F using (R)-5-(bromomethyl)-N-(cyclopropyl(5-fluoro-6-methylpyridin-2-yl)methyl)-4'-fluoro-2'-methyl-[1,1'-biphenyl]-3-carboxamide (50 mg, 0.10 mmol), 1-methyl-1H-imidazol-2-amine (15 mg, 0.15 mmol) and DIPEA (36 µL, 0.20 mmol). LCMS method 2: R$_T$=1.36 min, MS (ES) 502.0 (M+H).

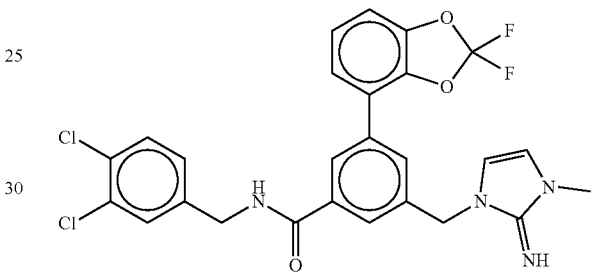

Example 168

N-(3,4-Dichlorobenzyl)-3-(2,2-difluorobenzo[d][1,3]dioxol-4-yl)-5-((2-imino-3-methyl-2,3-dihydro-1H-imidazol-1-yl)methyl)benzamide

Step A. Preparation of 3-bromo-N-(3,4-dichlorobenzyl)-5-(hydroxymethyl)benzamide The title compound (2.1 g, 43%) was prepared following the procedure described in Example 1 Step C using 3-bromo-5-hydroxymethylbenzoic acid (2.00 g, 12.65 mmol) and 3,4-dichlorophenyl)methanamine (2.44 g, 13.90 mmol). $^1$H NMR (400 MHz, D$_6$-DMSO) 9.1 (t, 1H, J=5.6 Hz), 7.9 (s, 1H), 7.8 (s, 1H), 7.6 (s, 1H), 7.5 (m, 2H), 7.2 (d, 1H, J=8.2 Hz), 5.3 (bs, 1H), 4.5 (s, 2H), 4.4 (d, 2H, J=6.0 Hz).

Step B. Preparation of 3-bromo-5-(bromomethyl)-N-(3,4-dichlorobenzyl)benzamide The title compound (2.2 g, 90%) was prepared following the procedure described in Example 1 Step D using 3-bromo-N-(3,4-dichlorobenzyl)-5-(hydroxymethyl)benzamide (2.1 g, 5.42 mmol).

Step C. Preparation of tert-butyl (E)-(1-(3-bromo-5-((3,4-dichlorobenzyl)carbamoyl)benzyl)-3-methyl-1,3-dihydro-2H-imidazol-2-ylidene)carbamate A solution of 3-bromo-5-(bromomethyl)-N-(3,4-dichlorobenzyl)benzamide (1.5 g, 3.30 mmol), DIPEA (1.28 mL, 7.26 mmol) and 1-methyl-1H-imidazol-2-amine (0.89 g, 6.60 mmol) in MeCN was refluxed for 18 h, cooled and concentrated. The residue was dissolved in THF (100 mL), and (BOC)$_2$O (0.86 g, 3.96 mmol) and DMAP (0.20 g, 1.65 mmol) was added. The reaction mixture was stirred for 18 h at ambient temperature then concentrated. The residue was purified by flash chromatography (Combi-flash Rf, Hex/EtOAc=0-90% gradient) to afford the title compound (0.81 g, 53%). $^1$H NMR (400 MHz, d$_6$-DMSO) 9.1 (t, 1H, J=6.0 Hz), 8.0 (s, 1H), 7.7 (s, 1H), 7.5 (m, 3H), 7.2 (m, 2H), 7.1 (s, 1H), 5.1 (s, 2H), 4.4 (d, 2H J=4.9 Hz), 3.3 (s, 3H), 1.3 (s, 9H).

Step D. Example 168

The title compound (0.03 g, 30%) was prepared following the procedure described in Example 1, Step A using tert-butyl (E)-(1-(3-bromo-5-((3,4-dichlorobenzyl)carbamoyl)benzyl)-3-methyl-1,3-dihydro-2H-imidazol-2-ylidene)carbamate (0.10 g. 0.18 mmol) and (2,2-difluorobenzo[d][1,3]dioxol-4-yl)boronic acid (0.05 g, 0.27 mmol) followed by deprotection of Boc group by TFA in DCM. LCMS: 98% 254 nm R$_T$=1.01 min, MS (ES) 545 (M+H).

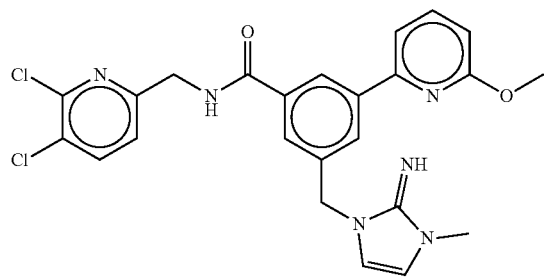

Example 169

N-(3,4-Dichlorobenzyl)-3-((2-imino-3-methyl-2,3-dihydro-1H-imidazol-1-yl)methyl)-5-(6-methoxypyridin-2-yl)benzamide The title compound (2 mg, 7%) was prepared following the procedure described in Example 1, Step A using tert-butyl (E)-(1-(3-bromo-5-((3,4-dichlorobenzyl)carbamoyl)benzyl)-3-methyl-1,3-dihydro-2H-imidazol-2-ylidene)carbamate (0.10 g. 0.18 mmol) and (6-methoxypyridin-2-yl)boronic acid (0.06 g, 0.27 mmol) followed by deprotection of Boc group by TFA in DCM. LCMS: 980% 254 nm R$_T$=0.99 min, MS (ES) 496 (M+H).

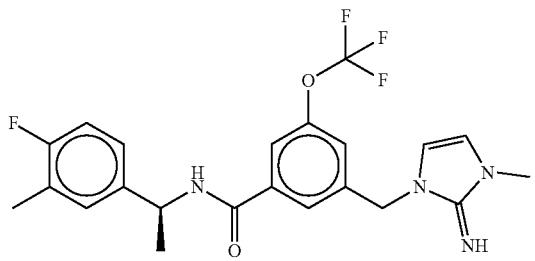

Example 170

(S)—N-(1-(4-Fluoro-3-methylphenyl)ethyl)-3-((2-imino-3-methyl-2,3-dihydro-1H-imidazol-1-yl)methyl)-5-(trifluoromethoxy)benzamide Step A. Preparation of tert-butyl (S,E)-(1-(3-((1-(4-fluoro-3-methylphenyl)ethyl)carbamoyl)-5-(trifluoromethoxy)benzyl)-3-methyl-1,3-dihydro-2H-imidazol-2-ylidene)carbamate The title compound (28.8 mg, 49% 2 step) was prepared from the procedure described in Example 33, Step A using (E)-3-((2-((tert-butoxycarbonyl)imino)-3-methyl-2,3-dihydro-1H-imidazol-1-yl)methyl)-5-(trifluoromethoxy)benzoic acid (35.0 mg, 0.08 mmol) and (S)-1-(4-fluoro-3-methylphenyl)ethan-1-amine (25.8 mL, 0.17 mmol). LCMS: R$_T$=1.431 min, MS (ES) 551.6 (M+H).

Step B. Example 170

The title compound (15.0 mg, 80%) was prepared from the procedure described in Example 84, Step H using tert-butyl (S,E)-(1-(3-((1-(4-fluoro-3-methylphenyl)ethyl)carbamoyl)-5-(trifluoromethoxy)benzyl)-3-methyl-1,3-dihydro-2H-imidazol-2-ylidene)carbamate (22.8 mg, 0.04 mmol). LCMS: R$_T$=1.290 min, MS (ES) 451.4 (M+H).

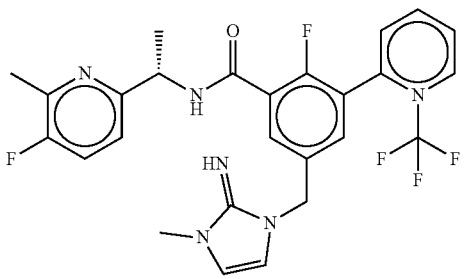

Example 171

(S)-2-Fluoro-N-(1-(4-fluoro-3-methylphenyl)ethyl)-5-((2-imino-3-methyl-2,3-dihydro-1H-imidazol-1-yl)methyl)-3-(2-(trifluoromethyl)pyridin-3-yl)benzamide Step A. Preparation of tert-butyl (S,E)-(1-(4-fluoro-3-((1-(4-fluoro-3-methylphenyl)ethyl)carbamoyl)-5-(2-(trifluoromethyl)pyridin-3-yl)benzyl)-3-methyl-1,3-dihydro-2H-imidazol-2-ylidene)carbamate The title compound (12.0 mg, 26% 2 step) was prepared from the procedure described in Example 33, Step A using (E)-5-((2-((tert-butoxycarbonyl)imino)-3-methyl-2,3-dihydro-1H-imidazol-1-yl)methyl)-2-fluoro-3-(2-(trifluoromethyl)pyridin-3-yl)benzoic acid (35.0 mg, 0.07 mmol) and (S)-1-(4-fluoro-3-methylphenyl)ethan-1-amine (21.7 mg, 0.14 mmol). LCMS: R$_T$=1.430 min, MS (ES) 630.6 (M+H).

Step B. Example 171

The title compound (8.2 mg, 810%) was prepared from the procedure described in Example 84, Step H using tert-butyl (S,E)-(l-(4-fluoro-3-((1-(4-fluoro-3-methylphenyl)ethyl)carbamoyl)-5-(2-(trifluoromethyl)pyridin-3-yl)benzyl)-3-methyl-1,3-dihydro-2H-imidazol-2-ylidene)carbamate (12.0 mg, 0.02 mmol). LCMS: $R_T$=1.302 min, MS (ES) 530.5 (M+H).

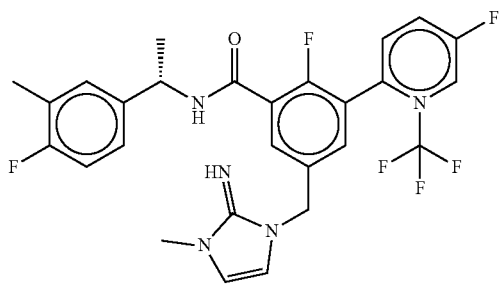

Example 172

(S)-2,4'-Difluoro-N-(1-(4-fluoro-3-methylphenyl)ethyl)-5-((2-imino-3-methyl-2,3-dihydro-1H-imidazol-1-yl)methyl)-2'-(trifluoromethyl)-[1,1'-biphenyl]-3-carboxamide Step A. Preparation of tert-butyl (S,Z)-(1-((4',6-difluoro-5-((1-(4-fluoro-3-methylphenyl)ethyl)carbamoyl)-2'-(trifluoromethyl)-[1,1'-biphenyl]-3-yl)methyl)-3-methyl-1,3-dihydro-2H-imidazol-2-ylidene)carbamate The title compound (14.6 mg, 32% 2 step) was prepared from the procedure described in Example 33, Step A using (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic acid (35.0 mg, 0.07 mmol) and (S)-1-(4-fluoro-3-methylphenyl)ethan-1-amine (21.0 mg, 0.14 mmol). LCMS: $R_T$=1.555 min, MS (ES) 647.6 (M+H).

Step B. Example 172

The title compound (10.3 mg, 83%) was prepared from the procedure described in Example 84, Step H using tert-butyl (S,Z)-(1-((4',6-difluoro-5-((1-(4-fluoro-3-methylphenyl)ethyl)carbamoyl)-2'-(trifluoromethyl)-[1,1'-biphenyl]-3-yl)methyl)-3-methyl-1,3-dihydro-2H-imidazol-2-ylidene)carbamate (14.6 mg, 0.02 mmol). LCMS: $R_T$=1.454 min, MS (ES) 547.5 (M+H).

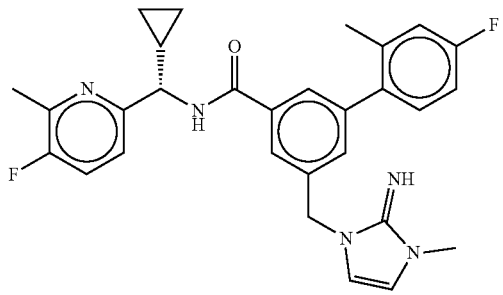

Example 173

(S)-1N-(Cyclopropyl(5-fluoro-6-methylpyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide Step A. Preparation of (S)-cyclopropyl(5-fluoro-6-methylpyridin-2-yl)methanamine hydrochloride The title compound (55 mg. 0.25 mmol) was prepared from the procedure described in Example 91, Step C using (S)—N—((S)-cyclopropyl(5-fluoro-6-methylpyridin-2-yl)methyl)-2-methylpropane-2-sulfinamide (the major diastereomer from Example 167, Step C) (72 mg, 0.25 mmol) and 4.0 M HCl in dioxane (0.63 mL, 2.5 mmol). LCMS method 2: $R_T$=0.19 min, MS (ES) 181.2 (M+H)

Step B. Preparation of (S)—N-(cyclopropyl(5-fluoro-6-methylpyridin-2-yl)methyl)-4'-fluoro-5-(hydroxymethyl)-2'-methyl-[1,1'-biphenyl]-3-carboxamide The title compound (88 mg, 100%) was prepared from the procedure described in Example 91, Step D using 4'-fluoro-5-(hydroxymethyl)-2'-methyl-[1,1'-biphenyl]-3-carboxylic acid (54 mg, 0.21 mmol) and (S)-cyclopropyl(5-fluoro-6-methylpyridin-2-yl)methanamine hydrochloride (54 mg, 0.25 mmol). LCMS method 2: $R_T$=1.68 min, MS (ES) 423.0 (M+H)

Step C. Preparation of (S)-5-(bromomethyl)-N-(cyclopropyl(5-fluoro-6-methylpyridin-2-yl)methyl)-4'-fluoro-2'-methyl-[1,1'-biphenyl]-3-carboxamide The title compound (112 mg, 100%) was prepared from the procedure described in Example 93, Step E using (S)—N-(cyclopropyl(5-fluoro-6-methylpyridin-2-yl)methyl)-4'-fluoro-5-(hydroxymethyl)-2'-methyl-[1,1'-biphenyl]-3-carboxamide (105 mg, 0.25 mmol) and PBr₃ (47 μL, 0.5 mmol). LCMS method 2: $R_T$=2.02 min, MS (ES) 484.9 (M+)

Step D. Example 173

The title compound (7 mg, 14%) was prepared from the procedure described in Example 91, Step F using (5)-5-(bromomethyl)-N-(cyclopropyl(5-fluoro-6-methylpyridin-2-yl)methyl)-4'-fluoro-2'-methyl-[1,1'-biphenyl]-3-carboxamide (50 mg, 0.10 mmol), 1-methyl-1H-imidazol-2-amine (15 mg, 0.15 mmol) and DIPEA (36 μL, 0.20 mmol). LCMS method 2: $R_T$=1.36 min, MS (ES) 502.0 (M+)

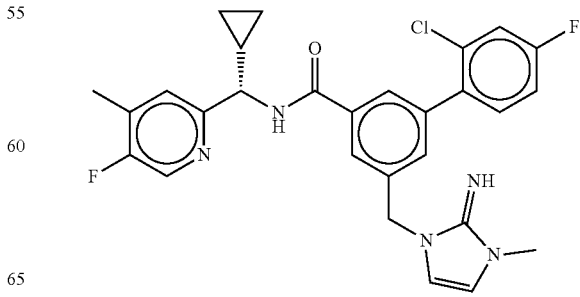

Example 174

(S)-2'-Chloro-N-(cyclopropyl(5-fluoro-4-methyl-pyridin-2-yl)methyl)-4'-fluoro-5-((2-imino-3-methyl-2,3-dihydro-1H-imidazol-1-yl)methyl)-[1,1'-biphenyl]-3-carboxamide Step A. Preparation of (S)-2'-chloro-N-(cyclopropyl (5-fluoro-4-methylpyridin-2-yl)methyl)-4'-fluoro-5-(hydroxymethyl)-[1,1'-biphenyl]-3-carboxamide The title compound (147 mg, 81%) was prepared from the procedure described in Example 91, Step D using 2'-chloro-4'-fluoro-5-(hydroxymethyl)-[1,1'-biphenyl]-3-carboxylic acid (100 mg, 0.236 mmol) and (S)-cyclopropyl(5-fluoro-4-methylpyridin-2-yl)methanamine hydrochloride (92 mg, 0.43 mmol). LCMS method 2: $R_T$=1.66 min, MS (ES) 442.9 (M+)

Step B. Preparation of (S)-5-(bromomethyl)-2'-chloro-N-(cyclopropyl(5-fluoro-4-methylpyridin-2-yl)methyl)-4'-fluoro-[1,1'-biphenyl]-3-carboxamide The title compound (55 mg, 37%) was prepared from the procedure described in Example 93, Step E using (S)-2'-chloro-N-(cyclopropyl(5-fluoro-4-methylpyridin-2-yl) methyl)-4'-fluoro-5-(hydroxymethyl)-[1,1'-biphenyl]-3-carboxamide (128 mg, 0.29 mmol) and PBr$_3$ (54 µL, 0.58 mmol). LCMS method 2: $R_T$=2.00 min, MS (ES) 504.9 (M+)

Step C. Example 174

The title compound (8 mg, 14%) was prepared from the procedure described in Example 91, Step F using (S)-5-(bromomethyl)-2'-chloro-N-(cyclopropyl(5-fluoro-4-methylpyridin-2-yl)methyl)-4'-fluoro-[1,1'-biphenyl]-3-carboxamide (55 mg, 0.11 mmol), 1-methyl-1H-imidazol-2-amine (16 mg, 0.16 mmol) and DIPEA (75 µL, 0.43 mmol) $^1$H NMR (CDCl$_3$) δ 8.27 (s, 1H), 7.88 (s, 1H), 7.83-7.81 (m, 2H), 7.44 (s, 1H), 7.32-7.29 (m, 1H), 7.22-7.16 (m, 2H), 7.06-7.02 (m, 1H), 6.32-6.30 (m, 2H), 5.13 (s, 2H), 4.62 (t, J=8.1 Hz, 1H), 3.46 (s, 3H), 2.3 (s, 3H), 1.37-1.28 (m, 1H), 0.61-0.49 (series of m, 3H), 0.44-0.38 (m, 1H). LCMS method 2: $R_T$=1.35 min, MS (ES) 522.0 (M+).

Example 175

(S)—N-(Cyclopropyl(4-fluoro-3-methylphenyl) ethyl)-3-(cyclopropylmethoxy)-5-((2-imino-3-methyl-2,3-dihydro-1H-imidazol-1-yl)methyl)benz-amide Step A. Preparation of methyl 3-hydroxy-5-methylbenzoate The title compound (1548 mg, 95%) was prepared from the procedure described in Example 84, Step E using 3-hydroxy-5-methylbenzoic acid (1000 mg, 6.57 mmol). LCMS: $R_T$=1.223 min, MS (ES) 167.2 (M+H).

Step B. Preparation of methyl 3-(cyclopropylmethoxy)-5-methylbenzoate (Bromomethyl)cyclopropane (1.17 mL, 12.1 mmol) and K$_2$CO$_3$ (2786.2 mg, 20.2 mmol) were added to a solution of methyl 3-hydroxy-5-methylbenzoate (670.0 mg, 4.0 mmol) in DMF (10.0 mL). The reaction mixture was stirred at 80° C. for 12 h and cooled to ambient temperature. The reaction mixture was filtered through the Celite and quenched with H$_2$O (5.0 mL). The mixture was extracted with CH$_2$Cl$_2$ (3×20.0 mL). The combined organics were dried over Na$_2$SO$_4$, filtered and concentrated under reduced pressure. The residue was purified by flash chromatography (Combi-flash Rf, Hex/EtOAc=0-100% gradient) to afford the title compound (579.7 mg, 65% yield). LCMS: $R_T$=1.774 min, MS (ES) 221.3 (M+H)

Step C. Preparation of methyl 3-(bromomethyl)-5-(cyclopropylmethoxy)benzoate

The title compound (608.4 mg, 77%) was prepared from the procedure described in Example 105, Step C using methyl 3-(cyclopropylmethoxy)-5-methylbenzoate (579.9 mg, 2.63 mmol). LCMS: $R_T$=1.818 min, MS (ES) 300.2 (M+H).

Step D. Preparation of methyl 3-(cyclopropyl-methoxy)-5-((2-imino-3-methyl-2,3-dihydro-1H-imidazol-1-yl)methyl)benzoate 1-Methyl-1H-imidazol-2-amine hydrochloride (296.3 mg, 3.1 mmol), KI (101.3 mg, 0.6 mmol), and DIPEA (1.77 mL, 10.2 mmol) were added to a solution of methyl 3-(bromomethyl)-5-(cyclopropylmethoxy)benzoate (608.4 mg, 2.0 mmol) in THF (6.0 mL). The reaction mixture was stirred at 90° C. for 12 h and cooled to ambient temperature to yield the crude title compound. LCMS: $R_T$=1.101 min, MS (ES) 316.4 (M+H).

Step E. Preparation of methyl (E)-3-((2-((tert-bu-toxycarbonyl)imino)-3-methyl-2,3-dihydro-1H-imi-dazol-1-yl)methyl)-5-(cyclopropylmethoxy)benzoate The title compound (629.9 mg, 74% 2 step) was prepared from the procedure described in Example 84, Step B using methyl 3-(cyclopropylmethoxy)-5-((2-imino-3-methyl-2,3-dihydro-1H-imidazol-1-yl)methyl)benzoate (641.4 mg, 2.0 mmol). LCMS: $R_T$=1.252 min, MS (ES) 416.5 (M+H).

Step F. Preparation of (E)-3-((2-((tert-butoxycarbo-nyl)imino)-3-methyl-2,3-dihydro-1H-imidazol-1-yl) methyl)-5-(cyclopropylmethoxy)benzoic Acid The crude mixture of title compound was prepared from the procedure described in Example 27, Step B using methyl

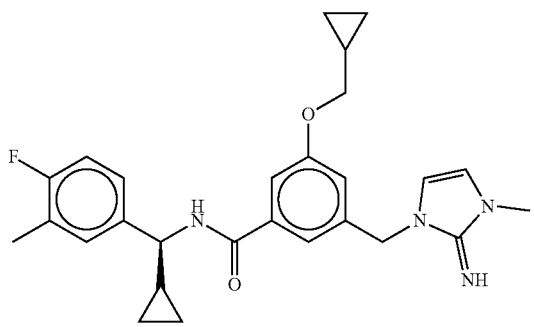

(E)-3-((2-((tert-butoxycarbonyl)imino)-3-methyl-2,3-dihydro-1H-imidazol-1-yl)methyl)-5-(cyclopropylmethoxy)benzoate (629.9 mg, 1.5 mmol). LCMS: $R_T$=1.150 min, MS (ES) 402.5 (M+H).

Step G. Preparation of tert-butyl (S,E)-(1-(3-((cyclopropyl(4-fluoro-3-methylphenyl)methyl)carbamoyl)-5-(cyclopropylmethoxy)benzyl)-3-methyl-1,3-dihydro-2H-imidazol-2-ylidene)carbamate The title compound (23.1 mg, 47% 2 step) was prepared from the procedure described in Example 33, Step A using (E)-3-((2-((tert-butoxycarbonyl)imino)-3-methyl-2,3-dihydro-1H-imidazol-1-yl)methyl)-5-(cyclopropylmethoxy)benzoic acid (35.0 mg, 0.09 mmol) and (S)-cyclopropyl(4-fluoro-3-methylphenyl)methanamine hydrochloride (28.2 mg, 0.13 mmol). LCMS: $R_T$=1.510 min, MS (ES) 563.7 (M+H).

Step H. Example 175

The title compound (9.2 mg, 48%) was prepared from the procedure described in Example 84, Step H using tert-butyl (S,E)-(1-(3-((cyclopropyl(4-fluoro-3-methylphenyl)methyl)carbamoyl)-5-(cyclopropylmethoxy)benzyl)-3-methyl-1,3-dihydro-2H-imidazol-2-ylidene)carbamate (24.2 mg, 0.04 mmol). LCMS: $R_T$=1.373 min, MS (ES) 463.6 (M+H).

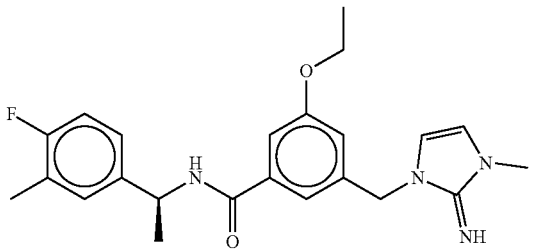

Example 176

(S)-3-Ethoxy-N-(1-(4-fluoro-3-methylphenyl)ethyl)-5-((2-imino-3-methyl-2,3-dihydro-1H-imidazol-1-yl)methyl)benzamide Step A. Preparation of methyl 3-ethoxy-5-methylbenzoate The title compound (563.8 mg, 71%) was prepared from the procedure described in Example 175, Step B using methyl 3-hydroxy-5-methylbenzoate (670.0 mg, 4.0 mmol) and bromoethane (0.87 mL, 12.1 mmol). LCMS: R-T=1.655 min, MS (ES) 195.2 (M+H).

Step B. Preparation of methyl 3-(bromomethyl)-5-ethoxybenzoate

The title compound (603.6 mg, 76%) was prepared from the procedure described in Example 105, Step C using methyl 3-ethoxy-5-methylbenzoate (563.8 mg, 2.9 mmol). LCMS: $R_T$=1.714 min, MS (ES) 274.1 (M+H).

Step C. Preparation of methyl 3-ethoxy-5-((2-imino-3-methyl-2,3-dihydro-1H-imidazol-1-yl)methyl)benzoate The crude title compound was prepared from the procedure described in Example 1, Step E using methyl 3-(bromomethyl)-5-ethoxybenzoate (603.6 mg, 2.2 mmol). LCMS: $R_T$=0.994 min, MS (ES) 290.3 (M+H).

Step D. Preparation of methyl (E)-3-((2-((tert-butoxycarbonyl)imino)-3-methyl-2,3-dihydro-1H-imidazol-1-yl)methyl)-5-ethoxybenzoate The title compound (824.9 mg, 95% 2 step) was prepared from the procedure described in Example 84, Step B using methyl 3-ethoxy-5-((2-imino-3-methyl-2,3-dihydro-1H-imidazol-1-yl)methyl)benzoate (639.4 mg, 2.2 mmol). LCMS: $R_T$=1.198 min, MS (ES) 390.5 (M+H).

Step E. Preparation of (E)-3-((2-((tert-butoxycarbonyl)imino)-3-methyl-2,3-dihydro-1H-imidazol-1-yl)methyl)-5-ethoxybenzoic Acid The crude title compound was prepared from the procedure described in Example 27, Step B using methyl (E)-3-((2-((tert-butoxycarbonyl)imino)-3-methyl-2,3-dihydro-1H-imidazol-1-yl)methyl)-5-ethoxybenzoate (400.0 mg, 1.03 mmol). LCMS: $R_T$=1.064 min, MS (ES) 376.4 (M+H).

Step F. Preparation of tert-butyl (S,E)-(1-(3-ethoxy-5-((1-(4-fluoro-3-methylphenyl)ethyl)carbamoyl)benzyl)-3-methyl-1,3-dihydro-2H-imidazol-2-ylidene)carbamate The title compound (21.8 mg, 45% 2 step) was prepared from the procedure described in Example 33, Step A using (E)-3-((2-((tert-butoxycarbonyl)imino)-3-methyl-2,3-dihydro-1H-imidazol-1-yl)methyl)-5-ethoxybenzoic acid (35.0 mg, 0.09 mmol) and (S)-1-(4-fluoro-3-methylphenyl)ethan-1-amine (28.6 mg, 0.19 mmol). LCMS: $R_T$=1.383 min, MS (ES) 511.6 (M+H).

Step G. Example 176

The title compound (14.9 mg, 84%) was prepared from the procedure described in Example 84, Step H using tert-butyl (S,E)-(1-(3-ethoxy-5-((1-(4-fluoro-3-methylphenyl)ethyl)carbamoyl)benzyl)-3-methyl-1,3-dihydro-2H-imidazol-2-ylidene)carbamate (21.8 mg, 0.04 mmol). $^1$H NMR (400 MHz, Chloroform-d) δ 7.39 (s, 1H), 7.34 (d, J=7.3 Hz, 1H), 7.24-7.15 (m, 2H), 6.95-6.87 (m, 1H), 6.82 (s, 1H), 6.19 (d, J=2.6 Hz, 11H), 6.17 (d, J=2.6 Hz, 11), 5.22 (p, J=7.1 Hz, 1H), 4.89-4.73 (m, 2H), 4.00 (q, J=6.9 Hz, 2H), 3.31 (s, 3H), 2.23 (d, J=1.7 Hz, 3H), 1.56 (d, J=7.0 Hz, 3H), 1.36 (t, J=7.0 Hz, 3H); LCMS: $R_T$=1.237 min, MS (ES) 411.5 (M+H).

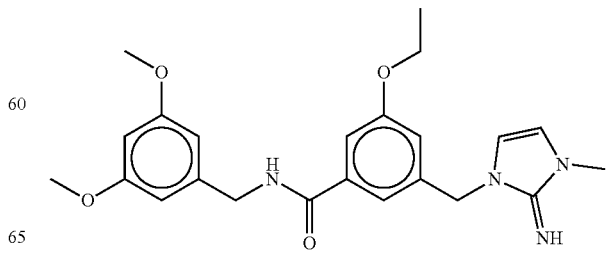

Example 177

N-(3,5-Diethoxybenzyl)-3-ethoxy-5-((2-imino-3-methyl-2,3-dihydro-1H-imidazol-1-yl)methyl)benzamide Step A. Preparation of tert-butyl (E)-(1-(3-((3,5-dimethoxybenzyl)carbamoyl)-5-ethoxybenzyl)-3-methyl-1,3-dihydro-2H-imidazol-2-ylidene)carbamate The title compound (23.8 mg, 48% 2 step) was prepared from the procedure described in Example 33, Step A using (E)-3-((2-((tert-butoxycarbonyl)imino)-3-methyl-2,3-dihydro-1H-imidazol-1-yl)methyl)-5-ethoxybenzoic acid (35.0 mg, 0.09 mmol) and (3,5-dimethoxyphenyl)methanamine (28.6 mg, 0.19 mmol). LCMS: $R_T$=1.262 min, MS (ES) 525.6 (M+H).

Step B. Example 177

The title compound (13.4 mg, 69%) was prepared from the procedure described in Example 84, Step H using tert-butyl (E)-(1-(3-((3,5-dimethoxybenzyl)carbamoyl)-5-ethoxybenzyl)-3-methyl-1,3-dihydro-2H-imidazol-2-ylidene)carbamate (23.8 mg, 0.05 mmol). $^1$H NMR (400 MHz, Chloroform-d) δ 7.55 (s, 1H), 7.36 (s, 1H), 7.31 (s, 1H), 6.82 (s, 1H), 6.51 (d, J=2.2 Hz, 2H), 6.32 (t, J=2.2 Hz, 1H), 6.17 (d, J=2.6 Hz, 1H), 6.16 (d, J=2.6 Hz, 1H), 4.80 (s, 2H), 4.53 (d, J=3.6 Hz, 2H), 4.01 (q, J=7.0 Hz, 2H), 3.74 (s, 6H), 3.28 (s, 3H), 1.37 (t, J=7.0 Hz, 3H); LCMS: $R_T$=1.120 min, MS (ES) 425.5 (M+H).

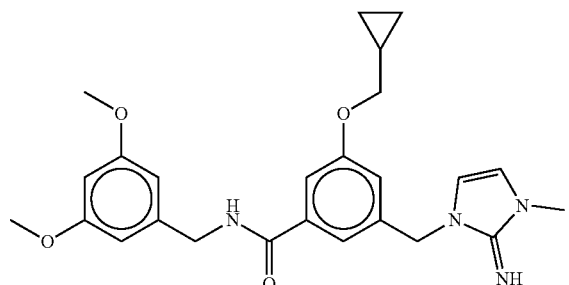

Example 178

3-(Cyclopropylmethoxy)-N-(3,5-dim ethoxybenzyl)-5-((2-imino-3-methyl-2,3-dihydro-1H-imidazol-1-yl)methyl)benzamide Step A. Preparation of tert-butyl (E)-(1-(3-(cyclopropylmethoxy)-5-((3,5-dimethoxybenzyl)carbamoyl)benzyl)-3-methyl-1,3-dihydro-2H-imidazol-2-ylidene)carbamate The title compound (22.6 mg, 47% 2 step) was prepared from the procedure described in Example 33, Step A using (E)-3-((2-((tert-butoxycarbonyl)imino)-3-methyl-2,3-dihydro-1H-imidazol-1-yl)methyl)-5-(cyclopropylmethoxy)benzoic acid (35.0 mg, 0.09 mmol) and (3,5-dimethoxyphenyl)methanamine (29.2 mg, 0.17 mmol). LCMS: $R_T$=1.341 min, MS (ES) 551.7 (M+H).

Step B. Example 178

The title compound (12.9 mg, 69%) was prepared from the procedure described in Example 84, Step H using tert-butyl (E)-(1-(3-(cyclopropylmethoxy)-5-((3,5-dimethoxybenzyl)carbamoyl)benzyl)-3-methyl-1,3-dihydro-2H-imidazol-2-ylidene)carbamate (21.8 mg, 0.04 mmol). $^1$H NMR (400 MHz, Chloroform-d) δ 7.57 (s, 1H), 7.42 (s, 1H), 7.33 (s, 1H), 6.87 (s, 1H), 6.53 (d, J=2.2 Hz, 2H), 6.35 (t, J=2.2 Hz, 1H), 6.22 (q, J=2.6 Hz, 2H), 4.85 (s, 2H), 4.55 (d, J=4.6 Hz, 2H), 3.82 (d, J=6.9 Hz, 2H), 3.77 (s, 6H), 3.34 (s, 3H), 1.24 (m, 1H), 0.72-0.57 (m, 2H), 0.34 (q, J=4.8 Hz, 2H); LCMS: $R_T$=1.189 min, MS (ES) 451.5 (M+H).

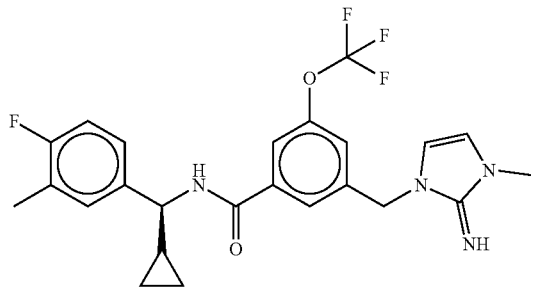

Example 179

(S)—N-(Cyclopropyl(4=fluoro-3-methylphenyl)methyl)-3-((2-imino-3-methyl-2,3-dihydro-1H-imidazol-1-yl)methyl)-5-(trifluoromethoxy)benzamide Step A. Preparation of tert-butyl (S,E)-(1-(3-((cyclopropyl(4-fluoro-3-methylphenyl)methyl)carbamoyl)-5-(trifluoromethoxy)benzyl)-3-methyl-1,3-dihydro-2H-imidazol-2-ylidene)carbamate The title compound (24.2 mg, 49% 2 step) was prepared from the procedure described in Example 33, Step A using (E)-3-((2-((tert-butoxycarbonyl)imino)-3-methyl-2,3-dihydro-1H-imidazol-1-yl)methyl)-5-(trifluoromethoxy)benzoic acid (35.0 mg, 0.08 mmol) and (5)-cyclopropyl(4-fluoro-3-methylphenyl)methanamine hydrochloride (27.3 mg, 0.13 mmol). LCMS: $R_T$=1.508 min, MS (ES) 577.6 (M+H).

Step B. Example 179

The title compound (11.4 mg, 57%) was prepared from the procedure described in Example 84, Step H using tert-butyl (S,E)-(1-(3-((cyclopropyl(4-fluoro-3-methylphenyl)methyl)carbamoyl)-5-(trifluoromethoxy)benzyl)-3-methyl-1,3-dihydro-2H-imidazol-2-ylidene)carbamate (24.2 mg, 0.04 mmol). LCMS: $R_T$=1.391 min, MS (ES) 477.5 (M+H).

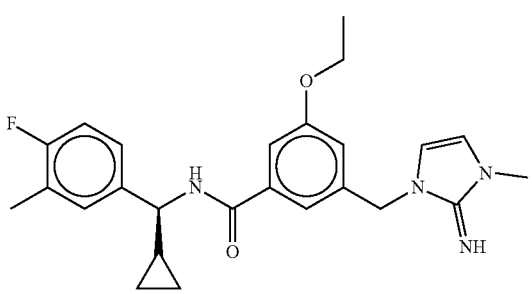

Example 180

(S)—N-(Cyclopropyl(4-fluoro-3-methylphenyl)methyl)-3-methoxy-5-((2-imino-3-methyl-2,3-dihydro-1H-imidazol-1-yl)methyl)benzamide Step A. Preparation of tert-butyl (S,E)-(1-(3-((cyclopropyl(4-fluoro-3-methylphenyl)methyl)carbamoyl)-5-ethoxybenzyl)-3-methyl-1,3-dihydro-2H-imidazol-2-ylidene)carbamate The title compound (32.7 mg, 65% 2 step) was prepared from the procedure described in Example 33, Step A using (E)-3-((2-((tert-butoxycarbonyl)imino)-3-methyl-2,3-dihydro-1H-imidazol-1-yl)methyl)-5-ethoxybenzoic acid (35.0 mg, 0.09 mmol) and (S)-cyclopropyl(4-fluoro-3-methylphenyl)methanamine hydrochloride (30.2 mg, 0.14 mmol). LCMS: $R_T$=1.436 min, MS (ES) 537.7 (M+H).

Step B. Example 180

The title compound (12.3 mg, 42%) was prepared from the procedure described in Example 84, Step H using tert-butyl (S,E)-(1-(3-((cyclopropyl(4-fluoro-3-methylphenyl)methyl)carbamoyl)-5-ethoxybenzyl)-3-methyl-1,3-dihydro-2H-imidazol-2-ylidene)carbamate (32.7 mg, 0.06 mmol). LCMS: $R_T$=1.290 min, MS (ES) 437.5 (M+H).

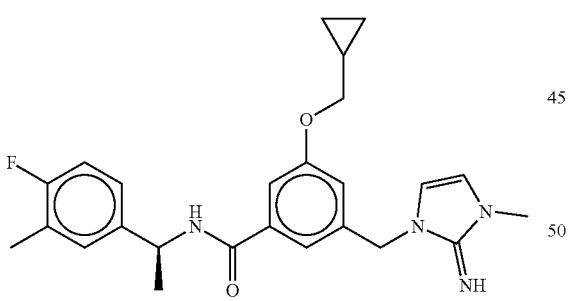

Example 181

(S)-3-(Cyclopropylmethoxy)-N-(1-(4-fluoro-3-methylphenyl)ethyl)-5-((2-imino-3-methyl-2,3-dihydro-1H-imidazol-1-yl)methyl)benzamide Step A. Preparation of tert-butyl (S,E)-(1-(3-(cyclopropylmethoxy)-5-((1-(4-fluoro-3-methylphenyl)ethyl)carbamoyl)benzyl)-3-ethyl-1,3-dihydro-2H-imidazol-2-ylidene)carbamate The title compound (21.0 mg, 44% 2 step) was prepared from the procedure described in Example 33, Step A using (E)-3-((2-((tert-butoxycarbonyl)imino)-3-methyl-2,3-dihydro-1H-imidazol-1-yl)methyl)-5-(cyclopropylmethoxy)benzoic acid (35.0 mg, 0.09 mmol) and (S)-1-(4-fluoro-3-methylphenyl)ethan-1-amine (29.2 mg, 0.17 mmol). LCMS: $R_T$=1.456 min, MS (ES) 537.7 (M+H).

Step B. Example 181

The title compound (12.4 mg, 72%) was prepared from the procedure described in Example 84, Step H using tert-butyl (S,E)-(1-(3-(cyclopropylmethoxy)-5-((1(4-fluoro-3-methylphenyl)ethyl)carbamoyl)benzyl)-3-methyl-1,3-dihydro-2H-imidazol-2-ylidene)carbamate (21.8 mg, 0.04 mmol). ¹H NMR (400 MHz, Chloroform-d) δ 7.43 (s, 1H), 7.34 (d, J=7.7 Hz, 1H), 7.24-7.15 (m, 2H), 6.97-6.87 (m, 1H), 6.84 (s, 1H), 6.20 (d, J=2.6 Hz, 1H), 6.19 (d, J=2.6 Hz, 1H), 5.21 (p, J=7.1 Hz, 1H), 4.92-4.74 (m, 2H), 3.82-3.74 (m, 2H), 3.33 (s, 3H), 2.23 (d, J=1.7 Hz, 3H), 1.56 (d, J=7.0 Hz, 3H), 1.30-1.14 (m, 1H), 0.67-0.53 (m, 2H), 0.31 (q, J=4.7 Hz, 2H); LCMS: $R_T$=1.300 min, MS (ES) 437.5 (M+H).

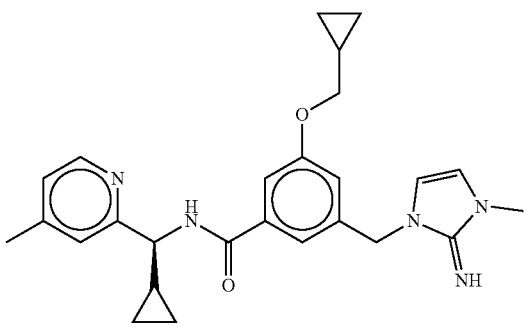

Example 182

(S)—N-(Cyclopropyl(4-methylpyridin-2-yl)methyl)-3-(cyclopropylmethoxy)-5-((2-imino-3-methyl-2,3-dihydro-1H-imidazol-1-yl)methyl)benzamide Step A. Preparation of tert-butyl (S,E)-(1-(3-((cyclopropyl(4-methylpyridin-2-yl)methyl)carbamoyl)-5-(cyclopropylmethoxy)benzyl)-3-methyl-1,3-dihydro-2H-imidazol-2-ylidene)carbamate The title compound (22.3 mg, 46% 2 step) was prepared from the procedure described in Example 33, Step A using (E)-3-((2-((tert-butoxycarbonyl)imino)-3-methyl-2,3-dihydro-1H-imidazol-1-yl)methyl)-5-(cyclopropylmethoxy)benzoic acid (35.0 mg, 0.09 mmol) and (S)-cyclopropyl(4-methylpyridin-2-yl)methanamine dihydrochloride (30.8 mg, 0.13 mmol). LCMS: $R_T$=1.141 min, MS (ES) 546.7 (M+H).

Step B. Example 182

The title compound (8.0 mg, 43%) was prepared from the procedure described in Example 84, Step H using tert-butyl (S,E)-(1-(3-((cyclopropyl(4-methylpyridin-2-yl)methyl)carbamoyl)-5-(cyclopropylmethoxy)benzyl)-3-methyl-1,3-dihydro-2H-imidazol-2-ylidene)carbamate (21.8 mg, 0.04 mmol). LCMS: $R_T$=0.997 min, MS (ES) 446.6 (M+H).

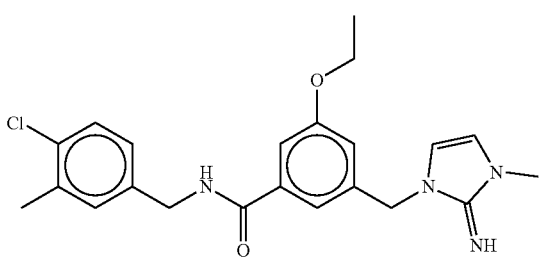

Example 183

N-(4-Chloro-3-methylbenzyl)-3-ethoxy-5-((2-imino-3-methyl-2,3-dihydro-1H-imidazol-1-yl)methyl)benzamide Step A. Preparation of tert-butyl (E)-(1-(3-((4-chloro-3-methyl benzyl)carbamoyl)-5-ethoxybenzyl)-3-methyl-1,3-dihydro-2H-imidazol-2-ylidene)carbamate The title compound (21.4 mg, 44% 2 step) was prepared from the procedure described in Example 33, Step A using (E)-3-((2-((tert-butoxycarbonyl)imino)-3-methyl-2,3-dihydro-1H-imidazol-1-yl)methyl)-5-ethoxybenzoic acid (35.0 mg, 0.09 mmol) and (4-chloro-3-methylphenyl)methanamine (0.03 mL, 0.19 mmol). LCMS: $R_T$=1.398 min, MS (ES) 514.0 (M+H).

Step B. Example 183

The title compound (15.3 mg, 88%) was prepared from the procedure described in Example 84, Step H using tert-butyl (E)-(1-(3-((4-chloro-3-methylbenzyl)carbamoyl)-5-ethoxybenzyl)-3-methyl-1,3-dihydro-2H-imidazol-2-ylidene)carbamate (21.4 mg, 0.04 mmol). $^1$H NMR (400 MHz, Chloroform-d) δ 7.91 (s, 1H), 7.39 (s, 1H), 7.32 (s, 1H), 7.20 (m, 2H), 7.10 (dd, J=8.1, 1.9 Hz, 1H), 6.80 (s, 1H), 6.17 (m, 2H), 4.78 (s, 2H), 4.49 (s, 2H), 3.99 (q, J=7.0 Hz, 2H), 3.26 (s, 3H), 2.29 (s, 3H), 1.36 (t, J=7.0 Hz, 3H). LCMS: $R_T$=1.255 min, MS (ES) 413.9 (M+H).

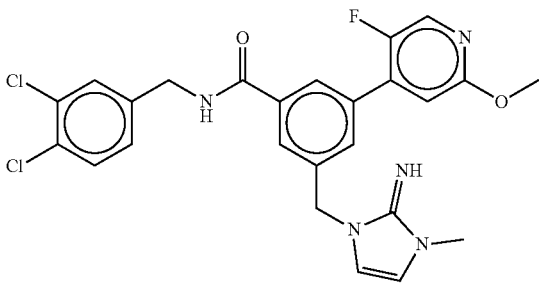

Example 184

N-(3,4-dichlorobenzyl)-3-(5-fluoro-2-methoxypyridin-4-yl)-5-((2-imino-3-methyl-2,3-dihydro-1H-imidazol-1-yl)methyl)benzamide The title compound (0.05, 49%) was prepared following the procedure described in Example 1, Step A using tert-butyl (E)-(1-(3-bromo-5-((3,4-dichlorobenzyl)carbamoyl)benzyl)-3-methyl-1,3-dihydro-2H-imidazol-2-ylidene)carbamate (0.10 g. 0.18 mmol) and (5-fluoro-2-methoxypyridin-4-yl)boronic acid (0.05 g, 0.27 mmol) followed by deprotection of Boc group by TFA in DCM. LCMS: 98% 254 nm $R_T$=0.96 min, MS (ES) 514 (M+H).

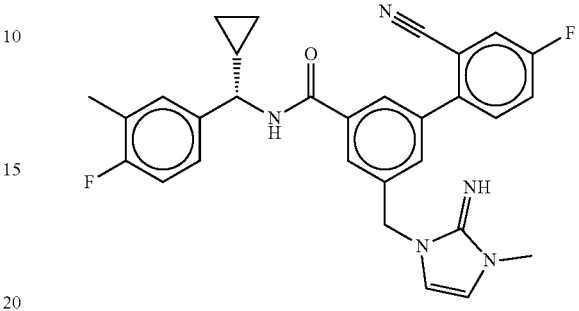

Example 185

(S)-2'-Cyano-N-(cyclopropyl(4-fluoro-3-methylphenyl)methyl)-4'-fluoro-5-((2-imino-3-methyl-2,3-dihydro-1H-imidazol-1-yl)methyl)-[1,1'-biphenyl]-3-carboxamide Step A. Preparation of methyl 5-(((tert-butyldiphenylsilyl)oxy)methyl)-2'-cyano-4'-fluoro-[1,1'-biphenyl]-3-carboxylate The title compound (1.57 g, 99%), was prepared from the procedure described in Example 1, Step A using methyl 3-(((tert-butyldiphenylsilyl)oxy)methyl)-5-(4,4,5,5-tetramethyl-1,3,2-dioxaborolan-2-yl)benzoate (1.6 g, 3.0 mmol) and 2-bromo-5-fluorobenzonitrile (0.9 g, 4.5 mmol). LCMS method 3: $R_T$=1.85 min, MS (ES) 523.9 (M+).

Step B. Preparation of methyl 2'-cyano-4'-fluoro-5-(hydroxymethyl)-[1,1'-biphenyl]-3-carboxylate TBAF 1.0 M in THF (6 mL, 6.0 mmol) was added to a solution of methyl 5-(((tert-butyldiphenylsilyl)oxy)methyl)-2'-cyano-4'-fluoro-[1,1'-biphenyl]-3-carboxylate (1.6 g, 3.0 mmol) in THF (10 mL). The reaction mixture was stirred at rt for 2 h, and quenched with water (5 mL). The mixture was extracted with EtOAc (3×10 mL). The combined organic layer was dried with MgSO$_4$ and concentrated. The residue was purified by flash chromatography (Combi-flash Rf, Hex/EtOAc=0-100% gradient) to afford the title compound (0.58 g, 68%).

Step C. Preparation of 2'-cyano-4'-fluoro-5-(hydroxymethyl)-[1,1'-biphenyl]-3-carboxylic Acid The title compound (0.5 g, 91%) was prepared from the procedure described in Example 139, Step B using methyl 2'-cyano-4'-fluoro-5-(hydroxymethyl)-[1,1-biphenyl]-3-carboxylate (0.58 g, 2.0 mmol).

Step D. Preparation of (S)-2'-cyano-N-(cyclopropyl (4-fluoro-3-methylphenyl)methyl)-4'-fluoro-5-(hydroxymethyl)-[1,1'-biphenyl]-3-carboxamide The title compound (0.38 g, 95%) was prepared from the procedure described in Example 91, Step D using 2'-cyano- 4'-fluoro-5-(hydroxymethyl)-[1,1'-biphenyl]-3-carboxylic acid (0.25 g, 0.92 mmol) and (5)-cyclopropyl(4-fluoro-3-methylphenyl)methanamine hydrochloride (0.30 g, 1.4 mmol). LCMS method 2: $R_T$=1.70 min, MS (ES) 333.0 (M+H)

Step E. Preparation of (S)-5-(bromomethyl)-2'-cyano-N-(cyclopropyl(4-fluoro-3-methylphenyl)methyl)-4'-fluoro-[1,1'-biphenyl]-3-carboxamide The title compound (0.26 g, 59%) was prepared from the procedure described in Example 139, Step D using (5)-2'-cyano-N-(cyclopropyl(4-fluoro-3-methylphenyl)methyl)-4'-fluoro-5-(hydroxymethyl)-[1,1'-biphenyl]-3-carboxamide (0.38 g, 0.88 mmol), PPh$_3$ (0.46 g, 1.76 mmol) and NBS (0.31 g, 1.76 mmol).

Step F. Example 185

The title compound (11 mg, 21%) was prepared from the procedure described in Example 91, Step F using (5)-5-(bromomethyl)-2'-cyano-N-(cyclopropyl(4-fluoro-3-methylphenyl)methyl)-4'-fluoro-[1,1'-biphenyl]-3-carboxamide (50 mg, 0.10 mmol), 1-methyl-1H-imidazol-2-amine (15 mg, 0.15 mmol) and DIPEA (70 µL, 0.40 mmol). $^1$H NMR (CDCl$_3$) δ 8.27 (s, 1H), 8.22 (d, J=7.9 Hz, 1H), 8.0 (bs, 1H), 7.57-7.54 (m, 1H), 7.50 (bs, 1H), 7.43-7.34 (series of m, 2H), 7.31-7.27 (m, 2H), 6.89 (t, J=9.2 Hz, 1H), 6.60 (d, J=2.5 Hz, 1H), 6.46 (d, J=2.5 Hz, 1H), 5.24 (s, 2H), 4.42 (t, J=8.6 Hz, 1H), 3.51 (s, 3H), 2.21 (s, 3H), 1.45-1.37 (m, 1H), 0.63-0.53 (m, 2H), 0.50-0.44 (m, 1H), 0.37-0.31 (m, 1H). LCMS method 2: $R_T$=1.37 min, MS (ES) 512.0 (M+H)

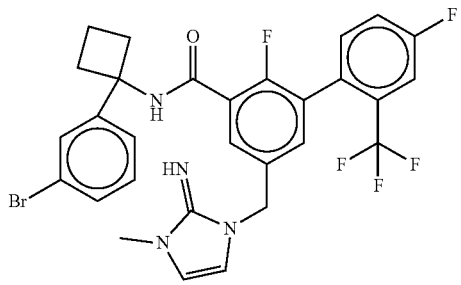

Example 186

N-(1-(3-Bromophenyl)cyclobutyl)-2,4'-difluoro-5-((2-imino-3-methyl-2,3-dihydro-1H-imidazol-1-yl)methyl)-2'-(trifluoromethyl)-[1,1'-biphenyl]-3-carboxamide Step A. Preparation of tert-butyl (Z)-(1-((5-((1-(3-bromophenyl)cyclobutyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate The title compound (13.2 mg, 43% 2 step) was prepared from the procedure described in Example 33, Step A using (Z)-5-((2-((tert-butoxycarbonyl)imino)-3-methyl-2,3-dihydro-1H-imidazol-1-yl)methyl)-2,4'-difluoro-2'-(trifluoromethyl)-[1,1'-biphenyl]-3-carboxylic acid (21.7 mg, 0.04 mmol) and 1-(3-bromophenyl)cyclobutan-1-amine (0.02 mL, 0.08 mmol). LCMS: $R_T$=1.694 min, MS (ES) 720.6 (M+H).

Step B. Example 186

The title compound (9.0 mg, 79%) was prepared from the procedure described in Example 84, Step H using tert-butyl (Z)-(1-((5-((1-(3-bromophenyl)cyclobutyl)carbamoyl)-4',6-difluoro-2'-(trifluoromethyl)-[1,1'-biphenyl]-3-yl)methyl)-3-methyl-1,3-dihydro-2H-imidazol-2-ylidene)carbamate (13.2 mg, 0.02 mmol). LCMS: $R_T$=1.567 min, MS (ES) 620.4 (M+H).

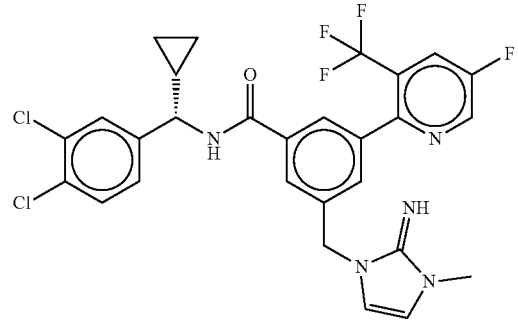

Example 187

((S)—N-(Cyclopropyl(3,4-dichlorophenyl)methyl)-3-(5-fluoro-3-(trifluoromethyl)pyridin-2-yl)-5-((2-imino-3-methyl-2,3-dihydro-1H-imidazol-1-yl)methyl)benzamide The title compound was prepared (25 mg, 0.042 mmol) according to the procedures described in Examples 72 and 60, Steps A-G substituting the hydrochloride salt of (S)-cyclopropyl(3,4-dichlorophenyl)methanamine (0.3 g, 1.1 mmol) in Step E. LC-MS: >95% 254 nm, $R_T$=1.075 min, MS (ES) 592.1 (M+H).

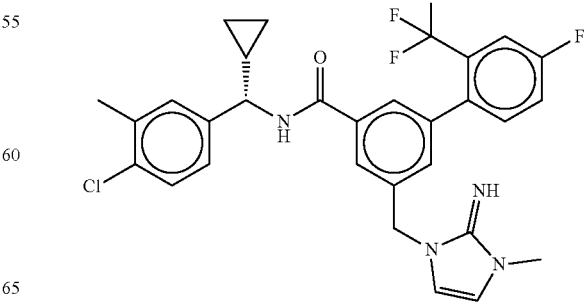

Example 188

(S)—N-(Cyclopropyl(4-fluoro-3-methylphenyl)methyl)-4'-fluoro-5-((2-imino-3-methyl-2,3-dihydro-1H-imidazol-1-yl)methyl)-2'-(trifluoromethyl)-[1,1'-biphenyl]3-carboxamide

Step A. Preparation of (S)—N-(cyclopropyl(4-fluoro-3-methylphenyl)methyl)-4'-fluoro-5-(hydroxymethyl)-2'-(trifluoromethyl)-[1,1'-biphenyl]-3-carboxamide The title compound (0.45 g, 99%) was prepared from the procedure described in Example 91, Step D using 4'-fluoro-5-(hydroxymethyl)-2'-(trifluoromethyl)-[1,1'-biphenyl]-3-carboxylic acid (0.30 g, 0.95 mmol) and (3)-cyclopropyl(4-fluoro-3-methylphenyl)methanamine hydrochloride (0.24 g, 1.2 mmol). LCMS method 2: R$_T$=1.85 min, MS (ES) 475.9 (M+)

Step B. Preparation of (S)-5-(bromomethyl)-N-(cyclopropyl(4-fluoro-3-methylphenyl)methyl)-4'-fluoro-2'-(trifluoromethyl)-[1,1'-biphenyl]-3-carboxamide The title compound (0.29 g, 570%) was prepared from the procedure described in Example 139, Step D using (S)—N-(cyclopropyl(4-fluoro-3-methylphenyl)methyl)-4'-fluoro-5-(hydroxymethyl)-2'-(trifluoromethyl)-[1,1'-biphenyl]-3-carboxamide (0.45 g, 0.95 mmol), PPh$_3$ (0.50 g, 1.89 mmol) and NBS (0.34 g, 1.89 mmol).

Step C. Example 188

The title compound (14 mg, 27%) was prepared from the procedure described in Example 91, Step F using (S)-5-(bromomethyl)-N-(cyclopropyl(4-fluoro-3-methylphenyl)methyl)-4'-fluoro-2'-(trifluoromethyl)-[1,1'-biphenyl]-3-carboxamide (50 mg, 0.093 mmol), 1-methyl-1H-imidazol-2-amine (13 mg, 0.14 mmol) and DIPEA (65 μL, 0.37 mmol). $^1$H NMR (CDCl$_3$) δ 8.0 (s, 1H), 7.77 (s, 1H), 7.61 (d, J=7.3 Hz, 1H), 7.44 (dd, J=9.1, 2.2 Hz, 1H), 7.23-7.24 (m, 5H), 6.92 (t, J=8.6 Hz, 1H), 6.34 (d, J=2.5 Hz, 1H), 6.31 (d, J=2.5 Hz, 1H), 5.05 (s, 2H), 4.45 (t, =8.2 Hz, 1H), 3.38 (s, 3H), 2.23 (s, 3H), 1.40-1.31 (m, 1H), 0.63-0.59 (m, 2H), 0.50-0.46 (m, 1H), 0.38-0.33 (m, 1H); LCMS method 2: R$_T$=1.54 min, MS (ES) 555.0 (M+1H).

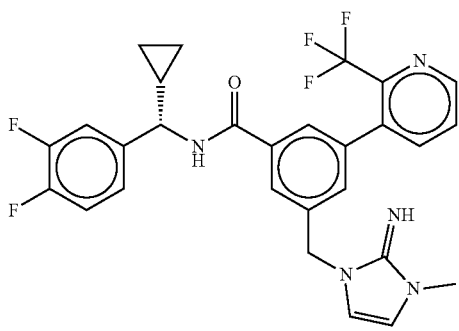

Example 189

(S)—N-(Cyclopropyl(3,4-difluorophenyl)methyl)-3-((2-imino-3-methyl-2,3-dihydro-1H-imidazol-1-yl)methyl)-5-(2-(trifluoromethyl)pyridin-3-yl)benzamide The title compound was prepared (14 mg, 0.026 mmol) according to the procedures described in Example 60, Steps A-G substituting the hydrochloride salt of (S)-cyclopropyl(3,4-difluorophenyl)methanamine (0.3 g, 1.4 mmol) in Step E. LC-MS: >95% 254 nm, R$_T$=0.993 min, MS (ES) 542.1 (M+H).

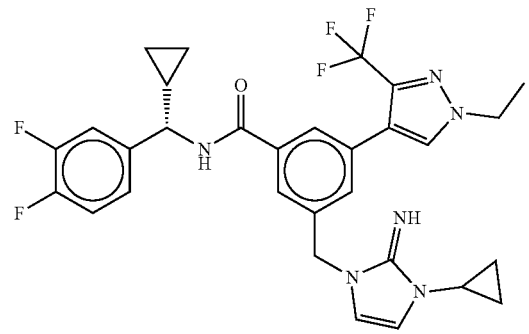

Example 190

(S)—N-(Cyclopropyl(3,4-difluorophenyl)methyl)-3-((3-cyclopropyl-2-imino-2,3-dihydro-1H-imidazol-1-yl)methyl)-5-(1-ethyl-3-(trifluoromethyl)-1H-pyrazol-4-yl)benzamide The title compound was prepared (18 mg, 0.031 mmol) according to the procedures described in Examples 162 and 60, Steps A-G substituting the hydrochloride salt of (S)-cyclopropyl(3,4-difluorophenyl)methanamine (0.3 g, 1.4 mmol) in Step E. LC-MS: >95% 254 nm, R$_T$=1.051 min, MS (ES) 585.2 (M+H).

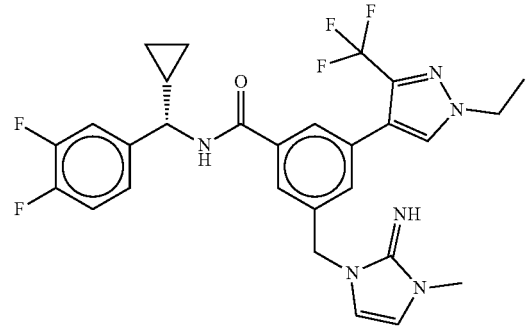

Example 191

(S)—N-(Cyclopropyl(3,4-difluorophenyl)ethyl)-3-(1-ethyl-3-(trifluoromethyl)-1H-pyrazol-4-yl)-5-((2-imino-3-methyl-2,3-dihydro-1H-imidazol-1-yl)methyl)benzamide The title compound was prepared (21 mg, 0.038 mmol) according to the procedures described in Examples 161 and 60, Steps A-G substituting the hydrochloride salt of (S)-cyclopropyl(3,4-difluorophenyl)methanamine (0.3 g, 1.4 mmol) in Step E. LC-MS: >95% 254 nm, $R_T$=1.011 min, MS (ES) 559.2 (M+H).

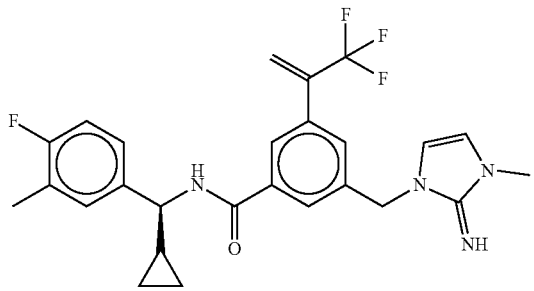

Example 192

(S)—N-(cyclopropyl(4-fluoro-3-methylphenyl)methyl)-3-((2-imino-3-methyl-2,3-dihydro-1H-imidazol-1-yl)methyl)-5-(3,3,3-trifluoroprop-1-en-2-yl)benzamide Step A. Preparation of methyl 3-(((tert-butyldiphenylsilyl)oxy)methyl)-5-(3,3,3-trifluoroprop-1-en-2-yl)benzoate The title compound (0.76 g, 81%) was prepared from the procedure described in Example 1, Step A using methyl 3-(((tert-butyl diphenyl silyl)oxy)methyl)-5-(4,4,5,5-tetramethyl-1,3,2-dioxaborolan-2-yl)benzoate (1.0 g, 1.9 mmol) and 2-bromo-3,3,3-trifluoroprop-1-ene (0.78 mL, 7.5 mmol). LCMS method 3: $R_T$=1.86 min, MS (ES) 499.0 (M+H).

Step B. Preparation of 3-(hydroxymethyl)-5-(3,3,3-trifluoroprop-1-en-2-yl)benzoic acid The title compound (118 mg, 32%) was prepared from the procedure described in Example 139, Step B using methyl 3-(((tert-butyldiphenylsilyl)oxy)methyl)-5-(3,3,3-trifluoroprop-1-en-2-yl)benzoate (750 mg, 1.50 mmol) and LiOH (180 mg, 7.5 mmol).

Step C. Preparation of (S)—N-(cyclopropyl(4-fluoro-3-methylphenyl)methyl)-3-(hydroxymethyl)-5-(3,33-trifluoroprop-1-en-2-yl)benzamide The title compound (0.14 g, 70%) was prepared from the procedure described in Example 91, Step D using 3-(hydroxymethyl)-5-(3,3,3-trifluoroprop-1-en-2-yl)benzoic acid (0.12 g, 0.48 mmol) and (S)-cyclopropyl(4-fluoro-3-methylphenyl)methanamine hydrochloride (0.12 g, 0.58 mmol). LCMS method 2: $R_T$=1.73 min, MS (ES) 408.0 (M+H).

Step D. Preparation of (S)-3-((cyclopropyl(4-fluoro-3-methylphenyl)methyl)carbamoyl)-5-(3,3,3-trifluoroprop-1-en-2-yl)benzyl methanesulfonate The title compound (83 mg, 99%) was prepared from the procedure described in Example 91, Step E using (S)—N-(cyclopropyl(4-fluoro-3-methylphenyl)methyl)-3-(hydroxymethyl)-5-(3,3,3-trifluoroprop-1-en-2-yl)benzamide (70 mg, 0.17 mmol), DIPEA (90 μL, 0.52 mmol), and methanesulfonyl chloride (20 μL, 0.26 mmol).

Step E. Example 192

The title compound (8 mg, 10%) was prepared from the procedure described in Example 91, Step F using (S)-3-((cyclopropyl(4-fluoro-3-methylphenyl)methyl)carbamoyl)-5-(3,3,3-trifluoroprop-1-en-2-yl)benzyl methanesulfonate (83 mg, 0.17 mmol), 1-methyl-1H-imidazol-2-amine (33 mg, 0.34 mmol) and DIPEA (118 μL, 0.68 mmol). LCMS method 2: $R_T$=1.41 min, MS (ES) 487.0 (M+H).

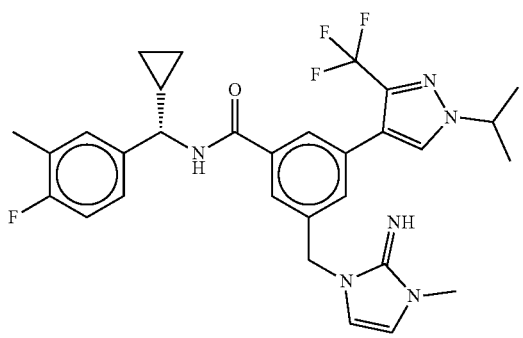

Example 193

(S)—N-(Cyclopropyl(4-fluoro-3-methylphenyl)methyl)-3-((2-imino-3-methyl-2,3-dihydro-1H-imidazol-1-yl)methyl)-5-(1-isopropyl-3-(trifluoromethyl)-1H-pyrazol-4-yl)benzamide The title compound was prepared (19 mg, 0.033 mmol) according to the procedures described in Example 60, Steps A-G substituting 4-bromo-1-isopropyl-3-(trifluoromethyl)-1H-pyrazole (1 g, 3.9 mmol) in Step C. LC-MS: >95% 254 nm, $R_T$=1.055 min, MS (ES) 569.2 (M+H).

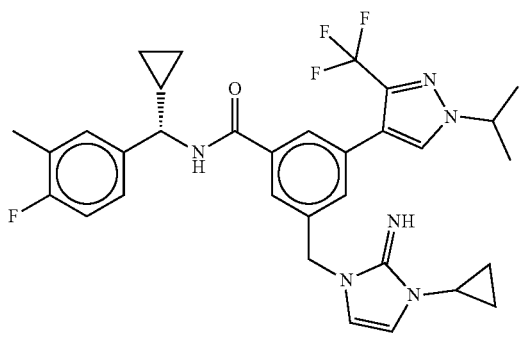

Example 194

(S)—N-(Cyclopropyl(4-fluoro-3-methylphenyl)methyl)-3-((3-cyclopropyl-2-imino-2,3-dihydro-1H-imidazol-1-yl)methyl)-5-(1-isopropyl-3-(trifluoromethyl)-1H-pyrazol-4-yl)benzamide The title compound was prepared (25 mg, 0.042 mmol) as a tan solid according to the procedures described in Examples 193 and 60, Steps A-G substituting 1-cyclopropyl-1H-imidazol-2-amine (13 mg, 0.11 mmol) in Step G. LC-MS: >95% 254 nm, $R_T$=1.071 min, MS (ES) 595.2 (M+H).

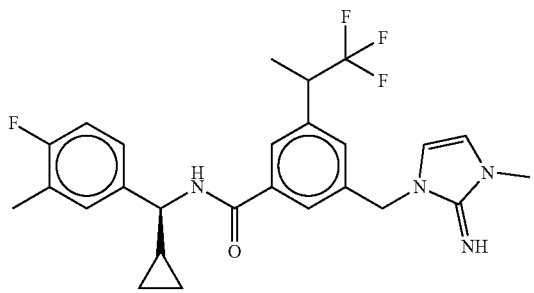
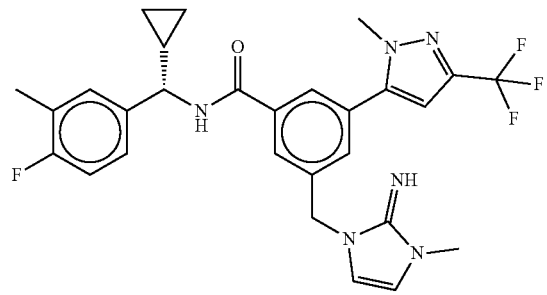

Example 195

N—((S)-Cyclopropyl(4-fluoro-3-methylphenyl)
methyl)-3-((2-imino-3-methyl-2,3-dihydro-1H-imi-
dazol-1-yl)methyl)-5-(1,1,1-trifluoropropan-2-yl)
benzamide Step A. Preparation of N—((S)-cyclopropyl(4-
fluoro-3-methylphenyl)methyl)-3-(hydroxymethyl)-
5-(1,1,1-trifluoropropan-2-yl)benzamide 10% Pd/C (5 mg) was added to a solution of (S)—N-(cyclopropyl(4-fluoro-3-methylphenyl)methyl)-3-(hydroxymethyl)-5-(3,3,3-trifluoroprop-1-en-2-yl)benzamide (70 mg, 0.17 mmol) in MeOH (5 mL). The reaction mixture was stirred under H$_2$ atmosphere at rt for 1.5 h then filtered. The filtrate was concentrated to dryness. The residue was purified by flash chromatography (Combi-flash Rf, Hex/EtOAc=0-100% gradient) to afford the title compound (20 mg, 28%). LCMS method 3: R$_T$=1.70 min, MS (ES) 410.0 (M+H).

Step B. Preparation of 3-(bromomethyl)-N—((S)-
cyclopropyl(4-fluoro-3-methylphenyl)methyl)-5-(1,
1,1-trifluoropropan-2-yl)benzamide The title compound (19 mg, 82) was prepared from the procedure described in Example 139, Step D using N—((S)-cyclopropyl(4-fluoro-3-methylphenyl)methyl)-3-(hydroxymethyl)-5-(1,1,1-trifluoropropan-2-yl)benzamide (20 mg, 0.049 mmol), PPh$_3$ (25 mg, 0.098 mmol) and NBS (17 mg, 0.098 mmol). LCMS method 2: R$_T$=1.97 min, MS (ES) 471.90 (M+)

Step C. Example 195

The title compound (1 mg, 7%) was prepared from the procedure described in Example 91, Step F using 3-(bromomethyl)-N—((S)-cyclopropyl(4-fluoro-3-methylphenyl)methyl)-5-(1,1,1-trifluoropropan-2-yl)benzamide (14 mg, 0.030 mmol), 1-methyl-1H-imidazol-2-amine (4 mg, 0.044 mmol) and DIPEA (21 g L, 0.19 mmol). $^1$H NMR (CDCl$_3$) δ 8.01 (s, 1H), 7.97 (d, J=7.9 Hz, 1H), 7.83 (s, 1H), 7.29-7.26 (m, 2H), 7.23 (d, J=7.6 Hz, 1H), 6.89 (t, J=8.8 Hz, 1H), 6.44 (d, J=2.5 Hz, 1H), 6.38 (d, J=2.5 Hz, 1H), 5.15-5.04 (m, 2H), 4.41 (t, J=8.5 Hz, 1H), 3.52 (s, 3H), 3.45-3.38 (m, 1H), 2.21 (s, 3H), 1.45 (dd, J=7.1, 2.8 Hz, 3H), 1.43-1.37 (s, 1H), 0.61-0.57 (m, 2H), 0.50-0.45 (m, 1H), 0.37-0.32 (m, 1H); LCMS method 2: R$_T$=1.41 min, MS (ES) 489.0 (M+H).

Example 196

(S)—N-(Cyclopropyl(4-fluoro-3-methylphenyl)
methyl)-3-((2-imino-3-methyl-2,3-dihydro-1H-imi-
dazol-1-yl)methyl)-5-(1-methyl-3-(trifluoromethyl)-
1H-pyrazol-5-yl)benzamide Step A. Preparation of methyl 3-(hydroxymethyl)-
5-(1-methyl-3-(trifluoromethyl)-1H-pyrazol-5-yl)
benzoate The title compound (373.5 mg, 64%) was prepared from the procedure described in Example 1, Step A using methyl 3-bromo-5-(hydroxymethyl)benzoate (450.0 mg, 1.84 mmol) and (1-methyl-3-(trifluoromethyl)-1H-pyrazol-5-yl) boronic acid (427.3 mg, 2.20 mmol). LCMS: R$_T$=1.441 min, MS (ES) 315.3 (M+H). $^1$H NMR (400 MHz, Chloroform-d) δ 8.12 (s, 1H), 8.01 (s, 1H), 7.65 (s, 1H), 6.61 (s, 1H), 4.83 (d, J=4.2 Hz, 2H), 3.95 (s, 3H), 3.93 (s, 3H).

Step B. Preparation of 3-(hydroxymethyl)-5-(1-
methyl-3-(trifluoromethyl)-1H-pyrazol-5-yl)benzoic
Acid The crude title compound was prepared from the procedure described in Example 27, Step B using methyl 3-(hydroxymethyl)-5-(1-methyl-3-(trifluoromethyl)-1H-pyrazol-5-yl)benzoate (373.5 mg, 1.19 mmol). LCMS: R$_T$=1.233 min, MS (ES) 301.2 (M+H).

Step C. Preparation of (S)—N-(cyclopropyl(4-
fluoro-3-methylphenyl)methyl)-3-(hydroxymethyl)-
5-(1-methyl-3-(trifluoromethyl)-1H-pyrazol-5-yl)
benzamide The crude title compound was prepared from the procedure described in Example 33, Step A using 3-(hydroxymethyl)-5-(1-methyl-3-(trifluoromethyl)-1H-pyrazol-5-yl)benzoic acid (35.0 mg, 0.12 mmol) and (S)-cyclopropyl(4-fluoro-3-methylphenyl)methanamine hydrochloride (30.2 mg, 0.14 mmol). LCMS: R$_T$=1.735 min, MS (ES) 462.5 (M+H).

Step D. Preparation of (S)-3-(bromomethyl)-N-
(cyclopropyl(4-fluoro-3-methylphenyl)methyl)-5-(1-
methyl-3-(trifluoromethyl)-1H-pyrazol-5-yl)benz-
amide The crude title compound was prepared from the procedure described in Example 27, Step D using (S)—N-(cyclopropyl(4-fluoro-3-methylphenyl)methyl)-3-(hydroxymethyl)-5-(1-methyl-3-(trifluoromethyl)-1H-pyrazol-5-yl)benzamide (53.8 mg, 0.12 mm ol). LCMS: R$_T$=2.002 min, MS (ES) 525.4 (M+H).

Step E. Example 196

The title compound (11.2 mg, 38% 4 step) was prepared from the procedure described in Example 175, Step D using (S)-3-(bromomethyl)-N-(cyclopropyl(4-fluoro-3-methylphenyl)methyl)-5-(1-methyl-3-(trifluoromethyl)-1H-pyrazol-5-yl)benzamide (28.0 mg, 0.05 mmol). LCMS: R$_T$=1.455 min, MS (ES) 541.6 (M+H).

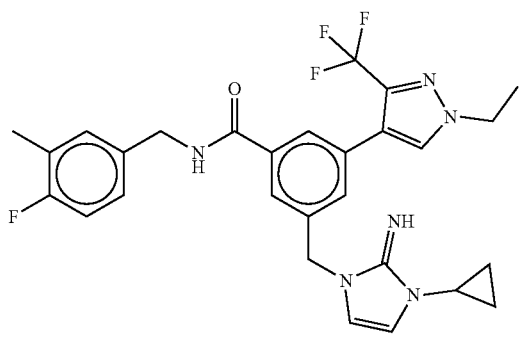

Example 197

3-((3-Cyclopropyl-2-imino-2,3-dihydro-1H-imidazol-1-yl)methyl)-5-(1-ethyl-3-(trifluoromethyl)-1H-pyrazol-4-yl)-N-(4-fluoro-3-methylbenzyl)benzamide The title compound was prepared (24 mg, 0.044 mmol) according to the procedures described in Example 60, Steps A-G substituting 4-bromo-1-ethyl-3-(trifluoromethyl)-11-pyrazole (1 g, 4.1 mmol) in Step C, (4-fluoro-3-methylphenyl)methanamine (0.5 g, 3.6 mmol) in Step E and 1-cyclopropyl-1H-imidazol-2-amine (13 mg, 0.11 mmol) in Step G. LC-MS: >95% 254 nm, R$_T$=0.972 min, MS (ES) 541.2 (M+H).

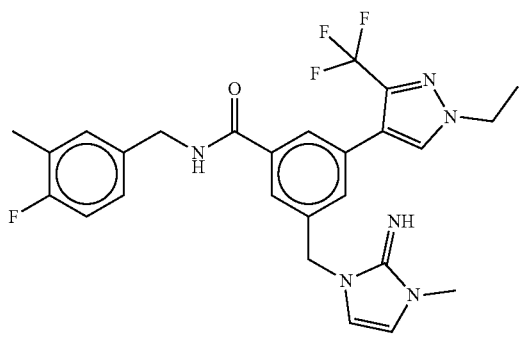

Example 198

3-(1-Ethyl-3-(trifluoromethyl)-1H-pyrazol-4-yl)-N-(4-fluoro-3-methylbenzyl)-5-((2-imino-3-methyl-2,3-dihydro-1H-imidazol-1-yl)methyl)benzamide The title compound was prepared (10 mg, 0.019 mmol) according to the procedures described in Example 60, Steps A-G substituting 4-bromo-1-ethyl-3-(trifluoromethyl)-1H-pyrazole (1 g, 4.1 mmol) in Step C and (4-fluoro-3-methylphenyl)methanamine (0.5 g, 3.6 mmol) in Step E. LC-MS: >95% 254 nm, R$_T$=0.955 min, MS (ES) 515.2 (M+H).

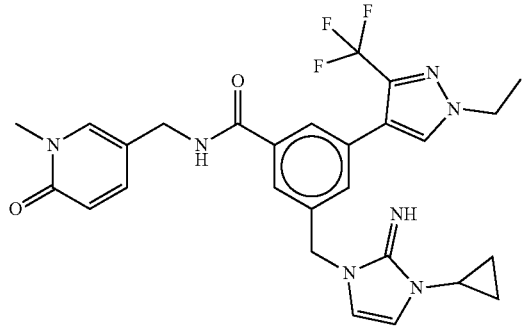

Example 199

3-((3-Cyclopropyl-2-imino-2,3-dihydro-1H-imidazol-1-yl)methyl)-5-(1-ethyl-3-(trifluoromethyl)-1H-pyrazol-4-yl)-N-((1-methyl-6-oxo-1,6-dihydropyridin-3-yl)methyl)benzamide The title compound was prepared (20 mg, 0.037 mmol) according to the procedures described in Examples 197 and 60, Steps A-G substituting 5-(aminomethyl)-1-methylpyridin-2(1H)-one (0.3 g, 2.17 mmol) in Step E. $^1$H NMR (400 MHz, Chloroform-d) δ 778 (t, J=1.6 Hz, 1H), 7.70 (t, J=1.6 Hz, 1H), 7.59 (d, J=1.1 Hz, 1H), 7.37 (d, J=17.5 Hz, 2H), 7.20-7.10 (m, 2H), 6.91 (dd, J=9.5, 8.3 Hz, 1H), 6.14 (q, J=2.7 Hz, 2H), 4.79 (s, 2H), 4.52 (s, 2H), 4.22 (q, J=7.3 Hz, 2H), 3.18 (s, 3H), 2.22 (d, J=2.0 Hz, 3H), 1.53 (t, J=7.3 Hz, 3H); LC-MS: >95% 254 nm, R$_T$=0.753 min, MS (ES) 540.2 (M+H).

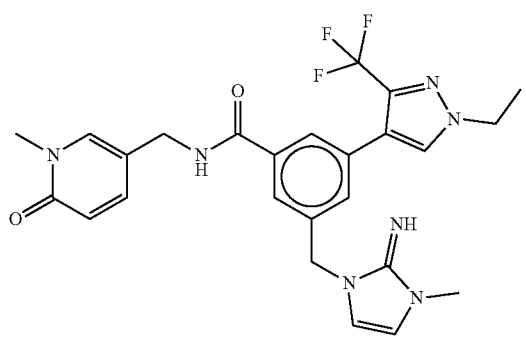

Example 200

3-(1-Ethyl-3-(trifluoromethyl)-1H-pyrazol-4-yl)-5-((2-imino-3-methyl-2,3-dihydro-1H-imidazol-1-yl)methyl)-N-((1-methyl-6-oxo-1,6-dihydropyridin-3-yl)methyl)benzamide The title compound was prepared (19 mg, 0.037 mmol) according to the procedures described in Examples 198 and 60, Steps A-G substituting 5-(aminomethyl)-1-methylpyridin-2(1H)-one (0.3 g, 2.17 mmol) in Step E. LC-MS: >95% 254 nm, R$_T$=0.690 min, MS (ES) 514.2 (M+H).

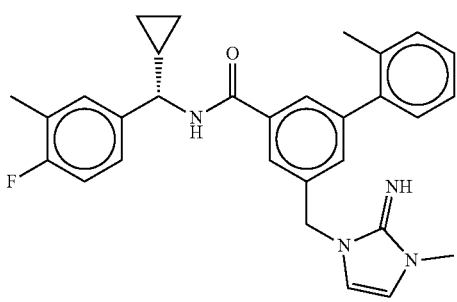

Example 201

(S)—N-(Cyclopropyl(4-fluoro-3-methylphenyl)methyl)-5-((2-imino-3-methyl-2,3-dihydro-1H-imidazol-1-yl)methyl)-2'-methyl-[1,1'-biphenyl]-3-carboxamide Step A. Preparation of methyl 5-(hydroxymethyl)-2'-methyl-[1,1'-biphenyl]-3-carboxylate The title compound (1.16 g, quant.), was prepared from the procedure described in Example 1, Step A using methyl 3-bromo-5-(hydroxymethyl)benzoate (1.0 g, 4.1 mmol) and o-tolylboronic acid (0.72 g, 5.3 mmol). LCMS method 2: $R_T$=1.55 min, MS (ES) 257.1 (M+H).

Step B. Preparation of 5-(hydroxymethyl)-2'-methyl-[1,1'-biphenyl]-3-carboxylic Acid The title compound (0.89, 850%) was prepared from the procedure described in Example 139, Step B using methyl 5-(hydroxymethyl)-2'-methyl-[1,1'-biphenyl]-3-carboxylate (1.1 g, 4.3 mmol). LCMS method 2: $R_T$=1.30 min, MS (ES) 243.1 (M+H).

Step C. Preparation of (S)—N-(cyclopropyl(4-fluoro-3-methylphenyl)methyl)-5-(hydroxymethyl)-2'-methyl-[1,1'-biphenyl]-3-carboxamide The title compound (0.31 g, 75%) was prepared from the procedure described in Example 91, Step D using 5-(hydroxymethyl)-2'-methyl-[1,1'-biphenyl]-3-carboxylic acid (0.25 g, 1.0 mmol) and (S)-cyclopropyl(4-fluoro-3-methylphenyl)methanamine hydrochloride (0.22 g, 1.0 mmol). LCMS method 2: $R_T$=1.79 min, MS (ES) 404.1 (M+H)

Step D. Preparation of (S)-5-(bromomethyl)-N-(cyclopropyl(4-fluoro-3-methylphenyl)methyl)-2'-methyl-[1,1'-biphenyl]-3-carboxamide The title compound (0.13 g, 73%) was prepared from the procedure described in Example 139, Step D using (S)—N-(cyclopropyl(4-fluoro-3-methylphenyl)methyl)-5-(hydroxymethyl)-2'-methyl-[1,1'-biphenyl]-3-carboxamide (0.15 g, 0.37 mmol). LCMS method 2: $R_T$=2.1 min, MS (ES) 465.9 (M+).

Step E. Example 201

The title compound (38 mg, 60%) was prepared from the procedure described in Example 91, Step F using (S)-5-(bromomethyl)-N-(cyclopropyl(4-fluoro-3-methylphenyl)methyl)-2'-methyl-[1,1'-biphenyl]-3-carboxamide (62 mg, 0.13 mmol), 1-methyl-1H-imidazol-2-amine (24 mg, 0.20 mmol) and DIPEA (91 μL, 0.53 mmol). LCMS method 2: $R_T$=1.49 min, MS (ES) 483.1 (M+).

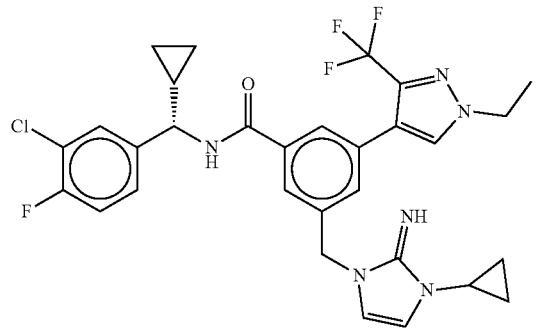

Example 202

(S)—N-((3-Chloro-4-fluorophenyl)(cyclopropyl)methyl)-3-((3-cyclopropyl-2-imino-2,3-dihydro-1H-imidazol-1-yl)methyl)-5-(1-ethyl-3-(trifluoromethyl)-1H-pyrazol-4-yl)benzamide The title compound was prepared (12 mg, 0.020 mmol) according to the procedures described in Examples 197 and 60, Steps A-G substituting the hydrochloride salt of (5)-(3-chloro-4-fluorophenyl)(cyclopropyl)methanamine (0.3 g, 1.3 mmol) in Step E. LC-MS: >95% 254 nm, $R_T$=1.046 min, MS (ES) 601.2 (M+H).

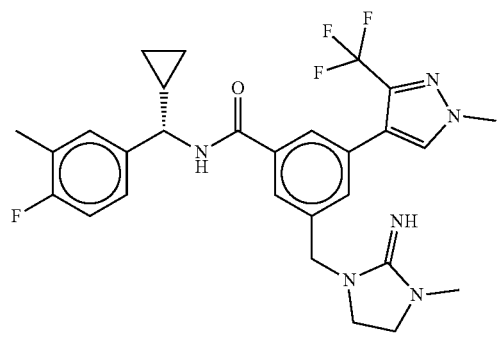

Example 203

(S)—N-(cyclopropyl(4-fluoro-3-methylphenyl)methyl)-3-((2-imino-3-methylimidazolidin-1-yl)methyl)-5-(1-methyl-3-(trifluoromethyl)-1H-pyrazol-4-yl)benzamide The title compound was prepared (7 ng, 0.013 mmol) according to the procedures described in Examples 125 and 60, Steps A-G substituting 1-methyl-4,5-dihydro-1H-imidazol-2-amine (12 rug, 0.12 mmol) in Step G. LC-MS: >95% 254 nm, $R_T$=0.933 min, MS (ES) 543.2 (M+H).

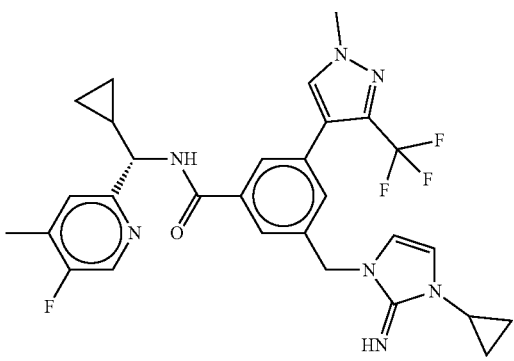

Example 204

(S)—N-(Cyclopropyl(5-fluoro-4-methy pyridin-2-yl)methyl)-3-((3-cyclopropyl-2-imino-2,3-dihydro-1H-imidazol-1-yl)methyl)-5-(1-methyl-3-(trifluoromethyl)-1H-pyrazol-4-yl)benzamide The title compound was prepared (17 mg, 0.03 mmol) according to the procedures described in Examples 125 and 60, Steps A-G substituting the hydrochloride salt of (S)-cyclopropyl(5-fluoro-4-methylpyridin-2-yl)methanamine (0.3 g, 1.4 mmol) in Step E and 1-cyclopropyl-1H-imidazol-2-amine (14 mg, 0.11 mmol) in Step G. LC-MS: >95% 254 nm, $R_T$=0.886 min, MS (ES) 568 (M+H).

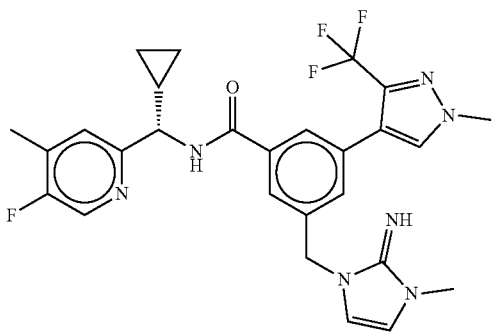

Example 205

(S)—N-(Cyclopropyl(5-fluoro-4-methylpyridin-2-yl)methyl)-3-((2-imino-3-methyl-2,3-dihydro-1H-imidazol-1-yl)methyl)-5-(1-methyl-3-(trifluoromethyl)-1H-pyrazol-4-yl)benzamide The title compound was prepared (25 mg, 0.046 mmol) according to the procedures described in Examples 125 and 60, Steps A-G substituting the hydrochloride salt of (S)-cyclopropyl(5-fluoro-4-methylpyridin-2-yl)methanamine (0.3 g, 1.4 mmol) in Step E. LC-MS: >95% 254 nm, $R_T$=0.878 min, MS (ES) 542 (M+H). LC-MS, >95% (254 nm), $R_t$=0.878 min, nm/z=542 [M+H]

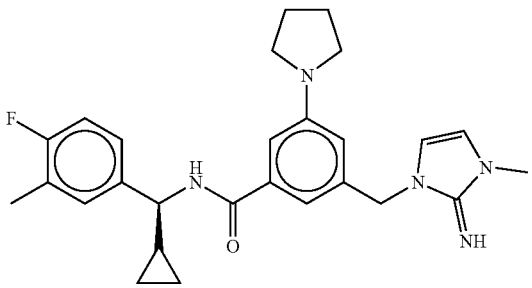

Example 206

(S)—N-(Cyclopropyl(4-fluoro-3-methylphenyl)methyl)-3-((2-imino-3-methyl-2,3-dihydro-1H-imidazol-1-yl)methyl)-5-(pyrrolidin-1-yl)benzamide Step A. Preparation of dimethyl 5-(pyrrolidin-1-yl)isophthalate Dimethyl 5-bromoisophthalate (1.0 g, 3.66 mmol), pyrrolidine (0.36 mL, 4.39 mmol), cesium carbonate (1.79 g, 5.49 mmol), rac-BINAP (0.11 g. 0.18 mmol), and palladium (II) acetate (0.04 g. 0.18 mmol) were combined in toluene (15 mL). The reaction was purged with Ar, sealed, and heated at 100° C. for 20 h then quenched with water (5 mL). The mixture was extracted with EtOAc (3×10 mL), and the combined organic layer was dried with $MgSO_4$ and concentrated. The residue was purified by flash chromatography (Combi-flash Rf, Hex/EtOAc=0-25% gradient) to afford the title compound (0.82 g, 85%). LCMS method 2: $R_T$=1.72 min, MS (ES) 264.1 (M+H).

Step B. Preparation of methyl 3-(hydroxymethyl)-5-(pyrrolidin-1-yl)benzoate

NaH (0.19 g, 5.1 mmol) was added to a solution of dimethyl 5-(pyrrolidin-1-yl)isophthalate (0.9 g, 3.4 mmol) in THF (10 mL). The reaction mixture was stirred for 30 min, and MeOH (0.75 mL, 18.4 mmol) was added. The reaction mixture was heated at 40° C. for 48 h then concentrated. The residue was purified by flash chromatography (Combi-flash Rf, Hex/EtOAc=0-50% gradient) to afford the title compound (0.34 g, 43%). LCMS method 2: $R_T$=1.33 min, MS (ES) 236.2 (M+H).

Step C. Preparation of 3-(hydroxymethyl)-5-(pyrrolidin-1-yl)benzoic acid

The title compound (222 mg, 100%) was prepared from the procedure described in Example 139, Step B using methyl 3-(hydroxymethyl)-5-(pyrrolidin-1-yl)benzoate (343 mg, 1.46 mmol).

Step D. Preparation of (S)—N-(cyclopropyl(4-fluoro-3-methylphenyl)methyl)-3-(hydroxymethyl)-5-(pyrrolidin-1-yl)benzamide The title compound (73 mg, 50%) was prepared from the procedure described in Example 91, Step D using 3-(hydroxymethyl)-5-(pyrrolidin-1-yl)benzoic acid (0.10 g, 0.38 mmol) and (S)-cyclopropyl(4-fluoro-3-methylphenyl)meth- Step E. Preparation of (S)-3-(bromomethyl)-N-(cyclopropyl(4-fluoro-3-methylphenyl)methyl)-5-(pyrrolidin-1-yl)benzamide The title compound (23 rug, 27%) was prepared from the procedure described in Example 139, Step D using (S)—N-(cyclopropyl(4-fluoro-3-methylphenyl)methyl)-3-(hydroxymethyl)-5-(pyrrolidin-1-yl)benzamide (73 mg, 0.19 mmol), PPh$_3$ (100 mg, 0.38 mmol) and NBS (67 mg, 0.38 mmol). LCMS method 2: R$_T$=1.99 min, MS (ES) 445.0 (M+).

Step F. Example 206

The title compound (10 rug, 42%) was prepared from the procedure described in Example 91, Step F using (S)-3-(bromomethyl)-N-(cyclopropyl(4-fluoro-3-methylphenyl)methyl)-5-(pyrrolidin-1-yl)benzamide (23 mg, 0.051 mmol), 1-methyl-1H-imidazol-2-amine (10 mg, 0.077 mmol) and DIPEA (36 μL, 0.21 mmol). LCMS method 2: R$_T$=1.41 min, MS (ES) 462.1 (M+H).

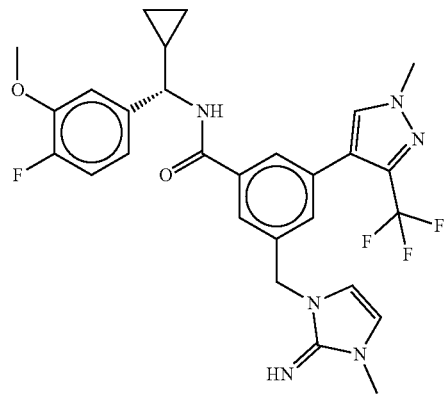

Example 207

(S)—N-(Cyclopropyl(4-fluoro-3-methoxyphenyl)methyl)-3-((2-imino-3-methyl-2,3-dihydro-1H-imidazol-1-yl)methyl)-5(1-ethyl-3-(trifluoromethyl)-1H-pyrazol-4-yl)benzamide The title compound was prepared (19 mg, 0.034 mmol) according to the procedures described in Examples 125 and 60, Steps A-G substituting the hydrochloride salt of (S)-cyclopropyl(4-fluoro-3-methoxyphenyl)methanamine (0.3 g, 1.3 mmol) in Step E. LC-MS: >95% 254 nm, R$_T$=0.951 min, MS (ES) 557 (M+H).

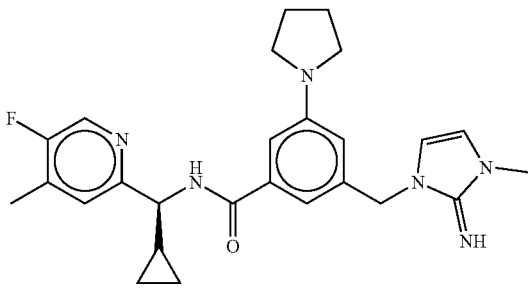

Example 208

(S)—N-(Cyclopropyl(5-fluoro-4-methylpyridin-2-yl)methyl)-3-((2-imino-3-methyl-2,3-dihydro-1H-imidazol-1-yl)methyl)-5-(pyrrolidin-1-yl)benzamide Step A. Preparation of (S)—N-(cyclopropyl(5-fluoro-4-methylpyridin-2-yl)methyl)-3-(hydroxymethyl)-5-(pyrrolidin-1-yl)benzamide The title compound (69 mg, 47%) was prepared from the procedure described in Example 91, Step D using 3-(hydroxymethyl)-5-(pyrrolidin-1-yl)benzoic acid, Example 206 Step C, (0.10 g, 0.38 mmol) and (S)-cyclopropyl(5-fluoro-4-methylpyridin-2-yl)methanamine hydrochloride (0.083 g, 0.38 mmol). LCMS method 2: R$_T$=1.44 min, MS (ES) 384.1 (M+H).

Step B. Preparation of (S)-3-(bromomethyl)-N-(cyclopropyl(5-fluoro-4-methylpyridin-2-yl)methyl)-5-(pyrrolidin-1-yl)benzamide The title compound (25 mg, 31%) was prepared from the procedure described in Example 139, Step D using (S)—N-(cyclopropyl(5-fluoro-4-methylpyridin-2-yl)methyl)-3-(hydroxymethyl)-5-(pyrrolidin-1-yl)benzamide (69 mg, 0.18 mmol), PPh$_3$ (94 mg, 0.36 mmol) and NBS (64 mg, 0.36 mmol).

Step C. Example 208

The title compound (4 mg, 17%) was prepared from the procedure described in Example 91, Step F using (S)-3-(bromomethyl)-N-(cyclopropyl(5-fluoro-4-methylpyridin-2-yl)methyl)-5-(pyrrolidin-1-yl)benzamide (25 mg, 0.056 mmol), 1-methyl-1H-imidazol-2-amine (11 mg, 0.084 mmol) and DIPEA (39 μL, 0.22 mmol). 1H NMR (CDCl$_3$) δ 8.28 (s, 1H), 7.35 (d, J=7.6 Hz, 1H), 7.13 (d, J=6.0 Hz, 1H), 6.94 (s, 1H), 6.90 (s, 1H), 6.51 (s, 1H), 6.08 (d, J=2.6 Hz, 1H), 6.04 (d, J=2.6 Hz, 1H), 4.69 (s, 2H), 4.63 (t, J=8.0 Hz, 1H), 3.30-3.26 (m, 4H), 3.23 (s, 3H), 2.31 (s, 3H), 2.01-1.97 (m, 4H), 1.32-1.24 (m, 1H), 0.62-0.49 (series of m, 3H), 0.43-0.39 (m, 1H). LCMS method 2: R$_T$=1.25 min, MS (ES) 463.0 (M+H).

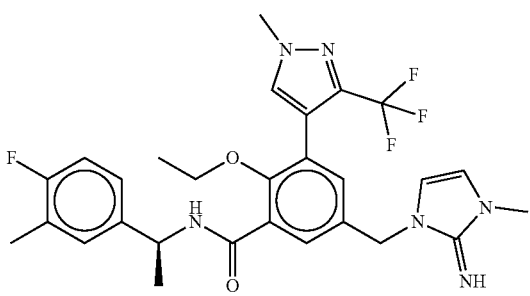

Example 209

(S)-2-Ethoxy-N-(1-(4-fluoro-3-methylphenyl)ethyl)-5-((2-imino-3-methyl-2,3-dihydro-1H-imidazol-1-yl)methyl)-3-(1-methyl-3-(trifluoromethyl)-1H-pyrazol-4-yl)benzamide Step A. Preparation of methyl 3-bromo-2-hydroxy-5-methylbenzoate $Br_2$ (0.3 mL, 6.0 mmol) was added to a solution of methyl 2-hydroxy-5-methylbenzoate (1000 mg, 6.0 mmol) in $CHCl_3$ (20.0 mL). The reaction mixture was stirred at ambient temperature for 4.5 h and quenched with $H_2O$ (5.0 mL). The reaction mixture was extracted with $CH_2Cl_2$ (3×5.0 mL). The combined organics were passed through the phase separator and concentrated under reduced pressure. The residue was purified by flash chromatography (Combiflash Rf, Hex/EtOAc=0-100?% gradient) to afford the title compound (1385 mg, 93%). LCMS: $R_T$=1.747 min, MS (ES) 246.1 (M+H).

Step B. Preparation of methyl 3-bromo-2-ethoxy-5-methylbenzoate

The title compound (1312 mg, 84%) was prepared from the procedure described in Example 175, Step B using methyl 3-bromo-2-hydroxy-5-methylbenzoate (1385 mg, 5.65 mmol) and bromoethane (1.27 mL, 17.0 mmol). $^1H$ NMR (400 MHz, Chloroform-d) δ 7.53 (s, 2H), 4.06 (q, J=7.0 Hz, 2H), 3.91 (s, 3H), 2.31 (s, 3H), 1.44 (t, J=7.0 Hz, 3H); LCMS: $R_T$=1.784 min, MS (ES) 274.1 (M+H).

Step C. Preparation of methyl 3-bromo-5-(bromomethyl)-2-ethoxybenzoate

The title compound (1622 mg) was prepared from the procedure described in Example 105, Step C using methyl 3-bromo-2-ethoxy-5-methylbenzoate (1311.7 mg, 4.80 mmol). LCMS: $R_T$=1.793 min, MS (ES) 353.0 (M+H).

Step D. Preparation of methyl 5-(acetoxymethyl)-3-bromo-2-ethoxybenzoate

NaOAc (756.0 mg, 9.21 mmol) was added to a solution of methyl 3-bromo-5-(bromomethyl)-2-ethoxybenzoate (1621.9 mg, 4.61 mmol) in MeOH (20.0 mL). The reaction mixture was stirred for 12 h at 64° C., cooled to ambient temperature and concentrated under reduced pressure to yield the crude title compound which was used for the next step without further purification. LCMS: $R_T$=1.645 min, MS (ES) 332.2 (M+H).

Step E. Preparation of methyl 3-bromo-2-ethoxy-5-(hydroxymethyl)benzoate

The titled product (485.2 mg, 36% 3 step) was synthesized according to the procedure described in Example 27, Step B. using methyl 5-(acetoxymethyl)-3-bromo-2-ethoxybenzoate (1526 mg, 4.61 mmol) and 1 M NaOH (5.0 mL). $^1H$ NMR (400 MHz, Chloroform-d) δ 7.64 (d, J=2.0 Hz, 1H), 7.61 (d, J=2.0 Hz, 1H), 4.57 (s, 2H), 4.01 (q, J=7.0 Hz, 2H), 3.86 (s, 3H), 1.40 (t, J=7.0 Hz, 3H); LCMS: $R_T$=1.334 min, MS (ES) 290.1 (M+H).

Step F. Preparation of 3-bromo-2-ethoxy-5-(hydroxymethyl)benzoic Acid

The crude title compound was prepared from the procedure described in Example 27, Step B using methyl 3-bromo-2-ethoxy-5-(hydroxymethyl)benzoate (485.2 mg, 1.68 mmol). LCMS: $R_T$=1.117 min, MS (ES) 276.1 (M+H).

Step G. Preparation of (S)-3-bromo-2-ethoxy-N-(1-(4-fluoro-3-methylphenyl)ethyl)-5-(hydroxymethyl)benzamide The title compound (171.8 mg, 76% 2 step) was prepared from the procedure described in Example 33, Step A using 3-bromo-2-ethoxy-5-(hydroxymethyl)benzoic acid (150.0 mg, 0.55 mm ol) and (S)-1-(4-fluoro-3-methylphenyl)ethan-1-amine (100.2 mg, 0.65 mmol). LCMS: $R_T$=1.694 min, MS (ES) 411.3 (M+H).

Step H. Preparation of (S)-2-ethoxy-N-(1-(4-fluoro-3-methylphenyl)ethyl)-5-(hydroxymethyl)-3-(1-methyl-3-(trifluoromethyl)-1H-pyrazol-4-yl)benzamide The title compound (48.6 mg, 24%) was prepared from the procedure described in Example 1, Step A using (S)-3-bromo-2-ethoxy-N-(1-(4-fluoro-3-methylphenyl)ethyl)-5-(hydroxymethyl)benzamide (171.8 mg, 0.42 mmol) and (1-methyl-3-(trifluoromethyl)-1H-pyrazol-4-yl)boronic acid (97.4 mg, 0.50 mmol). LCMS: $R_T$=1.667 min, MS (ES) 480.5 (M+H).

Step I. Preparation of (S)-5-(bromomethyl)-2-ethoxy-N-(1-(4-fluoro-3-methylphenyl)ethyl)-3-(1-methyl-3-(trifluoromethyl)-1H-pyrazol-4-yl)benzamide The crude title compound was prepared from the procedure described in Example 27, Step D using (S)-2-ethoxy-N-(1-(4-fluoro-3-methylphenyl)ethyl)-5-(hydroxymethyl)-3-(1-methyl-3-(trifluoromethyl)-1H-pyrazol-4-yl)benzamide (48.6 mg, 0.10 mmol). LCMS: $R_T$=1.938 min, MS (ES) 543.4 (M+H).

Step J. Example 209

The title compound (18.9 mg, 66% 2 step) was prepared from the procedure described in Example 175, Step D using (S)-5-(bromomethyl)-2-ethoxy-N-(1-(4-fluoro-3-methylphenyl)ethyl)-3-(1-methyl-3-(trifluoromethyl)-1H-pyrazol-4-yl)benzamide (27.5 mg, 0.05 mmol). LCMS: $R_T$=1.392 min, MS (ES) 559.6 (M+H).

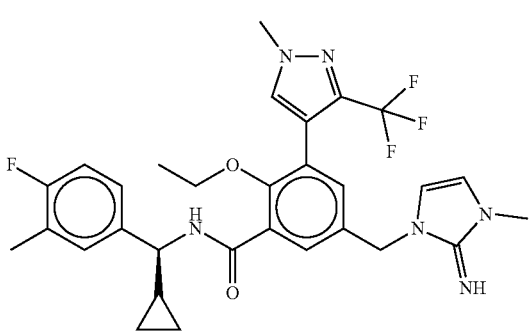

Example 210

(S)—N-(Cyclopropyl(4-fluoro-3-methylphenyl)methyl)-2-ethoxy-5-((2-iminio-3-methyl-2,3-dihydro-1H-imidazol-1-yl)methyl)-3-(1-methyl-3-(trifluoromethyl)-1H-pyrazol-4-yl)benzamide Step A. Preparation of (S)-3-bromo-N-(cyclopropyl(4-fluoro-3-methylphenyl)methyl)-2-ethoxy-5-(hydroxymethyl)benzamide The title compound (188.6 mg, 86% 2 step) was prepared from the procedure described in Example 33, Step A using 3-bromo-2-ethoxy-5-(hydroxymethyl)benzoic acid (150.0 mg, 0.55 mmol) and (S)-cyclopropyl(4-fluoro-3-methylphenyl)methanamine hydrochloride (129.3 mg, 0.60 mmol). LCMS: $R_T$=1.784 min, MS (ES) 437.3 (M+H).

Step B. Preparation of (S)—N-(cyclopropyl(4-fluoro-3-methylphenyl)methyl)-2-ethoxy-5-(hydroxymethyl)-3-(1-methyl-3-(trifluoromethyl)-1H-pyrazol-4-yl)benzamide The title compound (197.0 mg, 90%) was prepared from the procedure described in Example 1, Step A using (S)-3-bromo-N-(cyclopropyl(4-fluoro-3-methylphenyl)methyl)-2-ethoxy-5-(hydroxymethyl)benzamide (188.6 mg, 0.77 mmol) and (1-methyl-3-(trifluoromethyl)-1H-pyrazol-4-yl)boronic acid (179.1 mg, 0.92 mmol). LCMS: $R_T$=1.744 min, MS (ES) 506.5 (M+H)

Step C. Preparation of (S)-5-(bromomethyl)-N-(cyclopropyl(4-fluoro-3-methylphenyl)methyl)-2-ethoxy-3-(1-methyl-3-(trifluoromethyl)-1H-pyrazol-4-yl)benzamide The crude title compound was prepared from the procedure described in Example 27, Step D using (S)—N-(cyclopropyl(4-fluoro-3-methylphenyl)methyl)-2-ethoxy-5-(hydroxymethyl)-3-(1-methyl-3-(trifluoromethyl)-1H-pyrazol-4-yl)benzamide (197.0 mg, 0.39 mmol). LCMS: $R_T$=2.002 min, MS (ES) 569.4 (M+H).

Step D. Example 210

The title compound (27.0 mg, 87% 2 step) was prepared from the procedure described in Example 175, Step D using (Si-5-(bromomethyl)-N-(cyclopropyl(4-fluoro-3-methylphenyl)methyl)-2-ethoxy-3-(1-methyl-3-(trifluoromethyl)-1H-pyrazol-4-yl)benzamide (30.0 mg, 0.05 mmol). H NMR (400 MHz, Chloroform-d) δ 8.41 (d, J.=7.8 Hz, 1H), 7.92 (d, J=2.3 Hz, 1H), 7.59 (s, 1H), 7.27 (d, J=2.1 Hz, 1H), 7.20 (t, J=7.3 Hz, 2H), 6.99-6.90 (m, 1H), 6.12 (q, J=2.7 Hz, 2H), 4.81 (s, 2H), 4.55 (t, 0.1=8.4 Hz, 1H), 3.98 (s, 3H), 3.67-3.58 (m, 1H), 3.58-3.49 (m, 1H), 3.23 (s, 3H), 2.25 (d, J=1.5 Hz, 3H), 1.22 (m, 1H), 1.02 (t, J=7.0 Hz, 3H), 0.62 (m, 2H), 0.56-0.47 (m, 1H), 0.44-0.33 (m, 1H); LCMS: $R_T$=1.462 min, MS (ES) 585.6 (M+H).

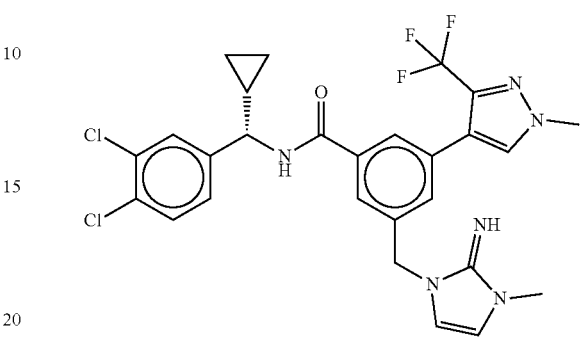

Example 211

(S)—N-(Cyclopropyl(3,4dichlorophenyl)methyl)-3-(2-imino-3-methylimidazolidin-1-yl)methyl)-5-(1-methyl-3-(trifluoromethyl)-1H-pyrazol-4-yl)benzamide The title compound was prepared (23 mg, 0.039 mmol) according to the procedures described in Examples 157 and 60, Steps A-G substituting 1-methyl-4,5-dihydro-1H-imidazol-2-amine (11 mg, 0.11 mmol) in Step G. LC-MS: >95% 254 nm, $R_T$=1.038 min, MS (ES) 579 (M+H).

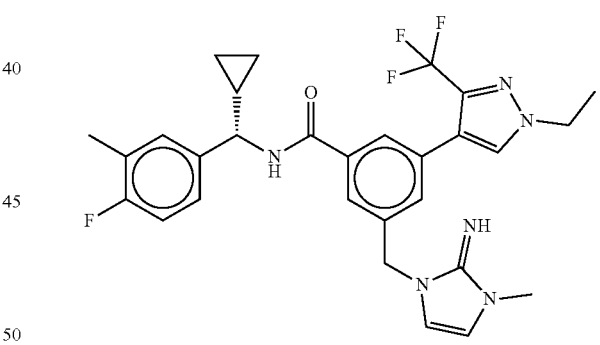

Example 212

(S)—N-(Cyclopropyl(4-fluoro-3-methylphenyl)methyl)-3-(1-ethyl-3-(trifluoromethyl)-1H-pyrazol-4-yl)-5-((2-imino-3-methylimidazolidin-1-yl)methyl)benzamide The title compound was prepared (10 mg, 0.018 mmol) according to the procedures described in Example 60, Steps A-G substituting 4-bromo-1-ethyl-3-(trifluoromethyl)-1H-pyrazole (1 g, 4.1 mmol) in Step C and 1-methyl-4,5-dihydro-1H-imidazol-2-amine (11 mg, 0.11 mmol) in Step G. LC-MS: >95% 254 nm, $R_T$=1.033 min, MS (ES) 557 (M+H).

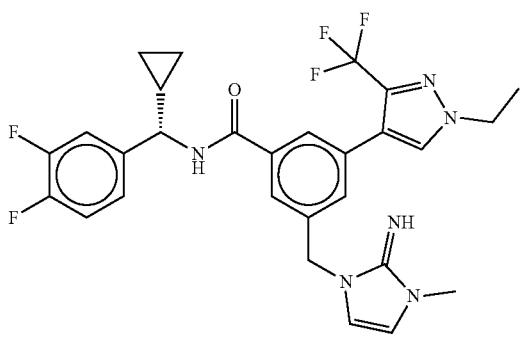

Example 213

(S)—N-(Cyclopropyl(3,4-difluorophenyl)methyl)-3-(1-ethyl-3-(trifluoromethyl)-1H-pyrazol-4-yl)-5-((2-imino-3-methylimidazolidin-1-yl)methyl)benzamide The title compound was prepared (16 mg, 0.029 mmol) according to the procedures described in Examples 191 and 60, Steps A-G substituting 1-methyl-4,5-dihydro-1H-imidazol-2-amine (11 mg, 0.11 mmol) in Step G. LC-MS: >95% 254 nm, $R_T$=1.002 min, MS (ES) 561 (M+H).

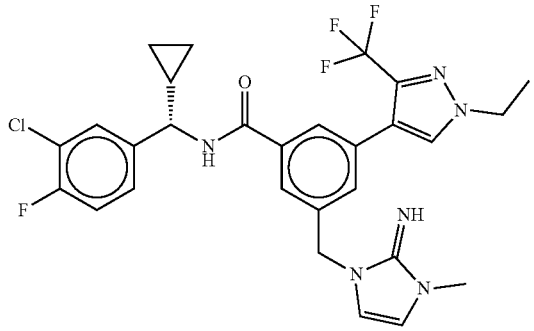

Example 214

(S)—N-((3-Chloro-4-fluorophenyl)(cyclopropyl)methyl)-3-(1-ethyl-3-(trifluoromethyl)-1H pyrazol-4-yl)-5-((2-imino-3-methylimidazolidin-1-yl)methyl)benzamide The title compound was prepared (13 mg, 0.023 mmol) according to the procedures described in Examples 202 and 60, Steps A-G substituting 1-methyl-4,5-dihydro-1H-imidazol-2-amine (11 mg, 0.11 mmol) in Step G. LC-MS: >95% 254 nm, $R_T$=1.046 min, MS (ES) 577 (M+H).

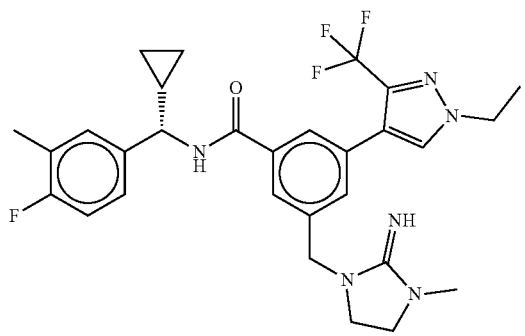

Example 215

(S)—N-(Cyclopropyl(4-fluoro-3-methylphenyl)methyl)-3-((2-imino-3-methylimidazolidin-1-yl)methyl)-5-(1-isopropyl-3-(trifluoromethyl)-1H-pyrazol-4-yl)benzamide Title compound was prepared (16 mg, 0.028 mmol) as a white solid according to the procedures described in Examples 193 and 60, Steps A-G substituting 1-methyl-4,5-dihydro-1H-imidazol-2-amine (11 mg, 0.11 mmol) in Step G. LC-MS: >95% 254 nm, $R_T$=1.046 min, MS (ES) 571 (M+H).

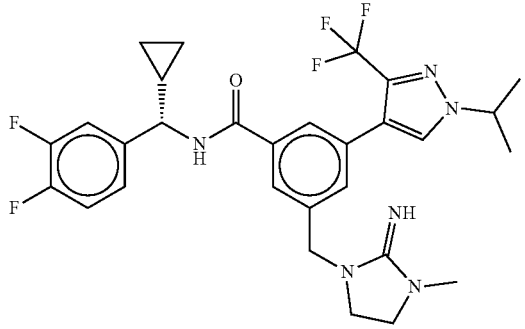

Example 216

(S)—N-(Cyclopropyl(3,4-difluorophenyl)methyl)-3-((2-imino-3-methylimidazolidin-1-yl)methyl)-5-(1-isopropyl-3-(trifluoromethyl)-1H-pyrazol-4-yl)benzamide The title compound was prepared (18 mg, 0.031 mmol) according to the procedures described in Example 60, Steps A-G substituting 4-bromo-1-isopropyl-3-(trifluoromethyl)-1H-pyrazole (1 g, 3.9 mmol) in Step C, the hydrochloride salt of (S)-cyclopropyl(3,4-difluorophenyl)methanamine (0.3 g, 1.4 mmol) in Step E and 1-methyl-4,5-dihydro-1H-imidazol-2-amine (11 mg, 0.11 mmol) in Step G. LC-MS: >95% 254 nm, $R_T$=1.048 min, MS (ES) 575 (M+H).

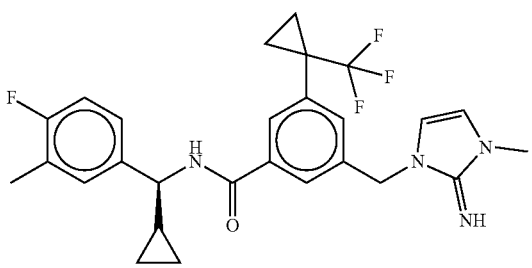

Example 217

(S)—N-(cyclopropyl(4-fluoro-3-methylphenyl) methyl)-3-((2imino-3-methyl-2,3-dihydro-1H-imidazol-1-yl)methyl)-5-(1-(trifluoromethyl)cyclopropyl) benzamide Step A. Preparation of 3-(((tert-butyldiphenylsilyl) oxy)methyl)-5-(3,3,3-trifluoroprop-1-en-2-yl)benzoic Acid The title compound (0.98 g, 65%) was prepared from the procedure described in Example 139, Step B using methyl 3-(((tert-butyldiphenylsilyl)oxy)methyl)-5-(3,3,3-trifluoroprop-1-en-2-yl)benzoate (1.5 g, 3.1 mmol) and LiOH (89 mg, 3.7 mmol).

Step B. Preparation of tert-butyl 3-(((tert-butyldiphenylsilyl)oxy)methyl)-5-(3,3,3-trifluoroprop-1-en-2-yl)benzoate DMAP (0.29 g, 2.4 mmol) and di-tert-butyl dicarbonate (0.69 mL, 3.0 mmol) were added to a solution of 3-(((tert-butyldiphenylsilyl)oxy)methyl)-5-(3,3,3-trifluoroprop-1-en-2-yl)benzoic acid (0.97 g, 2.0 mmol) in THF (20 mL). The reaction was stirred at rt for 20 h then concentrated. The residue was purified by flash chromatography (Combi-flash Rf, Hex/EtOAc=0-1% gradient) to afford the title compound (0.49 g, 40%).

Step C. Preparation of tert-butyl 3-(((tert-butyldiphenylsilyl)oxy)methyl)-5-(1-(trifluoromethyl)cyclopropyl)benzoate 1.0 M LiHMDS in THF (3.6 mL, 3.6 mmol) was added to a −78° C. solution of tert-butyl 3-(((tert-butyldiphenylsilyl)oxy)methyl)-5-(3,3,3-trifluoroprop-1-en-2-yl)benzoate (0.49 g, 0.9 mmol) and methyl (diphenyl)sulfonium tetrafluoroborate (0.52 mg, 1.8 mmol) in THF (5 mL). The reaction was kept at −78° C. for 2 h then quenched by addition water (0.5 mL). The mixture was extracted with EtOAc (3×5 mL) and the combined organic layer was dried with MgSO$_4$ and concentrated. The residue was purified by flash chromatography (Combi-flash Rf, Hex/EtOAc=0-10% gradient) to afford the title compound (0.22 g, 45%).

Step D. Preparation of 3-(((tert-butyldiphenylsilyl) oxy)methyl)-5-(1-(trifluoromethyl)cyclopropyl)benzoic Acid TFA (0.15 mL, 2.0 mmol) was added to a solution of tert-butyl 3-(((tert-butyldiphenylsilyl)oxy)methyl)-5-(1-(trifluoromethyl)cyclopropyl)benzoate (0.11 g, 0.2 mmol) in DCM (4 mL). The reaction was stirred for 1 h then concentrated to provide the title compound (0.1 g, 99%)

Step E. Preparation of (S)-3-(((tert-butyldiphenylsilyl)oxy)methyl)-N-(cyclopropyl(4-fluoro-3-methylphenyl)methyl)-5-(1-(trifluoromethyl)cyclopropyl) benzamide The title compound (90 mg, 68%) was prepared from the procedure described in Example 91, Step D using 3-(((tert-butyldiphenylsilyl)oxy)methyl)-5-(1-(trifluoromethyl)cyclopropyl)benzoic acid (0.10 g, 0.20 mmol) and (S)-cyclopropyl(4-fluoro-3-methylphenyl)methanamine hydrochloride (64 mg, 0.30 mmol).

Step F. Preparation of (S)—N-(cyclopropyl(4-fluoro-3-methylphenyl)methyl)-3-(hydroxyethyl)-5-(1-(trifluoromethyl)cyclopropyl)benzamide 1.0 M TBAF in THF (0.27 mL, 0.27 mmol) was added to a solution of(S)-3-(((tert-butyldiphenylsilyl)oxy)methyl)-N-(cyclopropyl(4-fluoro-3-methylphenyl)methyl)-5-(1-(trifluoromethyl)cyclopropyl)benzamide (90 mg, 0.14 mmol) in THF (2 mL). After 30 min the reaction mixture was concentrated. The residue was purified by flash chromatography (Combi-flash Rf Hex/EtOAc=0-100% gradient) to afford the title compound (50 mg, 87%). LCMS method 2: R$_T$=1.73 min, MS (ES) 422.1 (M+H).

Step G. Preparation of (S)-3-(bromomethyl)-N-(cyclopropyl(4-fluoro-3-methylphenyl)methyl)-5-(1-(trifluoromethyl)cyclopropyl)benzamide The title compound (20 mg, 34%) was prepared from the procedure described in Example 139, Step D using (S)—N-(cyclopropyl(4-fluoro-3-methylphenyl)methyl)-3-(hydroxymethyl)-5-(1-(trifluoromethyl)cyclopropyl)benzamide (50 mg, 0.12 mmol), triphenylphosphine (62 mg, 0.24 mmol) and N-Bromosuccinimide (42 mg, 0.24 mmol).

Step H. Example 217

The title compound (5 mg, 24%) was prepared from the procedure described in Example 91, Step F using (S)-3-(bromomethyl)-N-(cyclopropyl(4-fluoro-3-methylphenyl) methyl)-5-(1-(trifluoromethyl)cyclopropyl)benzamide (20 mg, 0.041 mmol), 1-methyl-1H-imidazol-2-amine (8 mg, 0,082 mmol) and DIPEA (21 µL, 0.12 mmol). $^1$H NMR (CDCl$_3$) δ 7.84 (s, 1H), 7.73 (s, 1H), 7.45 (s, 1H), 7.25-7.21 (m, 2H), 7.06-7.01 (m, 1H), 6.95 (t, J=8.8 Hz, 1H), 6.17 (d, J=2.6 Hz, 1H), 6.11 (d, J=2.6 Hz, 1H), 4.83 (s, 2H), 4.47 (t, J=8.5 Hz, 1H), 3.24 (s, 3H), 2.26 (s, 3H), 1.38-1.35 (m, 2H) 1.32-1.26 (m, 1H), 1.05-1.01 (m, 2H), 0.66-0.61 (m, 2H), 0.53-0.48 (m, 1H), 0.42-0.37 (m, 1H). LCMS method 2: R$_T$T=1.44 min, MS (ES) 501.0 (M+H).

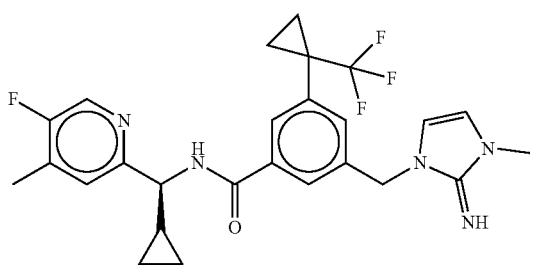

Example 218

(S)—N-(cyclopropyl(5-fluoro-4-methylpyridin-2-yl) methyl)-3-((2-imino-3-methyl-2,3-dihydro-1H-imidazol-1-yl)methyl)-5-(1-(trifluoromethyl)cyclopropyl)benzamide The title compound was prepared according to the procedures described in Example 217 Steps A through H, substituting (S)-cyclopropyl(5-fluoro-4-methylpyridin-2-yl)methanamine hydrochloride for (S)-cyclopropyl(4-fluoro-3-methylphenyl)methanamine hydrochloride in Step E. $^1$H NMR (CDCl$_3$) δ 8.30 (s, 1H), 7.82 (s, 1H), 7.68 (s, 1H), 7.51-7.48 (m, 2H), 7.14 (d, J=6.0 Hz, 1H), 6.11 (d, J=2.7 Hz, 1H), 6.04 (d, J=2.7 Hz, 1H), 4.80 (s, 2H), 4.62 (t, J=8.2 Hz, 1H), 3.22 (s, 3H), 2.32 (s, 3H), 1.39-1.36 (m, 2H), 1.33-1.27 (m, 1H), 1.06-1.03 (m, 2H), 0.63-058 (m, 2H), 0.56-0.51 (nm, 1H), 0.44-0.38 (m, 1H). LCMS method 2: R$_T$=1.30 min, MS (ES) 502.0 (M+H).

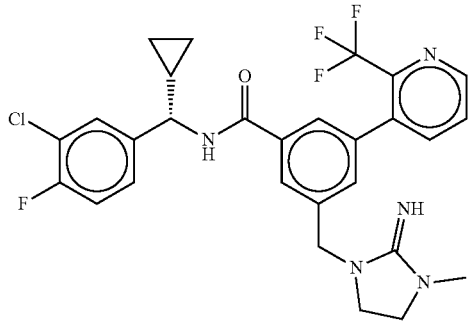

Example 219

(S)—N-((3-chloro-4-fluorophenyl)(cyclopropyl)methyl)-3-((2-imino-3-methylimidazolidin 1-yl)methyl)-5-(2-(trifluoromethyl)pyridin-3-yl)benzamide Title compound was prepared (6 mg, 0.011 mmol) as a white solid according to the procedures described in Example 60, Steps A-G substituting the hydrochloride salt of (S)-(3-chloro-4-fluorophenyl)(cyclopropyl)methanamine (0.3 g, 1.3 mmol) in Step E, and 1-methyl-4,5-dihydro-1H-imidazol-2-amine (9 mg, 0.09 mmol) in Step G. LC-MS, >95% (254 nm), Rt=1.007 min, m/z=560 (M+H).

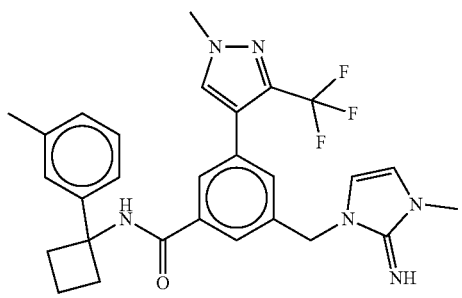

Example 220

3-((2-Imino-3-methyl-2,3-dihydro-1H-imidazol-1-yl)methyl)-5-(1-methyl-3-(trifluoromethyl)-1H-pyrazol-4-yl)-N-(1-(m-tolyl)cyclobutyl)benzamide Step A. Preparation of methyl 3-(hydroxymethyl)-5-(1-methyl-3-(trifluoromethyl)-1H-pyrazol-4-yl) benzoate The title compound (451.6 mg, 88%) was prepared from the procedure described in Example 1, Step A using methyl 3-bromo-5-(hydroxymethyl)benzoate (400.0 mg, 1.63 mmol) and (1-methyl-3-(trifluoromethyl)-1H-pyrazol-4-yl) boronic acid (379.8 mg, 1.96 mmol). LCMS: R$_T$=1.337 min, MS (ES) 315.3 (M+H).

Step B. Preparation of 3-(hydroxymethyl)-5-(1-methyl-3-(trifluoromethyl)-1H-pyrazol-4-yl)benzoic Acid The crude title compound was prepared from the procedure described in Example 27, Step B using methyl 3-(hydroxymethyl)-5-(1-methyl-3-(trifluoromethyl)-1H-pyrazol-4-yl)benzoate (451.6 mg, 1.44 mmol). LCMS: R$_T$=1.159 min, MS (ES) 301.2 (M+H).

Step C. Preparation of N-(1-(3-bromophenyl)cyclobutyl)-3-(hydroxymethyl)-5-(1-methyl-3-(trifluoromethyl)-1H-pyrazol-4-yl)benzamide The title compound (499.3 mg, 98% 2 step) was prepared from the procedure described in Example 33, Step A using 3-(hydroxymethyl)-5-(1-methyl-3-(trifluoromethyl)-1H-pyrazol-4-yl)benzoic acid (300.0 mg, 1.00 mmol) and 1-(3-bromophenyl)cyclobutan-1-amine (271.1 mg, 1.20 mmol). LCMS: R$_T$=1.693 min, MS (ES) 509.3 (M+H).

Step D. Preparation of 3-(hydroxymethyl)-5-(1-methyl-3-(trifluoromethyl)-1H-pyrazol-4-yl)-N-(1-(m-tolyl)cyclobutyl)benzamide The title compound (38.7 mg, 88%) was prepared from the procedure described in Example 1, Step A using N-(1-(3-bromophenyl)cyclobutyl)-3-(hydroxymethyl)-5-(1-methyl-3-(trifluoromethyl)-1H-pyrazol-4-yl)benzamide (50.0 mg, 0.1 mmol) and methyl boronic acid (29.4 mg, 0.49 mmol). LCMS: R$_T$=1.642 min, MS (ES) 444.5 (M+H).

Step E. Preparation of 3-(bromomethyl)-5-(1-methyl-3-(trifluoromethyl)-1H-pyrazol-4-yl)-N-(1-(m-tolyl)cyclobutyl)benzamide The crude title compound was prepared from the procedure described in Example 27, Step D using 3-(hydroxymethyl)-5-(1-methyl-3-(trifluoromethyl)-1H-pyrazol-4-yl)-N-(1-(m-tolyl)cyclobutyl)benzamide (38.7 mg, 0.09 mmol). LCMS: R$_T$=1.925 min, MS (ES) 507.4 (M+H).

Step F. Example 220

The title compound (11.7 mg, 51% 2 step) was prepared from the procedure described in Example 175, Step D using 3-(bromomethyl)-5-(1-methyl-3-(trifluoromethyl)-1H-pyrazol-4-yl)-N-(1-(m-tolyl)cyclobutyl)benzamide (22.0 mg, 0.04 mmol). LCMS: R$_T$=1.366 min, MS (ES) 523.6 (M+H).

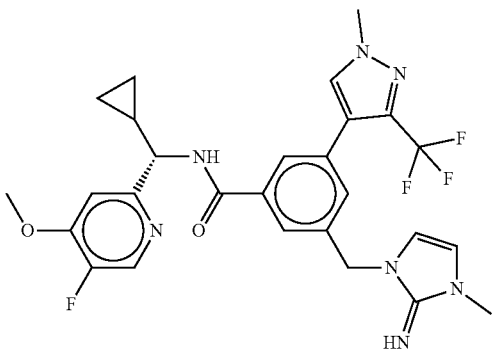

Example 221

(S)—N-(Cyclopropyl(5-fluoro-4-methoxypyridin-2-yl) methyl)-3-((2-imino-3-methyl-2,3-dihydro-1-imidazol-1-yl)methyl)-5-(1-methyl-3-(trifluoromethyl)-1H-pyrazol-4-yl)benzamide Step A. Preparation of (S,E)-N-((5-fluoro-4-methoxypyridin-2-yl)methylene)-2-methylpropane-2-sulfinamide The title compound was prepared according to the procedures described in Example 167 Steps A through B, substituting 2-bromo-5-fluoro-4-methoxypyridine for 6-bromo-3-fluoro-2-methylpyridine in Step A.

Step B. Preparation of (S)—N—((S)-cyclopropyl(5-fluoro-4-methoxypyridin-2-yl)methyl)-2-methylpropane-2-sulfinamide The title compound (90 mg, 39%) was prepared as the major diastereomer according to the procedure described in Example 91, Step B using (S,E)-N-((5-fluoro-4-methoxypyridin-2-yl)methylene)-2-methylpropane-2-sulfinamide (0.2 g, 0.77 mmol), and 1.0 M Cyclopropyl magnesium bromide solution in 2-methyltetrahydrofuran (1.55 mL, 1.55 mmol). LCMS method 2: $R_T$=1.23 min, MS (ES) 201.0 (M+H).

Step C. Preparation of (S)-cyclopropyl(5-fluoro-4-methoxypyridin-2-yl)methanamine dihydrochloride The title compound (80 mg, 97%) was prepared from the procedure described in Example 91, Step C using (S)—N—((S)-cyclopropyl(5-fluoro-4-methoxypyridin-2-yl)methyl)-2-methylpropane-2-sulfinamide (90 mg, 0.3 mmol) and 4.0 N HCl in dioxane solution (0.75 mL, 3 mmol), Step D. Preparation of (S)—N-(cyclopropyl(5-fluoro-4-methoxypyridin-2-yl)methyl)-3-(hydroxymethyl)-5-(1-methyl-3-(trifluoromethyl)-1H-pyrazol-4-yl)benzamide The title compound (75 mg, 52%) was prepared from the procedure described in Example 91, Step D using 3-(hydroxymethyl)-5-(1-methyl-3-(trifluoromethyl)-1H-pyrazol-4-yl)benzoic acid (90 mg, 0.30 mmol) and (S)-cyclopropyl (5-fluoro-4-methoxypyridin-2-yl)methanamine dihydrochloride (89 mg, 0.30 mmol). LCMS method 2: $R_T$=1.37 min, MS (ES) 479.0 (M+H).

Step E. Preparation of (S)-3-(bromomethyl)-N-(cyclopropyl(5-fluoro-4-methoxypyridin-2-yl)methyl)-5-(1-methyl-3-(trifluoromethyl)-1H-pyrazol-4-yl)benzamide The title compound (40 mg, 50%) was prepared from the procedure described in Example 139, Step D using (S)—N-(cyclopropyl(5-fluoro-4-m ethoxypyridin-2-yl)methyl)-3-(hydroxymethyl)-5-(1-methyl-3-(trifluoromethyl)-1H-pyrazol-4-yl)benzamide (75 mg, 0.16 mmol), PPh$_3$ (82 mg, 0.31 mmol) and NBS (55 mg, 0.31 mmol). LCMS method 2: $R_T$=1.70 min, MS (ES) 540.9 (M+).

Step F. Example 221

The title compound (9 mg, 21%) was prepared from the procedure described in Example 91, Step F using (S)-3-(bromomethyl)-N-(cyclopropyl(5-fluoro-4-methoxypyridin-2-yl)methyl)-5-(1-methyl-3-(trifluoromethyl)-1H-pyrazol-4-yl)benzamide (40 mg, 0.074 mmol), 1-methyl-1H-imidazol-2-amine (14 mg, 0.11 mmol) and DIPEA (51 μL, 0.29 mmol). $^1$H NMR (CDCl$_3$) δ 8.27 (d, J=3.0 Hz, 1H), 7.76 (s, 1H), 7.73 (s, 1H), 7.63 (d, J=8.1 Hz, 1H), 7.55 (s, 1H), 7.39 (s, 1H), 6.89 (d, J=5.9 Hz, 1H), 6.11 (d, J=2.6 Hz, 1H), 6.08 (d, J=2.6 Hz, 1H), 4.82 (s, 2H), 4.66 (t, J=8.2 Hz, 1H), 3.98 (s, 3H), 3.96 (s, 3H), 3.21 (s, 3H), 1.35-1.27 (m, 1H), 0.64-0.53 (m, 3H), 0.46-0.40 (m, 1H). LCMS method 2: $R_T$=1.18 min, MS (ES) 558.0 (M+H).

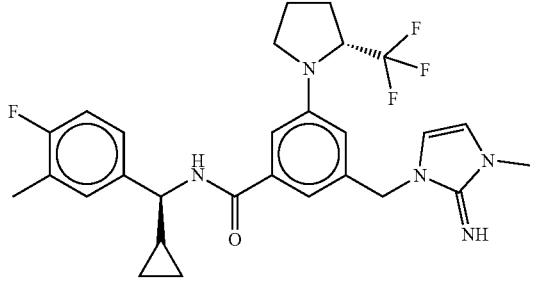

Example 222

N—((S)-Cyclopropyl(4-fluoro-3-methylphenyl) methyl)-3-((2-imino-3-methyl-2,3-dihydro-1H-imidazol-1-yl)methyl)-5-((R)-2-(trifluoromethyl)pyrrolidin-1-yl)benzamide Step A: Preparation of 3-bromo-5-(hydroxymethyl)benzoic Acid The title compound (0.66 g, 100%) was prepared from the procedure described in Example 139, Step B using methyl 3-bromo-5-(hydroxymethyl)benzoate (0.7 g, 2.9 mmol) and LiOH (68 mg, 2.9 mmol). LCMS method 2: $R_T$=1.04 min, MS (ES) 231.0 (M-f).

Step B: Preparation of (S)-3-bromo-N-(cyclopropyl (4-fluoro-3-methylphenyl)methyl)-5-(hydroxymethyl)benzamide The title compound (0.9 g 80%) was prepared from the procedure described in Example 91, Step D using 3-bromo-5-(hydroxymethyl)benzoic acid (0.66 g, 2.86 mmol) and (5)-cyclopropyl(4-fluoro-3-methylphenyl)methanamine hydrochloride (0.68 g, 3.1 mmol). LCMS method 2: $R_T$=1.64 min, MS (ES) 391.9 (M+).

Step C: Preparation of (S)-3-bromo-5-(bromomethyl)-N-(cyclopropyl(4-fluoro-3-methylphenyl)methyl)benzamide The title compound (0.79 g, 76%) was prepared from the procedure described in Example 139, Step D using (S)-3-bromo-N-(cyclopropyl(4-fluoro-3-methylphenyl)methyl)-5-(hydroxymethyl)benzamide (0.9 g, 2.3 mmol), PPh$_3$ (1.2 g, 4.6 mmol) and NBS (0.81 g, 4.6 mmol). LCMS method 2: $R_T$=1.95 min, MS (ES) 455.8 (M+).

Step D: Preparation of (S)-3-bromo-N-(cyclopropyl(4-fluoro-3-methylphenyl)methyl)-5-((2-imino-3-methyl-2,3-dihydro-1H-imidazol-1-yl)methyl)benzamide (S)-3-bromo-5-(bromomethyl)-N-(cyclopropyl(4-fluoro-3-methylphenyl)methyl)benzamide (500 mg, 1.10 mmol), 1-methyl-1H-imidazol-2-amine hydrochloride (183 mg, 1.37 mmol), DIPEA (0.76 mL, 4.39 mmol) and potassium iodide (72 mg, 0.44 mmol) were combined in MeCN (20 mL) and stirred at rt overnight. The reaction was concentrated and the crude product was dissolved in DCM (10 mL) and 1M aq. Na$_2$CO$_3$ (2 mL). The DCM layer was concentrated to give the title compound (0.62 g, 96%).

Step E: Preparation of tert-butyl (S,E)-(1-(3-bromo-5-((cyclopropyl(4-fluoro-3-methylphenyl)methyl)carbamoyl)benzyl)benzyl)-3-methyl-1,3-dihydro-2H-imidazol-2-ylidene)carbamate DIPEA (0.69 mL, 3.97 mmol) and di-tert-butyl dicarbonate (0.46 mL, 1.99 mmol) were added to a solution of (S)-3-bromo-N-(cyclopropyl(4-fluoro-3-methylphenyl)methyl)-5-((2-imino-3-methyl-2,3-dihydro-1H-imidazol-1-yl)methyl)benzamide (0.62 g, 1.32 mmol) in MeCN (20 mL). The reaction was heated at 50° C. for 4 h then concentrated. The crude product was dissolved in DCM (40 mL) and 1M aq. Na$_2$CO$_3$ (5 mL). The DCM layer was separated and concentrated to dryness. The residue was purified by flash chromatography (Combi-flash Rf, DCM/MeOH=0-10% gradient) to afford the title compound (0.43 g, 57%). LCMS method 2: $R_T$=1.48 min, MS (ES) 570.9 (M+).

Step F: Preparation of tert-butyl ((E)-1-(3-(((S)-cyclopropyl(4-fluoro-3-methylphenyl)methyl)carbamoyl)-5-((R)-2-(trifluoromethyl)pyrrolidin-1-yl)benzyl)-3-methyl-1,3-dihydro-2H-imidazol-2-ylidene)carbamate Tert-butyl (S,E)-(1-(3-bromo-5-((cyclopropyl(4-fluoro-3-methylphenyl)methyl) carbamoyl)benzyl)benzyl)-3-methyl-1,3-dihydro-2H-imidazol-2-ylidene)carbamate (50 mg, 0.088 mmol), (R)-2-(trifluoromethyl)pyrrolidine hydrochloride (17 rug, 0.096 mmol), sodium t-butoxide (18 mg, 0.188 mmol), allylpalladium (II) chloride dimer (1 mg), and Cy-BippyPhos (4 mg) were combined in dioxane (1 mL). The reaction was purged with Ar, capped, and heated at 65° C. for 4 h then concentrated. The residue was purified by flash chromatography (Combi-flash Rf, DCM/MeOH=0-8% gradient) to afford the title compound (25 mg, 45%). LCMS method 2: $R_T$=1.67 min, MS (ES) 630.0 (M+H).

Step G. Example 222

To a solution of tert-butyl ((E)-1-(3-(((S)-cyclopropyl(4-fluoro-3-methylphenyl)methyl)carbamoyl)-5-((R)-2-(trifluoromethyl)pyrrolidin-1-yl)benzyl)-3-methyl-1,3-dihydro-2H-imidazol-2-ylidene)carbamate (25 mg, 0.040 mmol) in THF (1 mL) was added 3 drops of conc. HCl. The reaction mixture was stirred at rt for 48 h then concentrated. The residue was purified by reverse phase HPLC (Phenomenex Gemini C18, H$_2$O/CH$_3$CN gradient from 5-95% CH$_3$CN, 0.1% TFA) to yield the title compound (3 mg, 16%). LCMS method 2: $R_T$=1.54 min, MS (ES) 530.0 (M+H).

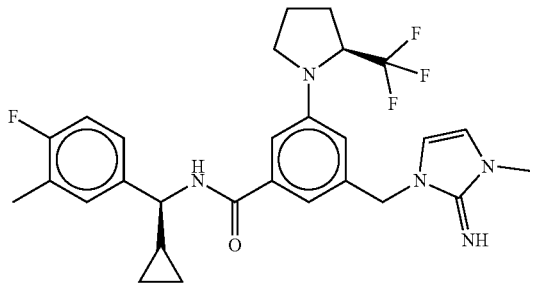

Example 223

N—((S)-cyclopropyl(4-fluoro-3-methylphenyl)methyl)-3-((2-imino-3-methyl-2,3-dihydro-1H-imidazol-1-yl)methyl)methyl)-5-((S)-2-(trifluoromethyl)pyrrolidin-1-yl)benzamide The title compound (2.5 mg) was prepared according to the procedures described in Example 222 Steps A through G, substituting (S)-2-(trifluoromethyl)pyrrolidine hydrochloride for (R)-2-(trifluoromethyl)pyrrolidine hydrochloride in Step F. LCMS method 2: $R_T$=1.52 min, MS (ES) 530.1 (M+H)

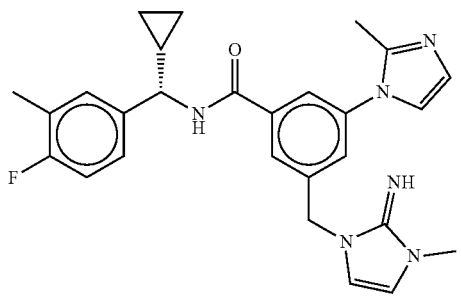

Example 224

(S)—N-(Cyclopropyl(4-fluoro-3-methylphenyl)methyl)-3-((2-imino-3-methyl-2,3-dihydro-H-imidazol-1-yl)methyl)-5-(2-methyl-1H-imidazol-1-yl)benzamide Step A: Preparation of tert-butyl (S,E)-(1-(3-((cyclopropyl(4-fluoro-3-methylphenyl)methyl)carbamoyl)-5-(2-methyl-1H-imidazol-1-yl)benzyl)-3-methyl-1,3-dihydro-2H-imidazol-2-ylidene)carbamate Tert-butyl (S,E)-(1-(3-bromo-5-((cyclopropyl(4-fluoro-3-methylphenyl)methyl) carbamoyl)benzyl)-3-methyl-1,3-dihydro-2H-imidazol-2-ylidene)carbamate (50 mg, 0.088 mmol), 2-methyl-1H-imidazole (7 mg, 0.088 mmol), $K_2CO_3$ (12 mg, 0.88 mmol), Copper(I) iodide (8 mg, 0.044 mmol), and L-proline (10 mg, 0.88 mmol) were combined in DMF (1 mL). The reaction was purged with Ar, capped, and heated at 130° C. for 16 h. The reaction was diluted with EtOAc and filtered through celite. The filtrate was washed with brine and concentrated. The residue was purified by flash chromatography (Combi-flash Rf, DCM/MeOH=0-5% gradient) to afford the title compound (10 mg, 20%). LCMS method 2: $R_T$=1.28 min, MS (ES) 574.0 (M+H).

Step B. Example 224

The title compound (3 mg, 32%) was prepared from the procedure described in Example 222, Step G using tert-butyl (S)-(1-(3-((cyclopropyl(4-fluoro-3-methylphenyl)methyl)carbamoyl)-5-(2-methyl-1H-imidazol-1-yl)benzyl)-3-methyl-1,3-dihydro-2H-imidazol-2-ylidene)carbamate (10 mg, 0.017 mmol). LCMS method 2: $R_T$=1.03 min, MS (ES) 473.11 (M+H).

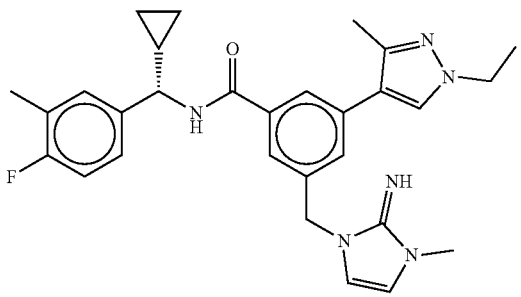

Example 225

(S)—N-(Cyclopropyl(4-fluoro-3-methylphenyl)methyl)-3-(1-ethyl-3-methyl-1H-pyrazol-4-yl)-5-((2-imino-3-methyl-2,3-dihydro-1H-imidazol-1-yl)methyl)benzamide Step A. methyl 3-(((tert-butyldiphenylsilyl)oxy)methyl)-5-(1-ethyl-3-methyl-1H-pyrazol-4-yl)benzoate The title compound (0.49 g, 50%), was prepared from the procedure described in Example 1, Step A using methyl 3-(((tert-butyldiphenylsilyl)oxy)methyl)-5-(4,4,5,5-tetramethyl-1,3,2-dioxaborolan-2-yl)benzoate (1.0 g, 1.88 mmol) and 4-bromo-1-ethyl-3-methyl-1H-pyrazole (0.53 g, 2.8 mmol). LCMS method 3: R-r=1.65 min, MS (ES) 513.0 (M+H).

Step B. Preparation of 3-(1-ethyl-3-methyl-1H-pyrazol-4-yl)-5-(hydroxymethyl)benzoic Acid The title compound (0.25 g, 99%) was prepared from the procedure described in Example 139, Step B using 3-(((tert-butyldiphenylsilyl)oxy)methyl)-5-(1-ethyl-3-methyl-1H-pyrazol-4-yl)benzoate (0.49 g, 0.95 mmol) and LiOH (0.11 g, 4.7 mmol).

Step C. Preparation of (S)—N-(cyclopropyl(4-fluoro-3-methylphenyl)methyl)-3-(1-ethyl-3-methyl-1H-pyrazol-4-yl)-5-(hydroxymethyl)benzamide The title compound (0.34 g, 85%) was prepared from the procedure described in Example 91, Step D using 3-(1-ethyl-3-methyl-1H-pyrazol-4-yl)-5-(hydroxymethyl)benzoic acid (0.25 g, 0.95 mmol) and (S)-cyclopropyl(4-fluoro-3-methylphenyl)methanamine hydrochloride (0.24 g, 1.1 mmol). LCMS method 2: $R_T$=1.52 min, MS (ES) 422.1 (M+H).

Step D: Preparation of (S)-3-(bromomethyl)-N-(cyclopropyl(4-fluoro-3-methylphenyl)methyl)-5-(1-ethyl-3-methyl-1H-pyrazol-4-yl)benzamide The title compound (123 mg, 63%) was prepared from the procedure described in Example 139, Step D using (S)—N-(cyclopropyl(4-fluoro-3-methylphenyl)methyl)-3-(1-ethyl-3-methyl-1H-pyrazol-4-yl)-5-(hydroxymethyl)benzamide (341 mg, 0.404 mmol), $PPh_3$ (212 mg, 0.81 mmol) and NBS (144 mg, 0.81 mmol). LCMS method 2: $R_T$=1.82 min, MS (ES) 483.9 (M+).

Step E. Example 225

The title compound (7 mg, 10%) was prepared from the procedure described in Example 91, Step F using (S)-3-(bromomethyl)-N-(cyclopropyl(4-fluoro-3-methylphenyl)methyl)-5-(1-ethyl-3-methyl-1H-pyrazol-4-yl)benzamide (60 mg, 0.12 mmol), 1-methyl-1H-imidazol-2-amine (24 mg, 0.19 mmol) and DIPEA (86 μL, 0.49 mmol). 1H NMR (CDCl$_3$) δ 7.74 (s, 1H), 7.57 (s, 1H), 7.51 (s, 1H), 7.38 (s, 1H), 7.26-7.21 (m, 2H), 6.96 (t, J=8.1 Hz, 1H), 6.87-6.83 (m, 1H), 6.13-6.11 (m, 2H), 4.82 (s, 2H), 4.53 (t, J=7.8 Hz, 1H), 4.13 (q, J=7.2 Hz, 2H), 3.21 (s, 3H), 2.36 (s, 3H), 2.27 (s, 3H), 1.49 (t, J=7.8 Hz, 3H), 1.30-1.21 (m, 1H), 0.66-0.62 (m, 2H), 0.54-0.50 (m, 1H), 0.44-0.39 (m, 1H). LCMS method 2: $R_T$=1.34 min, MS (ES) 501.0 (M+H).

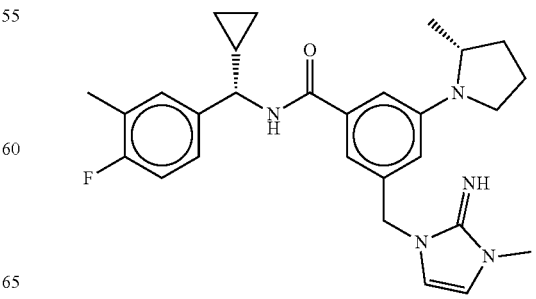

Example 226

N—((S)-Cyclopropyl(4-fluoro-3-methylphenyl)methyl)-3-((2-imino-3-methyl-2,3-dihydro-1H-imidazol-1-yl)methyl)-5-((R)-2-m ethylpyrrolidin-1-yl)benzamide The title compound (2.6 mg) was prepared according to the procedures described in Example 222 Steps A through G, substituting (R)-2-(methyl)pyrrolidine for (R)-2-(trifluoromethyl)pyrrolidine hydrochloride in Step F. LCMS method 2: $R_T$=1.35 min, MS (ES) 476.1 (M+H).

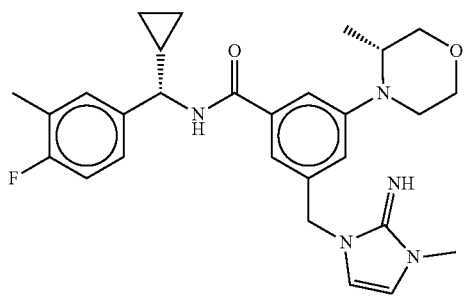

Example 227

N—((S)-cyclopropyl(4-fluoro-3-methylphenyl)methyl)-3-((2-imino-3-methyl-2,3-dihydro-1H-imidazol-1-yl)methyl)-5-((R)-3-methylmorpholino)benzamide The title compound (4 mg) was prepared according to the procedures described in Example 222 Steps A through G, substituting (R)-3-(methyl)morpholine for (R)-2-(trifluoromethyl)pyrrolidine hydrochloride in Step F. LCMS method 2: $R_T$=1.27 min, MS (ES) 492.1 (M+H).

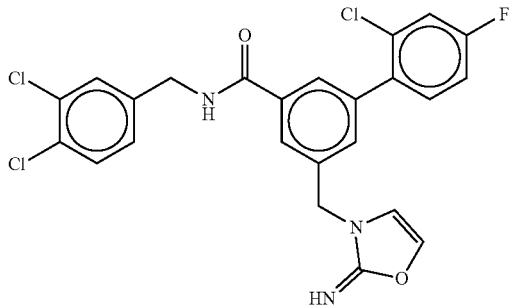

Example 228

2'-Chloro-N=(3,4-dichlorobenzyl)-4'-fluoro-5-((2-iminooxazol-3(2H)-yl)methyl)-[1,1'-biphenyl]-3-carboxamide

Step A. Preparation of methyl 2'-chloro-4'-fluoro-5-(hydroxymethyl)-[1,1'-biphenyl]-3-carboxylate The title compound (0.09 g, 0.21 mmol) was prepared following the procedure described in Example 1, Step A using methyl 3-bromo-5-(hydroxymethyl)benzoate (1 eq.) and (2-chloro-4-fluorophenyl)boronic acid (1.5 eq).

Step B. Preparation of 2'-chloro-4'-fluoro-5-(hydroxymethyl)-[1,1'-biphenyl]-3-carboxylic Acid The title compound (1.40 g, 98%) was prepared following the procedure described in Example 1, Step B using methyl 2'-chloro-4'-fluoro-5-(hydroxymethyl)-[1,1'-biphenyl]-3-carboxylate (1.50 g, 5.10 mmol).

Step C. Preparation of 2'-chloro-N-(3,4-dichlorobenzyl)-4'-fluoro-5-(hydroxymethyl)-[1,1'-biphenyl]-3-carboxamide The title compound (1.20 g, 53%) was prepared following the procedure described in Example 2, Step C using 2'-chloro-4'-fluoro-5-(hydroxymethyl)-[1,1'-biphenyl]-3-carboxylic acid (1.45 g, 5.19 mmol) and (3,4-dichlorophenyl)methanamine (0.30 g, 2.10 mmol).

Step D. Preparation of 5-(bromomethyl)-2'-chloro-N-(3,4-dichlorobenzyl)-4'-fluoro-[1,1'-biphenyl]-3-carboxamide The title compound (0.79 g, 69%) was prepared following the procedure described in Example 27, Step D using 2'-chloro-N-(3,4-di chlorobenzyl)-4'-fluoro-5-(hydroxymethyl)-[1,1'-biphenyl]-3-carboxamide (1.0 g, 2.28 mmol) in toluene.

Step E. Example 228

The title compound (1 mg, 2%) was prepared following the procedure described in Example 1, Step E using 5-(bromomethyl)-2'-chloro-N-(3,4-dichlorobenzyl)-4'-fluoro-[1,1'-biphenyl]-3-carboxamide (0.05 g, 0.10 mmol), oxazol-2(3H)-imine (0.02 g, 0.2 mmol), and DIPEA (0.04 mL, 0.25 mmol). LCMS: 98% 254 nm $R_T$=1.20 min, MS (ES) 505 (M+2H).

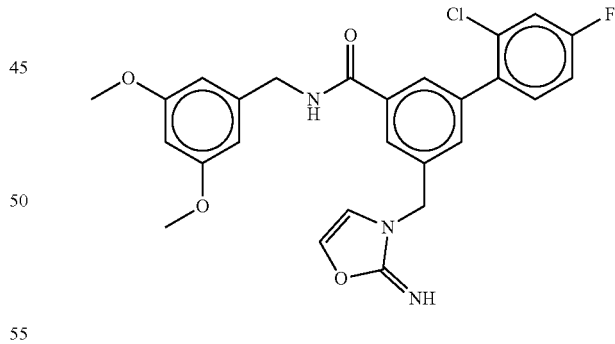

Example 229

N-(3,5-Dimethoxybenzyl)-4'-fluoro-5-((2-iminooxazol-3(2H)-yl)methyl)-2'-methyl-[1,1'-biphenyl]-3-carboxamide The title compound was prepared (31 mg, 0.065 mmol) according to the procedures described in Example 1, Steps A-E substituting (4-fluoro-2-methylphenyl)boronic acid (5 g, 32.4 mmol) in Step A, (3,5-dimethoxyphenyl)methanamine (0.3 g, 1.8 mmol) in Step C and oxazol-2-amine (37 mg, 0.32 mmol) in Step E. LC-MS: >95% 254 nm, $R_T$=0.945 min, MS (ES) 477 (M+H).

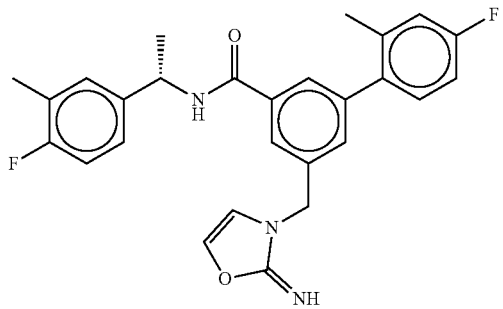

Example 230

(S)-4'-Fluoro-N-(1-(4-fluoro-3-methylphenyl)ethyl)-5-((2-iminooxazol-3(2H)-yl)methyl)-2'-methyl-[1,1'-biphenyl]-3-carboxamide The title compound was prepared (4 mg, 0.01 mmol) according to the procedures described in Examples 30 and 1, Steps A-E substituting oxazol-2-amine (8 mg, 0.08 mmol) in Step E. LC-MS: >95% 254 nm, $R_T$=1.019 min, MS (ES) 463 (M+H).

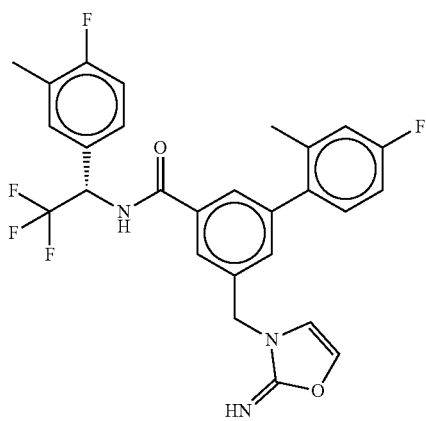

Example 231

(S)-4'-Fluoro-5-((2-iminooxazol-3(2H)-yl)methyl)-2'-methyl-N-(2,2,2-trifluoro-1-(4-fluoro-3-methylphenyl)ethyl)-[1,1'-biphenyl]-3-carboxamide The title compound was prepared (9 mg, 0.018 mmol) according to the procedures described in Examples 45 and 1, Steps A-E substituting oxazol-2-amine (10 mg, 0.11 mmol) in Step E. LC-MS: >95%° 254 nm, $R_T$=1.066 min, MS (ES) 517 (M+H).

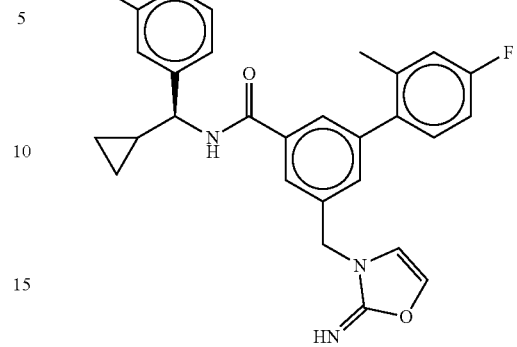

Example 232

(S)—N-(Cyclopropyl(4-fluoro-3-methylphenyl)methyl)-4'-fluoro-5-((2-iminooxazol-3(2H)-yl)methyl)-2'-methyl-[1,1'-biphenyl]-3-carboxamide The title compound was prepared (5 mg, 0.01 mmol) according to the procedures described in Examples 45 and 1, Steps A-E substituting oxazol-2-amine (7 mg, 0.08 mmol) in Step E. LC-MS: >95% 254 nm, $R_T$=1.041 min, MS (ES) 489 (M+H).

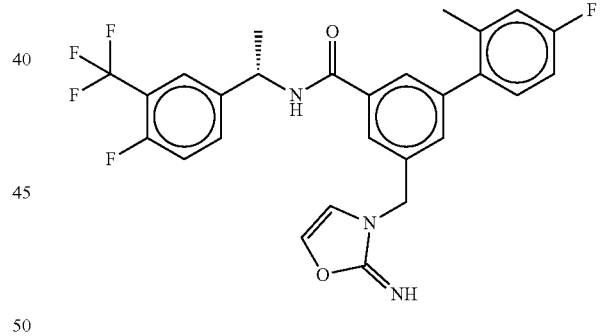

Example 233

(S)-4'-Fluoro-N-(1-(4-fluoro-3-(trifluoromethyl)phenyl)ethyl)-5-((2-iminooxazol-3(2H)-yl)methyl)-2'-methyl-[1,1'-biphenyl]-3-carboxamide The title compound was prepared (10 mg, 0.019 mmol) according to the procedures described in Examples 31 and 1, Steps A-E substituting oxazol-2-amine (7 mg, 0.08 mmol) in Step E. LC-MS: >95% 254 nm, $R_T$=1.050 min, MS (ES) 517 (M+H).

375

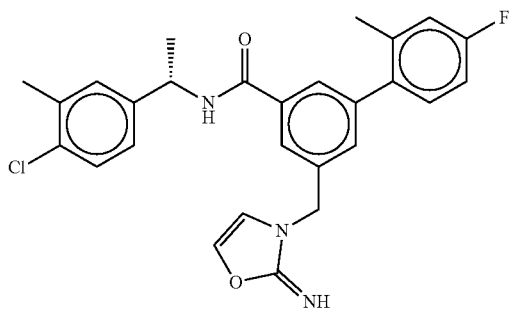

Example 234

(S)—N-(1-(4-Chloro-3-methylphenyl)ethyl)-4'-fluoro-5-((2-iminooxazol-3(2H)-yl)methyl)-2'-methyl-[1,1'-biphenyl]-3-carboxamide The title compound was prepared (15 mg, 003 mmol) according to the procedures described in Example 1, Steps A-E substituting (4-fluoro-2-methylphenyl)boronic acid (5 g, 32.4 mmol) in Step A, (S)-1-(4-chloro-3-methylphenyl)ethan-1-amine (0.15 g, 0.72 mmol) in Step C and oxazol-2-amine (12 mg, 0.14 mmol) in Step E. LC-MS: >95% 254 nm, $R_T$=1.045 min, MS (ES) 479 (M+H).

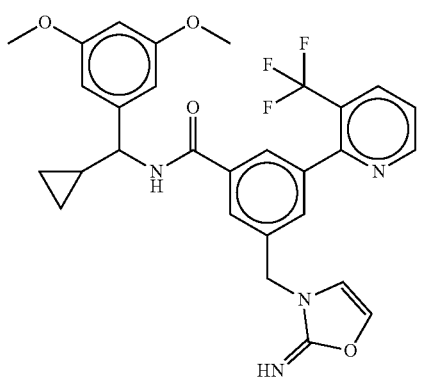

Example 235

N-(Cyclopropyl(3,5-dimethoxyphenyl)methyl)-3-((2-iminooxazol-3(2H)-yl)methyl)-5-(3-(trifluoromethyl)pyridin-2-yl)benzamide The title compound was prepared (37 mg, 0.067 mmol) according to the procedures described in Examples 61 and 60, Steps A-G substituting oxazol-2-amine (16 mg, 0.19 mmol) in Step G. LC-MS: >95% 254 nm, $R_T$=0.915 min, MS (ES) 553 (M+H).

376

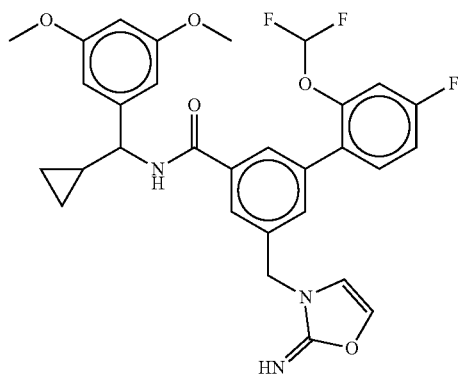

Example 236

N-(Cyclopropyl(3,5-dimethoxyphenyl)methyl)-2'-(difluoromethoxy)-4'-fluoro-5-((2-iminooxazol-3(2H)-yl)methyl)-[1,1'-biphenyl]-3-carboxamide The title compound was prepared (59 mg, 0.1 mmol) according to the procedures described in Examples 63 and 60, Steps A-G substituting oxazol-2-amine (32 mg, 0.38 mmol) in Step G. LC-MS: >95% 254 nm, $R_T$=0.999 min, MS (ES) 568 (M+H).

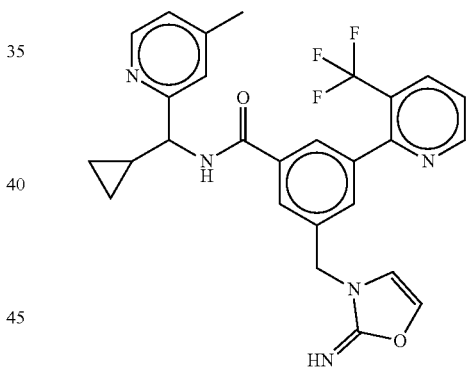

Example 237

N-(Cyclopropyl(4-methylpyridin-2-yl)methyl)-3-((2-iminooxazol-3(2H)-yl)methyl)-5-(3-(trifluoromethyl)pyridin-2-yl)benzamide The title compound was prepared (30 mg, 0.059 mmol) according to the procedures described in Example 60 Steps A-G substituting 2-bromo-3-(trifluoromethyl)pyridine (1 g, 4.4 mmol) in Step C, the dihydrochloride salt of cyclopropyl (4-methylpyridin-2-yl)methanamine (0.3 g, 1.3 mmol) in Step E and oxazol-2-amine (32 mg, 0.38 mmol) in Step G. LC-MS: >95% 254 nm, $R_T$=0.710 min, MS (ES) 508 (M+H).

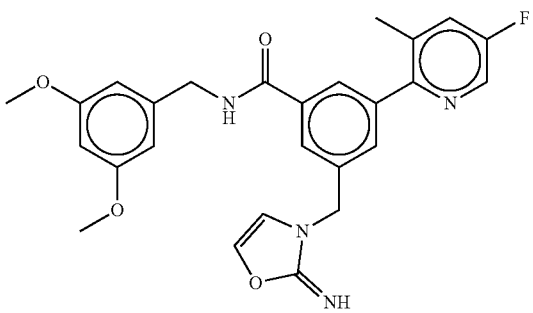

Example 238

N-(3,5-Dimethoxybenzyl)-3-(5-fluoro-3-methylpyridin-2-yl)-5-((2-iminooxazol-3(2H)-yl)methyl)benzamide The title compound was prepared (25 mg, 0.052 mmol) according to the procedures described in Examples 67 and 60, Steps A-G substituting oxazol-2-amine (18 mg, 0.22 mmol) in Step G. LC-MS: >95% 254 nm, $R_T$=0.837 min, MS (ES) 477 (M+H).

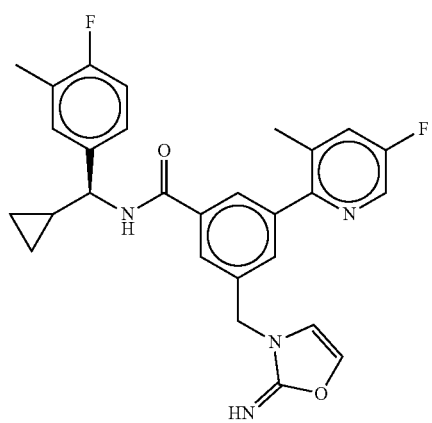

Example 240

(S)—N-(Cyclopropyl(4-fluoro-3-methylphenyl)methyl)-3-(5-fluoro-3-methylpyridin-2-yl)-5-((2-iminooxazol-3(2H)-yl)methyl)benzamide The title compound was prepared (64 mg, 0.131 mmol) according to the procedures described in Examples 66 and 60, Steps A-G substituting oxazol-2-amine (36 mg, 0.43 mmol) in Step G. LC-MS: >95% 254 nm, $R_T$=0.947 min, MS (ES) 490 (M+H).

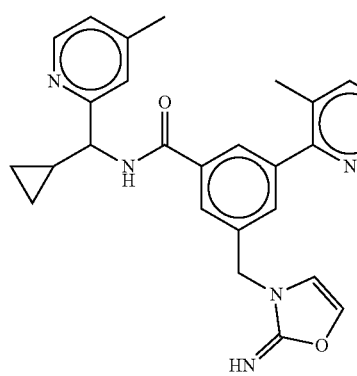

Example 239

N-(Cyclopropyl(4-methylpyridin-2-yl)methyl)-3-(5-fluoro-3-methylpyridin-2-yl)-5-((2-iminooxazol-3(2H)-yl)methyl)benzamide The title compound was prepared (19 mg, 0.040 mmol) according to the procedures described in Examples 69 and 60, Steps A-G substituting oxazol-2-amine (18 mg, 0.21 mmol) in Step G. LC-MS: >95% 254 nm, $R_T$=0.687 min, MS (ES) 473 (M+H).

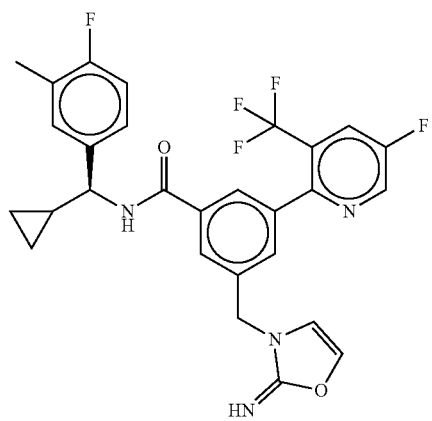

Example 241

(S)—N-(Cyclopropyl(4-fluoro-3-methylphenyl)methyl)-3-(5-fluoro-3-(trifluoromethyl)pyridin-2-yl)-5-((2-iminooxazol-3(2H)-yl)methyl)benzamide The title compound was prepared (48 mg, 0.088 mmol) according to the procedures described in Examples 72 and 60, Steps A-G substituting oxazol-2-amine (27 mg, 0.32 mmol) in Step G. LC-MS: >95% 254 nm, $R_T$=0.984 min, MS (ES) 560 (M+H).

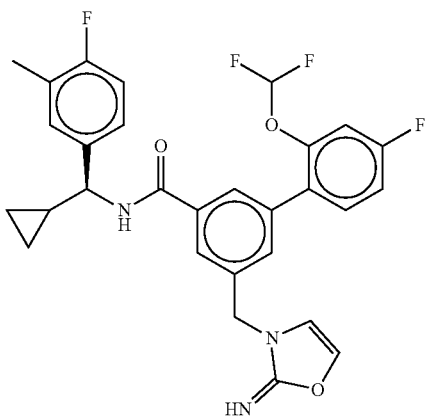

Example 242

(S)—N-(Cyclopropyl(4-fluoro-3-methylphenyl)methyl)-2'-(difluoromethoxy)-4'-fluoro-5-((2-iminooxazol-3(2 h)-yl)methyl)-[1,1'-biphenyl]-3-carboxamide The title compound was prepared (67 mg, 0.12 mmol) according to the procedures described in Examples 73 and 60, Steps A-G substituting oxazol-2-amine (24.5 mg, 0.3 mmol) in Step G. LC-MS: >95% 254 nm, R-r=1.074 min, MS (ES) 557 (M+H).

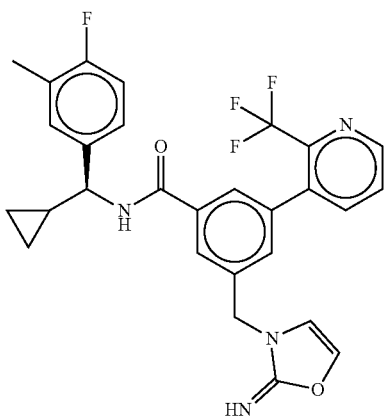

Example 243

(S)—N-(Cyclopropyl(4-fluoro-3-methylphenyl)methyl)-3-((2-iminooxazol-3(2H)-yl)methyl)-5-(2-(trifluoromethyl)pyridin-3-yl)benzamide The title compound was prepared (46 mg, 0.09 mmol) according to the procedures described in Example 60, Steps A-G substituting oxazol-2-amine (19 mg, 0.23 mmol) in Step G. $^1$H NMR (400 MHz, Chloroform-d) δ 8.74 (d, J=4.1 Hz, 1H), 7.84 (s, 1H), 7.79-7.67 (m, 2H), 7.55 (dd, J=7, 8, 4.7 Hz, 1H), 7.39 (s, 1H), 7.22 (t, J=5.3 Hz, 2H), 6.96 (t, J=8.8 Hz, 1H), 6.70 (d, J=7.5 Hz, 1H), 6.64 (d, J=1.8 Hz, 1H), 6.34 (d, J=1.8 Hz, 1H), 4.79 (s, 2H), 4.52 (t, J=8.3 Hz, 1H), 2.26 (s, 3H), 1.24 (m, 1H), 0.64 (dd, J=8.1, 4.0 Hz, 2H), 0.52 (dd, J=9.3, 4.5 Hz, 1H), 0.42 (s, 1H); $^{19}$F NMR (376 MHz, Chloroform-d) δ −60.97, −119.49; LC-MS: >95% 254 nm, $R_T$=0.955 min, MS (ES) 526 (M+H).

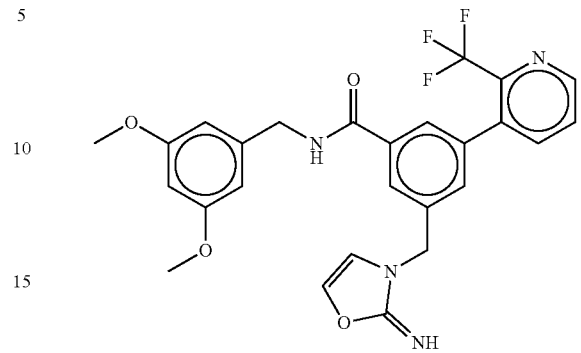

Example 244

N-(3,5-Dimethoxybenzyl)-3-((2-iminooxazol-3(2H)-yl)methyl)-5-(2-(trifluoromethyl)pyridin-3-yl)benzamide The title compound was prepared (34 mg, 0.066 mmol) according to the procedures described in Example 60, Steps A-G substituting (3,5-dimethoxyphenyl)methanamine (0.3 g, 1.8 mmol) in Step E and oxazol-2-amine (24 mg, 0.29 mmol) in Step G. LC-MS: >95% 254 nm, $R_T$=0.835 min, MS (ES) 514 (M+H).

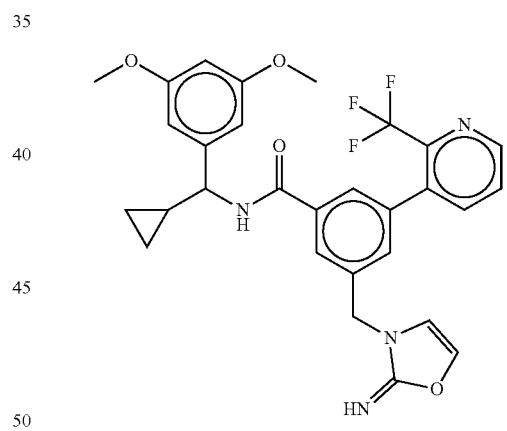

Example 245

N-(Cyclopropyl(3,5-dimethoxyphenyl)methyl)-3-((2-iminooxazol-3(2H)-yl)methyl)-5-(2-(trifluoromethyl)pyridin-3-yl)benzamide The title compound was prepared (17 mg, 0.031 mmol) according to the procedures described in Example 60, Steps A-G substituting the hydrochloride salt of cyclopropyl(3,5-dimethoxyphenyl)methanamine (0.2 g, 0.82 mmol) in Step E and oxazol-2-amine (14 mg, 0.17 mmol) in Step G. LC-MS: >95% 254 nm, $R_T$=0.916 min, MS (ES) 554 (M+H).

381

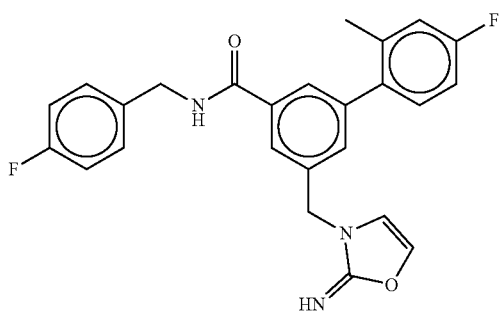

Example 246

4'-Fluoro-N-(4-fluorobenzyl)-5-((2-iminooxazol-3(2H)-yl)methyl)-2'-methyl-[1,1'-biphenyl]-3-carboxamide The title compound was prepared (53 mg, 0.12 mmol) according to the procedures described in Examples 89 and 1, Steps A-E substituting oxazol-2-amine (27 mg, 0.33 mmol) in Step E. LC-MS: >95% 254 nm, $R_T$=0.958 min, MS (ES) 451 (M+H).

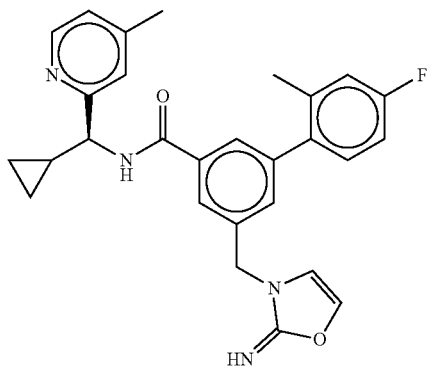

Example 247

(S)—N-(Cyclopropyl(4-methylpyridin-2-yl)methyl)-4'-fluoro-5-((2-iminooxazol-3(2H)-yl)methyl)-2'-methyl-[1,1'-biphenyl]-3-carboxamide The title compound (7 mg, 130%) was prepared from the procedure described in Example 91, Step F using (S)-(5-((cyclopropyl(4-methylpyridin-2-yl)methyl)carbamoyl)-4'-fluoro-2'-methyl-[1,1'-biphenyl]-3-yl)methyl methanesulfonate (54 mg, 0.12 mmol), oxazol-2-amine (15 mg, 0.17 mmol) and DIPEA (40 µL, 0.23 mmol). $^1$H NMR (CDCl$_3$) δ 8.40 (d, J=4.5 Hz, 1H), 7.79 (s, 1H), 7.75 (d, J=7.5 Hz, 1H), 7.69 (s, 1H), 7.35 (s, 1H), 7.18-7.15 (m, 1H), 7.10 (s, 1H), 7.03 (d, J=5.3 Hz, 1H), 6.99-6.91 (m, 2H), 6.63 (d, J=1.9 Hz, 1H), 6.33 (d, J=1.9 Hz, 1H), 4.79 (s, 2H), 4.69 (t, J=8.1 Hz, 1H), 2.36 (s, 3H), 2.22 (s, 3H), 1.33-1.26 (m, 1H), 0.67-0.40 (series of m, 4H). LCMS method 2: $R_T$=0.98 min, MS (ES) 471.0 (M+H).

382

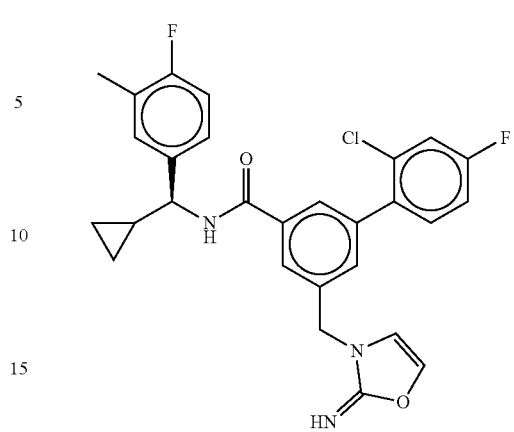

Example 248

(S)-2'-Chloro-N-(cyclopropyl(4-fluoro-3-methylphenyl)methyl)-4'-fluoro-5-((2-iminooxazol-3(2H)-yl)methyl)-[1,1'-biphenyl]-3-carboxamide The title compound was prepared (61 mg, 0.12 mmol) according to the procedures described in Examples 141 and 1, Steps A-E substituting oxazol-2-amine (23 mg, 0.28 mmol) in Step E. LC-MS: >95% 254 nm, $R_T$=1.051 min, MS (ES) 508.5 (M+H).

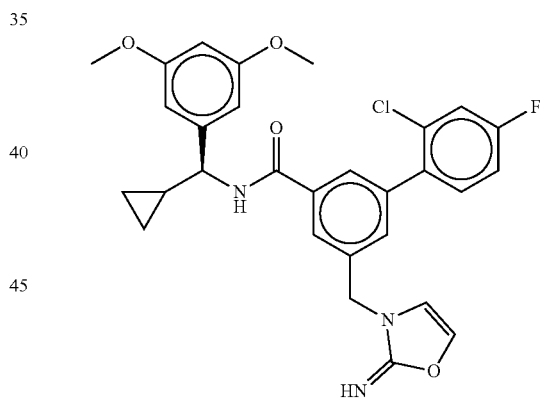

Example 249

2'-Chloro-N-(cyclopropyl(3,5-dimethoxyphenyl)methyl)-4'-fluoro-5-((2-iminooxazol-3(2H)-yl)methyl)-[1,1'-biphenyl]-3-carboxamide The title compound was prepared (58 mg, 0.11 mmol) according to the procedures described in Examples 141 and 1, Steps A-E substituting the hydrochloride salt of cyclopropyl(3,5-dimethoxyphenyl)methanamine (0.2 g, 0.82 mmol) in Step C and oxazol-2-amine (23 mg, 0.28 mmol) in Step E. LC-MS: >95% 254 nm, $R_T$=0.992 min, MS (ES) 536.2 (M+H).

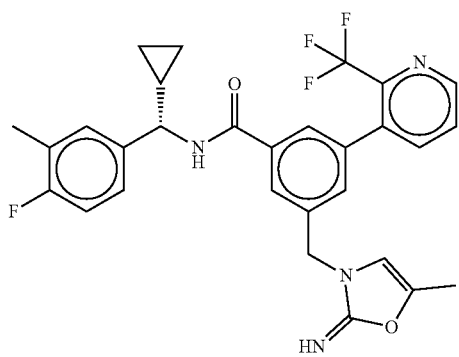

Example 250

(S)—N-(Cyclopropyl(4-fluoro-3-methylphenyl)
methyl)-3-((2-imino-5-methyloxazol-3(2H)-yl)
methyl)-5-(2-(trifluoromethyl)pyridin-3-yl)benz-
amide The title compound was prepared (9 mg, 0.017 mmol) according to the procedures described in Example 60, Steps A-G substituting 5-methyloxazol-2-amine (11 mg, 0.12 mmol) in Step G. LC-MS: >95% 254 nm, $R_T$=0.968 min, MS (ES) 539.2 (M+H).

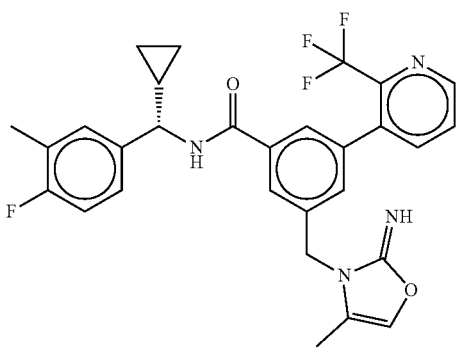

Example 252

(S)—N-(Cyclopropyl(4-fluoro-3-methylphenyl)
methyl)-3-((2-imino-4-methyloxazol-3(2H)-yl)
methyl)-5-(2-(trifluoromethyl)pyridin-3-yl)benz-
amide The title compound was prepared (6 mg, 0.011 mmol) according to the procedures described in Example 60, Steps A-G substituting 4-methyloxazol-2-amine (11 mg, 0.12 mmol) in Step G. LC-MS: >95% 254 nm, $R_T$ r 0.906 min, MS (ES) 539.2 (M+H).

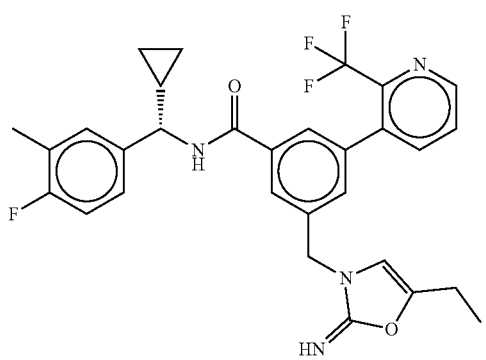

Example 251

(S)—N-(Cyclopropyl(4-fluoro-3-methylphenyl)
methyl)-3-((5-ethyl-2-iminooxazol-3(2H)-yl)
methyl)-5-(2-(trifluoromethyl)pyridin-3-yl)benz-
amide The title compound was prepared (11 mg, 0.019 mmol) according to the procedures described in Example 60, Steps A-G substituting 5-ethyloxazol-2-amine (13 mg, 0.12 mmol) in Step G. LC-MS, >95% (254 nm), Rt=0.992 min, m/z=553.2 (M+H)

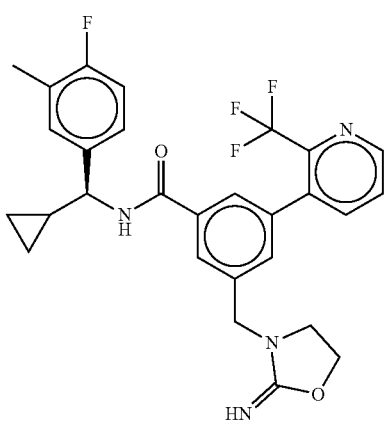

Example 253

(S)-(Cyclopropyl(4-fluoro-3-methylphenyl)methyl)-
3-((2-iminooxazolidin-3-yl)methyl)-5-(2-(trifluo-
romethyl)pyridin-3-yl)benzamide The title compound was prepared (4 mg, 0.008 mmol) according to the procedures described in Example 60, Steps A-G substituting 4,5-dihydrooxazol-2-amine (7 mg, 0.08 mmol) in Step G. LC-MS: >95% 254 nm, $R_T$=0.953 min, MS (ES) 527.2 (M+H).

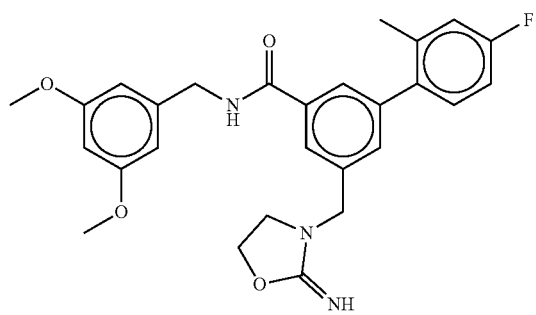

Example 254

N-(3,5-Dimethoxybenzyl)-4'-fluoro-5-((2-iminooxazolidin-3-yl)methyl)-2'-ethyl-[1,1'-biphenyl]-3-carboxamide The title compound was prepared (5 mg, 0.01 mmol) according to the procedures described in Examples 229 and 1, Steps A-E substituting 4,5-dihydrooxazol-2-amine (7 mg, 0.08 mmol) in Step E. LC-MS: >95% 254 nm, $R_T$=0.925 min, MS (ES) 480.2 (M+H).

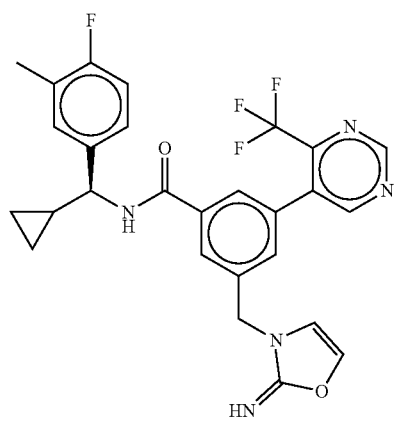

Example 255

(S)—N-(Cyclopropyl(4-fluoro-3-methylphenyl)methyl)-3-((2-iminooxazol-3(2H)-yl)methyl)-5-(4-(trifluoromethyl)pyrimidin-5-yl)benzamide The title compound was prepared (22 mg, 0.042 mmol) according to the procedures described in Examples 123 and 60, Steps A-G substituting oxazol-2-amine (16 mg, 0.29 mmol) in Step G. LC-MS: >95% 254 nm, $R_T$=0.953 min, MS (ES) 526.1 (M+H).

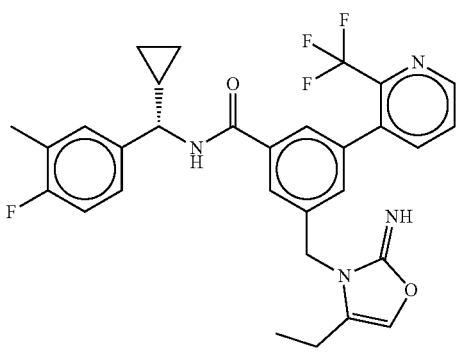

Example 256

(S)—N-(Cyclopropyl(4-fluoro-3-methylphenyl)methyl)-3-((4-ethyl-2-iminooxazol-3(2H)-yl)methyl)-5-(2-(trifluoromethyl)pyridin-3-yl)benzamide The title compound was prepared (7 mg, 0.013 mmol) according to the procedures described in Example 60, Steps A-G substituting 4-ethyloxazol-2-amine (13 mg, 0.12 mmol) in Step G. LC-MS: >95% 254 nm, $R_T$=0.990 min, MS (ES) 553.3 (M+H).

Example 257

(S)—N-(1-(3-Chloro-4-fluorophenyl)ethyl)-3-((2-iminooxazol-3(2H)-yl)methyl)-5-(2-(trifluoromethyl)pyridin-3-yl)benzamide The title compound was prepared (25 mg, 0.048 mmol) according to the procedures described in Examples 124 and 60, Steps A-G substituting oxazol-2-amine (14 mg, 0.16 mmol) in Step G. LC-MS: >95% 254 nm, $R_T$=0.912 min, MS (ES) 519.1 (M+H).

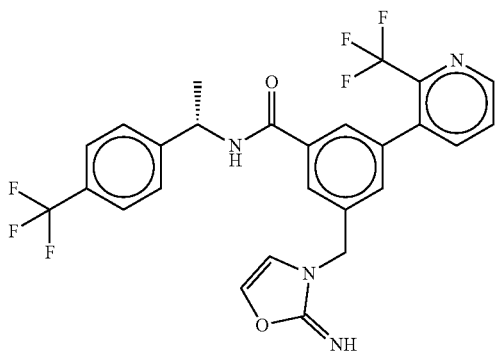

Example 258

(S)-3-((2-Iminooxazol-3(2H)-yl)methyl)-1-(1-(4-(trifluoromethyl)phenyl)ethyl)-5-(2-(trifluoromethyl)pyridin-3-yl)benzamide The title compound was prepared (31 mg, 0.058 mmol) according to the procedures described in Examples 126 and 60, Steps A-G substituting oxazol-2-amine (15 mg, 0.18 mmol) in Step G. LC-MS: >95% 254 nm, $R_T$=0.942 min, MS (ES) 535.2 (M+H).

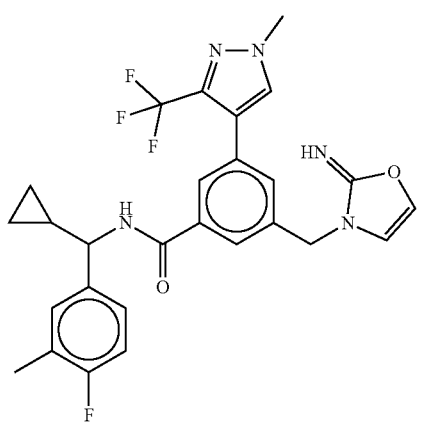

Example 259

(S)—N-(Cyclopropyl(4-fluoro-3-methylphenyl)methyl)-3-((2-iminooxazol-3(2H)-yl)methyl)-5-(1-methyl-3-(trifluoromethyl)-1H-pyrazol-4-yl)benzamide The title compound was prepared (37 mg, 0.07 mmol) according to the procedures described in Examples 124 and 60, Steps A-G substituting oxazol-2-amine (16 mg, 0.19 mmol) in Step G. LC-MS: >95% 254 nm, $R_T$=0.939 min, MS (ES) 528.1 (M+H).

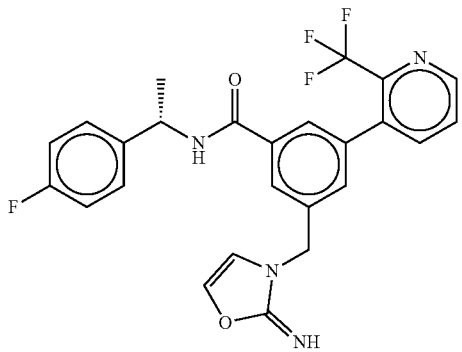

Example 260

(S)—N-(1-(4-Fluorophenyl)ethyl)-3-((2-iminooxazol-3(2H)-yl)methyl)-5-(2-(trifluoromethyl)pyridin-3-yl)benzamide The title compound was prepared (21 mg, 0.043 mmol) according to the procedures described in Example 60, Steps A-G substituting the hydrochloride salt of (S)-1-(4-fluorophenyl)ethan-1-amine in Step E (0.2 g, 1.1 mmol) and oxazol-2-amine in (15 mg, 0.18 mmol) in Step G. LC-MS: >95% 254 nm, $R_T$=0.870 min, MS (ES) 484.2 (M+H).

Example 261

(S)—N-(Cyclopropyl(4-fluoro-3-methylphenyl)methyl)-3-(2-(difluoromethoxy)pyridin-3-yl)-5-((2-iminooxazol-3(2H)-yl)methyl)benzamide The title compound was prepared (14 mg, 0.027 mmol) according to the procedures described in Examples 127 and 60, Steps A-G substituting oxazol-2-amine (11 mg, 0.14 mmol) in Step G. LC-MS: >95% 254 nm, $R_T$=0.984 min, MS (ES) 523.4 (M+H).

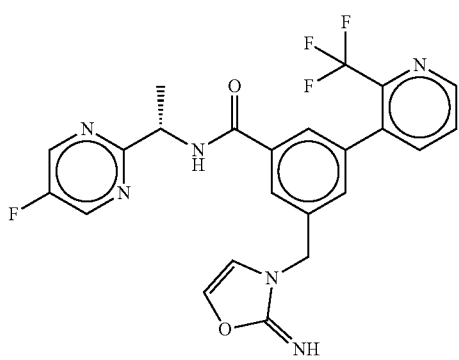

Example 262

(S)—N-(1-(5-Fluoropyrimidin-2-yl)ethyl)-3-((2-iminooxazol-3(2H)-yl)methyl)-5-(2-(trifluoromethyl)pyridin-3-yl)benzamide The title compound was prepared (42 mg, 0.086 mmol) according to the procedures described in Examples 130 and 60, Steps A-G substituting oxazol-2-amine (24 mg, 0.29 mmol) in Step G. LC-MS: >95% 254 nm, $R_T$=0.703 min, MS (ES) 487.1 (M+H).

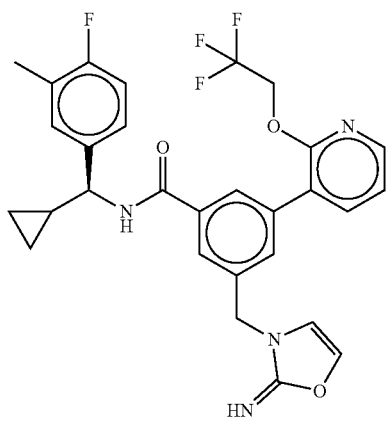

Example 263

(S)—N-(Cyclopropyl(4-fluoro-3-methylphenyl)methyl)-3-((2-iminooxazol-3(2H)-yl)methyl)-5-(2-(2,2,2-trifluoroethoxy)pyridin-3-yl)benzamide The title compound was prepared (28 mg, 0.05 mmol) according to the procedures described in Examples 135 and 60, Steps A-G substituting oxazol-2-amine (18 mg, 0.22 mmol) in Step G. $^1$H NMR (400 MHz, Chloroform-d) δ 8.13 (dd, J=4.9, 1.8 Hz, 1H), 8.01 (t, J=1.7 Hz, 1H), 7.97 (d, J=1.7 Hz, 1H), 7.76 (d, J=7.7 Hz, 1H), 7.71 (dd, J=7.4, 1.9 Hz, 1H), 7.59 (t, J=1.6 Hz, 1H), 7.27 (d, J=2.2 Hz, 1H), 7.26-7.21 (m, 1H), 7.06 (dd, J=7.4, 4.9 Hz, 1H), 6.89 (dd, J=9.6, 8.3 Hz, 1H), 6.43-6.36 (m, 2H), 5.12 (s, 2H), 4.78 (qd, J=8.7, 2.4 Hz, 2H), 4.44-4.38 (m, 1H), 3.45 (s, 3H), 2.21 (d, J=1.9 Hz, 3H), 1.35 (dddd, J=12.9, 9.5, 8.1, 4.9 Hz, 1H), 0.59 (hd, J=8.6, 4.2 Hz. 2H), 0.46 (dd, J=9.9, 4.6 Hz, 1H), 0.38-0.32 (m, 1H); LC-MS: >95% 254 nm, $R_T$=1.106 min, MS (ES) 570.2 (M+H).

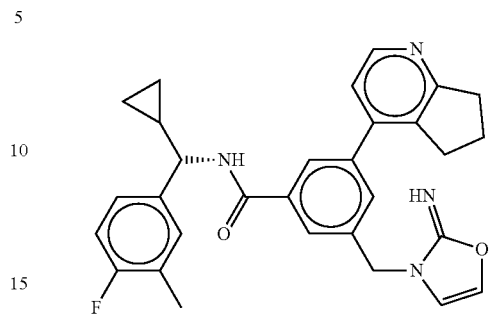

Example 264

(S)—N-(Cyclopropyl(4-fluoro-3-methylphenyl)ethyl)-3-(6,7-dihydro-5H-cyclopenta[b]pyridin-4-yl)-5-((2-iminooxazol-3(2H)-yl)methyl)benzamide The title compound was prepared (55 mg, 0.12 mmol) according to the procedures described in Examples 136 and 60, Steps A-G substituting oxazol-2-amine (24 mg, 0.28 mmol) in Step G. LC-MS: >95% 24 nm, $R_T$=0.814 min, MS (ES) 492 (M+H).

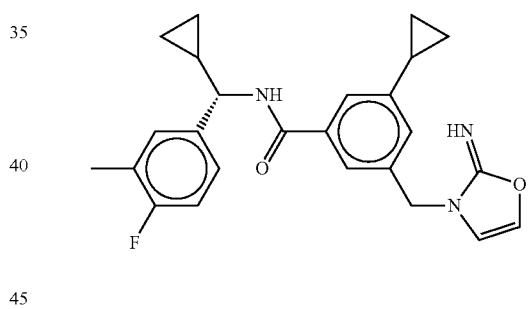

Example 265

(S)-3-cyclopropyl-N-(cyclopropyl(4-fluoro-3-methylphenyl)methyl)-5-((2-iminooxazol-3(2H)-yl)methyl)benzamide The title compound (5 mg, 9%) was prepared from the procedure described in Example 91, Step F using (S)-3-(bromomethyl)-5-cyclopropyl-N-(cyclopropyl(4-fluoro-3-methylphenyl)methyl)benzamide (50 mg, 0.12 mmol), oxazol-2-amine (15 mg, 0.17 mmol) and DIPEA (42 µL, 0.24 mmol) $^1$H NMR (CDCl$_3$) δ 7.50 (s, 1H), 7.44 (s, 1H), 7.23-7.19 (m, 2H), 7.13 (s, 1H), 6.96 (t, J=8.8 Hz, 1H), 6.66-6.3 (m, 1H), 6.63 (d, J=1.9 Hz, 1H), 6.30 (d, J=1.9 Hz, 1H), 4.69 (s, 2H), 4.51 (t, J=8.5 Hz, 1H), 2.26 (s, 3H), 1.96-1.89 (m, 1H), 1.27-1.20 (m, 1H), 1.02-0.97 (m, 2H), 0.75-0.71 (m, 2H), 0.67-0.62 (m, 2H), 0.53-0.49 (m, 1H), 0.44-0.39 (m, 1H) LCMS method 2: $R_T$=1.23 min, MS (ES) 420.0 (M+H).

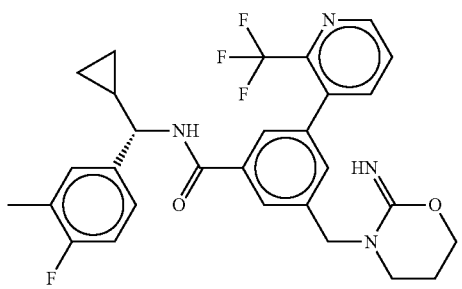

Example 266

(S)—N-(Cyclopropyl(4-fluoro-3-methylphenyl)methyl)-3-((2-imino-1,3-oxazinan-3-yl)methyl)-5-(2-(trifluoromethyl)pyridin-3-yl)benzamide The title compound was prepared (17 mg, 0.031 mmol) according to the procedures described in Example 60, Steps A-G substituting 5,6-dihydro-4H-1,3-oxazin-2-amine (12 mg, 0.12 mmol) in Step G. LC-MS: >95% 254 nm, $R_T$=0.949 min, MS (ES) 541.2 (M+H).

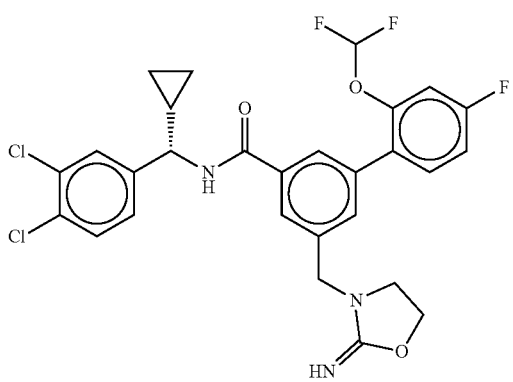

Example 267

(S)—N-(Cyclopropyl(3,4-dichlorophenyl)methyl)-2'-(difluoromethoxy)-4'-fluoro-5-((2-iminooxazolidin-3-yl)methyl)-[1,1'-biphenyl]-3-carboxamide The title compound was prepared (5 mg, 0.086 mmol) according to the procedures described in Examples 150 and 60, Steps A-G substituting 4,5-dihydrooxazol-2-amine (10 mg, 0.11 mmol) in Step G. LC-MS: >95% 254 nm, $R_T$=1.461 min, MS (ES) 577.1 (M+H).

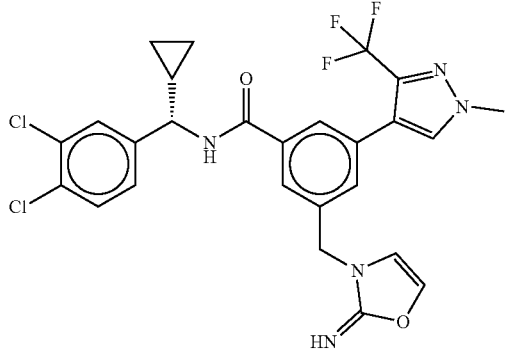

Example 268

(S)—N-(Cyclopropyl(3,4-dichlorophenyl)methyl)-3-((2-iminooxazol-3(2H)-yl)methyl)-5-(1-methyl-3-(trifluoromethyl)-1 t-pyrazol-4-yl)benzamide The title compound was prepared (16 mg, 0.028 mmol) according to the procedures described in Examples 157 and 60, Steps A-G substituting oxazol-2-amine (9 mg, 0.11 mmol) in Step G. $^1$H NMR (400 MHz, Chloroform-d) δ 7.81 (t, J=1.7 Hz, 2H), 7.58-7.53 (m, 2H), 7.45 (s, 1H), 7.39 (d, J=8.3 Hz, 1H), 7.28 (dd, J=8.3, 2.1 Hz, 2H), 7.13 (d, J=7.4 Hz, 1H), 6.75 (d, J=1.9 Hz, 1H), 6.43 (d, J=1.9 Hz, 1H), 4.90-4.78 (m, 2H), 4.48-4.41 (m, 1H), 3.99 (s, 3H), 0.68 (d, J=8.0 Hz, 2H), 0.50 (dt, J=7.7, 4.6 Hz, 1H), 0.43 (q, J=7.8, 5.3 Hz, 1H); LC-MS: >95% 254 nm, $R_T$=0.978 min, MS (ES) 564.1 (M+H).

Example 269

(S)—V—N-(Cyclopropyl(3,4-dichlorophenyl)methyl)-3-((2-iminooxazolidin-3-yl)methyl)-5-(1-methyl-3-(trifluoromethyl)-1H-pyrazol-4-yl)benzamide The title compound was prepared (7 mg, 0.012 mmol) according to the procedures described in Examples 157 and 60, Steps A-G substituting 4,5-dihydrooxazol-2-amine (10 mg, 0.11 mmol) in Step G. LC-MS: >95% 254 nm, $R_T$=0.989 min, MS (ES) 566 (M+H).

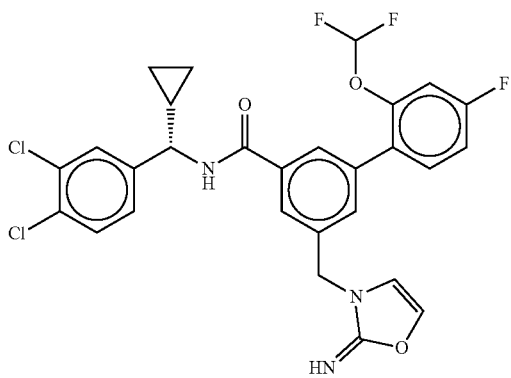

Example 270

(S)—N-(Cyclopropyl(3,4-dichlorophenyl)ethyl)-2'-(difluoromethoxy)-4'-fluoro-5-((2-iminooxazol-3(2)-yl)methyl)-[1,1'-biphenyl]-3-carboxamide The title compound was prepared (11 mg, 0.036 mmol) according to the procedures described in Examples 150 and 60, Steps A-G substituting oxazol-2-amine (9 mg, 0.10 mmol) in Step G. LC-MS: >95% 254 nm, $R_T$=1.490 min, MS (ES) 576 (M+H).

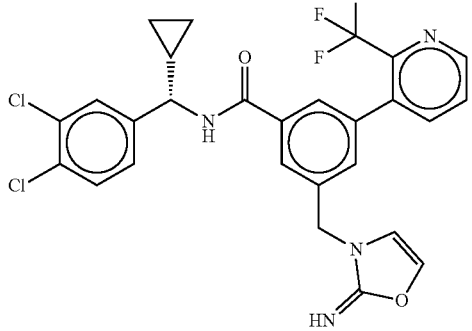

Example 271

(S)—N-(Cyclopropyl(3,4-dichlorophenyl)methyl)-3-((2-iminooxazol-3(2H)-yl)methyl)-5-(2-(trifluoromethyl)pyridin-3-yl)benzamide The title compound was prepared (19 mg, 0.033 mmol) according to the procedures described in Examples 153 and 60, Steps A-G substituting oxazol-2-amine (9 mg, 0.10 mmol) in Step G. LC-MS: >95% 254 nm, $R_T$=0.999 min, MS (ES) 561.1 (M+H).

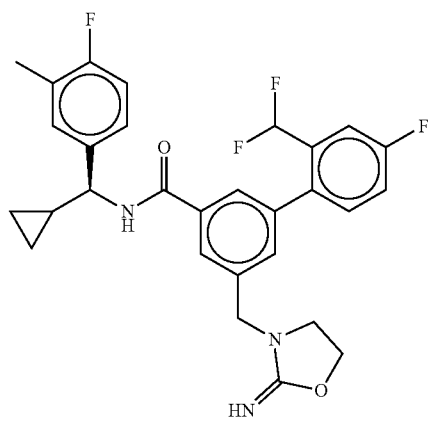

Example 272

(S)—N-(Cyclopropyl(4-fluoro-3-methylphenyl)methyl)-2'-(difluoromethyl)-4'-fluoro-5-((2-iminooxazolidin-3-yl)methyl)-[1,1'-biphenyl]-3-carboxamide The title compound was prepared (18 mg, 0.034 mmol) according to the procedures described in Examples 154 and 60, Steps A-G substituting 4,5-dihydrooxazol-2-amine (14 mg, 0.15 mmol) in Step G. LC-MS: >95% 254 nm, $R_T$=1.030 min MS (ES) 526.2 (M+H).

Example 273

(S)—N-(Cyclopropyl(4-fluoro-3-methylphenyl)methyl)-2'-(difluoromethoxy)-4'-fluoro-5-((2-iminooxazolidin-3-yl)methyl)-[1,1'-biphenyl]-3-carboxamide The title compound was prepared (20 mg, 0.037 mmol) according to the procedures described in Examples 73 and 60, Steps A-G substituting 4,5-dihydrooxazol-2-amine (12 mg, 0.13 mmol) in Step G. LC-MS: >95% 254 nm, $R_T$=1.029 min, MS (ES) 542.2 (M+H).

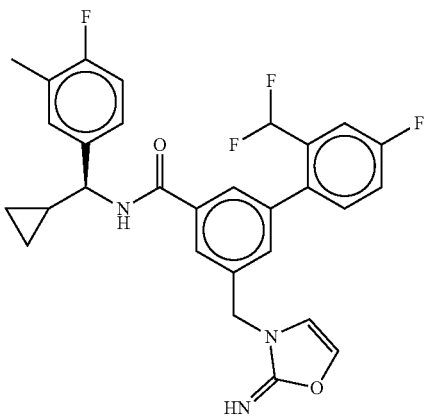

Example 274

(S)—N-(Cyclopropyl(4-fluoro-3-methylphenyl)
methyl)-2'-(difluoromethyl)-4'-fluoro-5-((2-iminoox-
azol-3(2H)-yl)methyl)-[1,1'-biphenyl]-3-carboxam-
ide The title compound was prepared (7 mg, 0.013 mmol) according to the procedures described in Examples 154 and 60, Steps A-G substituting oxazol-2-amine (8 mg, 0.10 mmol) in Step G. LC-MS: >95% 254 nm, $R_T$=1.024 min, MS (ES) 524.2 (M+H).

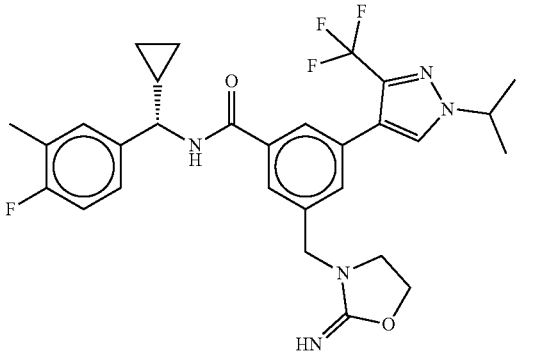

Example 275

(S)—N-(Cyclopropyl(4-fluoro-3-methylphenyl)
methyl)-3-((2iminooxazolidin-3-yl)methyl)-5-(1-
isopropyl-3-(trifluoromethyl)-1H-pyrazol-4-yl)benz-
amide The title compound was prepared (10 mg, 0.018 mmol) according to the procedures described in Examples 193 and 60, Steps A-G substituting 5-dihydrooxazol-2-amine (10 mg, 0.11 mmol) in Step G. LC-MS: >95% 254 nm, $R_T$=1.027 min, MS (ES) 558.2 (M+H).

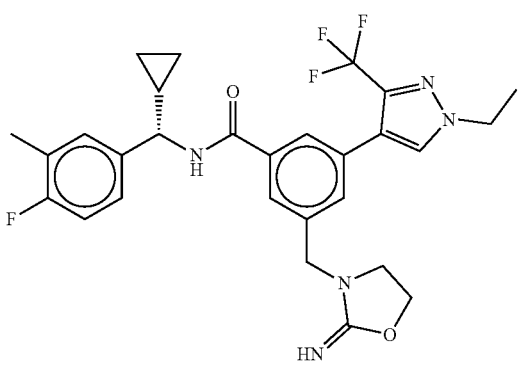

Example 276

(S)—N-(Cyclopropyl(4-fluoro-3-methylphenyl)
methyl)-3-(1-ethyl-3-(trifluoromethyl) H-pyrazol-4-
yl)-5-((2-iminooxazolidin-3-yl)methyl)benzamide The title compound was prepared (21 mg, 0.039 mmol) according to the procedures described in Examples 212 and 60, Steps A-G substituting 5-dihydrooxazol-2-amine (10 mg, 0.11 mmol) in Step G. LC-MS: >95% 254 nm, $R_T$=0.990 min, MS (ES) 543.2 (M+H).

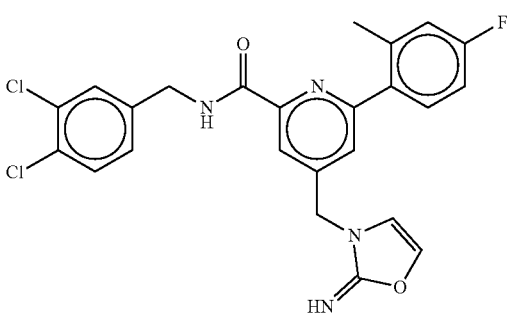

Example 277

N-(3,4-Dichlorobenzyl)-6-(4-fluoro-2-methylphe-
nyl)-4-((2-iminooxazol-3(2H)-yl)methyl)picolina-
mide A solution of 4-(bromomethyl)-N-(3,4-dichlorobenzyl)-6-(4-fluoro-2-methylphenyl)picolinamide (0.03 g, 0.06 mmol) and oxazol-2(3H)-imine (0.02 g, 0.25 mmol) in MeCN (5 ml) was stirred for 18 h at 50° C. then concentrated under reduced pressure. The residue was purified by reverse phase HPLC (Phenomenex Gemini C18, H₂O/CH₃CN gradient from 30-90% CH₃CN, 0.1% TFA) to yield the title compound (3 mg, 9%). LCMS: 98% 254 nm $R_T$=1.40 min, MS (ES) 485 (M+H).

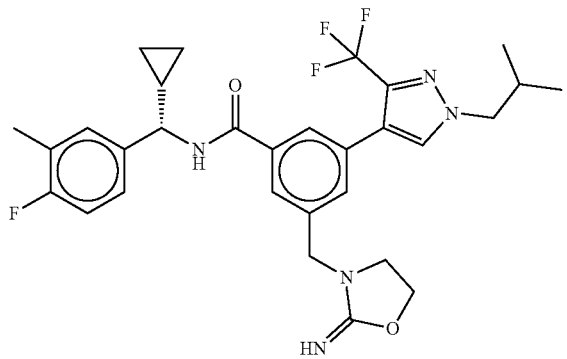

Example 278

(S)—N-(Cyclopropyl(4-fluoro-3-methylphenyl)methyl)-3-((2-iminooxazolidin-3-yl)methyl)-5-(1-isobutyl-3-(trifluoromethyl)-1H-pyrazol-4-yl)benzamide The title compound was prepared (13 mg, 0.022 mmol) according to the procedures described in Examples 163 and 60, Steps A-G substituting 5-dihydrooxazol-2-amine (8 mg, 0.09 mmol) in Step G. LC-MS: >95% 254 nm, $R_T$=1.078 min, MS (ES) 572.2 (M+H).

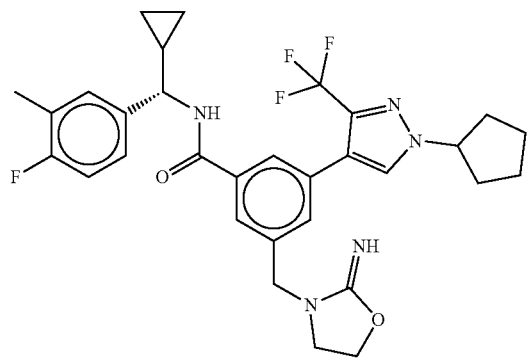

Example 279

(S)-3-(1-Cyclopentyl-3-(trifluoromethyl)-1H-pyrazol-4-yl)-N-(cyclopropyl(4-fluoro-3-methylphenyl)methyl)-5-((2-iminooxazolidin-3-yl)methyl)benzamide The title compound was prepared (9 mg, 0.015 mmol) according to the procedures described in Examples 164 and 60, Steps A-G substituting 5-dihydrooxazol-2-amine (8 mg, 0.09 mmol) in Step G. LC-MS: >95% 254 nm, $R_T$=1.105 min, MS (ES) 548.2 (M+H).

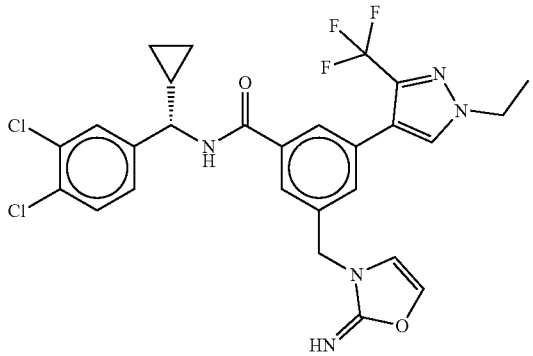

Example 280

(S)—N-(Cyclopropyl(3,4-dichlorophenyl)methyl)-3-(1-ethyl-3-(trifluoromethyl)-1H-pyrazol-4-yl)-5-((2-iminooxazol-3(2H)-yl)methyl)benzamide The title compound was prepared (27 mg, 0.047 mmol) according to the procedures described in Examples 161 and 60, Steps A-G substituting oxazol-2-amine (12 mg, 0.14 mmol) in Step G. LC-MS: >95% 254 nm, $R_T$=1.022 min, MS (ES) 578.1 (M+H).

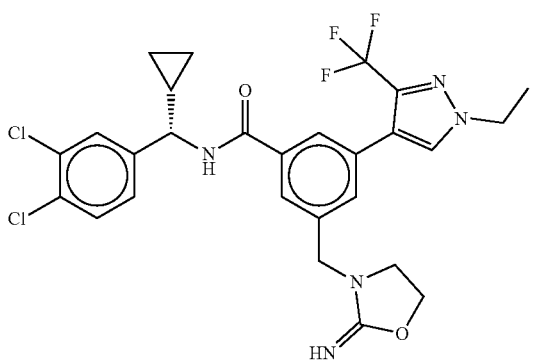

Example 281

(S)—N-(Cyclopropyl(3,4-dichlorophenyl)methyl)-3-(1-ethyl-3-(trifluoromethyl)-1H-pyrazol-4-yl)-5-((2-iminooxazolidin-3-yl)methyl)benzamide The title compound was prepared (16 mg, 0.027 mmol) according to the procedures described in Examples 161 and 60, Steps A-G substituting 5-dihydrooxazol-2-amine (13 mg, 0.14 mmol) in Step G. LC-MS: >95% 254 nm, $R_T$=1.044 min, MS (ES) 580.1 (M+H).

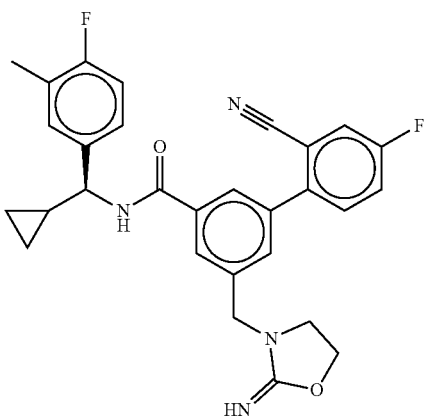

Example 282

(S)-2'-Cyano-N-(cyclopropyl(4-fluoro-3-methylphenyl)methyl)-4'-fluoro-5-((2-iminooxazolidin-3-yl)methyl)-[1,1'-biphenyl]-3-carboxamide The title compound (19 mg, 25%) was prepared from the procedure described in Example 91, Step F using (S)-5-(bromomethyl)-2'-cyano-N-(cyclopropyl(4-fluoro-3-methylphenyl)methyl)-4'-fluoro-[1,1'-biphenyl]-3-carboxamide (75 mg, 0.15 mmol), 4,5-dihydrooxazol-2-amine hydrochloride (37 mg, 0.30 mmol) and DIPEA (105 µL, 0.61 mmol). $^1$H NMR (CDCl$_3$) δ 7.86 (overlapping s, 2H), 7.67 (s, 1H), 7.58-7.54 (m, 1H), 7.49-7.46 (m, 1H), 7.42-7.37 (m, 1H), 7.26-7.21 (m, 2H), 6.97 (t, J=8.8 Hz, 1H), 6.81 (d, J=8.1 Hz, 1H), 4.57 (s, 2H), 4.54 (t, J=8.5 Hz, 1H), 4.27 (t, J=7.3 Hz, 2H), 3.47 ((t, J=7.3 Hz, 2H), 2.27 (s, 3H), 1.31-1.22 (m, 1H), 0.69-0.62 (m, 2H), 0.56-0.52 (m, 1H), 0.44-0.40 (m, 1H). LCMS method 2: R$_T$=1.45 min, MS (ES) 501.0 (M+H).

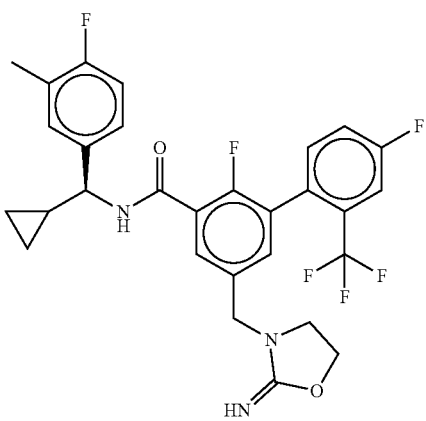

Example 283

(S)—N-(Cyclopropyl(4-fluoro-3-methylphenyl)methyl)-2,4'-difluoro-5-((2-iminooxazolidin-3-yl)methyl)-2'-(trifluoromethyl)-[1,1'-biphenyl]-3-carboxamide Step A. Preparation of methyl 2,4'-difluoro-5-(((2-hydroxyethyl)amino)methyl)-2'-(trifluoromethyl)-[1,1'-biphenyl]-3-carboxylate 2-Aminoethan-1-ol (0.09 mL, 1.55 mmol) was added to a solution of methyl 5-(bromomethyl)-2,4'-difluoro-2'-(trifluoromethyl)-[1,1'-biphenyl]-3-carboxylate (527.0 mg, 1.29 mmol) in DMF (10.0 mL). The reaction mixture was stirred at ambient temperature for 1 h and quenched with H$_2$O (5.0 mL). The reaction mixture was extracted with CH$_2$C$_2$(3× 10.0 mL). The combined organics were dried over Na$_2$SO$_4$ and concentrated under reduced pressure. The residue was purified by flash chromatography (Combi-flash Rf, DCM/MeOH=0-20% gradient) to afford the title compound (336.6 mg, 67%). LCMS: R$_T$=1.180 min, MS (ES) 390.3 (M+H).

Step B. Preparation of 2,4'-difluoro-5-(((2-hydroxyethyl)amino)methyl)-2'-(trifluoromethyl)-[1,1'-biphenyl]-3-carboxylic acid The crude title compound was prepared from the procedure described in Example 27, Step B using methyl 2,4'-difluoro-5-(((2-hydroxyethyl)amino)methyl)-2'-(trifluoromethyl)-[1,1'-biphenyl]-3-carboxylate (336.6 mg, 0.86 mmol). LCMS: R$_T$=1.031 min, MS (ES) 376.3 (M+H).

Step C. Preparation of (S)—N-(cyclopropyl(4-fluoro-3-methylphenyl)methyl)-2,4'-difluoro-5-(((2-hydroxyethyl)amino)methyl)-2'-(trifluoromethyl)-[1,1'-biphenyl]-3-carboxamide The title compound (33.4 mg, 46% 2 step) was prepared from the procedure described in Example 33, Step A using 2,4'-difluoro-5-(((2-hydroxyethyl)amino)methyl)-2'-(trifluoromethyl)-[1,1'-biphenyl]-3-carboxyli c acid (50.0 mg, 0.13 mmol) and (S)-cyclopropyl(4-fluoro-3-methylphenyl)methanamine hydrochloride (57.5 mg, 0.27 mmol). $^1$H NMR (400 MHz, Chloroform-) δ 9.18 (br s, 1H), 8.18 (dd, J=15.0, 5.1 Hz, 1H), 7.49 (d, J=8.6 Hz, 1H), 7.45 (d, J=5.7 Hz, 1H), 7.32 (dd, J=11.6, 7.5 Hz, 2H), 7.21-7.06 (m, 2H), 6.91 (t, J=8.8 Hz, 1H), 5.30 (br s, 2H), 4.46 (t, J=7.7 Hz, 1H), 4.13 (s, 2H), 3.74 (s, 2H), 3.01 (s, 2H), 2.21 (s, 3H), 1.16 (m, 1H), 0.59 (m, 2H), 0.39 (m, 2H); LCMS: R$_T$=1.493 min, MS (ES) 537.5 (M+H).

Step D. Example 283

CNBr (0.02 mL, 0.22 mmol) was added to a solution of (S)—N-(cyclopropyl(4-fluoro-3-methylphenyl)methyl)-2,4'-difluoro-5-(((2-hydroxyethyl)amino)methyl)-2'-(trifluoromethyl)-[1,1'-biphenyl]-3-carboxamide (24.0 mg, 0.04 mmol) in DMF (0.7 mL). The reaction mixture was stirred at ambient temperature for 12 h, quenched with H$_2$O (1.0 mL) and extracted with CH$_2$Cl$_2$ (3×3.0 mL). The combined organics were dried over Na$_2$SO$_4$ and concentrated under reduced pressure. The residue was purified by reverse phase HPLC (Phenomenex Gemini C18, H$_2$O/CH$_3$CN gradient from 5-95% CH$_3$CN, 0.1% TFA) to yield the title compound (3.7 mg, 14%). LCMS: R$_T$=1.827 min, MS (ES) 562.5 (M+H).

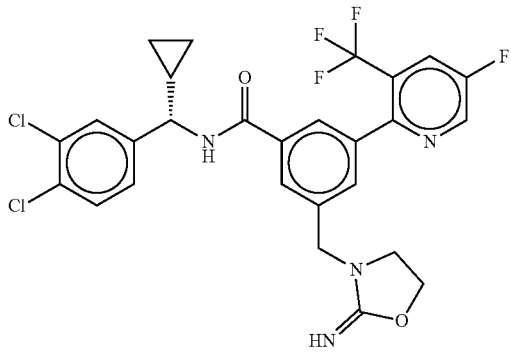

Example 284

(S)—N-(Cyclopropyl(3,4-dichlorophenyl)methyl)-3-(5-fluoro-3-(trifluoromethyl)pyridin-2-yl)-5-((2-iminooxazolidin-3-yl)methyl)benzamide The title compound was prepared (20 mg, 0.035 mmol) according to the procedures described in Examples 72 and 60, Steps A-G substituting the hydrochloride salt of (S)-cyclopropyl(3,4-dichlorophenyl)methanamine (0.3 g, 1.1 mmol) in Step E and 5-dihydrooxazol-2-amine (12 mg, 0.14 mmol) in Step G. LC-MS: >95% 254 nm, $R_T$=1.069 min, MS (ES) 581.1 (M=H),

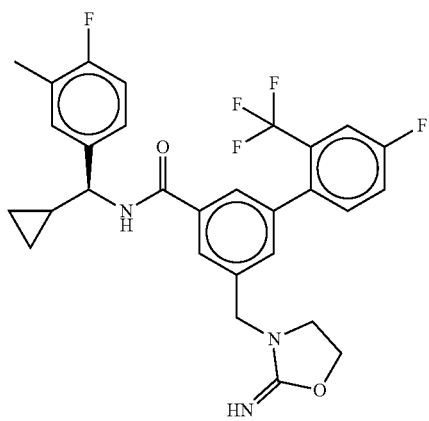

Example 285

(S)—N-(Cyclopropyl(4-fluoro-3-methylphenyl)methyl)-4'-fluoro-5-((2-iminooxazolidin-3-yl)methyl)-2'-(trifluoromethyl)-[1,1'-biphenyl]-3-carboxamide The title compound (9 mg, 12%) was prepared from the procedure described in Example 91, Step F using (5)-5-(bromomethyl)-N-(cyclopropyl(4-fluoro-3-methylphenyl)methyl)-4'-fluoro-2'-(trifluoromethyl)-[1,1'-biphenyl]-3-carboxamide (75 mg, 0.14 mmol), 4,5-dihydrooxazol-2-amine hydrochloride (34 mg, 0.38 mmol) and DIPEA (97 µL, 0.56 mmol). $^1$H NMR (DMSO d$_6$) δ 9.04 (d, J=8.1 Hz, 1H), 7.90 (s, 1H), 7.81 (s, 1H), (7.79-7.76 (m, 1H), 7.67-7.63 (m, 1H), 7.57-7.54 (m, 1H), 7.42 (s, 1H), 7.33 (d, J=7.7 Hz, 1H), 7.31-7.27 (m, 1H), 7.08 (t, J=9.4 Hz, 1H), 4.48 (s, 2H), 4.33 (t, J=8.9 Hz, 1H), 4.17 (t, J=7.4 Hz, 2H), 3.30 (t, J=7.4 Hz, 2H), 2.22 (s, 3H), 1.35-1.27 (m, 1H), 0.56-0.52 (m, 2H), 0.40-0.35 (m, 2H). LCMS method 2: $R_T$=1.53 min, MS (ES) 543.9 (M+).

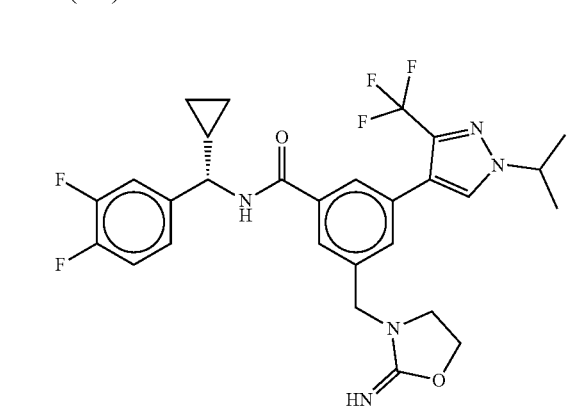

Example 286

(S)—N-(Cyclopropyl(3,4difluorophenyl)methyl)-3-((2-iminooxazolidin-3-yl)methyl)-5-(1-isopropyl-3-(trifluoromethyl)-1H-pyrazol-4-yl)benzamide The title compound was prepared (9 mg, 0.016 mmol) according to the procedures described in Examples 216 and 60, Steps A-G substituting 5-dihydrooxazol-2-amine (13 mg, 0.14 mmol) in Step G. LC-MS: >95% 254 nm, $R_T$=1.044 min, MS (ES) 562.2 (M+H).

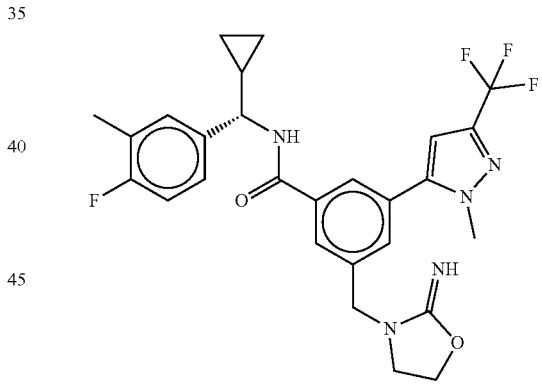

Example 287

(S)—N-(Cyclopropyl(4-fluoro-3-methylphenyl)methyl)-3-((2-iminooxazolidin-3-yl)methyl)-5-(1-methyl-3-(trifluoromethyl)-1H-pyrazol-5-yl)benzamide 4,5-Dihydrooxazol-2-amine (9.3 mg, 0.11 mmol) and DIPEA (0.01 mL, 0.05 mmol) were added to a solution of (S)-3-(bromomethyl)-N-(cyclopropyl(4-fluoro-3-methylphenyl)methyl)-5-(1-methyl-3-(trifluoromethyl)-1H-pyrazol-5-yl)benzamide (28.0 mg, 0.05 mmol) in CH$_3$CN (1.0 mL). The reaction mixture was stirred at ambient temperature for 12 h, quenched with 0.5 mL of H$_2$O, and extracted with CH$_2$Cl$_2$ (3×3.0 mL). The combined organics were passed through the phase separator then concentrated under reduced pressure. The residue was purified by reverse phase HPLC (Phenomenex Gemini C18, H₂O/CH₃CN gradient from 5-95% CH₃CN, 0.1% TFA) to yield the title compound (7.5 mg, 26% 4 step). LCMS: $R_T$=1.445 min, MS (ES) 530.5 (M+H).

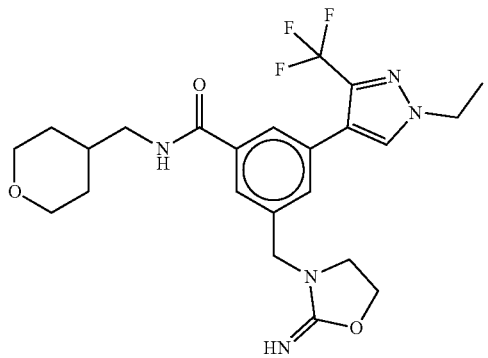

Example 288

3-(1-Ethyl-3-(trifluoromethyl)-1H-pyrazol-4-yl)-5-((2-iminooxazolidin-3-yl)methyl)-N-((tetrahydro-2H-pyran-4-yl)methyl)benzamide Step A. Preparation of 3-(1-ethyl-3-(trifluoromethyl)-1-pyrazol-4-yl)-5-(hydroxymethyl)-N-((tetrahydro-2H-pyran-4-yl)methyl)benzamide The title compound (95 mg, 92%) was prepared according to the procedure outlined for Example 78 Step C, using 3-(1-ethyl-3-(trifluoromethyl)-1H-pyrazol-4-yl)-5-(hydroxymethyl)benzoic acid (79 mg, 0.25 mmol) and 4-aminomethyltetrahydropyran (36 µL, 0.30 mmol). LCMS: $R_T$=0.84 min, MS (ES) 412.3 (M+H).

Step B. Preparation of 3-(bromomethyl)-5-(1-ethyl-3-(trifluoromethyl)-1H-pyrazol-4-yl)-N-((tetrahydro-2H-pyran-4-yl)methyl)benzamide The title compound (67 mg, 610%) was prepared according to the procedure outlined for Example 78 Step D, from 3-(1-ethyl-3-(trifluoromethyl)-1H-pyrazol-4-yl)-5-(hydroxymethyl)-N-((tetrahydro-2H-pyran-4-yl)methyl)benzamide (95 mg, 0.23 mmol). LCMS: 1.07 min, MS (ES) 476.5 (M+H).

Step C. Example 288

3-(Bromomethyl)-5-(1-ethyl-3-(trifluoromethyl)-1H-pyrazol-4-yl)-N-((tetrahydro-2H-pyran-4-yl)methyl)benzamide (47 mg, 0.10 mmol), 4,5-dihydrooxazol-2-amine hydrochloride (25 mg, 0.20 mmol), DIPEA (52 µL, 0.30 mmol) and KI (5 mg) were taken in MeCN (0.5 mL) and stirred at rt for 16 h. The mixture was concentrated and purified by reverse phase HPLC (Phenomenex Gemini C18, H₂O/CH₃CN gradient from 30-90% CH₃CN, 0.1% TFA) to yield the title compound (5 mg, 10%). LCMS: $R_T$=1.00 min, MS (ES) 479.5 (M+H).

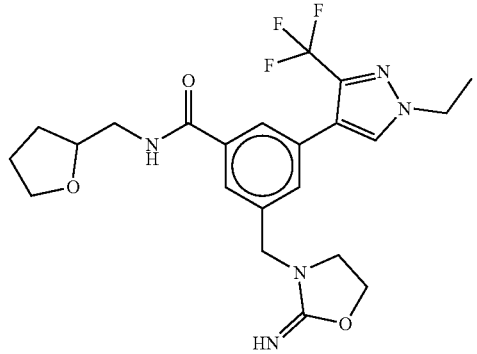

Example 289

3-(1-Ethyl-3-(trifluoromethyl)-1H-pyrazol-4-yl)-5-((2-iminooxazolidin-3-yl)methyl)-N-((tetrahydrofuran-2-yl)methyl)benzamide Step A. Preparation of 3-(1-ethyl-3-(trifluoromethyl)-1H-pyrazol-4-yl)-5-(hydroxymethyl)-N-((tetrahydrofuran-2-yl)methyl)benzamide The title compound (41 mg, 41%) was prepared according to the procedure outlined for Example 78 Step C, using 3-(1-ethyl-3-(trifluoromethyl)-1H-pyrazol-4-yl)-5-(hydroxymethyl)benzoic acid (79 mg, 0.25 mmol) and (tetrahydrofuran-2-yl)methanamine (36 µL, 0.30 mmol). LCMS: $R_T$=0.89 min, MS (ES) 398.4 (M+H)⁺.

Step B. Preparation of 3-(bromomethyl)-5-(1-ethyl-3-(trifluoromethyl)-1H-pyrazol-4-yl)-N-((tetrahydrofuran-2-yl)methyl)benzamide The title compound (32 mg, 72%) was prepared according to the procedure outlined for Example 78 Step D, from 3-(1-ethyl-3-(trifluoromethyl)-1H-pyrazol-4-yl)-5-(hydroxymethyl)-N-((tetrahydrofuran-2-yl)methyl)benzamide (41 mg, 0.10 mmol). LCMS: $R_T$=1.07 min, MS (ES) 460, 462 (M+H).

Step C. Example 289

The title compound (8 mg, 25%) was prepared according to the procedure outlined for Example 288 Step C, from 3-(bromomethyl)-5-(1-ethyl-3-(trifluoromethyl)-1H-pyrazol-4-yl)-N-((tetrahydrofuran-2-yl)methyl)benzamide (32 mg, 0.07 mmol). LCMS: $R_T$=0.98 min, MS (ES) 466.5 (M+H).

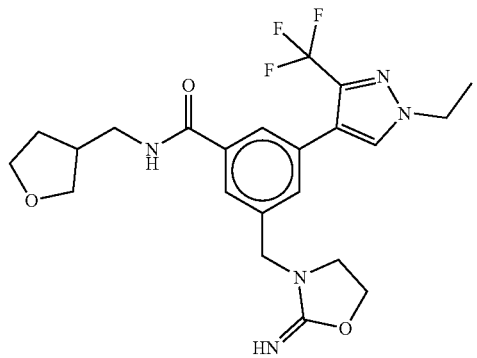

Example 290

3-(1-Ethyl-3-(trifluoromethyl)-1H-pyrazol-4-yl)-5-((2-iminooxazolidin-3-yl)methyl)-N-((tetrahydrofuran-3-yl)methyl)benzamide Step A. Preparation of 3-(1-ethyl-3-(trifluoromethyl)-1H-pyrazol-4-yl)-5-(hydroxymethyl)-N-((tetrahydrofuran-3-yl)methyl)benzamide The title compound (87 mg, 87%) was prepared according to the procedure outlined for Example 78 Step C, using 3-(i-ethyl-3-(trifluoromethyl)-1H-pyrazol-4-yl)-5-(hydroxymethyl)benzoic acid (79 mg, 0.25 mmol) and (tetrahydrofuran-3-yl)methanamine hydrochloride (41 mg, 0.30 mmol). LCMS: $R_T$=0.85 min, MS (ES) 398.4 (M+H).

Step B. Preparation of 3-(bromomethyl)-5-(1-ethyl-3-(trifluoromethyl)-1H-pyrazol-4-yl)-N-((tetrahydrofuran-3-yl)methyl)benzamide The title compound (69 mg, 68%) was prepared according to the procedure outlined for Example 78 Step D, from 3-(1-ethyl-3-(trifluoromethyl)-1H-pyrazol-4-yl)-5-(hydroxymethyl)-N-((tetrahydrofuran-3-yl)methyl)benzamide (87 mg, 0.22 mmol). LCMS: 1.07 min, MS (ES) 460, 462 (M+H).

Step C. Example 290

The title compound (7 mg, 15%) was prepared according to the procedure outlined for Example 288 Step C, from 3-(bromomethyl)-5-(1-ethyl-3-(trifluoromethyl)-1H-pyrazol-4-yl)-N-((tetrahydrofuran-3-yl)methyl)benzamide (46 mg, 0.10 mmol). LCMS: $R_T$=0.98 min, MS (ES) 466.5 (M+H)$^+$.

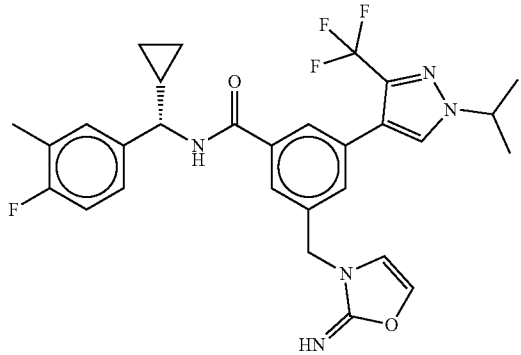

Example 291

(S)—N-(Cyclopropyl(4-fluoro-3-methylphenyl)methyl)-3-((2-iminooxazol-3(2H)-yl)methyl)-5-(1-isopropyl-3-(trifluromethyl)-1H-pyrazol-4-yl)benzamide The title compound was prepared (11 mg, 0.02 mmol) according to the procedures described in Examples 193 and 60, Steps A-G substituting oxazol-2-amine (8 mg, 0.09 mmol) in Step G. LC-MS: >95% 254 nm, $R_T$=1.049 min, MS (ES) 556.2 (M+H).

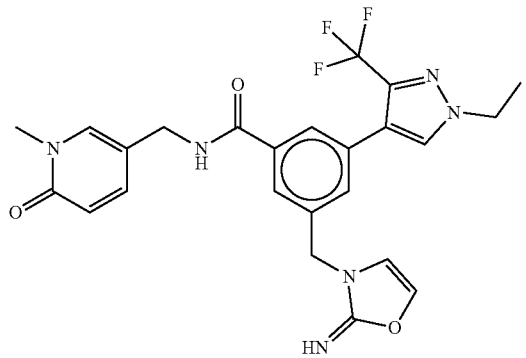

Example 292

3-(1-Ethyl-3-(trifluoromethyl)-1H-pyrazol-4-yl)-5-((2-iminooxazol-3(2H)-yl)methyl)-N-((1-methyl-6-oxo-1,6-dihydropyridin-3-yl)methyl)benzamide The title compound was prepared (13 mg, 0.026 mmol) according to the procedures described in Examples 199 and 60, Steps A-G substituting oxazol-2-amine (10 mg, 0.12 mmol) in Step G. $^1$H NMR (400 MHz, Chloroform-d) δ 7.79 (t, J=1.7 Hz, 1H), 7.70 (t, J=1.6 Hz, 1H), 7.58 (d, J=1.0 Hz, 1H), 7.44 (d, J=1.8 Hz, 1H), 7.38-7.33 (m, 2H), 7.24 (d, J=5.8 Hz, 1H), 6.64 (d, J=1.9 Hz, 1H), 6.49 (dd, J=8.9, 1.1 Hz, 1H), 6.34 (d, J=1.9 Hz, 1H), 4.71 (s, 2H), 4.34 (d, J=5.8 Hz, 2H), 4.23 (q, J=7.3 Hz, 2H), 3.48 (s, 3H), 1.54 (t, J=7.4 Hz, 3H); LCMS: >95% 254 nm, $R_T$=0.111 min, MS (ES) 503.1 (M+H).

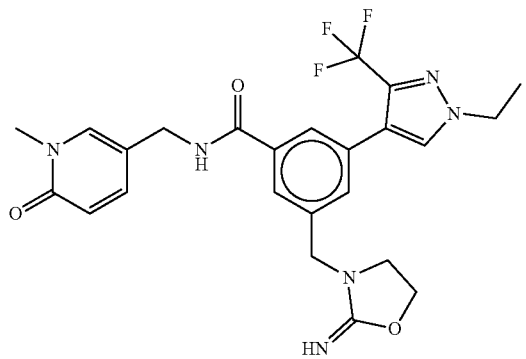

Example 293

3-(1-Ethyl-3-(trifluoromethyl)-1H-pyrazol-4-yl)-5-((2-iminooxazolidin-3-yl)methyl)-N-(1-methyl-6-oxo-1,6-dihydropyridin-3-yl)methyl)benzamide The title compound was prepared (4 mg, 0.008 mmol) according to the procedures described in Examples 199 and 60, Steps A-G substituting 5-dihydrooxazol-2-amine (11 mg, 0.12 mmol) in Step G. LC-MS: >95% 254 nm, $R_T$=0.105 min, MS (ES) 501.1 (M+H).

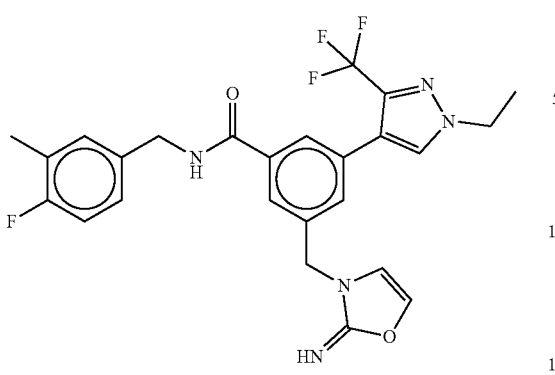

Example 294

3-(1-Ethyl-3-(trifluoromethyl)-1H-pyrazol-4-yl)-N-(4-fluoro-3-methylbenzyl)-5-((2-iminooxazol-3(2H)-yl)methyl)benzamide The title compound was prepared (14 mg, 0.028 mmol) according to the procedures described in Examples 198 and 60, Steps A-G substituting oxazol-2-amine (10 mg, 0.12 mmol) in Step G. LC-MS: >95% 254 nm, $R_T$=0.932 min, MS (ES) 502.1 (M+H).

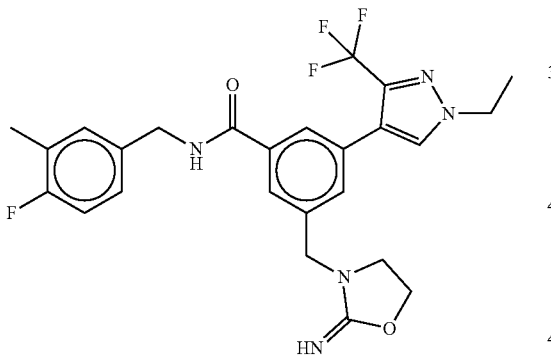

Example 295

3-(1-Ethyl-3-(trifluoromethyl)-1H-pyrazol-4-yl)-N-(4-fluoro-3-methylbenzyl)-5-((2-iminooxazolidin-3-yl)methyl)benzamide The title compound was prepared (10 mg, 0.019 mmol) according to the procedures described in Examples 198 and 60, Steps A-G substituting 5-dihydrooxazol-2-amine (10 mg, 0.12 mmol) in Step G. $^1$H NMR (400 MHz, Chloroform-d) δ 7.75 (d, J=1.7 Hz, 1H), 7.69 (d, J=1.7 Hz, 1H), 7.58 (d, J=1.0 Hz, 1H), 7.48 (d, J=1.9 Hz, 1H), 7.16 (td, J=7.5, 2.2 Hz, 2H), 6.99-6.95 (m, 1H), 6.76 (d, J=6.0 Hz, 1H), 4.56 (d, J=5.7 Hz, 2H), 4.48 (s, 3H), 4.26-4.22 (m, 4H), 3.41-3.36 (m, 2H), 2.25 (d, J=2.0 Hz, 2H), 1.57-1.54 (m, 3H); LC-MS: >95% 254 nm, $R_T$=0.943 min, MS (ES) 504.1 (M+H).

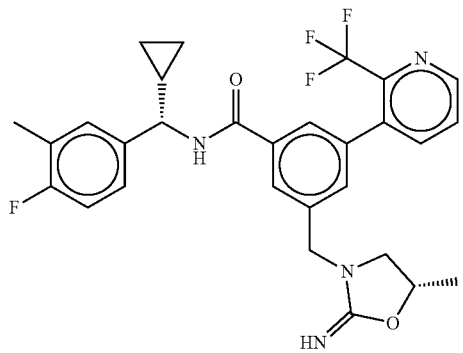

Example 296

N—((S)-cyclopropyl(4-fluoro-3-methylphenyl)methyl)-3-(((S)-2-imino-5-methyloxazolidin-3-yl)methyl)-5-(2-(trifluoromethyl)pyridin-3-yl)benzamide Step A. Preparation of methyl 3-(hydroxymethyl)-5-(2-(trifluoromethyl)pyridin-3-yl)benzoate The title compound (487.9 mg, 85%) was prepared from the procedure described in Example 1, Step A using methyl 3-bromo-5-(hydroxymethyl)benzoate (450.0 mg, 1.84 mmol) and (2-(trifluoromethyl)pyridin-3-yl)boronic acid (420.7 mg, 2.20 mmol). $^1$H NMR (400 MHz, Chloroform-d) δ 8.77-8.71 (m, 1H), 8.11 (s, 1H), 7.93 (s, 1H), 7.73 (d, J=7.8 Hz, 1H), 7.56 (d, J=8.0 Hz, 2H), 4.82 (d, J=5.0 Hz, 2H), 3.93 (s, 3H); LCMS: $R_T$=1.332 min, MS (ES) 312.3 (M+H).

Step B. Preparation of 3-(hydroxymethyl)-5-(2-(trifluoromethyl)pyridin-3-yl)benzoic Acid The crude title compound was prepared from the procedure described in Example 27, Step B using methyl 3-(hydroxymethyl)-5-(2-(trifluoromethyl)pyridin-3-yl)benzoate (488.0 mg, 1.57 mmol). LCMS: $R_T$=1.111 min, MS (ES) 298.2 (M+H).

Step C. Preparation of (S)—N-(cyclopropyl(4-fluoro-3-methylphenyl)methyl)-3-(hydroxymethyl)-5-(2-(trifluoromethyl)pyridin-3-yl)benzamide The title compound (641.9 mg, 89% 2 step) was prepared from the procedure described in Example 33, Step A using 3-(hydroxymethyl)-5-(2-(trifluoromethyl)pyridin-3-yl)benzoic acid (465.9 mg, 1.57 mmol) and (S)-cyclopropyl(4-fluoro-3-methylphenyl)methanamine hydrochloride (405.7 mg, 1.88 mmol). $^1$H NMR (400 MHz, Chloroform-d) δ 8.74 (d, J=4.5 Hz, 1H), 7.85 (s, 1H), 7.73 (d, J=7.7 Hz, 1H), 7.69 (s, 1H), 7.55 (dd, J=7.7, 4.7 Hz, 1H), 7.47 (s, 1H), 7.25-7.18 (m, 2H), 6.96 (t, J=8.7 Hz, 1H), 6.62 (m, 1H), 4.81 (s, 2H), 4.54 (t, J=8.3 Hz, 1H), 2.26 (s, 3H), 1.23 (m, 1H), 0.65 (m, 2H), 0.52 (m, 1H), 0.42 (m, 1H); LCMS: $R_T$=1.639 min, MS (ES) 459.5 (M+H).

Step D. Preparation of (S)-3-(bromomethyl)-N-(cyclopropyl(4-fluoro-3-methylphenyl)methyl)-5-(2-(trifluoromethyl)pyridin-3-yl)benzamide The title compound (84.1 mg, 73%) was prepared from the procedure described in Example 27, Step D using (S)—N-(cyclopropyl(4-fluoro-3-methylphenyl)methyl)-3-(hydroxymethyl)-5-(2-(trifluoromethyl)pyridin-3-yl)benzamide (100.0 mg, 0.22 mmol). LCMS: $R_T$=1.912 min, MS (ES) 522.4 (M+H).

Step E. Preparation of N—((S)-cyclopropyl(4-fluoro-3-methylphenyl)methyl)-3-(((((S)-2-hydroxypropyl)amino)methyl)-5-(2-(trifluoromethyl)pyridin-3-yl)benzamide The title compound (37.2 mg, 91%) was prepared from the procedure described in Example 283, Step A using (S)-3-(bromomethyl)-N-(cyclopropyl(4-fluoro-3-methylphenyl)methyl)-5-(2-(trifluoromethyl)pyridin-3-yl)benzamide (41.0 mg, 0.08 mmol) and (S)-1-aminopropan-2-ol (0.02 mL, 0.2 mmol). LCMS: $R_T$=1.294 min, MS (ES) 516.6 (M+H).

Step F. Example 296

The title compound (20.4 mg, 71%) was prepared from the procedure described in Example 283, Step D using N—((S)-cyclopropyl(4-fluoro-3-methylphenyl)methyl)-3-(((((S)-2-hydroxypropyl)amino)methyl)-5-(2-(trifluoromethyl)pyridin-3-yl)benzamide (27.2 mg, 0.05 mmol). $^1$H NMR (400 MHz, Chloroform-d) δ 8.73 (d, J=4.2 Hz, 1H), 7.84 (s, 1H), 7.73 (d, J=7.7 Hz, 1H), 7.70 (s, 1H), 7.54 (dd, J=7, 7, 4.7 Hz, 1H), 7.42 (s, 1H), 7.25-7.18 (m, 2H), 6.99-6.89 (m, 2H), 4.60-4.42 (m, 4H), 3.47 (t, J=7.9 Hz, 1H), 2.97 (t, J=7.7 Hz, 1H), 2.26 (s, 3H), 1.36 (d, J=6.2 Hz, 3H), 1.24 (m, 1H), 0.63 (m, 2H), 0.52 (m, 1H), 0.41 (m, 1H); LCMS: $R_T$=1.366 min, MS (ES) 541.6 (M+H).

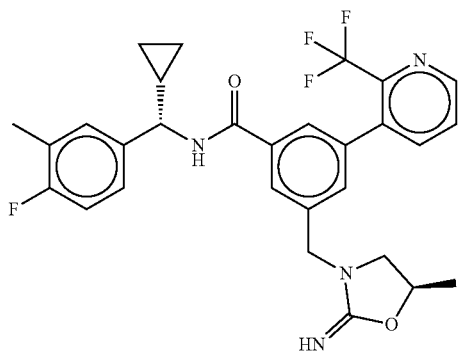

Example 297

N—((S)-cyclopropyl(4-fluoro-3-methylphenyl)methyl)-3-(((R)-2-imino-5-methyloxazolidin-3-yl)methyl)-5-(2-(trifluoromethyl)pyridin-3-yl)benzamide Step A. Preparation of N—((S)-cyclopropyl(4-fluoro-3-methylphenyl)methyl)-3-(((((R)-2-hydroxypropyl)amino)methyl)-5-(2-(trifluoromethyl)pyridin-3-yl)benzamide The title compound (22.3 mg, 59%) was prepared from the procedure described in Example 283, Step A using (S)-3-(bromomethyl)-N-(cyclopropyl(4-fluoro-3-methylphenyl)methyl)-5-(2-(trifluoromethyl)pyridin-3-yl)benzamide (38.1 mg, 0.07 mmol) and (R)-1-aminopropan-2-ol (0.01 mL, 0.18 mmol). LCMS: $R_T$=1.332 min, MS (ES) 516.6 (M+H).

Step B. Example 297

The title compound (13.4 mg, 89%) was prepared from the procedure described in Example 283, Step D using N—((S)-cyclopropyl(4-fluoro-3-methylphenyl)methyl)-3-(((((R)-2-hydroxypropyl)amino)methyl)-5-(2-(trifluoromethyl)pyridin-3-yl)benzamide (14.2 mg, 0.03 mmol). $^1$H NMR (400 MHz, Chloroform-) δ 8.76-8.70 (m, 1H), 7.83 (s, 1H), 7.77-7.71 (m, 1H), 7.69 (s, 1H), 7.55 (dd, J=7.8, 4.7 Hz, 1H), 7.43 (s, 1H), 7.25-7.18 (m, 2H), 6.99-6.92 (m, 1H), 6.78 (d, J=7.6 Hz, 1H), 4.63-4.42 (m, 4H), 3.46 (t, J=7.8 Hz, 1H), 2.99-2.92 (m, 1H), 2.26 (d, J=1.7 Hz, 3H), 1.36 (d, J=6.2 Hz, 3H), 1.31-1.18 (m, 1H), 0.64 (m, 2H), 0.52 (m, 1H), 0.42 (m, 1H); LCMS: $R_T$=1.381 min, MS (ES) 541.6 (M+H).

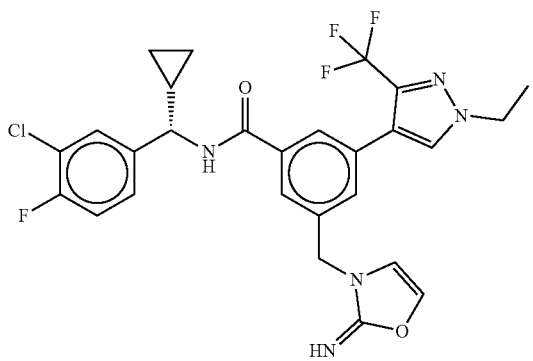

Example 298

(S)—N-((3-Chloro-4-fluorophenyl)(cyclopropyl)methyl)-3-(1-ethyl-3-(trifluoromethyl)-1H-pyrazol-4-yl)-5-((2-iminooxazol-3(2H)-yl)methyl)benzamide The title compound was prepared (5 mg, 0.09 mmol) according to the procedures described in Examples 202 and 60, Steps A-G substituting oxazol-2-amine (8 mg, 0.09 mmol) in Step G. LC-MS: >95% 254 nm, $R_T$=1.012 min, MS (ES) 562.1 (M+H).

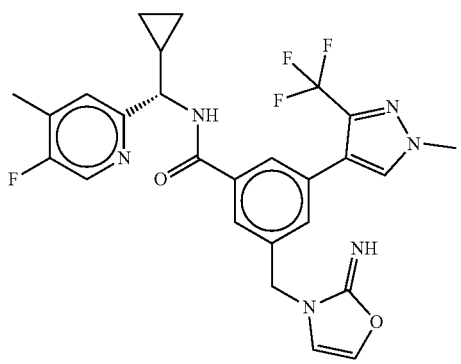

Example 299

(S)—N-(Cyclopropyl(5-fluoro-4-methylpyridin-2-yl)methyl)-3-((2-iminooxazol-3(2H)-yl)methyl)-5-(1-methyl-3-(trifluoromethyl)-1H-pyrazol-4-yl)benzamide

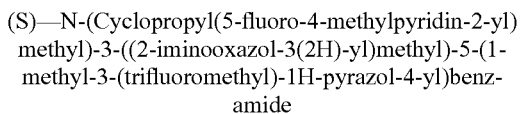

The title compound was prepared (19 mg, 0.036 mmol) according to the procedures described in Examples 204 and 60, Steps A-G substituting oxazol-2-amine (10 mg, 0.11 mmol) in Step G. LC-MS: >95% 254 nm, $R_T$=0.813 min, MS (ES) 529.2 (M+H).

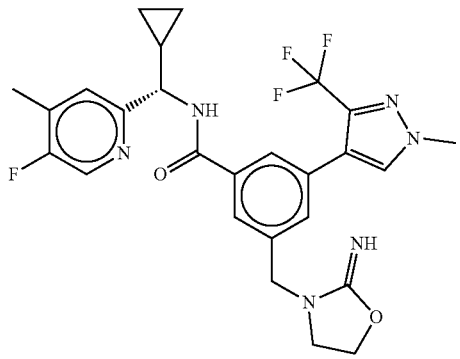

Example 300

(S)—N-(Cyclopropyl(5-fluoro-4-methylpyridin-2-yl)methyl)-3-((2-iminooxazolidin-3-yl)methyl)-5-(1-methyl-3-(trifluoromethyl)-1H-pyrazol-4-yl)benzamide

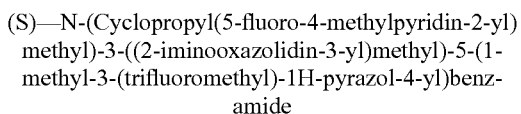

The title compound was prepared (10 mg, 0.019 mmol) according to the procedures described in Examples 204 and 60, Steps A-G substituting 5-dihydrooxazol-2-amine (10 mg, 0.11 mmol) in Step G. LC-MS: >95% 254 nm, $R_T$=0.840 min, MS (ES) 531 (M+H).

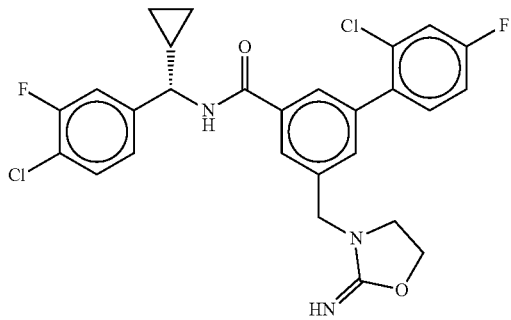

Example 301

(S)-2'-Chloro-N-((4-chloro-3-fluorophenyl)(cyclopropyl)methyl)-4'-fluoro-5-((2-iminooxazolidin-3-yl)methyl)-[1,1'-biphenyl]-3-carboxamide

Step A. Preparation of (S)-2'-chloro-N-((4-chloro-3-fluorophenyl)(cyclopropyl)methyl)-4'-fluoro-5-(hydroxymethyl)-[1,1'-biphenyl]-3-carboxamide The title compound (200 mg, 60%) was prepared from the procedure described in Example 91, Step D using 2'-chloro-4'-fluoro-5-(hydroxymethyl)-[1,1'-biphenyl]-3-carboxylic acid (0.2 g, 0.71 mmol) and (S)-(4-chloro-3-fluorophenyl)(cyclopropyl) methanamine hydrochloride (0.17 g, 0.71 mmol). LCMS method 2: $R_T$=1.85 min, MS (ES) 461.8 (M+).

Step B. Preparation of (S)-5-(bromomethyl)-2'-chloro-N-((4-chloro-3-fluorophenyl)(cyclopropyl)methyl)-4'-fluoro-[1,1'-biphenyl]-3-carboxamide The title compound (0.18 mg, 78%) was prepared from the procedure described in Example 139, Step D using (S)-2'-chloro-N-((4-chloro-3-fluorophenyl)(cyclopropyl)methyl)-4'-fluoro-5-(hydroxymethyl)-[1,1'-biphenyl]-3-carboxamide (0.20 g, 0.43 mmol), PPh$_3$ (0.23 g, 0.86 mmol) and NBS (0.15 g, 0.86 mmol). LCMS method 2: $R_T$=1.94 min, MS (ES) 415.9 (M+).

Step C. Example 301

The title compound (9 mg, 12%) was prepared from the procedure described in Example 91, Step F using (S)-5-(bromomethyl)-2'-chloro-N-((4-chloro-3-fluorophenyl)(cyclopropyl)methyl)-4'-fluoro-[1,1'-biphenyl]-3-carboxamide (84 mg, 0.16 mmol), 4,5-dihydrooxazol-2-amine hydrochloride (29 mg, 0.24 mmol) and DIPEA (110 μL, 0.64 mmol). LCMS method 2: $R_T$=1.51 min, MS (ES) 529.1 (M+)

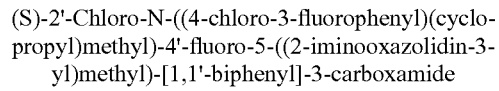

Example 302

(S)-2-Ethoxy-N-(1-(4-fluoro-3-methylphenyl)ethyl)-5-((2-iminooxazolidin-3-yl)methyl)-3-(1-methyl-3-(trifluoromethyl)-1H-pyrazol-4-yl)benzamide

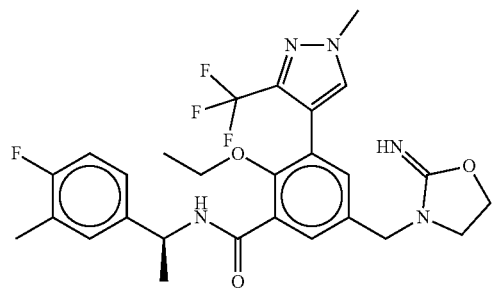

The title compound (5.0 mg, 18% 2 step) was prepared from the procedure described in Example 287 using (5)-5-(bromomethyl)-2-ethoxy-N-(1-(4-fluoro-3-methylphenyl)ethyl)-3-(1-methyl-3-(trifluoromethyl)-1H-pyrazol-4-yl)benzamide (27.5 mg, 0.05 mmol). LCMS: $R_T$=1.344 min, MS (ES) 548.6 (M+H).

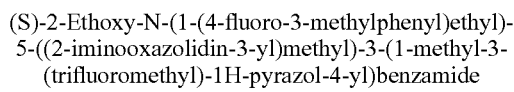

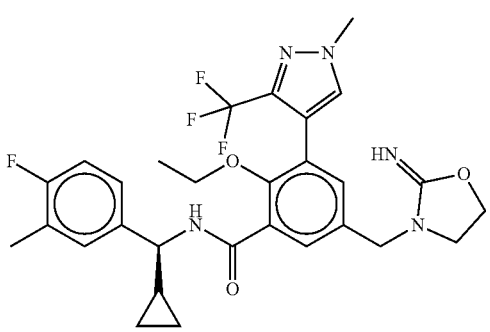

Example 303

(S)—N-(Cyclopropyl(4-fluoro-3-methylphenyl)methyl)-2-ethoxy-5-((2-iminooxazolidin-3-yl)methyl)-3-(1-methyl-3-(trifluoromethyl)-1H-pyrazol-4-yl)benzamide The title compound (5.8 mg, 19%) was prepared from the procedure described in Example 287 using (S)-5-(bromomethyl)-N-(cyclopropyl(4-fluoro-3-methylphenyl)methyl)-2-ethoxy-3-(1-methyl-3-(trifluoromethyl)-1H-pyrazol-4-yl) benzamide (30.0 mg, 0.05 mmol). $^1$H NMR (400 MHz, Chloroform-) δ 8.39 (d, J=7.7 Hz, 1H), 7.98 (d, J=1.9 Hz, 1H), 7.62 (s, 1H), 7.42 (s, 1H), 7.22 (t, J=7.4 Hz, 2H), 6.96 (t, J=8.8 Hz, 1H), 4.58 (t, J=8.4 Hz, 1H), 4.50 (s, 2H), 4.26 (t, J=7.5 Hz, 2H), 4.02 (s, 3H), 3.70-3.61 (m, 1H), 3.59-3.50 (m, 1H), 3.39 (t, J=7.5 Hz, 2H), 2.26 (s, 3H), 1.25 (m, 1H), 1.03 (t, J=7.0 Hz, 3H), 0.64 (m, 2H), 0.56 (s, 1H), 0.44-0.36 (m, 1H); LCMS: $R_T$=1.449 min, MS (ES) 574.6 (M+H).

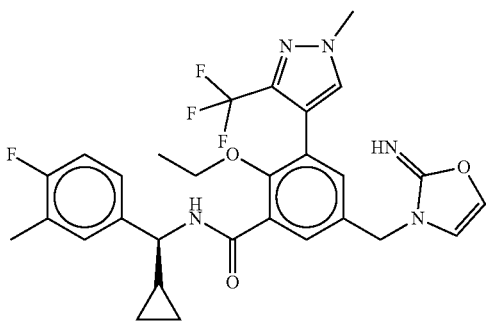

Example 304

(S)—N-(Cyclopropyl(4-fluoro-3-methylphenyl) methyl)-2-ethoxy-5-((2-iminooxazolidin-3-yl) methyl)-3-(1-methyl-3-(trifluoromethyl)-1H-pyrazol-4-yl)benzamide Oxazol-2-amine (13.3 mg, 0.16 mmol) and DIPEA (0.05 mL, 0.26 mmol) were added to a solution of (S)-5-(bromomethyl)-N-(cyclopropyl(4-fluoro-3-methylphenyl) methyl)-2-ethoxy-3-(1-methyl-3-(trifluoromethyl)-1H-pyrazol-4-yl)benzamide (30.0 mg, 0.05 mmol) in CH$_3$CN (1.0 mL). The reaction mixture was stirred at 90° C. for 12 h. After cooling to ambient temperature, the crude reaction mixture was concentrated under reduced pressure. The residue was purified by reverse phase HPLC (Phenomenex Gemini C18, H$_2$O/CH$_3$CN gradient from 5-950 CH$_3$CN, 0.1% TFA) to yield the title compound (8.7 mg, 28%), $^1$H NMR (400 MHz, Chloroform-d) δ 8.38 (d, J=7.9 Hz, 1H), 7.99 (d, J=2.3 Hz, 1H), 7.59 (s, 1H), 7.36 (d, J=1.9 Hz, 1H), 7.21 (m, 2H), 7.00-6.91 (m, 1H), 6.62 (d, J=1.8 Hz, 1H), 6.32 (d, J=1.8 Hz, 1H), 4.71 (s, 2H), 4.58 (t, J=8.4 Hz, 1H), 4.01 (s, 3H), 3.69-3.60 (m, 1H), 3.59-3.50 (m, 1H), 2.26 (S, 3H), 1.23 (m, 1H), 1.03 (t, J=7.0 Hz, 3H), 0.69-0.58 (m, 2H), 0.59-0.48 (m, 1H), 0.47-0.35 (m, 1H); LCMS: $R_T$=1.453 min, MS (ES) 572.6 (M+H).

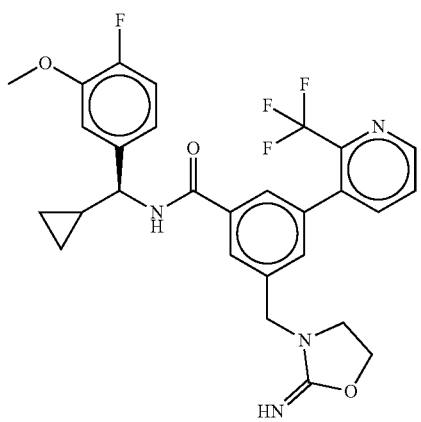

Example 305

(S)—N-(Cyclopropyl(4-fluoro-3-methoxyphenyl) methyl)-3-((2-iminooxazolidin-3-yl)methyl)-5-(2-(trifluoromethyl)pyridin-3-yl)benzamide The title compound was prepared (9 mg, 0.017 mmol) according to the procedures described in Example 60, Steps A-G substituting (S)-cyclopropyl(4-fluoro-3-methoxyphenyl)methanamine (0.3 g, 1.3 mmol) in Step E and 5-dihydrooxazol-2-amine (8 mg, 0.09 mmol) in Step G. LC-MS: >95% 254 nm, $R_T$=0.929 min, MS (ES) 543 (M+H).

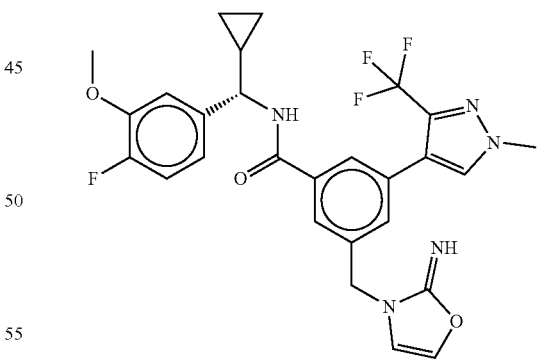

Example 306

(S)—N-(Cyclopropyl(5-fluoro-4-methoxypyridin-2-yl)methyl)-3-((2-iminooxazol-3(2H)-yl)methyl)-5-(1-methyl-3-(trifluoromethyl)-1H-pyrazol-4-yl)benzamide The title compound (9 mg, 120) was prepared from the procedure described in Example 91, Step F using (S)-3-

(bromomethyl)-N-(cyclopropyl(5-fluoro-4-methoxypyridin-2-yl)methyl)-5-(1-methyl-3-(trifluoromethyl)-1H-pyrazol-4-yl)benzamide (40 mg, 0.07 mmol), oxazol-2-amine (9 mg, 0.11 mmol) and DIPEA (50 4 µL, 0.30 mmol). $^1$H NMR (CDCl$_3$) δ 8.28 (d, J=2.9 Hz, 1H), 7.78 (s, 1H), 7.75 (s, 1H), 7.56 (m, 2H), 7.47 (s, 1H), 6.89 (d, J=6.9 Hz, 1H), 6.64 (d, J=1.7 Hz, 1H), 6.33 (d, J.=1.7 Hz, 1H), 4.78 (s, 2H), 4.67 (t, J=8.6 Hz, 1H), 4.0 (s, 3H), 3.96 (s, 3H), 1.33-1.22 (m, 1H), 0.65-0.53 (m, 3H), 0.47-0.41 (m, 1H); LCMS method 2: R$_T$=1.17 min, MS (ES) 544.9 (M+).

4.57 (d, J=5.6 Hz, 2H), 3.78 (s, 6H), 3.53 (t, J=6.8 Hz, 2H), 3.15 (t, J=6.8 Hz, 2H), 2.22 (s, 3H); LC-MS: >95% 254 nm, R$_T$=0.932 min, MS (ES) 494.2 (M+H).

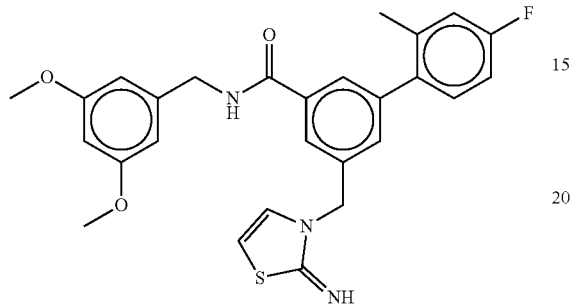

Example 307

N-(3,5-Dimethoxybenzyl)-4'-fluoro-5-((2-iminothiazol-3(2H)-yl)methyl)-2'-methyl-[1,1'-biphenyl]-3-carboxamide The title compound was prepared (62 mg, 0.13 mmol) according to the procedures described in Examples 229 and 1, Steps A-E substituting thiazol-2-amine (32 mg, 0.32 mmol) in Step E. LC-MS: >95% 254 nm, R$_T$=0.961 min, MS (ES) 493 (M+H).

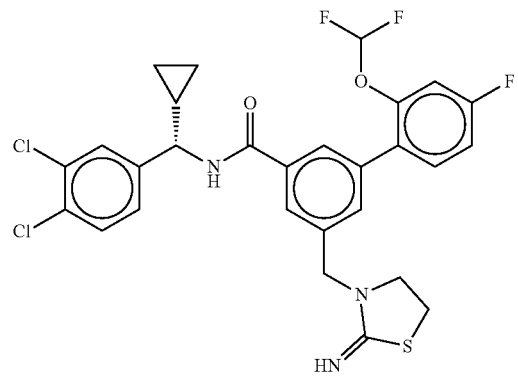

Example 309

(S)—N-(Cyclopropyl(3,4-dichlorophenyl)methyl)-2'-(difluoromethoxy)-4'-fluoro-5-((2-iminothiazolidin-3-yl)methyl)-[1,1'-biphenyl]-3-carboxamide The title compound was prepared (20 mg, 0.034 mmol) according to the procedures described in Examples 150 and 60, Steps A-G substituting 4,5-dihydrothiazol-2-amine (11 mg, 0.1 mmol) in Step G. LC-MS: >95% 254 nm, R$_T$=1.482 min, MS (ES) 594.1 (M+H).

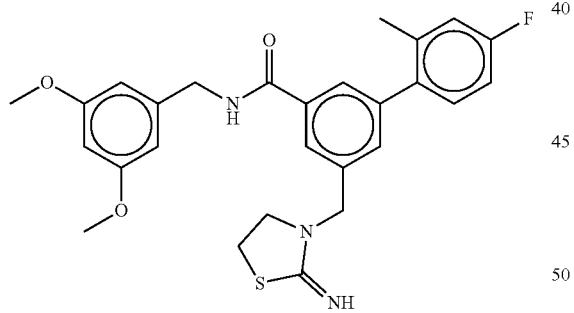

Example 308

N-(3,5-Dimethoxybenzyl)-4'-fluoro-5-((2-iminothiazolidin-3-yl)methyl)-2'-methyl-[1,1'-biphenyl]-3-carboxamide The title compound was prepared (13 mg, 0.024 mmol) according to the procedures described in Examples 229 and 1, Steps A-E substituting 4,5-dihydrothiazol-2-amine (8 mg, 0.08 mmol) in Step E. $^1$H NMR (400 MHz, Chloroform-d) δ 7.71 (t, J=1.7 Hz, 1H), 7.60 (t, J=1.7 Hz, 1H), 7.37 (t, J=1.7 Hz, 1H), 7.15 (dd, J=8.4, 5.9 Hz, 1H), 7.00-6.89 (m, 2H), 6.50 (d, J=2.3 Hz, 3H), 6.38 (t, J=2.3 Hz, 1H), 4.63 (s, 2H),

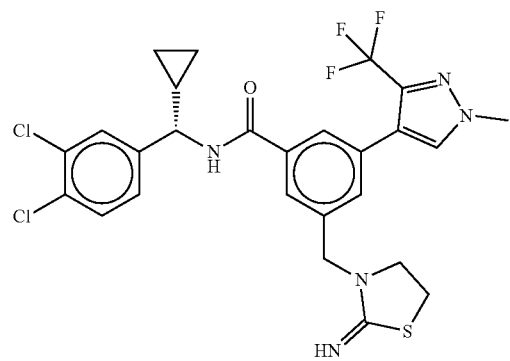

Example 310

(S)—N-(Cyclopropyl(3,4-dichlorophenyl)methyl)-3-((2-iminothiazolidin-3-yl)methyl)-5-(1-methyl-3-(trifluoromethyl)-1H-pyrazol-4-yl)benzamide The title compound was prepared (20 mg, 0.034 mmol) according to the procedures described in Examples 157 and 60, Steps A-G substituting 4,5-dihydrothiazol-2-amine (11 mg, 0.1 mmol) in Step G. LC-MS: >95% 254 nm, R$_T$=0.982 min, MS (ES) 582.1 (M+H).

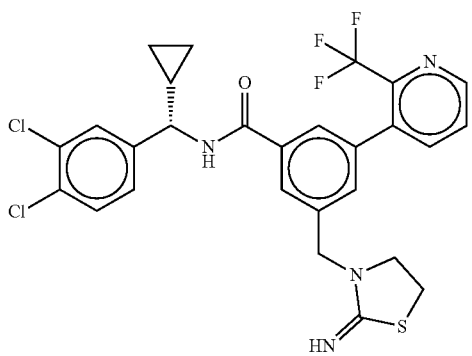

Example 311

(S)—N-(Cyclopropyl(3,4-dichlorophenyl)methyl)-3-((2-iminothiazolidin-3-yl)methyl)-5-(2-(trifluoromethyl)pyridin-3-yl)benzamide The title compound was prepared (23 mg, 0.040 mmol) according to the procedures described in Examples 153 and 60, Steps A-G substituting 4,5-dihydrothiazol-2-amine (11 mg, 0.11 mmol) in Step G. LC-MS: >95% 254 nm, $R_T$=1.002 min, MS (ES) 579 (M+H).

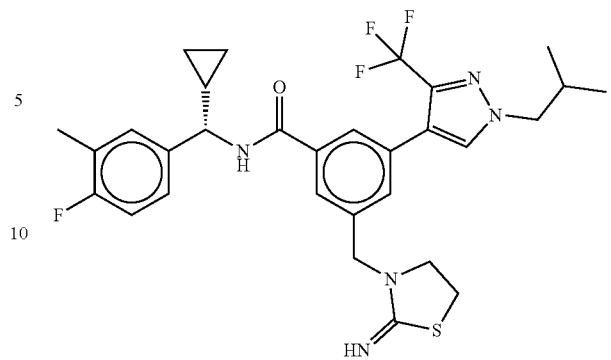

Example 313

(S)—N-(Cyclopropyl(4-fluoro-3-methylphenyl)methyl)-3-((2-iminothiazolidin-3-yl)methyl)-5-(1-isobutyl-3-(trifluoromethyl)-1H-pyrazol-4-yl)benzamide The title compound was prepared (16 mg, 0.027 mmol) according to the procedures described in Examples 163 and 60, Steps A-G substituting 4,5-dihydrothiazol-2-amine (9 mg, 0.09 mmol) in Step G. LC-MS: >95% 254 nm, $R_T$=1.058 min, MS (ES) 588.2 (M+H).

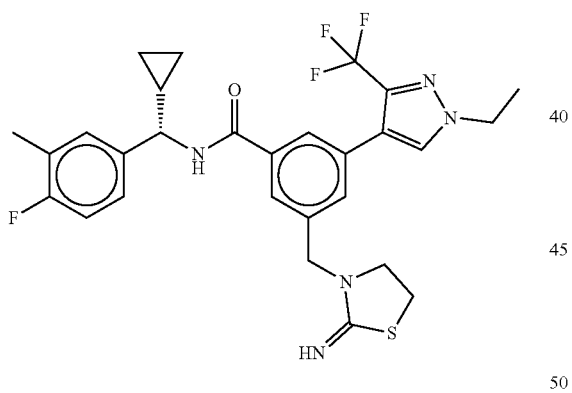

Example 312

(S)—N-(Cyclopropyl (4-fluoro-3-methylphenyl)methyl)-3-(1-ethyl-3-(trifluoromethyl)-1H-pyrazol-4-yl)-5-((2-iminothiazolidin-3-yl)methyl)benzamide The title compound was prepared (21 mg, 0.038 mmol) according to the procedures described in Examples 160 and 60, Steps A-G substituting 4,5-dihydrothiazol-2-amine (11 mg, 0.11 mmol) in Step G. LC-MS: >95% 254 nm, $R_T$=1.001 min, MS (ES) 560.2 (M+H).

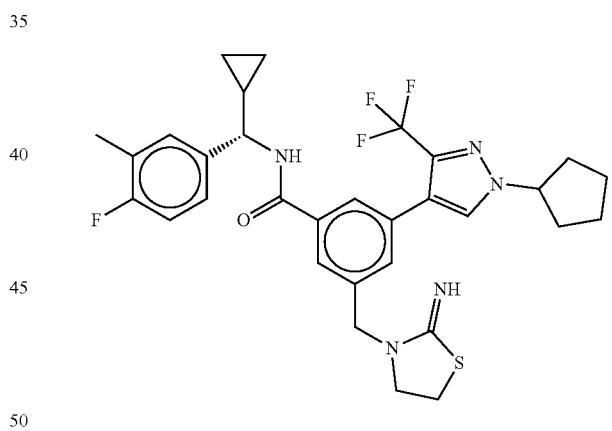

Example 314

(S)-3-(1-Cyclopentyl-3-(trifluoromethyl)-1H-pyrazol-4-yl)-N-(cyclopropyl(4-fluoro-3-methylphenyl)methyl)-5-((2-iminothiazolidin-3-yl)methyl)benzamide The title compound was prepared (9 mg, 0.015 mmol) according to the procedures described in Examples 264 and 60, Steps A-G substituting 4,5-dihydrothiazol-2-amine (9 mg, 0.09 mmol) in Step G. LC-MS: >95% 254 nm, $R_T$=1084 min, MS (ES) 600.2 (M+H).

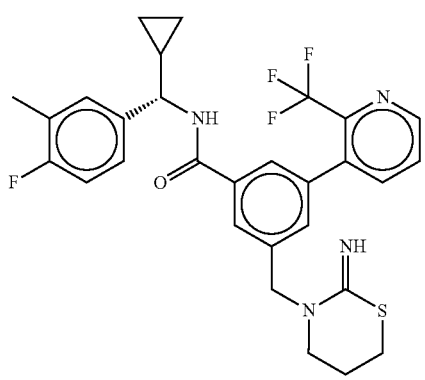

Example 315

(S)—N-(Cyclopropyl(4-fluoro-3-methylphenyl)methyl)-3-((2-imino-1,3-thiazinan-3-yl)methyl)-5-(2-(trifluoromethyl)pyridin-3-yl)benzamide The title compound was prepared (5 mg, 0.009 mmol) according to the procedures described in Example 60, Steps A-G substituting 5,6-dihydro-4H-1,3-thiazin-2-amine (13 mg, 0.12 mmol) in Step G. LC-MS: >95% 254 nm, $R_T$=0.932 min, MS (ES) 557.6 (M+H).

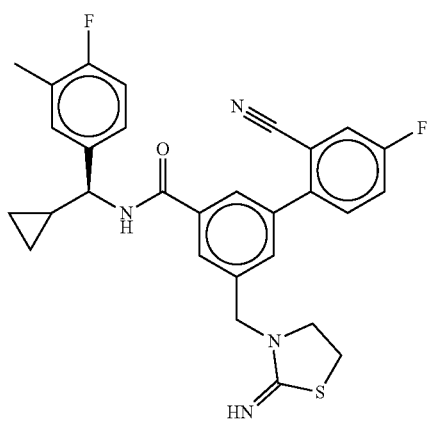

Example 316

(S)-2'-Cyano-N-(cyclopropyl(4-fluoro-3-methylphenyl)ethyl)-4'-fluoro-5-((2-iminothiazolidin-3-yl)methyl)-[1,1'-biphenyl]-3-carboxamide The title compound (32 mg, 61%) was prepared from the procedure described in Example 91, Step F using (S)-5-(bromomethyl)-2'-cyano-N-(cyclopropyl(4-fluoro-3-methylphenyl)methyl)-4'-fluoro-[1,1'-biphenyl]-3-carboxamide (50 mg, 0.10 mmol), 4,5-dihydrothiazol-2-amine (15 mg, 0.15 mmol) and DIPEA (70 μL, 0.40 mmol). $^1$H NMR (CDCl$_3$) δ 7.84-7.82 (m, 2H), 7.64 (s, 1H), 7.56-7.53 (m, 1H), 7.49-7.47 (m, 1H), 7.42-7.37 (m, 1H), 7.25-7.21 (m, 2H), 6.97 (t, J=8.9 Hz, 1H), 6.68 (d, J=8.1 Hz, 1H), 4.69 (s, 2H), 4.55 (t, J=7.4 Hz, 1H), 3.61 (t, J=6.9 Hz, 2H), 3.20 (t, J=6.9 Hz, 2H), 2.28 (s, 3H), 1.31-1.22 (m, 1), 0.68-0.63 (m, 2H), 0.56-0.51 (m, 1H), 0.45-0.41 (m, 1H); LCMS method 2: $R_T$=1.44 min, MS (ES) 517.0 (M+H).

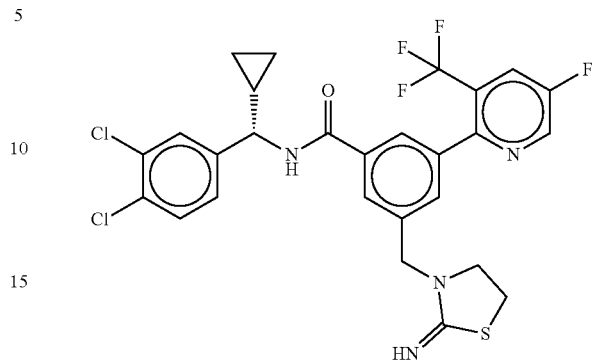

Example 317

(S)—N-(Cyclopropyl(3,4-dichlorophenyl)methyl)-3-(5-fluoro-3-(trifluoromethyl)pyridin-2-yl)-5-((2-iminothiazolidin-3-yl)methyl)benzamide The title compound was prepared (14 mg, 0.023 mmol) according to the procedures described in Examples 284 and 60, Steps A-G substituting 4,5-dihydrothiazol-2-amine (7 mg, 0.07 mmol) in Step G. LC-MS: >95% 254 nm, $R_T$=1.087 min, MS (ES) 597.1 (M+H).

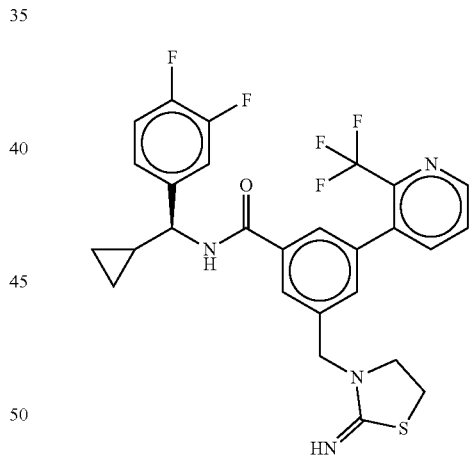

Example 318

(S)—N-(Cyclopropyl(3,4-difluorophenyl)methyl)-3-((2-iminothiazolidin-3-yl)methyl)-5-(2-(trifluoromethyl)pyridin-3-yl)benzamide The title compound was prepared (20 mg, 0.037 mmol) according to the procedures described in Examples 189 and 60, Steps A-G substituting 4,5-dihydrothiazol-2-amine (12 mg, 0.12 mmol) in Step G. LC-MS: >95% 254 nm, $R_T$=0.966 min, MS (ES) 547.1 (M+H).

421

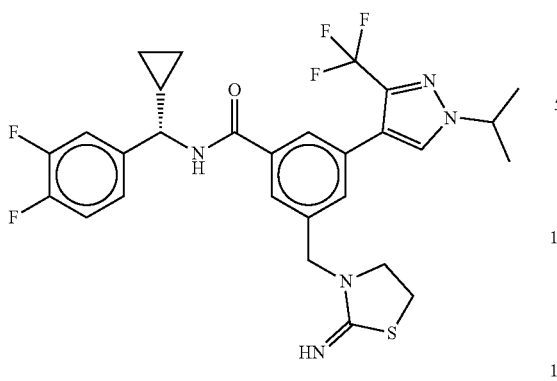

Example 319

(S)—N-(Cyclopropyl(3,4-difluorophenyl)methyl)-3-((2-iminothiazolidin-3-yl)methyl)-5-(1-isopropyl-3-(trifluoromethyl)-1H-pyrazol-4-yl)benzamide The title compound was prepared (17 mg, 0.029 mmol) according to the procedures described in Examples 216 and 60, Steps A-G substituting 4,5-dihydrothiazol-2-amine (11 mg, 0.11 mmol) in Step G. LC-MS: >95% 254 nm, $R_T$=1.041 min, MS (ES) 578.1 (M+H).

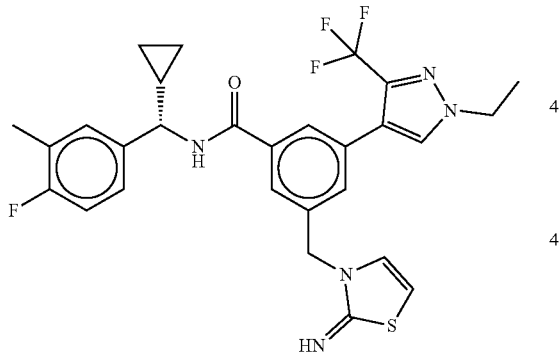

Example 320

(S)—N-(Cyclopropyl(4-fluoro-3-methylphenyl)methyl)-3-(1-ethyl-3-(trifluoromethyl)-1H-pyrazol-4-yl)-5-((2-iminothiazol-3(2H)-yl)methyl)benzamide The title compound was prepared (12 mg, 0.022 mmol) according to the procedures described in Examples 160 and 60, Steps A-G substituting thiazol-2-amine (9 mg, 0.09 mmol) in Step G. LC-MS: >95% 254 nm, $R_T$=1.006 min, MS (ES) 558.1 (M+H).

422

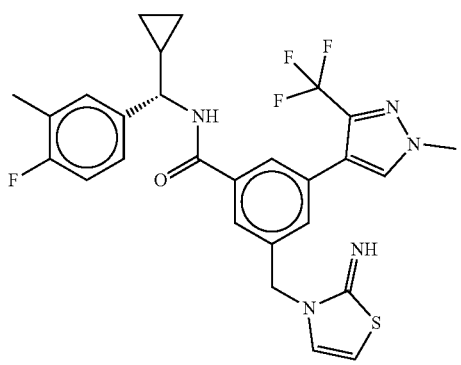

Example 321

(S)—N-(Cyclopropyl(4-fluoro-3-methylphenyl)methyl)-3-((2-iminothiazol-3(2H)-yl)methyl)-5-(1-methyl-3-(trifluoromethyl)-1H-pyrazol-4-yl)benzamide The title compound was prepared (14 mg, 0.026 mmol) according to the procedures described in Examples 125 and 60, Steps A-G substituting thiazol-2-amine (10 mg, 0.10 mmol) in Step G. $^1$H NMR (400 MHz, Chloroform-d) δ 7.70 (dt, J.=12.4, 1.7 Hz, 2H), 7.54 (d, J=1.2 Hz, 1H), 7.45 (s, 1H), 7.21 (dd, J=8.8, 5.7 Hz, 2H), 7.01-6.93 (m, 1H), 6.56-6.49 (m, 1H), 6.39 (d, J=5.0 Hz, 1H), 5.80 (d, J=5.0 Hz, 1H), 4.95 (s, 2H), 4.53 (t, J=8.3 Hz, 1H), 3.99 (s, 3H), 2.27 (d, J=2.0 Hz, 3H), 1.26-1.20 (m, 1H), 0.72-061 (m, 2H), 0.53 (dp, J=13.2, 4.8, 4.3 Hz, 1H), 0.42 (dtd, J=11.0, 5.7, 5.1, 4.0 Hz, 1H); LC-MS: >95% 254 nm, $R_T$=0.979 min, MS (ES) 544.5 (M+H).

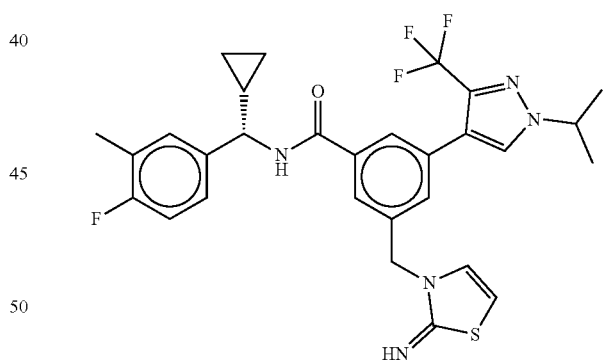

Example 322

(S)—N-(Cyclopropyl(4-fluoro-3-methylphenyl)methyl)-3-((2-iminothiazol-3(2H)-yl)methyl)-5-(1-isopropyl-3-(trifluoromethyl)-1H-pyrazol-4-yl)benzamide The title compound was prepared (19 mg, 0.033 mmol) according to the procedures described in Examples 193 and 60, Steps A-G substituting thiazol-2-amine (10 mg, 0.10 mmol) in Step G. LC-MS: >950% 254 nm, $R_T$=1.037 min, MS (ES) 572.2 (M+H).

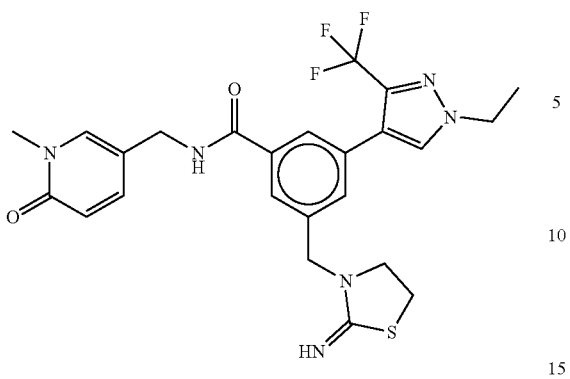

Example 323

3-(1-Ethyl-3-(trifluoromethyl)-1H-pyrazol-4-yl)-5-((2-iminothiazolidin-3-yl)methyl)-N-((1-methyl-6-oxo-1,6-dihydropyridin-3-yl)methyl)benzamide The title compound was prepared (20 mg, 0.038 mmol) according to the procedures described in Examples 199 and 60, Steps A-G substituting 4,5-dihydrothiazol-2-amine (12 mg, 0.12 mmol) in Step G. LC-MS: >95% 254 nm, R$_T$=0.109 min, MS (ES) 519.1 (M+H).

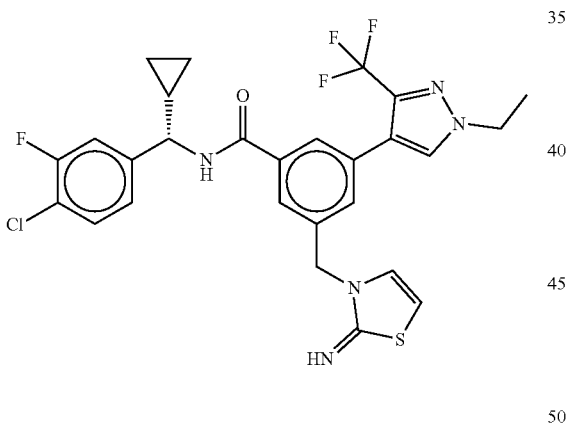

Example 324

(S)—N-((4-Chloro-3-fluorphenyl)(cyclopropyl)methyl)-3-(1-ethyl-3-(trifluoromethyl)-1H-pyrazol-4-yl)-5-((2-iminothiazol-3(2H)-yl)methyl)benzamide The title compound was prepared (10 mg, 0.017 mmol) according to the procedures described in Example 60, Steps A-G substituting 4-bromo-1-ethyl-3-(trifluoromethyl)-1H-pyrazole (1 g, 4.1 mmol) in Step C, the hydrochloride salt of (S)-(4-chloro-3-fluorophenyl)(cyclopropyl)methanamine (0.3 g, 1.3 mmol) in Step E, and thiazol-2-amine (9 mg, 0.09 mmol) in Step G. LC-MS: >95% 254 nm, R$_T$=1.002 min, MS (ES) 578.1 (M+H).

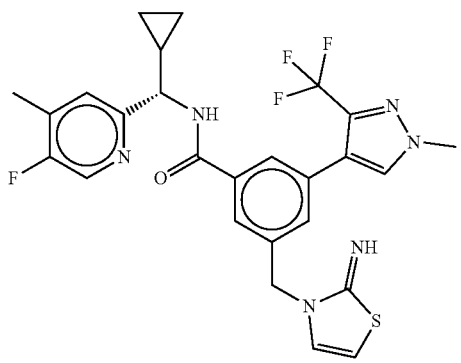

Example 325

(S)—N-(Cyclopropyl(5-fluoro-4-methylpyridin-2-yl)methyl)-3-((2-iminothiazol-3(2H)-yl)methyl)-5-(1-methyl-3-(trifluoromethyl)-1H-pyrazol-4-yl)benzamide The title compound was prepared (19 mg, 0.033 mmol) according to the procedures described in Examples 204 and 60, Steps A-G substituting thiazol-2-amine (11 mg, 0.11 mmol) in Step G. LC-MS: >95% 254 nm, R$_T$=0.842 min, MS (ES) 545 (M+H).

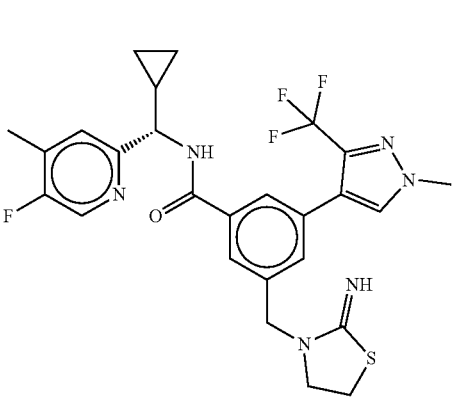

Example 326

(S)—N-(Cyclopropyl(5-fluoro-4-methylpyridin-2-yl)methyl)-3-((2-iminothiazolidin-3-yl)methyl)-5-(1-methyl-3-(trifluoromethyl)-1H-pyrazol-4-yl)benzamide The title compound was prepared (15 mg, 0.023 mmol) according to the procedures described in Examples 204 and 60, Steps A-G substituting 4,5-dihydrothiazol-2-amine (12 mg, 0.12 mmol) in Step G. LC-MS: >95% 254 nm, R$_T$=0.840 min, MS (ES) 547 (M+H)

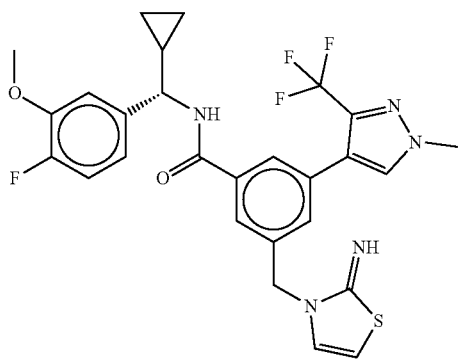

Example 327

(S)—N-(Cyclopropyl(4-fluoro-3-methoxyphenyl)methyl)-3-((2-iminothiazol-3(2H)-yl)methyl)-5-(1-methyl-3-(trifluoromethyl)-1H-pyrazol-4-yl)benzamide The title compound was prepared (16 mg, 0.029 mmol) according to the procedures described in Examples 207 and 60, Steps A-G substituting thiazol-2-amine (12 mg, 0.12 mmol) in Step G. LC-MS: >95% 254 nm, $R_T$=0.941 min, MS (ES) 560 (M+H).

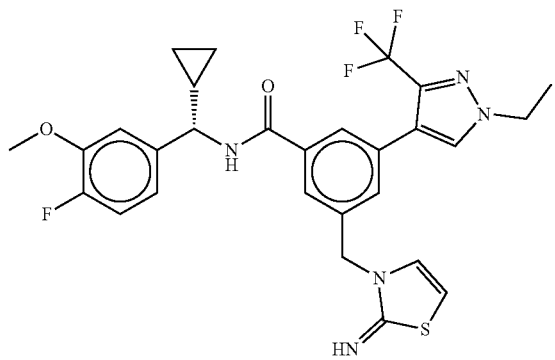

Example 328

(S)—N-(Cyclopropyl(4-fluoro-3-methoxyphenyl)methyl)-3-(1-ethyl-3-(trifluoromethyl)-1H-pyrazol-4-yl)-5-((2-iminothiazol-3(2H)-yl)methyl)benzamide The title compound was prepared (12 mg, 0.021 mmol) according to the procedures described in Examples 207 and 60, Steps A-G substituting 4-bromo-1-ethyl-3-(trifluoromethyl)-1H-pyrazole (1 g, 4.1 mmol) in Step C and thiazol-2-amine (9 mg, 0.09 mmol) in Step G. LC-MS: >950% 254 nm, $R_T$=0.985 min, MS (ES) 574.1 (M+H).

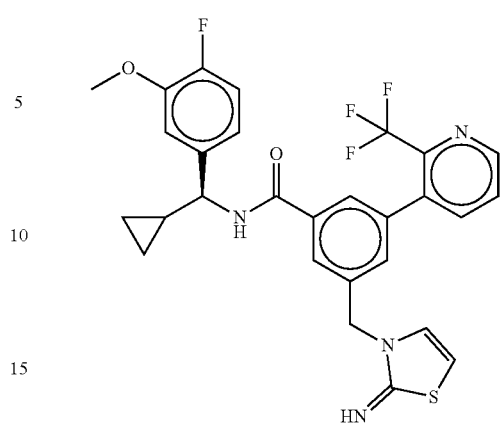

Example 329

(S)—(Cyclopropyl(4-fluoro-3-methoxyphenyl)methyl)-3-((2-iminothiazol-3(2H)-yl)methyl)-5-(2-(trifluoromethyl)pyridin-3-yl)benzamide The title compound was prepared (5 mg, 0.014 mmol) according to the procedures described in Examples 305 and 60, Steps A-G substituting thiazol-2-amine (12 mg, 0.12 mmol) in Step G. LC-MS: >95% 254 nm, $R_T$=0.929 min, MS (ES) 557 (M+H).

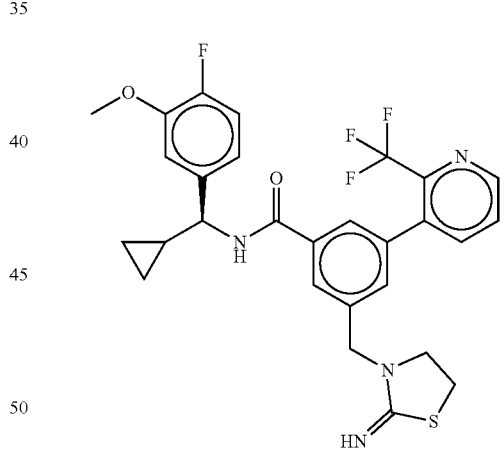

Example 330

((S)—N-(Cyclopropyl(4-fluoro-3-methoxyphenyl)methyl)-3-((2-iminothiazolidin-3-yl)methyl)-5-(2-(trifluoromethyl)pyridin-3-yl)benzamide The title compound was prepared (14 mg, 0.024 mmol) according to the procedures described in Examples 305 and 60, Steps A-G substituting 4,5-dihydrothiazol-2-amine (9 mg, 0.09 mmol) in Step G. LC-MS: >95% 254 nm, $R_T$=0.939 min, MS (ES) 541 (M+H).

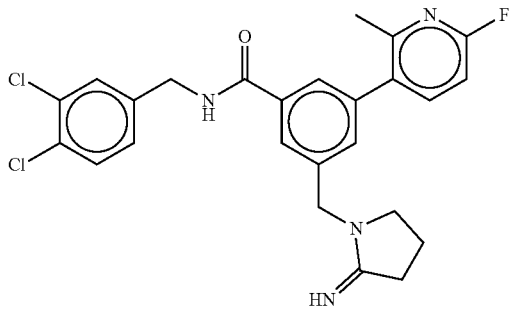

Example 331

N-(3,4-Dichlorobenzyl)-3-(6-fluoro-2-methylpyridin-3-yl)-5-((2-iminopyrrolidin-1-yl)methyl)benzamide The title compound (20 mg, 25%) was prepared following the procedure described in Example 1, Step E using 3-(bromomethyl)-N-(3,4-dichlorobenzyl)-5-(6-fluoro-2-methylpyridin-3-yl)benzamide (0.05 g, 0.10 mmol), pyrrolidin-2-imine.HCl (0.03 g, 0.21 mmol), and DIPEA (0.04 mL, 0.21 mmol). LCMS: 98% 254 nm $R_T$=0.93 min, MS (ES) 486 (M+H).

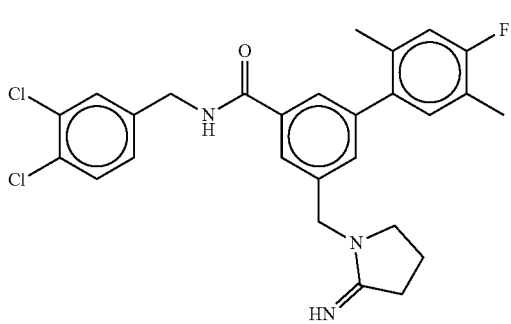

Example 332

N-(3,4-Dichlorobenzyl)-4'-fluoro-5-((2-iminopyrrolidin-1-yl)methyl)-2',5'-dimethyl-[1,1'-biphenyl]-3-carboxamide Step A. Preparation of 3-bromo-N-(3,4-dichlorobenzyl)-5-(hydroxymethyl)benzamide The title compound (1.05 g, 60%) was prepared following the procedure described in Example 1, Step C using 3-bromo-5-hydroxymethylbenzoic acid (1.00 g, 4.37 mmol) and (3,4-dichlorophenyl)methanamine (2.44 g, 13.90 mmol).

Step B. Preparation of N-(3,4-dichlorobenzyl)-4'-fluoro-5-(hydroxymethyl)-2',5'-dimethyl-[1,1'-biphenyl]-3-carboxamide The title compound (0.24 g, quant) was prepared following the procedure described in Example 1, Step A using 3-bromo-N-(3,4-dichlorobenzyl)-5-(hydroxymethyl)benzamide (0.20 g, 0.5 mmol) and (4-fluoro-2,5-dimethylphenyl)boronic acid (0.13 g, 0.77 mmol).

Step C. Preparation of N-(3,4-dichlorobenzyl)-4'-fluoro-2',5'-dimethyl-5-(methylsulfonamidoethyl)-[1,1'-biphenyl]-3-carboxamide The title compound was prepared following the procedure described in Example 11 Step B using N-(3,4-dichlorobenzyl)-4'-fluoro-5-(hydroxymethyl)-2',5'-dimethyl-[1,1'-biphenyl]-3-carboxamide (0.08 g 0.18 mmol) and methanesulfonyl chloride (0.025 g, 0.22 mmol).

Step D. Example 332

The title compound (0.06 g, 580% 2 steps) was prepared following the procedure described in Example 1, Step E using N-(3,4-dichlorobenzyl)-4'-fluoro-2',5'-dimethyl-5-(methylsulfonamidomethyl)-[1,1'-biphenyl]-3-carboxamide, pyrrolidin-2-imine-HCl (0.04 g, 0.36 mmol), and DIPEA (0.1 mL, 0.55 mmol). $^{1}$-1 NMR (400 MHz, $D_6$-DMSO) 9.2 (t, 1H, J=6.0), 9.1 (s, 1H), 7.8 (s, 2H), 7.6 (m, 4H), 7.5 (s, 1H), 7.3 (d, 1H, J=7.3 Hz), 7.2 (d, 1H, J=7.7 Hz), 7.1 (d, 1H, J=10.5 Hz), 4.8 (s, 2H), 4.5 (d, 2H, J=5.6 Hz), 3.6 (t, 2H, J=7.0), 2.9 (t, 2H, J=8.0 Hz), 2.3 (s, 3H), 2.2 (s, 3H), 2.0 (t, 2H, J=7.0 Hz); LCMS: 98% 254 nm $R_T$=1.10 min, MS (ES) 501 (M+H).

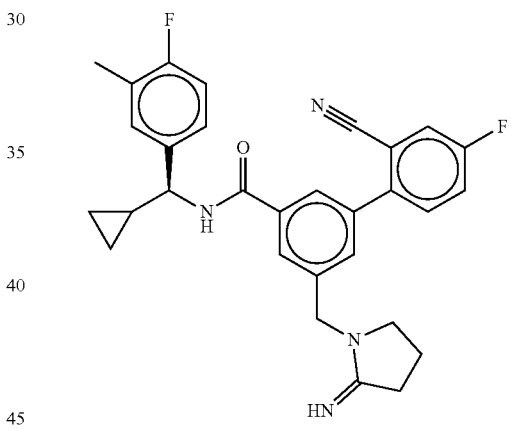

Example 333

(S)-2'-Cyano-N-(cyclopropyl(4-fluoro-3-methylphenyl)methyl)-4'-fluoro-5-((2-iminopyrrolidin-1-yl)methyl)-[1,1'-biphenyl]-3-carboxamide The title compound (19 mg, 37%) was prepared from the procedure described in Example 91, Step F using (S)-5-(bromomethyl)-2'-cyano-N-(cyclopropyl(4-fluoro-3-methylphenyl)methyl)-4'-fluoro-[1,1'-biphenyl]-3-carboxamide (50 mg, 0.10 mmol), 3,4-dihydro-2H-pyrrol-5-amine hydrochloride (18 mg, 0.15 mmol) and DIPEA (70 μL, 0.40 mmol). $^1$H NMR (CDCl$_3$) δ 7.84-7.82 (m, 2H), 7.60 (s, 1H), 7.56-7.52 (m, 1H), 7.48-7.45 (m, 1H), 7.40-7.36 (m, 1H), 7.25-7.21 (m, 2H), 6.97 (t, J=8.9 Hz, 1H), 6.68 (d, J=8.1 Hz, 1H), 4.60 (s, 2H), 4.55 (t, J=7.4 Hz, 1H), 3.37 (t, J=6.9 Hz, 2H), 2.57 (t, J=8.0 Hz, 2H), 2.28 (s, 3H), 2.0-1.93 (m, 2H), 1.31-1.22 (m, 1), 0.68-0.63 (m, 2H), 0.56-0.51 (m, 1H), 0.45-0.41 (in, 1H); LCMS method 2: $R_T$=1.47 min, MS (ES) 499.0 (M+H).

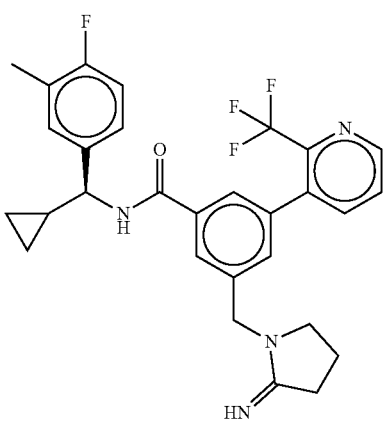

Example 334

(S)—N-(Cyclopropyl(4-fluoro-3-methylphenyl)methyl)-3-((2-iminopyrrolidin-1-yl)methyl)-5-(2-(trifluoromethyl)pyridin-3-yl)benzamide The title compound was prepared (10 mg, 0.019 mmol) according to the procedures described in Example 60, Steps A-G substituting 3,4-dihydro-2H-pyrrol-5-amine (10 mg, 0.12 mmol) in Step G. LC-MS: >95% 254 nm, $R_T$=0.938 min, MS (ES) 525 (M+H)

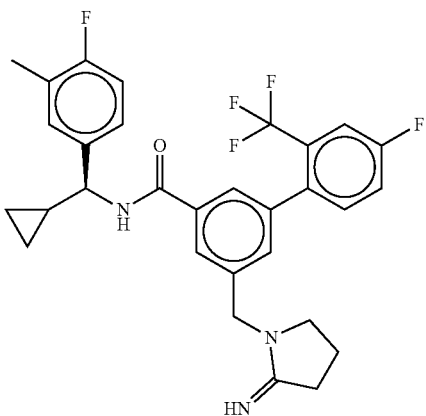

Example 335

(S)—N-(Cyclopropyl(4-fluoro-3-methylphenyl)methyl)-4'-fluoro-5-((2-iminopyrrolidin-1-yl)methyl)-2'-(trifluoromethyl)-[1,1'-biphenyl]-3-carboxamide The title compound (20 mg, 40%) was prepared from the procedure described in Example 91, Step F using (S)-5-(bromomethyl)-N-(cyclopropyl(4-fluoro-3-methylphenyl)methyl)-4'-fluoro-2'-(trifluoromethyl)-[1,1'-biphenyl]-3-carboxamide (50 mg, 0.093 mmol), 3,4-dihydro-2H-pyrrol-5-amine hydrochloride (17 mg, 0.14 mmol) and DIPEA (65 µL, 0.37 mmol). $^1$H NMR (CDCl$_3$) δ 7.79 (s, 1H), 7.63 (s, 1H), 7.47-7.44 (m, 1H), 7.34 (s, 1H) 7.33-7.29 (m, 1H), 7.28-7.20 (m, 3H), 6.96 (t, J=8.5 Hz, 1H), 6.73 (d, J=7.5 Hz, 1H), 4.58 (s, 2H), 4.53 (t, J=8.0 Hz, 1H), 3.28 (t, J=8.0 Hz, 2H), 2.55 (t, J=7.7 Hz, 2H), 2.27 (s, 3H), 1.98-1.90 (m, 2H), 1.29-1.21 (m, 1H), 0.66-0.62 (m, 2H), 0.54-0.49 (m, 1H), 0.43-0.39 (m, 1H); LCMS method 2: $R_T$=1.56 min, MS (ES) 541.9 (M+).

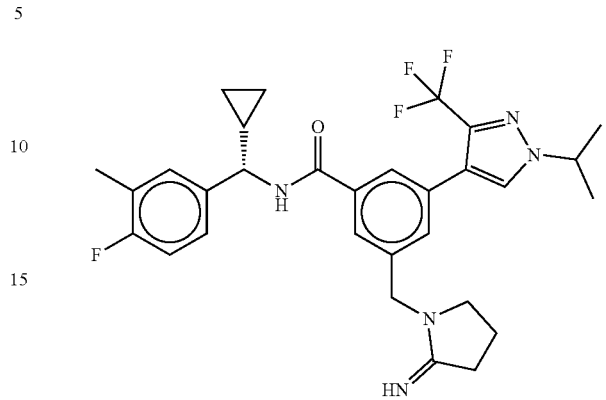

Example 336

(S)—N-(Cyclopropyl(4-fluoro-3-methylphenyl)methyl)-3-((2-iminopyrrolidin-1 yl)methyl)-5-(1-isopropyl-3-(trifluoromethyl)-1H-pyrazol-4-yl)benzamide The title compound was prepared (12 mg, 0.022 mmol) according to the procedures described in Examples 193 and 60, Steps A-G substituting 3,4-dihydro-2H-pyrrol-5-amine (10 mg, 0.12 mmol) in Step G. T1 NMR (400 MHz, Chloroform-d) δ 7.72 (d, J=1.7 Hz, 1H), 7.66 (t, J=1.6 Hz, 1H), 7.60 (d, J=1.1 Hz, 1H), 7.46 (s, 1H), 7.26-7.19 (m, 2H), 6.96 (dd, J=9.6, 8.1 Hz, 1H), 6.66 (d, J=7.7 Hz, 1H), 4.62-4.53 (m, 4H), 3.30 (t, J=6.8 Hz, 2H), 2.56 (t, J=7.9 Hz, 2H), 2.27 (d, J=2.0 Hz, 3H), 2.01-1.91 (m, 2H), 1.56 (d, J=6.7 Hz, 6H), 1.25-1.21 (m, 1H), 0.69-0.60 (m, 2H), 0.57-0.50 (m, 1H), 0.46-0.39 (m, 1H); LC-MS: >95% 254 nm, $R_T$=1.060 min, MS (ES) 556.2 (M+H).

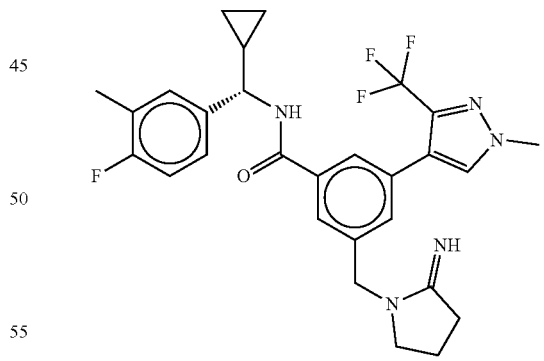

Example 337

(S)—N-(Cyclopropyl(4-fluoro-3-methylphenyl)methyl)-3-((2-iminopyrrolidin-1-yl)methyl)-5-(1-methyl-3-(trifluoromethyl)-1H-pyrazol-4-yl)benzamide The title compound was prepared (8 mg, 0.015 mmol) according to the procedures described in Examples 125 and 60, Steps A-G substituting 3,4-dihydro-2H-pyrrol-5-amine (10 mg, 0.12 mmol) in Step G. LC-MS: >95% 254 nm, $R_T$=0.984 min, MS (ES) 528 (M+H).

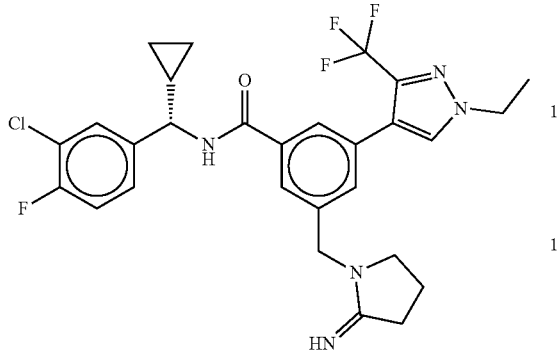

Example 338

(S)—N-((3-Chloro-4-fluorophenyl)(cyclopropyl) methyl)-3-(1-ethyl-3-(trifluoromethyl)-1H-pyrazol-4-yl)-5-((2-iminopyrrolidin-1-yl)methyl)benzamide The title compound was prepared (11 mg, 0.02 mmol) according to the procedures described in Examples 202 and 60, Steps A-G substituting 3,4-dihydro-2H-pyrrol-5-amine (8 mg, 0.09 mmol) in Step G. LC-MS: >95% 254 nm, $R_T$=1.021 min, MS (ES) 562.2 (M+H).

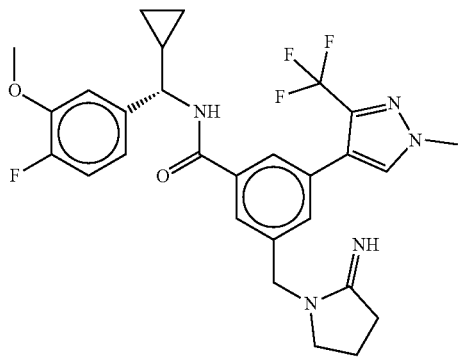

Example 339

(S)—N-(Cyclopropyl(4-fluoro-3-methoxyphenyl) methyl)-3-((2-iminopyrrolidin-1-yl)methyl)-5-(1-methyl-3-(trifluoromethyl)-1H-pyrazol-4-yl)benzamide The title compound was prepared (16 mg, 0.029 mmol) according to the procedures described in Examples 207 and 60, Steps A-G substituting 3,4-dihydro-2H-pyrrol-5-amine (8 mg, 0.09 mmol) in Step G. LC-MS: >95% 254 nm, $R_T$=0.945 min, MS (ES) 544 (M+H).

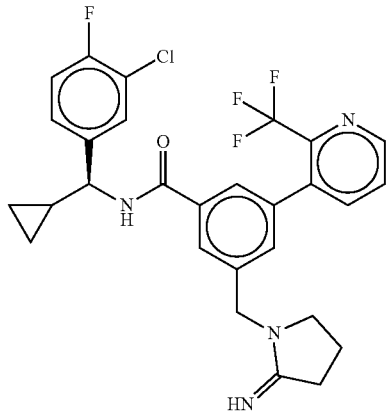

Example 340

(S)—N-((3-Chloro-4-fluorophenyl)(cyclopropyl) methyl)-3-((2-iminopyrrolidin-1-yl)methyl)-5-(2-(trifluoromethyl)pyridin-3-yl)benzamide The title compound was prepared (13 mg, 0.024 mmol) according to the procedures described in Examples 219 and 60, Steps A-G substituting 3,4-dihydro-2H-pyrrol-5-amine (8 mg, 0.09 mmol) in Step G. LC-MS: >95% 254 nm, $R_T$=0.989 min, MS (ES) 545 (M+H).

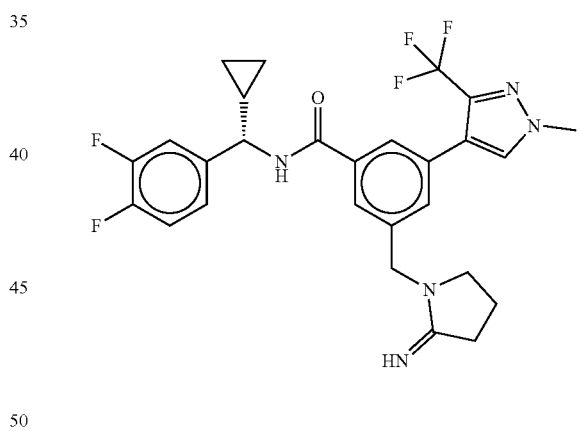

Example 341

(S)—N-(Cyclopropyl(3,4-difluorophenyl)methyl)-3-((2-iminopyrrolidin-1-yl)methyl)-5-(1-methyl-3-(trifluoromethyl)-1H-pyrazol-4-yl)benzamide The title compound was prepared (9 mg, 0.017 mmol) according to the procedures described in Examples 125 and 60, Steps A-G substituting the hydrochloride salt of (S)-cyclopropyl(3,4-difluorophenyl)methanamine (0.3 g, 1.4 mmol) in Step E and 3,4-dihydro-2H-pyrrol-5-amine (8 mg, 0.09 mmol) in Step G. LC-MS: >95% 254 nm, $R_T$=0.960 min, MS (ES) 532 (M+H).

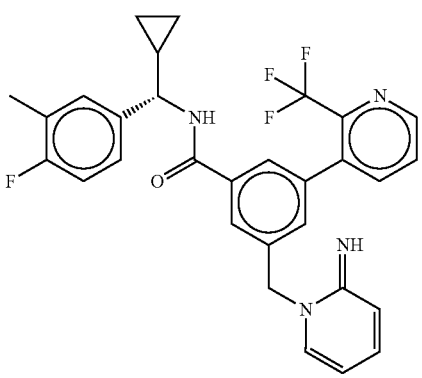

Example 342

(S)—N-(Cyclopropyl(4-fluoro-3-methylphenyl)methyl)-3-((2-iminopyridin-1(2H)-yl)methyl)-5-(2-(trifluoromethyl)pyridin-3-yl)benzamide Pyridin-2-amine (9.0 mg, 0.1 mmol) and DIPEA (0.04 mL, 0.24 mmol) were added to a solution of (S)-3-(bromomethyl)-N-(cyclopropyl(4-fluoro-3-methylphenyl)methyl)-5-(2-(trifluoromethyl)pyridin-3-yl)benzamide (25.0 mg, 0.05 mmol) in CH$_3$CN (1.0 mL). The reaction mixture was stirred at 90° C. for 12 h. After cooling to ambient temperature, the crude reaction mixture was concentrated under reduced pressure. The residue was purified by reverse phase HPLC (Phenomenex Gemini C18, H$_2$O/CH$_3$CN gradient from 5-95% CH$_3$CN, 0.1% TFA) to yield the title compound (8.9 mg, 34%). $^1$H NMR (400 MHz, Chloroform-d) δ 8.72 (d, J=3.6 Hz, 1H), 7.92 (s, 1H), 7.71 (d, J=7.8 Hz, 1H), 7.69 (s, 1H), 7.53 (dd, J=7, 8, 4.7 Hz, 1H), 7.30 (s, 1H), 7.23 (m, 2H), 7.06 (s, 1H), 7.02-6.91 (m, 2H), 6.85 (ddd, J=8.2, 6.4, 1.5 Hz, 1H), 6.40 (d, J=9.2 Hz, 1H), 5.83 (t, J=6.3 Hz, 1H), 5.20 (s, 2H), 4.50 (t, J=8.4 Hz, 1H), 2.25 (s, 3H), 1.27 (m, 1H), 0.62 (m, 2H), 0.51 (m, 1H), 0.40 (m, 1H); LCMS: R$_T$=1.369 min, MS (ES) 535.6 (M+H).

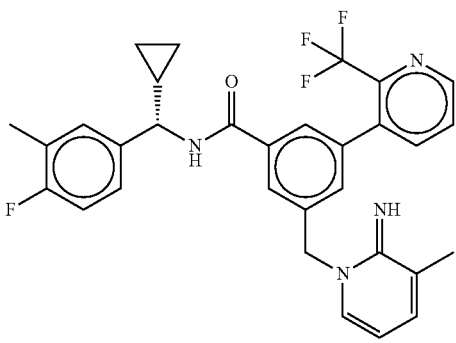

Example 343

(S)—N-(Cyclopropyl(4-fluoro-3-methylphenyl)methyl)-3-((2-imino-3-methylpyridin-1(2H)-yl)methyl)-5-(2-(trifluoromethyl)pyridin-3-yl)benzamide The title compound (6.7 mg, 21%) was prepared from the procedure described in Example 342 using (S)-3-(bromomethyl)-N-(cyclopropyl(4-fluoro-3-methylphenyl)methyl)-5-(2-(trifluoromethyl)pyridin-3-yl)benzamide (30.0 mg, 0.06 mmol) and 3-methylpyridin-2-amine (0.01 mL, 0.12 mmol). $^1$H NMR (400 MHz, Chloroform-d) δ 8.72 (d, J=3.6 Hz, 1H), 7.93 (s, 1H), 7.72 (d, J=6.9 Hz, 1H), 7.69 (s, 1H), 7.53 (dd, J=7.8, 4.7 Hz, 1H), 7.31 (s, 11H), 7.22 (m, 2H), 6.97 (m, 3H), 6.86 (d, J=6.5 Hz, 1H), 5.84 (t, J=6.7 Hz, 1H), 5.30 (s, 2H), 4.51 (t, J=8.3 Hz, 1H), 2.25 (d, J=1.6 Hz, 3H), 2.04 (s, 3H), 1.27 (m, 1H), 0.63 (m, 2H), 0.51 (m, 1H), 0.40 (m, 1H); LCMS: R$_T$=1.383 min, MS (ES) 549.6 (M+H).

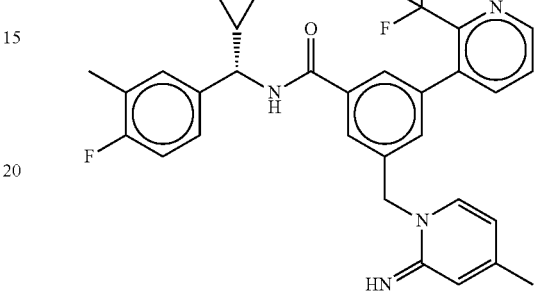

Example 344

(S)—N-(Cyclopropyl(4-fluoro-3-methylphenyl)methyl)-3-((2-imino-4-methylpyridin-1(2H)-yl)methyl)-5-(2-(trifluoromethyl)pyridin-3-yl)benzamide The title compound (10.7 mg, 33%) was prepared from the procedure described in Example 342 using (S)-3-(bromomethyl)-N-(cyclopropyl (4-fluoro-3-methylphenyl)methyl)-5-(2-(trifluoromethyl)pyridin-3-yl)benzamide (30.0 mg, 0.06 mmol) and 4-methylpyridin-2-amine (0.01 mL, 0.12 mmol). LCMS: R$_T$=1.389 min, MS (ES) 549.6 (M+H).

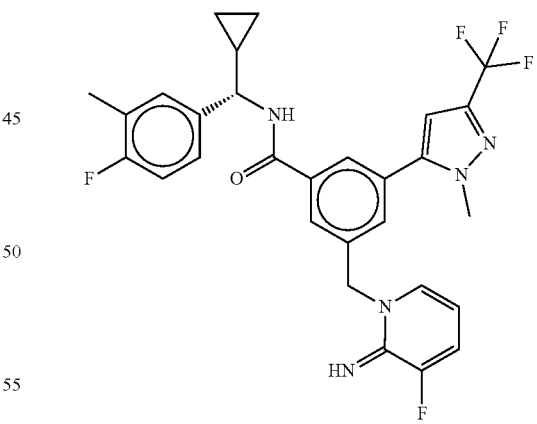

Example 345

(S)—N-(Cyclopropyl (4-fluoro-3-methylphenyl)methyl)-3-((3-fluoro-2-iminopyridin-1(2H)-yl)methyl)-5-(1-methyl-3-(trifluoromethyl)-1H-pyrazol-5-yl)benzamide The title compound (4.5 mg, 16%) was prepared from the procedure described in Example 342 using (S)-3-(bromomethyl)-N-(cyclopropyl(4-fluoro-3-methylphenyl)methyl)-5-(1-methyl-3-(trifluoromethyl)-1H-pyrazol-5-yl)benzamide (25.0 mg, 0.05 mmol) and 3-fluoropyridin-2-amine (10.7 mg, 0.10 mmol). LCMS: R$_T$=1.460 min, MS (ES) 556.6 (M+H).

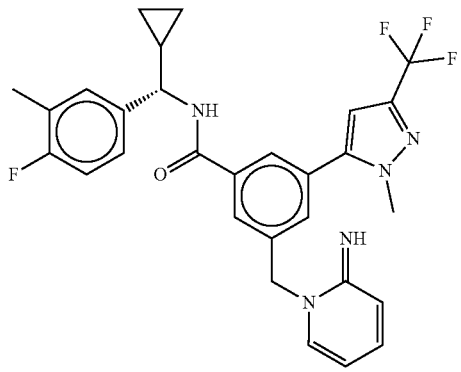

Example 346

(S)—N-(Cyclopropyl(4-fluoro-3-methylphenyl)methyl)-3-((2-iminopyridin-(2H)-yl)methyl)-5-(1-methyl-3-(trifluoromethyl)-1H-pyrazol-5-yl)benzamide The title compound (6.9 mg, 26%) was prepared from the procedure described in Example 342 using (S)-3-(bromomethyl)-N-(cyclopropyl(4-fluoro-3-methylphenyl)methyl)-5-(1-methyl-3-(trifluoromethyl)-1H-pyrazol-5-yl)benzamide (25.0 mg, 0.05 mmol) and pyridin-2-amine (9.0 mg, 0.10 mmol). $^1$H NMR (400 MHz, Chloroform-d) δ 7.91 (s, 1H), 7.75 (s, 1H), 7.40 (s, 1H), 7.22 (t, J=6.6 Hz, 2H), 7.01 (d, J=6.8 Hz, 1H), 6.95 (t, J=8.9 Hz, 2H), 6.92-6.83 (m, 1H), 6.55 (s, 1H), 6.43 (d, J=9.1 Hz, 1H), 5.86 (t, J=6.5 Hz, 1H), 5.20 (s, 2H), 4.50 (t, J=8.4 Hz, 1H), 3.85 (s, 3H), 2.25 (d, J=1.5 Hz, 3H), 1.28 (m, 1H), 0.64 (m, 2H), 0.52 (m, 1H), 0.41 (m, 1H); LCMS: R$_T$=1.459 min, MS (ES) 538.6 (M+H).

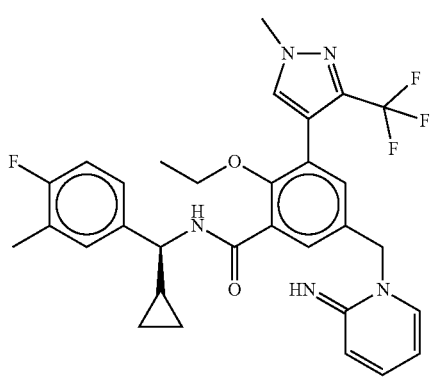

Example 347

(S)—N-(Cyclopropyl(4-fluoro-3-methylphenyl)methyl)-2-ethoxy-5-((2-iminopyridin-(2H)-yl)methyl)-3-(1-methyl-3-(trifluoromethyl)-1H-pyrazol-4-yl)benzamide The title compound (8.8 mg, 28%) was prepared from the procedure described in Example 342 using (S)-5-(bromomethyl)-N-(cyclopropyl(4-fluoro-3-methylphenyl)methyl)-2-ethoxy-3-(1-methyl-3-(trifluoromethyl)-1H-pyrazol-4-yl)benzamide (30.0 mg, 0.05 mmol) and pyridin-2-amine (14.9 mg, 0.16 mmol). $^1$H NMR (400 MHz, Chloroform-d) δ 8.38 (d, J=7.8 Hz, 1H), 7.96 (d, J=2.3 Hz, 1H), 7.58 (s, 1H), 7.38-7.32 (m, 1H), 7.20 (t, J=6.8 Hz, 2H), 6.95 (t, J=7.6 Hz, 2H), 6.84-6.78 (m, 1H), 6.38 (d, J=9.2 Hz, 1H), 5.78 (t, J=6.4 Hz, 1H), 5.11 (s, 2H), 4.56 (t, J=8.4 Hz, 1H), 3.99 (s, 3H), 3.67-3.59 (m, 1H), 3.58-3.50 (m, 1H), 2.25 (s, 3H), 1.22 (m, 1H), 1.02 (t, J=7.0 Hz, 3H), 0.62 (m, 2H), 0.53 (m, 1H), 0.41 (m, 1H); LCMS: RT=1.428 min, MS (ES) 582.6 (M+H).

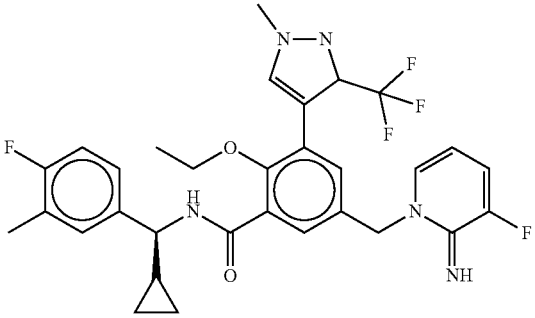

Example 348

N—((S)-Cyclopropyl(4-fluoro-3-methylphenyl)methyl)-2-ethoxy-5-((3-fluoro-2-iminopyridin-1(2H)-yl)methyl)-3-(1-methyl-3-(trifluoromethyl)-1,3-dihydro-2λ2-pyrazol-4-yl)benzamide The title compound (3.9 mg, 12%) was prepared from the procedure described in Example 342 using (S)-5-(bromomethyl)-N-(cyclopropyl(4-fluoro-3-methylphenyl)methyl)-2-ethoxy-3-(1-methyl-3-(trifluoromethyl)-1H-pyrazol-4-yl)benzamide (30.0 mg, 0.05 mmol) and 3-fluoropyridin-2-amine (11.8 mg, 0.11 mmol). $^1$H NMR (400 MHz, Chloroform-d) δ 8.37 (d, J=7.8 Hz, 1H), 7.98 (d, J=2.3 Hz, 1H), 7.59 (s, 1H), 7.38-7.33 (m, 1H), 7.20 (t, J=6.9 Hz, 2H), 6.95 (t, J=8.8 Hz, 1H), 6.79 (d, J=7.0 Hz, 1H), 6.61-6.50 (m, 1H), 5.62 (td, J=7.1, 5.0 Hz, 1H), 5.15 (s, 2H), 4.57 (t, J=8.4 Hz, 1H), 4.01 (s, 3H), 3.69-3.60 (m, 1H), 3.59-3.49 (m, 1H), 2.26 (s, 3H), 1.21 (m, 1H), 1.03 (t, J=7.0 Hz, 3H), 0.63 (m, 2H), 0.52 (m, 1H), 0.45-0.36 (m, 1H); LCMS: R$_T$=1.444 min, MS (ES) 600.6 (M+H).

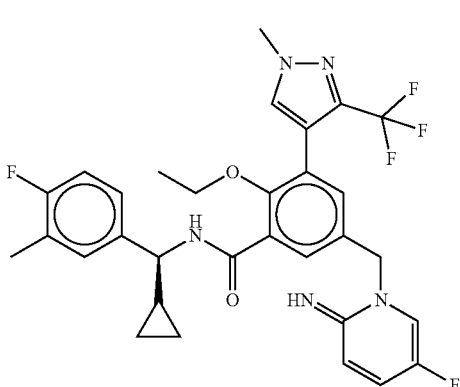

Example 349

(S)—N-(Cyclopropyl(4-fluoro-3-methylphenyl)
methyl)-2-ethoxy-5-((5-fluoro-2-iminopyridin-1
(2H)-yl)methyl)-3-(1-methyl-3-(trifluoromethyl)-
1H-pyrazol-4-yl)benzamide The title compound (2.6 mg, 8%) was prepared from the procedure described in Example 342 using (S)-5-(bromomethyl)-N-(cyclopropyl(4-fluoro-3-methylphenyl)methyl)-2-ethoxy-3-(1-methyl-3-(trifluoromethyl)-1H-pyrazol-4-yl)benzamide (30.0 mg, 0.05 mmol) and 5-fluoropyridin-2-amine (11.8 mg, 0.11 mmol). $^1$H NMR (400 MHz, Chloroform-d) δ 8.39 (d, J=7.9 Hz, 1H), 7.97 (d, J=2.3 Hz, 1H), 7.59 (s, 1H), 7.36 (s, 1H), 7.21 (t, J=6.8 Hz, 2H), 6.96 (t, J=8.9 Hz, 1H), 6.87-6.83 (m, 1H), 6.80 (ddd, J=9.5, 6.7, 2.7 Hz, 1H), 6.38 (dd, J=9.9, 5.4 Hz, 1H), 5.05 (s, 2H), 4.57 (t, J=8.4 Hz, 1H), 4.00 (s, 3H), 3.69-3.60 (m, 1H), 3.59-3.50 (m, 1H), 2.26 (s, 3H), 1.22 (m, 1H), 1.03 (t, J=7.0 Hz, 3H), 0.68-0.59 (m, 2H), 0.53 (m, 1H), 0.42 (m, 1H); LCMS: $R_T$=1.490 min, MS (ES) 600.6 (M+H).

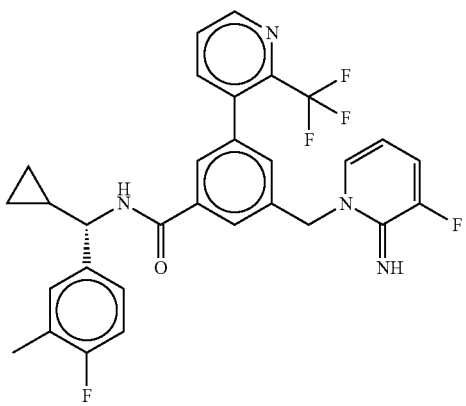

Example 350

(S)—N-(Cyclopropyl(4-fluoro-3-methylphenyl)
methyl)-3-((3-fluoro-2-iminopyridin-1(2H)-yl)
methyl)-5-(2-(trifluoromethyl)pyridin-3-yl)benz-
amide The title compound (3.5 mg, 11%) was prepared from the procedure described in Example 342 using (S)-3-(bromomethyl)-N-(cyclopropyl(4-fluoro-3-methylphenyl)methyl)-5-(2-(trifluoromethyl)pyridin-3-yl)benzamide (30.0 mg, 0.06 mmol) and 3-fluoropyridin-2-amine (12.9 mg, 0.12 mmol). LCMS: $R_T$=1.375 min, MS (ES) 553.6 (M+H).

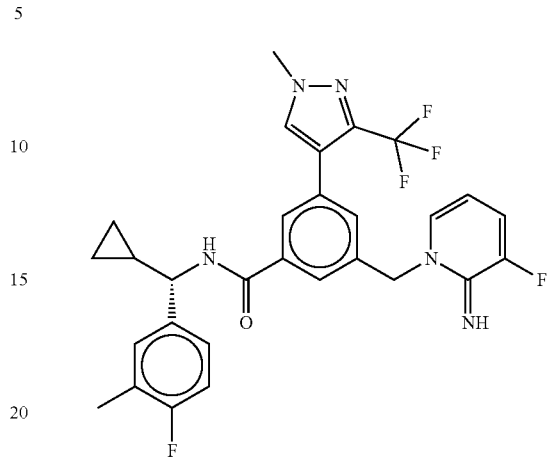

Example 351

(S)—N-(Cyclopropyl(4-fluoro-3-methylphenyl)methyl)-
3-((3-fluoro-2-iminopyridin-1(2H)-yl)methyl)-5-(1-methyl-
3-(trifluoromethyl)-1H-pyrazol-4-yl)benzamide Step A. Preparation of (S)—N-(cyclopropyl(4-
fluoro-3-methylphenyl)methyl)-3-(hydroxymethyl-5-
(1-methyl-3-(trifluoromethyl)-1H-pyrazol-4-yl)benz-
amide The title compound (429.8 mg, 93%) was prepared from the procedure described in Example 33, Step A using 3-(hydroxymethyl)-5-(1-methyl-3-(trifluoromethyl)-1H-pyrazol-4-yl)benzoic acid (300.0 mg, 1.00 mmol) and (S)-cyclopropyl(4-fluoro-3-methylphenyl)methanamine hydrochloride (258.6 mg, 1.20 mmol). LCMS: $R_T$=1.644 min, MS (ES) 462.5 (M+H).

Step B. Preparation of (S)-3-(bromomethyl)-N-(cy-
clopropyl(4-fluoro-3-methylphenyl)methyl)-5-(1-
methyl-3-(trifluoromethyl)-1H-pyrazol-4-yl)benz-
amide The title compound (371.5 mg, 62%) was prepared from the procedure described in Example 27, Step D using (S)—N-(cyclopropyl(4-fluoro-3-methylphenyl)methyl)-3-(hydroxymethyl)-5-(1-methyl-3-(trifluoromethyl)-1H-pyrazol-4-yl)benzamide (522.4 mg, 1.13 mmol). LCMS: $R_T$=1.902 min, MS (ES) 525.4 (M+H).

Step C. Example 351

The title compound (8.5 mg, 26%) was prepared from the procedure described in Example 342 using (S)-3-(bromomethyl)-N-(cyclopropyl(4-fluoro-3-methylphenyl)methyl)-5-(1-methyl-3-(trifluoromethyl)-1H-pyrazol-4-yl)benzamide (30.0 mg, 0.06 mmol) and 3-fluoropyridin-2-amine (19.2 mg, 0.17 mmol). LCMS: $R_T$=1.417 min, MS (ES) 556.6 (M+H).

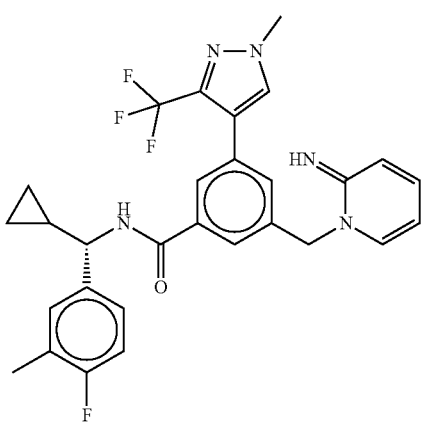

Example 352

(S)—N-(cyclopropyl(4-fluoro-3-methylphenyl)methyl)-3-((2-iminopyridin-1(2H)-yl)methyl)-5-(1-methyl-3-(trifluoromethyl)-1H-pyrazol-4-yl)benzamide The title compound (13.4 mg, 32%) was prepared from the procedure described in Example 342 using (S)-3-(bromomethyl)-N-(cyclopropyl(4-fluoro-3-methylphenyl)methyl)-5-(1-methyl-3-(trifluoromethyl)-1H-pyrazol-4-yl)benzamide (40.0 mg, 0.08 mmol) and pyridin-2-amine (21.5 mg, 0.23 mmol). LCMS: $R_T$=1.370 min, MS (ES) 538.6 (M+H).

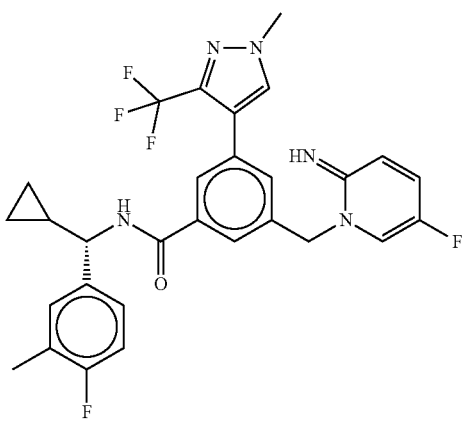

Example 353

(S)—N-(cyclopropyl(4-fluoro-3-methylphenyl)methyl)-3-((5-fluoro-2-iminopyridin-1(2H)-yl)methyl)-5-(1-methyl-3-(trifluoromethyl)-1H-pyrazol-4-yl)benzamide The title compound (10.3 mg, 32%) was prepared from the procedure described in Example 342 using (S)-3-(bromomethyl)-N-(cyclopropyl(4-fluoro-3-methylphenyl)methyl)-5-(1-methyl-3-(trifluoromethyl)-1H-pyrazol-4-yl)benzamide (30.0 mg, 0.06 mmol) and 5-fluoropyridin-2-amine (19.2 mg, 0.17 mmol). DIPEA was not added to this reaction mixture. The reaction mixture was stirred at 60° C. for 12 h. LCMS: $R_T$=1.462 min, MS (ES) 556.6 (M+H).

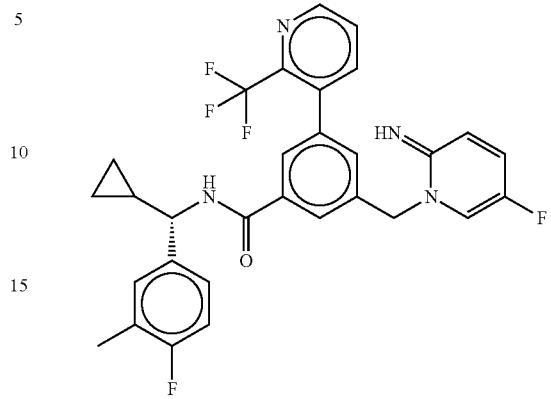

Example 354

(S)—N-(cyclopropyl(4-fluoro-3-methylphenyl)methyl)-3-((5-fluoro-2-iminopyridin-1(2H)-yl)methyl)-5-(2-(trifluoromethyl)pyridin-3-yl)benzamide The title compound (14.9 mg, 46%) was prepared from the procedure described in Example 353 using (S)-3-(bromomethyl)-N-(cyclopropyl(4-fluoro-3-methylphenyl)methyl)-5-(2-(trifluoromethyl)pyridin-3-yl)benzamide (30.0 mg, 0.06 mmol) and 5-fluoropyridin-2-amine (12.9 mg, 0.12 mmol). LCMS: $R_T$=1.434 min, MS (ES) 553.6 (M+H).

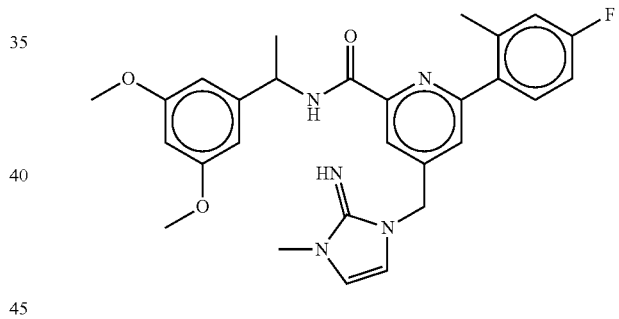

Example 355

N-(1-(3,5-Dimethoxyphenyl)ethyl)-6-(4-fluoro-2-methylphenyl)-4-((2-imino-3-methyl-2,3-dihydro-1H-imidazol-1-yl)methyl)picolinamide Step A. Preparation of N-(1-(3,5-dimethoxyphenyl)ethyl)-6-(4-fluoro-2-methylphenyl)-4-(hydroxymethyl)picolinamide The title compound (0.09 g, 57%) was prepared following the procedure described in Example 1, Step C using 6-(4-fluoro-2-methylphenyl)-4-(hydroxymethyl)picolinic acid (0.09 g, 0.35 mmol) and 1-(3,5-dimethoxyphenyl)ethan-1-amine (0.05 g, 0.38 mmol).

Step B. Preparation of 4-(bromomethyl)-N-(1-(3,5-dimethoxyphenyl)ethyl)-6-(4-fluoro-2-methylphenyl)picolinamide The title compound was prepared following the procedure described in Example 1, Step D using crude N-(1-(3,5- dimethoxyphenyl)ethyl)-6-(4-fluoro-2-methylphenyl)-4-(hydroxymethyl)picolinamide (0.09 g, 0.20 mmol) and 1M PBr₃ in DCM (0.20 mL, 0.20 mmol).

Step C. Example 355

The title compound (0.07 g, 66% 2 steps) was prepared following the procedure described in Example 1, Step E using 4-(bromomethyl)-N-(1-(3,5-dimethoxyphenyl)ethyl)-6-(4-fluoro-2-methylphenyl)picolinamide, 1-methyl-1H-imidazol-2-amine (0.04 g, 0.38 mmol), and DIPEA (0.14 mL, 0.80 mmol). LCMS: 98% 254 nm R$_T$=0.95 min, MS (ES) 504 (M+H).

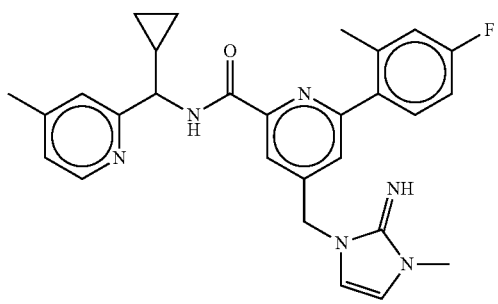

Example 356

N-(Cyclopropyl(4-methylpyridin-2-yl)methyl)-6-(4-fluoro-2-methylphenyl)-4-((2-imino-3-methyl-2,3-dihydro-1H-imidazol-1-yl)methyl)picolinamide Step A. Preparation of N-(cyclopropyl(4-methyl-pyridin-2-yl)methyl)-6-(4-fluoro-2-methylphenyl)-4-(hydroxymethyl)picolinamide The title compound (0.09 g, 75%) was prepared following the procedure described in Example 1, Step C using 6-(4-fluoro-2-methylphenyl)-4-(hydroxymethyl)picolinic acid (0.06 g, 0.35 mmol) and cyclopropyl(4-methylpyridin-2-yl)methanamine 2HCl (0.05 g, 0.38 mmol).

Step B. Preparation of 4-(bromomethyl)-N-(cyclopropyl(4-methylpyridin-2-yl)methyl)-6-(4-fluoro-2-methylphenyl)picolinamide The title compound was prepared following the procedure described in Example 1, Step D using N-(cyclopropyl(4-methylpyridin-2-yl)methyl)-6-(4-fluoro-2-methylphenyl)-4-(hydroxymethyl)picolinamide (0.09 g, 0.23 mmol) and 1M PBr₃ in DCM (0.25 mL, 0.25 mmol).

Step C. Example 356

The title compound (0.03 g, 25% 2 steps) was prepared following the procedure described in Example 1, Step E using crude 4-(bromomethyl)-N-(cyclopropyl(4-methyl-pyridin-2-yl)methyl)-6-(4-fluoro-2-methylphenyl)picolinamide, 1-methyl-1H-imidazol-2-amine (0.04 g, 0.38 mmol), and DIPEA (0.14 mL, 0.80 mmol). ¹H NMR (400 MHz, D₆-DMSO) δ 9.0 (d, 1H, J=9.1 Hz), 8.2 (d, 1H, J=5.2 Hz), 7.9 (d, 1H, J=8.4 Hz), 7.7 (d, 1H, J=8.4 Hz), 7.6 (s, 1H), 7.5 (s, 1H), 7.3 (m, 2H), 7.2 (t, 1H, J=7.2 Hz), 7.0 (m, 2H), 6.9 (d, 1H, J=4.9 Hz), 6.0 (s, 2H), 4.3 (t, 1H, J=8.2 Hz), 3.1 (s, 3H), 2.1 (s, 3H), 2.0 (s, 3H), 1.0 (m, 1H), 0.2 (m, 4H); LCMS: 98% 254 nm R$_T$=0.94 min, MS (ES) 507 (M+Na).

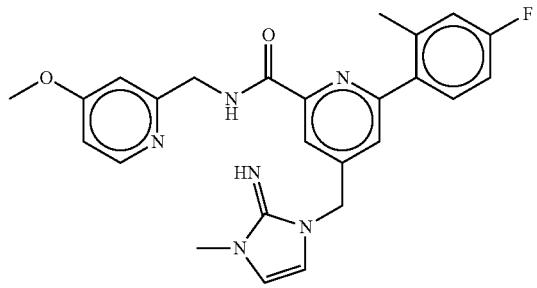

Example 357

6-(4-Fluoro-2-methylphenyl)-4-((2-imino-3-methyl-2,3-dihydro-1H-imidazol-1-yl)methyl)-N-((4-methoxypyridin-2-yl)methyl)picolinamide Step A. Preparation of 6-(4-fluoro-2-methylphenyl)-4-(hydroxymethyl)-N-((4-methoxypyridin-2-yl)methyl)picolinamide The title compound (0.08 g, 57%) was prepared following the procedure described in Example 1, Step C using 6-(4-fluoro-2-methylphenyl)-4-(hydroxymethyl)picolinic acid (0.06 g, 0.35 mmol) and (4-methoxypyridin-2-yl)methanamine (0.05 g, 0.38 mmol).

Step B. Preparation of (4-(bromomethyl)-6-(4-fluoro-2-methylphenyl)-N-((4-methoxypyridin-2-yl)methyl)picolinamide The title compound was prepared following the procedure described in Example 1, Step D using crude 6-(4-fluoro-2-methylphenyl)-4-(hydroxymethyl)-N-((4-methoxypyridin-2-yl)methyl)picolinamide (0.08 g, 0.20 mmol) and 1M PBr₃ in DCM (0.22 mL, 0.22 mmol).

Step C. Example 357

The title compound (0.04 g, 44% 2 steps) was prepared following the procedure described in Example 1, Step E using (4-(bromomethyl)-6-(4-fluoro-2-methylphenyl)-N-((4-methoxypyridin-2-yl)methyl)picolinamide, 1-methyl-1H-imidazol-2-amine (0.04 g, 0.38 mmol), and DIPEA (0.14 mL, 0.80 mmol). LCMS: 980% 254 nm R$_T$=1.00 min, MS (ES) 461 (M+H).

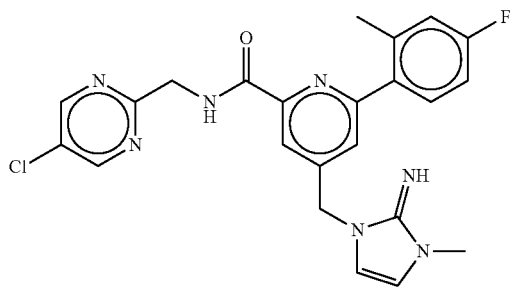

Example 358

N-((5-Chloropyrimidin-2-yl)methyl)-6-(4-fluoro-2-methylphenyl)-4-((2-imino-3-methyl-2,3-dihydro-1H-imidazol-1-yl)methyl)picolinamide Step A. Preparation of N-((5-chloropyrimidin-2-yl)methyl)-6-(4-fluoro-2-methylphenyl)-4-(hydroxymethyl)picolinamide The title compound (0.08 g, 57%) was prepared following the procedure described in Example 1, Step C using 6-(4-fluoro-2-methylphenyl)-4-(hydroxymethyl)picolinic acid (0.06 g, 0.35 mmol) and ((5-chloropyrimidin-2-yl)methanamine.HCl (0.07 g, 0.38 mmol).

Step B. Preparation of 4-(bromomethyl)-N-((5-chloropyrimidin-2-yl)methyl)-6-(4-fluoro-2-methylphenyl)picolinamide The title compound was prepared following the procedure described in Example 1, Step D using crude N-((5-chloropyrimidin-2-yl)methyl)-6-(4-fluoro-2-methylphenyl)-4-(hydroxymethyl)picolinamide (0.08 g, 0.21 mmol) and 1M PBr$_3$ in DCM (0.23 mL, 0.23 mmol).

Step C. Example 358

The title compound (9 mg, 9% 2 steps) was prepared following the procedure described in Example 1, Step E using 4-(bromomethyl)-N-((5-chloropyrimidin-2-yl)methyl)-6-(4-fluoro-2-methylphenyl)picolinamide, 1-methyl-1H-imidazol-2-amine (0.04 g, 0.38 mmol), and DIPEA (0.14 mL, 0.80 mmol). LCMS: 98% 254 nm R$_T$=0.98 min, MS (ES) 482 (M+H).

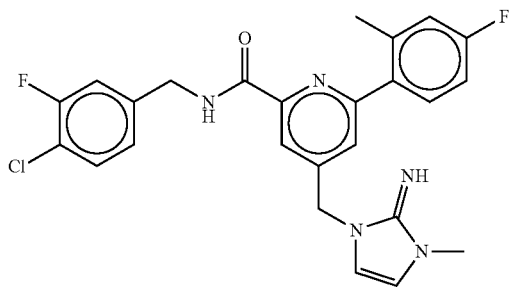

Example 359

N-(4-Chloro-3-fluorobenzyl)-6-(4-fluoro-2-methylphenyl)-4-((2-imino-3-methyl-2,3-dihydro-1H-imidazol-1-yl)methyl)picolinamide Step A. Preparation of N-(4-chloro-3-fluorobenzyl)-6-(4-fluoro-2-methylphenyl)-4-(hydroxymethyl)picolinamide The title compound (0.12 g, 87%) was prepared following the procedure described in Example 1, Step C using 6-(4-fluoro-2-methylphenyl)-4-(hydroxymethyl)picolinic acid (0.06 g, 0.35 mmol) and (4-chloro-3-fluorophenyl)methanamine (0.06 g, 0.38 mmol).

Step B. Preparation of 4-(bromomethyl)-N-(4-chloro-3-fluorobenzyl)-6-(4-fluoro-2-methylphenyl)picolinamide The title compound was prepared following the procedure described in Example 1, Step D using crude N-(4-chloro-3-fluorobenzyl)-6-(4-fluoro-2-methylphenyl)-4-(hydroxymethyl)picolinamide (0.12 g, 0.30 mmol) and 1M PBr$_3$ in DCM (0.33 mL, 0.33 mmol).

Step C. Example 357

The title compound (0.07 g, 49% 2 steps) was prepared following the procedure described in Example 1, Step E using 4-(bromomethyl)-N-(4-chloro-3-fluorobenzyl)-6-(4-fluoro-2-methylphenyl)picolinamide, 1-methyl-1H-imidazol-2-amine (0.04 g, 0.38 mmol), DIPEA (0.14 mL, 0.80 mmol). LCMS: 98% 254 nm R$_T$=0.98 min, MS (ES) 482 (M+H).

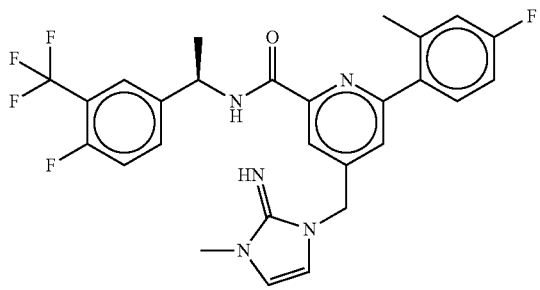

Example 360

(R)-6-(4-fluoro-2-methylphenyl)-N-(1-(4-fluoro-3-(trifluoromethyl)phenyl)ethyl)-4-((2-imino-3-methyl-2,3-dihydro-1H-imidazol-1-yl)methyl)picolinamide Step A. Preparation of (R)-6-(4-fluoro-2-methylphenyl)-N-(1-(4-fluoro-3-(trifluoromethyl)phenyl)ethyl)-4-(hydroxymethyl)picolinamide The title compound (0.09 g, 52%) was prepared following the procedure described in Example 1, Step C using 6-(4-fluoro-2-methylphenyl)-4-(hydroxymethyl)picolinic acid (0.06 g, 0.35 mmol) and (R)-1-(4-fluoro-3-(trifluoromethyl)phenyl)ethan-1-amine.HCl (0.08 g, 0.38 mmol).

Step B. Preparation of (R)-4-(bromomethyl)-6-(4-fluoro-2-methylphenyl)-N-(1-(4-fluoro-3-(trifluoromethyl)phenyl)ethyl)picolinamide The title compound was prepared following the procedure described in Example 1, Step D using crude (R)-6-(4-fluoro-2-methylphenyl)-N-(1-(4-fluoro-3-(trifluoromethyl)phenyl)ethyl)-4-(hydroxymethyl)picolinamide (0.09 g, 0.20 mmol) and 1M PBr$_3$ in DCM (0.23 mL, 0.23 mmol).

Step C. Example 360

The title compound (0.04 g, 44% 2 steps) was prepared following the procedure described in Example 1, Step E using (R)-4-(bromomethyl)-6-(4-fluoro-2-methylphenyl)-N-(1-(4-fluoro-3-(trifluoromethyl)phenyl)ethyl)picolinamide, 1-methyl-1H-imidazol-2-amine (0.04 g, 0.38 mmol), and DIPEA (0.14 mL, 0.80 mmol). LCMS: 98% 254 nm $R_T$=1.00 min, MS (ES) 530 (M+H).

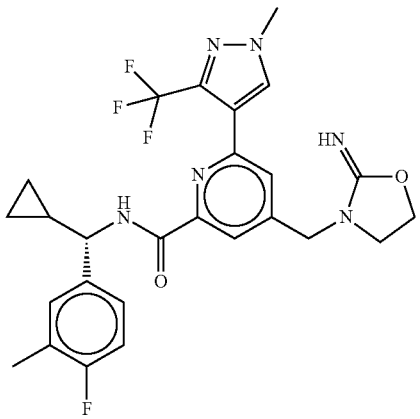

Example 361

(S)—N-(Cyclopropyl(4-fluoro-3-methylphenyl)methyl)-4-((2-iminooxazolidin-3-yl)methyl)-6-(1-methyl-3-(trifluoromethyl)-1H-pyrazol-4-yl)picolinamide Step A. Preparation of methyl 6-chloro-4-(((2-hydroxyethyl)amino)methyl)picolinate The title compound (198.9 mg, 43%) was prepared from the procedure described in Example 283, Step A using methyl 4-(bromomethyl)-6-chloropicolinate (500.0 mg, 2.00 mmol) and 2-aminoethan-1-ol (0.36 mL, 5.99 mmol). LCMS: $R_T$=0.154 min, MS (ES) 245.7 (M+H).

Step B. Preparation of 6-chloro-4-(((2-hydroxyethyl)amino)methyl)picolinic acid

The crude title compound was prepared from the procedure described in Example 27, Step B using methyl 6-chloro-4-(((2-hydroxyethyl)amino)methyl)picolinate (198.9 mg, 0.81 mmol). LCMS: $R_T$=0.187 min, MS (ES) 231.7 (M+H).

Step C. Preparation of (S)-6-chloro-N-(cyclopropyl(4-fluoro-3-methylphenyl)methyl)-4-(((2-hydroxyethyl)amino)methyl)picolinamide The title compound (159.7 mg, 87%) was prepared from the procedure described in Example 33, Step A using 6-chloro-4-(((2-hydroxyethyl)amino)methyl)picolinic acid (187.5 mg, 0.47 mmol) and (S)-cyclopropyl(4-fluoro-3-methylphenyl)methanamine hydrochloride (151.1 mg, 0.70 mmol). $^1$H NMR (400 MHz, Chloroform-d) 9.11 (br s, 1H), 8.11 (d, J=7.7 Hz, 1H), 7.92 (s, 1H), 6.95-6.82 (m, 2H), 6.88 (br s, 1H), 6.67 (t, J=8.9 Hz, 1H), 4.10 (t, J=8.3 Hz, 1H), 3.95 (s, 2H), 3.53 (s, 2H), 2.84 (s, 2H), 1.97 (s, 3H), 1.02 (m, 1H), 0.41 (m, 2H), 0.17 (m, 2H); LCMS: $R_T$=1.225 min, MS (ES) 392.9 (M+H).

Step D. Preparation of (S)—N-(cyclopropyl(4-fluoro-3-methylphenyl)methyl)-4-(((2-hydroxyethyl)amino)methyl)-6-(1-methyl-3-(trifluoromethyl)-1H-pyrazol-4-yl)picolinamide The title compound (17.5 mg, 8%) was prepared from the procedure described in Example 1, Step A using (S)-6-chloro-N-(cyclopropyl(4-fluoro-3-methylphenyl)methyl)-4-(((2-hydroxyethyl)amino)methyl)picolinamide (159.7 mg, 0.41 mmol) and (1-methyl-3-(trifluoromethyl)-1H-pyrazol-4-yl)boronic acid (94.8 mg, 0.49 mmol). LCMS: $R_T$=1.484 min, MS (ES) 506.5 (M+H).

Step E. Example 361

The title compound (5.2 mg, 28%) was prepared from the procedure described in Example 283, Step D using (S)—N-(cyclopropyl(4-fluoro-3-methylphenyl)methyl)-4-(((2-hydroxyethyl)amino)methyl)-6-(1-methyl-3-(trifluoromethyl)-1H-pyrazol-4-yl)picolinamide (17.5 mg, 0.03 mmol). $^1$H NMR (400 MHz, Chloroform-d) δ 8.66 (d, J=8.1 Hz, 1H), 7.97 (s, 1H), 7.89 (s, 1H), 7.63 (s, 1H), 7.25-7.16 (m, 2H), 6.95 (t, J=8.9 Hz, 1H), 4.53 (m, 3H), 4.27 (t, J=7.4 Hz, 2H), 4.03 (s, 3H), 3.43 (t, J=7.4 Hz, 2H), 2.26 (s, 3H), 1.28 (m, 1H), 0.67-0.59 (m, 2H), 0.44 (m, 2H); LCMS: $R_T$=1.455 min, MS (ES) 531.5 (M+H).

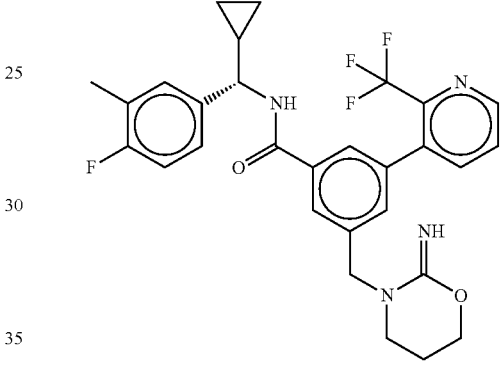

Example 362

(S)—N-(Cyclopropyl(4-fluoro-3-methylphenyl)methyl)-3-((2-imino-1,3-oxazinan-3-yl)methyl)-5-(2-(trifluoromethyl)pyridin-3-yl)benzamide The title compound was prepared (17 mg, 0.031 mmol) according to the procedures described in Example 60, Steps A-G substituting 5,6-dihydro-4H-1,3-oxazin-2-amine (12 mg, 0.12 mmol) in Step G. LC-MS: >95% 254 nm, $R_T$=0.949 min, MS (ES) 541.2 (M+H).

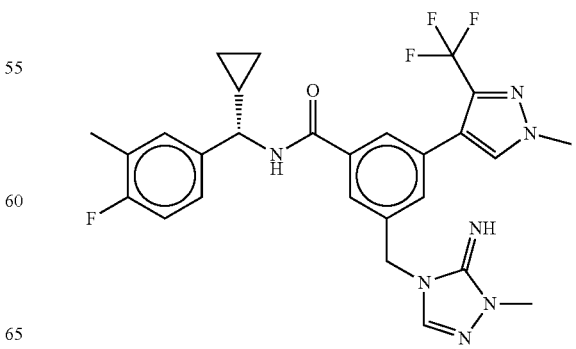

Example 363

(S)—N-(Cyclopropyl(4-fluoro-3-methylphenyl)methyl)-3-((5-imino-1-methyl-1,5-dihydro-4H-1,2,4-triazol-4-yl)methyl)-5-(1-methyl-3-(trifluoromethyl)-H-pyrazol-4-yl)benzamide The title compound (24.7 mg, 77%) was prepared from the procedure described in Example 353 using (S)-3-(bromomethyl)-N-(cyclopropyl(4-fluoro-3-methylphenyl)methyl)-5-(1-methyl-3-(trifluoromethyl)-1H-pyrazol-4-yl)benzamide (30.0 mg, 0.06 mmol) and 1-methyl-1H-1,2,4-triazol-5-amine (12.9 mg, 0.12 mmol). $^1$H NMR (400 MHz, Chloroform-d) δ 7.79-7.74 (m, 2H), 7.55 (s, 1H), 7.39 (s, 1H), 7.22 (m, 3H), 7.02 (d, J=7.7 Hz, 1H), 6.94 (t, J=9.0 Hz, 1H), 4.85 (s, 2H), 4.50 (t, J=8.3 Hz, 1H), 3.96 (s, 3H), 3.42 (s, 3H), 2.24 (d, J=1.5 Hz, 3H), 1.26 (m, 1H), 0.62 (m, 2H), 0.50 (m, 1H), 0.40 (m, 1H); LCMS: $R_T$=1.393 min, MS (ES) 542.6 (M+H).

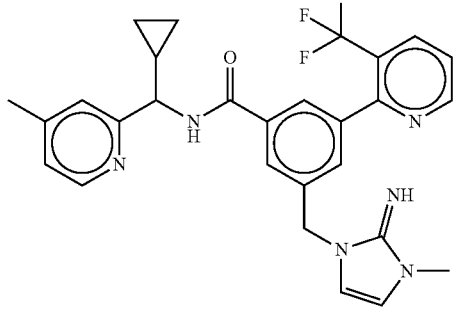

Example 364

N-(Cyclopropyl(4-methylpyridin-2-yl)methyl)-3-((2-imino-3-methyl-2,3-dihydro-1H-imidazol-1-yl)methyl)-5-(3-(trifluoromethyl)pyridin-2-yl)benzamide The title compound was prepared (72 mg, 0.14 mmol) according to the procedures described in Example 60, Steps A-G substituting 2-bromo-3-(trifluoromethyl)pyridine (1 g, 4.4 mmol) in Step C and the dihydrochloride salt of cyclopropyl(4-methylpyridin-2-yl)methanamine (0.3 g, 1.3 mmol) in Step E. LC-MS: >95% 254 nm, $R_T$=0.682 min, MS (ES) 521 (M+H).

Example 365

N-(3,5-Dimethoxybenzyl)-2-(4-fluoro-2-methylphenyl)-6-((2-imino-3-methyl-2,3-dihydro-1H-imidazol-1-yl)methyl)isonicotinamide

Step A. Preparation of 2-chloro-4-(methoxycarbonyl)-6-methylpyridine 1-oxide To a solution of methyl 2-chloro-6-methylisonicotinate (800 mg, 4.31 mmol) in benzene (22 mL) at rt was added mCPBA (1.06 g, 4.74 mmol). The resulting mixture was stirred at rt for 3 days. Then additional mCPBA (495 mg, 2.21 mmol) was added, and the reaction was stirred additional 15 h then concentrated. The residue was dissolved in EtOAc and the solution was washed with sat. aq. NaHCO$_3$, dried over Na$_2$SO$_4$, and concentrated. The residue was purified by flash chromatography (Combi-flash Rf, Hex/EtOAc=0-90% gradient) to afford the title compound (650 mg, 74%). $^1$H NMR (400 MHz, CDCl$_3$) δ 8.01 (d, J=2.4 Hz, 1H), 7.81 (d, J=2.4 Hz, 1H), 3.95 (s, 3H), 2.59 (s, 3H).

Step B. Preparation of methyl 2-(acetoxymethyl)-6-chloroisonicotinate

A solution of 2-chloro-4-(methoxycarbonyl)-6-methylpyridine 1-oxide (154 mg, 0.76 mmol) in acetic anhydride (2 mL) was heated in Microwave reactor at 100° C. for 2.5 h. Then sat. aq. NaHCO$_3$ was added, and the mixture was stirred at rt for 1 h. The mixture was extracted with EtOAc. The combined organic layers were dried over Na$_2$SO$_4$ and concentrated. The residue was purified by flash chromatography (Combi-flash Rf, Hex/EtOAc=0-25% gradient) to afford the title compound (94 mg, 50%). $^1$H NMR (400 MHz, CDCl$_3$) δ 7.83 (s, 1H), 7.82 (s, 1H), 5.24 (s, 2H), 3.99 (s, 3H), 2.20 (s, 3H).

Step C. Preparation of methyl 2-(acetoxymethyl)-6-(4-fluoro-2-methylphenyl)isonicotinate To a solution of methyl 2-(acetoxymethyl)-6-chloroisonicotinate (92 mg, 0.38 mmol) in toluene (2 mL)/EtOH (2 mL) was added 4-fluoro-2 methylphenylboronic acid (88 mg, 0.57 mmol), 2 M Na$_2$CO$_3$ (380 µL, 0.76 mmol), and Pd(PPh$_3$)$_4$ (27 mg, 0.023 mmol). The resulting mixture was stirred under Ar at 82° C. overnight and diluted with EtOAc. The resulting solution was washed with water, dried over Na$_2$SO$_4$, and concentrated. The residue was purified by flash chromatography (Combi-flash Rf, Hex/EtOAc=0-50% gradient) to afford a mixture (100 mg) containing the title compound and transesterification products, which was used without further purification.

Step D. Preparation of 2-(4-fluoro-2-methylphenyl)-6-(hydroxymethyl)isonicotinic acid To a solution of the crude (100 mg, ~0.32 mmol) from Step C in THF (3 mL) at rt was added water (1 mL) and LiOH (31 mg, 1.28 mmol). The resulting mixture was stirred overnight, then acidified with 1 M HCl to pH≈3. The mixture was extracted with EtOAc. The combined organic layers were dried (Na$_2$SO$_4$) and concentrated to provide the desired product (103 mg) as HCl salt which was used without further purification: LC-MS, >90% (254 nm), $R_T$=0.69 min, MS (ES) 262.4 (M+H).

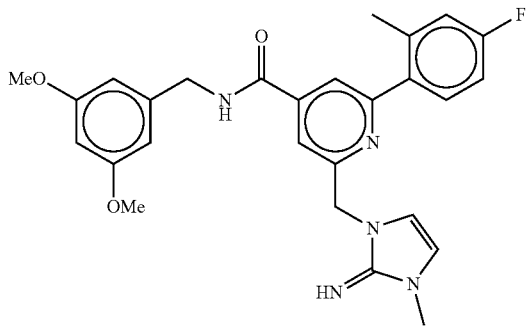

Step E. Preparation of N-(3,5-dimethoxybenzyl)-2-(4-fluoro-2-methylphenyl)-6-(hydroxymethyl)isonicotinamide The title compound (87 mg, 55% 3 step) was prepared from the procedure described in Example 1, Step C using 2-(4-fluoro-2-methylphenyl)-6-(hydroxymethyl)isonicotinic acid (103 mg, 0.32 mmol) and 3,5-dimethoxybenzyl amine. $^{1}$H NMR (400 MHz, CDCl$_{3}$) δ 7.65 (s, 1H), 7.55 (s, 1H), 7.38 (dd, J=6.0, 8.4 Hz, 1H), 7.00 (m, 2H), 6.63 (brs, 1H), 6.49 (d, J=2.4 Hz, 2H), 6.40 (t, J=2.4 Hz, 1H), 4.85 (s, 2H), 4.58 (d, J=5.6 Hz, 2H), 3.79 (s, 6H), 3.60 (brs, 1H), 2.36 (s, 3H).

Step F. Preparation of 2-(bromomethyl)-N-(3,5-dimethoxybenzyl)-6-(4-fluoro-2-methylphenyl)isonicotinamide The title compound (45 mg, 79%) was prepared from the procedure described in Example 27, Step D using N-(3,5-dimethoxybenzyl)-2-(4-fluoro-2-methylphenyl)-6-(hydroxymethyl)isonicotinamide (48 mg, 0.12 mmol) $^{1}$H NMR (400 MHz, CDCl$_{3}$) δ 7.71 (s, 1H), 7.63 (s, 1H), 7.38 (dd, J=6.0, 8.4 Hz, 1H), 7.00 (m, 2H), 6.57 (brs, 1H), 6.50 (d, J=2.4 Hz, 2H), 6.41 (t, J=2.4 Hz, 1H), 4.62 (s, 2H), 4.59 (d, J=5.6 Hz, 2H), 3.80 (s, 6H), 2.38 (s, 3H).

Step G. Example 365

The title compound (16.2 mg, 45%) was prepared from the procedure described in Example 28, Step F. $^{1}$H NMR (400 MHz, CDCl$_{3}$) δ 7.74 (s, 1H), 7.72 (s, 1H), 7.37 (dd, J=6.0, 8.4 Hz, 1H), 6.97 (m, 2H), 6.50 (d, J=2.0 Hz, 2H), 6.36 (m, 2H), 6.19 (d, J=2.8 Hz, 1H), 4.99 (s, 2H), 4.56 (s, 2H), 3.77 (s, 6H), 3.26 (s, 3H), 2.34 (s, 3H); LC-MS, >95% 254 nm, R$_{T}$=0.99 min, MS (ES) 490 (M+H).

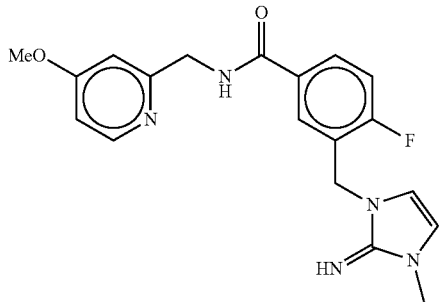

Example 366

4-Fluoro-3-((2-imino-3-methyl-2,3-dihydro-1H-imidazol-1-yl)methyl)-N-((4-methoxypyridin-2-yl)methyl)benzamide

Step A. Preparation of methyl 3-(bromomethyl)-4-fluorobenzoate

The title compound (3.60 g, 49%) was prepared from the procedure described in Example 5, Step A using methyl 4-fluoro-3-methylbenzoate (5.00 g, 29.7 mmol) and NBS (5.50 g, 30.9 mmol). $^{1}$H NMR (400 MHz, D$_{6}$-DMSO) δ 8.2 (dd 1H, =2.2 Hz), 8.0 (m, 1H), 7.4 (t, 1H, J=9.1 Hz), 4.8 (s, 3H), 3.8 (s, 3H).

Step B. Preparation of 4-fluoro-3-(hydroxymethyl)benzoic acid

A solution of methyl 3-(bromomethyl)-4-fluorobenzoate (0.48 g, 1.9 mmol) and NaOAc (1.57 g, 19.00 mmol) in MeCN (30 mL)/H$_{2}$O (1 mL) was heated to reflux for 18 h then concentrated. The residue was dissolved in DCM, washed with water and concentrated. The crude was saponified following the procedure described in Example 1, Step B to yield the title compound (0.27 g, 82%).

Step C. Preparation of 4-fluoro-3-(hydroxymethyl)-N-((4-methoxypyridin-2-yl)methyl)benzamide The title compound (0.37 g, 82%) was prepared from the procedure described in Example 2, Step C using 4-fluoro-3-(hydroxymethyl)benzoic acid (0.27 g, 1.56 mmol) and (4-methoxypyridin-2-yl)methanamine (0.26 g, 1.72 mmol).

Step D. Preparation of 3-(bromomethyl)-4-fluoro-N-((4-methoxypyridin-2-yl)methyl)benzamide The title compound (0.20 g, 44%) was prepared from the procedure described in Example 60, Step F using 4-fluoro-3-(hydroxymethyl)-N-((4-methoxypyridin-2-yl)methyl)benzamide (0.37 g, 1.27 mmol).

Step E. Example 366

The title compound (0.02 g, 41%) was prepared from the procedure described in Example 1, Step E using 3-(bromomethyl)-4-fluoro-N-((4-methoxypyridin-2-yl)methyl)benzamide (0.05 g, 0.14 mmol) and 1-methyl-1H-imidazol-2-amine (0.03 g, 0.27 mmol). LCMS: 98% 254 nm R$_{T}$=0.71 min, MS (ES) 370 (M+H).

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, *arachis* oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

Mixed lineage leukemia (MLL) presents a heterogeneous group of acute myeloid leukemia and acute lymphoblastic leukemia bearing features of more than one hematopoietic cell lineages. MLL accounts for about 80% of infant acute leukemia cases (Tomizawa, 2007) and 10% of all acute leukemia cases (Marschalek, 2011). MLL leukemia patients have a poor prognosis with overall 5-year survival ratio around 35% (Dimartino, 1999; Pui, 2003; Tomizawa, 2007).

MLL is composited of heterogeneous cell lineages with different molecular biology, cell biology and immunology features. However, MLL does share a common feature, which involves the chromosomal rearrangement of Mixed Lineage Leukemia (MLL) gene. MLL gene locates on chromosome 11q23 and the encoded MLL protein is a homolog of *Drosophila* trithorax (Trx) (Thachuk, 1992). Wild type MLL binds to regulatory regions of homeox (HOX) genes (Milne, 2005) through the amino terminal fragment while the catalytic C-terminal domain catalyzes the Histone 3 lysine 4 (H3K4) methylation via interaction with WDR5 and up regulates target genes transcription (Nakamura, 2002; Yokoyama, 2004; Milne, 2002). Wild type MLL in conjunction with WDR5 is required for maintenance HOX genes expression and is widely expressed not only during embryo development but also in adult tissues including myeloid and lymphoid cells (Butler, 1997; Yu, 1998). Reciprocal translocations of MLL gene result in-frame fusion of 5'-end MLL with the 3'-end of another partner gene. A common feature of MLL1 abnormality in leukemia is the preservation of one wild-type MLL1 allele. Currently, more than 80 partner genes have been identified, with MLL-AF4, MLL-AF9 and MLL-ENL being the three most frequently found fusion genes (Pui, 2003; herein incorporated by reference in its entirety). Expression of MLL fusion proteins promotes over expression of target genes such as HOXA9 and MEIS1, which blocks differentiation, enhances blast expansion and ultimately leads to leukemic transformation (Caslini, 2007; Yokoyama, 2005). The numerous chromosomal translocation of MLL gene and partner genes diversity add to the complexity to MLL leukemia treatment, though HOX9 and MEIS1 overexpression are commonly observed among MLL leukemia patients, each rearrangement leading to distinct dysregulated target gene expression patterns and downstream events (Slany, 2009). Clinical studies reveal that MLL of different chromosomal translocations are associated with different prognosis and are treated differently under current protocols (Tamai, 2010; Balgobind, 2011; Pigazzi, 2011).

Intrinsic HMT activity of MLL1 is extremely low and requires a complex assembly of WDR5, RbBP5, ASH2L, and DPY30 protein partners for effective H3K4 trimethylation, so called WRAD complex. The binding of MLL1 to WDR5 (WD40 repeat protein 5) is particularly critical for HMT activity and occurs through a conserved arginine containing motif on MLL1 called the "Win" or WDR5 interaction motif. Thus, targeting inhibitors of the MLL1-WDR5 interaction at the WIN site in order to block MLL1 methyltransferase activity could represent a promising therapeutic strategy for treating MLL leukemia patients. Peptidomimetics have been discovered that bind tightly to WDR5 at the MLL site, inhibit MLL1 methyltransferase activity, and block proliferation of MLL1 cells by inducing cell-cycle arrest, apoptosis, and myeloid differentiation (Cao, et al. Molecular Cell, 2014, 53, 247-261.) In addition, altered gene expression patterns similar to MLL1 deletion are observed, supporting a role for MLL1 activity in regulating MLL1-dependent leukemia transcription. Thus, interruption of the WDR5-MLL1 interaction may be a useful strategy for treating patients with MLL leukemias. The molecules described herein will target this interaction and could provide an attractive therapeutic approach to develop novel drugs for leukemias with translocations of MLL gene and other leukemias with upregulation of target genes. It also appreciated that WDR5 has been implicated in other cancer types and may utilize the WIN-site for other chromatin regulatory complexes outside and/or overlapping with WRAD complex. As such the WIN-site inhibitors described herein may have utility in multiple cancer types through mechanisms of action involving both direct competitive WIN-site antagonism, or through allosteric inhibition of higher complexes wherein WDR5 is dependent for their proliferative activity and tumor formation. Examples include breast cancer (Dai, X. et al. PLoS One, 2015), MYC-driven tumor types (Thomas, et al. Molecular Cell, 2015), bladder cancer (Chen, X. et al. Nature, Scientific Reports, 2015), neuroblastoma (Sun, Y. et al. Cancer Research, 2015), and pancreatic cancer (Carugo, A. et al. Cell Reports, 2016).

The disclosed compounds and compositions may be used in methods for treatment of MLL related cancers. The methods of treatment may comprise administering to a subject in need of such treatment a composition comprising a therapeutically effective amount of the compound of formula (I).

In one aspect, disclosed is a method of treating cancer, the method comprising administration of a therapeutically effective amount of a compound of formula (I), or a pharmaceutically acceptable salt thereof to a subject in need thereof.

In certain embodiments, the cancer being treated is associated with dysfunction of MLL.

In certain embodiments, the cancer is at least one of leukemia, ovarian cancer, breast cancer, colorectal cancer, pancreatic cancer, gastric cancer, stomach cancer, lung cancer, cervical cancer, uterine cancer, cancers of the blood, and cancers of the lymphatic system.

In another aspect, disclosed is a method of disrupting the protein-protein interaction between WDR5 and MLL1, the method comprising administration of a therapeutically effective amount of a compound of formula (I), or a pharmaceutically acceptable salt thereof to a subject in need thereof.

The compositions can be administered to a subject in need thereof to bind WDR5 and modulate MLL, to treat a variety of diverse cancers. The present disclosure is directed to methods for administering the composition to inhibit the protein-protein interaction between WDR5 its binding partners such chromatin, cognate transcription and other regulatory factors, including for example the histone methyltransferase MLL1.

The compositions may be useful for treating certain cancers in humans and animals related to MLL dysfunction. Treatment of such cancers can be effected by modulating MLL1 in a subject, by administering a compound or composition of the invention, either alone or in combination with another active agent as part of a therapeutic regimen to a subject in need thereof.

Disruption of the the interaction between WDR5 and its binding partners (such as MLL1) can lead to treatment and reduction of cancer or tumor growth, and/or reduce metastasis of cancerous or tumor cells. Accordingly, the disclosed compositions can be used in methods that treat and/or prevent cancer or tumors in a subject administered the composition. The method can treat cancer or tumor based growth and can be any type of cancer such as, but not limited to, leukemia (mixed-lineage leukemia), ovarian cancer, breast cancer, colorectal cancer, pancreatic cancer, gastric cancer, stomach cancer, lung cancer, cervical cancer, uterine cancer, cancers of the blood, and cancers of the lymphatic system.

In some embodiments, the administered composition to a subject in need thereof can mediate reduction, clearance or prevention of additional growth of tumor cells by disrupting the ability of MLL1, another transcription factor, or chromatin to associate with WDR5, thereby reducing growth/proliferation of tumor cells, but does not have an effect on normal cells.

In some embodiments, the administered composition can increase tumor free survival, reduce tumor mass, slow tumor growth, increase tumor survival, or a combination thereof in the subject. The administered composition can reduce tumor volume in the subject in need thereof. The administered composition can increase tumor free survival in the subject after administration of the composition.

In some embodiments, the composition can be administered to clear or eliminate the cancer or tumor expressing the one or more oncogenes without damaging or causing illness or death in the subject administered the composition.

A. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

B. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds. For example, the compound of Formula (I) can be combined with a variety of different anti-cancer drugs such as chemotherapeutics, anti-tumor agents, and anti-proliferative agents.

Further, the compound of formula (I) can be combined with the following, but not limited to, actinomycins, alkylating agents, anthracyclines, antifolates, antiestrogen agents, anti-metabolites, anti-androgens, antimicrotubule agents, aromatase inhibitors, bleomycins, bromodomain inhibitors, $Ca^{2+}$ adenosine triphosphate (ATP)ase inhibitors, cytosine analogs, deltoids/retinoids, dihydrofolate reductase inhibitors, deoxyribonucleic acid (DNA) topoisomerase inhibitors, dopaminergic neurotoxins, glucocorticoids, histone deacetylase inhibitors, hormonal therapies, immunotherapeutic agents, inosine monophosphate (IMP) dehydrogenase inhibitors, isoprenylation inhibitors, luteinizing hormone-releasing hormone agonists, mammalian target of rapamycin (mtor) inhibitors, multi-drug resistance (MDR) inhibitors, mitomycins, photodyamic therapies, proteasome inhibitors, platinum containing compounds, radiation, receptor tyrosine kinase inhibitors, ribonucleotide reductase inhibitors, thrombospondin mimetics, uracil analogs, *vinca* alkaloids, vitamin D3 analogs, γ-radiation, DOTIL inhibitors, agents targeting epigenetic mechanisms, or an additional chemotherapeutic agent such as N-Ac-Sar-Gly-Val-D-alloIlle-Thr-Nva-Ile-Arg-Pro-NHCH2CH3 or a salt thereof, actinomycin D, AG13736, 17-allylamino-17-demethoxygeldanamycin, 9-aminocamptothecin, N-(4-(3-amino-1H-indazol-4-yl)phenyl)-N-(2-fluoro-5-methylphenyl)urea or a salt thereof, N-(4-(4-aminothieno[2,3-d]

pyrimidin-5-yl)phenyl}-N-(2-fluoro-5-(trifluoromethyl) phenyl)urea or a salt thereof, temozolomide, nedaplatin, satraplatin, triplatin tetranitrate, procarbazine, altretamine, mitozolomide, anastozole, AP-23573, asparaginase, azacitidine, bevacizurnab, bicalutamide, bleomycin a2, bleomycin b2, bortezemib, busulfan, campathecins, carboplatin, carmustine (BCNU), CB1093, cetuximab, CHOP (C: Cytoxan® (cyclophosphamide); H: Adriamycin® (hydroxydoxorubicin); O: Vincristine (Oncovin®); P: prednisone), chlorambucil, CHIR258, cisplatin, CNF-101, CNF-1001, CNF-2024, CP547632, crisnatol, cytarabine, cyclophosphamide, cytosine arabinoside, daunorubicin, dacarbazine, dactinomycin, dasatinib, daunorubicin, deferoxamine, demethoxyhypocrellin A, depsipeptide, dexamethasone, 17-dimethylaminoethylamino-17-demethoxygeldanamycin, docetaxel, doxifluridine, doxorubicin, EB 1089, epothilone D, epirubicin, 5-ethynyl-1-13-D-ribofuranosylimidazole-4-carboxamide (EICAR), erlotinib, etoposide, everolimus, 5-fluorouracil (5-FU), floxuridine, fludarabine, flutamide, gefitinib, geldanamycin, gemcitabine, goserelin, N-(2-(4-hydroxyanilino)-3-pyridinyl)-4-methoxybenzenesulfonamide or a salt thereof, hydroxyurea, idarubicin, ifosfamide, imatinab, interferon-a, interferon-y, IPI-504, irinotecan, KH 1060, lapatanib, leucovorin calcium, LAQ824, leuprolide acetate, letrozole, lomustine (CCNU), lovastatin, megestrol, melphalan, mercaptopurine, methotrexate, 1-methyl-4-phenylpyridinium, MG132, mitomycin, mitoxantrone, MLN518, MLN4924, MS-275, mycophenolic acid, mitomycin C, nitrosoureas, oprelvekin, oxaliplatin, paclitaxel, PARP inhibitors (e.g., rucaparib, niraparib, olaparib, iniparib, talazoparib, and veliparib), PD98059, peplomycin, photosensitizer Pc4, phtalocyanine, pirarubicin, plicamycin, prednisone, procarbizine, PTK787, PU24FC1, PU3, radicicol, raloxifene, rapamycin, ratitrexed, retinoids such as pheuretinide, ribavirin, rituximab (Rituxin®), sorafenib, staurosporine, steroids such as dexamethasone and prednisone, suberoylanilide hydroxamic acid, tamoxifen, taxol, temozolamide, teniposide, thapsigargin, thioguanine, thrombospondin-1, tiazofurin, topotecan, trapoxin, trastuzumab, treosulfan, trichostatin A, trimetrexate, trofosfamide, tumor necrosis factor, valproic acid, VER49009, verapamil, vertoporfin, vinblastine, vincristine, vindesine, vinorelbine vitamin D3, VX-680, zactima, ZK-EPO, zorubicin, bevacizumab, enzastaurin, temsirolimus, cilengitide, lapatinib, sunitinib, axitinib, pazopanib, vemurafenib, dabrafenib, JQ1 or combinations thereof.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

5. Biological Activity

The in vitro modulation of WDR5 protein was determined as follows.
MLL Peptide Binding Assay
General Provided compounds of the present invention can be demonstrated to compete for binding with fluorescently labeled peptides derived from relevant MLL protein.

Fluorescence Polarization Anisotropy Competition Assay

A fluorescence polarization anisotropy (FPA) assay that measures the displacement of either a FITC-labeled MLL-derived peptide or a more potent 10mer-Thr-FAM probe in response to compound treatment is performed (Karatas et al. J. Med. Chem. 2010, 5179.). The assay is run in 384-well format and is read on a BioTek Cytation. Compounds are run as 2 replicates on the left and right sides of the plate; therefore a plate can accommodate 16 compounds in a 10-point, 3-fold dilution scheme, plus positive and negative controls. Replicate values are fit to a 4-parameter fit in XLFit to generate a single $IC_{50}$ value for each compound that is then converted to a $K_i$ value. Experiments are repeated to generate a $2^{nd}$, independent $K_i$ value; values from the two experiments are averaged to produce the reported $K_i$ value for the compound. The assay performs with an average Z' value of 0.7, and is tolerant of up to 5% DMSO.

FPA Assay protocol adopted from Karatas et al. (J. Med. Chem. 2010, 5179; J. Amer. Chem. Soc. 2013, 669.): WDR5 (A23, residues 24-334), is expressed and purified in sufficient quantities for screening. FITC-MLL peptide (FITC-GSARAEVHLRKS) and 10mer-Thr-FAM (ARTEVHL-RKS-(Ahx-AhxXLys-(5-FAM))) were purchased from GeneScript and used without additional purification. FITC-MLL peptide is used at 50 nM, while WDR5 is added at the $K_i$ value of the protein:peptide interaction (WDR5-WIN $K_i$=2.5 µM). 10mer-Thr-FAM peptide is used at 4 nM, while WDR5 is added at the $K_i$ value of the protein:peptide interaction (WDR5-10mer-Thr $K_i$=4 nM).

Stock compounds are dispensed in barcoded 384-well plates as 30 mM solutions in DMSO. This plate is used as the source plate for the Echo Liquid Handler, which distributes the compounds to the assay plate (black, flat-bottom; Greiner) in a 10-point, 3-fold dilution scheme with a top concentration of 100 µM (5 nM low concentration) in a final volume of 50 µL. Both the top concentration and the dilution scheme can be adjusted to fit the anticipated potency of the compounds.

For the FITC-MLL assay, 2.5 µM WDR5 and 50 nM FITC-MLL peptide in assay buffer (1x Phosphate Buffered Saline, pH 6.0, 300 mM NaCl, 0.5 mM TCEP, 0.1% CHAPS) is added to all compound-containing wells and to columns 2, 24 (negative control, 0% inhibition). 2 µL of 50 nM FITC-MLL peptide alone in assay buffer is added to columns 1, 23 (positive control, 100% inhibition). For the 10mer-Thr-FAM assay, a similar addition protocol is performed, using 4 nM WDR5 and 4 nM 10mer-Thr-FAM peptide in assay buffer (1x Phosphate Buffered Saline pH 6.0, 300 mM NaCl, 0.5 mM TCEP, 0.1% CHAPS).

The plate is covered, shielded from light, and incubated for 60 min at room temperature, with rocking. Anisotropy is measured at excitation wavelength 480 nm and emission wavelength 535 nm using an EnVision Multi-label plate reader (PerkinElmer, Wellesley, Mass., USA) or a BioTek Cytation 3 (BioTek, Winooski, Vt., USA). Fluorescence anisotropy is plotted against compound concentration to generate an $IC_{50}$ (inhibitor concentration at which 50% of bound peptide is displaced) by fitting the data to a 4-parameter logistic model using XLFit software (Guildford, Surrey, UK). $IC_{50}$ is converted to a binding dissociation constant ($K_i$ value) according to the formula of Wang Z. FEBS Lett (1996) 3, 245.

$$K_i = [I]_{50}/([L]_{50}/K_d + [P]_0/K_d + 1)$$

where $[I]_{50}$ is the concentration of the free inhibitor at 50% inhibition, $[L]_{50}$ is the concentration of the free labeled ligand at 50% inhibition, $[P]_0$ is the concentration of the free protein at 0% inhibition, $K_d$ represents the dissociation constant of the FITC-MLL or 10mer-Thr-FAM probe for WDR5. Total fluorescence is also measured, to rule out compounds that are inherently fluorescent or able to act as quenchers in the assay.

TR-FRET Binding Assay

A Time-Resolved Fluorescence Resonance Energy Transfer (TR-FRET) assay that measures the displacement of the 10mer-Thr-FAM probe in response to compound treatment was performed for compounds wherein the IC50 from FPA assay using 10mer-Thr-FAM was below the lower assay IC50 limit ~1 nM. Excess 10mer-Thr-FAM probe was utilized with His-tagged WDR5 in conjunction with a commercial anti-His antibody containing a Terbium label. The LanthaScreen™ Elite Tb-anti-HIS Antibody from Thermo-Fisher Scientific was used for this purpose. This Th-anti-HIS has an excitation/emission of 340 nm and 490 nm, respectively. The 10mer-Thr-FAM probe when bound to WDR5 will undergo a FRET interaction with the Tb-anti-HIS and emit at 520 nm. The ratio of the 520 and 495 signals are then utilized to generate a dose-response curve to calculate an IC50 value. By virtue of FRET there is little to no background fluorescence interference from 10mer-Thr-FAM probe allowing an excess of the probe to be used permitting an increase in the lower limit of the calculated Ki when testing against highly potent inhibitors with Ki<<1 nM. WDR5-His Tag (A23, residues 24-334) is expressed and purified in our lab in sufficient quantities for screening. 10mer-Thr-FAM peptide is used anywhere from 15 to 150 nM depending on the window of sensitivity required. WDR5-His tag protein is used at 2 nM. A source plate is prepared using an Echo Liquid Handler, which distributes the compounds to the assay plate (white, flat-bottom; Opti-Plate) in a 10-point, 3-fold dilution schemes with a top concentration of either 5 or 20 µM depending on the anticipated potency of the compounds, in a final volume of 20 µL. A final target (WDR5)/Tb-Ab concentration of 2 nM/1 nM is dispensed from appropriate stock solutions, respectively. The final DMSO concentration in each well of the assay plate is 1% or lower. As before the plate is covered, shielded from light, and incubated for 60 minutes at room temperature with rocking. Anisotropy is then measured on a Biotek Cytation 3 at excitation wavelength of 340 nm, and emission wavelengths of 495 nm and 520 nm. Working buffer conditions (pH 7.0) are similar to that in FPA above. TR-FRET signal is plotted and IC50 and Ki values are calculated in the same manner as the fluorescence polarization anisotropy based competition assays. The results for representative compounds are shown in Table 2.

TABLE 2

$K_i$ for Exemplified Compounds for Inhibition of WDR5 by TR-FRET assay

| Example | $K_i$ (nM) | Example | $K_i$ (nM) | Example | $K_i$ (nM) | Example | $K_i$ (nM) |
|---|---|---|---|---|---|---|---|
| 1 | <0.1 | 92 | 0.72 | 183 | 0.71 | 275 | <0.1 |
| 2 | <0.1 | 93 | 1.9 | 184 | 0.56 | 276 | <0.1 |
| 3 | <0.1 | 94 | 36 | 185 | <0.1 | 277 | >33 |
| 4 | 0.34 | 95 | 20 | 186 | <0.1 | 278 | 0.34 |
| 5 | 0.35 | 96 | 27 | 187 | <0.1 | 279 | 0.61 |
| 6 | 24 | 97 | 0.14 | 188 | <0.1 | 280 | <0.1 |
| 7 | 0.80 | 98 | 0.06 | 189 | <0.1 | 281 | <0.1 |
| 8 | 0.27 | 99 | 1.1 | 190 | 0.11 | 282 | 0.21 |
| 9 | 0.15 | 100 | 0.71 | 191 | <0.1 | 283 | 0.02 |
| 10 | 1.5 | 101 | 0.45 | 192 | <0.1 | 284 | 0.11 |
| 11 | 0.83 | 102 | 0.32 | 193 | <0.1 | 285 | <0.1 |

TABLE 2-continued $K_i$ for Exemplified Compounds for Inhibition of WDR5 by TR-FRET assay

| Example | $K_i$ (nM) | Example | $K_i$ (nM) | Example | $K_i$ (nM) | Example | $K_i$ (nM) |
|---|---|---|---|---|---|---|---|
| 12 | 1.2 | 103 | 20 | 194 | <0.1 | 286 | <0.1 |
| 13 | 2.7 | 104 | 0.13 | 195 | <0.1 | 287 | <0.1 |
| 14 | 6.0 | 105 | <0.1 | 196 | <0.1 | 288 | 8.7 |
| 15 | 2.7 | 106 | 0.34 | 197 | <0.1 | 289 | 31 |
| 16 | 0.49 | 107 | 0.23 | 198 | <0.1 | 290 | 20 |
| 17 | 0.94 | 108 | <0.1 | 199 | 0.30 | 291 | <0.1 |
| 18 | 3.5 | 109 | <0.1 | 200 | 0.15 | 292 | 1.1 |
| 19 | 0.35 | 110 | 0.10 | 201 | <0.1 | 293 | 0.54 |
| 20 | 2.5 | 111 | <0.1 | 202 | <0.1 | 294 | <0.1 |
| 21 | 0.64 | 112 | 29 | 203 | <0.1 | 295 | <0.1 |
| 22 | 6.4 | 113 | >33 | 204 | <0.1 | 296 | 7.0 |
| 23 | 5.7 | 114 | <0.1 | 205 | <0.1 | 297 | 2.3 |
| 24 | 25 | 115 | <0.1 | 206 | 0.34 | 298 | <0.1 |
| 25 | 1.3 | 116 | 0.40 | 207 | <0.1 | 299 | <0.1 |
| 26 | 0.72 | 117 | 0.15 | 208 | 0.59 | 300 | <0.1 |
| 27 | 1.5 | 118 | 0.83 | 209 | <0.1 | 301 | <0.1 |
| 28 | 0.35 | 119 | 0.16 | 210 | <0.1 | 302 | <0.1 |
| 29 | 0.28 | 120 | <0.1 | 211 | <0.1 | 303 | <0.1 |
| 30 | <0.1 | 121 | >33 | 212 | <0.1 | 304 | <0.1 |
| 31 | 0.17 | 122 | >33 | 213 | <0.1 | 305 | <0.1 |
| 32 | 0.88 | 123 | 0.18 | 214 | <0.1 | 306 | <0.1 |
| 33 | 0.99 | 124 | 1.0 | 215 | <0.1 | 307 | 0.95 |
| 34 | 16 | 125 | <0.1 | 216 | <0.1 | 308 | 0.45 |
| 35 | 1.3 | 126 | 2.5 | 217 | <0.1 | 309 | 0.77 |
| 36 | 8.5 | 127 | 0.21 | 218 | <0.1 | 310 | <0.1 |
| 37 | 0.40 | 128 | 23 | 219 | <0.1 | 311 | 1.49 |
| 38 | 3.7 | 129 | >33 | 220 | <0.1 | 312 | <0.1 |
| 39 | 17 | 130 | >33 | 221 | <0.1 | 313 | 1.2 |
| 40 | 133 | 131 | <0.1 | 222 | 0.33 | 314 | 4.0 |
| 41 | 33 | 132 | 0.13 | 223 | 1.3 | 315 | 1.0 |
| 42 | 10 | 133 | >33 | 224 | 0.14 | 316 | 0.91 |
| 43 | 8423 | 134 | 38 | 225 | <0.1 | 317 | 0.28 |
| 44 | 9.2 | 135 | 0.83 | 226 | 7.1 | 318 | 0.29 |
| 45 | 0.74 | 136 | <0.1 | 227 | 2.1 | 319 | 0.32 |
| 46 | 1.3 | 137 | >33 | 228 | >33 | 320 | <0.1 |
| 47 | 0.88 | 138 | 1.1 | 229 | 0.21 | 321 | <0.1 |
| 48 | 26 | 139 | 0.18 | 230 | 0.06 | 322 | <0.1 |
| 49 | 22 | 140 | 10 | 231 | 0.62 | 323 | 1.8 |
| 50 | 27 | 141 | <0.1 | 232 | 0.06 | 324 | <0.1 |
| 51 | 17 | 142 | <0.1 | 233 | 1.5 | 325 | <0.1 |
| 52 | 0.19 | 143 | <0.1 | 234 | 1.0 | 326 | <0.1 |
| 53 | 0.56 | 144 | 1.14 | 235 | 3.5 | 327 | <0.1 |
| 54 | <0.1 | 145 | 0.95 | 236 | 0.16 | 328 | <0.1 |
| 55 | 1.8 | 146 | 10 | 237 | 7.5 | 330 | 0.22 |
| 56 | 1.2 | 147 | 0.37 | 238 | 2.9 | 331 | 0.30 |
| 57 | >33 | 148 | 0.29 | 239 | 5.3 | 332 | 19 |
| 58 | 0.93 | 149 | 0.56 | 240 | 10 | 333 | 0.39 |
| 59 | 0.58 | 150 | 0.13 | 241 | 6.0 | 334 | <0.1 |
| 60 | <0.1 | 151 | 0.59 | 242 | <0.1 | 335 | <0.1 |
| 61 | 2.8 | 152 | 8.9 | 243 | <0.1 | 336 | <0.1 |
| 62 | 0.29 | 153 | 0.33 | 244 | <0.1 | 337 | <0.1 |
| 63 | 0.10 | 154 | <0.1 | 245 | <0.1 | 338 | <0.1 |
| 64 | 0.59 | 155 | 1.4 | 246 | 182 | 339 | <0.1 |
| 65 | 0.63 | 156 | <0.1 | 247 | 0.14 | 340 | <0.1 |
| 66 | 0.12 | 157 | <0.1 | 248 | <0.1 | 341 | 0.35 |
| 67 | 3.9 | 158 | <0.1 | 249 | <0.1 | 342 | <0.1 |
| 68 | 0.35 | 159 | <0.1 | 250 | 0.40 | 343 | 0.51 |
| 69 | 2.4 | 160 | <0.1 | 251 | 1.24 | 344 | 0.48 |
| 70 | 1.1 | 161 | <0.1 | 252 | 21 | 345 | 2.4 |
| 71 | 0.33 | 162 | <0.1 | 253 | <0.1 | 346 | 1.6 |
| 72 | 0.05 | 163 | 0.68 | 254 | 0.12 | 347 | <0.1 |
| 73 | 0.14 | 164 | 1.4 | 255 | 0.62 | 348 | <0.1 |
| 74 | 0.64 | 165 | 0.14 | 256 | 2.7 | 349 | <0.1 |
| 75 | 1.2 | 166 | <0.1 | 257 | 2.0 | 350 | 0.12 |
| 76 | <0.1 | 167 | 0.21 | 258 | 5.8 | 351 | <0.1 |
| 77 | 0.18 | 168 | 27 | 259 | <0.1 | 352 | <0.1 |
| 78 | 5.9 | 169 | 23 | 260 | 25 | 353 | <0.1 |
| 79 | 4.3 | 170 | 0.22 | 261 | 0.28 | 354 | <0.1 |
| 80 | 20 | 171 | 0.13 | 262 | >33 | 355 | 3.57 |
| 81 | 13 | 172 | <0.1 | 263 | 0.29 | 356 | 182 |
| 82 | 20 | 173 | 0.89 | 265 | 0.78 | 357 | 1.3 |
| 83 | 7.1 | 174 | <0.1 | 266 | 16 | 358 | 5.5 |
| 84 | 0.12 | 175 | 0.11 | 267 | 0.18 | 359 | 8.7 |
| 85 | <0.1 | 176 | 0.50 | 268 | <0.1 | 360 | 1.0 |

TABLE 2-continued

K$_i$ for Exemplified Compounds for Inhibition of WDR5 by TR-FRET assay

| Example | K$_i$ (nM) | Example | K$_i$ (nM) | Example | K$_i$ (nM) | Example | K$_i$ (nM) |
|---|---|---|---|---|---|---|---|
| 86 | 0.11 | 177 | 3.9 | 269 | <0.1 | 361 | 0.77 |
| 87 | 0.80 | 178 | 3.3 | 270 | 0.18 | 362 | 0.72 |
| 88 | 3.4 | 179 | <0.1 | 271 | 0.72 | 363 | <0.1 |
| 89 | 15 | 180 | 0.13 | 272 | <0.1 | 364 | 4.3 |
| 90 | 0.46 | 181 | 0.35 | 273 | <0.1 | 365 | 0.55 |
| 91 | <0.1 | 182 | 1.0 | 274 | <0.1 | 366 | 13 |

Among other things, these data demonstrate the utility of representative compounds as selective inhibitors of the activity of WDR5 protein to bind peptides from relevant MLL domain.

Cellular Viability of Human Tumor Cell Lines

Anti-Proliferative Activity Using MLL-Harboring Cell Lines.

MV4:11 cells are grown in RPMI-1640 media supplemented with 10% FBS and 1% penicillin/streptomycin. Viability assays are performed by dispensing 3600 cells/ml into each well of an opaque 384-well plate and adding compounds at the indicated concentrations in a final volume of 32 μL and a final concentration of DMSO of 0.1% for all samples. After a set incubation period, 7 day protocol, the viability of cells in each well is assessed using the CellTiter-Glo assay (Promega), read on a GloMax 96 Microplane Luminometer (Promega). Serial dilutions of each cell type are included in all assays to generate standard curves and determine assay measurements are taken within the dynamic range of the instrument. GI$_{50}$ values are calculated based on three biological replicates, each with three technical replicates. Data are expressed as mean plus/minus S.E.M.

TABLE 3

GI$_{50}$ (in μM) for representative compounds on cellular proliferation of MV4:11 human cancer cell lines

| Example | GI$_{50}$ (μM) |
|---|---|
| 1 | 0.30 |
| 3 | 0.55 |
| 5 | 0.24 |
| 8 | 0.17 |
| 9 | 0.22 |
| 10 | 2.3 |
| 22 | 14 |
| 23 | 6.2 |
| 25 | 6.1 |
| 26 | 0.79 |
| 27 | 3.1 |
| 28 | 1.3 |
| 29 | 0.78 |
| 30 | 0.10 |
| 31 | 0.30 |
| 32 | 1.5 |
| 33 | 4.9 |
| 34 | 30 |
| 35 | 9.0 |
| 37 | 3.8 |
| 38 | 6.0 |
| 39 | 30 |
| 42 | 28 |
| 44 | 22 |
| 45 | 1.8 |
| 46 | 5.9 |
| 47 | 6.7 |
| 52 | 0.51 |
| 53 | 0.58 |
| 54 | <0.1 |
| 55 | 1.8 |
| 56 | 0.45 |
| 59 | 0.46 |
| 60 | <0.1 |
| 61 | 4.2 |
| 62 | 0.80 |
| 63 | 0.46 |
| 64 | 0.93 |
| 65 | 0.30 |
| 66 | 0.51 |
| 67 | 3.8 |
| 68 | 2.7 |
| 69 | 5.1 |
| 70 | 2.4 |
| 71 | 1.9 |
| 72 | 0.18 |
| 73 | 1.8 |
| 74 | 4.5 |
| 75 | 12 |
| 76 | 0.26 |
| 77 | 1.2 |
| 84 | 2.1 |
| 91 | 0.21 |
| 97 | 0.25 |
| 98 | 0.16 |
| 102 | 2.16 |
| 104 | 14 |
| 105 | 0.40 |
| 107 | 0.95 |
| 108 | 0.31 |
| 109 | <0.1 |
| 111 | 0.30 |
| 114 | 0.30 |
| 115 | <0.1 |
| 116 | 0.57 |
| 117 | 0.31 |
| 118 | 6.3 |
| 119 | 7.6 |
| 120 | 0.22 |
| 121 | 5.9 |
| 122 | 4.2 |
| 125 | 0.18 |
| 127 | 0.73 |
| 131 | 0.14 |
| 132 | 0.61 |
| 139 | 0.73 |
| 141 | <0.1 |
| 142 | <0.1 |
| 143 | 0.17 |
| 147 | 0.84 |
| 154 | 0.12 |
| 156 | 0.47 |
| 157 | 0.10 |
| 158 | 0.17 |
| 159 | 0.19 |
| 160 | <0.1 |
| 161 | <0.1 |
| 162 | 0.13 |
| 166 | 0.36 |
| 172 | 0.16 |
| 174 | <0.1 |
| 175 | 0.32 |
| 179 | 0.23 |
| 185 | 0.61 |
| 186 | 0.58 |
| 187 | 0.44 |
| 188 | <0.1 |
| 189 | 0.12 |
| 190 | 0.19 |
| 191 | 0.08 |
| 192 | 0.50 |
| 193 | <0.1 |
| 194 | <0.1 |
| 195 | 0.94 |
| 196 | <0.1 |

TABLE 3-continued

GI$_{50}$ (in μM) for representative compounds on cellular proliferation of MV4:11 human cancer cell lines

| Example | GI$_{50}$ (μM) |
|---|---|
| 198 | <0.1 |
| 199 | 0.94 |
| 200 | 0.71 |
| 201 | 0.14 |
| 202 | <0.1 |
| 203 | <0.1 |
| 204 | <0.1 |
| 205 | <0.1 |
| 207 | <0.1 |
| 209 | <0.1 |
| 210 | <0.1 |
| 211 | <0.1 |
| 212 | <0.1 |
| 213 | <0.1 |
| 214 | <0.1 |
| 215 | <0.1 |
| 216 | <0.1 |
| 217 | <0.1 |
| 219 | <0.1 |
| 220 | 0.22 |
| 221 | <0.1 |
| 227 | 0.94 |
| 229 | 0.55 |
| 230 | 0.64 |
| 231 | 0.87 |
| 232 | 0.21 |
| 233 | 1.1 |
| 234 | 0.87 |
| 235 | 3.1 |
| 236 | 0.45 |
| 238 | 3.8 |
| 239 | 5.3 |
| 241 | 12 |
| 242 | 0.12 |
| 243 | <0.1 |
| 244 | 0.30 |
| 245 | 0.18 |
| 247 | 0.27 |
| 248 | 0.12 |
| 249 | 0.37 |
| 250 | 0.57 |
| 253 | <0.1 |
| 254 | 0.34 |
| 259 | <0.1 |
| 261 | 0.73 |
| 268 | <0.1 |
| 269 | <0.1 |
| 272 | 0.10 |
| 273 | 0.14 |
| 274 | <0.1 |
| 275 | <0.1 |
| 276 | <0.1 |
| 280 | <0.1 |
| 281 | <0.1 |
| 282 | 0.20 |
| 283 | 0.12 |
| 284 | 0.27 |
| 285 | <0.1 |
| 286 | <0.1 |
| 287 | 0.10 |
| 291 | <0.1 |
| 292 | 0.71 |
| 293 | 0.48 |
| 294 | <0.1 |
| 295 | <0.1 |
| 298 | <0.1 |
| 299 | <0.1 |
| 300 | <0.1 |
| 301 | 0.27 |
| 302 | <0.1 |
| 303 | <0.1 |
| 305 | <0.1 |
| 306 | 0.41 |
| 307 | 0.91 |
| 308 | 0.63 |
| 309 | 0.96 |
| 310 | 0.17 |
| 312 | <0.1 |
| 320 | <0.1 |
| 321 | <0.1 |
| 322 | 0.15 |
| 324 | <0.1 |
| 325 | <0.1 |
| 327 | <0.1 |
| 328 | <0.1 |
| 331 | 0.95 |
| 332 | 1.4 |
| 333 | 0.52 |
| 334 | <0.1 |
| 335 | <0.1 |
| 336 | <0.1 |
| 337 | <0.1 |
| 338 | <0.1 |
| 339 | 0.10 |
| 340 | <0.1 |
| 341 | 0.10 |
| 342 | <0.1 |
| 343 | 0.25 |
| 344 | 0.68 |
| 347 | <0.1 |
| 348 | <0.1 |
| 349 | <0.1 |
| 350 | 0.14 |
| 351 | <0.1 |
| 352 | <0.1 |
| 355 | 1.19 |
| 361 | 0.94 |
| 364 | 7.8 |
| 365 | 6.0 |
| 366 | 30 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I)

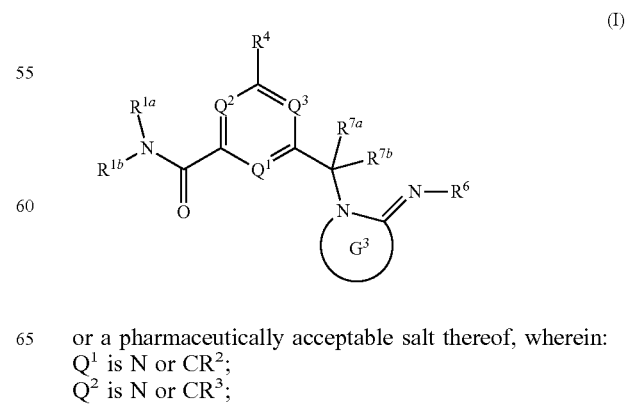

or a pharmaceutically acceptable salt thereof, wherein:
Q$^1$ is N or CR$^2$;
Q$^2$ is N or CR$^3$;

$Q^3$ is N or $CR^5$;
$R^{1a}$ is $G^1$ or —$(CR^aR^b)_n$-$G^1$;
n is 1, 2, or 3;
$R^a$ is hydrogen, $C_{1-4}$alkyl, $C_{1-4}$haloalkyl, $C_{3-6}$carbocycle, or —$C_{1-3}$alkylene-C(O)$YR^{20}$;
Y is O, NH, or $NC_{1-4}$alkyl;
$R^{20}$ is H, $C_{1-4}$alkyl, $C_{3-6}$cycloalkyl, or —$C_{1-3}$alkylene-$R^{30}$;
$R^{30}$ is C(O)$C_{1-4}$alkyl, C(O)$C_{3-6}$cycloalkyl, or phenyl, wherein the $C_{3-6}$cycloalkyl and phenyl are optionally substituted with 1-4 substituents independently selected from the group consisting of halogen, $C_{1-4}$alkyl, —$OC_{1-4}$alkyl, and $C_{1-4}$haloalkyl;
$R^b$ is hydrogen or $C_{1-4}$alkyl;
or alternatively $R^a$ and $R^b$ together with the carbon atom to which they are attached form a ring selected from a 3-8 membered saturated or partially unsaturated carbocyclic ring, a 3-8 membered saturated or partially unsaturated heterocyclic ring having 1-4 heteroatoms independently selected from nitrogen, oxygen, or sulfur;
or alternatively $R^a$ and $R^b$ are taken together to form an oxo group;
$R^{1b}$ is hydrogen, $C_{1-4}$alkyl, $C_{3-6}$cycloalkyl, or —$C_{1-3}$alkylene-$C_{3-6}$cycloalkyl;
$G^1$ is 6- to 12-membered aryl, a 5- to 12-membered heteroaryl, a 4- to 12-membered heterocyclyl, or a $C_{3-10}$carbocycle optionally fused to a phenyl or to a 5- to 6-membered heteroaryl, wherein $G^1$ is optionally substituted with 1-5 substituents independently selected from the group consisting of halogen, $C_{1-6}$alkyl, $C_{1-6}$haloalkyl, oxo, —$OR^{1c}$, —$NR^{1c}R^{1d}$, —$SR^{1c}$, cyano, —C(O)$OR^{1c}$, —C(O)$NR^{1c}R^{1d}$, —C(O)$R^{1e}$, —$SOR^{1e}$, —$SO_2R^{1e}$, —$SO_2NR^{1c}R^{1d}$, —$NR^{1c}$C(O)$R^{1e}$, —$NR^{1c}$C(O)$OR^{1d}$, —$NR^{1c}$C(O)$NR^{1c}R^{1d}$, —$NR^{1c}S(O)_2R^{1e}$, —$NR^{1c}S(O)_2NR^{1c}R^{1d}$, $C_{3-8}$cycloalkyl, and —$C_{1-3}$alkylene-$C_{3-8}$cycloalkyl, wherein the $C_{3-5}$cycloalkyl and —$C_{1-3}$alkylene-$C_{3-8}$cycloalkyl are optionally substituted with 1-4 substituents independently selected from $C_{1-4}$alkyl and halogen;
$R^2$ is hydrogen, halogen, $C_{1-4}$alkyl, or $C_{1-6}$haloalkyl;
$R^3$ is hydrogen, halogen, $C_{1-4}$alkyl, $C_{1-4}$haloalkyl, —$OR^{3a}$, —$NR^{3a}R^{3b}$, —$SR^{3a}$, cyano, —C(O)$OR^{3a}$, —C(O)$NR^{3a}R^{3b}$, —C(O)$R^{3c}$, —$SOR^{3c}$, —$SO_2R^{3c}$, —$SO_2NR^{3a}R^{3b}$, —$NR^{3a}$C(O)$R^{3c}$, —$NR^{3a}$C(O)$OR^{3b}$, —$NR^{3a}$C(O)$NR^{3a}R^{3b}$, —$NR^{3a}S(O)_2R^{3c}$, —$NR^{3a}S(O)_2NR^{3a}R^{3b}$, $C_{3-8}$cycloalkyl, or —$C_{1-3}$alkylene-$C_{3-8}$cycloalkyl, wherein the $C_{3-8}$cycloalkyl and —$C_{1-3}$alkylene-$C_{3-8}$cycloalkyl are optionally substituted with 1-4 substituents independently selected from $C_{1-4}$alkyl and halogen;
$R^4$ is hydrogen, halogen, $C_{1-6}$alkyl, $C_{1-6}$haloalkyl, $C_{1-6}$haloalkenyl, -L-$R^x$, $G^2$, -L-$G^2$, or -L-$C_{1-3}$alkyl ene-$G^2$;
L is O, S, —$NR^{4a}$—, —S(O)—, —$S(O)_2$—, —$S(O)_2NR^{4a}$—, —C(O)$NR^{4a}$—, —C(O)—, —$NR^{4a}$C(O)—, —$NR^{4a}$C(O)O—, —$NR^{4a}$C(O)$NR^{4a}$—, —$NR^{4a}S(O)_2$—, or —$NR^{4a}S(O)_2NR^{4a}$—;
$R^x$ is hydrogen, $C_{1-6}$alkyl, or $C_{1-6}$haloalkyl;
$G^2$ is a $C_{3-10}$carbocycle, a 6- to 12-membered aryl, a 5- to 12-membered heteroaryl, or a 4- to 12-membered heterocycle, wherein $G^2$ is optionally substituted with 1-5 substituents independently selected from the group consisting of halogen, $C_{1-6}$alkyl, $C_{1-6}$haloalkyl, oxo, —$OR^{4b}$, —$NR^{4b}R^{4c}$, —$SR^{4b}$, cyano, —C(O)$OR^{4b}$, —C(O)$NR^{4b}R^{4c}$, —C(O)$R^{4d}$, —$SOR^{4d}$, —$SO_2R^{4d}$, —$SO_2NR^{4b}R^{4c}$, —$NR^{4b}$C(O)$R^{4d}$, —$NR^{4b}$C(O)$OR^{4c}$, —$NR^{4b}$C(O)$NR^{4b}R^{4c}$, —$NR^{4b}S(O)_2R^{4d}$, —$NR^{4b}$ $S(O)_2NR^{4b}R^{4c}$, $C_{3-8}$cycloalkyl, and —$C_{1-3}$alkylene-$C_{3-8}$cycloalkyl, wherein the $C_{3-8}$cycloalkyl and —$C_{1-3}$alkylene-$C_{3-8}$cycloalkyl are optionally substituted with 1-4 substituents independently selected from $C_{1-4}$alkyl and halogen;
$R^5$ is hydrogen, halogen, $C_{1-4}$alkyl, $C_{1-4}$haloalkyl, —$OR^{5a}$, —$NR^{5a}R^{5b}$, —$SR^{5a}$, cyano, —C(O)$OR^{5a}$, —C(O)$NR^{5a}R^{5b}$, —C(O)$R^{5c}$, —$SOR^{5c}$, —$SO_2R^{5c}$, —$SO_2NR^{5a}R^{5b}$, —$NR^{5a}$C(O)$R^{5c}$, —$NR^{5a}$C(O)$OR^{5b}$, —$NR^{5a}$C(O)$NR^{5a}R^{5b}$, —$NR^{5a}S(O)_2R^{5c}$, —$NR^{5a}$ $S(O)_2NR^{5a}R^{5b}$, $C_{3-8}$cycloalkyl, or —$C_{1-3}$alkylene-$C_{3-8}$cycloalkyl, wherein the $C_{3-8}$cycloalkyl and —$C_{1-3}$alkylene-$C_{3-8}$cycloalkyl are optionally substituted with 1-4 substituents independently selected from $C_{1-4}$alkyl and halogen;
$G^3$ is

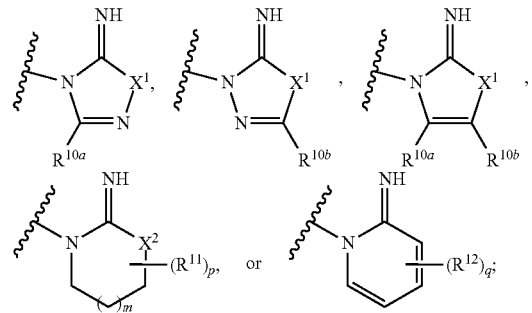

$X^1$ is $NR^{13}$, O, or S;
$X^2$ is C($R^{14a}YR^{14b}$), $NR^{13}$, O, or S;
$R^{10a}$ and $R^{10b}$ are independently hydrogen, $C_{1-4}$alkyl, or $C_{1-6}$haloalkyl;
$R^{11}$, at each occurrence, is independently halogen, $C_{1-4}$alkyl or $C_{1-4}$haloalkyl;
$R^{12}$, at each occurrence, is independently halogen, $C_{1-4}$alkyl or $C_{1-4}$haloalkyl;
$R^{13}$ is hydrogen, $C_{1-4}$alkyl $C_{1-4}$haloalkyl $C_{3-8}$cycloalkyl, $C_{1-3}$alkylene-$C_{3-5}$cycloalkyl, or phenyl, the phenyl and cycloalkyl-containing substituents being further optionally substituted with 1-4 substituents independently selected from halogen, $C_{1-4}$alkyl $C_{1-4}$haloalkyl, OH, and —$OC_{1-4}$alkyl;
$R^{14a}$ and $R^{14b}$ are independently hydrogen or $C_{1-4}$alkyl;
m is 0, 1, or 2;
p and q are each independently 0, 1, 2, 3, or 4;
$R^6$ is hydrogen, C(O)$C_{1-4}$alkyl, or C(O)$OC_{1-4}$alkyl;
$R^{7a}$ and $R^{7b}$ are independently selected from hydrogen, halogen, $C_{1-4}$alkyl, and $C_{1-4}$haloalkyl, or $R^{7a}$ and $R^{7b}$ are taken together to form an oxo group; and
$R^{1c}$, $R^{1d}$, $R^{1e}$, $R^{3a}$, $R^{3b}$, $R^{3c}$, $R^{4a}$, $R^{4b}$, $R^{4c}$, $R^{4d}$, $R^{5a}$, $R^{5b}$, and $R^{5c}$, at each occurrence, are independently hydrogen, $C_{1-6}$alkyl, $C_{1-6}$haloalkyl, $C_{3-5}$cycloalkyl, or —$C_{1-6}$alkylene-$C_{3-8}$cycloalkyl, wherein the $C_{3-5}$cycloalkyl and —$C_{1-6}$alkylene-$C_{3-8}$cycloalkyl are optionally substituted with 1-4 substituents independently selected from $C_{1-4}$alkyl and halogen, wherein alternatively $R^{1c}$ and $R^{1d}$, $R^{3a}$ and $R^{3b}$, $R^{4b}$ and $R^{4c}$, and/or $R^{5a}$ and $R^{5b}$, each together with a common nitrogen atom to which each attaches form a 4- to 8-membered saturated or partially unsaturated heterocyclic ring, optionally substituted with 1-4 substituents independently selected from $C_{1-4}$alkyl, $C_{1-4}$haloalkyl, oxo, —OH, and —$OC_{1-4}$alkyl.

2. The compound of claim 1, or a pharmaceutically acceptable salt thereof, wherein $G^3$ is

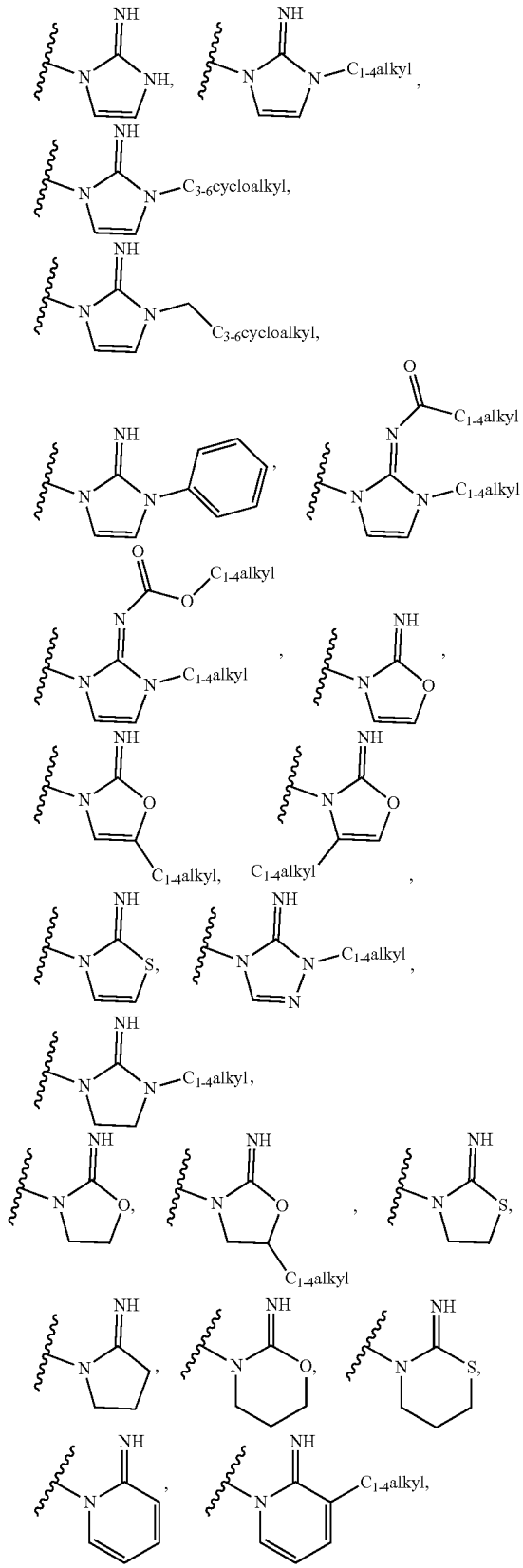

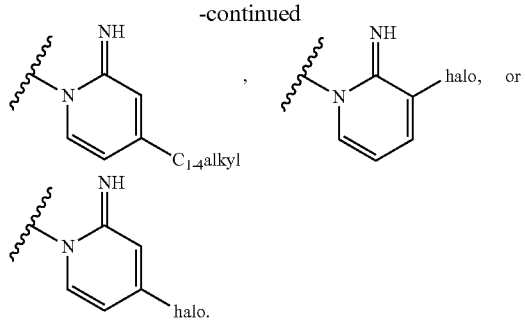

3. The compound of claim 1, or a pharmaceutically acceptable salt thereof, wherein:
$R^{1a}$ is $G^{1a}$ or $-(CR^aR^b)-G^{1b}$;
$G^{1a}$ is a 9- to 10-membered heteroaryl or a $C_{3-7}$carbocycle optionally fused to a phenyl, wherein $G^{1a}$ is optionally substituted with 1-4 substituents independently selected from the group consisting of halogen, $C_{1-6}$alkyl, $C_{1-6}$haloalkyl, oxo, $-OR^{1c}$, $-NR^{1c}R^{1d}$, $-SR^{1c}$, cyano, $-C(O)OR^{1c}$, $-C(O)NR^{1c}R^{1d}$, $-C(O)R^{1e}$, $-SOR^{1e}$, $-SO_2R^{1e}$, $-SO_2NR^{1c}R^{1d}$, $-NR^{1c}C(O)R^{1e}$, $-NR^{1c}C(O)OR^{1d}$, $-NR^{1c}C(O)NR^{1c}R^{1d}$, $-NR^{1c}S(O)_2R^{1e}$, $-NR^{1c}S(O)_2NR^{1c}R^{1d}$, $C_{3-8}$cycloalkyl, and $-C_{1-3}$alkylene-$C_{3-8}$cycloalkyl, wherein the $C_{3-5}$cycloalkyl and $-C_{1-3}$alkylene-$C_{3-8}$cycloalkyl are optionally substituted with 1-4 substituents independently selected from $C_{1-4}$alkyl and halogen; and
$G^{1b}$ is phenyl, a 5- to 6-membered heteroaryl, or a 4- to 8-membered heterocyclyl, wherein $G^{1b}$ is optionally substituted with 1-4 substituents independently selected from the group consisting of halogen, $C_{1-6}$alkyl, $C_{1-6}$haloalkyl, oxo, $-OR^{1c}$, $-NR^{1c}R^{1d}$, $-SR^{1c}$, cyano, $-C(O)OR^{1c}$, $-C(O)NR^{1c}R^{1d}$, $-C(O)R^{1e}$, $-SOR^{1e}$, $-SO_2R^{1e}$, $-SO_2NR^{1c}R^{1d}$, $-NR^{1c}C(O)R^{1e}$, $-NR^{1c}C(O)OR^{1d}$, $-NR^{1c}C(O)NR^{1c}R^{1d}$, $-NR^{1c}S(O)_2R^{1e}$, $-NR^{1c}S(O)_2NR^{1c}R^{1d}$, $C_{3-8}$cycloalkyl, and $-C_{1-3}$alkylene-$C_{3-8}$cycloalkyl, wherein the $C_{3-8}$cycloalkyl and $-C_{1-3}$alkylene-$C_{3-8}$cycloalkyl are optionally substituted with 1-4 substituents independently selected from $C_{1-4}$alkyl and halogen.

4. The compound of claim 3, or a pharmaceutically acceptable salt thereof, wherein:
$G^{1a}$ is
  a) a 5-membered monocyclic heteroaryl fused to a phenyl;
  b) $C_{3-7}$cycloalkyl; or
  c) a $C_{5-7}$cycloalkyl fused to a phenyl;
  wherein $G^{1a}$ is optionally substituted with 1-4 substituents independently selected from halogen, $C_{1-4}$alkyl, $C_{1-4}$haloalkyl, and $-OR^{1c}$; and
$G^{1b}$ is
  a) phenyl;
  b) a 5- to 6-membered heteroaryl; or
  c) a 4- to 8-membered heterocyclyl;
  wherein $G^{1b}$ is optionally substituted with 1-4 substituents independently selected from halogen, $C_{1-4}$alkyl, $C_{1-4}$haloalkyl, oxo, and $-OR^{1c}$.

5. The compound of claim 4, or a pharmaceutically acceptable salt thereof, wherein
$G^{1a}$ is
  a) a 5-membered monocyclic heteroaryl containing 1-2 heteroatoms selected from O, N, and S, the heteroaryl being fused to a phenyl;

b) C$_{3-7}$cycloalkyl; or c) a C$_{5-7}$cycloalkyl fused to a phenyl, wherein the C$_{5-7}$cycloalkyl fused to a phenyl is optionally substituted with 1-2 substituents independently selected from halogen, C$_{1-4}$alkyl, or trifluoromethyl, and —OR$^{1c}$;

G$^{1b}$ is a) phenyl optionally substituted with 1-3 substituents independently selected from the group consisting of halogen, C$_{1-4}$alkyl, C$_{1-4}$haloalkyl, and —OR$^{1c}$;

b) a 5- to 6-membered heteroaryl optionally substituted with 1-3 substituents independently selected from the group consisting of halogen, C$_{1-6}$alkyl, C$_{1-6}$haloalkyl, and —OR$^{1c}$;

c) a 4- to 8-membered saturated heterocyclyl containing one oxygen atom; or d) a pyridone optionally substituted with C$_{1-4}$alkyl; and R$^{1c}$ is C$_{1-4}$alkyl.

6. The compound of claim 1, or a pharmaceutically acceptable salt thereof, wherein R$^{1a}$ is G$^{1a}$ and G$^{1a}$ is

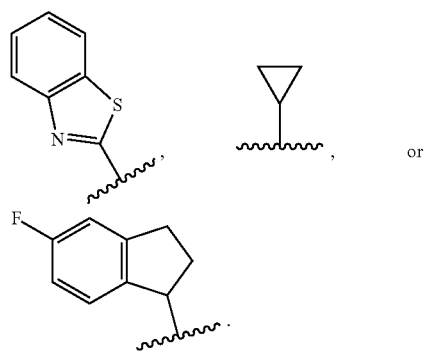

7. The compound of claim 1, or a pharmaceutically acceptable salt thereof, wherein R$^{1a}$ is —(CR$^a$R$^b$)-G$^{1b}$; and G$^{1b}$ is

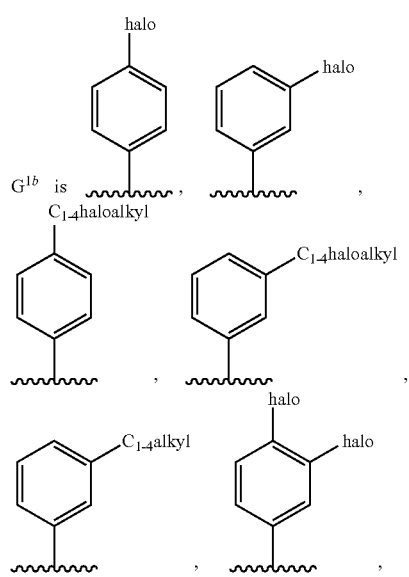

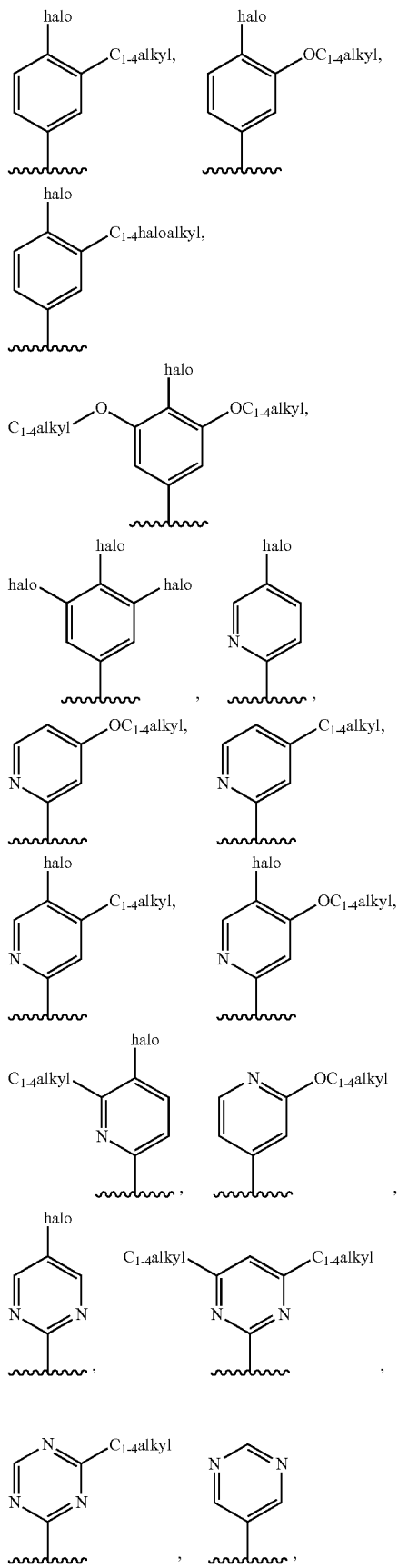

473

-continued

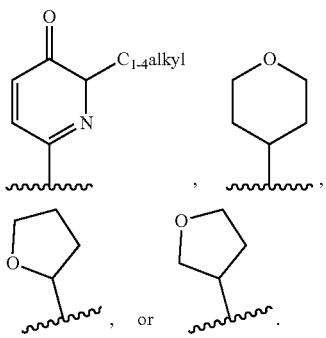

8. The compound of claim 7, or a pharmaceutically acceptable salt thereof, wherein G$^{1b}$ is

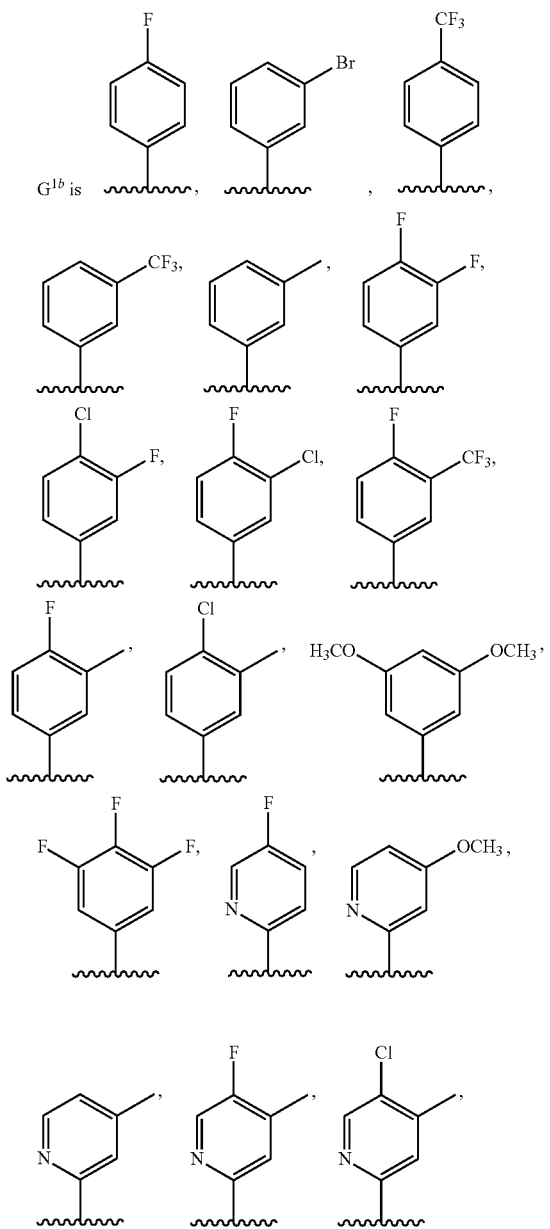

474

-continued

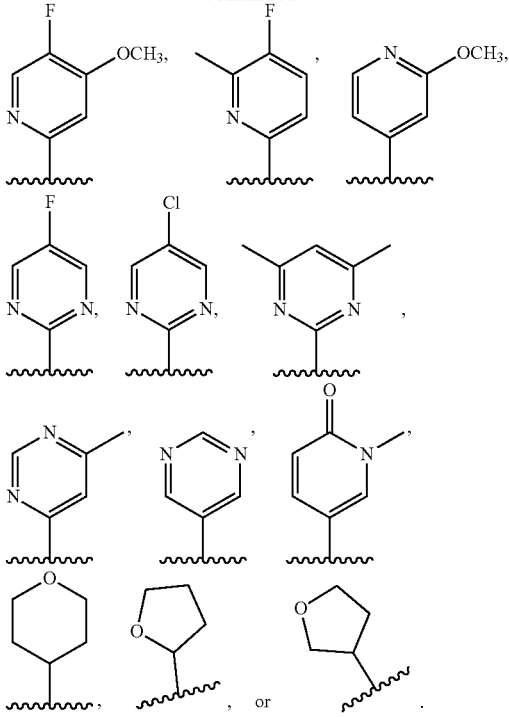

9. The compound of claim 1, or a pharmaceutically acceptable salt thereof, wherein:
R$^4$ is hydrogen, C$_{1-6}$haloalkyl, C$_{1-6}$haloalkenyl, -L-R$^x$, G$^2$, or -L-C$_{1-3}$alkylene-G$^2$;
L is O; and
R$^x$ is C$_{1-6}$alkyl or C$_{1-6}$haloalkyl.

10. The compound of claim 9, or a pharmaceutically acceptable salt thereof, wherein:
G$^2$ is a C$_{3-7}$carbocycle, a 6- to 10-membered aryl, a 5- to 10-membered heteroaryl, or a 4- to 10-membered heterocycle, wherein G$^2$ is optionally substituted with 1-3 substituents independently selected from halogen, C$_{1-6}$alkyl, C$_{1-6}$haloalkyl, oxo, —OR$^{4b}$, cyano, —C(O)OR$^{4b}$, —C(O)NR$^{4b}$R$^{4c}$, and C$_{3-8}$cycloalkyl, wherein the C$_{3-8}$cycloalkyl is optionally substituted with 1-4 substituents independently selected from C$_{1-4}$alkyl and halogen.

11. The compound of claim 1, or a pharmaceutically acceptable salt thereof, wherein:
Q$^1$ is CR$^2$;
Q$^2$ is CR$^3$; and
Q$^3$ is CR$^5$.

12. The compound of claim 1, or a pharmaceutically acceptable salt thereof, wherein:
Q$^1$ is CR$^2$;
Q$^2$ is N; and
Q$^3$ is CR$^5$.

13. The compound of claim 1, or a pharmaceutically acceptable salt thereof, wherein R$^2$ is hydrogen.

14. The compound of claim 1, or a pharmaceutically acceptable salt thereof, wherein R$^3$ is hydrogen, halogen, or —OR$^{3a}$.

15. The compound of claim 1, or a pharmaceutically acceptable salt thereof, wherein R$^5$ is hydrogen or halogen.

16. The compound of claim 1, selected from the group consisting of

- N-(3,4-dichlorobenzyl)-3-(6-fluoro-2-methylpyridin-3-yl)-5-((2-imino-3-methyl-2,3-dihydro-1H-imidazol-1-yl)methyl)benzamide;
- N-(cyclopropyl(4-methylpyridin-2-yl)methyl)-3-((2-imino-3-methyl-2,3-dihydro-1H-imidazol-1-yl)methyl)-5-(2-methoxy-5-methylpyridin-3-yl)benzamide;
- N-(cyclopropyl(4-methylpyridin-2-yl)methyl)-3-(6-fluoro-2-methylpyridin-3-yl)-5-((2-imino-3-methyl-2,3-dihydro-1H-imidazol-1-yl)methyl)benzamide;
- 3-((2-imino-3-methyl-2,3-dihydro-1H-imidazol-1-yl)methyl)-5-(2-methoxy-5-methylpyridin-3-yl)-N-((4-methoxypyridin-2-yl)methyl)benzamide;
- N-(3,4-dichlorobenzyl)-6-(4-fluoro-2-methylphenyl)-4-((2-imino-3-methyl-2,3-dihydro-1H-imidazol-1-yl)methyl)picolinamide;
- N-(3,4-dichlorobenzyl)-6-(4-fluoro-2-methylphenyl)-4-((2-imino-2,3-dihydro-1H-imidazol-1-yl)methyl)picolinamide;
- N-(cyclopropyl(4-methylpyridin-2-yl)methyl)-3-((2-imino-3-methyl-2,3-dihydro-1H-imidazol-1-yl)methyl)-5-(2-methylpyridin-4-yl)benzamide;
- 3-((2-imino-3-methyl-2,3-dihydro-1H-imidazol-1-yl)methyl)-N-((4-methoxypyridin-2-yl)methyl)-5-(3-methylpyridin-4-yl)benzamide;
- N-(cyclopropyl(4-methylpyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide;
- 5-((2-imino-3-methyl-2,3-dihydro-1H-imidazol-1-yl)methyl)-2'-methoxy-N-((4-methoxypyridin-2-yl)methyl)-5'-methyl-[1,1'-biphenyl]-3-carboxamide;
- N-(cyclopropyl(4-methylpyridin-2-yl)methyl)-3-((2-imino-3-methyl-2,3-dihydro-1H-imidazol-1-yl)methyl)-5-(1-methyl-1H-pyrrol-2-ylbenzamide;
- N-(cyclopropyl(4-methylpyridin-2-yl)methyl)-3-((2-imino-3-methyl-2,3-dihydro-1H-imidazol-1-yl)methyl)-5-(1-methyl-1H-pyrazol-5-yl)benzamide;
- N-(cyclopropyl(4-methylpyridin-2-yl)methyl)-3-((2-imino-3-methyl-2,3-dihydro-1H-imidazol-1-yl)methyl)-5-(3-methoxypyridin-4-yl)benzamide;
- N-(cyclopropyl(4-methylpyridin-2-yl)methyl)-3-((2-imino-3-methyl-2,3-dihydro-1H-imidazol-1-yl)methyl)-5-(2-methoxypyridin-4-yl)benzamide;
- N-(cyclopropyl(4-methylpyridin-2-yl)methyl)-3-((2-imino-3-methyl-2,3-dihydro-1H-imidazol-1-yl)methyl)-5-(4-methylpyridin-3-yl)benzamide;
- N-(4-chloro-3-methylbenzyl)-3-((2-imino-3-methyl-2,3-dihydro-1H-imidazol-1-yl)methyl)-5-(3-methylpyridin-4-yl)benzamide;
- N-(4-chloro-3-methylbenzyl)-3-((2-imino-3-methyl-2,3-dihydro-1H-imidazol-1-yl)methyl)-5-(1-methyl-1H-pyrazol-5-yl)benzamide;
- N-(4-chloro-3-methylbenzyl)-3-((2-imino-3-methyl-2,3-dihydro-1H-imidazol-1-yl)methyl)-5-(2-methylpyridin-4-yl)benzamide;
- N-(4-chloro-3-methylbenzyl)-3-((2-imino-2,3-dihydro-1H-imidazol-1-yl)methyl)-5-(1-methyl-1H-pyrrol-2-yl)benzamide;
- N-(4-chloro-3-methylbenzyl)-3-((2-imino-3-methyl-2,3-dihydro-1H-imidazol-1-yl)methyl)-5-(3-methoxypyridin-4-yl)benzamide;
- N-(3,4-dichlorobenzyl)-3-((2-imino-3-methyl-2,3-dihydro-1H-imidazol-1-yl)methyl)-5-(1-methyl-1H-pyrrol-2-ylbenzamide;
- N-(3,4-dichlorobenzyl)-3-((2-imino-3-methyl-2,3-dihydro-1H-imidazol-1-yl)methyl)-5-(2-methylpyridin-4-yl)benzamide;
- N-(3,4-dichlorobenzyl)-3-((2-imino-3-methyl-2,3-dihydro-1H-imidazol-1-yl)methyl)-5-(3-methoxypyridin-4-yl)benzamide;
- N-(3,4-dichlorobenzyl)-3-((2-imino-3-methyl-2,3-dihydro-1H-imidazol-1-yl)methyl)-5-(2-methoxypyridin-4-yl)benzamide;
- N-(3,4-dichlorobenzyl)-3-((2-imino-3-methyl-2,3-dihydro-1H-imidazol-1-yl)methyl)-5-(3-methylpyridin-4-yl)benzamide;
- N-(3,4-dichlorobenzyl)-3-((2-imino-3-methyl-2,3-dihydro-1H-imidazol-1-yl)methyl)-5-(1-methyl-1H-pyrazol-5-yl)benzamide;
- N-(3,4-dichlorobenzyl)-3-((2-imino-3-methyl-2,3-dihydro-1H-imidazol-1-yl)methyl)-5-(5-methyl-1H-indazol-4-yl)benzamide;
- N-(3,4-dichlorobenzyl)-2',4'-difluoro-5-((2-imino-3-methyl-2,3-dihydro-1H-imidazol-1-yl)methyl)-6'-methyl-[1,1'-biphenyl]-3-carboxamide;
- (R)-4'-fluoro-N-(1-(4-fluoro-3-methylphenyl)ethyl)-5-((2-imino-3-methyl-2,3-dihydro-1H-imidazol-1-yl)methyl)-2'-methyl-[1,1'-biphenyl]-3-carboxamide;
- (S)-4'-fluoro-N-(1-(4-fluoro-3-methylphenyl)ethyl)-5-((2-imino-3-methyl-2,3-dihydro-1H-imidazol-1-yl)methyl)-2'-methyl-[1,1'-biphenyl]-3-carboxamide;
- (S)-4'-fluoro-N-(1-(4-fluoro-3-(trifluoromethyl)phenyl)ethyl)-5-((2-imino-3-methyl-2,3-dihydro-1H-imidazol-1-yl)methyl)-2'-methyl-[1,1'-biphenyl]-3-carboxamide;
- (R)-4'-fluoro-N-(1-(4-fluoro-3-(trifluoromethyl)phenyl)ethyl)-5-((2-imino-3-methyl-2,3-dihydro-1H-imidazol-1-yl)methyl)-2'-methyl-[1,1'-biphenyl]-3-carboxamide;
- N-(4-chloro-3-methylbenzyl)-3-((2-imino-3-methyl-2,3-dihydro-1H-imidazol-1-yl)methyl)-5-(5-methyl-1H-indazol-4-yl)benzamide;
- N-(3,5-dimethoxybenzyl)-3-((2-imino-3-methyl-2,3-dihydro-1H-imidazol-1-yl)methyl)-N-methyl-5-(5-methyl-1H-indazol-4-yl)benzamide;
- N-(3,5-dimethoxybenzyl)-3-((2-imino-3-methyl-2,3-dihydro-1H-imidazol-1-yl)methyl)-5-(5-methyl-1H-indazol-4-yl)benzamide;
- N-(cyclopropyl(4-methylpyridin-2-yl)methyl)-3-((2-imino-3-methyl-2,3-dihydro-1H-imidazol-1-yl)methyl)-5-(2-methylpyridin-3-yl)benzamide;
- 3-((2-imino-3-methyl-2,3-dihydro-1H-imidazol-1-yl)methyl)-5-(2-methylpyridin-3-yl)-N-((6-methylpyrimidin-4-yl)methyl)benzamide;
- N-(dicyclopropylmethyl)-3-((2-imino-3-methyl-2,3-dihydro-1H-imidazol-1-yl)methyl)-5-(2-methylpyridin-3-ylbenzamide;
- 3-((2-imino-3-methyl-2,3-dihydro-1H-imidazol-1-yl)methyl)-5-(2-methylpyridin-3-yl)-N-(pyrimidin-5-ylmethyl)benzamide;
- 3-((2-imino-3-methyl-2,3-dihydro-1H-imidazol-1-yl)methyl)-N-((2-methoxypyridin-4-yl)methyl)-5-(2-methylpyridin-3-yl)benzamide;
- N-((4,6-dimethylpyrimidin-2-yl)methyl)-3-((2-imino-3-methyl-2,3-dihydro-1H-imidazol-1-yl)methyl)-5-(2-methylpyridin-3-yl)benzamide;
- 3-((2-imino-3-methyl-2,3-dihydro-1H-imidazol-1-yl)methyl)-N-((4-methoxypyridin-2-yl)methyl)-5-(2-methylpyridin-3-yl)benzamide;

N-((5-chloropyrimidin-2-yl)methyl)-3-((2-imino-3-methyl-2,3-dihydro-1H-imidazol-1-yl)methyl)-5-(2-methylpyridin-3-yl)benzamide;
(S)-4'-fluoro-5-((2-imino-3-methyl-2,3-dihydro-1H-imidazol-1-yl)methyl)-2'-methyl-N-(2,2,2-trifluoro-1-(4-fluoro-3-methylphenyl)ethyl)-[1,1'-biphenyl]-3-carboxamide;
N-(4-chloro-3-methylbenzyl)-3-((2-imino-3-methyl-2,3-dihydro-1H-imidazol-1-yl)methyl)-5-(3-methyl-1H-indazol-4-yl)benzamide;
N-(cyclopropyl(4-methylpyridin-2-yl)methyl)-3-((2-imino-3-methyl-2,3-dihydro-1H-imidazol-1-yl)methyl)-5-(5-methyl-1H-indazol-4-yl)benzamide;
N-(3,5-dimethoxybenzyl)-3-((2-imino-3-methyl-2,3-dihydro-1H-imidazol-1-yl)methyl)-N-methyl-5-(2-methylpyridin-4-yl)benzamide;
N-(dicyclopropylmethyl)-3-((2-imino-3-methyl-2,3-dihydro-1H-imidazol-1-yl)methyl)-5-(2-methylpyridin-4-yl)benzamide;
N-((4,6-dimethylpyrimidin-2-yl)methyl)-3-((2-imino-3-methyl-2,3-dihydro-1H-imidazol-1-yl)methyl)-5-(2-methylpyridin-4-yl)benzamide;
N-((5-chloropyrimidin-2-yl)methyl)-3-((2-imino-3-methyl-2,3-dihydro-1H-imidazol-1-yl)methyl)-5-(2-methylpyridin-4-yl)benzamide;
N-(3,5-dimethoxybenzyl)-2',4'-difluoro-5-((2-imino-3-methyl-2,3-dihydro-1H-imidazol-1-yl)methyl)-6'-methyl-[1,1'-biphenyl]-3-carboxamide;
N-(4-chloro-3-methylbenzyl)-2',4'-difluoro-5-((2-imino-3-methyl-2,3-dihydro-1H-imidazol-1-yl)methyl)-6'-methyl-[1,1'-biphenyl]-3-carboxamide;
(S)—N-(cyclopropyl(4-fluoro-3-methylphenyl)methyl)-4'-fluoro-5-((2-imino-3-methyl-2,3-dihydro-1H-imidazol-1-yl)methyl)-2'-methyl-[1,1'-biphenyl]-3-carboxamide;
N-(1-(5-chloro-4-methylpyridin-2-yl)ethyl)-6-(4-fluoro-2-methylphenyl)-4-((2-imino-3-methyl-2,3-dihydro-1H-imidazol-1-yl)methyl)picolinamide;
N-(4-chloro-3-methylbenzyl)-6-(4-fluoro-2-methylphenyl)-4-((2-imino-3-methyl-2,3-dihydro-1H-imidazol-1-yl)methyl)picolinamide;
N-(benzo[d]thiazol-2-yl)-4'-fluoro-5-((2-imino-3-methyl-2,3-dihydro-1H-imidazol-1-yl)methyl)-2'-methyl-[1,1'-biphenyl]-3-carboxamide;
(R)—N-(1-(3,4-dichlorophenyl)ethyl)-6-(4-fluoro-2-methylphenyl)-4-((2-imino-3-methyl-2,3-dihydro-1H-imidazol-1-yl)methyl)picolinamide;
N-(4-chloro-3-methylbenzyl)-4'-fluoro-5-((2-imino-3-methyl-2,3-dihydro-1H-imidazol-1-yl)methyl)-2',6'-dimethyl-[1,1'-biphenyl]-3-carboxamide;
(S)-3-(Cyclopropanecarboximidamidomethyl)-N-(cyclopropyl(4-fluoro-3-methylphenyl)methyl)-5-(1-ethyl-3-(trifluoromethyl)-1H-pyrazol-4-yl)benzamide;
N-(cyclopropyl(3,5-dimethoxyphenyl)methyl)-3-((2-imino-3-methyl-2,3-dihydro-1H-imidazol-1-yl)methyl)-5-(3-(trifluoromethyl)pyridin-2-ylbenzamide;
2'-(difluoromethoxy)-N-(3,5-dimethoxybenzyl)-4'-fluoro-5-((2-imino-3-methyl-2,3-dihydro-1H-imidazol-1-yl)methyl)-[1,1'-biphenyl]-3-carboxamide;
N-(cyclopropyl(3,5-dimethoxyphenyl)methyl)-2'-(difluoromethoxy)-4'-fluoro-5-((2-imino-3-methyl-2,3-dihydro-1H-imidazol-1-yl)methyl)-[1,1'-biphenyl]-3-carboxamide;
(S)—N-(cyclopropyl(4-fluoro-3-methylphenyl)methyl)-3-((2-imino-3-methyl-2,3-dihydro-1H-imidazol-1-yl)methyl)-5-(3-(trifluoromethyl)pyridin-2-yl)benzamide;
N-(3,5-dimethoxybenzyl)-4'-fluoro-5-((2-imino-3-methyl-2,3-dihydro-1H-imidazol-1-yl)methyl)-2',6'-dimethyl-[1,1'-biphenyl]-3-carboxamide;
(S)—N-(cyclopropyl(4-fluoro-3-methylphenyl)methyl)-3-(5-fluoro-3-methylpyridin-2-yl)-5-((2-imino-3-methyl-2,3-dihydro-1H-imidazol-1-yl)methyl)benzamide;
N-(3,5-dimethoxybenzyl)-3-(5-fluoro-3-methylpyridin-2-yl)-5-((2-imino-3-methyl-2,3-dihydro-1H-imidazol-1-yl)methyl)benzamide;
N-(cyclopropyl(3,5-dimethoxyphenyl)methyl)-3-(5-fluoro-3-methylpyridin-2-yl)-5-((2-imino-3-methyl-2,3-dihydro-1H-imidazol-1-yl)methyl)benzamide;
N-(cyclopropyl(4-methylpyridin-2-yl)methyl)-3-(5-fluoro-3-methylpyridin-2-yl)-5-((2-imino-3-methyl-2,3-dihydro-1H-imidazol-1-yl)methyl)benzamide;
N-(4-chloro-3-methylbenzyl)-3-(5-fluoro-3-methylpyridin-2-yl)-5-((2-imino-3-methyl-2,3-dihydro-1H-imidazol-1-yl)methyl)benzamide;
N-(cyclopropyl(4-methylpyridin-2-yl)methyl)-2'-(difluoromethoxy)-4'-fluoro-5-((2-imino-3-methyl-2,3-dihydro-1H-imidazol-1-yl)methyl)-[1,1'-biphenyl]-3-carboxamide;
(S)—N-(cyclopropyl(4-fluoro-3-methylphenyl)methyl)-3-(5-fluoro-3-(trifluoromethyl)pyridin-2-yl)-5-((2-imino-3-methyl-2,3-dihydro-1H-imidazol-1-yl)methyl)benzamide;
(S)—N-(cyclopropyl(4-fluoro-3-methylphenyl)methyl)-2'-(difluoromethoxy)-4'-fluoro-5-((2-imino-3-methyl-2,3-dihydro-1H-imidazol-1-yl)methyl)-[1,1'-biphenyl]-3-carboxamide;
N-(cyclopropyl(3,5-dimethoxyphenyl)methyl)-3-(5-fluoro-3-(trifluoromethyl)pyridin-2-yl)-5-((2-imino-3-methyl-2,3-dihydro-1H-imidazol-1-yl)methyl)benzamide;
N-(cyclopropyl(4-methylpyridin-2-yl)methyl)-3-(5-fluoro-3-(trifluoromethyl)pyridin-2-yl)-5-((2-imino-3-methyl-2,3-dihydro-1H-imidazol-1-yl)methyl)benzamide;
N-(4-chloro-3-methylbenzyl)-3-((2-imino-3-methyl-2,3-dihydro-1H-imidazol-1-yl)methyl)-5-(2-(trifluoromethyl)pyridin-3-yl)benzamide;
N-(cyclopropyl(4-methylpyridin-2-yl)methyl)-3-((2-imino-3-methyl-2,3-dihydro-1H-imidazol-1-yl)methyl)-5-(2-(trifluoromethyl)pyridin-3-yl)benzamide;
N-(3,5-dimethoxybenzyl)-3-(6-fluoro-4-methylpyridin-3-yl)-5-((2-imino-3-methyl-2,3-dihydro-1H-imidazol-1-yl)methyl)benzamide;
N-(4-chloro-3-methylbenzyl)-3-(6-fluoro-4-methylpyridin-3-yl)-5-((2-imino-3-methyl-2,3-dihydro-1H-imidazol-1-yl)methyl)benzamide;
N-(4-chloro-3-methylbenzyl)-3-((2-imino-3-methyl-2,3-dihydro-1H-imidazol-1-yl)methyl)-5-(2-methyl-6-oxo-1,6-dihydropyridin-3-yl)benzamide;
N-(3,5-dimethoxybenzyl)-3-((2-imino-3-methyl-2,3-dihydro-1H-imidazol-1-yl)methyl)-5-(4-methyl-6-oxo-1,6-dihydropyridin-3-ylbenzamide;
N-(3,4-dichlorobenzyl)-3-((2-imino-3-methyl-2,3-dihydro-1H-imidazol-1-yl)methyl)-5-(4-methyl-6-oxo-1,6-dihydropyridin-3-ylbenzamide;
N-(4-chloro-3-methylbenzyl)-3-((2-imino-3-methyl-2,3-dihydro-1H-imidazol-1-yl)methyl)-5-(4-methyl-6-oxo-1,6-dihydropyridin-3-yl)benzamide;
3-(3,4-dichlorophenyl)-3-(4'-fluoro-5-((2-imino-3-methyl-2,3-dihydro-1H-imidazol-1-yl)methyl)-2'-(trifluoromethyl)-[1,1'-biphenyl]-3-carboxamido)propanoic acid;

N-(1-(3,4-dichlorophenyl)-3-oxo-3-((2-oxobutyl)amino) propyl)-4'-fluoro-5-((2-imino-3-methyl-2,3-dihydro-1H-imidazol-1-yl)methyl)-2'-(trifluoromethyl)-[1,1'-biphenyl]-3-carboxamide;

N-(1-(3,4-dichlorophenyl)-3-((3,5-dimethoxybenzyl) amino)-3-oxopropyl)-4'-fluoro-5-((2-imino-3-methyl-2,3-dihydro-1H-imidazol-1-yl)methyl)-2'-(trifluoromethyl)-[1,1'-biphenyl]-3-carboxamide;

4'-fluoro-N-(4-fluoro-3-methylbenzyl)-5-((2-imino-3-methyl-2,3-dihydro-1H-imidazol-1-yl)methyl)-2'-methyl-[1,1'-biphenyl]-3-carboxamide;

4'-fluoro-5-((2-imino-3-methyl-2,3-dihydro-1H-imidazol-1-yl)methyl)-2'-methyl-N-(3,4,5-trifluorobenzyl)-[1,1'-biphenyl]-3-carboxamide;

4'-fluoro-N-(4-fluorobenzyl)-5-((2-imino-3-methyl-2,3-dihydro-1H-imidazol-1-yl)methyl)-2'-methyl-[1,1'-biphenyl]-3-carboxamide;

N-(3,4-dichlorobenzyl)-5-((2-imino-3-methyl-2,3-dihydro-1H-imidazol-1-yl)methyl)-2'-(trifluoromethyl)-[1,1'-biphenyl]-3-carboxamide;

(S)—N-(cyclopropyl(4-methylpyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide;

N-(3,4-dichlorobenzyl)-5-((2-imino-3-methyl-2,3-dihydro-1H-imidazol-1-yl)methyl)-2'-methyl-[1,1'-biphenyl]-3-carboxamide;

(R)—N-(cyclopropyl(4-methoxypyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide;

(S)—N-(cyclopropyl(4-fluoro-3-methylphenyl)methyl)-3-((2-imino-3-methyl-2,3-dihydro-1H-imidazol-1-yl)methyl)-5-(5,6,7,8-tetrahydroquinazolin-4-yl)benzamide;

N-(cyclopropyl(4-methylpyridin-2-yl)methyl)-3-((2-imino-3-methyl-2,3-dihydro-1H-imidazol-1-yl)methyl)-5-(5,6,7,8-tetrahydroquinazolin-4-yl)benzamide;

N-(cyclopropyl(3,5-dimethoxyphenyl)methyl)-3-((2-imino-3-methyl-2,3-dihydro-1H-imidazol-1-yl)methyl)-5-(5,6,7,8-tetrahydroquinazolin-4-yl)benzamide;

(S)—N-(cyclopropyl(4-methoxypyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide;

N-(3,5-dimethoxybenzyl)-4'-fluoro-5-((2-imino-3-methyl-2,3-dihydro-1H-imidazol-1-yl)methyl)-2'-(trifluoromethyl)-[1,1'-biphenyl]-3-carboxamide;

N-(4-chloro-3-methylbenzyl)-6-(4-fluoro-2-(trifluoromethyl)phenyl)-4-((2-imino-3-methyl-2,3-dihydro-1H-imidazol-1-yl)methyl)picolinamide;

N-(3,5-dimethoxybenzyl)-6-(4-fluoro-2-(trifluoromethyl) phenyl)-4-((2-imino-3-methyl-2,3-dihydro-1H-imidazol-1-yl)methyl)picolinamide;

N-(cyclopropyl(4-methylpyridin-2-yl)methyl)-6-(4-fluoro-2-(trifluoromethyl)phenyl)-4-((2-imino-3-methyl-2,3-dihydro-1H-imidazol-1-yl)methyl)picolinamide;

(S)—N-(cyclopropyl(4-fluoro-3-methylphenyl)methyl)-3-((2-imino-3-methyl-2,3-dihydro-1H-imidazol-1-yl)methyl)-5-(1-isopropyl-1H-pyrazol-5-yl)benzamide;

(R)—N-(cyclopropyl(4-methylpyridin-2-yl)methyl)-3-((2-imino-3-methyl-2,3-dihydro-1H-imidazol-1-yl)methyl)-5-(1-isopropyl-1H-pyrazol-5-yl)benzamide;

3-(3,4-dichlorophenyl)-3-(6-(4-fluoro-2-(trifluoromethyl)phenyl)-4-((2-imino-3-methyl-2,3-dihydro-1H-imidazol-1-yl)methyl)picolinamido)propanoic acid;

N-(cyclopropyl(4-methylpyridin-2-yl)methyl)-2,4'-difluoro-5-((2-imino-3-methyl-2,3-dihydro-1H-imidazol-1-yl)methyl)-2'-(trifluoromethyl)-[1,1'-biphenyl]-3-carboxamide;

methyl 3-(3,4-dichlorophenyl)-3-(6-(4-fluoro-2-(trifluoromethyl)phenyl)-4-((2-imino-3-methyl-2,3-dihydro-1H-imidazol-1-yl)methyl)picolinamido)propanoate;

(S)—N-(cyclopropyl(4-fluoro-3-methylphenyl)methyl)-6-(4-fluoro-2-(trifluoromethylphenyl)-4-((2-imino-3-methyl-2,3-dihydro-1H-imidazol-1-yl)methyl)picolinamide;

N-(3,5-dimethoxybenzyl)-2,4'-difluoro-5-((2-imino-3-methyl-2,3-dihydro-1H-imidazol-1-yl)methyl)-2'-(trifluoromethyl)-[1,1'-biphenyl]-3-carboxamide;

(S)—N-(cyclopropyl(4-fluoro-3-methylphenyl)methyl)-2,4'-difluoro-5-((2-imino-3-methyl-2,3-dihydro-1H-imidazol-1-yl)methyl)-2'-(trifluoromethyl)-[1,1'-biphenyl]-3-carboxamide;

methyl 3-(3,4-dichlorophenyl)-3-(2,4'-difluoro-5-((2-imino-3-methyl-2,3-dihydro-1H-imidazol-1-yl) methyl)-2'-(trifluoromethyl)-[1,1'-biphenyl]-3-carboxamido)propanoate;

N-(4-chloro-3-methylbenzyl)-2,4'-difluoro-5-((2-imino-3-methyl-2,3-dihydro-1H-imidazol-1-yl)methyl)-2'-(trifluoromethyl)-[1,1'-biphenyl]-3-carboxamide;

N-(3,4-dichlorobenzyl)-3-((2-imino-3-methyl-2,3-dihydro-1H-imidazol-1-yl)methyl)-5-(2-methyl-6-oxo-1,6-dihydropyridin-3-yl)benzamide;

(S)—N-(cyclopropyl(4-fluoro-3-methylphenyl)methyl)-3-(6-fluoro-4-methylpyridin-3-yl)-5-((2-imino-3-methyl-2,3-dihydro-1H-imidazol-1-yl)methyl)benzamide;

(S)—N-(cyclopropyl(4-fluoro-3-methylphenyl)methyl)-3-((3-ethyl-2-imino-2,3-dihydro-1H-imidazol-1-yl) methyl)-5-(2-(trifluoromethyl)pyridin-3-yl)benzamide;

(S)—N-(cyclopropyl(4-fluoro-3-methylphenylmethyl)-4-((3-cyclopropyl-2-imino-2,3-dihydro-1H-imidazol-1-yl)methyl)-5-(2-(trifluoromethyl)pyridin-3-yl)benzamide;

N-(3,5-dimethoxybenzyl)-5-((3-ethyl-2-imino-2,3-dihydro-1H-imidazol-1-yl)methyl)-4'-fluoro-2'-methyl-[1,1'-biphenyl]-3-carboxamide;

5-((3-cyclopropyl-2-imino-2,3-dihydro-1H-imidazol-1-yl)methyl)-N-(3,5-dimethoxybenzyl)-4'-fluoro-2'-methyl-[1,1'-biphenyl]-3-carboxamide;

N-(cyclopropyl(3,5-dimethoxyphenyl)methyl)-3-((2-imino-3-methyl-2,3-dihydro-1H-imidazol-1-yl) methyl)-5-(1-isopropyl-1H-pyrazol-5-yl)benzamide;

(S)—N-(cyclopropyl(4-fluoro-3-methylphenyl)methyl)-4-((2-imino-3-methyl-2,3-dihydro-1H-imidazol-1-yl) methyl)-2'-(trifluoromethyl)-[2,3'-bipyridine]-6-carboxamide;

(S)—N-(cyclopropyl(4-methylpyridin-2-yl)methyl)-2,4'-difluoro-5-((2-imino-3-methyl-2,3-dihydro-1H-imidazol-1-yl)methyl)-2'-(trifluoromethyl)-[1,1'-biphenyl]-3-carboxamide;

(E)-3-((2-(acetylimino)-3-methyl-2,3-dihydro-1H-imidazol-1-yl)methyl)-N-(3,4-dichlorobenzyl)-5-(6-fluoro-2-methylpyridin-3-yl)benzamide;

ethyl (1-(3-((3,4-dichlorobenzyl)carbamoyl)-5-(6-fluoro-2-methylpyridin-3-yl)benzyl)-3-methyl-1,3-dihydro-2H-imidazol-2-ylidene)carbamate;

(S)—N-(cyclopropyl(4-fluoro-3-methylphenyl)methyl)-3-((2-imino-3-methyl-2,3-dihydro-1H-imidazol-1-yl)methyl)-5-(4-(trifluoromethyl)pyrimidin-5-yl)benzamide;

(S)—N-(1-(3-chloro-4-fluorophenyl)ethyl)-3-((2-imino-3-methyl-2,3-dihydro-1H-imidazol-1-yl)methyl)-5-(2-(trifluoromethyl)pyridin-3-yl)benzamide;

(S)—N-(cyclopropyl(4-fluoro-3-methylphenyl)methyl)-3-((2-imino-3-methyl-2,3-dihydro-1H-imidazol-1-yl)methyl)-5-(1-methyl-3-(trifluoromethyl)-1H-pyrazol-4-yl)benzamide;

(S)-3-((2-imino-3-methyl-2,3-dihydro-1H-imidazol-1-yl)methyl)-N-(1-(4-(trifluoromethyl)phenyl)ethyl)-5-(2-(trifluoromethyl)pyridin-3-yl)benzamide;

(S)—N-(cyclopropyl(4-fluoro-3-methylphenyl)methyl)-3-(2-(difluoromethoxy)pyridin-3-yl)-5-((2-imino-3-methyl-2,3-dihydro-1H-imidazol-1-yl)methyl)benzamide;

(S)—N-(cyclopropyl(5-fluoropyridin-2-yl)methyl)-3-((2-imino-3-methyl-2,3-dihydro-1H-imidazol-1-yl)methyl)-5-(2-(trifluoromethyl)pyridin-3-yl)benzamide;

(S)—N-(5-fluoro-2,3-dihydro-1H-inden-1-yl)-3-((2-imino-3-methyl-2,3-dihydro-1H-imidazol-1-yl)methyl)-5-(2-(trifluoromethyl)pyridin-3-yl)benzamide;

(S)—N-(1-(5-fluoropyrimidin-2-yl)ethyl)-3-((2-imino-3-methyl-2,3-dihydro-1H-imidazol-1-yl)methyl)-5-(2-(trifluoromethyl)pyridin-3-yl)benzamide;

(S)—N-(cyclopropyl(4-fluoro-3-methylphenyl)methyl)-2-fluoro-5-((2-imino-3-methyl-2,3-dihydro-1H-imidazol-1-yl)methyl)-3-(2-(trifluoromethyl)pyridin-3-yl)benzamide;

(S)—N-(cyclopropyl(4-methylpyridin-2-yl)methyl)-2-fluoro-5-((2-imino-3-methyl-2,3-dihydro-1H-imidazol-1-yl)methyl)-3-(2-(trifluoromethyl)pyridin-3-yl)benzamide;

N-(3,5-dimethoxybenzyl)-4'-fluoro-5-((2-imino-3-phenyl-2,3-dihydro-1H-imidazol-1-yl)methyl)-2'-methyl-[1,1'-biphenyl]-3-carboxamide;

5-((3-(cyclopropylmethyl)-2-imino-2,3-dihydro-1H-imidazol-1-yl)methyl)-N-(3,5-dimethoxybenzyl)-4'-fluoro-2'-methyl-[1,1'-biphenyl]-3-carboxamide;

(S)—N-(cyclopropyl(4-fluoro-3-methylphenyl)methyl)-3-((2-imino-3-methyl-2,3-dihydro-1H-imidazol-1-yl)methyl)-5-(2-(2,2,2-trifluoroethoxy)pyridin-3-yl)benzamide;

(S)—N-(cyclopropyl(4-fluoro-3-methylphenyl)methyl)-3-(6,7-dihydro-5H-cyclopenta[b]pyridin-4-yl)-5-((2-imino-3-methyl-2,3-dihydro-1H-imidazol-1-yl)methyl)benzamide;

(S)—N-(cyclopropyl(4-fluoro-3-methylphenyl)methyl)-3-((2-imino-3-phenyl-2,3-dihydro-1H-imidazol-1-yl)methyl)-5-(2-(trifluoromethyl)pyridin-3-yl)benzamide;

(S)—N-(cyclopropyl(4-fluoro-3-methylphenyl)methyl)-3-((3-(cyclopropylmethyl)-2-imino-2,3-dihydro-1H-imidazol-1-yl)methyl)-5-(2-(trifluoromethyl)pyridin-3-yl)benzamide;

(S)-3-cyclopropyl-N-(cyclopropyl(4-fluoro-3-methylphenyl)methyl)-5-((2-imino-3-methyl-2,3-dihydro-1H-imidazol-1-yl)methyl)benzamide;

N-(3,4-dichlorobenzyl)-3-(6-fluoro-2-methylpyridin-3-yl)-5-((2-imino-3-methyl-2,3-dihydro-1H-imidazol-1-yl)methyl)-N-methylbenzamide;

(S)-2'-chloro-N-(cyclopropyl(4-fluoro-3-methylphenyl)methyl)-5-((3-cyclopropyl-2-imino-2,3-dihydro-1H-imidazol-1-yl)methyl)-4'-fluoro-[1,1'-biphenyl]-3-carboxamide;

(S)—N-(Cyclopropyl(4-fluoro-3-methylphenylmethyl)-4-((3-cyclopropyl-2-imino-2,3-dihydro-1H-imidazol-1-yl)methyl)-5-(1-methyl-3-(trifluoromethyl)-1H-pyrazol-4-yl);

(S)—N-(Cyclopropyl(4-fluoro-3-methylphenylmethyl)-4-((2-imino-3-methylimidazolidin-1-yl)methyl)-5-(2-(trifluoromethyl)pyridin-3-yl)benzamide;

(S)—N-(cyclopropyl(4-fluoro-3-methylphenylmethyl)-4-((2-imino-3-methylimidazolidin-1-yl)methyl)-5-(2-(trifluoromethyl)pyridin-3-yl)benzamide];

N-(3,5-dimethoxybenzyl)-3-((2-imino-3-methyl-2,3-dihydro-1H-imidazol-1-yl)methyl)-5-(trifluoromethoxy)benzamide;

N-(cyclopropyl(4-methylpyridin-2-yl)methyl)-3-((2-imino-3-methyl-2,3-dihydro-1H-imidazol-1-yl)methyl)-5-(trifluoromethoxy)benzamide;

(S)-3-(3-((2-imino-3-methyl-2,3-dihydro-1H-imidazol-1-yl)methyl)-5-(trifluoromethoxy)benzamido)-3-(3-(trifluoromethyl)phenyl)propanoic acid;

N-(4-chloro-3-methylbenzyl)-3-((2-imino-3-methyl-2,3-dihydro-1H-imidazol-1-yl)methyl)-5-(trifluoromethoxy)benzamide;

(S)-3-(2,4'-difluoro-5-((2-imino-3-methyl-2,3-dihydro-1H-imidazol-1-yl)methyl)-2'-(trifluoromethyl)-[1,1'-biphenyl]-3-carboxamido)-3-(3-(trifluoromethyl)phenyl)propanoic acid;

(S)—N-(cyclopropyl(4-methylpyridin-2-yl)methyl)-3-((2-imino-3-methyl-2,3-dihydro-1H-imidazol-1-yl)methyl)-5-(trifluoromethoxy)benzamide;

(S)—N-(cyclopropyl(3,4-dichlorophenyl)methyl)-2'-(difluoromethoxy)-4'-fluoro-5-((2-imino-3-methyl-2,3-dihydro-1H-imidazol-1-yl)methyl)-[1,1'-biphenyl]-3-carboxamide;

(S)—N-(cyclopropyl(3,4-dichlorophenyl)methyl)-5-((3-cyclopropyl-2-imino-2,3-dihydro-1H-imidazol-1-yl)methyl)-2'-(difluoromethoxy)-4'-fluoro-[1,1'-biphenyl]-3-carboxamide;

N3'-(3,5-dimethoxybenzyl)-4-fluoro-5'-((2-imino-3-methyl-2,3-dihydro-1H-imidazol-1-yl)methyl)-[1,1'-biphenyl]-2,3'-dicarboxamide;

(S)—N-(cyclopropyl(3,4-dichlorophenyl)methyl)-3-((2-imino-3-methyl-2,3-dihydro-1H-imidazol-1-yl)methyl)-5-(2-(trifluoromethyl)pyridin-3-yl)benzamide;

(S)—N-(cyclopropyl(4-fluoro-3-methylphenyl)methyl)-2'-(difluoromethyl)-4'-fluoro-5-((2-imino-3-methyl-2,3-dihydro-1H-imidazol-1-yl)methyl)-[1,1'-biphenyl]-3-carboxamide;

(S)—N-(cyclopropyl(3,4-dichlorophenyl)methyl)-3-((3-cyclopropyl-2-imino-2,3-dihydro-1H-imidazol-1-yl)methyl)-5-(2-(trifluoromethyl)pyridin-3-yl)benzamide;

(S)—N-(cyclopropyl(4-fluoro-3-methylphenyl)methyl)-5-((3-cyclopropyl-2-imino-2,3-dihydro-1H-imidazol-1-yl)methyl)-2'-(difluoromethoxy)-4'-fluoro-[1,1'-biphenyl]-3-carboxamide;

(S)—N-(cyclopropyl(3,4-dichlorophenyl)methyl)-3-((2-imino-3-methyl-2,3-dihydro-1H-imidazol-1-yl)methyl)-5-(1-methyl-3-(trifluoromethyl)-1H-pyrazol-4-yl)benzamide;

(S)—N-(cyclopropyl(4-fluoro-3-methylphenyl)methyl)-5-((3-cyclopropyl-2-imino-2,3-dihydro-1H-imidazol-1-yl)methyl)-2'-(difluoromethyl)-4'-fluoro-[1,1'-biphenyl]-3-carboxamide;

(S)—N-(cyclopropyl(3,4-dichlorophenyl)methyl)-3-((3-cyclopropyl-2-imino-2,3-dihydro-1H-imidazol-1-yl)methyl)-5-(1-methyl-3-(trifluoromethyl)-1H-pyrazol-4-yl)benzamide;

(S)—N-(cyclopropyl(4-fluoro-3-methylphenylmethyl)-4-((3-cyclopropyl-2-imino-2,3-dihydro-1H-imidazol-1-yl)methyl)-5-(1-ethyl-3-(trifluoromethyl)-1H-pyrazol-4-yl)benzamide;

(S)—N-(cyclopropyl(3,4-dichlorophenyl)methyl)-3-(1-ethyl-3-(trifluoromethyl)-1H-pyrazol-4-yl)-5-((2-imino-3-methyl-2,3-dihydro-1H-imidazol-1-yl)methyl)benzamide;

(S)—N-(cyclopropyl(3,4-dichlorophenyl)methyl)-3-((3-cyclopropyl-2-imino-2,3-dihydro-1H-imidazol-1-yl)methyl)-5-(1-ethyl-3-(trifluoromethyl)-1H-pyrazol-4-yl)benzamide;

(S)—N-(cyclopropyl(4-fluoro-3-methylphenyl)methyl)-3-((3-cyclopropyl-2-imino-2,3-dihydro-1H-imidazol-1-yl)methyl)-5-(1-isobutyl-3-(trifluoromethyl)-1H-pyrazol-4-yl)benzamide;

(S)-3-(1-cyclopentyl-3-(trifluoromethyl)-1H-pyrazol-4-yl)-N-(cyclopropyl(4-fluoro-3-methylphenyl)methyl)-5-((3-cyclopropyl-2-imino-2,3-dihydro-1H-imidazol-1-yl)methyl)benzamide;

(S)—N-(cyclopropyl(4-fluoro-3-methylphenyl)methyl)-3-((2-imino-3-methyl-2,3-dihydro-1H-imidazol-1-yl)methyl)-5-(1-isobutyl-3-(trifluoromethyl)-1H-pyrazol-4-yl)benzamide;

(S)-3-cyclobutyl-N-(cyclopropyl(4-fluoro-3-methylphenyl)methyl)-5-((2-imino-3-methyl-2,3-dihydro-1H-imidazol-1-yl)methyl)benzamide;

(R)—N-(cyclopropyl(5-fluoro-6-methylpyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide;

N-(3,4-dichlorobenzyl)-3-(2,2-difluorobenzo[d][1,3]dioxol-4-yl)-5-((2-imino-3-methyl-2,3-dihydro-1H-imidazol-1-yl)methyl)benzamide;

N-(3,4-dichlorobenzyl)-3-((2-imino-3-methyl-2,3-dihydro-1H-imidazol-1-yl)methyl)-5-(6-methoxypyridin-2-yl)benzamide;

(S)—N-(1-(4-fluoro-3-methylphenyl)ethyl)-3-((2-imino-3-methyl-2,3-dihydro-1H-imidazol-1-yl)methyl)-5-(trifluoromethoxy)benzamide;

(S)-2-fluoro-N-(1-(4-fluoro-3-methylphenyl)ethyl)-5-((2-imino-3-methyl-2,3-dihydro-1H-imidazol-1-yl)methyl)-3-(2-(trifluoromethyl)pyridin-3-yl)benzamide;

(S)-2,4'-difluoro-N-(1-(4-fluoro-3-methylphenyl)ethyl)-5-((2-imino-3-methyl-2,3-dihydro-1H-imidazol-1-yl)methyl)-2'-(trifluoromethyl)-[1,1'-biphenyl]-3-carboxamide;

(S)—N-(cyclopropyl(5-fluoro-6-methylpyridin-2-yl)methyl)-4'-fluoro-5-((2-imino-3-methyl-2,3-dihydro-1H-imidazol-1-yl)methyl)-2'-methyl-[1,1'-biphenyl]-3-carboxamide;

(S)-2'-chloro-N-(cyclopropyl(5-fluoro-4-methylpyridin-2-yl)methyl)-4'-fluoro-5-((2-imino-3-methyl-2,3-dihydro-1H-imidazol-1-yl)methyl)-[1,1'-biphenyl]-3-carboxamide;

(S)—N-(cyclopropyl(4-fluoro-3-methylphenyl)methyl)-3-(cyclopropylmethoxy)-5-((2-imino-3-methyl-2,3-dihydro-1H-imidazol-1-yl)methyl)benzamide;

(S)-3-ethoxy-N-(1-(4-fluoro-3-methylphenyl)ethyl)-5-((2-imino-3-methyl-2,3-dihydro-1H-imidazol-1-yl)methyl)benzamide;

N-(3,5-dimethoxybenzyl)-3-ethoxy-5-((2-imino-3-methyl-2,3-dihydro-1H-imidazol-1-yl)methyl)benzamide;

3-(cyclopropylmethoxy)-N-(3,5-dimethoxybenzyl)-5-((2-imino-3-methyl-2,3-dihydro-1H-imidazol-1-yl)methyl)benzamide;

(S)—N-(cyclopropyl(4-fluoro-3-methylphenyl)methyl)-3-((2-imino-3-methyl-2,3-dihydro-1H-imidazol-1-yl)methyl)-5-(trifluoromethoxy)benzamide;

(S)—N-(cyclopropyl(4-fluoro-3-methylphenyl)methyl)-3-ethoxy-5-((2-imino-3-methyl-2,3-dihydro-1H-imidazol-1-yl)methyl)benzamide;

(S)-3-(cyclopropylmethoxy)-N-(1-(4-fluoro-3-methylphenyl)ethyl)-5-((2-imino-3-methyl-2,3-dihydro-1H-imidazol-1-yl)methyl)benzamide;

(S)—N-(cyclopropyl(4-methylpyridin-2-yl)methyl)-3-(cyclopropylmethoxy)-5-((2-imino-3-methyl-2,3-dihydro-1H-imidazol-1-yl)methyl)benzamide;

N-(4-chloro-3-methylbenzyl)-3-ethoxy-5-((2-imino-3-methyl-2,3-dihydro-1H-imidazol-1-yl)methyl)benzamide;

N-(3,4-dichlorobenzyl)-3-(5-fluoro-2-methoxypyridin-4-yl)-5-((2-imino-3-methyl-2,3-dihydro-1H-imidazol-1-yl)methyl)benzamide;

(S)-2'-cyano-N-(cyclopropyl(4-fluoro-3-methylphenyl)methyl)-4'-fluoro-5-((2-imino-3-methyl-2,3-dihydro-1H-imidazol-1-yl)methyl)-[1,1'-biphenyl]-3-carboxamide;

N-(1-(3-bromophenyl)cyclobutyl)-2,4'-difluoro-5-((2-imino-3-methyl-2,3-dihydro-1H-imidazol-1-yl)methyl)-2'-(trifluoromethyl)-[1,1'-biphenyl]-3-carboxamide;

(S)—N-(cyclopropyl(3,4-dichlorophenyl)methyl)-3-(5-fluoro-3-(trifluoromethyl)pyridin-2-yl)-5-((2-imino-3-methyl-2,3-dihydro-1H-imidazol-1-yl)methyl)benzamide;

(S)—N-(cyclopropyl(4-fluoro-3-methylphenyl)methyl)-4'-fluoro-5-((2-imino-3-methyl-2,3-dihydro-1H-imidazol-1-yl)methyl)-2'-(trifluoromethyl)-[1,1'-biphenyl]-3-carboxamide;

(S)—N-(cyclopropyl(3,4-difluorophenyl)methyl)-3-((2-imino-3-methyl-2,3-dihydro-1H-imidazol-1-yl)methyl)-5-(2-(trifluoromethyl)pyridin-3-yl)benzamide;

(S)—N-(cyclopropyl(3,4-difluorophenyl)methyl)-3-((3-cyclopropyl-2-imino-2,3-dihydro-1H-imidazol-1-yl)methyl)-5-(1-ethyl-3-(trifluoromethyl)-1H-pyrazol-4-yl)benzamide;

(S)—N-(cyclopropyl(3,4-difluorophenyl)methyl)-3-(1-ethyl-3-(trifluoromethyl)-1H-pyrazol-4-yl)-5-((2-imino-3-methyl-2,3-dihydro-1H-imidazol-1-yl)methyl)benzamide;

(S)—N-(cyclopropyl(4-fluoro-3-methylphenyl)methyl)-3-((2-imino-3-methyl-2,3-dihydro-1H-imidazol-1-yl)methyl)-5-(3,3,3-trifluoroprop-1-en-2-ylbenzamide;

(S)—N-(cyclopropyl(4-fluoro-3-methylphenyl)methyl)-3-((2-imino-3-methyl-2,3-dihydro-1H-imidazol-1-yl)methyl)-5-(1-isopropyl-3-(trifluoromethyl)-1H-pyrazol-4-yl)benzamide;

(S)—N-(cyclopropyl(4-fluoro-3-methylphenylmethyl)-4-((3-cyclopropyl-2-imino-2,3-dihydro-1H-imidazol-1-yl)methyl)-5-(1-isopropyl-3-(trifluoromethyl)-1H-pyrazol-4-yl)benzamide;

N—((S)-cyclopropyl(4-fluoro-3-methylphenyl)methyl)-3-((2-imino-3-methyl-2,3-dihydro-1H-imidazol-1-yl)methyl)-5-(l, 1,1-trifluoropropan-2-yl)benzamide;

(S)—N-(cyclopropyl(4-fluoro-3-methylphenyl)methyl)-3-((2-imino-3-methyl-2,3-dihydro-1H-imidazol-1-yl)methyl)-5-(1-methyl-3-(trifluoromethyl)-1H-pyrazol-5-yl)benzamide;

3-((3-cyclopropyl-2-imino-2,3-dihydro-1H-imidazol-1-yl)methyl)-5-(1-ethyl-3-(trifluoromethyl)-1H-pyrazol-4-yl)-N-(4-fluoro-3-methylbenzyl)benzamide;

3-(1-ethyl-3-(trifluoromethyl)-1H-pyrazol-4-yl)-N-(4-fluoro-3-methylbenzyl)-5-((2-imino-3-methyl-2,3-dihydro-1H-imidazol-1-yl)methyl)benzamide;

3-((3-cyclopropyl-2-imino-2,3-dihydro-1H-imidazol-1-yl)methyl)-5-(1-ethyl-3-(trifluoromethyl)-1H-pyrazol-4-yl)-N-((1-methyl-6-oxo-1,6-dihydropyridin-3-yl)methyl)benzamide;

3-(1-ethyl-3-(trifluoromethyl)-1H-pyrazol-4-yl)-5-((2-imino-3-methyl-2,3-dihydro-1H-imidazol-1-yl)methyl)-N-((1-methyl-6-oxo-1,6-dihydropyridin-3-yl)methyl)benzamide;

(S)—N-(cyclopropyl(4-fluoro-3-methylphenyl)methyl)-5-((2-imino-3-methyl-2,3-dihydro-1H-imidazol-1-yl)methyl)-2'-methyl-[1,1'-biphenyl]-3-carboxamide;

(S)—N-((3-chloro-4-fluorophenyl)(cyclopropyl)methyl)-3-((3-cyclopropyl-2-imino-2,3-dihydro-1H-imidazol-1-yl)methyl)-5-(1-ethyl-3-(trifluoromethyl)-1H-pyrazol-4-yl)benzamide;

(S)—N-(cyclopropyl(4-fluoro-3-methylphenylmethyl)-4-((2-imino-3-methylimidazolidin-1-yl)methyl)-5-(1-methyl-3-(trifluoromethyl)-1H-pyrazol-4-yl)benzamide;

(S)—N-(cyclopropyl(5-fluoro-4-methylpyridin-2-yl)methyl)-3-((3-cyclopropyl-2-imino-2,3-dihydro-1H-imidazol-1-yl)methyl)-5-(1-methyl-3-(trifluoromethyl)-1H-pyrazol-4-yl)benzamide; (S)—N-(cyclopropyl(5-fluoro-4-methylpyridin-2-yl)methyl)-3-((2-imino-3-methyl-2,3-dihydro-1H-imidazol-1-yl)methyl)-5-(1-methyl-3-(trifluoromethyl)-1H-pyrazol-4-yl)benzamide;

(S)—N-(cyclopropyl(4-fluoro-3-methylphenyl)methyl)-3-((2-imino-3-methyl-2,3-dihydro-1H-imidazol-1-yl)methyl)-5-(pyrrolidin-1-ylbenzamide;

(S)—N-(cyclopropyl(4-fluoro-3-methoxyphenyl)methyl)-3-((2-imino-3-methyl-2,3-dihydro-1H-imidazol-1-yl)methyl)-5-(1-methyl-3-(trifluoromethyl)-1H-pyrazol-4-yl)benzamide;

(S)—N-(cyclopropyl(5-fluoro-4-methylpyridin-2-yl)methyl)-3-((2-imino-3-methyl-2,3-dihydro-1H-imidazol-1-yl)methyl)-5-(pyrrolidin-1-ylbenzamide;

(S)-2-ethoxy-N-(1-(4-fluoro-3-methylphenyl)ethyl)-5-((2-imino-3-methyl-2,3-dihydro-1H-imidazol-1-yl)methyl)-3-(1-methyl-3-(trifluoromethyl)-1H-pyrazol-4-yl)benzamide;

(S)—N-(cyclopropyl(4-fluoro-3-methylphenyl)methyl)-2-ethoxy-5-((2-imino-3-methyl-2,3-dihydro-1H-imidazol-1-yl)methyl)-3-(1-methyl-3-(trifluoromethyl)-1H-pyrazol-4-yl)benzamide;

(S)—N-(cyclopropyl(3,4-dichlorophenyl)methyl)-3-((2-imino-3-methylimidazolidin-1-yl)methyl)-5-(1-methyl-3-(trifluoromethyl)-1H-pyrazol-4-yl)benzamide;

(S)—N-(cyclopropyl(4-fluoro-3-methylphenyl)methyl)-3-(1-ethyl-3-(trifluoromethyl)-1H-pyrazol-4-yl)-5-((2-imino-3-methylimidazolidin-1-yl)methyl)benzamide;

(S)—N-(cyclopropyl(3,4-difluorophenyl)methyl)-3-(1-ethyl-3-(trifluoromethyl)-1H-pyrazol-4-yl)-5-((2-imino-3-methylimidazolidin-1-yl)methyl)benzamide;

(S)—N-((3-chloro-4-fluorophenyl)(cyclopropyl)methyl)-3-(1-ethyl-3-(trifluoromethyl)-1H-pyrazol-4-yl)-5-((2-imino-3-methylimidazolidin-1-yl)methyl)benzamide;

(S)—N-(cyclopropyl(4-fluoro-3-methylphenylmethyl)-4-((2-imino-3-methylimidazolidin-1-yl)methyl)-5-(1-isopropyl-3-(trifluoromethyl)-1H-pyrazol-4-yl)benzamide;

(S)—N-(cyclopropyl(3,4-difluorophenyl)methyl)-3-((2-imino-3-methylimidazolidin-1-yl)methyl)-5-(1-isopropyl-3-(trifluoromethyl)-1H-pyrazol-4-yl)benzamide;

(S)—N-(cyclopropyl(4-fluoro-3-methylphenyl)methyl)-3-((2-imino-3-methyl-2,3-dihydro-1H-imidazol-1-yl)methyl)-5-(1-(trifluoromethyl)cyclopropyl)benzamide;

(S)—N-(cyclopropyl(5-fluoro-4-methylpyridin-2-yl)methyl)-3-((2-imino-3-methyl-2,3-dihydro-1H-imidazol-1-yl)methyl)-5-(1-(trifluoromethyl)cyclopropyl)benzamide;

(S)—N-((3-chloro-4-fluorophenyl)(cyclopropyl)methyl)-3-((2-imino-3-methylimidazolidin-1-yl)methyl)-5-(2-(trifluoromethyl)pyridin-3-yl)benzamide;

3-((2-imino-3-methyl-2,3-dihydro-1H-imidazol-1-yl)methyl)-5-(1-methyl-3-(trifluoromethyl)-1H-pyrazol-4-yl)-N-(1-(m-tolyl)cyclobutyl)benzamide;

(S)—N-(cyclopropyl(5-fluoro-4-methoxypyridin-2-yl)methyl)-3-((2-imino-3-methyl-2,3-dihydro-1H-imidazol-1-yl)methyl)-5-(1-methyl-3-(trifluoromethyl)-1H-pyrazol-4-yl)benzamide;

N—((S)-cyclopropyl(4-fluoro-3-methylphenyl)methyl)-3-((2-imino-3-methyl-2,3-dihydro-1H-imidazol-1-yl)methyl)-5-((R)-2-(trifluoromethyl)pyrrolidin-1-ylbenzamide;

N—((S)-cyclopropyl(4-fluoro-3-methylphenyl)methyl)-3-((2-imino-3-methyl-2,3-dihydro-1H-imidazol-1-yl)methyl)-5-((S)-2-(trifluoromethyl)pyrrolidin-1-ylbenzamide;

(S)—N-(cyclopropyl(4-fluoro-3-methylphenyl)methyl)-3-((2-imino-3-methyl-2,3-dihydro-1H-imidazol-1-yl)methyl)-5-(2-methyl-1H-imidazol-1-ylbenzamide;

(S)—N-(cyclopropyl(4-fluoro-3-methylphenyl)methyl)-3-(1-ethyl-3-methyl-1H-pyrazol-4-yl)-5-((2-imino-3-methyl-2,3-dihydro-1H-imidazol-1-yl)methyl)benzamide;

N—((S)-cyclopropyl(4-fluoro-3-methylphenyl)methyl)-3-((2-imino-3-methyl-2,3-dihydro-1H-imidazol-1-yl)methyl)-5-((R)-2-m ethylpyrrolidin-1-ylbenzamide;

N—((S)-cyclopropyl(4-fluoro-3-methylphenyl)methyl)-3-((2-imino-3-methyl-2,3-dihydro-1H-imidazol-1-yl)methyl)-5-((R)-3-methylmorpholino)benzamide;

2'-chloro-N-(3,4-dichlorobenzyl)-4'-fluoro-5-((2-iminooxazol-3(2H)-yl)methyl)-[1,1'-biphenyl]-3-carboxamide;

N-(3,5-dimethoxybenzyl)-4'-fluoro-5-((2-iminooxazol-3(2H)-yl)methyl)-2'-methyl-[1,1'-biphenyl]-3-carboxamide;

(S)-4'-fluoro-N-(1-(4-fluoro-3-methylphenyl)ethyl)-5-((2-iminooxazol-3(2H)-yl)methyl)-2'-methyl-[1,1'-biphenyl]-3-carboxamide;

(S)-4'-fluoro-5-((2-iminooxazol-3(2H)-yl)methyl)-2'-methyl-N-(2,2,2-trifluoro-1-(4-fluoro-3-methylphenyl)ethyl)-[1,1'-biphenyl]-3-carboxamide;

(S)—N-(cyclopropyl(4-fluoro-3-methylphenyl)methyl)-4'-fluoro-5-((2-iminooxazol-3(2H)-yl)methyl)-2'-methyl-[1,1'-biphenyl]-3-carboxamide;

(S)-4'-fluoro-N-(1-(4-fluoro-3-(trifluoromethyl)phenyl)ethyl)-5-((2-iminooxazol-3(2H)-yl)methyl)-2'-methyl-[1,1'-biphenyl]-3-carboxamide;

(S)—N-(1-(4-chloro-3-methylphenyl)ethyl)-4'-fluoro-5-((2-iminooxazol-3(2H)-yl)methyl)-2'-methyl-[1,1'-biphenyl]-3-carboxamide;

N-(cyclopropyl(3,5-dimethoxyphenyl)methyl)-3-((2-iminooxazol-3(2H)-yl)methyl)-5-(3-(trifluoromethyl)pyridin-2-yl)benzamide;

N-(cyclopropyl(3,5-dimethoxyphenyl)methyl)-2'-(difluoromethoxy)-4'-fluoro-5-((2-iminooxazol-3(2H)-yl)methyl)-[1,1'-biphenyl]-3-carboxamide;
N-(cyclopropyl(4-methylpyridin-2-yl)methyl)-3-((2-iminooxazol-3(2H)-yl)methyl)-5-(3-(trifluoromethyl)pyridin-2-yl)benzamide;
N-(3,5-dimethoxybenzyl)-3-(5-fluoro-3-methylpyridin-2-yl)-5-((2-iminooxazol-3(2H)-yl)methyl)benzamide;
N-(cyclopropyl(4-methylpyridin-2-yl)methyl)-3-(5-fluoro-3-methylpyridin-2-yl)-5-((2-iminooxazol-3(2H)-yl)methyl)benzamide;
(S)—N-(cyclopropyl(4-fluoro-3-methylphenyl)methyl)-3-(5-fluoro-3-methylpyridin-2-yl)-5-((2-iminooxazol-3(2H)-yl)methyl)benzamide;
(S)—N-(cyclopropyl(4-fluoro-3-methylphenyl)methyl)-3-(5-fluoro-3-(trifluoromethyl)pyridin-2-yl)-5-((2-iminooxazol-3(2H)-yl)methyl)benzamide;
(S)—N-(cyclopropyl(4-fluoro-3-methylphenyl)methyl)-2'-(difluoromethoxy)-4'-fluoro-5-((2-iminooxazol-3(2H)-yl)methyl)-[1,1'-biphenyl]-3-carboxamide;
(S)—N-(cyclopropyl(4-fluoro-3-methylphenyl)methyl)-3-((2-iminooxazol-3(2H)-yl)methyl)-5-(2-(trifluoromethyl)pyridin-3-yl)benzamide; N-(3,5-dimethoxybenzyl)-3-((2-iminooxazol-3(2H)-yl)methyl)-5-(2-(trifluoromethyl)pyridin-3-yl)benzamide;
N-(cyclopropyl(3,5-dimethoxyphenyl)methyl)-3-((2-iminooxazol-3(2H)-yl)methyl)-5-(2-(trifluoromethyl)pyridin-3-yl)benzamide;
4'-fluoro-N-(4-fluorobenzyl)-5-((2-iminooxazol-3(2H)-yl)methyl)-2'-methyl-[1,1'-biphenyl]-3-carboxamide;
(S)—N-(cyclopropyl(4-methylpyridin-2-yl)methyl)-4'-fluoro-5-((2-iminooxazol-3(2H)-yl)methyl)-2'-methyl-[1,1'-biphenyl]-3-carboxamide;
(S)-2'-chloro-N-(cyclopropyl(4-fluoro-3-methylphenyl)methyl)-4'-fluoro-5-((2-iminooxazol-3(2H)-yl)methyl)-[1,1'-biphenyl]-3-carboxamide;
2'-chloro-N-(cyclopropyl(3,5-dimethoxyphenyl)methyl)-4'-fluoro-5-((2-iminooxazol-3(2H)-yl)methyl)-[1,1'-biphenyl]-3-carboxamide;
(S)—N-(cyclopropyl(4-fluoro-3-methylphenyl)methyl)-3-((2-imino-5-methyloxazol-3(2H)-yl)methyl)-5-(2-(trifluoromethyl)pyridin-3-yl)benzamide;
(S)—N-(cyclopropyl(4-fluoro-3-methylphenyl)methyl)-3-((5-ethyl-2-iminooxazol-3(2H)-yl)methyl)-5-(2-(trifluoromethyl)pyridin-3-yl)benzamide;
(S)—N-(cyclopropyl(4-fluoro-3-methylphenylmethyl)-4-((2-imino-4-methyloxazol-3(2H)-yl)methyl)-5-(2-(trifluoromethyl)pyridin-3-yl)benzamide;
(S)—N-(cyclopropyl(4-fluoro-3-methylphenyl)methyl)-3-((2-iminooxazolidin-3-yl)methyl)-5-(2-(trifluoromethyl)pyridin-3-yl)benzamide;
N-(3,5-dimethoxybenzyl)-4'-fluoro-5-((2-iminooxazolidin-3-yl)methyl)-2'-methyl-[1,1'-biphenyl]-3-carboxamide;
(S)—N-(cyclopropyl(4-fluoro-3-methylphenyl)methyl)-3-((2-iminooxazol-3(2H)-yl)methyl)-5-(4-(trifluoromethyl)pyrimidin-5-yl)benzamide;
(S)—N-(cyclopropyl(4-fluoro-3-methylphenyl)methyl)-3-((4-ethyl-2-iminooxazol-3(2H)-yl)methyl)-5-(2-(trifluoromethyl)pyridin-3-yl)benzamide;
(S)—N-(1-(3-chloro-4-fluorophenyl)ethyl)-3-((2-iminooxazol-3(2H)-yl)methyl)-5-(2-(trifluoromethyl)pyridin-3-yl)benzamide;
(S)-3-((2-iminooxazol-3(2H)-yl)methyl)-N-(1-(4-(trifluoromethyl)phenyl)ethyl)-5-(2-(trifluoromethyl)pyridin-3-yl)benzamide;
(S)—N-(cyclopropyl(4-fluoro-3-methylphenyl)methyl)-3-((2-iminooxazol-3(2H)-yl)methyl)-5-(1-methyl-3-(trifluoromethyl)-1H-pyrazol-4-yl)benzamide;
(S)—N-(1-(4-fluorophenyl)ethyl)-3-((2-iminooxazol-3(2H)-yl)methyl)-5-(2-(trifluoromethyl)pyridin-3-yl)benzamide;
(S)—N-(cyclopropyl(4-fluoro-3-methylphenyl)methyl)-3-(2-(difluoromethoxy)pyridin-3-yl)-5-((2-iminooxazol-3(2H)-yl)methyl)benzamide;
(S)—N-(1-(5-fluoropyrimidin-2-yl)ethyl)-3-((2-iminooxazol-3(2H)-yl)methyl)-5-(2-(trifluoromethyl)pyridin-3-yl)benzamide;
(S)—N-(cyclopropyl(4-fluoro-3-methylphenyl)methyl)-3-((2-iminooxazol-3(2H)-yl)methyl)-5-(2-(2,2,2-trifluoroethoxy)pyridin-3-yl)benzamide;
(S)—N-(cyclopropyl(4-fluoro-3-methylphenyl)methyl)-3-(6,7-dihydro-5H-cyclopenta[b]pyridin-4-yl)-5-((2-iminooxazol-3(2H)-yl)methyl)benzamide;
(S)-3-cyclopropyl-N-(cyclopropyl(4-fluoro-3-methylphenyl)methyl)-5-((2-iminooxazol-3(2H)-yl)methyl)benzamide;
(S)—N-(cyclopropyl(4-fluoro-3-methylphenyl)methyl)-3-((2-imino-1,3-oxazinan-3-yl)methyl)-5-(2-(trifluoromethyl)pyridin-3-yl)benzamide;
(S)—N-(cyclopropyl(3,4-dichlorophenyl)methyl)-2'-(difluoromethoxy)-4'-fluoro-5-((2-iminooxazolidin-3-yl)methyl)-[1,1'-biphenyl]-3-carboxamide;
(S)—N-(cyclopropyl(3,4-dichlorophenyl)methyl)-3-((2-iminooxazol-3(2H)-yl)methyl)-5-(1-methyl-3-(trifluoromethyl)-1H-pyrazol-4-yl)benzamide;
(S)—N-(cyclopropyl(3,4-dichlorophenyl)methyl)-3-((2-iminooxazolidin-3-yl)methyl)-5-(1-methyl-3-(trifluoromethyl)-1H-pyrazol-4-yl)benzamide;
(S)—N-(cyclopropyl(3,4-dichlorophenyl)methyl)-2'-(difluoromethoxy)-4'-fluoro-5-((2-iminooxazol-3(2H)-yl)methyl)-[1,1'-biphenyl]-3-carboxamide;
(S)—N-(cyclopropyl(3,4-dichlorophenyl)methyl)-3-((2-iminooxazol-3(2H)-yl)methyl)-5-(2-(trifluoromethyl)pyridin-3-yl)benzamide;
(S)—N-(cyclopropyl(4-fluoro-3-methylphenyl)methyl)-2'-(difluoromethyl)-4'-fluoro-5-((2-iminooxazolidin-3-yl)methyl)-[1,1'-biphenyl]-3-carboxamide;
(S)—N-(cyclopropyl(4-fluoro-3-methylphenyl)methyl)-2'-(difluoromethoxy)-4'-fluoro-5-((2-iminooxazolidin-3-yl)methyl)-[1,1'-biphenyl]-3-carboxamide;
(S)—N-(cyclopropyl(4-fluoro-3-methylphenyl)methyl)-2'-(difluoromethyl)-4'-fluoro-5-((2-iminooxazol-3(2H)-yl)methyl)-[1,1'-biphenyl]-3-carboxamide;
(S)—N-(cyclopropyl(4-fluoro-3-methylphenyl)methyl)-3-((2-iminooxazolidin-3-yl)methyl)-5-(1-isopropyl-3-(trifluoromethyl)-1H-pyrazol-4-yl)benzamide;
(S)—N-(cyclopropyl(4-fluoro-3-methylphenyl)methyl)-3-(1-ethyl-3-(trifluoromethyl)-1H-pyrazol-4-yl)-5-((2-iminooxazolidin-3-yl)methyl)benzamide;
N-(3,4-dichlorobenzyl)-6-(4-fluoro-2-methylphenyl)-4-((2-iminooxazol-3(2H)-yl)methyl)picolinamide;
(S)—N-(cyclopropyl(4-fluoro-3-methylphenyl)methyl)-3-((2-iminooxazolidin-3-yl)methyl)-5-(1-isobutyl-3-(trifluoromethyl)-1H-pyrazol-4-yl)benzamide;
(S)-3-(1-cyclopentyl-3-(trifluoromethyl)-1H-pyrazol-4-yl)-N-(cyclopropyl(4-fluoro-3-methylphenyl)methyl)-5-((2-iminooxazolidin-3-yl)methyl)benzamide;
(S)—N-(cyclopropyl(3,4-dichlorophenyl)methyl)-3-(1-ethyl-3-(trifluoromethyl)-1H-pyrazol-4-yl)-5-((2-iminooxazol-3(2H)-yl)methyl)benzamide;

(S)—N-(cyclopropyl(3,4-dichlorophenyl)methyl)-3-(1-ethyl-3-(trifluoromethyl)-1H-pyrazol-4-yl)-5-((2-iminooxazolidin-3-yl)methyl)benzamide;
(S)-2'-cyano-N-(cyclopropyl(4-fluoro-3-methylphenyl)methyl)-4'-fluoro-5-((2-iminooxazolidin-3-yl)methyl)-[1,1'-biphenyl]-3-carboxamide;
(S)—N-(cyclopropyl(4-fluoro-3-methylphenyl)methyl)-2,4'-difluoro-5-((2-iminooxazolidin-3-yl)methyl)-2'-(trifluoromethyl)-[1,1'-biphenyl]-3-carboxamide;
(S)—N-(cyclopropyl(3,4-dichlorophenyl)methyl)-3-(5-fluoro-3-(trifluoromethyl)pyridin-2-yl)-5-((2-iminooxazolidin-3-yl)methyl)benzamide;
(S)—N-(cyclopropyl(4-fluoro-3-methylphenyl)methyl)-4'-fluoro-5-((2-iminooxazolidin-3-yl)methyl)-2'-(trifluoromethyl)-[1,1'-biphenyl]-3-carboxamide;
(S)—N-(cyclopropyl(3,4-difluorophenyl)methyl)-3-((2-iminooxazolidin-3-yl)methyl)-5-(1-isopropyl-3-(trifluoromethyl)-1H-pyrazol-4-yl)benzamide;
(S)—N-(cyclopropyl(4-fluoro-3-methylphenyl)methyl)-3-((2-iminooxazolidin-3-yl)methyl)-5-(1-methyl-3-(trifluoromethyl)-1H-pyrazol-5-yl)benzamide;
3-(1-ethyl-3-(trifluoromethyl)-1H-pyrazol-4-yl)-5-((2-iminooxazolidin-3-yl)methyl)-N-((tetrahydro-2H-pyran-4-yl)methyl)benzamide;
3-(1-ethyl-3-(trifluoromethyl)-1H-pyrazol-4-yl)-5-((2-iminooxazolidin-3-yl)methyl)-N-((tetrahydrofuran-2-yl)methyl)benzamide;
3-(1-ethyl-3-(trifluoromethyl)-1H-pyrazol-4-yl)-5-((2-iminooxazolidin-3-yl)methyl)-N-((tetrahydrofuran-3-yl)methyl)benzamide;
(S)—N-(cyclopropyl(4-fluoro-3-methylphenyl)methyl)-3-((2-iminooxazol-3(2H)-yl)methyl)-5-(1-isopropyl-3-(trifluoromethyl)-1H-pyrazol-4-yl)benzamide;
3-(1-ethyl-3-(trifluoromethyl)-1H-pyrazol-4-yl)-5-((2-iminooxazol-3(2H)-yl)methyl)-N-((1-methyl-6-oxo-1,6-dihydropyridin-3-yl)methyl)benzamide;
3-(1-ethyl-3-(trifluoromethyl)-1H-pyrazol-4-yl)-5-((2-iminooxazolidin-3-yl)methyl)-N-((1-methyl-6-oxo-1,6-dihydropyridin-3-yl)methyl)benzamide;
3-(1-ethyl-3-(trifluoromethyl)-1H-pyrazol-4-yl)-N-(4-fluoro-3-methylbenzyl)-5-((2-iminooxazol-3(2H)-yl)methyl)benzamide;
3-(1-ethyl-3-(trifluoromethyl)-1H-pyrazol-4-yl)-N-(4-fluoro-3-methylbenzyl)-5-((2-iminooxazolidin-3-yl)methyl)benzamide;
N—((S)-cyclopropyl(4-fluoro-3-methylphenyl)methyl)-3-(((S)-2-imino-5-methyloxazolidin-3-yl)methyl)-5-(2-(trifluoromethyl)pyridin-3-yl)benzamide;
N—((S)-cyclopropyl(4-fluoro-3-methylphenyl)methyl)-3-(((R)-2-imino-5-methyloxazolidin-3-yl)methyl)-5-(2-(trifluoromethyl)pyridin-3-yl)benzamide;
(S)—N-((3-chloro-4-fluorophenyl)(cyclopropyl)methyl)-3-(1-ethyl-3-(trifluoromethyl)-1H-pyrazol-4-yl)-5-((2-iminooxazol-3(2H)-yl)methyl)benzamide;
(S)—N-(cyclopropyl(5-fluoro-4-methylpyridin-2-yl)methyl)-3-((2-iminooxazol-3(2H)-yl)methyl)-5-(1-methyl-3-(trifluoromethyl)-1H-pyrazol-4-yl)benzamide;
(S)—N-(cyclopropyl(5-fluoro-4-methylpyridin-2-yl)methyl)-3-((2-iminooxazolidin-3-yl)methyl)-5-(1-methyl-3-(trifluoromethyl)-1H-pyrazol-4-yl)benzamide;
(S)-2'-chloro-N-((4-chloro-3-fluorophenyl)(cyclopropyl)methyl)-4'-fluoro-5-((2-iminooxazolidin-3-yl)methyl)-[1,1'-biphenyl]-3-carboxamide;
(S)-2-ethoxy-N-(1-(4-fluoro-3-methylphenyl)ethyl)-5-((2-iminooxazolidin-3-yl)methyl)-3-(1-methyl-3-(trifluoromethyl)-1H-pyrazol-4-yl)benzamide;
(S)—N-(cyclopropyl(4-fluoro-3-methylphenyl)methyl)-2-ethoxy-5-((2-iminooxazolidin-3-yl)methyl)-3-(1-methyl-3-(trifluoromethyl)-1H-pyrazol-4-yl)benzamide;
(S)—N-(cyclopropyl(4-fluoro-3-methylphenyl)methyl)-2-ethoxy-5-((2-iminooxazol-3(2H)-yl)methyl)-3-(1-methyl-3-(trifluoromethyl)-1H-pyrazol-4-yl)benzamide;
(S)—N-(cyclopropyl(4-fluoro-3-methoxyphenyl)methyl)-3-((2-iminooxazolidin-3-yl)methyl)-5-(2-(trifluoromethyl)pyridin-3-yl)benzamide;
(S)—N-(cyclopropyl(5-fluoro-4-methoxypyridin-2-yl)methyl)-3-((2-iminooxazol-3(2H)-yl)methyl)-5-(1-methyl-3-(trifluoromethyl)-1H-pyrazol-4-yl)benzamide;
N-(3,5-dimethoxybenzyl)-4'-fluoro-5-((2-iminothiazol-3(2H)-yl)methyl)-2'-methyl-[1,1'-biphenyl]-3-carboxamide;
N-(3,5-dimethoxybenzyl)-4'-fluoro-5-((2-iminothiazolidin-3-yl)methyl)-2'-methyl-[1,1'-biphenyl]-3-carboxamide;
(S)—N-(cyclopropyl(3,4-dichlorophenyl)methyl)-2'-(difluoromethoxy)-4'-fluoro-5-((2-iminothiazolidin-3-yl)methyl)-[1,1'-biphenyl]-3-carboxamide;
(S)—N-(cyclopropyl(3,4-dichlorophenyl)methyl)-3-((2-iminothiazolidin-3-yl)methyl)-5-(1-methyl-3-(trifluoromethyl)-1H-pyrazol-4-yl)benzamide;
(S)—N-(cyclopropyl(3,4-dichlorophenyl)methyl)-3-((2-iminothiazolidin-3-yl)methyl)-5-(2-(trifluoromethyl)pyridin-3-yl)benzamide;
(S)—N-(cyclopropyl(4-fluoro-3-methylphenyl)methyl)-3-(1-ethyl-3-(trifluoromethyl)-1H-pyrazol-4-yl)-5-((2-iminothiazolidin-3-yl)methyl)benzamide;
(S)—N-(cyclopropyl(4-fluoro-3-methylphenyl)methyl)-3-((2-iminothiazolidin-3-yl)methyl)-5-(1-isobutyl-3-(trifluoromethyl)-1H-pyrazol-4-yl)benzamide;
(S)-3-(1-cyclopentyl-3-(trifluoromethyl)-1H-pyrazol-4-yl)-N-(cyclopropyl(4-fluoro-3-methylphenyl)methyl)-5-((2-iminothiazolidin-3-yl)methyl)benzamide;
(S)—N-(cyclopropyl(4-fluoro-3-methylphenyl)methyl)-3-((2-imino-1,3-thiazinan-3-yl)methyl)-5-(2-(trifluoromethyl)pyridin-3-yl)benzamide;
(S)-2'-cyano-N-(cyclopropyl(4-fluoro-3-methylphenyl)methyl)-4'-fluoro-5-((2-iminothiazolidin-3-yl)methyl)-[1,1'-biphenyl]-3-carboxamide;
(S)—N-(cyclopropyl(3,4-dichlorophenyl)methyl)-3-(5-fluoro-3-(trifluoromethyl)pyridin-2-yl)-5-((2-iminothiazolidin-3-yl)methyl)benzamide;
(S)—N-(cyclopropyl(3,4-difluorophenyl)methyl)-3-((2-iminothiazolidin-3-yl)methyl)-5-(2-(trifluoromethyl)pyridin-3-yl)benzamide;
(S)—N-(cyclopropyl(3,4-difluorophenyl)methyl)-3-((2-iminothiazolidin-3-yl)methyl)-5-(1-isopropyl-3-(trifluoromethyl)-1H-pyrazol-4-yl)benzamide;
(S)—N-(cyclopropyl(4-fluoro-3-methylphenyl)methyl)-3-(1-ethyl-3-(trifluoromethyl)-1H-pyrazol-4-yl)-5-((2-iminothiazol-3(2H)-yl)methyl)benzamide;
(S)—N-(cyclopropyl(4-fluoro-3-methylphenyl)methyl)-3-((2-iminothiazol-3(2H)-yl)methyl)-5-(1-methyl-3-(trifluoromethyl)-1H-pyrazol-4-yl)benzamide;
(S)—N-(cyclopropyl(4-fluoro-3-methylphenyl)methyl)-3-((2-iminothiazol-3(2H)-yl)methyl)-5-(1-isopropyl-3-(trifluoromethyl)-1H-pyrazol-4-yl)benzamide;

3-(1-ethyl-3-(trifluoromethyl)-1H-pyrazol-4-yl)-5-((2-iminothiazolidin-3-yl)methyl)-N-((1-methyl-6-oxo-1,6-dihydropyridin-3-yl)methyl)benzamide;

(S)—N-((4-chloro-3-fluorophenyl)(cyclopropyl)methyl)-3-(1-ethyl-3-(trifluoromethyl)-1H-pyrazol-4-yl)-5-((2-iminothiazol-3(2H)-yl)methyl)benzamide;

(S)—N-(cyclopropyl(5-fluoro-4-methylpyridin-2-yl)methyl)-3-((2-iminothiazol-3(2H)-yl)methyl)-5-(1-methyl-3-(trifluoromethyl)-1H-pyrazol-4-yl)benzamide;

(S)—N-(cyclopropyl(5-fluoro-4-methylpyridin-2-yl)methyl)-3-((2-iminothiazolidin-3-yl)methyl)-5-(1-methyl-3-(trifluoromethyl)-1H-pyrazol-4-yl)benzamide;

(S)—N-(cyclopropyl(4-fluoro-3-methoxyphenyl)methyl)-3-((2-iminothiazol-3(2H)-yl)methyl)-5-(1-methyl-3-(trifluoromethyl)-1H-pyrazol-4-yl)benzamide;

(S)—N-(cyclopropyl(4-fluoro-3-methoxyphenyl)methyl)-3-(1-ethyl-3-(trifluoromethyl)-1H-pyrazol-4-yl)-5-((2-iminothiazol-3(2H)-yl)methyl)benzamide;

(S)—N-(cyclopropyl(4-fluoro-3-methoxyphenyl)methyl)-3-((2-iminothiazol-3(2H)-yl)methyl)-5-(2-(trifluoromethyl)pyridin-3-yl)benzamide;

(S)—N-(cyclopropyl(4-fluoro-3-methoxyphenyl)methyl)-3-((2-iminothiazolidin-3-yl)methyl)-5-(2-(trifluoromethyl)pyridin-3-yl)benzamide;

N-(3,4-dichlorobenzyl)-3-(6-fluoro-2-methylpyridin-3-yl)-5-((2-iminopyrrolidin-1-yl)methyl)benzamide;

N-(3,4-dichlorobenzyl)-4'-fluoro-5-((2-iminopyrrolidin-1-yl)methyl)-2',5'-dimethyl-[1,1'-biphenyl]-3-carboxamide;

(S)-2'-cyano-N-(cyclopropyl(4-fluoro-3-methylphenyl)methyl)-4'-fluoro-5-((2-iminopyrrolidin-1-yl)methyl)-[1,1'-biphenyl]-3-carboxamide;

(S)—N-(cyclopropyl(4-fluoro-3-methylphenyl)methyl)-3-((2-iminopyrrolidin-1-yl)methyl)-5-(2-(trifluoromethyl)pyridin-3-yl)benzamide;

(S)—N-(cyclopropyl(4-fluoro-3-methylphenyl)methyl)-4'-fluoro-5-((2-iminopyrrolidin-1-yl)methyl)-2'-(trifluoromethyl)-[1,1'-biphenyl]-3-carboxamide;

(S)—N-(cyclopropyl(4-fluoro-3-methylphenyl)methyl)-3-((2-iminopyrrolidin-1-yl)methyl)-5-(1-isopropyl-3-(trifluoromethyl)-1H-pyrazol-4-yl)benzamide;

(S)—N-(cyclopropyl(4-fluoro-3-methylphenyl)methyl)-3-((2-iminopyrrolidin-1-yl)methyl)-5-(1-methyl-3-(trifluoromethyl)-1H-pyrazol-4-yl)benzamide;

(S)—N-((3-chloro-4-fluorophenyl)(cyclopropyl)methyl)-3-(1-ethyl-3-(trifluoromethyl)-1H-pyrazol-4-yl)-5-((2-iminopyrrolidin-1-yl)methyl)benzamide;

(S)—N-(cyclopropyl(4-fluoro-3-methoxyphenyl)methyl)-3-((2-iminopyrrolidin-1-yl)methyl)-5-(1-methyl-3-(trifluoromethyl)-1H-pyrazol-4-yl)benzamide;

(S)—N-((3-chloro-4-fluorophenyl)(cyclopropyl)methyl)-3-((2-iminopyrrolidin-1-yl)methyl)-5-(2-(trifluoromethyl)pyridin-3-yl)benzamide;

(S)—N-(cyclopropyl(3,4-difluorophenyl)methyl)-3-((2-iminopyrrolidin-1-yl)methyl)-5-(1-methyl-3-(trifluoromethyl)-1H-pyrazol-4-yl)benzamide;

(S)—N-(cyclopropyl(4-fluoro-3-methylphenyl)methyl)-3-((2-iminopyridin-1(2H)-yl)methyl)-5-(2-(trifluoromethyl)pyridin-3-yl)benzamide;

(S)—N-(cyclopropyl(4-fluoro-3-methylphenyl)methyl)-3-((2-imino-3-methylpyridin-1(2H)-yl)methyl)-5-(2-(trifluoromethyl)pyridin-3-yl)benzamide;

(S)—N-(cyclopropyl(4-fluoro-3-methylphenyl)methyl)-3-((2-imino-4-m ethylpyridin-1(2H)-yl)methyl)-5-(2-(trifluoromethyl)pyridin-3-yl)benzamide;

(S)—N-(cyclopropyl(4-fluoro-3-methylphenyl)methyl)-3-((3-fluoro-2-iminopyridin-1(2H)-yl)methyl)-5-(1-methyl-3-(trifluoromethyl)-1H-pyrazol-5-ylbenzamide;

(S)—N-(cyclopropyl(4-fluoro-3-methylphenyl)methyl)-3-((2-iminopyridin-1(2H)-yl)methyl)-5-(1-methyl-3-(trifluoromethyl)-1H-pyrazol-5-yl)benzamide;

(S)—N-(cyclopropyl(4-fluoro-3-methylphenyl)methyl)-2-ethoxy-5-((2-iminopyridin-1(2H)-yl)methyl)-3-(1-methyl-3-(trifluoromethyl)-1H-pyrazol-4-yl)benzamide;

N—((S)-cyclopropyl(4-fluoro-3-methylphenyl)methyl)-2-ethoxy-5-((3-fluoro-2-iminopyridin-1(2H)-yl)methyl)-3-(1-methyl-3-(trifluoromethyl)-1,3-dihydro-2λ2-pyrazol-4-yl)benzamide;

(S)—N-(cyclopropyl(4-fluoro-3-methylphenyl)methyl)-2-ethoxy-5-((5-fluoro-2-iminopyridin-1(2H)-yl)methyl)-3-(1-methyl-3-(trifluoromethyl)-1H-pyrazol-4-yl)benzamide;

(S)—N-(cyclopropyl(4-fluoro-3-methylphenyl)methyl)-3-((3-fluoro-2-iminopyridin-1(2H)-yl)methyl)-5-(2-(trifluoromethyl)pyridin-3-yl)benzamide;

(S)—N-(cyclopropyl(4-fluoro-3-methylphenyl)methyl)-3-((3-fluoro-2-iminopyridin-1(2H)-yl)methyl)-5-(1-methyl-3-(trifluoromethyl)-1H-pyrazol-4-yl)benzamide;

(S)—N-(cyclopropyl(4-fluoro-3-methylphenyl)methyl)-3-((2-iminopyridin-1(2H)-yl)methyl)-5-(1-methyl-3-(trifluoromethyl)-1H-pyrazol-4-yl)benzamide;

(S)—N-(cyclopropyl(4-fluoro-3-methylphenyl)methyl)-3-((5-fluoro-2-iminopyridin-1(2H)-yl)methyl)-5-(1-methyl-3-(trifluoromethyl)-1H-pyrazol-4-yl)benzamide;

(S)—N-(cyclopropyl(4-fluoro-3-methylphenyl)methyl)-3-((5-fluoro-2-iminopyridin-1(2H)-yl)methyl)-5-(2-(trifluoromethyl)pyridin-3-yl)benzamide;

N-(1-(3,5-dimethoxyphenyl)ethyl)-6-(4-fluoro-2-methylphenyl)-4-((2-imino-3-methyl-2,3-dihydro-1H-imidazol-1-yl)methyl)picolinamide;

N-(cyclopropyl(4-methylpyridin-2-yl)methyl)-6-(4-fluoro-2-methylphenyl)-4-((2-imino-3-methyl-2,3-dihydro-1H-imidazol-1-yl)methyl)picolinamide;

6-(4-fluoro-2-methylphenyl)-4-((2-imino-3-methyl-2,3-dihydro-1H-imidazol-1-yl)methyl)-N-((4-methoxypyridin-2-yl)methyl)picolinamide;

N-((5-chloropyrimidin-2-yl)methyl)-6-(4-fluoro-2-methylphenyl)-4-((2-imino-3-methyl-2,3-dihydro-1H-imidazol-1-yl)methyl)picolinamide;

N-(4-chloro-3-fluorobenzyl)-6-(4-fluoro-2-methylphenyl)-4-((2-imino-3-methyl-2,3-dihydro-1H-imidazol-1-yl)methyl)picolinamide;

(R)-6-(4-fluoro-2-methylphenyl)-N-(1-(4-fluoro-3-(trifluoromethyl)phenyl)ethyl)-4-((2-imino-3-methyl-2,3-dihydro-1H-imidazol-1-yl)methyl)picolinamide;

(S)—N-(cyclopropyl(4-fluoro-3-methylphenyl)methyl)-4-((2-iminooxazolidin-3-yl)methyl)-6-(1-methyl-3-(trifluoromethyl)-1H-pyrazol-4-yl)picolinamide;

(S)—N-(cyclopropyl(4-fluoro-3-methylphenyl)methyl)-3-((2-imino-1,3-oxazinan-3-yl)methyl)-5-(2-(trifluoromethyl)pyridin-3-yl)benzamide;

(S)—N-(cyclopropyl(4-fluoro-3-methylphenyl)methyl)-3-((5-imino-1-methyl-1,5-dihydro-4H-1,2,4-triazol-4-yl)methyl)-5-(1-methyl-3-(trifluoromethyl)-1H-pyrazol-4-yl)benzamide;

N-(cyclopropyl(4-methylpyridin-2-yl)methyl)-3-((2-imino-3-methyl-2,3-dihydro-1H-imidazol-1-yl)methyl)-5-(3-(trifluoromethyl)pyridin-2-ylbenzamide;

N-(3,5-dimethoxybenzyl)-2-(4-fluoro-2-methylphenyl)-6-((2-imino-3-methyl-2,3-dihydro-1H-imidazol-1-yl)methyl)isonicotinamide; and 4-fluoro-3-((2-imino-3-methyl-2,3-dihydro-1H-imidazol-1-yl)methyl)-N-((4-methoxypyridin-2-yl)methyl)benzamide;

or a pharmaceutically acceptable salt thereof.

17. A pharmaceutical composition comprising the compound of claim 1, or a pharmaceutically acceptable salt thereof, and a pharmaceutically acceptable carrier.

18. A method of treating acute myeloid leukemia comprising administering to a subject in need thereof, a therapeutically effective amount of the compound of claim 1, or a pharmaceutically acceptable salt thereof.

19. A method of inhibiting cancer cell proliferation in acute myeloid cells, comprising administering to a subject in need thereof, the compound of claim 1, or a pharmaceutically acceptable salt thereof, in an amount effective to inhibit the cancer cell proliferation in acute myeloid cells.

20. The compound of claim 5, or a pharmaceutically acceptable salt thereof, wherein $R^a$ is hydrogen, $C_{1-2}$alkyl, $C_{1-2}$haloalkyl, $C_{3-4}$carbocycle, —$C_{1-3}$alkylene-C(O)OH, —$C_{1-3}$alkylene-C(O)O$C_{1-4}$alkyl, or —$C_{1-3}$alkylene-C(O)Y$R^{20}$;

$R^{20}$ is —$C_{1-3}$alkylene-$R^{30}$; and $R^{30}$ is C(O)$C_{1-4}$alkyl or phenyl, wherein the phenyl is optionally substituted with 1-4 substituents independently selected from the group consisting of halogen, $C_{1-4}$alkyl, —O$C_{1-4}$alkyl, and $C_{1-4}$haloalkyl.

* * * * *